United States Patent
Perez et al.

(10) Patent No.: US 10,864,367 B2
(45) Date of Patent: Dec. 15, 2020

(54) METHODS FOR USING AN ELECTRICAL DERMAL PATCH IN A MANNER THAT REDUCES ADVERSE PATIENT REACTIONS

(71) Applicant: Elira, Inc., St. Louis, MO (US)

(72) Inventors: Raul E. Perez, St. Louis, MO (US); Peter I. Hong, Valencia, CA (US); Steven Diianni, Groveland, MA (US); Luis Jose Malave, San Marcos, CA (US); Brad Stengel, Kirkwood, MO (US)

(73) Assignee: Elira, Inc., St. Louis, MO (US)

( * ) Notice: Subject to any disclaimer, the term of this patent is extended or adjusted under 35 U.S.C. 154(b) by 519 days.

(21) Appl. No.: 15/716,866

(22) Filed: Sep. 27, 2017

(65) Prior Publication Data

US 2018/0078754 A1  Mar. 22, 2018

Related U.S. Application Data

(63) Continuation-in-part of application No. 15/702,676, filed on Sep. 12, 2017, now Pat. No. 10,335,302,
(Continued)

(51) Int. Cl.
*A61N 1/04* (2006.01)
*A61N 1/36* (2006.01)
(Continued)

(52) U.S. Cl.
CPC .......... *A61N 1/0492* (2013.01); *A61B 5/0002* (2013.01); *A61B 5/0036* (2018.08);
(Continued)

(58) Field of Classification Search
CPC .... A61N 1/0456; A61N 1/36; A61N 1/36007; A61N 1/36014; A61N 1/36034; A61N 1/36085
(Continued)

(56) References Cited

U.S. PATENT DOCUMENTS 3,411,507 A  11/1968  Wingrove
3,978,865 A   9/1976  Trabucco
(Continued)

FOREIGN PATENT DOCUMENTS

CA  2764610 A1  12/2010
CA  2885175 A1   2/2014
(Continued)

OTHER PUBLICATIONS

Camilleri et al, "Effect of somatovisceral reflexes and selective dermatomal stimulation on postcibal antral pressure activity", Gastroenterology Unit, Mayo Clinic, Rochester, Minnesota 55905, Jul. 1984.
(Continued)

*Primary Examiner* — John R Downey
(74) *Attorney, Agent, or Firm* — Novel IP

(57) ABSTRACT

The disclosed electrical stimulation system generates interventions to assist patients in complying with a diet. The wearable device includes a microprocessor, electrical stimulator and at least one electrode configured to deliver electrical stimulation to the epidermis, through a range of 0.1 mm to 10 mm or a range of 0.1 mm to 20 mm of the dermis, of a T2 dermatome to a T12 dermatome or meridian of the patient, a C5 to a T1 dermatome across the hand and/or arm, and/or the upper chest regions. The device is adapted to provide electrical stimulation as per stimulation protocols and to communicate wirelessly with a companion control device configured to monitor and record appetite patterns of the patient and generate interventions. The control device is also configured to monitor, record, and modify stimulation parameters of the stimulation protocols.

21 Claims, 126 Drawing Sheets

Related U.S. Application Data which is a continuation-in-part of application No. 15/590,750, filed on May 9, 2017, now Pat. No. 10,376,145, which is a continuation-in-part of application No. 15/370,944, filed on Dec. 6, 2016, now Pat. No. 9,956,393, which is a continuation-in-part of application No. 15/204,752, filed on Jul. 7, 2016, now Pat. No. 10,154,922, which is a continuation-in-part of application No. 15/052,791, filed on Feb. 24, 2016, now Pat. No. 10,118,035, and a continuation-in-part of application No. 15/052,784, filed on Feb. 24, 2016, now Pat. No. 10,143,840, and a continuation-in-part of application No. 15/052,791, filed on Feb. 24, 2016, now Pat. No. 10,118,035, which is a continuation-in-part of application No. 15/052,784, filed on Feb. 24, 2016, now Pat. No. 10,143,840.

(60) Provisional application No. 62/532,317, filed on Jul. 13, 2017, provisional application No. 62/413,213, filed on Oct. 26, 2016, provisional application No. 62/393,486, filed on Sep. 12, 2016, provisional application No. 62/378,393, filed on Aug. 23, 2016, provisional application No. 62/341,917, filed on May 26, 2016, provisional application No. 62/326,541, filed on Apr. 22, 2016, provisional application No. 62/248,059, filed on Oct. 29, 2015, provisional application No. 62/247,113, filed on Oct. 27, 2015, provisional application No. 62/246,526, filed on Oct. 26, 2015, provisional application No. 62/242,957, filed on Oct. 16, 2015, provisional application No. 62/242,944, filed on Oct. 16, 2015, provisional application No. 62/242,957, filed on Oct. 16, 2015, provisional application No. 62/240,808, filed on Oct. 13, 2015, provisional application No. 62/237,356, filed on Oct. 5, 2015, provisional application No. 62/189,805, filed on Jul. 8, 2015, provisional application No. 62/189,800, filed on Jul. 8, 2015, provisional application No. 62/161,362, filed on May 14, 2015, provisional application No. 62/161,353, filed on May 14, 2015, provisional application No. 62/141,328, filed on Apr. 1, 2015, provisional application No. 62/141,333, filed on Apr. 1, 2015, provisional application No. 62/133,526, filed on Mar. 16, 2015, provisional application No. 62/133,530, filed on Mar. 16, 2015, provisional application No. 62/120,082, filed on Feb. 24, 2015, provisional application No. 62/120,067, filed on Feb. 24, 2015.

(51) Int. Cl.
| | |
|---|---|
| *A61B 5/00* | (2006.01) |
| *A61B 5/04* | (2006.01) |
| *A61B 5/11* | (2006.01) |
| A61B 5/0205 | (2006.01) |
| A61N 1/05 | (2006.01) |

(52) U.S. Cl.
CPC ........ *A61B 5/04001* (2013.01); *A61B 5/1118* (2013.01); *A61B 5/42* (2013.01); *A61B 5/4836* (2013.01); *A61B 5/4848* (2013.01); *A61B 5/6833* (2013.01); *A61N 1/36014* (2013.01); *A61N 1/36034* (2017.08); A61B 5/02055 (2013.01); A61B 2562/0219 (2013.01); A61N 1/0456 (2013.01); A61N 1/0502 (2013.01); A61N 1/36007 (2013.01)

(58) Field of Classification Search
USPC .................................. 607/2, 40, 45
See application file for complete search history.

(56) References Cited

U.S. PATENT DOCUMENTS

| | | | |
|---|---|---|---|
| 4,256,115 A | 3/1981 | Bilitch | |
| 4,646,744 A | 3/1987 | Capel | |
| 4,979,517 A | 12/1990 | Grossman | |
| 5,067,495 A | 11/1991 | Brehm | |
| 5,188,104 A | 2/1993 | Wernicke | |
| 5,263,480 A | 11/1993 | Wernicke | |
| 5,282,468 A | 2/1994 | Klepinski | |
| 5,324,287 A | 6/1994 | Szeles | |
| 5,374,279 A | 12/1994 | Duffin | |
| 5,386,084 A | 1/1995 | Risko | |
| D357,069 S | 4/1995 | Plahn | |
| 5,423,872 A | 6/1995 | Cigaina | |
| 5,458,626 A | 10/1995 | Krause | |
| 5,514,175 A | 5/1996 | Kim | |
| 5,518,155 A | 5/1996 | Gallagher | |
| 5,540,730 A | 7/1996 | Terry, Jr. | |
| 5,669,790 A | 9/1997 | Carson | |
| 5,690,691 A | 11/1997 | Chen | |
| 5,700,282 A | 12/1997 | Zabara | |
| 5,716,385 A | 2/1998 | Mittal | |
| 5,716,392 A | 2/1998 | Bourgeois | |
| 5,782,874 A | 7/1998 | Loos | |
| 5,836,994 A | 11/1998 | Bourgeois | |
| 5,868,141 A | 2/1999 | Ellias | |
| 5,919,220 A | 7/1999 | Stieglitz | |
| 6,041,258 A | 3/2000 | Cigaina | |
| 6,065,154 A | 5/2000 | Hulings | |
| 6,083,249 A | 7/2000 | Familoni | |
| 6,097,982 A * | 8/2000 | Glegyak | A61N 1/3904 607/5 |
| 6,097,984 A | 8/2000 | Douglas | |
| 6,104,955 A | 8/2000 | Bourgeois | |
| 6,129,685 A | 10/2000 | Howard, III | |
| 6,141,588 A | 10/2000 | Cox | |
| 6,146,391 A | 11/2000 | Cigaina | |
| 6,169,924 B1 | 1/2001 | Meloy | |
| 6,178,349 B1 | 1/2001 | Kieval | |
| 6,179,756 B1 | 1/2001 | Bertolucci | |
| 6,192,889 B1 | 2/2001 | Morrish | |
| 6,228,103 B1 | 5/2001 | Grey | |
| 6,243,607 B1 | 6/2001 | Mintchev | |
| 6,246,912 B1 | 6/2001 | Sluijter | |
| 6,266,564 B1 | 7/2001 | Hill | |
| 6,272,383 B1 | 8/2001 | Grey | |
| 6,282,443 B1 | 8/2001 | Mann | |
| 6,282,448 B1 | 8/2001 | Katz | |
| 6,321,124 B1 | 11/2001 | Cigaina | |
| 6,327,503 B1 | 12/2001 | Familoni | |
| 6,356,786 B1 | 3/2002 | Rezai | |
| 6,356,787 B1 | 3/2002 | Rezai | |
| 6,361,550 B2 | 3/2002 | Grey | |
| 6,366,813 B1 | 4/2002 | DiLorenzo | |
| 6,381,495 B1 | 4/2002 | Jenkins | |
| 6,381,496 B1 | 4/2002 | Meadows | |
| 6,381,497 B1 | 4/2002 | Knowlton | |
| 6,393,324 B2 | 5/2002 | Gruzdowich | |
| 6,438,423 B1 | 8/2002 | Rezai | |
| 6,487,446 B1 | 11/2002 | Hill | |
| 6,521,309 B1 | 2/2003 | Chen | |
| 6,535,760 B1 | 3/2003 | Grey | |
| 6,535,764 B2 | 3/2003 | Imran | |
| 6,540,789 B1 | 4/2003 | Silverman | |
| 6,542,776 B1 | 4/2003 | Gordon | |
| 6,564,101 B1 | 5/2003 | Zikria | |
| 6,567,695 B1 | 5/2003 | Gruzdowich | |
| 6,571,127 B1 | 5/2003 | Ben-Haim | |
| 6,582,449 B2 | 6/2003 | Grey | |
| 6,587,719 B1 | 7/2003 | Barrett | |
| 6,591,137 B1 | 7/2003 | Fischell | |
| 6,600,953 B2 | 7/2003 | Flesler | |

(56) References Cited

U.S. PATENT DOCUMENTS

| | | | |
|---|---|---|---|
| 6,606,518 B1 | 8/2003 | Cigaina | |
| 6,606,523 B1 | 8/2003 | Jenkins | |
| 6,609,025 B2 | 8/2003 | Barrett | |
| 6,615,084 B1 | 9/2003 | Cigaina | |
| 6,658,297 B2 | 12/2003 | Loeb | |
| 6,658,298 B2 | 12/2003 | Gruzdowich | |
| 6,671,557 B1 * | 12/2003 | Gliner | A61N 1/36021 607/2 |
| 6,684,104 B2 | 1/2004 | Gordon | |
| 6,684,105 B2 | 1/2004 | Cohen | |
| 6,687,543 B1 | 2/2004 | Isaac | |
| 6,718,202 B2 | 4/2004 | Mann | |
| 6,735,480 B2 | 5/2004 | Giuntoli | |
| 6,754,536 B2 | 6/2004 | Swoyer | |
| 6,775,573 B2 | 8/2004 | Schuler | |
| 6,802,868 B2 | 10/2004 | Silverman | |
| 6,819,956 B2 | 11/2004 | DiLorenzo | |
| 6,826,428 B1 | 11/2004 | Chen | |
| 6,862,479 B1 | 3/2005 | Whitehurst | |
| 6,876,885 B2 | 4/2005 | Swoyer | |
| 6,879,859 B1 | 4/2005 | Boveja | |
| 6,892,098 B2 | 5/2005 | Ayal | |
| 6,895,278 B1 | 5/2005 | Gordon | |
| 6,895,279 B2 | 5/2005 | Loeb | |
| 6,907,295 B2 | 6/2005 | Gross | |
| 6,947,792 B2 | 9/2005 | Ben-Haim | |
| 6,952,613 B2 | 10/2005 | Swoyer | |
| 6,993,391 B2 | 1/2006 | Flesler | |
| 6,994,095 B2 | 2/2006 | Burnett | |
| 7,006,871 B1 | 2/2006 | Darvish | |
| 7,016,735 B2 | 3/2006 | Imran | |
| 7,020,531 B1 | 3/2006 | Colliou | |
| 7,043,295 B2 | 5/2006 | Starkebaum | |
| 7,044,979 B2 | 5/2006 | Silverman | |
| 7,054,690 B2 | 5/2006 | Imran | |
| 7,076,305 B2 | 7/2006 | Imran | |
| 7,089,061 B2 | 8/2006 | Grey | |
| 7,096,070 B1 | 8/2006 | Jenkins | |
| 7,107,100 B2 | 9/2006 | Imran | |
| 7,120,497 B2 | 10/2006 | Ben-Haim | |
| 7,120,498 B2 | 10/2006 | Imran | |
| 7,120,499 B2 | 10/2006 | Thrope | |
| 7,127,288 B2 | 10/2006 | Sturman | |
| 7,155,278 B2 | 12/2006 | King | |
| 7,167,750 B2 | 1/2007 | Knudson | |
| 7,171,266 B2 | 1/2007 | Gruzdowich | |
| 7,171,276 B2 | 1/2007 | Giuntoli | |
| 7,176,218 B2 | 2/2007 | Irwin | |
| 7,177,693 B2 | 2/2007 | Starkebaum | |
| 7,194,301 B2 | 3/2007 | Jenkins | |
| 7,200,443 B2 | 4/2007 | Faul | |
| 7,209,787 B2 | 4/2007 | DiLorenzo | |
| 7,221,978 B2 | 5/2007 | Ben-Haim | |
| 7,228,167 B2 | 6/2007 | Kara | |
| 7,231,254 B2 | 6/2007 | DiLorenzo | |
| 7,236,822 B2 | 6/2007 | Dobak, III | |
| 7,239,912 B2 | 7/2007 | Dobak, III | |
| 7,242,984 B2 | 7/2007 | DiLorenzo | |
| 7,252,665 B2 | 8/2007 | Starkebaum | |
| 7,277,758 B2 | 10/2007 | DiLorenzo | |
| 7,282,050 B2 | 10/2007 | Starkebaum | |
| 7,282,509 B2 | 10/2007 | Irwin | |
| 7,292,889 B2 | 11/2007 | Gordon | |
| 7,299,091 B2 | 11/2007 | Barrett | |
| 7,310,557 B2 | 12/2007 | Maschino | |
| 7,321,793 B2 | 1/2008 | BenEzra | |
| 7,324,851 B1 | 1/2008 | DiLorenzo | |
| 7,324,853 B2 | 1/2008 | Ayal | |
| 7,326,787 B2 | 2/2008 | By | |
| 7,330,753 B2 | 2/2008 | Policker | |
| 7,336,993 B1 | 2/2008 | Szeles | |
| 7,340,306 B2 | 3/2008 | Barrett | |
| 7,346,390 B1 | 3/2008 | Tumey | |
| 7,346,398 B2 | 3/2008 | Gross | |
| 7,347,868 B2 | 3/2008 | Burnett | |
| 7,359,751 B1 | 4/2008 | Erickson | |
| 7,364,591 B2 | 4/2008 | Silverman | |
| 7,371,215 B2 | 5/2008 | Colliou | |
| 7,376,467 B2 | 5/2008 | Thrope | |
| 7,403,820 B2 | 7/2008 | DiLorenzo | |
| 7,430,450 B2 | 9/2008 | Imran | |
| 7,437,195 B2 | 10/2008 | Policker | |
| 7,444,183 B2 | 10/2008 | Knudson | |
| 7,483,746 B2 | 1/2009 | Lee | |
| 7,483,754 B2 | 1/2009 | Imran | |
| 7,489,969 B2 | 2/2009 | Knudson | |
| 7,502,649 B2 | 3/2009 | Ben-Haim | |
| 7,509,174 B2 | 3/2009 | Imran | |
| 7,509,175 B2 | 3/2009 | Sparks | |
| 7,512,442 B2 | 3/2009 | Flesler | |
| 7,519,433 B2 | 4/2009 | Foley | |
| 7,529,582 B1 | 5/2009 | DiLorenzo | |
| 7,545,740 B2 | 6/2009 | Zelig | |
| 7,551,599 B2 | 6/2009 | Levit | |
| 7,551,964 B2 * | 6/2009 | Dobak, III | A61N 1/36085 607/2 |
| 7,561,922 B2 | 7/2009 | Cohen | |
| 7,590,452 B2 | 9/2009 | Imran | |
| 7,599,736 B2 | 10/2009 | DiLorenzo | |
| 7,608,578 B2 | 10/2009 | Miller | |
| 7,613,515 B2 | 11/2009 | Knudson | |
| 7,616,996 B2 | 11/2009 | Imran | |
| 7,620,454 B2 | 11/2009 | Dinsmoor | |
| 7,620,455 B2 | 11/2009 | Maschino | |
| 7,623,924 B2 | 11/2009 | Narciso, Jr. | |
| 7,623,928 B2 | 11/2009 | DiLorenzo | |
| 7,627,384 B2 | 12/2009 | Ayal | |
| 7,629,466 B2 | 12/2009 | By | |
| 7,630,769 B2 | 12/2009 | Knudson | |
| 7,634,317 B2 | 12/2009 | Ben-David | |
| 7,643,887 B2 | 1/2010 | Imran | |
| 7,651,596 B2 | 1/2010 | Petisce | |
| 7,657,310 B2 | 2/2010 | Buras | |
| 7,660,637 B2 | 2/2010 | Szeles | |
| 7,664,551 B2 | 2/2010 | Cigaina | |
| 7,670,279 B2 | 3/2010 | Gertner | |
| 7,672,727 B2 | 3/2010 | Donders | |
| 7,676,270 B2 | 3/2010 | Imran | |
| 7,680,540 B2 | 3/2010 | Jensen | |
| 7,689,276 B2 | 3/2010 | Dobak | |
| 7,689,277 B2 | 3/2010 | Dobak, III | |
| 7,689,284 B2 | 3/2010 | Imran | |
| 7,691,152 B2 | 4/2010 | Silverman | |
| 7,693,577 B2 | 4/2010 | Knudson | |
| 7,702,386 B2 | 4/2010 | Dobak | |
| 7,702,394 B2 | 4/2010 | Imran | |
| 7,706,874 B2 | 4/2010 | Maschino | |
| 7,711,402 B2 | 5/2010 | Shults | |
| 7,713,574 B2 | 5/2010 | Brister | |
| 7,720,540 B2 | 5/2010 | Knudson | |
| 7,729,771 B2 | 6/2010 | Knudson | |
| 7,734,341 B2 | 6/2010 | Shuros | |
| 7,734,355 B2 | 6/2010 | Cohen | |
| 7,736,392 B2 | 6/2010 | Starkebaum | |
| 7,737,109 B2 | 6/2010 | Miller | |
| 7,738,961 B2 | 6/2010 | Sharma | |
| 7,742,818 B2 | 6/2010 | Dinsmoor | |
| 7,745,216 B2 | 6/2010 | Pang | |
| 7,747,322 B2 | 6/2010 | Imran | |
| 7,747,325 B2 | 6/2010 | DiLorenzo | |
| 7,756,582 B2 | 7/2010 | Imran | |
| 7,761,130 B2 | 7/2010 | Simpson | |
| 7,771,352 B2 | 8/2010 | Shults | |
| 7,778,703 B2 | 8/2010 | Gross | |
| 7,778,711 B2 | 8/2010 | Ben-David | |
| 7,783,333 B2 | 8/2010 | Brister | |
| 7,787,948 B2 | 8/2010 | Ross | |
| 7,792,562 B2 | 9/2010 | Shults | |
| 7,803,195 B2 | 9/2010 | Levy | |
| 7,807,641 B2 | 10/2010 | Pang | |
| 7,822,486 B2 | 10/2010 | Foster | |
| 7,828,728 B2 | 11/2010 | Boock | |
| 7,831,287 B2 | 11/2010 | Brister | |
| 7,835,796 B2 | 11/2010 | Maschino | |

(56) References Cited

U.S. PATENT DOCUMENTS

| | | |
|---|---|---|
| 7,844,338 B2 | 11/2010 | Knudson |
| 7,844,346 B2 | 11/2010 | Cohen |
| 7,853,329 B2 | 12/2010 | DiLorenzo |
| 7,856,273 B2 | 12/2010 | Maschino |
| 7,869,867 B2 | 1/2011 | Armstrong |
| 7,869,884 B2 | 1/2011 | Scott |
| 7,869,885 B2 | 1/2011 | Begnaud |
| 7,881,763 B2 | 2/2011 | Brauker |
| 7,885,697 B2 | 2/2011 | Brister |
| 7,885,709 B2 | 2/2011 | Ben-David |
| 7,885,711 B2 | 2/2011 | Ben-Ezra |
| 7,890,185 B2 | 2/2011 | Cohen |
| 7,894,906 B2 | 2/2011 | Shuros |
| 7,899,511 B2 | 3/2011 | Shults |
| 7,899,540 B2 | 3/2011 | Maschino |
| 7,899,541 B2 | 3/2011 | Cowan |
| 7,901,354 B2 | 3/2011 | Shults |
| 7,904,175 B2 | 3/2011 | Scott |
| 7,904,176 B2 | 3/2011 | Ben-Ezra |
| 7,930,035 B2 | 4/2011 | DiLorenzo |
| 7,937,144 B2 | 5/2011 | Dobak |
| 7,937,145 B2 | 5/2011 | Dobak |
| 7,937,158 B2 | 5/2011 | Erickson |
| 7,941,221 B2 | 5/2011 | Foley |
| 7,946,976 B2 | 5/2011 | Gertner |
| 7,949,381 B2 | 5/2011 | Brister |
| 7,962,214 B2 | 6/2011 | Byerman |
| 7,962,220 B2 | 6/2011 | Kolafa |
| 7,963,907 B2 | 6/2011 | Gertner |
| 7,966,071 B2 | 6/2011 | Ben-Haim |
| 7,974,693 B2 | 7/2011 | Ben-David |
| 7,974,696 B1 | 7/2011 | DiLorenzo |
| 7,974,701 B2 | 7/2011 | Armstrong |
| 7,976,554 B2 | 7/2011 | Newell |
| 7,979,127 B2 | 7/2011 | Imran |
| 7,983,761 B2 | 7/2011 | Giuntoli |
| 7,986,995 B2 | 7/2011 | Knudson |
| 7,996,079 B2 | 8/2011 | Armstrong |
| 8,001,974 B2 | 8/2011 | Makower |
| 8,010,204 B2 | 8/2011 | Knudson |
| 8,019,422 B2 | 9/2011 | Imran |
| 8,024,035 B2 | 9/2011 | Dobak, III |
| 8,032,198 B2 | 10/2011 | VanAntwerp |
| 8,032,223 B2 | 10/2011 | Imran |
| 8,046,085 B2 | 10/2011 | Knudson |
| 8,048,169 B2 | 11/2011 | Burnett |
| 8,048,170 B2 | 11/2011 | Silverman |
| 8,060,174 B2 | 11/2011 | Simpson |
| 8,060,197 B2 | 11/2011 | Ben-David |
| 8,065,021 B2 | 11/2011 | Gross |
| RE43,039 E | 12/2011 | Brister |
| 8,070,673 B2 | 12/2011 | Gertner |
| 8,070,768 B2 | 12/2011 | Kim |
| 8,070,824 B2 | 12/2011 | Burnett |
| 8,073,543 B2 | 12/2011 | Pyles |
| 8,086,318 B2 | 12/2011 | Strother |
| 8,088,132 B2 | 1/2012 | Roslin |
| 8,095,218 B2 | 1/2012 | Gross |
| 8,103,349 B2 | 1/2012 | Donders |
| 8,116,881 B2 | 2/2012 | Cohen |
| 8,126,538 B2 | 2/2012 | Shuros |
| 8,138,204 B2 | 3/2012 | Irwin |
| 8,145,299 B2 | 3/2012 | Dobak, III |
| 8,145,318 B2 | 3/2012 | Van Herk |
| 8,150,508 B2 | 4/2012 | Craig |
| 8,160,709 B2 | 4/2012 | Soffer |
| RE43,399 E | 5/2012 | Simpson |
| 8,172,857 B2 | 5/2012 | Fogel |
| 8,185,206 B2 | 5/2012 | Starkebaum |
| 8,187,297 B2 | 5/2012 | Makower |
| 8,190,261 B2 | 5/2012 | Imran |
| 8,192,455 B2 | 6/2012 | Brazzini |
| 8,204,591 B2 | 6/2012 | Ben-David |
| 8,204,603 B2 | 6/2012 | Maschino |
| 8,211,186 B2 | 7/2012 | Belhe |
| 8,219,188 B2 | 7/2012 | Craig |
| 8,219,201 B2 | 7/2012 | Ben-Haim |
| 8,229,534 B2 | 7/2012 | Brister |
| 8,239,027 B2 | 8/2012 | Imran |
| 8,260,426 B2 | 9/2012 | Armstrong |
| 8,260,439 B2 | 9/2012 | DiUbaldi |
| 8,265,758 B2 | 9/2012 | Policker |
| 8,280,505 B2 | 10/2012 | Craig |
| 8,282,598 B2 | 10/2012 | Belhe |
| 8,295,926 B2 | 10/2012 | Dobak, III |
| 8,295,932 B2 | 10/2012 | Bitton |
| 8,301,256 B2 | 10/2012 | Policker |
| 8,306,627 B2 | 11/2012 | Armstrong |
| 8,321,030 B2 | 11/2012 | Maniak |
| 8,326,438 B2 | 12/2012 | Ayal |
| 8,340,760 B2 | 12/2012 | Dobak, III |
| 8,340,772 B2 | 12/2012 | Vase |
| 8,342,183 B2 | 1/2013 | Makower |
| 8,353,925 B2 | 1/2013 | Makower |
| 8,356,605 B2 | 1/2013 | Makower |
| 8,360,069 B2 | 1/2013 | Kim |
| 8,364,229 B2 | 1/2013 | Simpson |
| 8,364,269 B2 | 1/2013 | Imran |
| 8,369,943 B2 | 2/2013 | Shuros |
| 8,369,952 B2 | 2/2013 | Knudson |
| 8,372,158 B2 | 2/2013 | Levy |
| 8,382,775 B1 | 2/2013 | Bender |
| 8,386,056 B2 | 2/2013 | BenDavid |
| 8,388,632 B2 | 3/2013 | Gambale |
| 8,394,463 B1 | 3/2013 | Chiu |
| 8,396,557 B2 | 3/2013 | DiLorenzo |
| 8,398,668 B2 | 3/2013 | Makower |
| 8,414,559 B2 | 4/2013 | Gross |
| 8,417,329 B2 | 4/2013 | Policker |
| 8,417,352 B2 | 4/2013 | Carroll |
| 8,423,114 B2 | 4/2013 | Simpson |
| 8,423,130 B2 | 4/2013 | Thrower |
| 8,427,953 B2 | 4/2013 | Solomon |
| 8,428,731 B2 | 4/2013 | Armstrong |
| 8,442,841 B2 | 5/2013 | Haddad |
| 8,447,403 B2 | 5/2013 | Sharma |
| 8,447,404 B2 | 5/2013 | Sharma |
| 8,457,747 B2 | 6/2013 | Terry, Jr. |
| 8,460,321 B2 | 6/2013 | Newell |
| 8,463,383 B2 | 6/2013 | Sakai |
| 8,463,385 B2 | 6/2013 | Pyles |
| 8,463,404 B2 | 6/2013 | Levi |
| 8,467,874 B2 | 6/2013 | Chen |
| 8,467,880 B2 | 6/2013 | Glukhovsky |
| 8,467,884 B2 | 6/2013 | Chen |
| 8,483,793 B2 | 7/2013 | Simpson |
| 8,494,637 B2 | 7/2013 | Cowan |
| 8,494,655 B2 | 7/2013 | Ayal |
| 8,512,731 B2 | 8/2013 | Yang |
| 8,515,519 B2 | 8/2013 | Brister |
| 8,523,773 B2 | 9/2013 | Shah |
| 8,524,736 B2 | 9/2013 | Irwin |
| 8,527,025 B1 | 9/2013 | Shults |
| 8,527,026 B2 | 9/2013 | Shults |
| 8,537,682 B2 | 9/2013 | Solomon |
| 8,538,532 B2 | 9/2013 | Starkebaum |
| 8,538,533 B2 | 9/2013 | Knudson |
| 8,538,534 B2 | 9/2013 | Soffer |
| 8,538,542 B2 | 9/2013 | Knudson |
| 8,541,232 B2 | 9/2013 | Porat |
| 8,543,184 B2 | 9/2013 | Boock |
| 8,543,210 B2 | 9/2013 | Sharma |
| 8,548,594 B2 | 10/2013 | Thimineur |
| 8,551,120 B2 | 10/2013 | Gambale |
| 8,556,925 B2 | 10/2013 | Makower |
| 8,560,039 B2 | 10/2013 | Simpson |
| 8,565,867 B2 | 10/2013 | Armstrong |
| 8,565,896 B2 | 10/2013 | Ben-David |
| 8,571,651 B2 | 10/2013 | Ben-Ezra |
| 8,571,653 B2 | 10/2013 | Ben-David |
| 8,579,988 B2 | 11/2013 | Burnett |
| 8,585,733 B2 | 11/2013 | Newell |
| 8,588,918 B2 | 11/2013 | Bighetti |
| 8,591,598 B2 | 11/2013 | Silverman |

(56) References Cited

U.S. PATENT DOCUMENTS

| | | |
|---|---|---|
| 8,594,811 B2 | 11/2013 | Chen |
| 8,609,082 B2 | 12/2013 | Ben-David |
| 8,612,016 B2 | 12/2013 | Kliger |
| 8,615,294 B2 | 12/2013 | Ben-David |
| 8,615,309 B2 | 12/2013 | Craig |
| 8,649,840 B2 | 2/2014 | Sheppard, Jr. |
| 8,655,444 B2 | 2/2014 | Ben-Haim |
| 8,657,885 B2 | 2/2014 | Burnett |
| 8,660,628 B2 | 2/2014 | Wang |
| 8,660,647 B2 | 2/2014 | Parnis |
| 8,660,666 B2 | 2/2014 | Craig |
| 8,663,338 B2 | 3/2014 | Burnett |
| 8,676,288 B2 | 3/2014 | Shults |
| 8,682,408 B2 | 3/2014 | Boock |
| 8,685,724 B2 | 4/2014 | Fulga |
| 8,694,118 B2 | 4/2014 | Armstrong |
| 8,700,177 B2 | 4/2014 | Strother |
| 8,702,641 B2 | 4/2014 | Belhe |
| 8,702,642 B2 | 4/2014 | Belhe |
| 8,712,529 B2 | 4/2014 | Sharma |
| 8,712,530 B2 | 4/2014 | Sharma |
| 8,715,181 B2 | 5/2014 | Brynelsen |
| 8,718,791 B2 | 5/2014 | Ben-David |
| 8,725,243 B2 | 5/2014 | DiLorenzo |
| 8,725,271 B2 | 5/2014 | Ayal |
| 8,738,126 B2 | 5/2014 | Craig |
| 8,738,137 B2 | 5/2014 | Dar |
| 8,755,888 B2 | 6/2014 | Voznesensky |
| 8,755,893 B2 | 6/2014 | Gross |
| 8,761,903 B2 | 6/2014 | Chen |
| 8,762,065 B2 | 6/2014 | DiLorenzo |
| 8,781,597 B2 | 7/2014 | DiLorenzo |
| 8,792,953 B2 | 7/2014 | Brister |
| 8,792,986 B2 | 7/2014 | Cigaina |
| 8,795,301 B2 | 8/2014 | Burnett |
| 8,798,753 B2 | 8/2014 | Sharma |
| 8,805,507 B2 | 8/2014 | Ben-Haim |
| 8,808,532 B2 | 8/2014 | Yang |
| 8,821,521 B2 | 9/2014 | Burnett |
| 8,821,584 B2 | 9/2014 | Burnett |
| 8,825,164 B2 | 9/2014 | Tweden |
| 8,828,201 B2 | 9/2014 | Simpson |
| 8,831,729 B2 | 9/2014 | Policker |
| 8,838,231 B2 | 9/2014 | Dobak, III |
| 8,850,687 B2 | 10/2014 | Shah |
| 8,850,688 B2 | 10/2014 | Shah |
| 8,862,233 B2 | 10/2014 | Knudson |
| 8,862,238 B2 | 10/2014 | Rahimi |
| 8,868,172 B2 | 10/2014 | Leyde |
| 8,874,205 B2 | 10/2014 | Simon |
| 8,874,218 B2 | 10/2014 | Terry, Jr. |
| 8,880,175 B2 | 11/2014 | Simon |
| 8,888,797 B2 | 11/2014 | Burnett |
| 8,897,878 B2 | 11/2014 | Shuros |
| 8,903,494 B2 | 12/2014 | Goldwasser |
| 8,903,502 B2 | 12/2014 | Perryman |
| 8,903,601 B2 | 12/2014 | Muirhead |
| 8,905,999 B2 | 12/2014 | Shuros |
| 8,909,355 B2 | 12/2014 | Ayal |
| 8,911,369 B2 | 12/2014 | Brister |
| 8,911,393 B2 | 12/2014 | Levy |
| 8,929,968 B2 | 1/2015 | Brister |
| 8,934,976 B2 | 1/2015 | Wong |
| 8,938,303 B1 | 1/2015 | Matsen |
| 8,958,872 B2 | 2/2015 | Ben-Haim |
| 8,968,177 B2 | 3/2015 | Silverman |
| 8,977,353 B2 | 3/2015 | Rousso |
| 9,002,458 B2 | 4/2015 | Pal |
| 9,014,811 B2 | 4/2015 | Pal |
| 9,042,988 B2 | 5/2015 | DiLorenzo |
| 9,044,199 B2 | 6/2015 | Brister |
| 9,113,801 B2 | 8/2015 | DiLorenzo |
| 9,168,375 B2 | 10/2015 | Rahimi |
| 9,233,244 B2 | 1/2016 | Pal |
| 9,320,900 B2 | 4/2016 | DiLorenzo |
| 9,345,880 B1 | 5/2016 | DiLorenzo |
| 9,375,573 B2 | 6/2016 | DiLorenzo |
| 9,403,001 B2 | 8/2016 | Simon |
| 9,409,030 B2 | 8/2016 | Perryman |
| 9,415,222 B2 | 8/2016 | DiLorenzo |
| 9,421,373 B2 | 8/2016 | DiLorenzo |
| 9,466,919 B2 | 10/2016 | Kiani |
| 2002/0087192 A1 | 7/2002 | Barrett |
| 2002/0143376 A1 | 10/2002 | Chinn |
| 2003/0018367 A1 | 1/2003 | DiLorenzo |
| 2003/0018369 A1 | 1/2003 | Thompson |
| 2003/0027998 A1 | 2/2003 | Holtzman |
| 2003/0144708 A1 | 7/2003 | Starkebaum |
| 2003/0181959 A1 | 9/2003 | Dobak |
| 2004/0098065 A1 | 5/2004 | Hagglof |
| 2004/0162594 A1 | 8/2004 | King |
| 2004/0254617 A1 | 12/2004 | Hemmerling |
| 2005/0075678 A1* | 4/2005 | Faul ............... A61N 1/36017 607/41 |
| 2005/0085743 A1* | 4/2005 | Hacker ............ A61B 5/0488 600/554 |
| 2006/0116736 A1 | 6/2006 | DiLorenzo |
| 2006/0149345 A1* | 7/2006 | Boggs, II ......... A61N 1/36007 607/118 |
| 2006/0161217 A1 | 7/2006 | Jaax |
| 2006/0167498 A1 | 7/2006 | DiLorenzo |
| 2006/0195153 A1 | 8/2006 | DiUbaldi |
| 2007/0027501 A1 | 2/2007 | Jensen |
| 2007/0060971 A1 | 3/2007 | Glasberg |
| 2007/0060991 A1 | 3/2007 | North |
| 2007/0093870 A1 | 4/2007 | Maschino |
| 2007/0123952 A1 | 5/2007 | Strother |
| 2007/0162085 A1 | 7/2007 | DiLorenzo |
| 2007/0213795 A1 | 9/2007 | Bradley |
| 2007/0233203 A1 | 10/2007 | Euliano |
| 2008/0132962 A1 | 6/2008 | DiUbaldi |
| 2008/0132969 A1 | 6/2008 | Bennett |
| 2008/0154179 A1 | 6/2008 | Cantor |
| 2008/0161874 A1* | 7/2008 | Bennett ........... A61N 1/36021 607/39 |
| 2008/0292685 A1 | 11/2008 | Wang |
| 2009/0054952 A1 | 2/2009 | Glukhovsky |
| 2009/0132018 A1 | 5/2009 | DiUbaldi |
| 2009/0157149 A1 | 6/2009 | Wahlgren |
| 2009/0182216 A1 | 7/2009 | Roushey |
| 2009/0182393 A1 | 7/2009 | Bachinski |
| 2009/0182394 A1 | 7/2009 | Bachinski |
| 2010/0025238 A1 | 2/2010 | Gottlieb |
| 2010/0036445 A1 | 2/2010 | Sakai |
| 2010/0072334 A1 | 3/2010 | Le Gette |
| 2010/0096259 A1 | 4/2010 | Zhang |
| 2010/0096278 A1 | 4/2010 | Shah |
| 2010/0106204 A1 | 4/2010 | Moffitt |
| 2010/0168820 A1 | 7/2010 | Maniak |
| 2010/0175992 A1 | 7/2010 | Shah |
| 2010/0185071 A1 | 7/2010 | Simpson |
| 2010/0228314 A1 | 9/2010 | Goetz |
| 2010/0280347 A1 | 11/2010 | Shah |
| 2010/0324620 A1 | 12/2010 | Libbus |
| 2011/0028815 A1 | 2/2011 | Simpson |
| 2011/0028816 A1 | 2/2011 | Simpson |
| 2011/0071589 A1* | 3/2011 | Starkebaum ...... A61N 1/36007 607/40 |
| 2011/0082356 A1 | 4/2011 | Yang |
| 2011/0091817 A1 | 4/2011 | Shah |
| 2011/0125214 A1 | 5/2011 | Goetz |
| 2011/0144465 A1 | 6/2011 | Shults |
| 2011/0208123 A1 | 8/2011 | Gray |
| 2011/0230735 A1 | 9/2011 | Wolfe |
| 2011/0257711 A1 | 10/2011 | Lindner |
| 2011/0270068 A1 | 11/2011 | Mehdizadeh |
| 2011/0270360 A1 | 11/2011 | Harris |
| 2011/0319734 A1 | 12/2011 | Gottlieb |
| 2012/0010651 A1 | 1/2012 | Thramann |
| 2012/0016392 A1 | 1/2012 | Silverman |
| 2012/0046533 A1 | 2/2012 | Voskanyan |
| 2012/0046534 A1 | 2/2012 | Simpson |
| 2012/0089045 A1 | 4/2012 | Seidl |
| 2012/0097554 A1 | 4/2012 | Shah |

(56) References Cited

U.S. PATENT DOCUMENTS

| | | |
|---|---|---|
| 2012/0116478 A1 | 5/2012 | Buhlmann |
| 2012/0121735 A1 | 5/2012 | Halford |
| 2012/0123496 A1 | 5/2012 | Schotzko |
| 2012/0172792 A1 | 7/2012 | Baynham |
| 2012/0228134 A1 | 9/2012 | Simpson |
| 2012/0277562 A1 | 11/2012 | Brister |
| 2012/0283800 A1 | 11/2012 | Perryman |
| 2013/0053665 A1 | 2/2013 | Hughes |
| 2013/0053666 A1 | 2/2013 | Hughes |
| 2013/0096641 A1 | 4/2013 | Strother |
| 2013/0109039 A1 | 5/2013 | Kristensen |
| 2013/0110201 A1 | 5/2013 | Bonde |
| 2013/0131478 A1 | 5/2013 | Simpson |
| 2013/0131753 A1 | 5/2013 | Simon |
| 2013/0150923 A1 | 6/2013 | Schnetz |
| 2013/0158624 A1 | 6/2013 | Bain |
| 2013/0178912 A1 | 7/2013 | Sharma |
| 2013/0231542 A1 | 9/2013 | Simpson |
| 2013/0245412 A1 | 9/2013 | Rong |
| 2013/0296996 A1 | 11/2013 | Wahlgren |
| 2013/0299350 A1 | 11/2013 | Rhodes |
| 2013/0304175 A1 | 11/2013 | Voegele |
| 2013/0310670 A1 | 11/2013 | Boock |
| 2013/0313130 A1 | 11/2013 | Little |
| 2013/0338729 A1 | 12/2013 | Spector |
| 2014/0001042 A1 | 1/2014 | Simpson |
| 2014/0005508 A1 | 1/2014 | Estes |
| 2014/0005759 A1 | 1/2014 | Fahey |
| 2014/0012115 A1 | 1/2014 | Li |
| 2014/0012157 A1 | 1/2014 | Gilhuly |
| 2014/0031837 A1 | 1/2014 | Perryman |
| 2014/0031895 A1 | 1/2014 | Rahimi |
| 2014/0046423 A1 | 2/2014 | Rajguru |
| 2014/0051906 A1 | 2/2014 | Chen |
| 2014/0081368 A1 | 3/2014 | Szeles |
| 2014/0081419 A1 | 3/2014 | Silverman |
| 2014/0088389 A1 | 3/2014 | Simpson |
| 2014/0094671 A1 | 4/2014 | Boock |
| 2014/0128702 A1 | 5/2014 | Brister |
| 2014/0128703 A1 | 5/2014 | Simpson |
| 2014/0163346 A1 | 6/2014 | Pesantez |
| 2014/0214118 A1* | 7/2014 | Greiner ............... A61N 1/3756 607/45 |
| 2014/0214126 A1 | 7/2014 | Greiner |
| 2014/0243634 A1 | 8/2014 | Huang |
| 2014/0296935 A1* | 10/2014 | Ferree ............... A61N 1/36021 607/46 |
| 2014/0303465 A1 | 10/2014 | Simpson |
| 2014/0303682 A1 | 10/2014 | Siff |
| 2014/0343386 A1 | 11/2014 | Boock |
| 2014/0343625 A1* | 11/2014 | O Laighin ............... A61N 1/14 607/48 |
| 2014/0367246 A1 | 12/2014 | Shah |
| 2015/0005841 A1 | 1/2015 | Pal |
| 2015/0025346 A1 | 1/2015 | Simpson |
| 2015/0073510 A1 | 3/2015 | Perryman |
| 2015/0088227 A1 | 3/2015 | Shishilla |
| 2015/0090589 A1 | 4/2015 | Estes |
| 2015/0094790 A1 | 4/2015 | Shishilla |
| 2015/0100106 A1 | 4/2015 | Shishilla |
| 2015/0122645 A1 | 5/2015 | Yang |
| 2015/0335885 A1 | 11/2015 | Schnetz |
| 2016/0015988 A1 | 1/2016 | Perryman |
| 2016/0023003 A1 | 1/2016 | Perryman |
| 2016/0023005 A1 | 1/2016 | Perryman |
| 2016/0206893 A1* | 7/2016 | Raymond ............ A61N 1/3912 |
| 2016/0213933 A1* | 7/2016 | Raymond ............ A61N 1/3912 |
| 2016/0213938 A1* | 7/2016 | Raymond ............ A61N 1/3906 |
| 2016/0235352 A1 | 8/2016 | DiLorenzo |
| 2017/0203095 A1 | 7/2017 | Bachinski |

FOREIGN PATENT DOCUMENTS

| | | |
|---|---|---|
| CN | 204147427 | 2/2015 |
| EP | 1629780 A1 | 3/2006 |
| EP | 2143465 B1 | 10/2012 |
| EP | 2298166 B1 | 1/2014 |
| EP | 2263744 B1 | 5/2014 |
| EP | 2879755 A1 | 6/2015 |
| EP | 2934419 | 5/2016 |
| WO | 1997041921 A1 | 11/1997 |
| WO | 1999003532 A2 | 1/1999 |
| WO | 1999038563 A1 | 8/1999 |
| WO | 2000061223 A1 | 10/2000 |
| WO | 2000061224 A1 | 10/2000 |
| WO | 2001052932 A1 | 7/2001 |
| WO | 2001058520 A1 | 8/2001 |
| WO | 2002009808 A1 | 2/2002 |
| WO | 2002032499 A1 | 4/2002 |
| WO | 2002043467 A2 | 6/2002 |
| WO | 2004011085 A1 | 2/2004 |
| WO | 2005041749 A2 | 5/2005 |
| WO | 2005102448 A2 | 11/2005 |
| WO | 2006118790 A2 | 11/2006 |
| WO | 2006118792 A1 | 11/2006 |
| WO | 2010144982 A1 | 12/2010 |
| WO | 2012040243 | 3/2012 |
| WO | 2012103519 | 8/2012 |
| WO | 2012138782 | 10/2012 |
| WO | 2014022215 A1 | 2/2014 |
| WO | 2014089299 | 6/2014 |
| WO | 2014153219 | 9/2014 |
| WO | 2014153223 | 9/2014 |
| WO | 2014153228 | 9/2014 |
| WO | 2014194200 | 12/2014 |
| WO | 2014194200 A1 | 12/2014 |
| WO | 2015033152 A2 | 3/2015 |
| WO | 2016138176 A1 | 9/2016 |
| WO | 2016138357 A1 | 9/2016 |
| WO | 2017002104 A1 | 1/2017 |
| WO | 2017205047 A2 | 11/2017 |

OTHER PUBLICATIONS

"Feasibility Assessment of Appetite Suppression Utilizing TENS Trial-1 (FAAST-1)", Protocol No. CD-001, Revision: Version Rev 02 (Nov. 20, 2015).

Hall WJ, O'Connor PC., "A pharmacological analysis of the response of dog anterior mesenteric vein to transmural electrical stimulation", IR J Med Sci. Jul.-Sep. 1972;141(7):113-9.

Lee SK et al, "Electroacupuncture may relax the sphincter of Oddi in humans", Gastrointest Endosc. Feb. 2001;53(2):211-6.

Lee GT., "A study of electrical stimulation of acupuncture locus tsusanli (St-36) on mesenteric microcirculation", Am J Chin Med (Gard City N Y). Jan. 1974;2(1):53-66.

Obuchowicz A, Obuchowicz E., "Plasma beta-endorphin and insulin concentrations in relation to body fat and nutritional parameters in overweight and obese prepubertal children", Int J Obes Relat Metab Disord. Sep. 1997;21(9):783-8.

Giovannini et al, "Unresponsiveness of the endorphinergic system to its physiological feedback in obesity", Appetite. Feb. 1991;16(1):39-43.

Wan et al, "The effectiveness of purgation and electroacupuncture in extrahepatic bile duct stone complicated with acute biliary pancreatitis: management of biliary stone pancreatitis through traditional Chinese medicine", Pancreas. Apr. 2011;40(3):483-4. doi: 10.1097/MPA.0b013e318205e52f.

Blaut et al, "The effect of transcutaneous nerve stimulation on intraductal biliary pressure in post-cholecystectomy patients with T-drainage", Eur J Gastroenterol Hepatol. Jan. 2003;15(1):21-6.

Kim MH, "A brief commentary: electroacupuncture may relax the contraction of sphincter of Oddi". The Journal of Alternative and Complementary Medicine. vol. 7, Supplement 1, 2001, pp. S-119-S-120.

Liu et al, "Effects of acupuncture on myoelectric activity of Oddi''s sphincter in humans", J Tradit Chin Med. Sep. 1993;13(3):189-90.

(56) References Cited

OTHER PUBLICATIONS

"D4.3: Satiety Methodology", Work Package 4, Project No. KBBE-2011-5-289800, Project Title: SATIN (Satiety Innovation), Lead Partner: University of Leeds (UNIVLEEDS). Nov. 13, 2012.
Jing Wang et al, "Effects of Cutaneous Gastric Electrical Stimulation on Gastric Emptying and Postprandial Satiety and Fullness in Lean and Obese Subjects", J Clin Gastroenterol vol. 44, No. 5, May/Jun. 2010.
Mark Johnson, "Transcutaneous electrical nerve stimulation (TENS)".
"ACUSLIM Control Your Appetite the Natural Way", Simply Good Health, Australia. Natural Remedies for Healthy Living, Nov. 21, 1997.
Furgala et al, "The effect of Transcutaneous Nerve Stimulation (TENS) on gastric electrical activity", Oct. 18, 2001, http://www.jpp.krakow.pl/journal/archive/12_01/articles/07_article.html.
Wang et al, "Effects of Cutaneous Gastric Electrical Stimulation on Gastric Emptying and Postprandial Satiety and Fullness in Lean and Obese Subjects", J Clin Gastroenterol, vol. 44, No. 5, May/Jun. 2010.
JM Lacey et al, "Acupuncture for the treatment of obesity: a review of the evidence", International Journal of Obesity (2003) 27, 419-427.
Philip V. Peplow et al, "Electroacupuncture for Control of Blood Glucose in Diabetes: Literature Review", J Acupunct Meridian Stud 2012;5(1):1-10.
Mohammad Ma'ani et al, "Nerve Supply of the Stomach and the Small Intestines", Anatomy-7, Apr. 21, 2015.
Camilleri et al, "Relation between antral motility and gastric emptying of solids and liquids in humans", The American journal of physiology, Dec. 1985.
Liu Zhicheng et al, "Effect of acupuncture on weight loss evaluated by adrenal function", Journal of Traditional Chinese Medicine 13 (3): 169-173, 1993.
J F Bergmann et al, "Correlation between echographic gastric emptying and appetite: influence of psyllium", Gut 1992; 33: 1042-1043.
Janssen et al, "Review article: the role of gastric motility in the control of food intake", Aliment Pharmacol Ther 2011; 33: 880-894.
Eva Haker et al, "Effect of sensory stimulation (acupuncture) on sympathetic and parasympathetic activities in healthy subjects", Journal of the Autonomic Nervous System 79 (2000) 52-59.
Stein Knardahl et al, "Sympathetic nerve activity after acupuncture in humans", Pain 75 (1998) 19-25.
Monique Ernst et al, "Sympathetic effects of manual and electrical acupuncture of the Tsusnali Knee Point: Comparison with the Hoku Hand point sympathetic effects", Experimental Neurology 94, 1-10 (1986).
DiLorenzo, Daniel John, "Chronic Intraneural Electrical Stimulation for Prosthetic Sensory Feedback", Proc. 1st Intl IEEE EMBS Conf Neural Eng, Mar. 20-22, 2003.
Sven Andersson, "The functional background in acupuncture effects", Scand J Rehab Med, Suppl 29: 31-60, 1993.
Akio Sato et al, "Somatosympathetic Reflexes : Afferent Fibers, Central Pathways, Discharge Characteristics", Physiological Reviews, vol. 53, No. 4, Oct. 1973.
Kazushi Nishijo et al, "Decreased heart rate by acupuncture stimulation in humans via facilitation of cardiac vagal activity and suppression of cardiac sympathetic nerve", Neuroscience Letters 227 (1997) 165-168.
D. Thomas et al, "Somatic sympathetic vasomotor changes documented by medical thermographic imaging during acupuncture analgesia", Clinical reheumatology, 1992, 11, 55-59.
Monique Ernst et al, "Sympathetic vasomotor changes induced by manual and electrical acupuncture of the Hoku Point visualized by thermography", Pain 21 (1985), 25-33.
Will Rosellini, "FDA gives nod to first fully-removable percutaneous peripheral nerve stimulation device", Peripheral Nerve Stimulation, Posted on Jul. 28, 2016.

DiLorenzo, Daniel John, "Development of a Chronically Implanted Microelectrode Array for Intraneural Electrical Stimulation for Prosthetic Sensory Feedback", MIT SM Thesis, 1999.
Zardetto-Smith et al., "Catecholamine and NPY Efferents From the Ventrolateral Medulla to the Amygdala in the Rat", Brain Research Bulletin, vol. 38, No. 3, 1995, pp. 253-260.
Barone et al., "Gastric Distension Modulates Hypothalamic Neurons Via a Sympathetic Afferent Path Through the Mesencephalic Periaqueductal Gray", Brain Research Bulletin, vol. 38, No. 3, 1995; pp. 239-251.
Brown et al., "Changes in Food Intake with Electrical Stimulation of the Ventromedial Hypothalamus in Dogs", Journal of Neurosurgery, vol. 60, 1984, pp. 1253-1257.
Daniel et al., "Criteria for Differentiation of Brown and White Fat in the Rat", Canadian Journal of Physiology and Pharmacology, vol. 47, Mar. 22, 1969; pp. 941-945.
Flaim et al., "Coupling of Signals to Brown Fat: .alpha.-and .beta.-Adrenergic Responses in Intact Rats", In Vivo Adrenergic Responses of Brown Adipose Tissue, 1976, pp. R101-R109.
Felton, D.L. and R.F. Jozefowicz, "Netter's Atlas of Human Neuroscience", Icon Learning Systems, Teterboro, NJ, 2004, p. 126.
Kolen et al., "Effects of spatially targeted transcutaneous electrical nerve stimulation using an electrode array that measures skin resistance on pain and mobility in patients with osteoarthritis in the knee: A randomized controlled trial." J. Pain, 153 (2012) 373-381, doi:10.1016/j.pain.2011.10.033.
Malesevic et al., "Classification of muscle twitch response using ANN: Application in multi-pad electrode optimization," IEEE 2010.
Malesevic et al., "Muscle twitch responses for shaping the multi-pad electrode for functional electrical stimulation," IEEE Journal of Automatic Control, University of Belgrade, vol. 20:53-58, 2010.
International Search Report for PCT Application No. PCT/US2016/019416, dated Jun. 21, 2016.
Li et al, "Acupuncture Effect and Central Autonomic Regulation", Hindawi Publishing Corporation, Evidence-Based Complementary and Alternative Medicine. vol. 2013, Article ID 267959, 6 pages.
"Obesity Treatment Using Neurostimulation", iRunway.com. Karthik Sankar. 2011, 7 pages.
Yao, Tai, "Acupuncture and Somatic Nerve Stimulation: Mechanism Underlying Effects on Cardiovascular and Renal Activities", Scand J Rehab Med, Suppl 29:7-18, 1993.
Derry et al., "Two Sympathetic Nerve Supplies to Brown Adipose Tissue of the Rat", Canadian Journal of Physiology and Pharmacology, vol. 47, 1969, pp. 57-63.
Takahashi et al., "Hypothalamic Regulation of Lipid Metabolism in the Rat: Effect of Hypothalamic Stimulation on Lipogenesis", Journal of the Autonomic Nervous System, vol. 6, 1982, pp. 225-235.
Yuan et al, "Hypothalamic Unitary Responses to Gastric Vagal Input from the Proximal Stomach", Am J Physiol Gastrointest Liver Physiol 262:G74-G80, 1992.
Astrup A, Buemann B, Christensen NJ, Toubro S, Thorbek G, Victor OJ, Quaade F., "The effect of ephedrine/caffeine mixture on energy expenditure and body composition in obese women", Metabolism vol. 41, No. 7 (July), (1992), pp. 686-688.
Astrup A, Toubro S, Christensen NJ, Quaade F., "Pharmacology of thermogenic drugs", Am.J.Clin.Nutr. (1992), pp. 246S-248S.
Tian D et al, "Study on the effect of transcutaneous electric nerve stimulation on obesity", Beijing Da Xue Xue Bao. Jun. 2003l¾ 35(3):2779.
Berthoud HR, Niijima A, Sauter JF, Jeanrenaud B., "Evidence for a role of the gastric, coeliac and hepatic branches in vagally stimulated insulin secretion in the rat", J.Auton.Nerv.Syst. (1983), pp. 97-110.
Bray GA, "Obesity, a disorder of nutrient partitioning: the Mona Lisa hypothesis", American Institute of Nutrition (1991), pp. 1146-1162.
Bray GA, "Genetic, hypothalamic and endocrine features of clinical and experimental obesity", Prog.Brain Res. (1992), pp. 333-340.
Bray GA., "Reciprocal relation of food intake and sympathetic activity: experimental observations and clinical implications", Int. J.Obes.Relat Metab Disord. (2000), pp. S8-17.

(56) References Cited

OTHER PUBLICATIONS

Bray GA, Gallagher TF, Jr., "Manifestations of hypothalamic obesity in man: a comprehensive investigation of eight patients and a review of the literature", Medicine (Baltimore) (1975), pp. 301-330.
Bray GA, York DA, Fisler JS., "Experimental obesity: a homeostatic failure due to defective nutrient stimulation of the sympathetic nervous system", Vitam.Horm. (1989), pp. 1-125.
Bruch H., "The Frohlich syndrome: report of the original case", 1939. Obes. Res. (1939), pp. 329-331.
Cigaina V, V, Saggioro A, Rigo V, V, Pinato G, Ischai S., "Long-term Effects of Gastric Pacing to Reduce Feed Intake in Swine" Obes. Surg. (1996), pp. 250-253.
HANS—Han's Acupoint Nerve Stimulator, http://thehanssite.com. 2012. BioBalance LLC.
Greenway FL, "The safety and efficacy of pharmaceutical and herbal caffeine and ephedrine use as a weight loss agent", Obes.Rev. (2001), pp. 199-211.
Inoue S, Bray GA, "The effects of subdiaphragmatic vagotomy in rats with ventromedial hypothalamic obesity", Endocrinology (1977), pp. 108-114.
Inoue S, Bray GA, Mullen YS, "Transplantation of pancreatic beta-cells prevents development of hypothalamic obesity in rats", Am.J.Physiol (1978), pp. E266-E271.
Jeanrenaud B., "Energy fuel and hormonal profile in experimental obesities", Experientia Suppl (1983), pp. 57-76.
King BM, Frohman LA, "The role of vagally-medicated hyperinsulinemia in hypothalamic obesity", Neurosci.Biobehay. Rev. (1982), pp. 205-214. [28] Kral JG. Vagotomy.
Niijima A, Rohner-Jeanrenaud F, Jeanrenaud B., "Role of ventromedial hypothalamus on sympathetic efferents of brown adipose tissue", Am.J.Physiol (1984), pp. R650-R654.
Pasquali R, Casimirri F, Melchionda N, Grossi G. Bortoluzzi L, Morselli Labate AM, Stefanini C, Raitano A., "Effects of chronic administration of ephedrine during very-low-calorie diets on energy expenditure, protein metabolism and hormone levels in obese subjects", Clin.Sci.(Lond) (1992), pp. 85-92.
Perkins MN, Rothwell NJ, Stock MJ, Stone TW., "Activation of brown adipose tissue thermogenesis by the ventromedial hypothalamus", Nature (1981), pp. 401-402.
Pories WJ, Swanson MS, MacDonald KG, Long SB, Morris PG, Brown BM, Barakat HA, deRamon RA, Israel G, Dolezal JM, "Who would have thought it? An operation proves to be the most effective therapy for adult-onset diabetes mellitus", Ann.Surg. (1995), pp. 339-350.
Reeves AG, Plum F., "Hyperphagia, rage, and dementia accompanying a ventromedial hypothalamic neoplasm", Arch.Neurol. (1969), pp. 616-624.
De Graaf et al, "Biomarkers of satiation and satiety", Am J Clin Nutr 2004;79:946-61.
Sakaguchi T, Bray GA, Eddlestone G., "Sympathetic activity following paraventricular or ventromedial hypothalamic lesions in rats", Brain Res.Bull. (1988), pp. 461-465.
Sauter JF, Berthoud HR, Jeanrenaud B. ,"A simple electrode for intact nerve stimulation and/or recording in semi-chronic rats", Pflugers Arch. (1983), pp. 68-69.
Seydoux J. ssimacopoulos-Jeannet F, Jeanrenaud B, Girardier L., "Alterations of brown adipose tissue in genetically obese (ob/ob) mice. I. Demonstration of loss of metabolic response to nerve stimulation and catecholamines and its partial recovery after fasting or cold adaptation", Endocrinology (1982), pp. 432-438.
Shimizu H, Shargill NS, Bray GA., "Adrenalectomy and response to corticosterone and MSH in the genetically obese yellow mouse", Am.J.Physiol (1989), pp. R494-R500. [38] Smith DK, Sarfeh J, Howard L. Truncal vagotomy.
Tokunaga K, Fukushima M, Kemnitz JW, Bray GA., "Effect of vagotomy on serum insulin in rats with paraventricular or ventromedial hypothalamic lesions", Endocrinology (1986), pp. 1708-1711.
York DA, Bray GA., "Dependence of hypothalamic obesity on insulin, the pituitary and the adrenal gland", Endocrinology (1972), pp. 885-894.

Yoshida T, Bray GA., "Catecholamine turnover in rats with ventromedial hypothalamic lesions", Am.J.Physiol (1984), pp. R558-R565.
"Stimulation of auricular acupuncture points in weight loss", Richards et al., Aust. Fam. Physician, Jul. 1998, 27 Suppl 2:S73-77.
Gibbons et al, "Validation of a new hand-held electronic data capture method for continuous monitoring of subjective appetite sensations", International Journal of Behavioral Nutrition and Physical Activity 2011, 8:57.
Biggs et al., "A Comparison of the Hypoalgesic Effects of Transcutaneous Electrical Nerve Stimulation (TENS) and Non-invasive Interactive Neurostimulation (InterX.RTM.) on Experimentally Induced Blunt Pressure Pain Using Healthy Human Volunteers", Neuromodulation 2012; 15: 93-99.
Jordan Kahn, "Hands on with 'i-Massager' iPhone-controlled electrical nerve stimulation and other iOS massage accessories", 9TO5Mac, http://9to5mac.com/2013/01/09/hands-on-with-i-massager-iphone-controlled-electrical-nerve-stimulation-and-other-ios-massage-accessories/ Jan. 9, 2013.
Malesevic et al., "INTFES: A multi-pad electrode system for selective transcutaneous electrical muscle stimulation". Sep. 2011.
Sauter et al., "Current threshold for nerve stimulation depends on electrical impedance of the tissue: a study of ultrasound-guided electrical nerve stimulation of the median nerve." Anesth Analg. Apr. 2009;108(4):1338-43. doi: 10.1213/ane.0b013e3181957d84.
Ronald Melzack, "Pain and the Neuromatrix in the Brain", Journal of Dental Education, vol. 65, No. 12, Dec. 2001.
Harrold et al, "Measuring appetite in humans", KissileffLaboratory for the Study of Human Ingestive Behaviour, School of Psychology, University of Liverpool. Jan. 29, 2008.
Jaime Ruiz-Tovar et al, "Percutaneous Electric Neurostimulation of Dermatome T7 Improves the Glycemic Profile in Obese and Type 2 Diabetic Patients", vol. 93. No. 07. Aug.-Sep. 2015, doi: 10.1016/j.cireng.2014.06.013.
Jaime Ruiz-Tovar et al, "Percutaneous Electrical Neurostimulation of Dermatome T6 for Appetite Reduction and Weight Loss in Morbidly Obese Patients", Obes Surg (2014) 24:205-211, DOI 10.1007/s11695-013-1091-z.
John K. DiBaise et al, "Impact of the Gut Microbiota on the Development of Obesity: Current Concepts", Am J Gastroenterol Suppl 2012; 1:22-27; doi: 10.1038/ajgsup.2012.5.
Lim et al, "Adipose Tissue: Ability to Respond to Nerve Stimulation in vitro", Department of Nutrition and Food Science, MIT, Cambirdge 39, Science, vol. 140. 1963.
Wenwen Zeng et al, "Sympathetic Neuro-adipose Connections Mediate Leptin-Driven Lipolysis", Cell 163, 84-94, Sep. 24, 2015, http://dx.doi.org/10.1016/j.cell.2015.08.055.
Kenneth Snow, "The Use of Transcutaneous Electrical Nerve Stimulationfor the Treatment of Painful Diabetic Neuropathy", 2012 NeuroMetrix, Inc., PN2203822 Rev C.
Diyar Hussein Tahir, "A comparison of high versus low intensity transcutaneous electrical nerve stimulation for chronic pain", Zanco J. Med. Sci., vol. 15, No. (2), 2011.
Obuchowicz A et al, "Plasma beta-endorphin and insulin concentrations in relation to body fat and nutritional parameters in overweight and obese prepubetral children", Int J Obes Relat Metab Disord. Sep. 1997, 21(9):783-8.
Livingstone et al, "Methodological issues in the assessment of satiety", Scandinavian Journal of NutritionlNaringsforskning vol. 44:98-1 03,2000.
Xing et al, "Gastric Electrical-Stimulation Effects on Canine Gastric Emptying, Food Intake, and Body Weight", Obesity Research vol. 11 No. 1 Jan. 2003.
Ruffin M et al, "Electrical stimulation of the ventromedial hypothalamus enhances both fat utilization and metabolic rate that precede and parallel the inhibition of feeding behavior", Brain Res. Oct. 30, 1999;846(1):23-9, PMID: 10536210.
Cigaina V, "Gastric pacing as therapy for morbid obesity: preliminary results", Obes Surg Jun. 2002;12(3):421, PMID: 11969102.
Shafshak TS, "Electroacupuncture and exercise in body weight reduction and their application in rehabilitating patients with knee osteoarthritis", Am J Chin Med. 1995;23(1):15-25, PMID: 7598088.

(56) References Cited

OTHER PUBLICATIONS

Michael Camilleri, "Peripheral Mechanisms in Appetite Regulation", Gastroenterology. May 2015 ; 148(6): 1219-1233. doi:10.1053/j.gastro.2014.09.016.
Guneli E, et al, "Possible involvement of ghrelin on pain threshold in obesity", Med Hypotheses, Mar. 2010;74(3):452-4, PMID 19883981.
Thomas O. Mundinger et al, "Direct Stimulation of Ghrelin Secretion by Sympathetic Nerves", Endocrinology, Jun. 2006, 147(6):2893-2901, doi: 10.1210/en.2005-1182.
Cigaina V et al, "Plasma ghrelin and gastric pacing in morbidly obese patients", Metabolism Clinical and Experimental 56 (2007) 1017-1021.
Flint et al, "Reproducibility, power and validity of visual analogue scales in assessment of appetite sensations in single test meal studies", International Journal of Obesity (2000) 24, 38-48.
Cigaina V et al, "Gastric Pacing for Morbid Obesity: Plasma Levels of Gastrointestinal Peptides and Leptin", Obesity Research vol. 11 No. 12 Dec. 2003.
Vander Tuig JG, Knehans AW, Romsos DR., "Reduced sympathetic nervous system activity in rats with ventromedial hypothalamic lesions", Life Sci. (1982), pp. 913-920.
Takahashi K, et al, "Methodology for detecting swallowing sounds", Dysphagia. 1994 Winter;9(1):54-62.
Brian Buntz, "Brain-Zapping Wearable Device Hits Market without FDA Clearance", Posted in Mobile Health by Brian Buntz on Jun. 4, 2015.
Biegler GMBH, Stivax Neurostimulation product brochure, http://www.biegler.com/en/stivax?file=files/biegler/manuals/stivax_brochure_en.pdf. Apr. 2016.
Eagle Advancement Institute, "Pulse Stimulation Treatment (PSTIM)", http://eagleadvancementinstitute.com/pstim/Overview.asp. 2014.
Ghoname et al, "The effect of stimulus frequency on the analgesic response to percutaneous electrical nerve stimulation in patients with chronic low back pain", Anesth Analg. Apr. 1999;88(4):841-6.
Takagi K1, Yamaguchi S, Ito M, Ohshima N., "Effects of electroacupuncture stimulation applied to limb and back on mesenteric microvascular hemodynamics", Jpn J Physiol. Jun. 2005;55(3):191-203. Epub Sep. 7, 2005.
Yamaguchi S1, Ito M, Ohshima N., "Effects of electrical stimulation of the dorsal skin on systemic and mesenteric microvascular hemodynamics in anesthetized rats", Jpn J Physiol. Jun. 2002;52(3):257-65.
Gomez et al, "Delayed Gastric Emptying as a Proposed Mechanism of Action During Intragastric Balloon Therapy: Results of a Prospective Study", Obesity, Sep. 2016; vol. 24, No. 9: 1849-1853.
Lerner et al, "Benefit-risk paradigm for clinical trial design of obesity devices: FDA proposal", Surgical Endoscopy, Dec. 18, 2012; 6 pages: DOI 10.1007/s00464-012-2724-3.
International Search Report for PCT Application No. PCT/US2017/031769, dated Nov. 27, 2017.
Office Action dated Jan. 30, 2017 for U.S. Appl. No. 15/370,944.
Office Action dated Aug. 14, 2017 for U.S. Appl. No. 15/370,944; (pp. 1-23).
Office Action dated Nov. 3, 2017 for U.S. Appl. No. 15/052,701; (pp. 1-22).
Notice of Allowanace dated Dec. 21, 2017 for U.S. Appl. No. 15/370,944; (pp. 1-5).
International Search Report for PCT Application No. PCT/US2017/058528, dated Feb. 1, 2018.

* cited by examiner

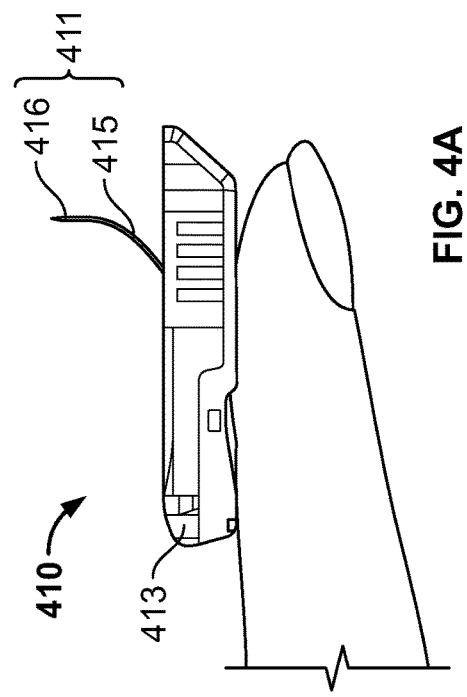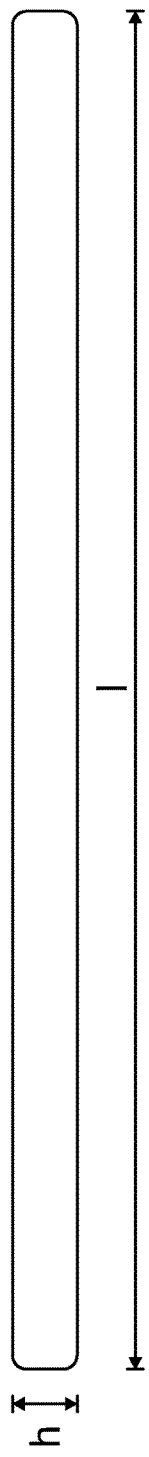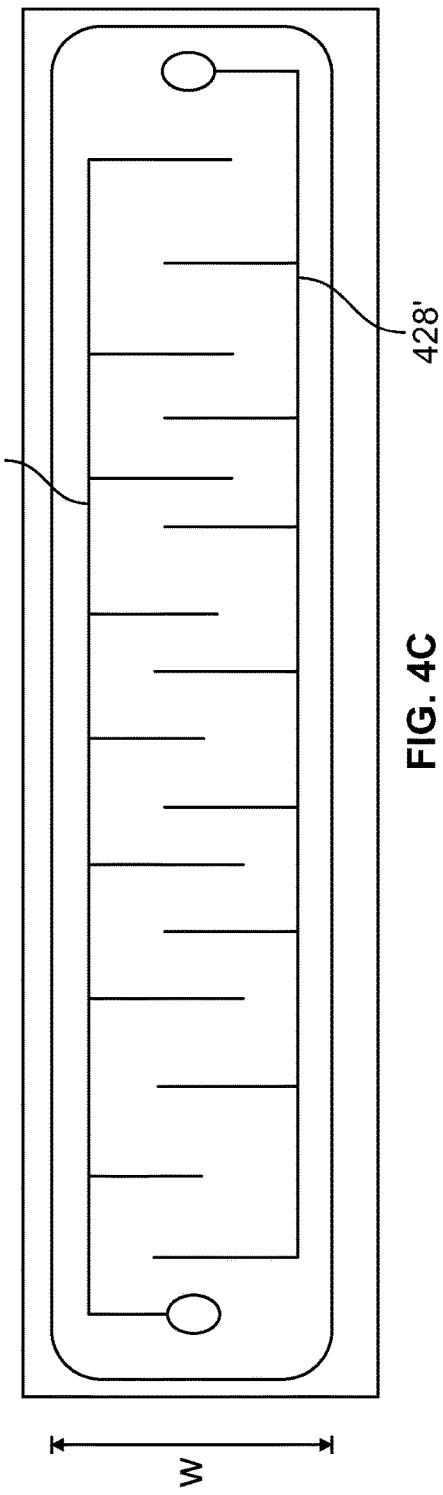
FIG. 4A
FIG. 4B
FIG. 4C

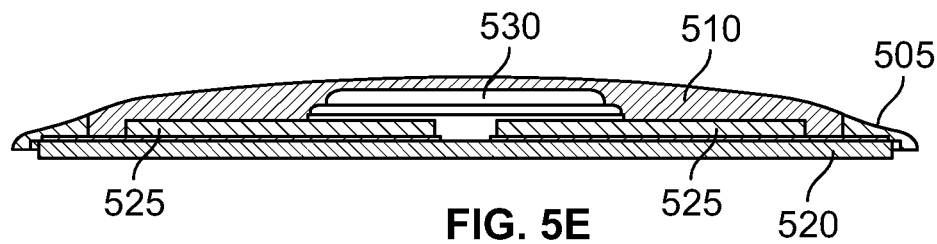
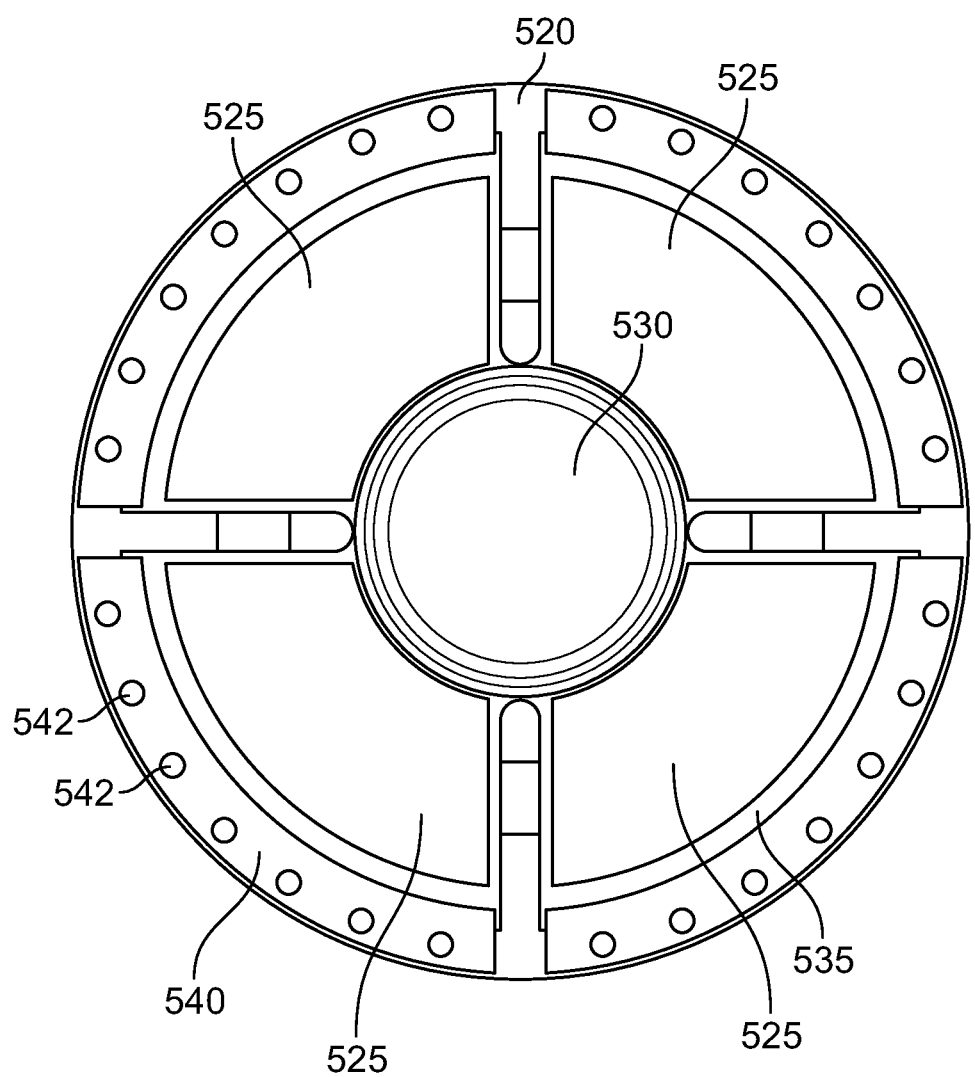

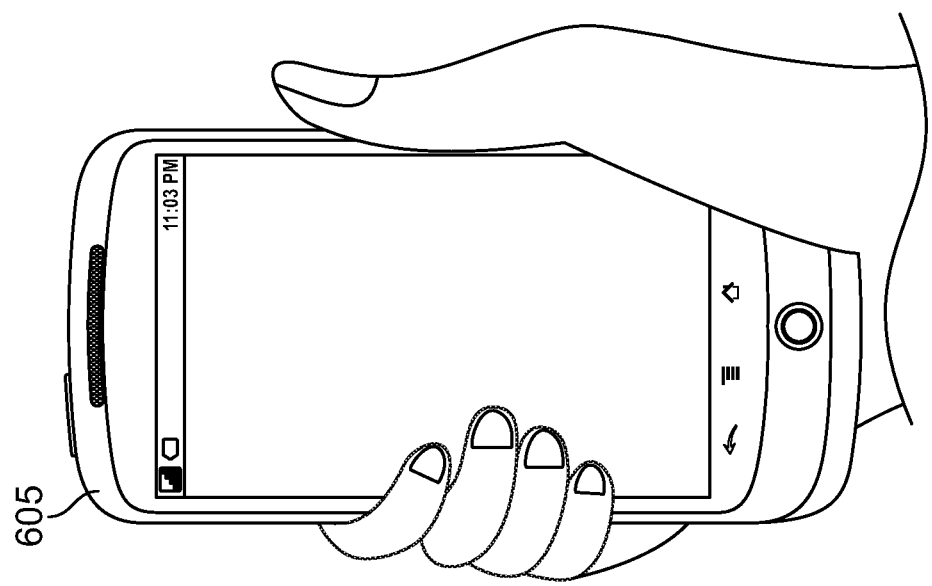
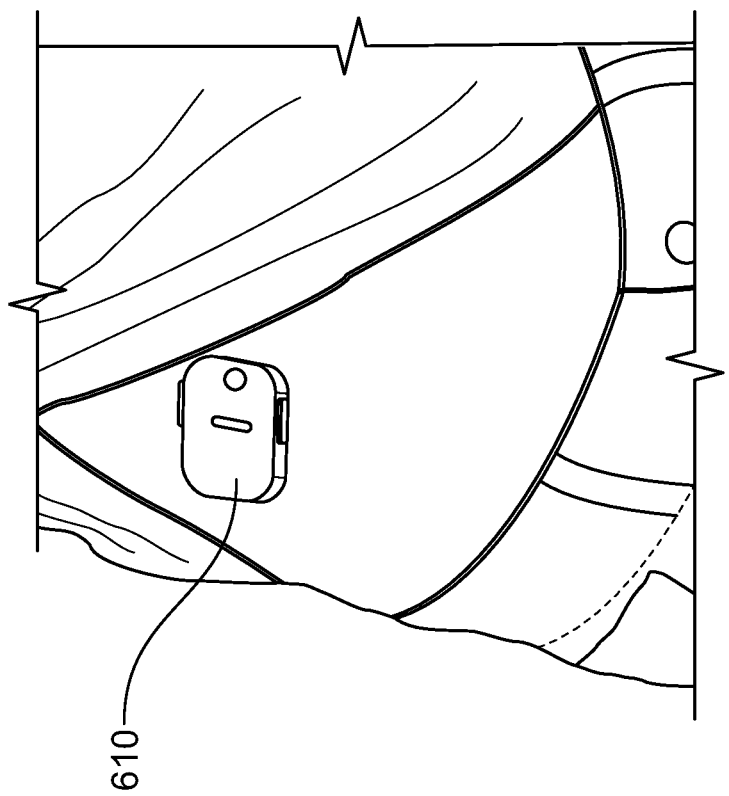
FIG. 6A

680 — Patient Obtains an Electro-Dermal Patch (EDP) Device from a Medical Professional

681 — Patient Pairs a Companion Device with the EDP and with a Separate Physiological Monitoring Device with Physiological Sensors, Configured to be Worn on the Human Body, Such as Around the Wrist, in Order to Monitor, Acquire, Record, and/or Transmit Physiological Data to the Companion Device

682 — Patient then Downloads, from an Online Marketplace, a First Application Designed to Configure the EDP to Achieve a First Objective Associated with a Specific Therapy

683 — Patient Positions EDP on His Body

684 — The First Application Configures the EDP for the First Objective by Establishing Certain Baseline Stimulation Parameters Designed to Achieve Said First Objective and by Titrating or Fine-tuning Said Stimulation Parameters Based on Patient Diary Input Into the Companion Device and/or Physiological Data Transmitted to the Companion Device by the Separate Monitoring Device

685 — After the First Objective has Been Achieved, the Patient then Downloads a Second Application, from an Online Marketplace, Designed to Reconfigure the EDP to Achieve a Second Objective Associate with the Specific Therapy

686 — The Second Application then Configures the EDP for the Second Objective by Establishing Certain Baseline Stimulation Parameters Designed to Achieve Said Second Objective and by Titrating or Fine-tuning Said Stimulation Parameters Based on Patient Diary Input into the Companion Device and/or Physiological Data Transmitted to the Companion Device by the Separate Monitoring Device

FIG. 6D

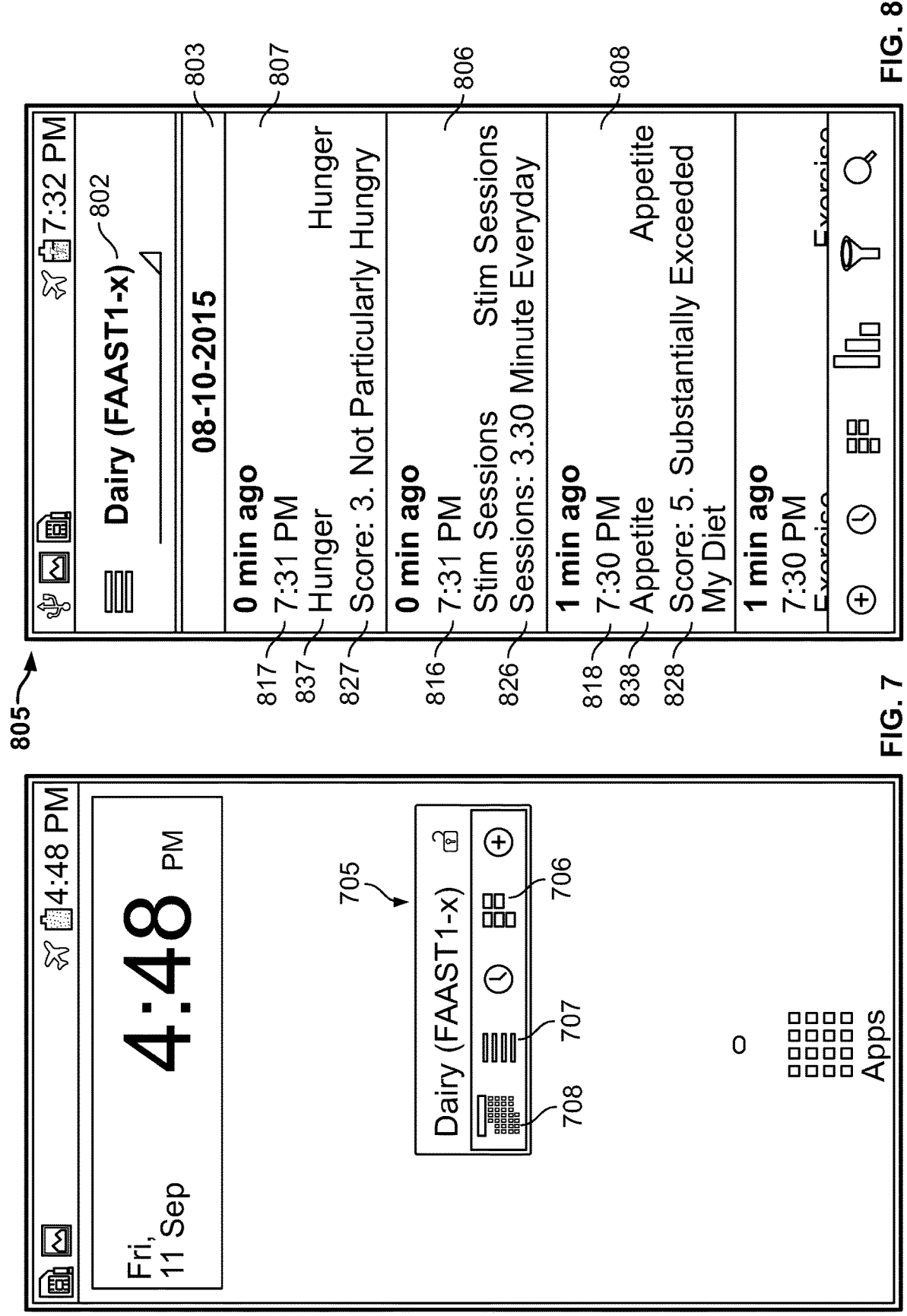

FIG. 11

← Dairy (FAAST1-x)

Time 08-10-2015  7:09 PM

Type Appetite   Appetite

Item 5. Substantially Excee

Score

5. Substantially Exceeded My Diet

4. Somewhat Exceeded My Diet

3. Followed My Diet

2. Ate A Little Less Than My Diet

1. Ate Substantially Less Than My Diet

FIG. 12

← Dairy (FAAST1-x)

Time 08-10-2015   2:13 PM

Type Exercise   Exercise

Item 5. Less Than 2,500 St

Score

5. Less Than 2,500 Steps Per Day 4. 2,500-5,000 Steps Per Day 3. 5,000-7,500 Steps Per Day 2. 7,500-10,000 Steps Per Day 1. More Than 10,000 Steps Per Day

FIG. 13

Diary (FAAST1-x) — 7:09 PM

- Time: 08-10-2015 — 7:09 PM
- Type: Hunger
- Item: Hunger
- Score: 5. Extremely Hungry M 5. Extremely Hungry Most of The Time
4. Frequently Hungry — 1310
3. Not Particularly Hungry
2. Almost Never Hungry
1. Not Hungry At All

FIG. 14

Diary (FAAST1-x) — 2:14 PM

- Time: 08-10-2015 — 2:14 PM
- Type: Stim Sessions
- Item: Stim Sessions
- Score: 1. 15 Minute E/O Day 1. 15 Minute E/O Day
2. 30 Minute E/O Day — 1410
3. 30 Minute Everyday
4. 30 Minute Twice/Day

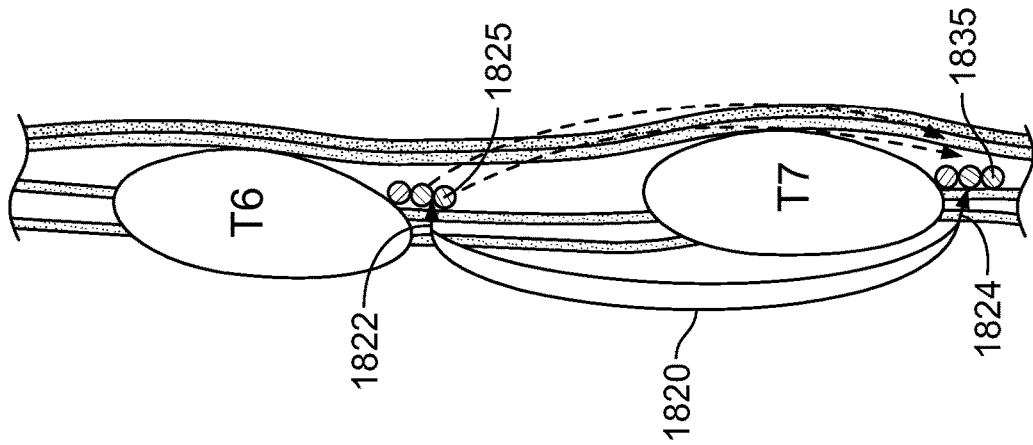
FIG. 18C  T-6+7 Stimulation
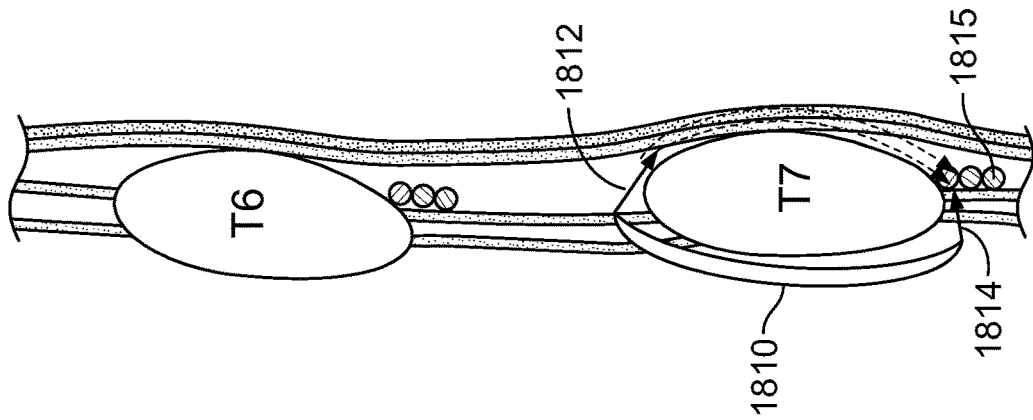
FIG. 18B  T-7 Stimulation
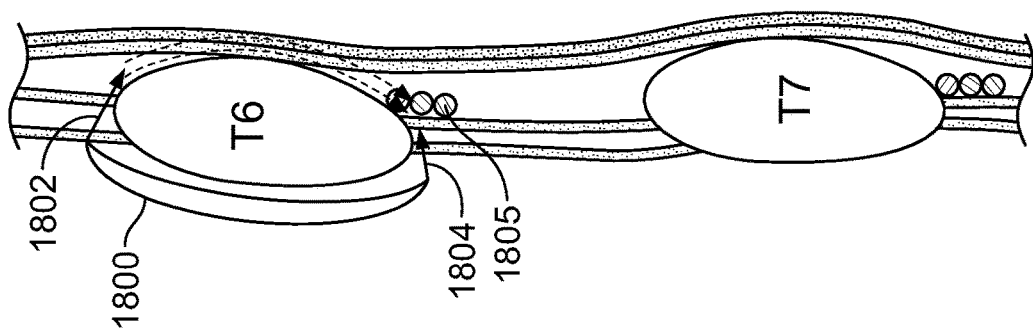
FIG. 18A  T-6 Stimulation

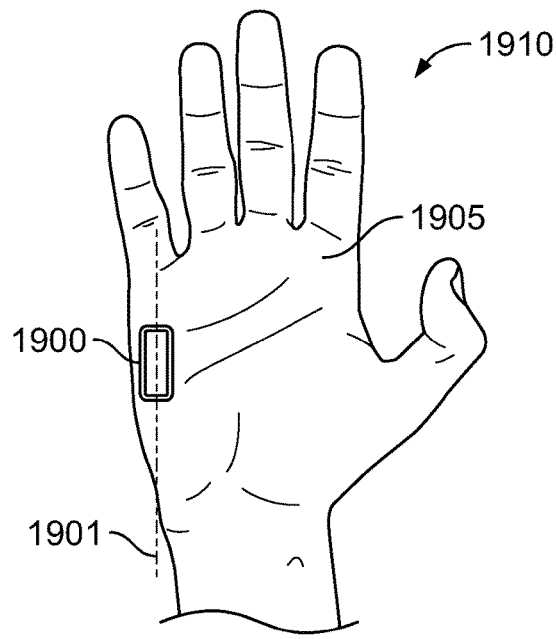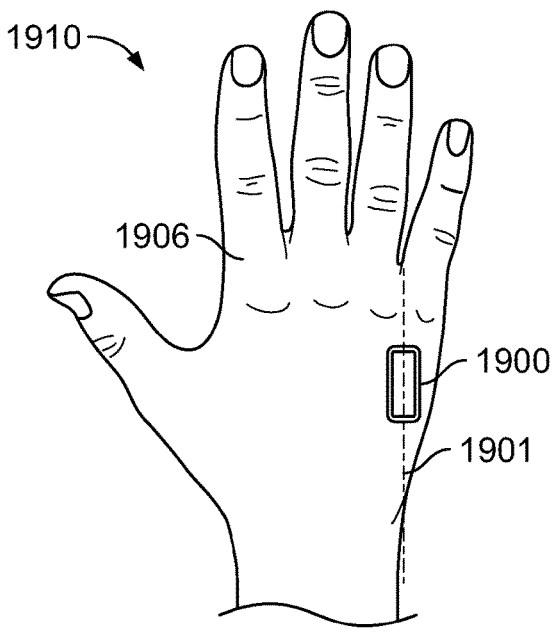
FIG. 19A  FIG. 19B
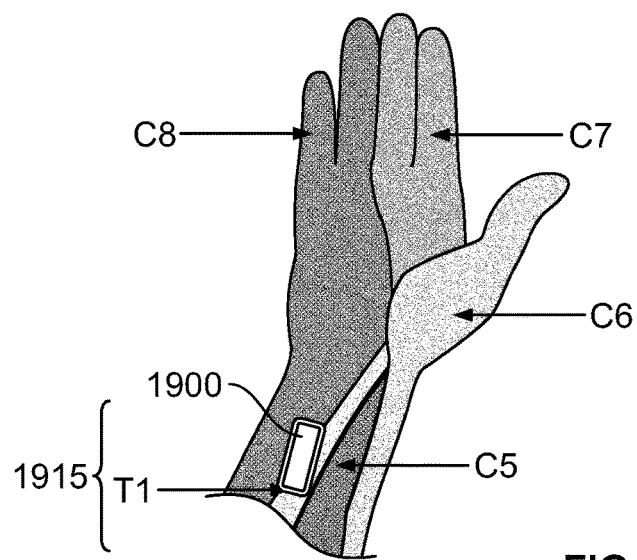
FIG. 19C

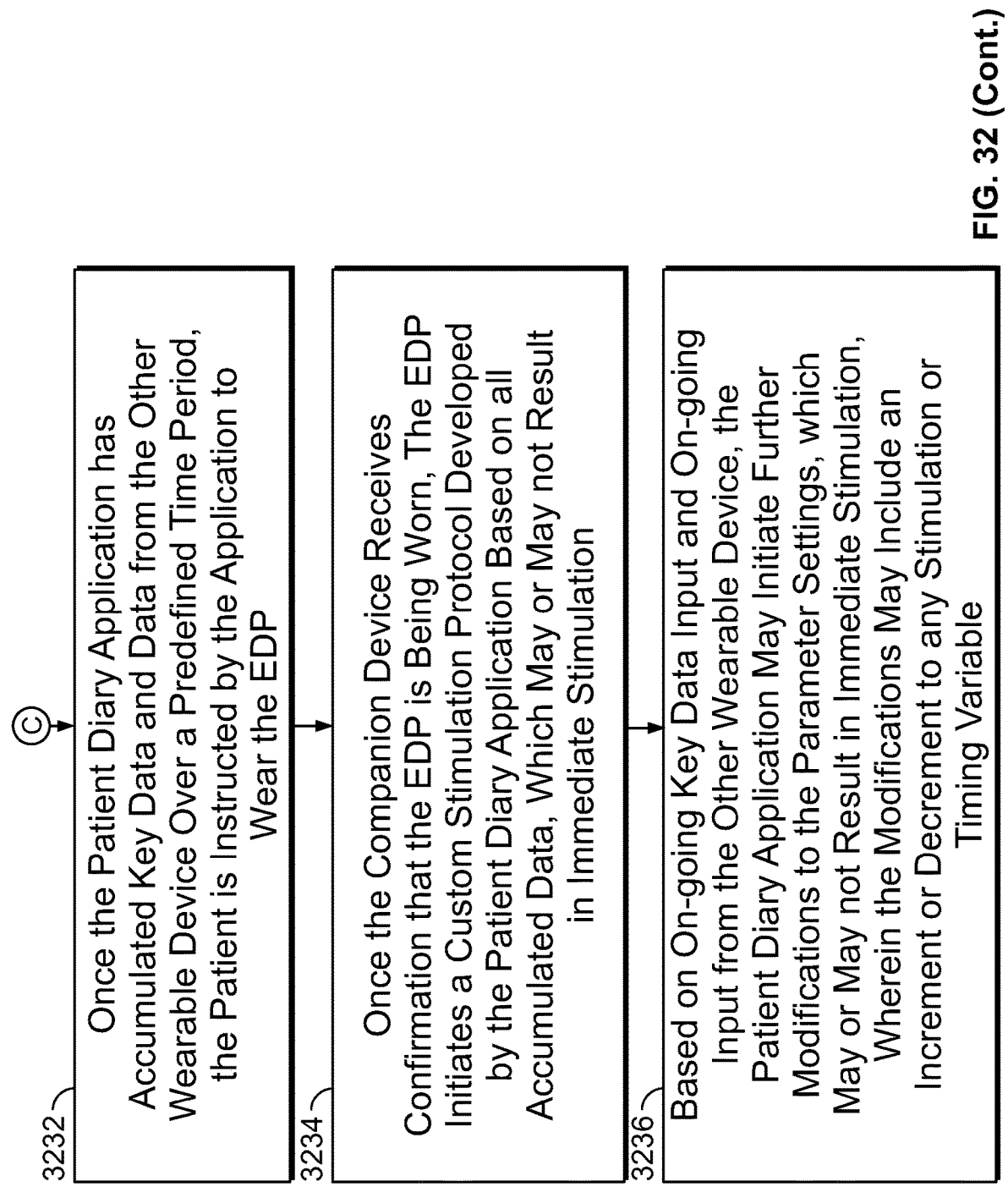

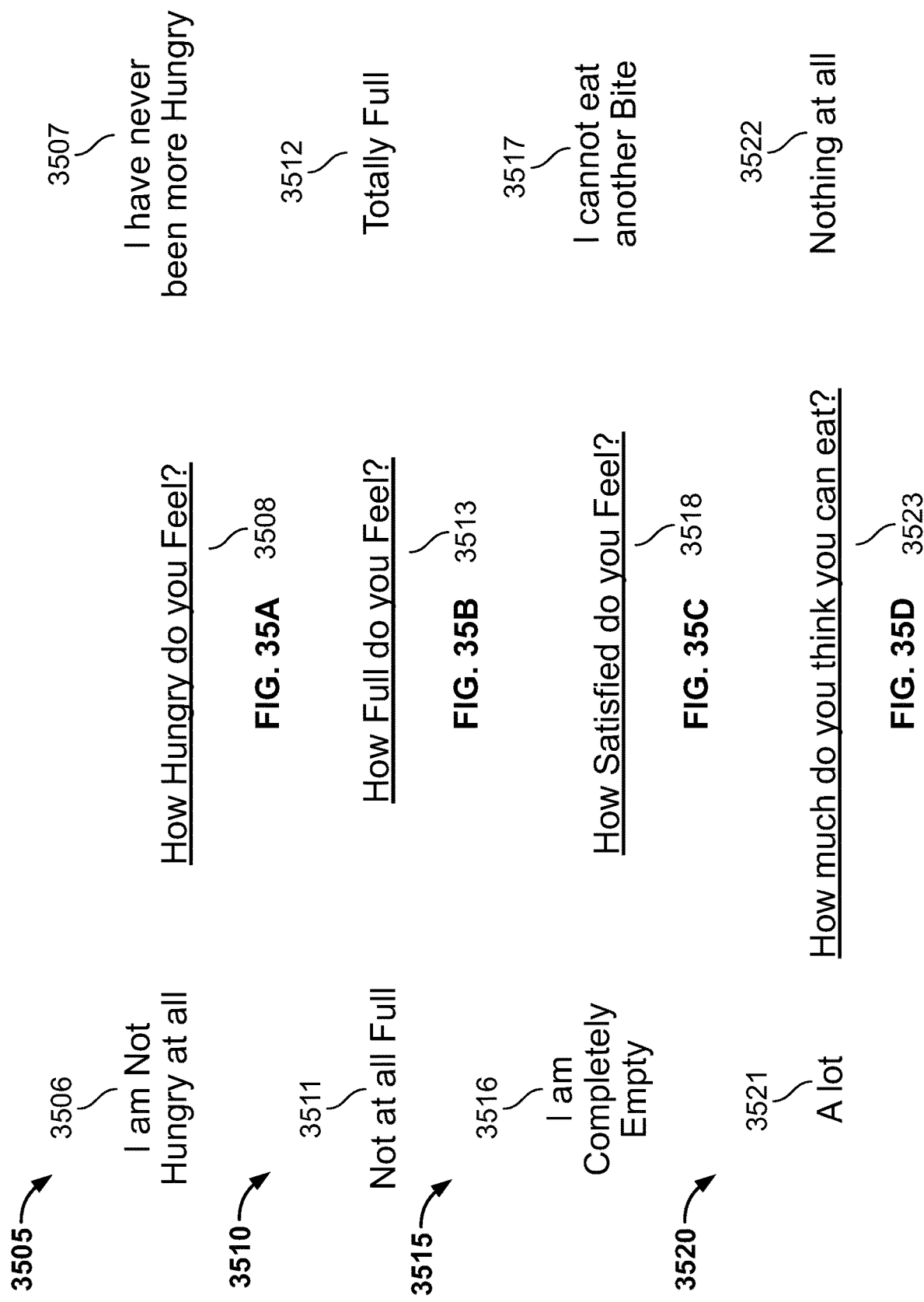

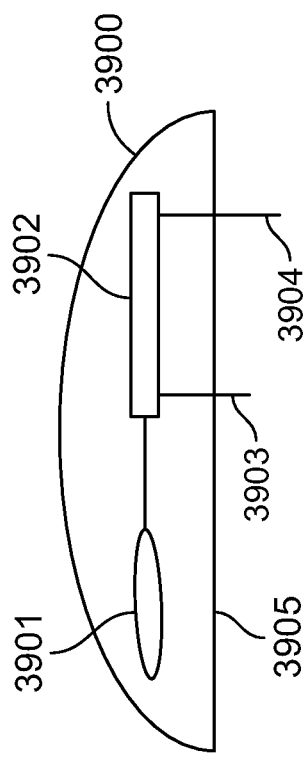
FIG. 39
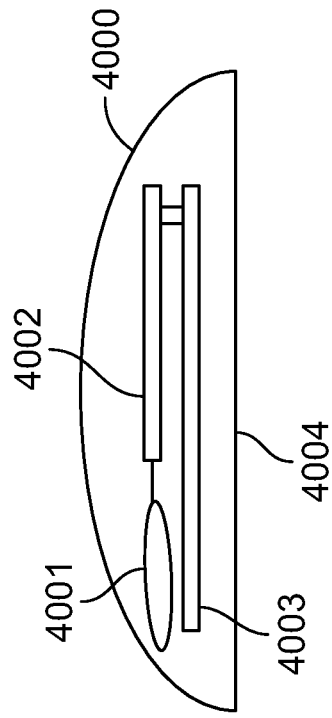
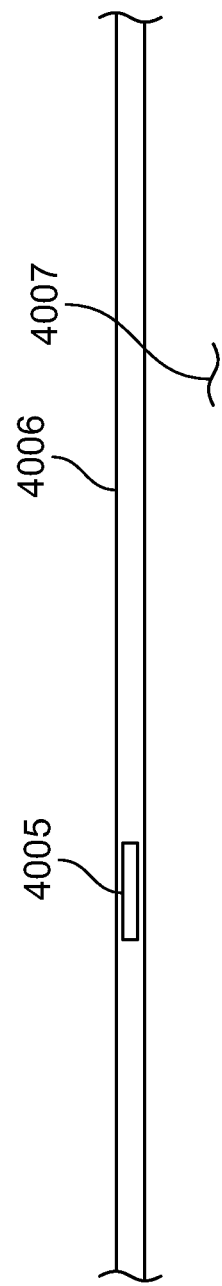
FIG. 40

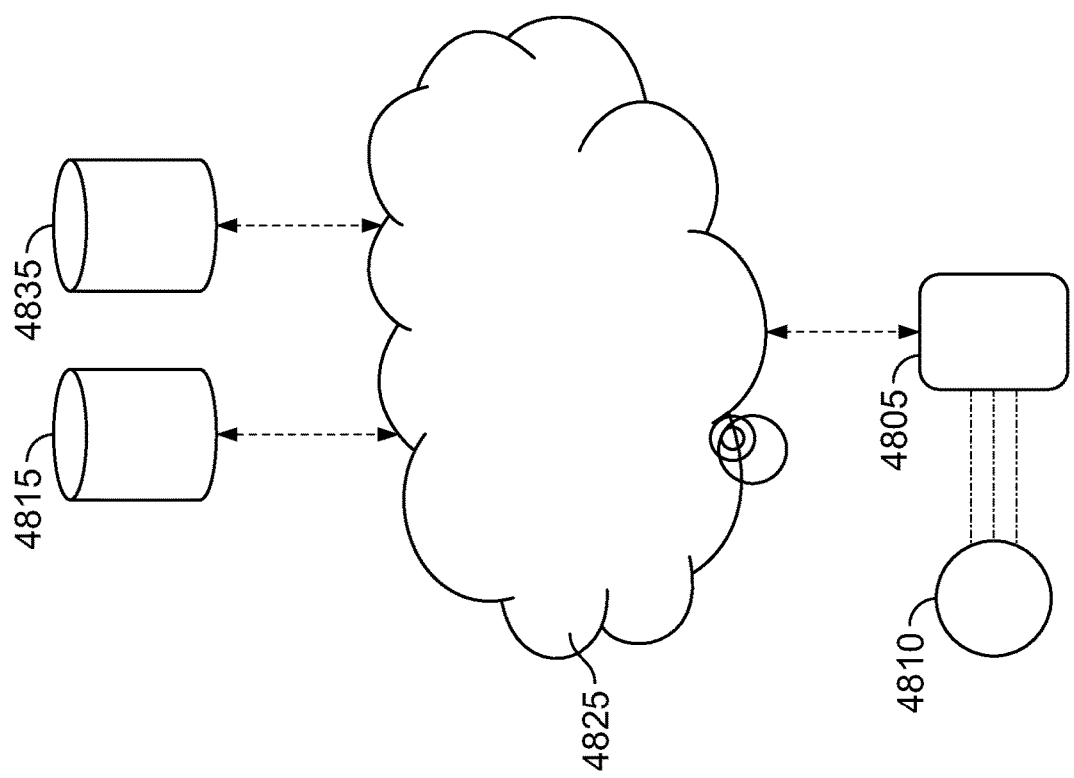

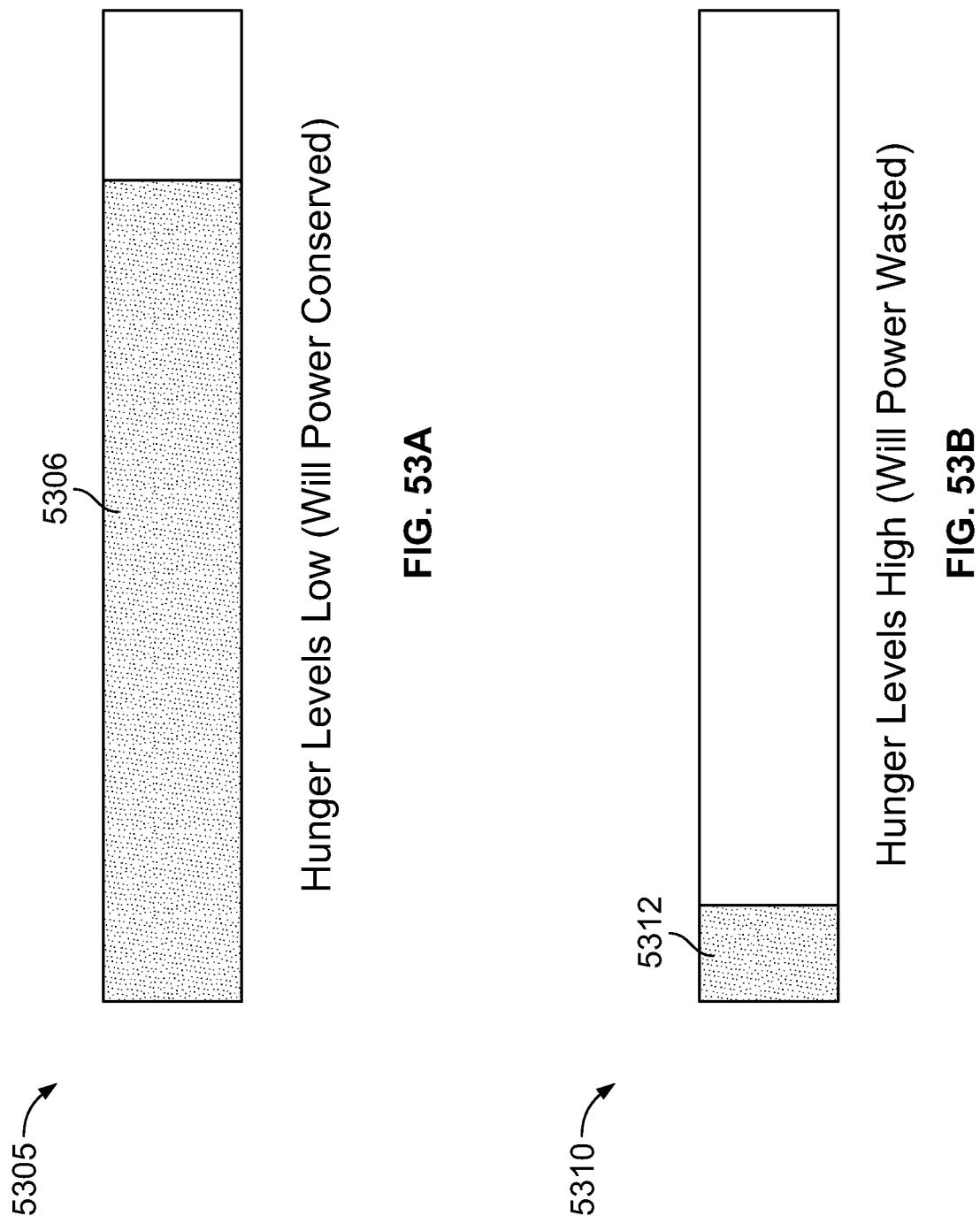

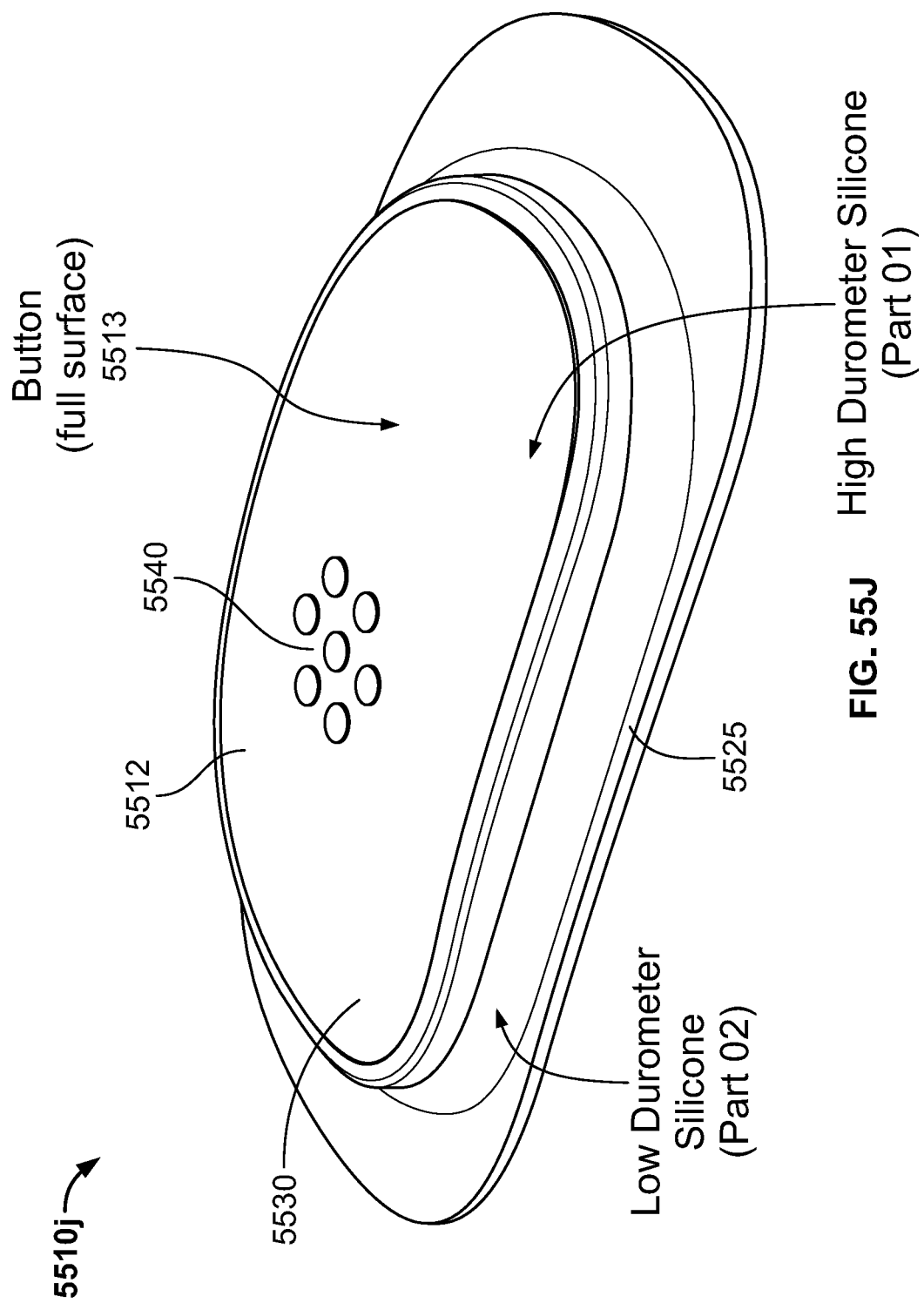

METHODS FOR USING AN ELECTRICAL DERMAL PATCH IN A MANNER THAT REDUCES ADVERSE PATIENT REACTIONS

CROSS-REFERENCE

The present application relies on, for priority, the following U.S. Provisional Patent Applications:

U.S. Patent Provisional Application No. 62/532,317, entitled "Systems and Methods for Engaging In Eating Interventions and Appetite Modulation Based on Closed Loop Glucose Monitoring" and filed on Jul. 13, 2017; and U.S. Patent Provisional Application No. 62/413,213, entitled "Systems and Methods for Enabling Appetite Modulation and/or Improving Dietary Compliance Using an Electro-Dermal Patch" and filed on Oct. 26, 2016.

The present application is also a continuation-in-part application of U.S. patent application Ser. No. 15/702,676, entitled "Systems and Methods for Using Transcutaneous Electrical Stimulation to Enable Dietary Interventions", and filed on Sep. 12, 2017, which relies on, for priority, the following U.S. Provisional Patent Applications:

U.S. Patent Provisional Application No. 62/532,317, entitled "Systems and Methods for Engaging In Eating Interventions and Appetite Modulation Based on Closed Loop Glucose Monitoring" and filed on Jul. 13, 2017; and U.S. Patent Provisional Application No. 62/413,213, entitled "Systems and Methods for Enabling Appetite Modulation and/or Improving Dietary Compliance Using an Electro-Dermal Patch" and filed on Oct. 26, 2016; and U.S. Patent Provisional Application No. 62/393,486, entitled "Systems and Methods for Enabling Appetite Modulation and/or Improving Dietary Compliance Using an Electro-Dermal Patch" and filed on Sep. 12, 2016.

U.S. patent application Ser. No. 15/702,676 is also a continuation-in-part application of U.S. patent application Ser. No. 15/590,750, entitled "Systems and Methods for Achieving Weight Loss Using a Transcutaneous Electro-Dermal Patch" and filed on May 9, 2017, which relies on, for priority, the following U.S. Provisional Patent Applications:

U.S. Patent Provisional Application No. 62/413,213, entitled "Systems and Methods for Enabling Appetite Modulation and/or Improving Dietary Compliance Using an Electro-Dermal Patch" and filed on Oct. 26, 2016;

U.S. Patent Provisional Application No. 62/393,486, entitled "Systems and Methods for Enabling Appetite Modulation and/or Improving Dietary Compliance Using an Electro-Dermal Patch" and filed on Sep. 12, 2016;

U.S. Patent Provisional Application No. 62/378,393, entitled "Systems and Methods for Enabling Appetite Modulation and/or Improving Dietary Compliance Using an Electro-Dermal Patch" and filed on Aug. 23, 2016; and U.S. Patent Provisional Application No. 62/341,917, entitled "Systems and Methods for Enabling Appetite Modulation and/or Improving Dietary Compliance Using an Electro-Dermal Patch" and filed on May 26, 2016.

U.S. patent application Ser. No. 15/590,750 is also a continuation-in-part application of U.S. patent application Ser. No. 15/370,944, entitled "Systems and Methods for Increasing A Delay in the Gastric Emptying Time for a Patient Using a Transcutaneous Electro-Dermal Patch" and filed on Dec. 6, 2016, which relies on, for priority, the following U.S. Provisional Patent Applications:

U.S. Patent Provisional Application No. 62/413,213, entitled "Systems and Methods for Enabling Appetite Modulation and/or Improving Dietary Compliance Using an Electro-Dermal Patch" and filed on Oct. 26, 2016;

U.S. Patent Provisional Application No. 62/393,486, entitled "Systems and Methods for Enabling Appetite Modulation and/or Improving Dietary Compliance Using an Electro-Dermal Patch" and filed on Sep. 12, 2016;

U.S. Patent Provisional Application No. 62/378,393, entitled "Systems and Methods for Enabling Appetite Modulation and/or Improving Dietary Compliance Using an Electro-Dermal Patch" and filed on Aug. 23, 2016;

U.S. Patent Provisional Application No. 62/341,917, entitled "Systems and Methods for Enabling Appetite Modulation and/or Improving Dietary Compliance Using an Electro-Dermal Patch" and filed on May 26, 2016; and U.S. Patent Provisional Application No. 62/326,541, entitled "Systems and Methods for Enabling Appetite Modulation and/or Improving Dietary Compliance Using an Electro-Dermal Patch" and filed on Apr. 22, 2016.

U.S. patent application Ser. No. 15/370,944 is also a continuation-in-part application of U.S. patent application Ser. No. 15/052,791, entitled "Systems and Methods for Enabling Appetite Modulation and/or Improving Dietary Compliance Using an Electro-Dermal Patch" and filed on Feb. 24, 2016.

U.S. patent application Ser. No. 15/370,944 is also a continuation-in-part application of U.S. patent application Ser. No. 15/052,784, entitled "Systems and Methods for Enabling Appetite Modulation and/or Improving Dietary Compliance Using an Electro-Dermal Patch" and filed on Feb. 24, 2016.

U.S. patent application Ser. No. 15/370,944 is also a continuation-in-part application of U.S. patent application Ser. No. 15/204,752, entitled "Systems and Method for Enabling Appetite Modulation and/or Improving Dietary Compliance Using Percutaneous Electrical Neurostimulation", filed on Jul. 7, 2016, which, in turn, is a continuation-in-part of both U.S. patent application Ser. No. 15/052,791, entitled "Systems and Methods for Enabling Appetite Modulation and/or Improving Dietary Compliance Using an Electro-Dermal Patch" and filed on Feb. 24, 2016 and U.S. patent application Ser. No. 15/052,784, entitled "Systems and Methods for Enabling Appetite Modulation and/or Improving Dietary Compliance Using an Electro-Dermal Patch" and filed on Feb. 24, 2016.

U.S. patent application Ser. No. 15/052,791; U.S. patent application Ser. No. 15/052,784 and thus, U.S. patent application Ser. No. 15/204,752 (as a CIP to the '791 and '784 applications) rely on the following applications, for priority:

U.S. Patent Provisional Application No. 62/248,059, entitled "Systems and Methods for Enabling Pain Management Using an Electro-Dermal Patch" and filed on Oct. 29, 2015;

U.S. Patent Provisional Application No. 62/247,113, entitled "Systems and Methods for Enabling Appetite Modulation Using an Electro-Dermal Patch" and filed on Oct. 27, 2015;

U.S. Patent Provisional Application No. 62/246,526, entitled "Systems and Methods for Enabling Appetite Modulation Using an Electro-Dermal Patch" and filed on Oct. 26, 2015;

U.S. Patent Provisional Application No. 62/242,957, entitled "Systems and Methods for Enabling Appetite Modulation Using an Electro-Dermal Patch" and filed on Oct. 16, 2015;

U.S. Patent Provisional Application No. 62/242,944, entitled "Systems and Methods for Enabling Appetite Modulation Using an Electro-Dermal Patch" and filed on Oct. 16, 2015;

U.S. Patent Provisional Application No. 62/240,808, entitled "Systems and Methods for Enabling Appetite Modulation Using an Electro-Dermal Patch" and filed on Oct. 13, 2015;

U.S. Patent Provisional Application No. 62/237,356, entitled "Systems and Methods for Enabling Appetite Modulation Using Transcutaneous Electrical Neurostimulation" and filed on Oct. 5, 2015;

U.S. Patent Provisional Application No. 62/189,805, entitled "Dermatome Stimulation System" and filed on Jul. 8, 2015;

U.S. Patent Provisional Application No. 62/189,800, entitled "Dermatome Stimulation Method" and filed on Jul. 8, 2015;

U.S. Patent Provisional Application No. 62/161,362, entitled "Dermatome Stimulation Method" and filed on May 14, 2015;

U.S. Patent Provisional Application No. 62/161,353, entitled "Dermatome Stimulation System" and filed on May 14, 2015;

U.S. Patent Provisional Application No. 62/141,333, entitled "Dermatome Stimulation Method" and filed on Apr. 1, 2015;

U.S. Patent Provisional Application No. 62/141,328, entitled "Dermatome Stimulation System" and filed on Apr. 1, 2015;

U.S. Patent Provisional Application No. 62/133,530, entitled "Dermatome Stimulation Method" and filed on Mar. 16, 2015;

U.S. Patent Provisional Application No. 62/133,526, entitled "Dermatome Stimulation System" and filed on Mar. 16, 2015;

U.S. Patent Provisional Application No. 62/120,082, entitled "Dermatome Stimulation Methods" and filed on Feb. 24, 2015; and U.S. Patent Provisional Application No. 62/120,067, entitled "Dermatome Stimulation System" and filed on Feb. 24, 2015.

The present application also relates to International Application Number PCT/US16/19416, entitled "Systems and Methods for Enabling Appetite Modulation and/or Improving Dietary Compliance Using an Electro-Dermal Patch" and filed on Feb. 24, 2016.

All of the above-mentioned applications are herein incorporated by reference in their entirety.

FIELD

The present specification relates generally to systems and methods of generating appropriate dietary interventions by providing transcutaneous electrical stimulation using an electrical dermal patch that is optimized for long term wearability. The disclosed systems deliver electrical stimulation to a predetermined area of the user's anatomy in a manner that is convenient, easy to use, and amenable to increased patient compliance. More particularly, the present specification relates to electrical stimulation devices comprising low profile, wearable, disposable skin patches that are easy to self-administer, programmable and monitorable using a mobile handheld device, and programmed to stimulate a patient's nerves from the external surface of the patient's epidermal layer or epidermis in a manner that decreases appetite and hunger, avoids nausea, minimizes habituation and enables increased compliance with a dietary regimen. The present specification further relates to a low profile, wearable, disposable skin patch that is capable of integrating with, and being controlled by, a plurality of different hardware devices or software applications depending on the type, extent, nature and scope of the nature and degree of dietary compliance required and the amount of weight loss desired and/or the need for long term weight maintenance.

BACKGROUND

Being obese, or overweight, is a condition that often results from an imbalance between food intake and caloric expenditure. Excessive weight increases the likelihood of several additional risks including cardiovascular complications (such as hypertension and hyperlipidemia), gallbladder disease, metabolic syndrome, cancer, polycystic ovary disease, pregnancy-related complications, arthritis-related complications and other orthopedic complications caused by stress on body joints. Obesity is also thought to be a primary cause of type 2 diabetes (T2DM) in many ethnicities.

Certain methods and systems of using electrical stimulation to modulate food intake have been disclosed in the art. In U.S. Pat. Nos. 8,538,532 and 8,185,206, serosal electrodes are surgically implanted in the gastrointestinal tract to cause impaired gastric myoelectric activity, retrograde propagation of gastric slow waves, suppression of antral contractions, and delayed gastric emptying. Gastric dysrhythmia has been shown to be associated with gastrointestinal symptoms and delayed gastric emptying which, in turn, is associated with weight loss. The electrical stimulation therapy is configured to cause at least partial gastric distention, thereby inducing a sensation of fullness and discouraging excessive food intake by the patient. The electrical stimulation therapy is delivered to the gastrointestinal tract of the patient by electrodes deployed by one or more implantable leads coupled to an electrical stimulator. The stimulation protocols require a significant amount of energy and are expressly designed to cause muscular contractions or otherwise electrically dysregulate gastric slow waves.

While potentially effective, such therapies require a medical professional to surgically place the device and/or administer the therapy and require a substantial amount of energy to cause muscular contractions or actual impairment of gastric slow waves. The patient must visit the medical professional at the onset of treatment to have the device placed and then periodically thereafter to have the therapy administered and/or device programming modified. The requirement for such frequent doctor visits is inconvenient for most patients and can have a detrimental effect on patient compliance.

With respect to prior art approaches that use electrical, external stimulation to suppress appetite, they do not have a combination of the following characteristics effective to enable a patient to independently administer the device and accompanying therapies: small footprint; administration by the patient; real-time or near real-time feedback from the patient (e.g. food intake, exercise, hunger) or from wearable devices, for example, a device, with physiological sensors, configured to be worn on the human body, such as around the wrist, in order to monitor, acquire, record, and/or transmit the physiological data; the ability to stimulate multiple times per day or week; daily, or on-demand, feedback from the device to the patient with respect to dietary compliance, exercise, calories burned; storage of stimulation parameters and other real-time inputs; effective dietary interventions, and an electrical stimulation profile and a footprint conducive to long term wearability. In addition, prior art therapies which have some degree of flexibility include an electrode which must be tethered via cables to a control or power box. Prior art therapies which are wireless are typically bulky, inflexible, and not amenable to being worn for long periods of time.

Because successful weight loss is, in the end, a matter of achieving a high degree of compliance with a dietary regimen, it is absolutely critical for a successful device to go beyond mere stimulation and combine wearability, physical comfort, ease of use, accurate interventions and integration of numerous data sources to provide a holistic and real-time view into a person's dietary compliance, in addition to effectively modulating the individual's gastric volume, rate of gastric emptying, appetite, hunger, satiety level, satiation level, and/or fullness.

Therefore, there is a need for a low profile, long lasting electrical neuro-stimulation device which is programmable, and is designed to be worn over a longer period of time. There is also a need for a device that can effectively integrate appetite management data with conventional weight management information, such as caloric expenditure and consumption.

There is a need for an electrical neuro-stimulation device which is wearable and can be controlled, programmed, and self-administered by the patient, thereby enabling greater patient independence. There is also a need for an electrical neuro-stimulation device which includes real-time or near real-time feedback from patient parameters including, but not limited to, exercise, diet, hunger, appetite, well-being and which will be able to obtain real-time or near real-time feedback from other wearable devices, for example, a device, with physiological sensors, configured to be worn on the human body, such as around the wrist, in order to monitor, acquire, record, and/or transmit the physiological data, allowing for frequent adjustability and customization of therapy to suppress appetite and therefore treat conditions of obesity, over-weight, eating disorders, metabolic syndrome. There is a need for an electro-stimulation device configured to intelligently trigger and initiate stimulation automatically and without on-going management by a user. There is a need for an electrical neuro-stimulation device having the ability to stimulate multiple times per day or per week, accelerating treatment effect and efficacy. There is a need for an electrical neuro-stimulation device which provides daily feedback from the device to the patient on such parameters as dietary compliance, and calories burned.

In addition, there is a need for an electrical neuro-stimulation device capable of storing stimulation parameters and other real-time inputs, such as diary and exercise monitoring, to provide a physician and the patient with real-time records and treatment profiles. Inputs from the electrical neuro-stimulation device and from other sources of information, for example, a device, with physiological sensors, configured to be worn on the human body, such as around the wrist, in order to monitor, acquire, record, and/or transmit the physiological data would be stored.

There is also a need to allow physicians to be able to flexibly program an electrical neuro-stimulation device and still direct the patient, allowing the patient to adjust device parameters (for greater patient independence) but within restricted bounds or predetermined parameters.

There is also a need for an electrical neuro-stimulation device which targets a rate of appetite or hunger suppression, does not require implantation, and does not require wires or remote electrodes to provide stimulation. There is a need for an electrical neuro-stimulation device which is remotely programmable, yet wireless, can flex at any point along its body, is waterproof, and is configured for extended or permanent wearability. There is also a need for a patient-administered, wearable electrical neuro-stimulation device directed toward suppressing post-prandial glucose levels and effectively modulating a plurality of hormones and microbiota related to gastrointestinal functionality. There is a need for an electrical neuro-stimulation device having a size, shape, and weight, and being composed of materials that effectively allow the device to be wearable. Such a device would eliminate the need for stimulation parameters requiring large power needs (which would make wearability impractical or impossible). There is also a need for an electrical neuro-stimulation device which is controllable by a companion device (such as a smartphone) and includes no visible or tactile user interface on the stimulation device itself. There is a need for an electrical neuro-stimulation device having unique electrical stimulation and footprint, based on electrode design and stimulation parameters, which would allow users to comfortably wear the device.

There is also a need for a holistic approach to managing a patient's caloric consumption and expenditure profile. Conventional approaches focus on caloric intake but do not analyze, monitor, or otherwise gather data on the important precursor to caloric intake, namely appetite or hunger levels. There are untapped benefits to integrating data relating to the appetite, hunger and/or craving levels, active suppression or control over appetite, caloric intake, weight gain, and caloric expenditure. These and other benefits shall be described in relation to the detailed description and figures.

SUMMARY

The following embodiments and aspects thereof are described and illustrated in conjunction with systems, tools and methods, which are meant to be exemplary and illustrative, and not limiting in scope. The present application discloses numerous embodiments.

The device may be used to treat a condition including any one of obesity, excess weight, eating disorders, metabolic syndrome and diabetes. In accordance with various aspects of the present specification, the electro-dermal patch device enables treating people with BMI (Body Mass Index) of 25 or greater (overweight being 25-30, obese being 30 and above, and morbid obesity being above 35).

The present specification discloses an electrical dermal patch adapted to be continuously worn by a patient for at least 24 hours, a housing comprising a controller in electrical communication with a pulse generator; and at least two electrodes adapted to be adhered to the patient's skin and in electrical communication with the pulse generator, wherein the controller comprises programmatic instructions that, when executed and transmitted to the pulse generator, cause the pulse generator to generate and transmit to the at least two electrodes a first electrical stimulation pulse and a second electrical stimulation pulse, wherein the first electrical pulse is defined by a first phase having a first polarity and a second phase having a second polarity that is opposite the first polarity, wherein the second electrical pulse follows the first electrical pulse and is defined by a third phase having a third polarity and a fourth phase having a fourth polarity that is opposite the third polarity, and wherein the second polarity is equal to the third polarity.

Optionally, the second electrical pulse follows the first electrical pulse after a predetermined wait period.

Optionally, the first polarity is positive, the second polarity is negative, the third polarity is negative, and the fourth polarity is positive.

Optionally, the first polarity is negative, the second polarity is positive, the third polarity is positive, and the fourth polarity is negative.

Optionally, each of the at least two electrodes comprise a hypoallergenic conductive gel with at least one adhesive surface.

Optionally, the electrode does not comprise imidazolidinyl urea or diazolidinyl urea.

Optionally, the electrode comprises carboxymethylcellulose polymer and propylene glycol.

Optionally, the at least one adhesive surface is adapted to adhere to the patient's skin and have a peel strength in a range of 1.0 to 2.1 newtons.

Optionally, the at least one adhesive surface is adapted to adhere to the patient's skin and have a total skin contact surface area in a range of 2 $cm^2$ to 4 $cm^2$.

Optionally, the at least two electrodes are positioned in a same plane parallel to the patient's skin and separated by a distance of 0.05 $cm^2$ to 0.4 $cm^2$.

Optionally, an amplitude of the first phase, the second phase, the third phase, and the fourth phase are equal and a pulse width of the first phase, the second phase, the third phase, and the fourth phase are equal.

Optionally, the predefined time interval is in a range of 1 minute to 10 minutes.

Optionally, an amplitude of the first phase and the fourth phase are equal, wherein a pulse width of the first phase and the fourth phase are equal, an amplitude of the second phase and the third phase are equal, wherein a pulse width of the second phase and the third phase are equal, and wherein at least one of the amplitude and the pulse width of the first phase is different from the amplitude and pulse width of the second phase.

Optionally, the first phase is defined by a waveform characterized by a first period and a second period, wherein the first period comprises a first 10 μs of the waveform and the second period comprises a remainder of the waveform and wherein said waveform is defined by a maximum amplitude during the first period and an amplitude less than said maximum amplitude during the second period.

Optionally, the maximum amplitude is in a range of 20 to 40 mA.

Optionally, the maximum amplitude is in a range of 20 to 40 mA and an average amplitude across said first period and second period is in a range of 10 mA to 20 mA.

Optionally, the pulse generator has a maximum compliance voltage in a range of 40 volts to 60 volts.

Optionally, at least one of the first phase, second phase, third phase, and fourth phase is defined by a waveform characterized by a first period, a second period, and a third period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a maximum amplitude and the second and third periods are defined by a remainder amplitude less than said maximum amplitude.

Optionally, the maximum amplitude is in a range of 20 mA to 40 mA.

Optionally, in the second period, a decay of the remainder amplitude is defined by a first negative slope having a first magnitude and, in the third period, a decay of said remainder amplitude is defined by a second negative slope having a second magnitude, wherein the first magnitude is less than the second magnitude.

Optionally, an average of the maximum amplitude and the remainder amplitude is in a range of 10 mA to 20 mA.

In some embodiments, the present specification discloses an electrical dermal patch adapted to be continuously worn by a patient for at least 1 day, a housing comprising a controller in electrical communication with a pulse generator; and two electrodes adapted to be adhered to the patient's skin, positioned in a same plane parallel to the patient's skin, separated by a distance of 0.05 $cm^2$ to 0.4 $cm^2$. and in electrical communication with the pulse generator, wherein the controller comprises programmatic instructions that, when executed and transmitted to the pulse generator, cause the pulse generator to generate and transmit to the at least two electrodes a first set of electrical stimulation pulses and a second set of electrical stimulation pulses and wherein each of the at least two electrodes comprise a hypoallergenic conductive gel with at least one adhesive surface, wherein the hypoallergenic conductive gel does not comprise imidazolidinyl urea or diazolidinyl urea and wherein the at least one adhesive surface is adapted to adhere to the patient's skin and have a total skin contact surface area in a range of 2 $cm^2$ to 4 $cm^2$.

Optionally, the electrode comprises carboxymethylcellulose polymer and propylene glycol.

Optionally, each of the electrical stimulation pulses is defined by a charged balanced biphasic waveform and wherein the first set of electrical stimulation pulses and second set of electrical stimulation pulses are separated by a predefined time interval.

Optionally, the predefined time interval is randomized and is at least 1 minute long.

Optionally, the pulse generator has a maximum compliance voltage in a range of 40 volts to 60 volts.

Optionally, each of the electrical stimulation pulses is defined by a waveform characterized by a first period, a second period, and a third period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a maximum amplitude and the second and third periods are defined by a remainder amplitude less than said maximum amplitude.

Optionally, the maximum amplitude of the electrical dermal patch is in a range of 20 mA to 40 mA.

Optionally, in the second period, a decay of said remainder amplitude is defined by a first negative slope having a first magnitude and, in the third period, a decay of said remainder amplitude is defined by a second negative slope having a second magnitude, wherein the first magnitude is less than the second magnitude.

Optionally, an average of the maximum amplitude and the remainder amplitude is in a range of 10 mA to 20 mA.

In some embodiments, the present specification discloses a method of using the electrical dermal patch of claim 1 comprising: programming the controller such that each of the electrical stimulation pulses comprises a pulse width in a range of 10 μsec to 10 msec, a pulse amplitude in a range of 100 μA to 100 mA, and a pulse frequency in a range of 1 Hz and 100 Hz; and determining if the patient experiences a change in appetite as a result of an application of said first set of electrical stimulation pulses or said second set of electrical stimulation pulses to the patient's skin, wherein the patient does not experience erythema, scaling, pruritus, folliculitis, or intertrigo at a point where said two electrodes adhere to the patient's skin.

Optionally, the method further comprises programming the controller such that each of the electrical stimulation pulses comprises a pulse width in a range of 10 μsec to 10 msec, a pulse amplitude in a range of 100 μA to 100 mA, and a pulse frequency in a range of 1 Hz and 100 Hz; and determining if the patient experiences a change in appetite as a result of an application of said first set of electrical stimulation pulses or said second set of electrical stimulation pulses to the patient's skin, wherein the patient does not experience erythema, scaling, pruritus, folliculitis, or intertrigo at a point where said two electrodes adhere to the patient's skin.

The present specification discloses a system to generate real-time interventions in response to a patient's degree of appetite, comprising: an electrical dermal patch comprising: a housing; a controller positioned within the housing; at least one electrode positioned in physical communication with the housing and adapted to be in electrical contact with the patient's skin; and, a pulse generator positioned within the housing and in electrical communication with the controller and said at least one electrode, wherein the pulse generator is configured to generate a plurality of stimulation sessions comprising a plurality of electrical pulses defined by stimulation parameters and wherein said stimulation parameters comprise a first pulse width in a range of 10 μsec to 10 msec, a first pulse amplitude in a range of 100 μA to 100 mA, and a first pulse frequency in a range of 1 Hz and 100 Hz; a first plurality of programmatic instructions stored in a non-transient memory in a client device separate from the electrical dermal patch, wherein, when executed, said first plurality of programmatic instructions is adapted to cause the client device to generate a prompt to the patient to input data indicative of the patient's degree of appetite via a microphone or a display of said client device; a second plurality of programmatic instructions stored in a non-transient memory in the client device or another device separate from the electrical dermal patch, wherein, when executed, said second plurality of programmatic instructions determines an appetite pattern of the patient based upon said inputted data; and a third plurality of programmatic instructions stored in a non-transient memory in the client device or another device separate from the electrical dermal patch, wherein, when executed, said third plurality of programmatic instructions determines an intervention and generates said intervention based on the appetite pattern.

Optionally, said intervention is causing at least one of a text-based message, video message, audio message, or graphic message to be transmitted to the patient via the client device.

Optionally, said intervention is modifying the stimulation parameters such that at least one of a pulse width is different than the first pulse width, a pulse amplitude is different than the first pulse amplitude, and a pulse frequency is different than the first pulse frequency.

Optionally, said second plurality of programmatic instructions determines an appetite pattern of the patient based upon the inputted data by determining a time window associated with each of the inputted data and, for each time window, determining if value ranges of all inputted data associated with the time window are within a predefined range around a value to constitute a pattern. The time window may be in a range of 1 to 3 hours.

Optionally, said second plurality of programmatic instructions determines an appetite pattern of the patient based upon the inputted data by determining a time window associated with each of the inputted data and, for each time window, determining if value ranges of all inputted data associated with the time window are not within a predefined range around a value to constitute a pattern.

Optionally, said second plurality of programmatic instructions determines an appetite pattern of the patient based upon the inputted data by determining a time window associated with each of the inputted data and, for each time window, determining if a number of individual inputted data values associated with the time window are sufficiently large to constitute a pattern.

Optionally, said second plurality of programmatic instructions determines an appetite pattern of the patient based upon the inputted data by determining a time window associated with each of the inputted data and, for each time window, determining if a number of individual inputted data values associated with the time window are too low to constitute a pattern. The time window may be in a range of 1 to 3 hours.

Optionally, the prompt is in a form of at least one of an audio message, video message, text message, and graphical message.

Optionally, the first plurality of programmatic instructions is adapted to cause the client device to generate the prompt at a first rate for a first time window and at a second rate after said first time window, wherein the second rate is less than the first rate. Optionally, the first rate is in a range of once per day to twenty four times per day and the first time window is in a range of 1 day to 1 month. Optionally, the first plurality of programmatic instructions is adapted to provide the patient with an option, via the display of the client device, to modify the first rate.

Optionally, said third plurality of programmatic instructions determines the intervention by processing the appetite pattern indicative of the patient's degree of appetite to determine if the patient's degree of appetite is expected to be greater than or less than a first threshold value at a future time window. Optionally, if the patient's degree of appetite is expected to be less than the first threshold value at the future time window, said third plurality of programmatic instructions does not generate the intervention during the future time window. Optionally, if the patient's degree of appetite is expected to be greater than the first threshold value at the future time window, said third plurality of programmatic instructions generates the intervention during the future time window. The intervention may cause at least one of a text-based message, video message, audio message, or graphic message to be transmitted to the patient via the client device. The intervention may modify the stimulation parameters such that at least one of a pulse width is different than the first pulse width, a pulse amplitude is different than the first pulse amplitude, and a pulse frequency is different than the first pulse frequency.

Optionally, when executed, the first plurality of programmatic instructions generates the prompt in a form of a visual analog scale and causes said prompt to be displayed on the client device, wherein each value along said visual analog scale is representative of a different degree of appetite. The visual analog scale may be a light bar having a sliding scale, wherein a first end of the sliding scale is indicative of a low degree of appetite and a second end of the sliding scale is indicative of a high degree of appetite.

Optionally, when executed, the first plurality of programmatic instructions generates the prompt in a form of a plurality of icons and wherein each of said plurality of icons is representative of a different degree of appetite.

Optionally, when executed, the first plurality of programmatic instructions generates the prompt in a form of auditory inquires and causes said auditory inquiries to be played via a speaker of said client device.

Optionally, when executed, the third plurality of programmatic instructions receives the appetite pattern of the patient and causes said appetite pattern to be displayed on the client device, wherein the appetite pattern is in a form of a graph having a time of day on a first axis, a calendar day on a second axis, and an icon representing a degree of the patient's appetite plotted on said graph in relation to said time of day and calendar day. Optionally, at least one of a size, shape, color, or pattern of the icon is indicative of the patient's degree of appetite.

Optionally, when executed, the third plurality of programmatic instructions receives a weight trend of the patient and the appetite pattern and determines a composite score of the patient, wherein said composite score is a function of the patient's historical degrees of appetite and weight trend, and causes said composite score to be displayed on the client device. Optionally, when executed, the third plurality of programmatic instructions is configured to cause the client device to transmit said composite score to an online affinity group, wherein the patient is a member of said online affinity group.

The present specification also discloses a system to generate real-time interventions in response to a patient's degree of appetite, comprising: an electrical dermal patch comprising: a housing; a controller positioned within the housing; at least one electrode in physical communication with the housing and adapted to be in electrical contact with the patient's skin; and, a pulse generator positioned within the housing and in electrical communication with the controller and said at least one electrode, wherein the pulse generator is configured to generate a plurality of stimulation sessions comprising a plurality of electrical pulses defined by stimulation parameters; a first plurality of programmatic instructions stored in a non-transient memory in a client device separate from the electrical dermal patch, wherein, when executed, said first plurality of programmatic instructions communicates with said electrical dermal patch and prompts the patient to input data indicative of the patient's degree of appetite via a microphone or display of said client device; and a second plurality of programmatic instructions stored in a non-transient memory in the client device or another device separate from the electrical dermal patch, wherein, when executed, the second plurality of programmatic instructions receives the data indicative of the patient's degree of appetite, processes the data indicative of the patient's degree of appetite to develop predictions of whether the patient's degree of appetite will be above or below a threshold value in a future time window, does not generate any intervention in the future time window if the patient's degree of appetite is expected to be below the threshold value, and causes a first intervention to be generated in the future time window if the patient's degree of appetite is expected to be above the threshold value.

Optionally, the first intervention is a signal that is generated by the second plurality of programmatic instructions and is transmitted to the electrical dermal patch in or before the future time window.

Optionally, the first intervention comprises at least one of graphics, text, audio, and video and said at least one of graphics, text, audio, and video comprises a pre-recorded message from an individual who is connected with the patient within a social network.

Optionally, the first intervention comprises at least one of graphics, text, audio, and video and said at least one of graphics, text, audio, and video comprises a real-time message from an individual who is connected with the patient within a social network.

The present specification also discloses an electrical dermal patch adapted to be continuously worn by a patient for at least 3 days, comprising: a housing comprising a controller in electrical communication with a pulse generator; and at least two electrodes adapted to be adhered to the patient's skin and in electrical communication with the pulse generator, wherein the controller comprises programmatic instructions that, when executed and transmitted to the pulse generator, cause the pulse generator to generate and transmit to the at least two electrodes a first set of electrical stimulation pulses and a second set of electrical stimulation pulses and wherein each of the at least two electrodes comprise a hypoallergenic conductive gel with at least one adhesive surface.

Optionally, the electrode does not comprise imidazolidinyl urea or diazolidinyl urea.

Optionally, the electrode comprises carboxymethylcellulose polymer and propylene glycol.

Optionally, the at least one adhesive surface is adapted to adhere to the patient's skin and have a peel strength in a range of 1.0 to 2.1 newtons.

Optionally, the at least one adhesive surface is adapted to adhere to the patient's skin and have a total skin contact surface area in a range of 2 $cm^2$ to 4 $cm^2$.

Optionally, the at least two electrodes are positioned in a same plane parallel to the patient's skin and separated by a distance of 0.05 $cm^2$ to 0.4 $cm^2$.

Optionally, each of the electrical stimulation pulses is defined by a charged balanced biphasic waveform and the first set of electrical stimulation pulses and second set of electrical stimulation pulses are separated by a predefined time interval. The predefined time interval may be in a range of 1 minute to 10 minutes.

Optionally, each of the electrical stimulation pulses is defined by a waveform characterized by a first period and a second period, wherein the first period comprises a first 10 μs of the waveform and the second period comprises a remainder of the waveform and said waveform is defined by a maximum amplitude during the first period and an amplitude less than said maximum amplitude during the second period. The maximum amplitude may be in a range of 20 to 50 mA. The maximum amplitude may be in a range of 20 to 50 mA and an average amplitude across said first period and second period may be in a range of 10 mA to 30 mA.

Optionally, the pulse generator has a maximum compliance voltage in a range of 40 volts to 60 volts. Optionally, each of the electrical stimulation pulses is defined by a waveform characterized by a first period, a second period, and a third period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a maximum amplitude and the second and third periods are defined by a remainder amplitude less than said maximum amplitude. Optionally, the maximum amplitude is in a range of 20 mA to 50 mA. Optionally, in the second period, a decay of said remainder amplitude is defined by a first negative slope having a first magnitude and, in the third period, a decay of said remainder amplitude is defined by a second negative slope having a second magnitude, wherein the first magnitude is less than the second magnitude. Optionally, an average of the maximum amplitude and the remainder amplitude is in a range of 10 mA to 30 mA.

The present specification also discloses an electrical dermal patch adapted to be continuously worn by a patient for at least 3 days, comprising: a housing comprising a controller in electrical communication with a pulse generator; and two electrodes adapted to be adhered to the patient's skin, positioned in a same plane parallel to the patient's skin, separated by a distance of 0.05 $cm^2$ to 0.4 $cm^2$. and in electrical communication with the pulse generator, wherein the controller comprises programmatic instructions that, when executed and transmitted to the pulse generator, cause the pulse generator to generate and transmit to the at least two electrodes a first set of electrical stimulation pulses and a second set of electrical stimulation pulses and wherein each of the at least two electrodes comprise a hypoallergenic conductive gel with at least one adhesive surface, wherein the hypoallergenic conductive gel does not comprise imidazolidinyl urea or diazolidinyl urea and wherein the at least one adhesive surface is adapted to adhere to the patient's skin and have a total skin contact surface area in a range of 2 $cm^2$ to 4 $cm^2$.

Optionally, the electrode comprises carboxymethylcellulose polymer and propylene glycol.

Optionally, each of the electrical stimulation pulses is defined by a charged balanced biphasic waveform and the first set of electrical stimulation pulses and second set of electrical stimulation pulses are separated by a predefined time interval. The predefined time interval may be randomized and is at least 1 minute.

Optionally, the pulse generator has a maximum compliance voltage in a range of 40 volts to 60 volts. Optionally, each of the electrical stimulation pulses is defined by a waveform characterized by a first period, a second period, and a third period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a maximum amplitude and the second and third periods are defined by a remainder amplitude less than said maximum amplitude. Optionally, the maximum amplitude is in a range of 20 mA to 50 mA. Optionally, in the second period, a decay of said remainder amplitude is defined by a first negative slope having a first magnitude and, in the third period, a decay of said remainder amplitude is defined by a second negative slope having a second magnitude, wherein the first magnitude is less than the second magnitude. Optionally, an average of the maximum amplitude and the remainder amplitude is in a range of 10 mA to 30 mA.

The present specification also discloses a method of using the electrical dermal patch described above, comprising: programming the controller such that each of the electrical stimulation pulses comprises a pulse width in a range of 10 μsec to 10 msec, a pulse amplitude in a range of 100 μA to 100 mA, and a pulse frequency in a range of 1 Hz and 100 Hz; and evaluating if the patient experiences a change in appetite as a result of an application of said first set of electrical stimulation pulses or said second set of electrical stimulation pulses to the patient's skin, wherein the patient does not experience erythema, scaling, pruritus, folliculitis, or intertrigo at a point where said two electrodes adhere to the patient's skin.

In some embodiments, the present specification discloses an electrical stimulation system, comprising: an electrical dermal patch comprising a housing, a controller positioned within the housing, at least one electrode positioned within the housing and adapted to be in electrical contact with the patient's skin, a pulse generator positioned within the housing and in electrical communication with the controller and said at least one electrode, wherein the pulse generator is configured to generate a plurality of stimulation sessions comprising a plurality of electrical pulses defined by stimulation parameters; and a first plurality of programmatic instructions stored in a non-transient memory in a client device separate from the electrical dermal patch, wherein, when executed by said client device, said first plurality of programmatic instructions communicates with said electrical dermal patch, acquires glucose status data of said patient, generates a modulation signal based upon said glucose status data and causes said modulation signal to be transmitted to the electrical dermal patch.

Optionally, the stimulation parameters comprise a pulse width in a range of 10 μsec to 10 msec, a pulse amplitude in a range of 100 μA to 100 mA, and a pulse frequency in a range of 1 Hz and 100 Hz.

Optionally, the modulation signal defines a second plurality of stimulation parameters, wherein said second plurality of stimulation parameters comprise a second pulse width in a range of 10 μsec to 10 msec, a second pulse amplitude in a range of 100 μA to 100 mA, and a second pulse frequency in a range of 1 Hz and 100 Hz and wherein at least one of the pulse width is different from the second pulse width, the pulse amplitude is different from the second pulse amplitude, and the pulse frequency is different from the second pulse frequency.

Optionally, the second plurality of stimulation parameters are selected such that, after applying a stimulation session defined by the second plurality of stimulation parameters, a glycemic indicator of the patient improves relative to the patient's said glycemic indicator prior to applying the stimulation session.

Optionally, the first plurality of programmatic instructions prompts the patient to input glucose status data by causing a visual analog scale to be displayed on said client device.

Optionally, when executed, the first plurality of programmatic instructions generates the modulation signal based upon a time of day.

Optionally, when executed, the first plurality of programmatic instructions acquires said glucose status data from a second device comprising a glucose sensor configured to periodically and automatically acquire said glucose status data and wirelessly communicate said glucose status data to said client device.

Optionally, the electrical dermal patch comprises a glucose sensor to periodically and automatically monitor and record said glucose status data of the patient.

Optionally, when executed, the first plurality of programmatic instructions prompts the patient to input data indicative of the patient's degree of appetite via a microphone or display of said client device.

Optionally, when executed, the first plurality of programmatic instructions generates a modulation signal based upon said glucose status data and said data indicative of the patient's degree of appetite.

In some embodiments, the present specification discloses an electrical stimulation system, comprising: an electrical dermal patch comprising a housing, a controller positioned within the housing, at least one electrode positioned within the housing and adapted to be in electrical contact with the patient's skin, a pulse generator positioned within the housing and in electrical communication with the controller and said at least one electrode, wherein the pulse generator is configured to generate a plurality of stimulation sessions comprising a plurality of electrical pulses defined by stimulation parameters; and a first plurality of programmatic instructions stored in a non-transient memory in a client device separate from the electrical dermal patch, wherein, when executed by said client device, said first plurality of programmatic instructions communicates with said electrical dermal patch, prompts the patient to input data indicative of the patient's degree of appetite via a microphone or display of said client device, acquires glucose status data of said patient, generates a modulation signal based upon said glucose status data and a time of day and causes said modulation signal to be transmitted to the electrical dermal patch.

Optionally, when executed, the first plurality of programmatic instructions prompts the patient to input said data indicative of the patient's degree of appetite by causing a visual analog scale to be displayed on said client device.

Optionally, when executed, the first plurality of programmatic instructions further generates the modulation signal based upon said data indicative of the patient's degree of appetite.

Optionally, the stimulation parameters comprise a session frequency, a session duration, a pulse width in a range of 10 μsec to 10 msec, a pulse amplitude in a range of 100 μA to 100 mA, and a pulse frequency in a range of 1 Hz and 100 Hz and wherein said modulation signal defines a second plurality of stimulation parameters, wherein said second plurality of stimulation parameters comprise a second session frequency, a second session duration, second pulse width in a range of 10 μsec to 10 msec, a second pulse amplitude in a range of 100 μA to 100 mA, and a second pulse frequency in a range of 1 Hz and 100 Hz.

Optionally, when executed, the first plurality of programmatic instructions receives said glucose status data before 11 am, examines said glucose status data to determine if a glucose level of the patient is greater than 100 mg/dl, and, based on said determination, generates said modulation signal configured to cause the electrical dermal patch to generate an electrical stimulation after 5 pm.

Optionally, when executed, the first plurality of programmatic instructions receives said glucose status data before 11 am, examines said glucose status data to determine if a glucose level of the patient is greater than 100 mg/dl, and, based on said determination, generates said modulation signal configured to cause the electrical dermal patch to generate an electrical stimulation after 5 pm, wherein said modulation signal comprises at least one of an increased second session frequency relative to the session frequency, an increased second session duration relative to the session duration, an increased second pulse amplitude relative to the pulse amplitude, and an increased second pulse frequency relative to the pulse frequency.

Optionally, when executed, the first plurality of programmatic instructions receives said glucose status data periodically throughout a day, examines said glucose status data to determine if a glucose level of the patient is greater than 140 mg/dl, and, based on said determination, generates said modulation signal configured to cause the electrical dermal patch to generate an electrical stimulation within two hours after determining the glucose level is greater than 140 mg/dl.

Optionally, when executed, the first plurality of programmatic instructions receives said glucose status data periodically throughout a day, examines said glucose status data to determine if a glucose level of the patient is greater than 140 mg/dl, examines data indicative of the patient's degree of appetite, and, based on said determination, generates said modulation signal configured to generate an electrical stimulation within two hours after determining the glucose level is greater than 140 mg/dl and the patient's degree of appetite is greater than a predefined number.

Optionally, when executed, the first plurality of programmatic instructions receives said glucose status data, examines said glucose status data to determine if a glucose level of the patient is less than 80 mg/dl, and, based on said determination, generates said modulation signal.

Optionally, when executed, the first plurality of programmatic instructions receives said glucose status data, examines said glucose status data to determine if a glucose level of the patient is less than 80 mg/dl, and, based on said determination, generates said modulation signal, wherein said modulation signal comprises at least one of a decreased second session frequency relative to the session frequency, a decreased second session duration relative to the session duration, a decreased second pulse amplitude relative to the pulse amplitude, and a decreased second pulse frequency relative to the pulse frequency.

Optionally, when executed, the first plurality of programmatic instructions receives said glucose status data, examines said glucose status data to determine if a rate of increase in a glucose level of the patient is more than 2 mg/dl per minute, and, based on said determination, generates said modulation signal.

Optionally, when executed, the first plurality of programmatic instructions receives said glucose status data, examines said glucose status data to determine if a rate of increase in a glucose level of the patient is more than 2 mg/dl per minute, and, based on said determination, generates said modulation signal, wherein said modulation signal comprises at least one of an increased second session frequency relative to the session frequency, an increased second session duration relative to the session duration, an increased second pulse amplitude relative to the pulse amplitude, and an increased second pulse frequency relative to the pulse frequency.

Optionally, the second plurality of stimulation parameters are selected such that, after applying a stimulation session defined by the second plurality of stimulation parameters, a glucose level of the patient is reduced by 20 mg/dl.

Optionally, the second plurality of stimulation parameters are selected such that, after applying a stimulation session defined by the second plurality of stimulation parameters, a level of hemoglobin A1C in the patient decreases by at least 1% relative to the patient's level of hemoglobin A1C prior to applying the stimulation session.

Optionally, the second plurality of stimulation parameters are selected such that, after applying a stimulation session defined by the second plurality of stimulation parameters, a hepatic gluconeogenesis of said patient is lowered by at least 1% relative to the hepatic gluconeogenesis prior to applying the stimulation session.

Optionally, the second plurality of stimulation parameters are selected such that, after applying a stimulation session defined by the second plurality of stimulation parameters, a degree of insulin resistance of the patient improves by at least 1% relative to the patient's degree of insulin resistance prior to applying the stimulation session.

Optionally, the second plurality of stimulation parameters are selected such that, after applying a stimulation session defined by the second plurality of stimulation parameters, a level of glucose homeostasis of the patient improves by at least 1% relative to the patient's glucose homeostasis prior to applying said stimulation session.

Optionally, the second plurality of stimulation parameters are selected such that, after applying a stimulation session defined by the second plurality of stimulation parameters, a level of HOMA-IR of the patient decreases by at least 4% compared to a level of HOMA-IR prior to applying said stimulation session.

In some embodiments, the present specification discloses a system to generate real-time interventions in response to a patient's degree of appetite, comprising: an electrical dermal patch comprising a housing, a controller positioned within the housing, at least one electrode positioned within the housing and adapted to be in electrical contact with the patient's skin, a pulse generator positioned within the housing and in electrical communication with the controller and said at least one electrode, wherein the pulse generator is configured to generate a plurality of stimulation sessions comprising a plurality of electrical pulses defined by stimulation parameters, wherein said stimulation parameters comprise a pulse width in a range of 10 μsec to 10 msec, a pulse amplitude in a range of 100 μA to 100 mA, and a pulse frequency in a range of 1 Hz and 100 Hz; a first plurality of programmatic instructions stored in a non-transient memory in a client device separate from the electrical dermal patch, wherein, when executed, said first plurality of programmatic instructions communicates with said electrical dermal patch, prompts the patient to input data indicative of the patient's degree of appetite via a microphone or display of said client device, and transmits said data indicative of the patient's degree of appetite to at least one server; and a second plurality of programmatic instructions stored in a non-transient memory in said at least one server, wherein, when executed, said second plurality of programmatic instructions receives the data indicative of the patient's degree of appetite, processes the data indicative of the patient's degree of appetite to determine if the patient's degree of appetite falls between a first threshold value and a second threshold value or between the second threshold value and a third threshold value, wherein each of the first threshold value, second threshold value, and third threshold value are different, causes a first intervention to be transmitted to the client device if the patient's degree of appetite falls between the first threshold value and the second threshold value and causes a second intervention to be transmitted to the client device if the patient's degree of appetite falls between the second threshold value and the third threshold value, wherein the first intervention is different from the second intervention and wherein each of the first intervention and second intervention is transmitted from the at least one server to the client device and presented to the patient via said client device.

Optionally, when executed, said first plurality of programmatic instructions generates a visual prompt in a form of a visual analog scale and causes said visual prompt to be displayed on the client device, wherein each value along said visual analog scale is representative of a different degree of appetite.

Optionally, when executed, said first plurality of programmatic instructions transmits to said electrical dermal patch a signal in response to said data indicative of the patient's degree of appetite.

Optionally, when executed, said first plurality of programmatic instructions generates a visual prompt in a form of a plurality of icons and causes said visual prompt to be displayed on the client device, wherein each of said plurality of icons is representative of a different degree of appetite.

Optionally, when executed, said first plurality of programmatic instructions generates a plurality of auditory inquires and causes said plurality of auditory inquiries to be played via a speaker of said client device.

Optionally, the first intervention comprises at least one of graphics, text, audio, and video and wherein said at least one of graphics, text, audio, and video comprises coaching instructions to assist the patient in achieving dietary compliance.

Optionally, the second intervention comprises at least one of graphics, text, audio, and video and wherein said at least one of graphics, text, audio, and video comprises messages from individuals who are connected with the patient within a social network.

Optionally, when executed, the second plurality of programmatic instructions processes the data indicative of the patient's degree of appetite to determine if the patient's degree of appetite falls between the third threshold value and a fourth threshold value, wherein the fourth threshold value is different than the first threshold value, the second threshold value, and the third threshold value and causes a third intervention to be transmitted to the client device if the patient's degree of appetite falls between the third threshold value and the fourth threshold value; wherein the third intervention is different from the first and second interventions and wherein the third intervention is transmitted from the at least one server to the client device and presented to the patient via said display.

Optionally, the first intervention comprises at least one of graphics, text, audio, and video and wherein said at least one of graphics, text, audio, and video comprises data indicative of the patient's appetite profile.

Optionally, the second intervention comprises at least one of graphics, text, audio, and video and wherein said at least one of graphics, text, audio, and video comprises a pre-recorded message from an individual who is connected with the patient within a social network.

Optionally, the third intervention comprises at least one of graphics, text, audio, and video and wherein said at least one of graphics, text, audio, and video comprises a real-time message from an individual who is connected with the patient within a social network.

Optionally, when executed, at least one of the first plurality of programmatic instructions and the second plurality of programmatic instructions receives a weight trend of the patient and a plurality of values indicative of the patient's historical degrees of appetite, determines a composite score of the patient, wherein said composite score is a function of the patient's historical degrees of appetite and weight trend, and causes said composite score to be displayed on the client device.

Optionally, when executed, at least one of the first plurality of programmatic instructions and the second plurality of programmatic instructions transmits said composite score to an online affinity group, wherein the patient is a member of said online affinity group.

Optionally, when executed, at least one of the first plurality of programmatic instructions and the second plurality of programmatic instructions receives a composite score of a member of an online affinity group, wherein said composite score of the member is a function of the member's historical appetite scores and weight trends and causes said composite score of the member to be displayed on the client device.

Optionally, when executed, at least one of the first plurality of programmatic instructions and the second plurality of programmatic instructions receives a weight trend of the patient, a plurality of values indicative of the patient's historical degrees of appetite, a plurality of values indicative of the patient's historical amount of exercise and a plurality of values indicative of the patient's historical well-being, determines a composite score of the patient, wherein said composite score is a function of the patient's historical degrees of appetite, weight trend, historical well-being, and historical amount of exercise, and causes said composite score to be displayed on the client device.

In some embodiments, the present specification discloses a system to generate real-time interventions in response to a patient's degree of appetite, comprising: an electrical dermal patch comprising a housing, a controller positioned within the housing, at least one electrode positioned within the housing and adapted to be in electrical contact with the patient's skin, a pulse generator positioned within the housing and in electrical communication with the controller and said at least one electrode, wherein the pulse generator is configured to generate a plurality of stimulation sessions comprising a plurality of electrical pulses defined by stimulation parameters, wherein said stimulation parameters comprise a pulse width in a range of 10 μsec to 10 msec, a pulse amplitude in a range of 100 μA to 100 mA, and a pulse frequency in a range of 1 Hz and 100 Hz; a first plurality of programmatic instructions stored in a non-transient memory in a client device separate from the electrical dermal patch, wherein, when executed, said first plurality of programmatic instructions communicates with said electrical dermal patch, prompts the patient to input data indicative of the patient's degree of appetite via a microphone or display of said client device, and transmits said data indicative of the patient's degree of appetite to at least one server; and a second plurality of programmatic instructions stored in a non-transient memory in said at least one server, wherein, when executed, said second plurality of programmatic instructions receives the data indicative of the patient's degree of appetite, processes the data indicative of the patient's degree of appetite to determine if the patient's degree of appetite is above or below a threshold value, does not cause any intervention to be transmitted to the client device if the patient's degree of appetite falls below the threshold value and causes a first intervention to be transmitted to the client device if the patient's degree of appetite is above the threshold value.

Optionally, when executed, at least one of the first plurality of programmatic instructions and second plurality of programmatic instructions processes the data indicative of the patient's degree of appetite to determine when, at a future time, said patient will be hungry.

Optionally, when executed, the first plurality of programmatic instructions transmits a signal to the electrical dermal patch positioned on the patient's skin based upon said future time.

Optionally, when executed, said first plurality of programmatic instructions generates a visual prompt in a form of a visual analog scale, wherein each value along said visual analog scale is representative of a different degree of appetite.

Optionally, the visual prompt is a light bar having a sliding scale, wherein one end of the sliding scale is indicative of a low degree of appetite and a second end of the sliding scale is indicative of a high degree of appetite.

Optionally, when executed, said first plurality of programmatic instructions transmits to said electrical dermal patch a signal in response to data indicative of said high degree of appetite.

Optionally, when executed, said first plurality of programmatic instructions generate a visual prompt in a form of a plurality of icons and wherein each of said plurality of icons is representative of a different degree of appetite.

Optionally, when executed, said first plurality of programmatic instructions generates a plurality of auditory inquires, via a speaker of said client device, to prompt a user to verbally respond with said data indicative of the patient's degree of appetite.

Optionally, the first intervention comprises at least one of graphics, text, audio, and video and wherein said at least one of graphics, text, audio, and video comprises coaching instructions to assist the patient in achieving dietary compliance.

Optionally, the first intervention comprises at least one of graphics, text, audio, and video and wherein said at least one of graphics, text, audio, and video comprises a pre-recorded message from an individual who is connected with the patient within a social network.

Optionally, the first intervention comprises at least one of graphics, text, audio, and video and wherein said at least one of graphics, text, audio, and video comprises a real-time message from an individual who is connected with the patient within a social network.

Optionally, when executed, at least one of the first plurality of programmatic instructions and the second plurality of programmatic instructions receives a weight trend of the patient and a plurality of values indicative of the patient's historical degrees of appetite, determines a composite score of the patient, wherein said composite score is a function of the patient's historical degrees of appetite and weight trend, and causes said composite score to be displayed on the client device.

Optionally, when executed, at least one of the first plurality of programmatic instructions and the second plurality of programmatic instructions transmits said composite score to an online affinity group, wherein the patient is a member of said online affinity group.

Optionally, when executed, at least one of the first plurality of programmatic instructions and the second plurality of programmatic instructions receives a composite score of a member of an online affinity group, wherein said composite score of the member is a function of the member's historical appetite scores and weight trends and causes said composite score of the member to be displayed on the client device.

Optionally, when executed, at least one of the first plurality of programmatic instructions and the second plurality of programmatic instructions receives a weight trend of the patient, a plurality of values indicative of the patient's historical degrees of appetite, a plurality of values indicative of the patient's historical amount of exercise and a plurality of values indicative of the patient's historical well-being, determines a composite score of the patient, wherein said composite score is a function of the patient's historical degrees of appetite, weight trend, historical well-being, and historical amount of exercise, and causes said composite score to be displayed on the client device.

In some embodiments, the present specification discloses a method of enabling a patient to achieve a weight loss objective, comprising: providing the patient with an electrical dermal patch comprising a housing, an electrical pulse generator positioned within the housing, and at least one electrode attached to said housing and in electrical communication with the electrical pulse generator, wherein said electrical pulse generator is configured to deliver electrical pulses having a pulse amplitude in a range of 5 mA to 45 mA; instructing the patient to secure the electrical dermal patch to the patient's skin; applying a plurality of stimulation sessions to the patient's skin using said electrical dermal patch over a duration of one week, wherein each of the plurality of stimulation sessions comprises said electrical pulses, wherein at least some of the plurality of stimulation sessions have a duration of at least 15 minutes, and wherein the plurality of stimulation sessions comprises at least one in said week; and instructing the patient to repeatedly apply said plurality of stimulation sessions until said weight loss objective is achieved.

Optionally, each of said electrical pulses is defined by a plurality of stimulation parameters and wherein said plurality of stimulation parameters comprises a pulse width in a range of 10 μsec to 10 msec and a pulse frequency in a range of 1 Hz and 100 Hz.

Optionally, a total energy delivered by the plurality of stimulation sessions applied over said one week is not less than 0.25 joules.

Optionally, the plurality of stimulation sessions comprises at least two in said week and wherein each of said two stimulation sessions occurs on different days of said week.

Optionally, a total energy delivered by one of said plurality of stimulation sessions does not exceed 6 joules.

Optionally, the plurality of stimulation sessions comprises at least seven in said week and wherein each of said seven stimulation sessions occurs on different days of said week.

Optionally, a first of said plurality of stimulation sessions is separated from a second of said plurality of stimulation sessions by an amount of time equal to or greater than one quarter of a duration of the second of said plurality of stimulation sessions.

Optionally, the method further comprises instructing the patient to repeatedly apply said plurality of stimulation sessions over a minimum of four weeks.

Optionally, the method further comprises causing the patient to lose a minimum of two pounds over said minimum of four weeks.

Optionally, the method further comprises instructing the patient to repeatedly apply said plurality of stimulation sessions over a minimum of four weeks and causing the patient to lose an amount of weight over said minimum of four weeks such that the patient maintains a loss of at least 90% of said amount of weight lost for at least 30 days after applying a last of said plurality of stimulation sessions.

Optionally, the method further comprises applying at least three of said plurality of stimulation sessions to the patient's skin each day using said electrical dermal patch, wherein each of the three of said plurality of stimulation sessions occurs on different days of said week, wherein said plurality of stimulation parameters, including said pulse width, said pulse frequency, and said pulse amplitude, are set such that an antral activity of the patient is slowed from a first level to a second level after applying at least one of said three of said plurality of stimulation sessions and wherein said second level of antral activity is maintained for at least 1 hour after applying a last of said plurality of stimulation sessions.

Optionally, the method further comprises generating, via the electrical dermal patch, at least one of a visual, auditory, and vibratory signal to the patient within 30 minutes before initiating one of said plurality of stimulation sessions.

Optionally, the method further comprises instructing the patient to manually trigger at least one of the plurality of stimulation sessions by generating at least one of a visual, auditory and vibratory signal using the electrical dermal patch within 30 minutes before initiating one of said plurality of stimulation sessions.

Optionally, the method further comprises instructing the patient to secure the electrical dermal patch to the patient's skin by generating at least one of a visual, auditory, and vibratory signal using the electrical dermal patch within 60 minutes before initiating one of said plurality of stimulation sessions.

Optionally, the method further comprises instructing the patient to secure the electrical dermal patch to the patient's skin by generating at least one of a visual, auditory, and vibratory signal using the electrical dermal patch within 60 minutes after initiating a wake up alarm.

In some embodiments, the present specification discloses a method of enabling a patient to achieve a weight loss objective, comprising: providing the patient with an electrical dermal patch comprising a housing, an electrical pulse generator positioned within the housing, and at least one electrode attached to said housing and in electrical communication with the electrical pulse generator, wherein said electrical pulse generator is configured to deliver electrical pulses having a pulse amplitude in a range of 5 mA to 45 mA, a pulse width in a range of 10 μsec to 10 msec, and a pulse frequency in a range of 1 Hz and 100 Hz; instructing the patient to secure the electrical dermal patch to the patient's skin; applying a plurality of stimulation sessions to the patient's skin using said electrical dermal patch over a duration of one week, wherein each of the plurality of stimulation sessions comprises said electrical pulses and has a duration of at least 15 minutes and wherein the plurality of stimulation sessions comprises at least two in said week occurring on different days of the week; and instructing the patient to repeatedly apply said plurality of stimulation sessions for a minimum of four weeks.

Optionally, said electrical dermal patch is programmed to apply at least a portion of said plurality of stimulation sessions between 6 am and 9 am, between 11 am and 2 pm or between 5 pm and 9 pm.

Optionally, a total energy delivered by the plurality of stimulation sessions applied over said one week is not less than 0.5 joules.

Optionally, a total energy delivered by one of said plurality of stimulation sessions does not exceed 6 joules.

Optionally, each of said plurality of stimulation sessions is separated from a subsequent one of said plurality of stimulation sessions by an amount of time equal to or greater than 25% of a duration of the subsequent one of said plurality of stimulation sessions.

Optionally, the method further comprises causing the patient to lose a minimum of two pounds over said minimum of four weeks.

Optionally, the method further comprises instructing the patient to repeatedly apply said plurality of stimulation sessions over a minimum of four weeks and causing the patient to lose an amount of weight over said minimum of four weeks such that the patient maintains a loss of at least 90% of said amount of weight lost for at least 30 days after applying a last of said plurality of stimulation sessions.

Optionally, the method further comprises applying at least two of said plurality of stimulation sessions to the patient's skin each day using said electrical dermal patch.

Optionally, the method further comprises generating, via the electrical dermal patch, at least one of a visual, auditory and vibratory signal to the patient within 30 minutes before initiating one of said plurality of stimulation sessions.

Optionally, the method further comprises instructing the patient to manually trigger at least one of the plurality of stimulation sessions by generating at least one of a visual, auditory and vibratory signal using the electrical dermal patch within 30 minutes before initiating one of said plurality of stimulation sessions.

Optionally, the method further comprises instructing the patient to secure the electrical dermal patch to the patient's skin by generating at least one of a visual, auditory and vibratory signal using the electrical dermal patch within 60 minutes before initiating one of said plurality of stimulation sessions.

In some embodiments, the present specification discloses a method of enabling a patient to achieve a weight loss objective, comprising: providing the patient with an electrical dermal patch comprising a housing, an electrical pulse generator positioned within the housing, and at least one electrode attached to said housing and in electrical communication with the electrical pulse generator, wherein said electrical pulse generator is configured to deliver electrical pulses having a pulse amplitude in a range of 5 mA to 45 mA, a pulse width in a range of 10 μsec to 10 msec, and a pulse frequency in a range of 1 Hz and 100 Hz; instructing the patient to secure the electrical dermal patch to the patient's skin on at least one of the patient's C5, C6, C7, C8, T1, T2, T3, T4, T5, T6, T7, T8, T9, T10, T11, and T12 frontal and lateral dermatomes; applying a plurality of stimulation sessions to the patient's skin using said electrical dermal patch over a duration of one week, wherein each of the plurality of stimulation sessions comprises said electrical pulses, wherein at least some of the plurality of stimulation sessions have a duration of at least 15 minutes, wherein the plurality of stimulation sessions comprises at least one in said week, and wherein a total energy delivered by any one of the plurality of stimulation sessions does not exceed 6 joules and a total energy delivered by all of the plurality of stimulation sessions applied over said one week is not less than 0.5 joules; and instructing the patient to repeatedly apply said plurality of stimulation sessions for a minimum of four weeks.

Optionally, said electrical dermal patch is programmed to apply at least a portion of said plurality of stimulation sessions between 6 am and 9 am, between 11 am and 2 pm or between 5 pm and 9 pm.

Optionally, the method further comprises applying at least two of said plurality of stimulation sessions to the patient's skin on different days of said week using said electrical dermal patch and wherein each of said at least two of said plurality of stimulation sessions has a duration of at least 15 minutes.

Optionally, the method further comprises generating, via the electrical dermal patch, at least one of a visual, auditory, and vibratory signal to the patient within 30 minutes before initiating one of said plurality of stimulation sessions.

Optionally, the method further comprises instructing the patient to manually trigger at least one of the plurality of stimulation sessions by generating at least one of a visual, auditory, and vibratory signal to the patient within 30 minutes before initiating one of said plurality of stimulation sessions.

Optionally, the method further comprises instructing the patient to secure the electrical dermal patch to the patient's skin by generating at least one of a visual, auditory, and vibratory signal to the patient within 60 minutes before initiating one of said plurality of stimulation sessions.

Optionally, none of said plurality of stimulation sessions applied to the patient's skin over said week has a duration for more than 12 hours and has said pulse amplitude greater than 45 mAmps.

In some embodiments, the present specification discloses an electrical dermal patch configured to cause a delay in emptying of a patient's stomach contents, comprising: a housing having a base surface, wherein said base surface is defined by a total base surface area epidermis; a controller positioned within the housing; at least one electrode having a base surface and attached to the base surface of said housing, wherein the base surface of the at least one electrode is adapted to be in electrical contact with said patient's epidermis and wherein at least one of the base surface of the at least one electrode and the base surface of the housing is adapted to be adhered to an epidermis of the patient; and a pulse generator positioned within the housing and in electrical communication with the controller and said at least one electrode, wherein the pulse generator is configured to generate a plurality of stimulation sessions, wherein each of said plurality of stimulation sessions comprises a plurality of electrical pulses and wherein each of said plurality of electrical pulses is defined by a plurality of stimulation parameters, said plurality of stimulation parameters being defined such that, after applying at least one of said plurality of stimulation sessions to the epidermis of the patient within 90 minutes of said patient consuming a meal, a post-prandial time to empty 50% of the patient's stomach contents increases by at least 5% relative to a post-prandial time to empty 50% of the patient's stomach contents without applying at least one of said plurality of stimulation sessions.

Optionally, said electrical dermal patch is adapted to be adhered to the epidermis of the patient such that an electrical field, generated by said plurality of stimulation sessions, directly contacts at least one of the patient's C5, C6, C7, C8, T1, T2, T3, T4, T5, T6, T7, T8, T9, T10, T11, and T12 frontal and lateral dermatomes, does not directly contact the patient's gastrointestinal tract, does not directly contact the patient's vagus nerve, and penetrates a range of 0.1 mm to 25 mm through the patient's epidermis.

Optionally, the base surface of the housing is not configured to be adhered to the patient's epidermis and is positioned less than 4 mm above the patient's epidermis and wherein the base surface of the at least one electrode is configured to be adhered to the patient's epidermis and has a maximum surface area contacting said epidermis of 10 in$^2$.

Optionally, the electrical dermal patch further comprises a second electrode and wherein the at least one electrode and second electrode are separated by a distance of less than 20 mm and wherein the housing, the at least one electrode, and the second electrode, in combination, have a height not exceeding 1 inch.

Optionally, said plurality of stimulation parameters are further defined such that each of said plurality of electrical pulses has a pulse width of less than 1 ms and wherein the at least one electrode is a foam electrode or a hydrocolloid electrode.

Optionally, said plurality of stimulation parameters are further defined such that, after applying at least one of said plurality of stimulation sessions to the epidermis of the patient within 90 minutes of said patient consuming the meal, the post-prandial time to empty 95% of the patient's stomach contents increases by at least 5% relative to the post-prandial time to empty 95% of the patient's stomach contents without applying at least one of said plurality of stimulation sessions.

Optionally, the electrical dermal patch further comprises a transceiver in communication with at least one of said controller and pulse generator and a plurality of programmatic instructions, stored in a non-transient computer readable memory of a device physically separate from said electrical dermal patch, wherein, when executed, said programmatic instructions acquire patient status data, generate a modulation signal based upon said patient status data, and wirelessly transmit said modulation signal from the device to the transceiver, wherein said modulation signal comprises data for modulating at least one of said plurality of stimulation parameters.

Optionally, said patient status data comprises at least one of the patient's hunger, the patient's hunger appetite, the patient's satiety level, the patient's satiation level, and a degree of well-being being experienced by the patient.

Optionally, said plurality of stimulation parameters are further defined such that, after applying at least one of said plurality of stimulation sessions to the epidermis of the patient, the patient's appetite or hunger decreases relative to the patient's appetite or hunger before applying said at least one of said plurality of stimulation sessions.

Optionally, said plurality of stimulation parameters are further defined such that, after applying at least one of said plurality of stimulation sessions to the epidermis of the patient, the patient's gastric retention increases by 5% relative to the patient's gastric retention before applying said at least one of said plurality of stimulation sessions.

Optionally, said plurality of stimulation parameters are further defined such that, after applying at least one of said plurality of stimulation sessions to the epidermis of the patient, the patient's postprandial plasma glucose concentration decreases by at least 5% relative to the patient's postprandial plasma glucose concentration without applying said at least one of said plurality of stimulation sessions.

In some embodiments, the present specification discloses an electrical dermal patch configured to cause a delay in gastric emptying of a patient having a body mass index of at least 25 comprising: a housing having a base surface, wherein said base surface is defined by a total base surface area; a controller positioned within the housing; at least one electrode having a base surface and attached to the base surface of said housing, wherein the base surface of the at least one electrode is adapted to be in electrical contact with said patient's epidermis and wherein at least one of the base surface of the at least one electrode and the base surface of the housing is adapted to be adhered to an epidermis of the patient; and a pulse generator positioned within the housing and in electrical communication with the controller and said at least one electrode, wherein the pulse generator is configured to generate a plurality of stimulation sessions, wherein each of said plurality of stimulation sessions comprises a plurality of electrical pulses and wherein each of said plurality of electrical pulses is defined by a plurality of stimulation parameters, said plurality of stimulation parameters being defined such that, after applying at least one of said plurality of stimulation sessions for at least 5 minutes to the epidermis of the patient within 90 minutes of said patient consuming a meal, a post-prandial time to empty 50% of the patient's stomach contents increases by at least 5 minutes relative to a post-prandial time to empty 50% of the patient's stomach contents without applying at least one of said plurality of stimulation sessions.

Optionally, said electrical dermal patch is adapted to be adhered to the epidermis of the patient such that an electrical field, generated by said plurality of stimulation sessions, directly contacts at least one of the patient's C5, C6, C7, C8, T1, T2, T3, T4, T5, T6, T7, T8, T9, T10, T11, and T12 frontal and lateral dermatomes, does not directly contact the patient's gastrointestinal tract, does not directly contact the patient's vagus nerve, and penetrates no more than 25 mm through the patient's epidermis.

Optionally, the base surface of the housing is not configured to be adhered to the patient's epidermis and is positioned less than 4 mm above the patient's epidermis and wherein the base surface of the at least one electrode is configured to be adhered to the patient's epidermis and has a maximum surface area contacting said epidermis of 10 in$^2$.

Optionally, the electrical dermal patch further comprises a second electrode and wherein the at least one electrode and second electrode are separated by a distance of less than 10 mm and wherein the housing, the at least one electrode, and the second electrode, in combination, have a height not exceeding 1 inch.

Optionally, the electrical dermal patch has a volume in a range from 0.10 in$^3$ to 0.5 in$^3$, a weight in a range from 10 grams to 80 grams, and a ratio of a surface area of the base surface of the at least one electrode to said weight in a range of 0.1 to 0.8 in$^2$ per gram weight of the electrical dermal patch.

Optionally, said plurality of stimulation parameters are further defined such that, after applying at least one of said plurality of stimulation sessions for at least 5 minutes to the epidermis of the patient within 90 minutes of said patient consuming the meal, the post-prandial time to empty 95% of the patient's stomach contents increases by at least 5 minutes relative to the post-prandial time to empty 95% of the patient's stomach contents without applying at least one of said plurality of stimulation sessions.

Optionally, the electrical dermal patch further comprises a transceiver in communication with at least one of said controller and pulse generator and a plurality of programmatic instructions, stored in a non-transient computer readable memory of a device physically separate from said electrical dermal patch, wherein, when executed, said programmatic instructions acquire patient status data, generate a modulation signal based upon said patient status data, and wirelessly transmit said modulation signal from the device to the transceiver, wherein said modulation signal comprises data for modulating at least one of said plurality of stimulation parameters.

Optionally, said patient status data comprises at least one of the patient's hunger, the patient's hunger appetite, the patient's satiety level, the patient's satiation level, and a degree of well-being being experienced by the patient.

Optionally, said plurality of stimulation parameters are further defined such that, after applying at least one of said plurality of stimulation sessions to the epidermis of the patient, the patient's appetite or hunger decreases relative to the patient's appetite or hunger before applying said at least one of said plurality of stimulation sessions and a nausea level of the patient does not increase relative to the patient's nausea level before applying said at least one of said plurality of stimulation sessions.

Optionally, said plurality of stimulation parameters are further defined such that, after applying at least one of said plurality of stimulation sessions to the epidermis of the patient, the patient's gastric retention increases by 5% relative to the patient's gastric retention before applying said at least one of said plurality of stimulation sessions.

Optionally, the electrical dermal patch further comprises an adhesive layer positioned a base surface of the at least one electrode and wherein, when the adhesive layer of the electrical dermal patch is configured to be adhered to the patient's epidermis, the electrical dermal patch has a peel strength in a range of 1.0 to 2.1 newtons.

Optionally, said plurality of stimulation parameters are further defined such that, after applying at least one of said plurality of stimulation sessions to the epidermis of the patient, a body weight of the patient reduces by at least 1% relative to a body weight of the patient before applying said at least one of said plurality of stimulation sessions.

Optionally, when executed, said programmatic instructions acquire a first stimulation protocol and use said first stimulation protocol to generate the modulation signal. Still optionally, when executed, said programmatic instructions acquire a second stimulation protocol, wherein said second stimulation protocol is different from the first stimulation protocol, and, using said second stimulation protocol, generate a second modulation signal, wherein said second modulation signal comprises data for modulating at least one of the plurality of stimulation parameters.

Optionally, the plurality of stimulation parameters comprise a first pulse width, a first pulse amplitude, a first pulse frequency, a first pulse shape, a first duty cycle, a first session duration, and a first session frequency, wherein the electrical dermal patch is configured to use the second modulation signal to modify at least one of the first pulse width, the first pulse amplitude, the first pulse frequency, the first pulse shape, the first duty cycle, the first session duration, and the first session frequency to yield a second pulse width, a second pulse amplitude, a second pulse frequency, a second pulse shape, a second duty cycle, a second session duration, or a second session frequency, and wherein at least one of the second pulse width is different from the first pulse width, the second pulse amplitude is different from the first pulse amplitude, the second pulse frequency is different from the first pulse frequency, the second pulse shape is different from the first pulse shape, the second duty cycle is different from the first duty cycle, the second session duration is different from the first session duration, and the second session frequency is different from the first session frequency.

In some embodiments, the present specification discloses an electrical dermal patch configured to cause a delay in gastric emptying of a patient comprising: a housing; a controller positioned within the housing; at least one electrode attached to said housing and adapted to be in electrical contact with said patient's epidermis, wherein the at least one electrode has a base surface defined by a total base surface area, wherein at least a portion of said total base surface area is adapted to be adhered to an epidermis of the patient, wherein said portion of the total base surface area adapted to be adhered to the epidermis of the patient is no greater than 10 in$^2$, and wherein said portion of the total base surface area is adapted to be adhered to the epidermis of the patient such that an electrical field, generated by a plurality of stimulation sessions, directly contacts at least one of the patient's C5, C6, C7, C8, T1, T2, T3, T4, T5, T6, T7, T8, T9, T10, T11, and T12 frontal and lateral dermatomes; and a pulse generator positioned within the housing and in electrical communication with the controller and said at least one electrode, wherein the pulse generator is configured to generate said plurality of stimulation sessions, wherein each of said plurality of stimulation sessions comprises a plurality of electrical pulses and wherein each of said plurality of electrical pulses is defined by a plurality of stimulation parameters, said plurality of stimulation parameters being defined such that, after applying at least one of said plurality of stimulation sessions for at least 5 minutes to the epidermis of the patient within 90 minutes of said patient consuming a meal, a post-prandial time to empty 50% of the patient's stomach contents increases by at least 5% relative to a post-prandial time to empty 50% of the patient's stomach contents without applying at least one of said plurality of stimulation sessions.

Optionally, the electrical dermal patch further comprises a transceiver in communication with at least one of said controller and pulse generator and a plurality of programmatic instructions, stored in a non-transient computer readable memory of a device physically separate from said electrical dermal patch, wherein, when executed, said programmatic instructions acquire patient status data, generate a modulation signal based upon said patient status data, and wirelessly transmit said modulation signal from the device to the transceiver, wherein said modulation signal comprises data for modulating at least one of said plurality of stimulation parameters.

Optionally, said patient status data comprises at least one of the patient's hunger, the patient's hunger appetite, the patient's satiety level, the patient's satiation level, and a degree of well-being being experienced by the patient.

Optionally, said plurality of stimulation parameters are further defined such that, after applying at least one of said plurality of stimulation sessions to the epidermis of the patient, the patient's gastric retention increases by 5% relative to the patient's gastric retention before applying said at least one of said plurality of stimulation sessions.

In some embodiments, the present specification discloses a method of modulating at least one of a patient's appetite, hunger, satiety level, or satiation level comprising: providing an electrical dermal patch adapted to adhere to the patient's epidermal layer, wherein said electrical dermal patch comprises a controller, at least one electrode adapted to be in electrical contact with said patient's epidermal layer, and a pulse generator in electrical communication with the controller and said at least one electrode; defining a plurality of stimulation parameters; and programming the pulse generator to generate a plurality of electrical pulses using said plurality of stimulation parameters, wherein said plurality of stimulation parameters are defined such that, after applying at least one stimulation to the patient's epidermal layer, at least one of the patient's appetite, hunger, satiety level, and satiation level is modified.

Optionally, after applying at least one stimulation to the patient's epidermal layer, the appetite of said patient decreases relative to the appetite of said patient prior to applying at least one stimulation.

Optionally, after applying at least one stimulation to the patient's epidermal layer, the hunger of said patient decreases relative to the hunger of said patient prior to applying at least one stimulation.

Optionally, after applying at least one stimulation to the patient's epidermal layer, the satiety level of said patient increases relative to the satiety level of said patient prior to applying at least one stimulation.

Optionally, after applying at least one stimulation to the patient's epidermal layer, the satiation level of said patient increases relative to the satiation level of said patient prior to applying at least one stimulation.

Optionally, after applying at least one stimulation to the patient's epidermal layer, the fullness level of said patient increases relative to the fullness level of said patient prior to applying at least one stimulation.

Optionally, said plurality of stimulation parameters are defined such that, after applying at least one stimulation to the patient's epidermal layer, the patient's appetite modulates from a first state to a second state, wherein the first state is defined by a pre-stimulation appetite profile comprising a first plurality of quantitative appetite measurements, wherein each of said first plurality of quantitative appetite measurements is determined, prior to stimulation, using a visual analog scale and is taken at different predefined times of day, wherein the second state is defined by a post-stimulation appetite profile comprising a second plurality of quantitative appetite measurements, wherein each of said second plurality of quantitative appetite measurements is determined, after stimulation, using said visual analog scale and is taken at different predefined times of day, and wherein, for a given predefined time of day, at least one of the second plurality of quantitative appetite measurements differs from at least one of the first plurality of quantitative appetite measurements by at least 5%, thereby representing a decrease in appetite of the patient.

Optionally, said plurality of stimulation parameters are defined such that, after applying at least one stimulation to the patient's epidermal layer, the patient's hunger modulates from a first state to a second state, wherein the first state is defined by a pre-stimulation hunger profile comprising a first plurality of quantitative hunger measurements, wherein each of said first plurality of quantitative hunger measurements is determined, prior to stimulation, using a visual analog scale and is taken at different predefined times of day, wherein the second state is defined by a post-stimulation hunger profile comprising a second plurality of quantitative hunger measurements, wherein each of said second plurality of quantitative hunger measurements is determined, after stimulation, using said visual analog scale and is taken at different predefined times of day, and wherein, for a given predefined time of day, at least one of the second plurality of quantitative hunger measurements differs from at least one of the first plurality of quantitative hunger measurements by at least 5%, thereby representing a decrease in hunger of the patient.

Optionally, said plurality of stimulation parameters are defined such that, after applying at least one stimulation to the patient's epidermal layer, the patient's satiety level modulates from a first state to a second state, wherein the first state is defined by a pre-stimulation satiety profile comprising a first plurality of quantitative satiety measurements, wherein each of said first plurality of quantitative satiety measurements is determined, prior to stimulation, using a visual analog scale and is taken at different predefined times of day, wherein the second state is defined by a post-stimulation satiety profile comprising a second plurality of quantitative satiety measurements, wherein each of said second plurality of quantitative satiety measurements is determined, after stimulation, using said visual analog scale and is taken at different predefined times of day, and wherein, for a given predefined time of day, at least one of the second plurality of quantitative satiety measurements differs from at least one of the first plurality of quantitative satiety measurements by at least 5%, thereby representing an increase in the satiety level of the patient.

Optionally, said plurality of stimulation parameters are defined such that, after applying at least one stimulation to the patient's epidermal layer, the patient's satiation level modulates from a first state to a second state, wherein the first state is defined by a pre-stimulation satiation profile comprising a first plurality of quantitative satiation measurements, wherein each of said first plurality of quantitative satiation measurements is determined, prior to stimulation, using a visual analog scale and is taken at different predefined times of day, wherein the second state is defined by a post-stimulation satiation profile comprising a second plurality of quantitative satiation measurements, wherein each of said second plurality of quantitative satiation measurements is determined, after stimulation, using said visual analog scale and is taken at different predefined times of day, and wherein, for a given predefined time of day, at least one of the second plurality of quantitative satiation measurements differs from at least one of the first plurality of quantitative satiation measurements by at least 5%, thereby representing an increase in the satiation level of the patient.

Optionally, said plurality of stimulation parameters are defined such that, after applying at least one stimulation to the patient's epidermal layer, the patient's fullness level modulates from a first state to a second state, wherein the first state is defined by a pre-stimulation fullness profile comprising a first plurality of quantitative fullness measurements, wherein each of said first plurality of quantitative fullness measurements is determined, prior to stimulation, using a visual analog scale and is taken at different predefined times of day, wherein the second state is defined by a post-stimulation fullness profile comprising a second plurality of quantitative fullness measurements, wherein each of said second plurality of quantitative fullness measurements is determined, after stimulation, using said visual analog scale and is taken at different predefined times of day, and wherein, for a given predefined time of day, at least one of the second plurality of quantitative fullness measurements differs from at least one of the first plurality of quantitative fullness measurements by at least 5%, thereby representing an increase in the fullness level of the patient.

Optionally, said plurality of stimulation parameters are defined such that, after applying at least one stimulation to the patient's epidermal layer, the patient's appetite modulates from a first state to a second state, wherein the first state is defined by a pre-stimulation appetite profile comprising a first plurality of quantitative appetite measurements, wherein each of said first plurality of quantitative appetite measurements is determined, prior to stimulation, using a visual analog scale and is taken at different predefined times of day, wherein said first plurality of quantitative appetite measurements collectively define a first area representative of said first state, wherein the second state is defined by a post-stimulation appetite profile comprising a second plurality of quantitative appetite measurements, wherein each of said second plurality of quantitative appetite measurements is determined, after stimulation, using said visual analog scale and is taken at different predefined times of day, wherein said second plurality of quantitative appetite measurements collectively define a second area representative of said second state, and wherein said first area differs from said second area by at least 5%, thereby representing a decrease in the appetite of the patient.

Optionally, said plurality of stimulation parameters are defined such that, after applying at least one stimulation to the patient's epidermal layer, the patient's hunger modulates from a first state to a second state, wherein the first state is defined by a pre-stimulation hunger profile comprising a first plurality of quantitative hunger measurements, wherein each of said first plurality of quantitative hunger measurements is determined, prior to stimulation, using a visual analog scale and is taken at different predefined times of day, wherein said first plurality of quantitative hunger measurements collectively define a first area representative of said first state, wherein the second state is defined by a post-stimulation hunger profile comprising a second plurality of quantitative hunger measurements, wherein each of said second plurality of quantitative hunger measurements is determined, after stimulation, using said visual analog scale and is taken at different predefined times of day, wherein said second plurality of quantitative hunger measurements collectively define a second area representative of said second state, and wherein said first area differs from said second area by at least 5%, thereby representing a decrease in the hunger of the patient.

Optionally, said plurality of stimulation parameters are defined such that, after applying at least one stimulation to the patient's epidermal layer, the patient's satiety level modulates from a first state to a second state, wherein the first state is defined by a pre-stimulation satiety profile comprising a first plurality of quantitative satiety measurements, wherein each of said first plurality of quantitative satiety measurements is determined, prior to stimulation, using a visual analog scale and is taken at different predefined times of day, wherein said first plurality of quantitative satiety measurements collectively define a first area representative of said first state, wherein the second state is defined by a post-stimulation satiety profile comprising a second plurality of quantitative satiety measurements, wherein each of said second plurality of quantitative satiety measurements is determined, after stimulation, using said visual analog scale and is taken at different predefined times of day, wherein said second plurality of quantitative satiety measurements collectively define a second area representative of said second state, and wherein said first area differs from said second area by at least 5%, thereby representing an increase in the satiety level of the patient.

Optionally, said plurality of stimulation parameters are defined such that, after applying at least one stimulation to the patient's epidermal layer, the patient's satiation level modulates from a first state to a second state, wherein the first state is defined by a pre-stimulation satiation profile comprising a first plurality of quantitative satiation measurements, wherein each of said first plurality of quantitative satiation measurements is determined, prior to stimulation, using a visual analog scale and is taken at different predefined times of day, wherein said first plurality of quantitative satiation measurements collectively define a first area representative of said first state, wherein the second state is defined by a post-stimulation satiation profile comprising a second plurality of quantitative satiation measurements, wherein each of said second plurality of quantitative satiation measurements is determined, after stimulation, using said visual analog scale and is taken at different predefined times of day, wherein said second plurality of quantitative satiation measurements collectively define a second area representative of said second state, and wherein said first area differs from said second area by at least 5%, thereby representing an increase in the satiation level of the patient.

Optionally, said plurality of stimulation parameters are defined such that, after applying at least one stimulation to the patient's epidermal layer, the patient's fullness level modulates from a first state to a second state, wherein the first state is defined by a pre-stimulation fullness profile comprising a first plurality of quantitative fullness measurements, wherein each of said first plurality of quantitative fullness measurements is determined, prior to stimulation, using a visual analog scale and is taken at different predefined times of day, wherein said first plurality of quantitative fullness measurements collectively define a first area representative of said first state, wherein the second state is defined by a post-stimulation fullness profile comprising a second plurality of quantitative fullness measurements, wherein each of said second plurality of quantitative fullness measurements is determined, after stimulation, using said visual analog scale and is taken at different predefined times of day, wherein said second plurality of quantitative fullness measurements collectively define a second area representative of said second state, and wherein said first area differs from said second area by at least 5%, thereby representing an increase in the fullness level of the patient.

Optionally, said plurality of stimulation parameters are defined such that, after applying at least one stimulation to the patient's epidermal layer, the patient's appetite modulates from a first state to a second state, wherein the patient's appetite in the second state is decreased relative to the patient's appetite in the first state, wherein said first state appetite is measured using a scale at predefined times of day over a first predefined period of time, wherein said second state appetite is measured, after stimulation is initiated, using said scale at said predefined times of day over a second predefined period of time, equal in duration to the first predefined period of time, and wherein said second state appetite decreases such that it is equal to, or less than, 95% of the first state appetite.

Optionally, said plurality of stimulation parameters are defined such that, after applying at least one stimulation to the patient's epidermal layer, the patient's hunger modulates from a first state to a second state, wherein the patient's hunger in the second state is decreased relative to the patient's hunger in the first state, wherein said first state hunger is measured using a scale at predefined times of day over a first predefined period of time, wherein said second state hunger is measured, after stimulation is initiated, using said scale at said predefined times of day over a second predefined period of time, equal in duration to the first predefined period of time, and wherein said second state hunger decreases such that it is equal to, or less than, 95% of the first state hunger.

Optionally, said plurality of stimulation parameters are defined such that, after applying at least one stimulation to the patient's epidermal layer, the patient's satiety level modulates from a first state to a second state, wherein the patient's satiety level in the second state is increased relative to the patient's satiety level in the first state, wherein said first state satiety level is measured using a scale at predefined times of day over a first predefined period of time, wherein said second state satiety level is measured, after stimulation is initiated, using said scale at said predefined times of day over a second predefined period of time, equal in duration to the first predefined period of time, and wherein said second state satiety level increases such that it is equal to, or greater than, 105% of the first state satiety level.

Optionally, said plurality of stimulation parameters are defined such that, after applying at least one stimulation to the patient's epidermal layer, the patient's satiation level modulates from a first state to a second state, wherein said first state satiation level is measured using a scale at predefined times of day over a first predefined period of time, wherein said second state satiation level is measured, after stimulation is initiated, using said scale at said predefined times of day over a second predefined period of time, equal in duration to the first predefined period of time, and wherein said second state satiation level increases such that it is equal to, or greater than, 105% of the first state satiation level.

Optionally, said plurality of stimulation parameters are defined such that, after applying at least one stimulation to the patient's epidermal layer, the patient's fullness level modulates from a first state to a second state, wherein said first state fullness level is measured using a scale at predefined times of day over a first predefined period of time, wherein said second state fullness level is measured, after stimulation is initiated, using said scale at said predefined times of day over a second predefined period of time, equal in duration to the first predefined period of time, and wherein said second state fullness level increases such that it is equal to, or greater than, 105% of the first state fullness level.

Optionally, said plurality of stimulation parameters are further selected such that, after at least one stimulation, an amount of the patient's antral motility reduces relative to the patient's antral motility before stimulation.

Optionally, said plurality of stimulation parameters are further selected such that, after at least one stimulation, an amount of the patient's gastric motility reduces relative to the patient's gastric motility before stimulation.

Optionally, said plurality of stimulation parameters are further selected such that, after at least one stimulation, a rate of the patient's gastric emptying reduces relative to a rate of the patient's gastric emptying before stimulation.

Optionally, said plurality of stimulation parameters are further selected such that, after at least one stimulation, the patient's appetite decreases, over a predefined period of time, relative to the patient's appetite before stimulation and a nausea level of the patient does not increase, over said predefined period of time, relative to a nausea level of the patient before stimulation.

Optionally, said plurality of stimulation parameters are further selected such that, after at least one stimulation, the patient's hunger decreases, over a predefined period of time, relative to the patient's hunger before stimulation and a nausea level of the patient does not increase, over said predefined period of time, relative to a nausea level of the patient before stimulation.

Optionally, said plurality of stimulation parameters are further selected such that, after at least one stimulation, the patient's satiety level increases, over a predefined period of time, relative to the patient's satiety level before stimulation and a nausea level of the patient does not increase, over said predefined period of time, relative to a nausea level of the patient before stimulation.

Optionally, said plurality of stimulation parameters are further selected such that, after at least one stimulation, the patient's satiation level increases, over a predefined period of time, relative to the patient's satiation level before stimulation and a nausea level of the patient does not increase, over said predefined period of time, relative to a nausea level of the patient before stimulation.

Optionally, said plurality of stimulation parameters are further selected such that, after at least one stimulation, the patient's fullness level increases, over a predefined period of time, relative to the patient's fullness level before stimulation and a nausea level of the patient does not increase, over said predefined period of time, relative to a nausea level of the patient before stimulation.

Optionally, said plurality of stimulation parameters are further selected such that, after at least one stimulation, the patient's appetite decreases, over a predefined period of time, relative to the patient's appetite before stimulation, wherein at least one of a dyspepsia level of the patient or a nausea level of the patient does not increase, over said predefined period of time, relative to at least one of a dyspepsia level or a nausea level of the patient before stimulation, and wherein said at least one stimulation does not cause the patient to experience a pain sensation.

Optionally, said plurality of stimulation parameters are further selected such that, after at least one stimulation, the patient's hunger decreases, over a predefined period of time, relative to the patient's hunger before stimulation, wherein at least one of a dyspepsia level of the patient or a nausea level of the patient does not increase, over said predefined period of time, relative to at least one of a dyspepsia level or a nausea level of the patient before stimulation, and wherein said at least one stimulation does not cause the patient to experience a pain sensation.

Optionally, said plurality of stimulation parameters are further selected such that, after at least one stimulation, the patient's satiety level increases, over a predefined period of time, relative to the patient's satiety level before stimulation, wherein at least one of a dyspepsia level of the patient or a nausea level of the patient does not increase, over said predefined period of time, relative to at least one of a dyspepsia level or a nausea level of the patient before stimulation, and wherein said at least one stimulation does not cause the patient to experience a pain sensation.

Optionally, said plurality of stimulation parameters are further selected such that, after at least one stimulation, the patient's satiation level increases, over a predefined period of time, relative to the patient's satiation level before stimulation, wherein at least one of a dyspepsia level of the patient or a nausea level of the patient does not increase, over said predefined period of time, relative to at least one of a dyspepsia level or a nausea level of the patient before stimulation, and wherein said at least one stimulation does not cause the patient to experience a pain sensation.

Optionally, said plurality of stimulation parameters are further selected such that, after at least one stimulation, the patient's fullness level increases, over a predefined period of time, relative to the patient's fullness level before stimulation, wherein at least one of a dyspepsia level of the patient or a nausea level of the patient does not increase, over said predefined period of time, relative to at least one of a dyspepsia level or a nausea level of the patient before stimulation, and wherein said at least one stimulation does not cause the patient to experience a pain sensation.

Optionally, said plurality of stimulation parameters are further selected such that, after at least one stimulation, a total body weight of the patient reduces by at least 1% relative to a total body weight of the patient before stimulation.

Optionally, said plurality of stimulation parameters are further selected such that, after at least one stimulation, an excess body weight of the patient reduces by at least 3% relative to an excess body weight of the patient before stimulation.

Optionally, said plurality of stimulation parameters are further selected such that, after at least one stimulation, a total body weight of the patient reduces by at least 1% relative to a total body weight of the patient before stimulation and a well-being level of the patient does not reduce more than 5% relative to a well-being level of the patient before stimulation.

Optionally, said plurality of stimulation parameters are further selected such that, after at least one stimulation, an excess body weight of the patient reduces by at least 3% relative to an excess body weight of the patient before stimulation and a well-being level of the patient does not reduce more than 5% relative to a well-being level of the patient before stimulation.

Optionally, said plurality of stimulation parameters are further selected such that, after at least one stimulation, a pre-prandial ghrelin level of the patient reduces by at least 3% relative to a pre-prandial ghrelin level of the patient before stimulation.

Optionally, said plurality of stimulation parameters are further selected such that, after at least one stimulation, a post-prandial ghrelin level of the patient reduces by at least 3% relative to a post-prandial ghrelin level of the patient before stimulation.

Optionally, said plurality of stimulation parameters are further selected such that, after at least one stimulation session, exercise output of the patient increases by at least 3% relative to the exercise output of the patient before stimulation.

Optionally, said plurality of stimulation parameters are further selected such that, after at least one stimulation, a glucagon-like peptide-1 level of the patient increases by at least 3% relative to a glucagon-like peptide-1 level of the patient before stimulation.

Optionally, said plurality of stimulation parameters are further selected such that, after at least one stimulation, a leptin level of the patient increases by at least 3% relative to a leptin level of the patient before stimulation.

Optionally, said plurality of stimulation parameters are further selected such that, after at least one stimulation, the patient's appetite decreases, over a predefined period of time, relative to the patient's appetite before stimulation and a nausea level of the patient does not increase by more than 10%, over said predefined period of time, relative to the nausea level of the patient before stimulation.

Optionally, said plurality of stimulation parameters are further selected such that, after at least one stimulation, a peptide YY level of the patient increases by at least 3% relative to a peptide YY level of the patient before stimulation.

Optionally, said plurality of stimulation parameters are further selected such that, after at least one stimulation, a lipopolysaccharide level of the patient reduces by at least 3% relative to a lipopolysaccharide level of the patient before stimulation.

Optionally, said plurality of stimulation parameters are further selected such that, after at least one stimulation, a motilin-related peptide level of the patient reduces by at least 3% relative to a motilin-related peptide level of the patient before stimulation.

Optionally, said plurality of stimulation parameters are further selected such that, after at least one stimulation, a cholecystokinin level of the patient increases by at least 3% relative to a cholecystokinin level of the patient before stimulation.

Optionally, said plurality of stimulation parameters are further selected such that, after at least one stimulation, a resting metabolic rate of the patient increases by at least 3% relative to a resting metabolic rate of the patient before stimulation.

Optionally, said plurality of stimulation parameters are further selected such that, after at least one stimulation, a plasma-beta endorphin level of the patient increases by at least 3% relative to a plasma-beta endorphin level of the patient before stimulation.

Optionally, said plurality of stimulation parameters are further selected such that, after at least one stimulation, the patient's hunger decreases, over a predefined period of time, relative to the patient's hunger before stimulation and a nausea level of the patient does not increase by more than 10%, over said predefined period of time, relative to the nausea level of the patient before stimulation.

Optionally, said plurality of stimulation parameters are further selected such that, after at least one stimulation, the patient's glucose homeostasis, or balance of insulin and glucagon, improves by at least 3% relative to the patient's glucose homeostasis before stimulation.

Optionally, said plurality of stimulation parameters are further selected such that, after at least one stimulation, the patient's level of hemoglobin A1c decreases by an amount equal to at least 0.3%.

Optionally, said plurality of stimulation parameters are further selected such that, after at least one stimulation, a triglyceride level of the patient decreases by at least 3% relative to a triglyceride level of the patient before stimulation.

Optionally, said plurality of stimulation parameters are further selected such that, after at least one stimulation, a total blood cholesterol level of the patient decreases by at least 3% relative to a total blood cholesterol level of the patient before stimulation.

Optionally, said plurality of stimulation parameters are further selected such that, after at least one stimulation, a glycemia level of the patient decreases by at least 3% relative to a glycemia level of the patient before stimulation.

Optionally, said plurality of stimulation parameters are further selected such that, after at least one stimulation, a degree of insulin resistance of the patient improves by at least 3% relative to a degree of insulin resistance of the patient before stimulation.

Optionally, said plurality of stimulation parameters are further selected such that, after at least one stimulation, a composition of the patient's gut microbiota modulates from a first state to a second state, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%.

Optionally, said plurality of electrical pulses comprise a pulse width in a range of 10 μsec to 100 msec, a pulse amplitude in a range of 100 μA to 500 mA, and a pulse frequency in a range of 1 Hz to 10,000 Hz.

Optionally, said plurality of electrical pulses comprise a pulse width in a range of 10 μsec to 10 msec and a pulse amplitude in a range of 15 mA to 30 mA.

Optionally, said plurality of electrical pulses comprise a pulse amplitude in a range of 100 μA to 100 mA.

Optionally, said plurality of electrical pulses comprise a pulse width in a range of 10 μsec to 100 msec and a pulse amplitude in a range of 5 mA to 45 mA.

Optionally, said pulse generator generates an electrical field and wherein the electrical field is adapted to penetrate, via the at least one electrode, a range of 0.1 mm to 25 mm through the patient's epidermal layer.

Optionally, said method further comprises: determining a central electrical stimulation reaction threshold for the patient; determining a spinal electrical stimulation reaction threshold for the patient; defining at least a portion of the plurality of stimulation parameters such that at least one of a pulse width, a pulse amplitude, and a pulse frequency is set above the spinal electrical stimulation reaction threshold but below the central electrical stimulation reaction threshold; and generating said plurality of electrical pulses, wherein said plurality of electrical pulses is defined by said pulse width, said pulse amplitude, and said pulse frequency.

Optionally, said method further comprises: determining a maximum tolerable electrical stimulation reaction threshold for the patient; determining a spinal electrical stimulation reaction threshold for the patient; defining at least a portion of the plurality of stimulation parameters such that at least one of a pulse width, a pulse amplitude, and a pulse frequency is set above the spinal electrical stimulation reaction threshold but below the maximum tolerable electrical stimulation reaction threshold; and generating said plurality of electrical pulses, wherein said plurality of electrical pulses is defined by said pulse width, said pulse amplitude, and said pulse frequency.

Optionally, the method further comprises: determining a central electrical stimulation reaction threshold for the patient; defining at least a portion of the plurality of stimulation parameters such that at least one of a pulse width, a pulse amplitude, and a pulse frequency is set below the central electrical stimulation reaction threshold; and generating said plurality of electrical pulses, wherein said plurality of electrical pulses is defined by said pulse width, said pulse amplitude, and said pulse frequency.

Optionally, the method further comprises determining a maximum tolerable electrical stimulation reaction threshold for the patient; defining at least a portion of the plurality of stimulation parameters such that at least one of a pulse width, a pulse amplitude, and a pulse frequency is set below the maximum tolerable electrical stimulation reaction threshold; and generating said plurality of electrical pulses, wherein said plurality of electrical pulses is defined by said pulse width, said pulse amplitude, and said pulse frequency.

Optionally, the method further comprises determining a placement for the electrical dermal patch on the patient by finding a midclavicular line of the patient, progressing downward from the midclavicular line to a bottom rib of a thoracic cage of the patient, moving further downward from the bottom rib to identify a placement spot, and placing a top center portion of the electrical dermal patch at the placement spot.

Optionally, the move further downward from the bottom rib to identify a placement spot is in a range of 1 cm to 6 cm.

Optionally, the method further comprises generating said plurality of electrical pulses such that at least one of the patient's C5, C6, C7, C8, T1, T2, T3, T4, T5, T6, T7, T8, T9, T10, T11, and T12 dermatomes is electrically stimulated.

Optionally, said method further comprises generating said plurality of electrical pulses such that at least one of the patient's C5, C6, C7, C8, T1, T2, T3, T4, T5, T6, T7, T8, T9, T10, T11, and T12 frontal and lateral dermatomes is electrically stimulated while, concurrent thereto, no portion of the patient's C5, C6, C7, C8, T1, T2, T3, T4, T5, T6, T7, T8, T9, T10, T11, and T12 posterior dermatomes is electrically stimulated.

Optionally, said method further comprises generating said plurality of electrical pulses such that at least one of the patient's C5, C6, C7, C8, T1, T2, T3, T4, T5, T6, T7, T8, T9, T10, T11, and T12 frontal and lateral dermatomes is electrically stimulated while, concurrent thereto, no portion of the patient's C5, C6, C7, C8, T1, T2, T3, T4, T5, T6, T7, T8, T9, T10, T11, or T12 posterior dermatomes is electrically stimulated.

Optionally, the method further comprises generating said plurality of electrical pulses such that at least one of the patient's C8 anterior or posterior dermatome located on the patient's hand, wrist, elbow, and fingers, C8 anterior or posterior dermatome located on the patient's arm, C8 dermatome located on the patient's upper trunk, T1 anterior or posterior dermatome located on the patient's arm, T1 anterior or posterior dermatome located on the patient's wrist, elbow, and hand, and T1 anterior or posterior dermatome located on the patient's upper trunk is electrically stimulated.

Optionally, the method further comprises generating said plurality of electrical pulses such that at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, and T10 frontal and lateral thoracic dermatome is electrically stimulated and any one of the patient's T2 posterior thoracic dermatome, T3 posterior thoracic dermatome, T4 posterior thoracic dermatome, T5 posterior thoracic dermatome, T6 posterior thoracic dermatome, T7 posterior thoracic dermatome, T8 posterior thoracic dermatome, T9 posterior thoracic dermatome, and T10 posterior thoracic dermatome is not electrically stimulated.

Optionally, the method further comprises generating said plurality of electrical pulses such that at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, or T10 frontal and lateral thoracic dermatome is electrically stimulated.

Optionally, the method further comprises causing an application to be installed on an external device, wherein said application is configured to acquire patient status data and to prompt, via said application, the patient to input said patient status data; using said application to generate a modulation signal based upon said patient status data, wherein said modulation signal comprises instructions for modulating at least one of the plurality of stimulation parameters, wherein said plurality of stimulation parameters comprise at least one of a pulse width, a pulse amplitude, a pulse frequency, a pulse shape, a duty cycle, a session duration, and a session frequency; using said application to wirelessly transmit said modulation signal from the external device to the electrical dermal patch; receiving said modulation signal at the electrical dermal patch; in said electrical dermal patch, using the modulation signal to modify at least one of said pulse width, pulse amplitude, pulse frequency, pulse shape, duty cycle, session duration, and session frequency to yield a first pulse width, a first pulse amplitude, a first pulse frequency, a first pulse shape, a first duty cycle, a first session duration, or a first session frequency; and in said electrical dermal patch, using the first pulse width, the first pulse amplitude, the first pulse frequency, the first pulse shape, the first duty cycle, the first session duration, or the first session frequency to generate said plurality of electrical pulses.

Optionally, said patient status data comprises at least one of a degree of hunger being experienced by the patient, a degree of appetite being experienced by the patient, a satiety level being experienced by the patient, a satiation level being experienced by the patient, a degree of dyspepsia being experienced by the patient, a degree of nausea being experienced by the patient and a degree of well-being being experienced by the patient.

Optionally, the method further comprises acquiring, via said application, a first stimulation protocol; and using said first stimulation protocol, within said application, to generate the modulation signal.

Optionally, the method further comprises acquiring, via said application, a second stimulation protocol, wherein said second stimulation protocol is different from the first stimulation protocol; using said second stimulation protocol, within said application, to generate a second modulation signal, wherein said second modulation signal comprises instructions for modulating at least one of the pulse width, the pulse amplitude, the pulse frequency, the pulse shape, the duty cycle, the session duration, and the session frequency; causing, via said application, said second modulation signal to be wirelessly transmitted from the external device to the electrical dermal patch; and receiving said second modulation signal at the electrical dermal patch; in said electrical dermal patch, using the second modulation signal to modify at least one of said pulse width, pulse amplitude, pulse frequency, pulse shape, duty cycle, session duration, and session frequency to yield at least one second pulse width, a second pulse amplitude, a second pulse frequency, a second pulse shape, a second duty cycle, a second session duration, and a second session frequency.

Optionally, the second pulse width is different from the first pulse width, wherein the electrical dermal patch uses the second pulse width to generate a second plurality of electrical pulses, and wherein the electrical dermal patch applies a stimulation to the patient's epidermal layer using said second plurality of electrical pulses.

Optionally, the second pulse amplitude is different from the first pulse amplitude, wherein the electrical dermal patch uses the second pulse amplitude to generate a second plurality of electrical pulses, and wherein the electrical dermal patch applies a stimulation to the patient's epidermal layer using said second plurality of electrical pulses.

Optionally, the second pulse frequency is different from the first pulse frequency, wherein the electrical dermal patch uses the second pulse frequency to generate a second plurality of electrical pulses, and wherein the electrical dermal patch applies a stimulation to the patient's epidermal layer using said second plurality of electrical pulses.

Optionally, the second pulse shape is different from the first pulse shape, wherein the electrical dermal patch uses the second pulse shape to generate a second plurality of electrical pulses, and wherein the electrical dermal patch applies a stimulation to the patient's epidermal layer using said second plurality of electrical pulses.

Optionally, the second duty cycle is different from the first duty cycle, wherein the electrical dermal patch uses the second duty cycle to generate a second plurality of electrical pulses, and wherein the electrical dermal patch applies a stimulation to the patient's epidermal layer using said second plurality of electrical pulses.

Optionally, the second session duration is different from the first session duration, wherein the electrical dermal patch uses the second session duration to generate a second plurality of electrical pulses, and wherein the electrical dermal patch applies a stimulation to the patient's epidermal layer using said second plurality of electrical pulses.

Optionally, the second session frequency is different from the first session frequency, wherein the electrical dermal patch uses the second session frequency to generate a second plurality of electrical pulses, and wherein the electrical dermal patch applies a stimulation to the patient's epidermal layer using said second plurality of electrical pulses.

Optionally, the method further comprises prompting, via an application installed on an external device, a user to input data; generating a signal based upon said data; causing said signal to be wirelessly transmitted from the external device to the electrical dermal patch; receiving said signal at the electrical dermal patch; and using said signal to modify at least one of said plurality of stimulation parameters, wherein said plurality of stimulation parameters comprise at least one of a pulse width, a pulse amplitude, a pulse frequency, a pulse shape, a duty cycle, a session duration, and a session frequency.

Optionally, said signal is generated based upon data inputted by the user and a plurality of values, each of said plurality of values represents a maximum numerical limit or minimum numerical limit to at least one of the pulse width, the pulse amplitude, the pulse frequency, the pulse shape, the duty cycle, the session duration, and the session frequency.

Optionally, the method further comprises using an application installed on an external device to acquire patient status data over a period of time, said patient status data including at least one of the appetite of the patient, the hunger of the patient, a level of well-being of the patient, a level of nausea of the patient, an amount of the patient's weight, an amount of calories consumed by the patient, and an amount of calories expended by the patient; after said period of time, generating a signal based upon said patient status data; causing the signal to be wirelessly transmitted to the electrical dermal patch; and, causing the plurality of electrical pulses to be generated using a second plurality of stimulation parameters, wherein said second plurality of stimulation parameters is determined based upon said signal and wherein said second plurality of stimulation parameters has at least one stimulation parameter that is different than at least one of the plurality of stimulation parameters.

Optionally, if the level of the appetite is above a threshold level, the second plurality of stimulations has at least one of a pulse width, a pulse amplitude, a pulse frequency, a pulse duty cycle, a pulse shape, a session duration, or a session frequency that is increased relative to at least one of a pulse width, a pulse amplitude, a pulse frequency, a pulse duty cycle, a pulse shape, a session duration, or a session frequency of the plurality of stimulation parameters.

Optionally, if the level of the appetite is below a threshold level, the second plurality of stimulations has at least one of a pulse width, a pulse amplitude, a pulse frequency, a pulse duty cycle, a pulse shape, a session duration, or a session frequency that is decreased relative to at least one of a pulse width, a pulse amplitude, a pulse frequency, a pulse duty cycle, a pulse shape, a session duration, or a session frequency of the plurality of stimulation parameters.

Optionally, if the level of nausea is above a threshold level, the second plurality of stimulations has at least one of a pulse width, a pulse amplitude, a pulse frequency, a pulse duty cycle, a pulse shape, a session duration, or a session frequency that is decreased relative to at least one of a pulse width, a pulse amplitude, a pulse frequency, a pulse duty cycle, a pulse shape, a session duration, or a session frequency of the plurality of stimulation parameters.

Optionally, if the level of the hunger is above a threshold level, the second plurality of stimulations has at least one of a pulse width, a pulse amplitude, a pulse frequency, a pulse duty cycle, a pulse shape, a session duration, or a session frequency that is increased relative to at least one of a pulse width, a pulse amplitude, a pulse frequency, a pulse duty cycle, a pulse shape, a session duration, or a session frequency of the plurality of stimulation parameters.

Optionally, if the level of hunger is below a threshold level, the second plurality of stimulations has at least one of a pulse width, a pulse amplitude, a pulse frequency, a pulse duty cycle, a pulse shape, a session duration, or a session frequency that is decreased relative to at least one of a pulse width, a pulse amplitude, a pulse frequency, a pulse duty cycle, a pulse shape, a session duration, or a session frequency of the plurality of stimulation parameters.

In some embodiments, the present specification discloses a method of enabling a person to comply with a diet plan comprising: providing an electrical dermal patch adapted to adhere to the person's epidermal layer, wherein said electrical dermal patch comprises a controller, at least one electrode adapted to be in electrical contact with said patient's epidermal layer, and a pulse generator in electrical communication with the controller and said at least one electrode; generating a plurality of electrical pulses having a treatment session duration and a treatment session frequency, wherein each of said plurality of electrical pulses is defined by a pulse width, a pulse amplitude, a pulse shape, a pulse frequency and wherein said pulse shape, pulse width, said pulse amplitude, and said pulse frequency are selected to enable the person to comply with the diet plan; using an application installed on an external device to acquire data over a period of time, said data including at least one of a timing of caloric consumption, an amount of caloric consumption, and a content of a caloric consumption; after said period of time, generating a signal, using said application, based upon said data; causing the signal to be transmitted to the electrical dermal patch; and generating a second plurality of electrical pulses using a plurality of stimulation parameters, said plurality of stimulation parameters being determined based upon said signal and including at least one of a second pulse width, a second pulse amplitude, a second pulse frequency, a second pulse duty cycle, a second pulse shape, a second treatment session duration, and a second treatment session frequency.

Optionally, the epidermal layer is positioned within a range of 0.1 mm to 25 mm from at least one of the person's C5, C6, C7, C8, T1, T2, T3, T4, T5, T6, T7, T8, T9, T10, T11, and T12 dermatomes.

Optionally, if the amount of caloric consumption varies from a predefined amount, the second pulse width is greater than the pulse width.

Optionally, if the amount of caloric consumption varies from a predefined amount, the second pulse amplitude is greater than the pulse amplitude.

Optionally, if the amount of caloric consumption varies from a predefined amount, the second pulse frequency is greater than the pulse frequency.

Optionally, if the amount of caloric consumption varies from a predefined amount, the second treatment session duration is greater than the treatment session duration.

Optionally, if the amount of caloric consumption varies from a predefined amount, the second treatment session frequency is greater than the treatment session frequency.

Optionally, the content of a caloric consumption includes at least one of an amount of carbohydrates, an amount of protein, an amount of fat, an amount of sugar, an amount of vitamins, an amount of minerals, and an amount of glycemic index.

Optionally, if at least one of the amount of carbohydrates, the amount of fat, the amount of sugar, and the amount of glycemic index varies from a predefined amount, the second pulse width is greater than the pulse width.

Optionally, if at least one of the amount of carbohydrates, the amount of fat, the amount of sugar, and the amount of glycemic index varies from a predefined amount, the second pulse amplitude is greater than the pulse amplitude.

Optionally, if at least one of the amount of carbohydrates, the amount of fat, the amount of sugar, and the amount of glycemic index varies from a predefined amount, the second pulse frequency is greater than the pulse frequency.

Optionally, if at least one of the amount of carbohydrates, the amount of fat, the amount of sugar, and the amount of glycemic index varies from a predefined amount, the second treatment session duration is greater than the treatment session duration.

Optionally, if at least one of the amount of carbohydrates, the amount of fat, the amount of sugar, and the amount of glycemic index varies from a predefined amount, the second treatment session frequency is greater than the treatment session frequency.

In some embodiments, the present specification discloses a method of enabling a person to comply with a diet plan comprising: providing an electrical dermal patch adapted to adhere to the person's epidermal layer, wherein said electrical dermal patch comprises a controller, at least one electrode adapted to be in electrical contact with said patient's epidermal layer, and a pulse generator in electrical communication with the controller and said at least one electrode; using said electrical dermal patch, generating a plurality of electrical pulses at a first predefined time of day; using an application installed on a device separate from said electrical dermal patch to acquire data over a period of time, said data including at least one of a timing of caloric consumption and an amount of caloric consumption; after said period of time, generating a signal, using said application, based upon said data; causing the signal to be transmitted to the electrical dermal patch; and generating a second plurality of electrical pulses using a plurality of stimulation parameters, said plurality of stimulation parameters being determined based upon said signal and including a second predefined time of day.

Optionally, the epidermal layer is positioned within a range of 0.1 mm to 25 mm from at least one of the person's C5, C6, C7, C8, T1, T2, T3, T4, T5, T6, T7, T8, T9, T10, T11, and T12 dermatomes.

Optionally, if the amount of caloric consumption varies from a predefined amount, the second plurality of electrical pulses are generated at the second predefined time of day, wherein the second predefined time of day is different from the first predefined time of day and is based on the timing of caloric consumption.

Optionally, the data further includes at least one of an amount of carbohydrates consumed by the person, an amount of fat consumed by the person, and an amount of sugar consumed by the person.

Optionally, if the amount of carbohydrates varies from a predefined amount, the second plurality of electrical pulses are generated at the second predefined time of day, wherein the second predefined time of day is different from the first predefined time of day and is based on the timing of caloric consumption.

Optionally, if the amount of fat varies from a predefined amount, the second plurality of electrical pulses are generated at the second predefined time of day, wherein the second predefined time of day is different from the first predefined time of day and is based on the timing of caloric consumption.

Optionally, if the amount of sugar varies from a predefined amount, the second plurality of electrical pulses are generated at the second predefined time of day, wherein the second predefined time of day is different from the first predefined time of day and is based on the timing of caloric consumption.

Optionally, the electrical dermal patch further comprises a transceiver and wherein said signal is caused to be transmitted to the electrical dermal patch wirelessly.

Optionally, the device is at least one of a mobile phone, a tablet computer, and a laptop computer.

In some embodiments, the present specification discloses a method of enabling a person to comply with a diet plan, said diet plan having at least one of a recommended timing of caloric consumption, a recommended content of caloric consumption, and a recommended amount of caloric consumption, comprising: providing an electrical dermal patch adapted to adhere to the person's epidermal layer, wherein said electrical dermal patch comprises a controller, at least one electrode adapted to be in electrical contact with said patient's epidermal layer, and a pulse generator in electrical communication with the controller and said at least one electrode; generating a plurality of electrical pulses at a first predefined time of day wherein said plurality of electrical pulses are defined by at least one of a pulse width, a pulse amplitude, a pulse frequency, a duty cycle, a pulse shape, a treatment session duration, and a treatment session frequency; using an application installed on a device separate from said electrical dermal patch to acquire data over a period of time, said data including at least one of a timing of caloric consumption, a content of caloric consumption, and an amount of caloric consumption; using said application to compare at least one of the timing of caloric consumption, the content of caloric consumption, and the amount of caloric consumption with at least one of the recommended timing of caloric consumption, recommended content of caloric consumption, and recommended amount of caloric consumption; generating a signal, using said application, based upon said comparison; causing the signal to be transmitted to the electrical dermal patch; and, generating a second plurality of electrical pulses using a plurality of stimulation parameters, said plurality of stimulation parameters being determined based upon said signal and including at least one of a second pulse width, a second pulse amplitude, a second pulse frequency, a second pulse duty cycle, a second pulse shape, a second treatment session duration, a second treatment session frequency, and a second predefined time of day.

Optionally, if the amount of caloric consumption varies from the recommended amount of caloric consumption by a predefined amount, the second pulse width is greater than the pulse width.

Optionally, if the amount of caloric consumption varies from the recommended amount of caloric consumption by a predefined amount, the second pulse amplitude is greater than the pulse amplitude.

Optionally, if the amount of caloric consumption varies from the recommended amount of caloric consumption by a predefined amount, the second pulse frequency is greater than the pulse frequency.

Optionally, if the amount of caloric consumption varies from the recommended amount of caloric consumption by a predefined amount, the second treatment session duration is greater than the treatment session duration.

Optionally, if the amount of caloric consumption varies from the recommended amount of caloric consumption by a predefined amount, the second treatment session frequency is greater than the treatment session frequency.

Optionally, the content of a caloric consumption includes at least one of an amount of carbohydrates, an amount of fat, an amount of sugar, and an amount of glycemic index.

Optionally, if at least one of the amount of carbohydrates, the amount of fat, the amount of sugar, and the amount of glycemic index varies from the recommended content of caloric consumption by a predefined amount, the second pulse width is greater than the pulse width.

Optionally, if at least one of the amount of carbohydrates, the amount of fat, the amount of sugar, and the amount of glycemic index varies from the recommended content of caloric consumption by a predefined amount, the second pulse amplitude is greater than the pulse amplitude.

Optionally, if at least one of the amount of carbohydrates, the amount of fat, the amount of sugar, and the amount of glycemic index varies from the recommended content of caloric consumption by a predefined amount, the second pulse frequency is greater than the pulse frequency.

Optionally, if at least one of if the amount of carbohydrates, the amount of fat, the amount of sugar, and the amount of glycemic index varies from the recommended content of caloric consumption by a predefined amount, the second treatment session duration is greater than the treatment session duration.

Optionally, if at least one of the amount of carbohydrates, the amount of fat, the amount of sugar, and the amount of glycemic index varies from the recommended content of caloric consumption by a predefined amount, the second treatment session frequency is greater than the treatment session frequency.

Optionally, the electrical dermal patch further comprises a transceiver and wherein said signal is caused to be transmitted to the electrical dermal patch wirelessly.

Optionally, said device is at least one of a mobile phone, a tablet computer, and a laptop computer.

In some embodiments, the present specification discloses a method of using an electrical dermal patch, adhered to a person's epidermal layer, to enable the person to comply with a diet plan, said diet plan being defined by at least one of a recommended timing of caloric consumption, a recommended content of caloric consumption, and a recommended amount of caloric consumption, comprising: generating a plurality of electrical pulses at a first predefined time of day, wherein said plurality of electrical pulses are defined by at least one of a pulse width, a pulse amplitude, a pulse frequency, a pulse duty cycle, a pulse shape, a treatment session duration, and a treatment session frequency; receiving data into an application installed on a device separate from said electrical dermal patch, said data including at least one of a timing of caloric consumption, a content of caloric consumption, and an amount of caloric consumption; using the application to compare at least one of the timing of caloric consumption, the content of caloric consumption, and the amount of caloric consumption with at least one of the recommended timing of caloric consumption, recommended content of caloric consumption, and recommended amount of caloric consumption; generating a signal, using said application, based upon said comparison; causing the signal to be transmitted to the electrical dermal patch; and generating a second plurality of electrical pulses using a plurality of stimulation parameters, said plurality of stimulation parameters being determined based upon said signal and including at least one of a second pulse width, a second pulse amplitude, a second pulse frequency, a second pulse duty cycle, a second pulse shape, a second treatment session duration, a second treatment session frequency, and a second predefined time of day.

Optionally, if the amount of caloric consumption varies from the recommended amount of caloric consumption by a predefined amount, the second pulse width is greater than the pulse width.

Optionally, if the amount of caloric consumption varies from the recommended amount of caloric consumption by a predefined amount, the second pulse amplitude is greater than the pulse amplitude.

Optionally, if the amount of caloric consumption varies from the recommended amount of caloric consumption by a predefined amount, the second pulse frequency is greater than the pulse frequency.

Optionally, if the amount of caloric consumption varies from the recommended amount of caloric consumption by a predefined amount, the second treatment session duration is greater than the treatment session duration.

Optionally, if the amount of caloric consumption varies from the recommended amount of caloric consumption by a predefined amount, the second treatment session frequency is greater than the treatment session frequency.

Optionally, if the amount of caloric consumption varies from the recommended amount of caloric consumption by a predefined amount, the second pulse width is less than the pulse width.

Optionally, if the amount of caloric consumption varies from the recommended amount of caloric consumption by a predefined amount, the second pulse amplitude is less than the pulse amplitude.

Optionally, if the amount of caloric consumption varies from the recommended amount of caloric consumption by a predefined amount, the second pulse frequency is less than the pulse frequency.

Optionally, if the amount of caloric consumption varies from the recommended amount of caloric consumption by a predefined amount, the second treatment session duration is less than the treatment session duration.

Optionally, if the amount of caloric consumption varies from the recommended amount of caloric consumption by a predefined amount, the second treatment session frequency is less than the treatment session frequency.

Optionally, the content of a caloric consumption includes at least one of an amount of carbohydrates, an amount of fat, an amount of sugar, and an amount of glycemic index.

Optionally, if at least one of the amount of carbohydrates, the amount of fat, the amount of sugar, or the amount of glycemic index varies from the recommended content of caloric consumption by a predefined amount, the second pulse width is greater than the pulse width.

Optionally, if the amount of carbohydrates, the amount of fat, the amount of sugar, or the amount of glycemic index varies from the recommended content of caloric consumption by a predefined amount, the second pulse amplitude is greater than the pulse amplitude.

Optionally, if the amount of carbohydrates, the amount of fat, the amount of sugar, or the amount of glycemic index varies from the recommended content of caloric consumption by a predefined amount, the second pulse frequency is greater than the pulse frequency.

Optionally, if the amount of carbohydrates, the amount of fat, the amount of sugar, or the amount of glycemic index varies from the recommended content of caloric consumption by a predefined amount, the second treatment session duration is greater than the treatment session duration.

Optionally, if the amount of carbohydrates, the amount of fat, the amount of sugar, or the amount of glycemic index varies from the recommended content of caloric consumption by a predefined amount, the second treatment session frequency is greater than the treatment session frequency.

Optionally, if at least one of the amount of carbohydrates, the amount of fat, the amount of sugar, or the amount of glycemic index varies from the recommended content of caloric consumption by a predefined amount, the second pulse width is less than the pulse width.

Optionally, if the amount of carbohydrates, the amount of fat, the amount of sugar, or the amount of glycemic index varies from the recommended content of caloric consumption by a predefined amount, the second pulse amplitude is less than the pulse amplitude.

Optionally, if the amount of carbohydrates, the amount of fat, the amount of sugar, or the amount of glycemic index varies from the recommended content of caloric consumption by a predefined amount, the second pulse frequency is less than the pulse frequency.

Optionally, if the amount of carbohydrates, the amount of fat, the amount of sugar, or the amount of glycemic index varies from the recommended content of caloric consumption by a predefined amount, the second treatment session duration is less than the treatment session duration.

Optionally, if the amount of carbohydrates, the amount of fat, the amount of sugar, or the amount of glycemic index varies from the recommended content of caloric consumption by a predefined amount, the second treatment session frequency is less than the treatment session frequency.

Optionally, the electrical dermal patch further comprises a transceiver and wherein said signal is caused to be transmitted to the electrical dermal patch wirelessly.

Optionally, said device is at least one of a mobile phone, a tablet computer, and a laptop computer.

In some embodiments, the present specification discloses a method of using an electrical dermal patch, adhered to an epidermal layer of a patient, to enable the patient to comply with a diet plan in order to achieve a target weight, comprising: generating a plurality of electrical pulses, wherein said plurality of electrical pulses is defined by at least one of a pulse width, a pulse amplitude, a pulse shape, a pulse frequency, a treatment session duration, and a treatment session frequency; using an application installed on a device external to said electrical dermal patch to acquire patient status data, said patient status data including data indicative of a weight of the patient; comparing the weight of the patient to the target weight; generating a signal, using said application, based upon said comparison; causing the signal to be transmitted to the electrical dermal patch; and, generating a second plurality of electrical pulses using a plurality of stimulation parameters, said plurality of stimulation parameters being determined based upon said signal and including at least one of a second pulse width, a second pulse shape, a second pulse amplitude, a second pulse frequency, a second treatment session duration, and a second treatment session frequency.

Optionally, if the weight of the patient is equal to or less than the target weight, at least one of the second pulse width, the second pulse amplitude, the second pulse frequency, the second treatment session duration, and the second treatment session frequency is decreased relative to at least one of the pulse width, the pulse amplitude, the pulse frequency, the treatment session duration, and the treatment session frequency.

Optionally, if the weight of the patient is greater than the target weight, at least one of the second pulse width, the second pulse amplitude, the second pulse frequency, the second treatment session duration, and the second treatment session frequency is increased relative to at least one of the pulse width, the pulse amplitude, the pulse frequency, the treatment session duration, and the treatment session frequency.

Optionally, the electrical dermal patch further comprises a transceiver and wherein said signal is caused to be transmitted to the electrical dermal patch wirelessly.

Optionally, said device is at least one of a mobile phone, a tablet computer, and a laptop computer.

In some embodiments, the present specification discloses a method of using an electrical dermal patch, adhered to an epidermal layer of a person, to enable the person to comply with a diet plan in order to achieve a target weight, comprising: generating, via said electrical dermal patch, a plurality of electrical pulses, wherein said plurality of electrical pulses is defined by at least one of a pulse width, a pulse amplitude, a pulse frequency, a treatment session duration, and a treatment session frequency; using an application installed on a device separate from the electrical dermal patch to acquire data, said data being indicative of at least one of an appetite of the person, a hunger of the person, a satiety level of the person, a satiation level of the person, and a fullness level of the person; generating a signal, using said application, based upon said data; causing the signal to be transmitted to the electrical dermal patch; and, generating a second plurality of electrical pulses using a plurality of stimulation parameters, said plurality of stimulation parameters being determined based upon said signal and including at least one of a second pulse width, a second pulse amplitude, a second pulse frequency, a second treatment session duration, and a second treatment session frequency.

Optionally, if the appetite of the person varies from a target appetite level by a predefined amount, at least one of the second pulse width, the second pulse amplitude, the second pulse frequency, the second treatment session duration, and the second treatment session frequency is increased relative to the pulse width, the pulse amplitude, the pulse frequency, the treatment session duration, and a second treatment session frequency.

Optionally, if the hunger of the person varies from a target hunger level by a predefined amount, at least one of the second pulse width, the second pulse amplitude, the second pulse frequency, the second treatment session duration, and the second treatment session frequency is increased relative to the pulse width, the pulse amplitude, the pulse frequency, the treatment session duration, and a second treatment session frequency.

Optionally, if the satiety level of the person varies from a target satiety level by a predefined amount, at least one of the second pulse width, the second pulse amplitude, the second pulse frequency, the second treatment session duration, and the second treatment session frequency is increased relative to the pulse width, the pulse amplitude, the pulse frequency, the treatment session duration, and a second treatment session frequency.

Optionally, if the satiation level of the person varies from a target satiation level by a predefined amount, at least one of the second pulse width, the second pulse amplitude, the second pulse frequency, the second treatment session duration, and the second treatment session frequency is increased relative to the pulse width, the pulse amplitude, the pulse frequency, the treatment session duration, and a second treatment session frequency.

Optionally, if the fullness level of the person varies from a target fullness level by a predefined amount, at least one of the second pulse width, the second pulse amplitude, the second pulse frequency, the second treatment session duration, and the second treatment session frequency is increased relative to the pulse width, the pulse amplitude, the pulse frequency, the treatment session duration, and a second treatment session frequency.

Optionally, if the appetite of the person varies from a target appetite level by a predefined amount, at least one of the second pulse width, the second pulse amplitude, the second pulse frequency, the second treatment session duration, and the second treatment session frequency is decreased relative to the pulse width, the pulse amplitude, the pulse frequency, the treatment session duration, and a second treatment session frequency.

Optionally, if the hunger of the person varies from a target hunger level by a predefined amount, at least one of the second pulse width, the second pulse amplitude, the second pulse frequency, the second treatment session duration, and the second treatment session frequency is decreased relative to the pulse width, the pulse amplitude, the pulse frequency, the treatment session duration, and a second treatment session frequency.

Optionally, if the satiety level of the person varies from a target satiety level by a predefined amount, at least one of the second pulse width, the second pulse amplitude, the second pulse frequency, the second treatment session duration, and the second treatment session frequency is decreased relative to the pulse width, the pulse amplitude, the pulse frequency, the treatment session duration, and a second treatment session frequency.

Optionally, if the satiation level of the person varies from a target satiation level by a predefined amount, at least one of the second pulse width, the second pulse amplitude, the second pulse frequency, the second treatment session duration, and the second treatment session frequency is decreased relative to the pulse width, the pulse amplitude, the pulse frequency, the treatment session duration, and a second treatment session frequency.

Optionally, if the fullness level of the person varies from a target fullness level by a predefined amount, at least one of the second pulse width, the second pulse amplitude, the second pulse frequency, the second treatment session duration, and the second treatment session frequency is decreased relative to the pulse width, the pulse amplitude, the pulse frequency, the treatment session duration, and a second treatment session frequency.

Optionally, the electrical dermal patch further comprises a transceiver and wherein said signal is caused to be transmitted to the electrical dermal patch wirelessly.

Optionally, said device is at least one of a mobile phone, a tablet computer, and a laptop computer.

In some embodiments, the present specification discloses a method of modulating at least one of a person's appetite, hunger, satiety level, or satiation comprising: providing an electrical dermal patch adapted to adhere to the person's epidermal layer, wherein said electrical dermal patch comprises a controller, at least one electrode adapted to be in electrical contact with said person's epidermal layer, and a pulse generator in electrical communication with the controller and said at least one electrode; defining a first plurality of stimulation parameters; generating a plurality of electrical pulses using said first plurality of stimulation parameters, wherein said first plurality of stimulation parameters are defined such that, after applying at least one stimulation to the patient's epidermal layer, at least one of the patient's appetite, hunger, satiety level, and satiation level is modified; using an application installed on a device separate from the electrical dermal patch to acquire data, said data being indicative of at least one of the person's appetite, hunger, satiety level, satiation level, fullness level, amount of caloric intake, weight, type of caloric intake, and timing of caloric intake; generating a signal, using said application, based upon said data; causing the signal to be transmitted to the electrical dermal patch; and generating a second plurality of electrical pulses using a second plurality of stimulation parameters, wherein said second plurality of stimulation parameters is determined.

Optionally, said first plurality of stimulation parameters and second plurality of stimulation parameters are further selected such that a post-stimulation daily caloric intake of said person decreases relative to a pre-stimulation daily caloric intake of said person, wherein said pre-stimulation daily caloric intake is a function of an amount of calories consumed by the person over a first predefined period of time prior to stimulation, and wherein said post-stimulation daily caloric intake is a function of an amount of calories consumed by the person over a second predefined period of time equal in duration to the first predefined period of time, after stimulation is initiated.

Optionally, said first plurality of stimulation parameters and second plurality of stimulation parameters are further selected such that a post-stimulation daily caloric intake of said person is less than 99% of a pre-stimulation daily caloric intake of said person, wherein said pre-stimulation daily caloric intake is a function of an amount of calories consumed by the person over a first predefined period of time prior to stimulation, and wherein said post-stimulation daily caloric intake is a function of an amount of calories consumed by the person over a second predefined period of time equal in duration to the first predefined period of time, after stimulation is initiated.

Optionally, said first plurality of stimulation parameters and second plurality of stimulation parameters are further selected such that, after at least one stimulation, the person's compliance with a target daily caloric intake increases relative to the person's compliance with the target daily caloric intake before stimulation.

Optionally, said first plurality of stimulation parameters and second plurality of stimulation parameters are further selected such that, after at least one stimulation, the person's daily caloric intake decreases to a range of 600 to 1600 calories from a daily caloric intake range greater than 1600 calories.

Optionally, said first plurality of stimulation parameters and second plurality of stimulation parameters are further selected such that, after at least one stimulation, the person's daily caloric intake decreases from over 2000 calories per day to under 2000 calories per day.

Optionally, said first plurality of electrical pulses and second plurality of electrical pulses comprise pulse widths in a range of 10 μsec to 100 msec, pulse amplitudes in a range of 100 μA to 500 mA, and pulse frequencies in a range of 1 Hz to 10,000 Hz.

Optionally, said first plurality of stimulation parameters and said second plurality of stimulation parameters are further selected such that, after at least one stimulation, a total body weight of the person reduces by at least 1% relative to a total body weight of the person before stimulation.

Optionally, said first plurality of stimulation parameters and said second plurality of stimulation parameters are further selected such that, after at least one stimulation, an excess body weight of the person reduces by at least 1% relative to an excess body weight of the person before stimulation.

Optionally, said first plurality of stimulation parameters and second plurality of stimulation parameters are further selected such that, after at least one stimulation, a total body weight of the person reduces by at least 1% relative to a total body weight of the person before stimulation and a well-being level of the person does not reduce more than 5% relative to a well-being level of the person before stimulation.

Optionally, said first plurality of stimulation parameters and second plurality of stimulation parameters are further selected such that, after at least one stimulation, an excess body weight of the person reduces by at least 1% relative to an excess body weight of the person before stimulation and a well-being level of the person does not reduce more than 5% relative to a well-being level of the person before stimulation.

Optionally, said first plurality of stimulation parameters and second plurality of stimulation parameters are further selected such that, after at least one stimulation, a pre-prandial ghrelin level of the person reduces by at least 1% relative to a pre-prandial ghrelin level of the person before stimulation.

Optionally, said first plurality of stimulation parameters and second plurality of stimulation parameters are further selected such that, after at least one stimulation, a post-prandial ghrelin level of the person reduces by at least 1% relative to a post-prandial ghrelin level of the person before stimulation.

Optionally, said first plurality of stimulation parameters and second plurality of stimulation parameters are further selected such that, after at least one stimulation session, exercise output of the patient increases by at least 1% relative to the exercise output of the patient before stimulation.

Optionally, said first plurality of stimulation parameters and second plurality of stimulation parameters are further selected such that, after at least one stimulation, a glucagon-like peptide-1 level of the person increases by at least 1% relative to a glucagon-like peptide-1 level of the person before stimulation.

Optionally, said first plurality of stimulation parameters and second plurality of stimulation parameters are further selected such that, after at least one stimulation, a leptin level of the person increases by at least 1% relative to a leptin level of the person before stimulation.

Optionally, said first plurality of stimulation parameters and second plurality of stimulation parameters are further selected such that, after at least one stimulation, the patient's appetite decreases, over a predefined period of time, relative to the patient's appetite before stimulation and a nausea level of the patient does not increase by more than 10%, over said predefined period of time, relative to the nausea level of the patient before stimulation.

Optionally, said first plurality of stimulation parameters and second plurality of stimulation parameters are further selected such that, after at least one stimulation, a peptide YY level of the person increases by at least 1% relative to a peptide YY level of the person before stimulation.

Optionally, said first plurality of stimulation parameters and second plurality of stimulation parameters are further selected such that, after at least one stimulation, a lipopolysaccharide level of the person reduces by at least 1% relative to a lipopolysaccharide level of the person before stimulation.

Optionally, said first plurality of stimulation parameters and second plurality of stimulation parameters are further selected such that, after at least one stimulation, a motilin-related peptide level of the person reduces by at least 1% relative to a motilin-related peptide level of the person before stimulation.

Optionally, said first plurality of stimulation parameters and second plurality of stimulation parameters are further selected such that, after at least one stimulation, a cholecystokinin level of the person increases by at least 1% relative to a cholecystokinin level of the person before stimulation.

Optionally, said first plurality of stimulation parameters and second plurality of stimulation parameters are further selected such that, after at least one stimulation, a resting metabolic rate of the person increases by at least 1% relative to a resting metabolic rate of the person before stimulation.

Optionally, said first plurality of stimulation parameters and second plurality of stimulation parameters are further selected such that, after at least one stimulation, a plasma-beta endorphin level of the person increases by at least 1% relative to a plasma-beta endorphin level of the person before stimulation.

Optionally, said first plurality of stimulation parameters and second plurality of stimulation parameters are further selected such that, after at least one stimulation, the patient's hunger decreases, over a predefined period of time, relative to the patient's hunger before stimulation and a nausea level of the patient does not increase by more than 10%, over said predefined period of time, relative to the nausea level of the patient before stimulation.

Optionally, said first plurality of stimulation parameters and second plurality of stimulation parameters are further selected such that, after at least one stimulation, the person's level of hemoglobin A1c decreases by an amount equal to at least 0.3%.

Optionally, said first plurality of stimulation parameters and second plurality of stimulation parameters are further selected such that, after at least one stimulation, a triglyceride level of the person decreases by at least 1% relative to a triglyceride level of the person before stimulation.

Optionally, said first plurality of stimulation parameters and second plurality of stimulation parameters are further selected such that, after at least one stimulation, a total blood cholesterol level of the person decreases by at least 1% relative to a total blood cholesterol level of the person before stimulation.

Optionally, said first plurality of stimulation parameters and second plurality of stimulation parameters are further selected such that, after at least one stimulation, a glycemia level of the person decreases by at least 1% relative to a glycemia level of the person before stimulation.

Optionally, said first plurality of stimulation parameters and second plurality of stimulation parameters are further selected such that, after at least one stimulation, a composition of the person's gut microbiota modulates from a first state to a second state, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 3%, and wherein the second level of firmicutes is less than the first level of firmicutes by at least 3%.

In some embodiments, the present specification discloses a method of enabling a person to comply with a diet plan comprising: providing an electrical dermal patch adapted to adhere to the person's epidermal layer, wherein said electrical dermal patch comprises a controller, at least one electrode adapted to be in electrical contact with said patient's epidermal layer, and a pulse generator in electrical communication with the controller and said at least one electrode; generating a plurality of electrical pulses having a treatment session duration and a treatment session frequency, wherein each of said plurality of electrical pulses is defined by pulse width, a pulse amplitude, a pulse shape, a pulse frequency and wherein said pulse shape, pulse width, said pulse amplitude, and said pulse frequency are selected to enable the person to comply with the diet plan; using an application installed on an external device to acquire data over a period of time, said data including at least one of a timing of caloric consumption, an amount of caloric consumption, a content of a caloric consumption, an appetite level, a timing of appetite, a hunger level, a satiety level, a satiation level, a fullness level, an amount of calories burned, and an activity level; after said period of time, generating a signal, using said application, based upon said data; causing the signal to be transmitted to the electrical dermal patch; generating a second plurality of electrical pulses using a plurality of stimulation parameters, said plurality of stimulation parameters being determined based upon said signal and including at least one of a second pulse width, a second pulse amplitude, a second pulse frequency, a second pulse duty cycle, a second pulse shape, a second treatment session duration, and a second treatment session frequency; using said application, causing at least a portion of at least one of said data and said plurality of stimulation parameters to be transmitted from said external device to a server; using said server to store said at least a portion of said data and said plurality of stimulation parameters in a database; using said server to associate at least a portion of said data and said plurality of stimulation parameters with an electronic profile of the patient; using said server to share said electronic profile of the patient with electronic profiles of other individuals; using said server to transmit to said application at least one of a timing of caloric consumption, an amount of caloric consumption, a content of a caloric consumption, an appetite level, a timing of appetite, a hunger level, a satiety level, a satiation level, a fullness level, an amount of calories burned, an activity level, and a plurality of stimulation parameters associated with one or more of said individuals; and visually displaying in said application at least one of a timing of caloric consumption, an amount of caloric consumption, a content of a caloric consumption, an appetite level, a timing of appetite, a hunger level, a satiety level, a satiation level, a fullness level, an amount of calories burned, an activity level, and a plurality of stimulation parameters associated with one or more of said individuals in association with or relative to at least one of the timing of caloric consumption, the amount of caloric consumption, the content of caloric consumption, the appetite level, the timing of appetite, the hunger level, the satiety level, the satiation level, the fullness level, the amount of calories burned, the activity level, and the plurality of stimulation parameters associated of the patient. It should be appreciated that server may refer to one or more computing devices, whether individually identifiable or collectively acting as a cloud service.

Optionally, in any of the above embodiments, the duty cycle may be between 1% and 100% and the pulse shape of any one of monophasic, biphasic, and sinusoidal. Additionally, in any of the above embodiments, each of the stimulation sessions may be further defined as having a stimulation session duration of 1 min to 120 min with 1 to 24 stimulation sessions per day and 2 to 168 stimulation sessions per week. The stimulation session duration may also range from 1 min to substantially continuously.

Optionally, in any of the above embodiments, the stimulation sessions are configured to provide alternating stimulation sessions between a first session having a first pulse frequency equal to less than a pivot frequency, such as 50 Hz or a frequency in a range of 25 to 75 Hz, followed by a second session having a second pulse frequency greater than the pivot frequency.

Optionally, said control device is further configured to monitor, record, and modify stimulation parameters of said stimulation protocol. The control device may comprise any one of a smartphone, tablet, and personal digital assistant and may be in data communication with a remote patient care facility or patient care personnel.

Optionally, said control device includes a graphical user interface screen configured to receive appetite, eating, weight, and activity information data from a patient and display said data on said screen. Still optionally, said control device is configured to generate and display a plurality of charts and graphs representative of said information data and, based upon said data, manage and generate prompts related to patient compliance on said graphical user interface screen.

Optionally, said control device is adapted to receive and integrate exercise and weight loss information from a third party device.

Optionally, said control device is configured to provide rescue stimulation sessions, wherein a rescue stimulation session is defined as an on-demand stimulation session applied at the onset of unplanned hunger events or potential occurrences of hunger events as determined by analyzing said data.

Optionally, said stimulation device includes at least one sensor and said control device is configured to modify said stimulation parameters based on data received from said at least one sensor. The sensor may include any one or combination of a glucose sensor, a neural sensor, an accelerometer, an impedance sensor, and a bio-impedance sensor.

The present specification also discloses a device for providing electrical stimulation from the external surface of the patient's epidermal layer through 5 mm, 10 mm, 15 mm, 20 mm, 25 mm or any increment therein of the dermis comprising: a housing comprising a microprocessor, a wireless transceiver, a pulse generator, a power management module, and at least one electrode extending from within the housing or an external surface of the housing; at least one conductive pad configured to be in electrical communication with the electrode and be placed on a skin surface of a patient, wherein said at least one electrode is positioned such that an electrical field generated by said at least one electrode is shallow and widely distributed over said skin surface, wherein shallow is defined as a depth of no more than 25 mm from said skin surface and widely distributed is defined as at least an area of attachment of said at least one conductive pad to said skin surface, further wherein said device provides a maximum output voltage of 500 V and a maximum output current of 500 mA.

The pad may have a shape including any one of irregular, rectangular, circular, square, elliptical, and triangular and wherein, at its longest, a length of the pad ranges from 2 to 4 inches, at its widest, a width or diameter of said pad ranges from 1.25 to 3 inches, and a thickness of approximately 0.2 inches. In another embodiment, the electrode/pad combination may have a shape including any one of irregular, rectangular, circular, square, elliptical, and triangular and wherein, at its widest, would between 0.25 to 5 inches in width, at its tallest would be between 0.25 to 5 inches in height, and at its thickest would be between 0.25 to 5 inches in thickness. In another embodiment, the device would comprise two of such electrode/pad combinations placed side by side.

The present specification also discloses a device for treating a condition, including at least one of obesity, overweight, eating disorders, metabolic syndrome and diabetes in a patient, wherein said device is configured to deliver electrical stimulation from the external surface of the patient's epidermal layer through a range of 0.1 mm to 25 mm, or any increment therein, of the dermis by applying electrical stimulation to any one of an epidermis of a T2 frontal thoracic dermatome, an epidermis of a T3 frontal thoracic dermatome, an epidermis of a T4 frontal thoracic dermatome, an epidermis of a T5 frontal thoracic dermatome, an epidermis of a T6 frontal thoracic dermatome, an epidermis of a T7 frontal thoracic dermatome, an epidermis of a T8 frontal thoracic dermatome, an epidermis of a T9 frontal thoracic dermatome, an epidermis of a T10 frontal thoracic dermatome, an epidermis of a T11 frontal thoracic dermatome, and an epidermis of a T12 frontal thoracic dermatome of said patient, further wherein electrical stimulation is increased based on data from a first parameter and electrical stimulation is decreased based on data from a second parameter. The first parameter may include any one of appetite, hunger, weight, body mass index (BMI), and body fat and said second parameter may include any one of nausea, dyspepsia, heartburn, and sensation at the site of stimulation.

The present specification also discloses a device for treating a condition, including at least one of obesity, overweight, eating disorders, metabolic syndrome and diabetes in a patient, wherein said device is configured to deliver electrical stimulation from the external surface of the patient's epidermal layer through a range of 0.1 mm to 25 mm, or any increment therein, of the dermis by applying electrical stimulation to any one of an epidermis of a T2 frontal thoracic dermatome, an epidermis of a T3 frontal thoracic dermatome, an epidermis of a T4 frontal thoracic dermatome, an epidermis of a T5 frontal thoracic dermatome, an epidermis of a T6 frontal thoracic dermatome, an epidermis of a T7 frontal thoracic dermatome, an epidermis of a T8 frontal thoracic dermatome, an epidermis of a T9 frontal thoracic dermatome, an epidermis of a T10 frontal thoracic dermatome, an epidermis of a T11 frontal thoracic dermatome, and an epidermis of a T12 frontal thoracic dermatome of said patient, further wherein electrical stimulation is decreased based on data indicative of excessive appetite loss, excessive hunger loss, an actual weight less than a target weight, an actual caloric intake less than a target caloric intake, an actual BMI less than a target BMI.

The present specification also discloses a device for treating a condition, including at least one of obesity, overweight, eating disorders, metabolic syndrome and diabetes in a patient, wherein said device is configured to deliver electrical stimulation from the external surface of the patient's epidermal layer through a range of 0.1 mm to 10 mm or a range of 0.1 mm to 20 mm of the dermis by applying electrical stimulation to any one of an epidermis of a T2 frontal thoracic dermatome, an epidermis of a T3 frontal thoracic dermatome, an epidermis of a T4 frontal thoracic dermatome, an epidermis of a T5 frontal thoracic dermatome, an epidermis of a T6 frontal thoracic dermatome, an epidermis of a T7 frontal thoracic dermatome, an epidermis of a T8 frontal thoracic dermatome, an epidermis of a T9 frontal thoracic dermatome, an epidermis of a T10 frontal thoracic dermatome, an epidermis of a T11 frontal thoracic dermatome, and an epidermis of a T12 frontal thoracic dermatome of said patient, further wherein said patient is stimulated with a first stimulation algorithm to induce weight loss and a second stimulation algorithm to maintain weight loss, wherein a first total stimulation energy per day of said first stimulation algorithm is greater than a second total stimulation energy per day of said second stimulation algorithm.

The present specification also discloses a device for suppressing appetite or food cravings in a patient, said device comprising: a device body having a length no greater than 5 inches, a width no greater than 2 inches, and a height no greater than 1.5 inches, preferably no greater than 0.35 inches, and comprising a microprocessor, a wireless transceiver, a pulse generator, a power management module, and at least one electrode extending along a bottom surface of said device body; and wherein said device is configured to deliver electrical stimulation from the external surface of the patient's epidermal layer through a range of 0.1 mm to 10 mm or a range of 0.1 mm to 20 mm of the dermis by applying electrical stimulation to any one of an epidermis of a T2 frontal thoracic dermatome, an epidermis of a T3 frontal thoracic dermatome, an epidermis of a T4 frontal thoracic dermatome, an epidermis of a T5 frontal thoracic dermatome, an epidermis of a T6 frontal thoracic dermatome, an epidermis of a T7 frontal thoracic dermatome, an epidermis of a T8 frontal thoracic dermatome, an epidermis of a T9 frontal thoracic dermatome, an epidermis of a T10 frontal thoracic dermatome, an epidermis of a T11 frontal thoracic dermatome, and an epidermis of a T12 frontal thoracic dermatome of said patient; and wherein said device is programmed with a stimulation protocol for providing electrical stimulation to said patient, wherein said stimulation protocol is configured to provide stimulation non-continuously and for at least two stimulation sessions per week, wherein each of said stimulation sessions has an on period of 10 to 120 minutes or substantially continuously.

In some embodiments, the present specification is directed toward a method of modulating a patient's glucose level, the method comprising: providing an electrical dermal patch adapted to adhere to the patient's epidermal layer, wherein said electrical dermal patch comprises a controller, at least one electrode adapted to be in electrical contact with said patient's epidermal layer, and a pulse generator in electrical communication with the controller and said at least one electrode; defining a plurality of stimulation parameters; providing a glucose sensor to the patient for continuously monitoring said patient's glucose level in a closed loop configuration; and programming the pulse generator to generate a plurality of electrical pulses using said plurality of stimulation parameters, and stimulating said patient based on a threshold glucose level, wherein after applying at least one stimulation to the patient's epidermal layer, the patient's glucose level is modified, and wherein said modification may result in a modification of said stimulation.

Optionally, stimulation is stopped once a predefined lower glucose level is achieved.

Optionally, an optimal or intense stimulation protocol is initiated if the patient's glucose level is higher than a predetermined threshold level.

Optionally, after at least one stimulation session, the level of hemoglobin A1C decreases by at least 1% with a p value of 0.05.

Optionally, after at least one stimulation session, the level of hemoglobin A1C is completely normalized.

Optionally, after at least one stimulation session, the level of hemoglobin A1C is ≤7.0%.

In some embodiments, the present specification discloses a method of modulating a patient's will power reserve, the method comprising: providing an electrical dermal patch adapted to adhere to the patient's epidermal layer, wherein said electrical dermal patch comprises a controller, at least one electrode adapted to be in electrical contact with said patient's epidermal layer, and a pulse generator in electrical communication with the controller and said at least one electrode; defining a plurality of stimulation parameters; and programming the pulse generator to generate a plurality of electrical pulses using said plurality of stimulation parameters, wherein said plurality of stimulation parameters are defined such that, after applying at least one stimulation to the patient's epidermal layer, the patient's will power reserve is modified, and wherein said will power reserve is a function of any one or a combination of at least the patient's hunger score, dietary compliance, level of exercise, appetite control, amount of calories consumed, type of calories consumed, timing of meals, and weight. Optionally, said will power reserve is an inverse function of hunger score.

Optionally, said will power reserve is a composite function of dietary will power and exercise will power, wherein said dietary will power is either an inverse function of hunger score or a directly proportional function of dietary compliance, and wherein said exercise will power is a directly proportional function of level of exercise.

Optionally, said dietary will power is a directly proportional composite function of dietary compliance and appetite control, and wherein said dietary compliance is a function of at least the amount of calories consumed and the type of calories consumed.

Optionally, one or both of the following occurs if the patient's appetite control and dietary compliance are low: a dietary will power graph is displayed to be in red zone, the electro dermal patch flashes red color using at least one LED.

Optionally, one or both of the following occurs if the patient's appetite control and dietary compliance increases: a dietary will power graph is displayed to be in yellow zone, the electro dermal patch flashes yellow color using at least one LED.

Optionally, one or both of the following occurs if the patient's appetite control and dietary compliance are high: a dietary will power graph is displayed to be in green zone, the electro dermal patch flashes green color using at least one LED.

Optionally, said will power reserve is an inverse function of an urge to eat profile of the patient, and wherein said urge to eat profile is a function of at least one of amount of calories consumed, type of calories consumed, timing of meals.

Optionally, said will power reserve is a composite function of at least two of amount of calories consumed, type of calories consumed, timing of meals, level of exercise, weight.

Optionally, said will power reserve is a composite function of hunger score improvement, dietary compliance and level of exercise.

Optionally, the patient is periodically presented with VAS light bars to record the patient's inputs related to success in maintaining a diet plan, success in limiting out-of-meal plan snacking, success in eating healthy foods, and success in controlling hunger.

Optionally, said will power reserve also includes at least one of bonus points earned for each hunger rescue bolus, bonus points earned for exercising, bonus points earned for filling out the patient's daily diary, bonus points earned for favorable daily weight change, bonus points earned for positive coaching of other patients within the patient's social network group.

Optionally, the patient provides input on a displayed light bar VAS to assess dietary will power on a periodic basis.

Optionally, the patient's will power reserve is displayed in the form of a graph.

Optionally, the patient is a member of an affinity group comprising a plurality of members, each of said members having an associated will power reserve profile generated from archived daily will power reserve of each member over a period of time. Optionally, a collective will power reserve of said affinity group is determined based on will power reserve of each member of the affinity group. Optionally, the collective will power reserve is an average of the will power reserve of each member of the affinity group.

Optionally, a member with at least a predefined minimum will power reserve is allowed to coach other members.

Optionally, a member's will power reserve above a predefined threshold results in at least one reward for the member.

Optionally, a member is allowed to subscribe to dietary plans, exercise regimes, and/or stimulation parameters of other members who have attained a predefined threshold will power reserve.

Optionally, a member's will power reserve enables the member to accumulate points and bonuses corresponding to a degree of will power reserve, and use said points and bonuses to earn a plurality of rewards and participate in games among members of the affinity group.

In some embodiments, the present specification discloses a method of stimulating a patient's somatovisceral reflex system comprising: providing an electrical dermal patch adapted to adhere to the patient's epidermal layer, wherein said electrical dermal patch comprises a controller, at least one electrode adapted to be in electrical contact with said patient's epidermal layer, and a pulse generator in electrical communication with the controller and said at least one electrode; defining a plurality of stimulation parameters; and programming the pulse generator to generate a plurality of electrical pulses using said plurality of stimulation parameters, wherein said plurality of stimulation parameters are defined such that, after applying at least one stimulation to the patient's epidermal layer, at least one of the patient's antral motility, gastric emptying, appetite, weight, ghrelin, insulin, and glycemia is modified.

Optionally, the stimulation of the patient's somatovisceral reflex system involves delivering said plurality of electrical pulses to at least one of the following dermatomes: T2-T12, C5-T1.

Optionally, the stimulation of the somatovisceral reflex system is enhanced by coinciding stimulation sessions with pre-prandial and/or post-prandial windows.

Optionally, said pre-prandial window relates to a first period involving secretion of ghrelin just prior to anticipated eating, and wherein said post-prandial window relates to a second period involving digestive activity after a meal.

Optionally, said first period spans approximately 60 minutes prior to anticipated eating, and wherein said second period spans approximately 2 hours after a meal.

Optionally, said first period spans approximately 60 minutes prior to anticipated eating, and wherein said second period spans approximately 60 minutes after a meal.

In some embodiments, the present specification discloses a method of modulating at least one of a person's appetite, hunger, satiety level, or satiation comprising: providing an electrical dermal patch adapted to adhere to the person's epidermal layer, wherein said electrical dermal patch comprises a controller, at least one electrode adapted to be in electrical contact with said person's epidermal layer, and a pulse generator in electrical communication with the controller and said at least one electrode; defining a first plurality of stimulation parameters, wherein said first plurality of stimulation parameters comprises a treatment session duration, a stimulation amplitude, and frequency of treatment sessions; generating a plurality of electrical pulses using said first plurality of stimulation parameters, wherein said first plurality of stimulation parameters are defined such that, after applying at least one stimulation to the patient's epidermal layer, at least one of the patient's appetite, hunger, satiety level, and satiation level is modified; using an application installed on a device separate from the electrical dermal patch to acquire data, said data being indicative of at least one of the person's appetite, hunger, satiety level, satiation level, fullness level, amount of caloric intake, weight, type of caloric intake, and timing of caloric intake; generating a signal, using said application, based upon said data; and causing the signal to be transmitted to the electrical dermal patch.

Optionally, the treatment session duration is in a range of 20 to 40 minutes.

Optionally, the stimulation amplitude is in a range of 10 mA to 30 mA.

Optionally, the frequency of treatment sessions is three times per day.

Optionally, the frequency of treatment sessions is configured to initiate in a range of 20 minutes to 90 minutes before the person's mealtimes.

Optionally, the application is configured to generate a graphical user interface comprising a visual bar and configured to receive, from the person, an input modifying a position of the visual bar based on a hunger level of the person and wherein, upon modifying the position of the visual bar, the application is configured to modify one or more of said first plurality of stimulation parameters.

Optionally, the device separate from the electrical dermal patch is at least one of a mobile phone, tablet computer, intelligent personal assistant, chat robot, chatter robot, chatterbot, chat bot, artificial conversational entities, artificial intelligence agent, talk bot, and chatterbox.

In some embodiments, the present specification discloses a method for enabling a TPM to prescribe, configure, manage, monitor and intervene an EDP device based stimulation therapy for a user.

Optionally, a user visits his TPM for a medical check-up or evaluation. Optionally, the TPM recommends an EDP device of the present specification to the user based on the user's medical condition, such as for example obesity or over-weight.

Optionally, the TPM downloads the HMA on the user's smartphone (that works as a companion device).

Optionally, the TPM assists the user in identifying appropriate areas of stimulation (and therefore, placement of the EDP device on the user's body), such as T6, C8 and/or T1 dermatomes for conditions of obesity, over-weight, eating disorders, metabolic syndrome and T7 for T2DM management, and also provides an orientation to the user regarding use and functions of the electro-dermal patch device. The EDP device is positioned on the identified location on the user's body.

Optionally, the TPM associates or links himself to the user, the user's EDP device and HMA, such as, by inputting his unique code into the user's HMA. Still optionally, the TPM pairs or syncs the user's smartphone with the user's EDP device.

Optionally, the TPM configures or programs the stimulation protocols and parameters, including various associated thresholds, ranges, related to planned therapy sessions as well as unplanned on-demand rescue sessions. The TPM may, optionally, also prescribe a low calorie planned diet for the user. Optionally, the HMA acknowledges that the configuration (by the TPM) is successful and the EDP device also optionally acknowledges successful configuration by, for example, vibratory, auditory and/or visual indications or signals (such as flashing LEDs of a specific color).

Optionally, the TPM delivers a first planned therapy session to the user in the presence of the TPM to ensure that the HMA or therapy configuration is conducive to the user.

Optionally, if the user feels fine after the first session, the user is allowed to leave to continue the therapy at home or if the user reports inconvenience or deterioration in well-being, such as due to a feeling of nausea, the TPM reprograms the stimulation protocols and parameters.

Optionally, at home, the user continues with the stimulation therapy and generates a plurality of health related information (such as, but not limited to, the user's weight, scores related to appetite, hunger, exercise, well-being (well-being profile including recorded nausea and/or dyspepsia events), values related to calories consumed, and individualized hunger profile (as a result of recorded unplanned hunger events and delivered rescue sessions) during therapy.

Optionally, if and when needed, the TPM modulates the stimulation parameters and protocols, for both planned as well as rescue sessions, based on the plurality of user's health related information while the user is continuing with the stimulation therapy at home. Optionally, the TPM also intervenes, by re-setting or reprogramming the EDP device and HMA and/or deactivating and reactivating the EDP device, when needed. Optionally, the user's stimulation is stopped, paused and/or the user prompted to revisit his TPM for re-evaluation of his medical condition or progress.

Optionally, a user has a plurality of options for purchasing the EDP device along with the TPM's services. Optionally, the TPM's fee schedule is enforced through his unique code that is valid only for the predefined period of time. Optionally, the TPM's fee is linked to the user achieving one or more therapeutic goals within a period of time.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 4A is a perspective view of an electro-dermal patch device configured to provide electrical stimulation therapy, in accordance with some embodiments;

FIG. 4B is a side perspective view of an electro-dermal patch device, in accordance with another embodiment of the present specification;

FIG. 4C is a bottom perspective view of the electro-dermal patch device of FIG. 4B;

FIG. 5E is a side cross-sectional view of the EDP device of FIG. 5D;

FIG. 5F is a top perspective view of the EDP device of FIG. 5A with the entire overmold removed;

FIG. 6A illustrates an electro-dermal patch device of the present specification, configured as a skin patch, placed at a lateral thoracic dermatome and being wirelessly controlled by a smartphone, in accordance with various embodiments;

FIG. 6D is a flow chart illustrating the steps involved in using one or more downloadable applications to configure and reconfigure stimulation provided by an electro-dermal patch (EDP) device, in accordance with one embodiment of the present specification;

FIG. 7 is a screen shot of a companion device depicting a diary widget, in accordance with one embodiment of the present specification;

FIG. 8 is a screen shot of a companion device depicting a list view of diary entries, in accordance with one embodiment of the present specification;

FIG. 11 is a screen shot of a companion device depicting an appetite entry screen, in accordance with one embodiment of the present specification;

FIG. 12 is a screen shot of a companion device depicting an exercise entry screen, in accordance with one embodiment of the present specification;

FIG. 13 is a screen shot of a companion device depicting a hunger entry screen, in accordance with one embodiment of the present specification;

FIG. 14 is a screen shot of a companion device depicting a stimulation session entry screen, in accordance with one embodiment of the present specification;

FIG. 15 is a screen shot of a companion device depicting a weight entry screen, in accordance with one embodiment of the present specification;

FIG. 16 is a screen shot of a companion device depicting a well-being entry screen, in accordance with one embodiment of the present specification;

FIG. 18A illustrates T6 stimulation using an electro-dermal patch device, in accordance with certain embodiments;

FIG. 18B illustrates T7 stimulation using an electro-dermal patch device, in accordance with certain embodiments;

FIG. 18C illustrates T6 and T7 stimulation using an electro-dermal patch device, in accordance with certain embodiments;

FIG. 19A illustrates C8 stimulation position of the ventral or front (palm) side of a user's hand using an electro-dermal patch, in accordance with certain embodiments;

FIG. 19B illustrates C8 stimulation position of the dorsal or back side of the user's hand using an electro-dermal patch, in accordance with certain embodiments;

FIG. 19C illustrates C8 and T1 stimulation position of the ventral side of the user's lower arm or wrist regions using an electro-dermal patch, in accordance with certain embodiments;

FIG. 35A is a Visual Analogue Scale (VAS) questionnaire for assessing a feeling of hunger or appetite, in accordance with an embodiment;

FIG. 35B is a VAS questionnaire for assessing a feeling of fullness, in accordance with an embodiment;

FIG. 35C is a VAS questionnaire for assessing a feeling of satiation, in accordance with an embodiment;

FIG. 35D is a VAS questionnaire for assessing a feeling of satiety, in accordance with an embodiment;

FIG. 39 is a side view illustration of an EDP device, in accordance with a less preferred embodiment;

FIG. 40 is a side view illustration of another EDP device, in accordance with a less preferred embodiment;

FIG. 42 is a side view illustration of yet another EDP device, in accordance with a less preferred embodiment;

FIG. 43 is an illustration of a percutaneous multi-electrode array that may be employed with the devices of the present specification;

FIG. 44 is a block diagram of a mobile electronics platform that may be employed with the devices of the present specification;

FIG. 45 is an illustration of an EDP device that receives wireless energy for stimulation, in accordance with a less preferred embodiment;

FIG. 46 is an illustration of another EDP device that receives wireless energy for stimulation, in accordance with a less preferred embodiment;

FIG. 47A is a bar graph illustrating mean cumulative changes of antral motility indices for various stimulation sessions, in accordance with an embodiment;

FIG. 47B is a bar graph illustrating maximum plasma endorphin levels measured for various stimulation sessions, in accordance with an embodiment;

FIG. 48A is a block diagram illustration of a Health Management Application (HMA) in communication with an Intelligent Personal Assistant (IPA) system, in accordance with embodiment;

FIG. 48B is a block diagram illustration of the HMA in communication with the IPA system, in accordance with another embodiment;

FIG. 48C is a block diagram illustration of the HMA, of the present specification, in communication with the IPA system as well as a Big Data database server, in accordance with an exemplary embodiment;

FIG. 49 is a flow chart illustrating exemplary steps involved in one embodiment of a method of using an electro-dermal patch device to automatically drive rescue therapy based on the user's individualized hunger profile or map;

FIG. 50 is a flow chart illustrating exemplary steps involved in one embodiment of a method of using an electro-dermal patch device to automatically titrate therapy based on the user's dynamic well-being profile;

Figure 51:
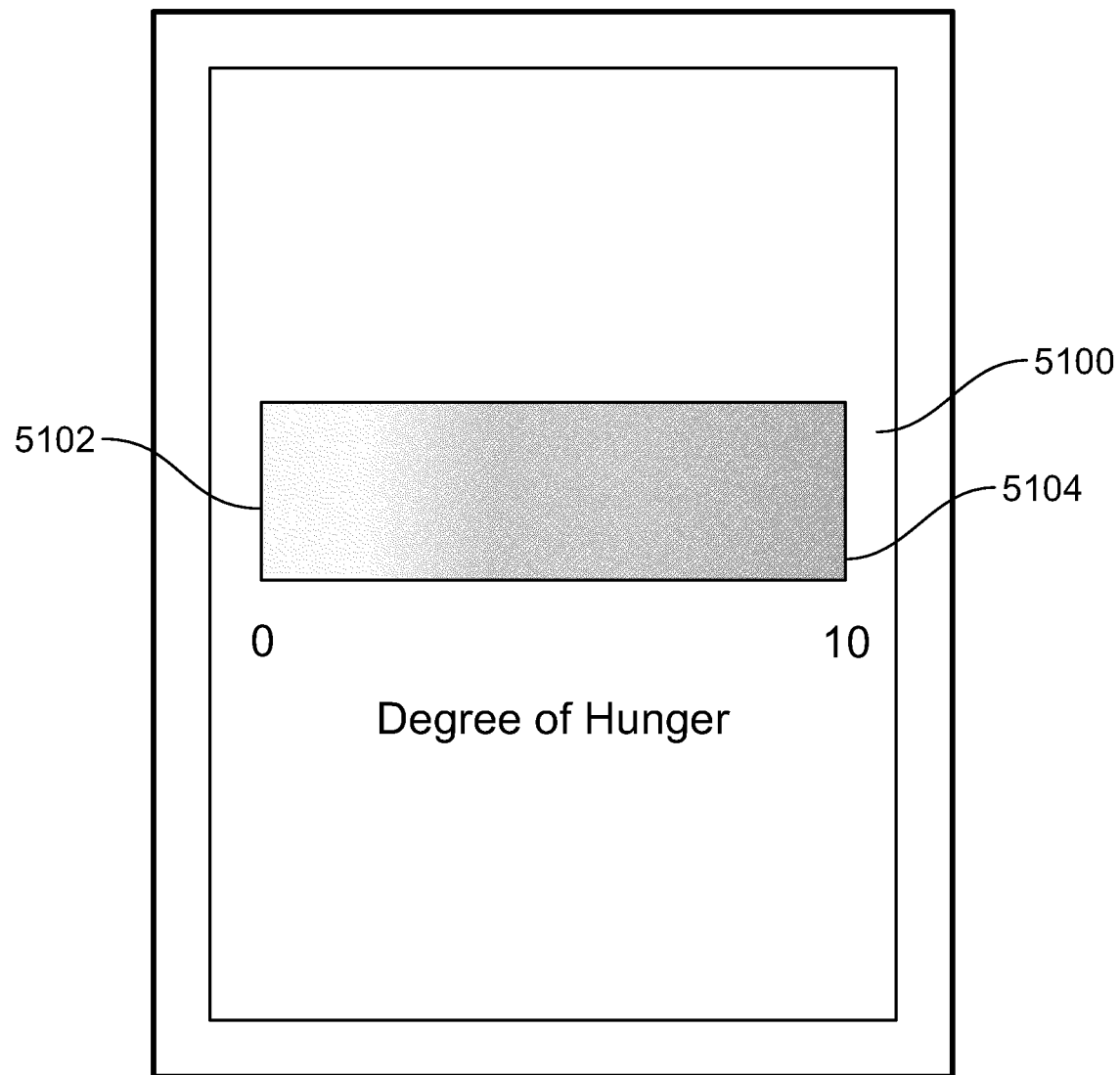
Figure 52:
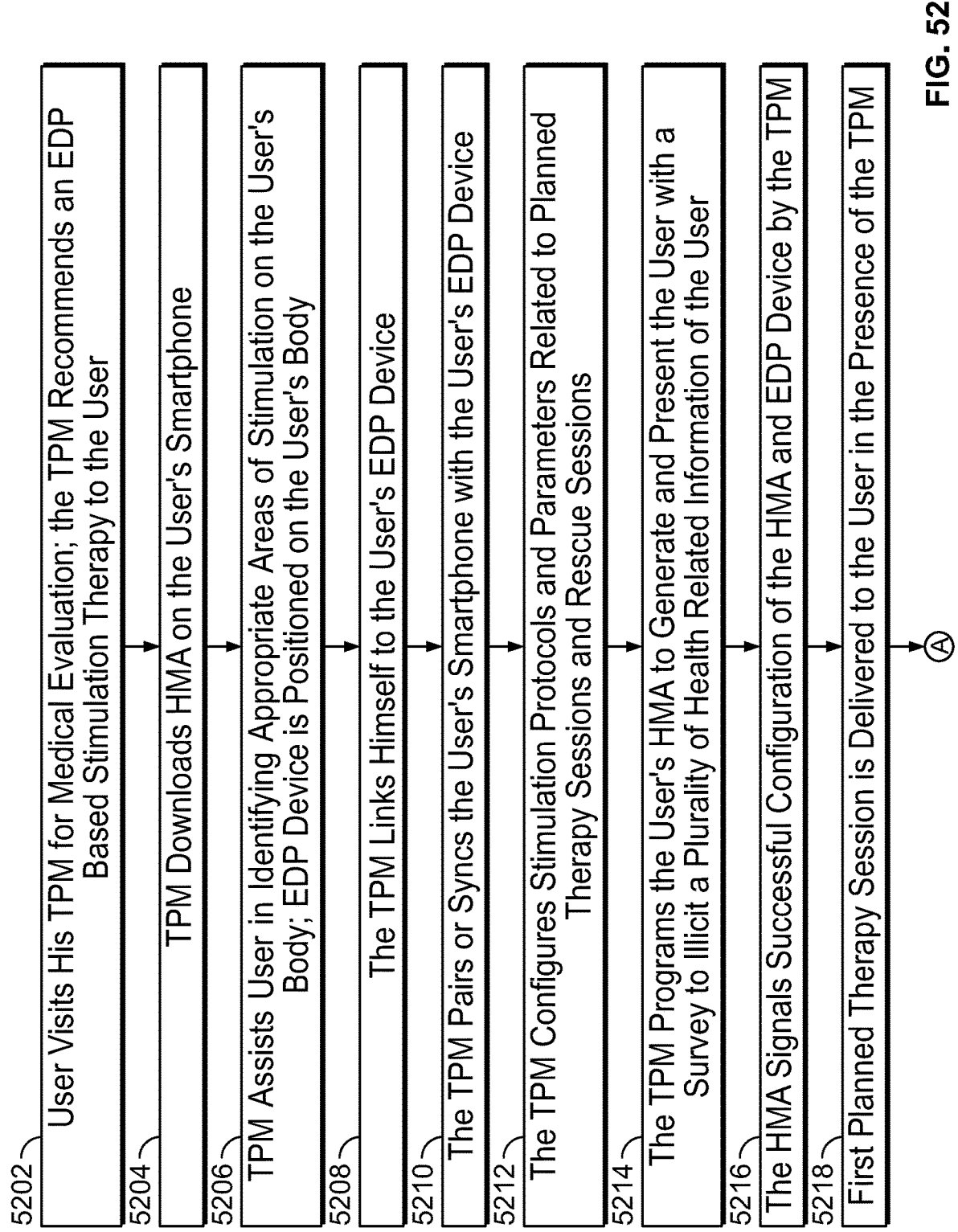
Figure 52:
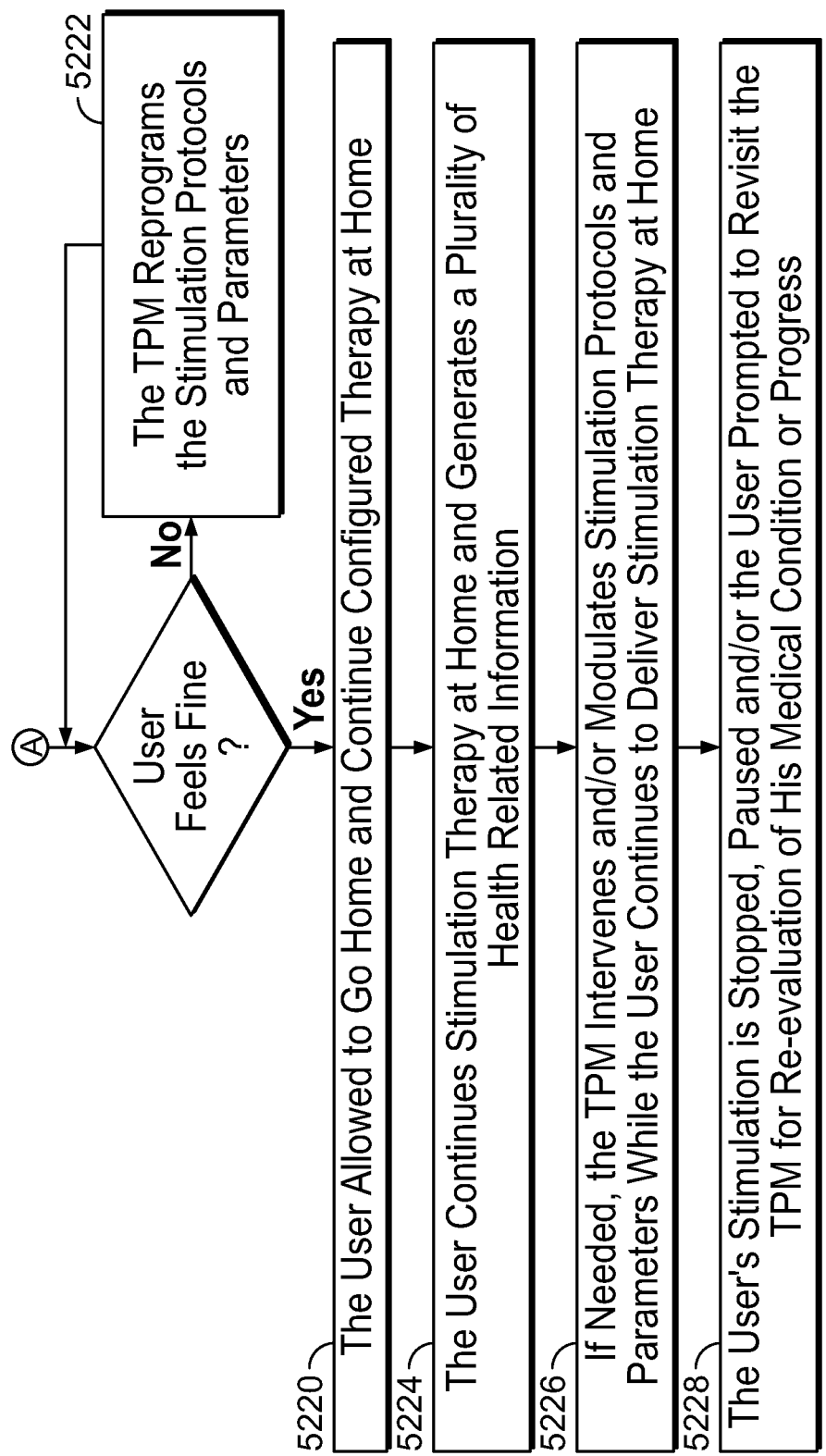
Figure 54B:
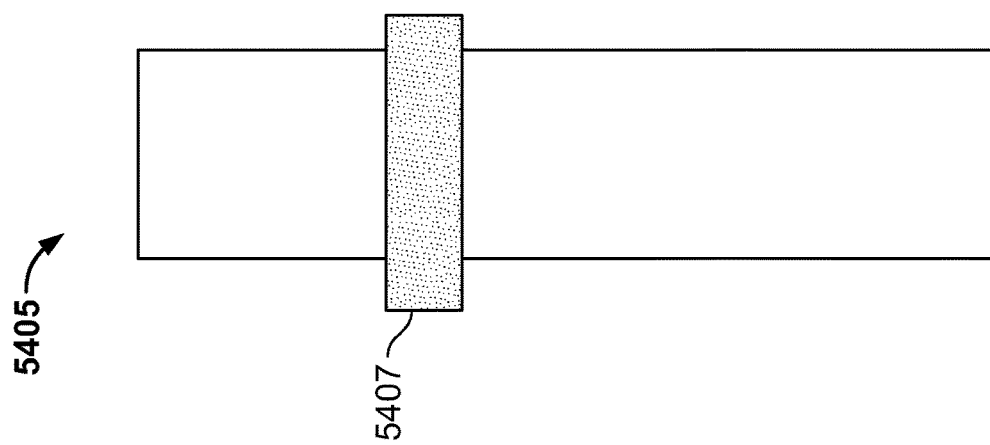
Figure 54A:
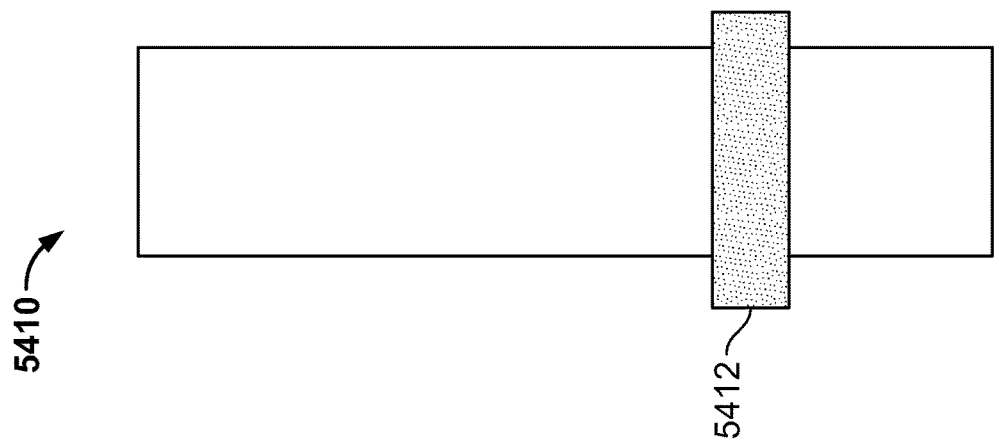
Figure 55A:
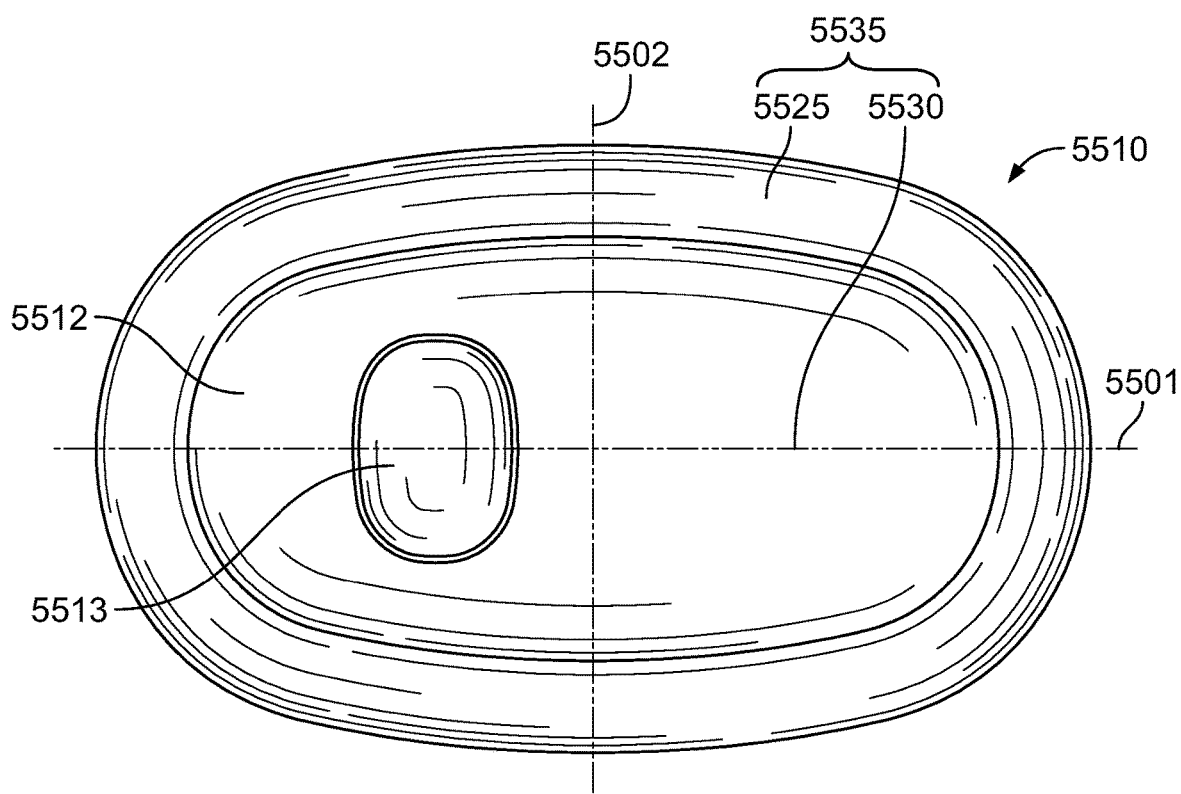
Figure 55B:
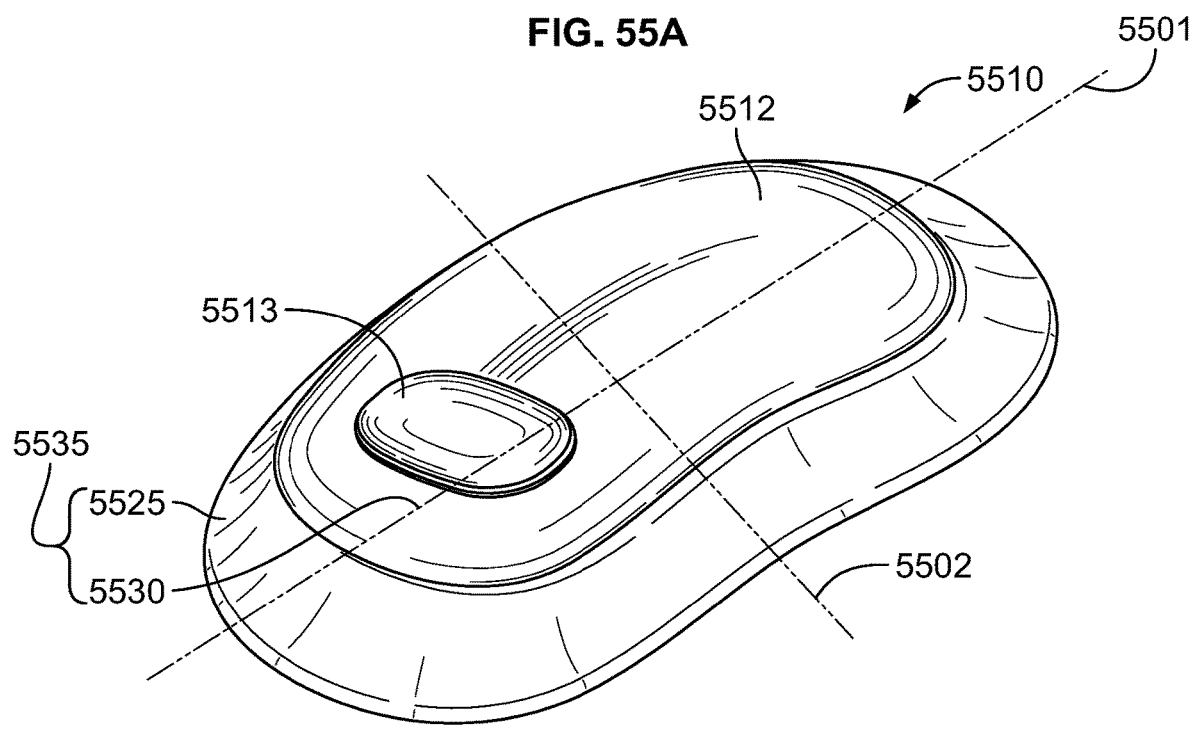
Figure 55C:
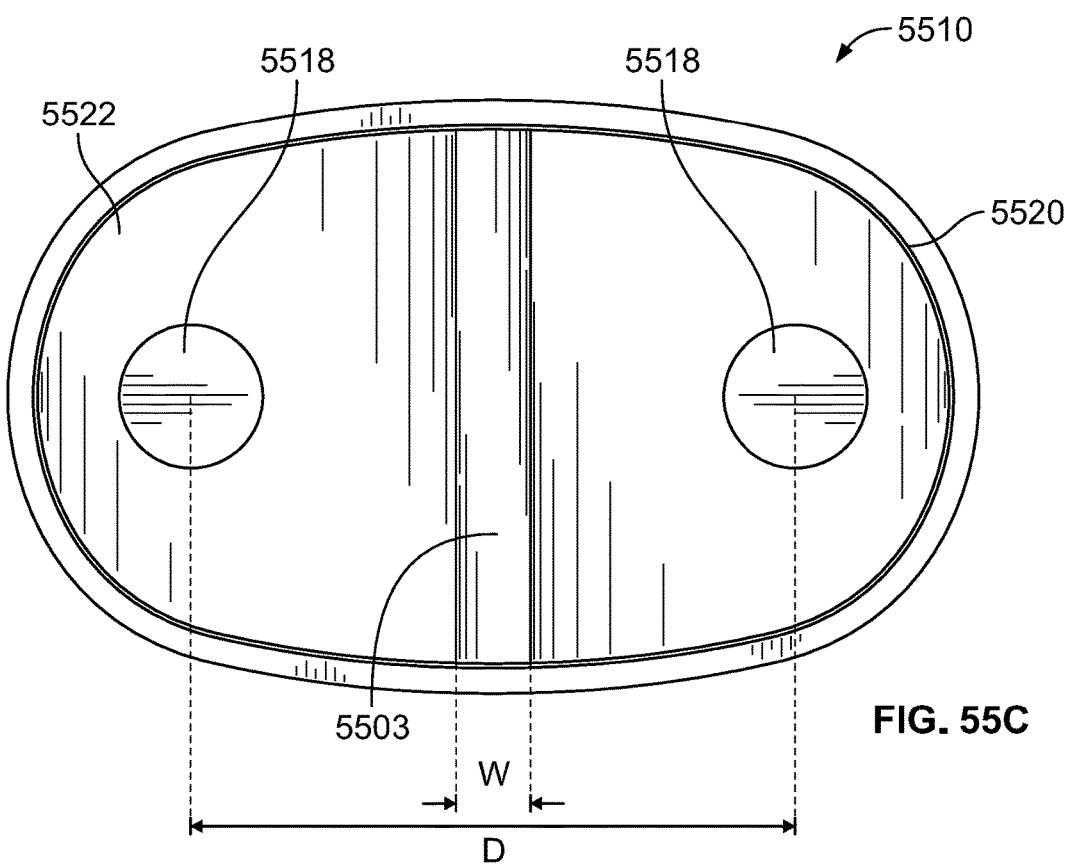
Figure 55D:
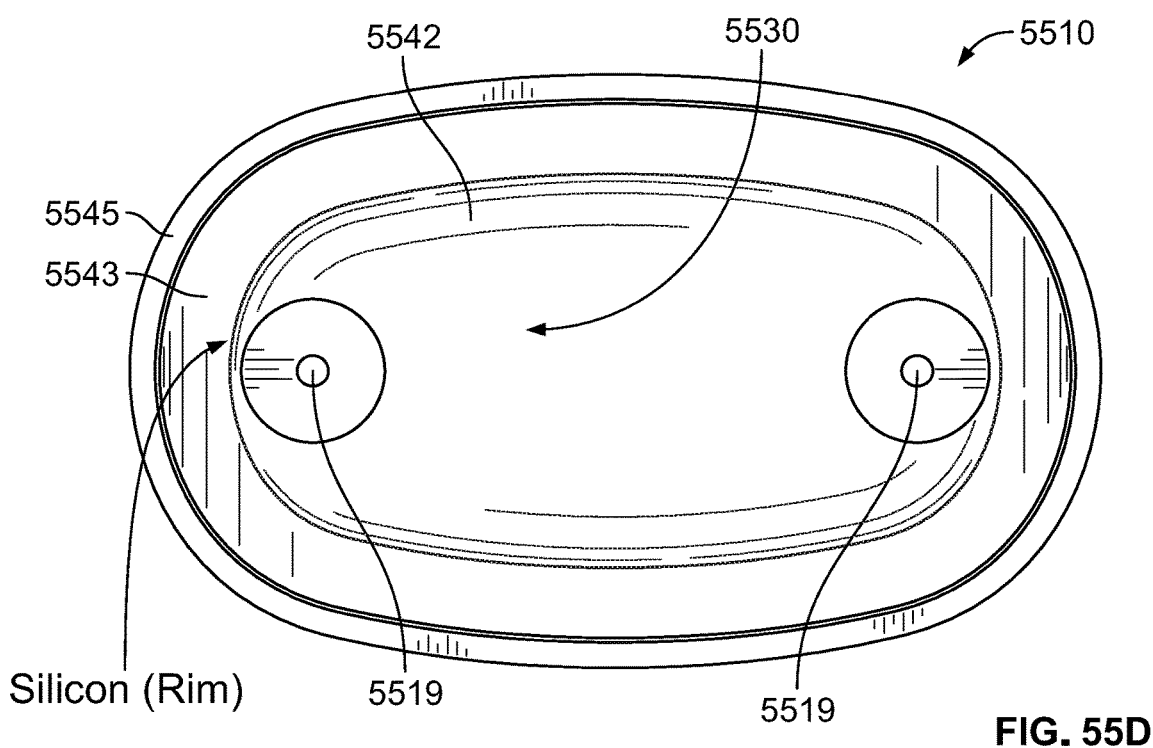
Figure 55E:
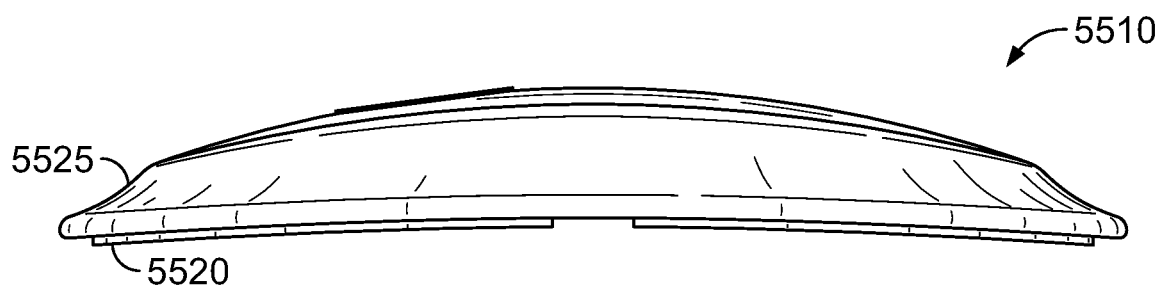
Figure 55F:
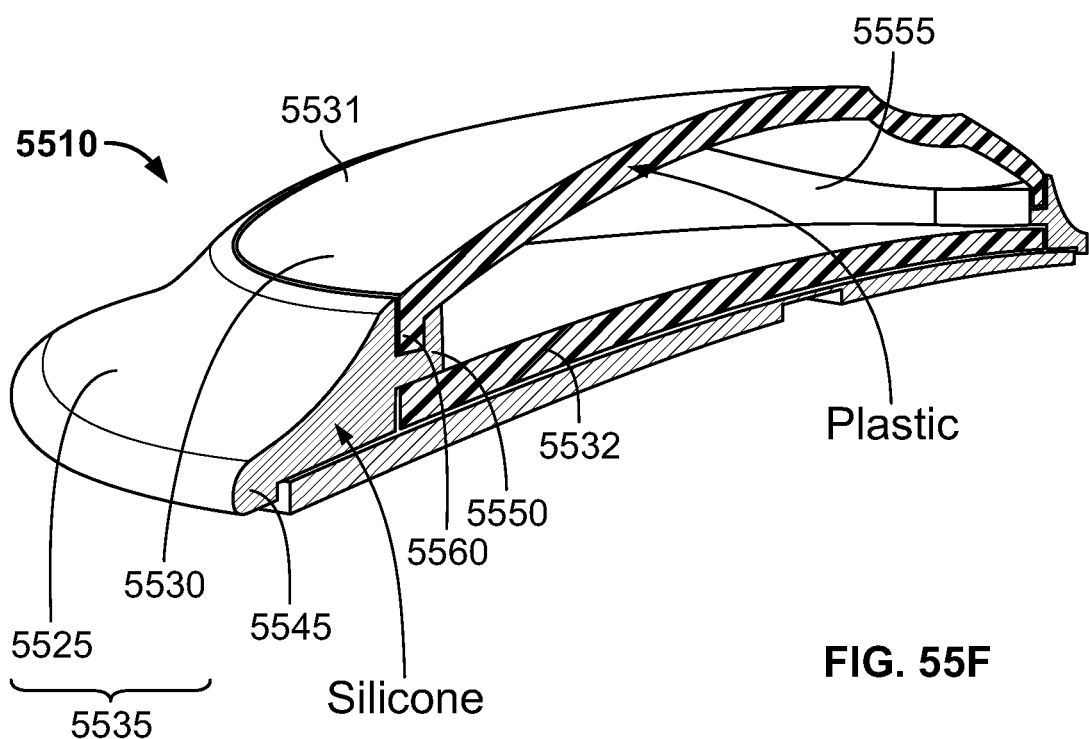
Figure 55G:
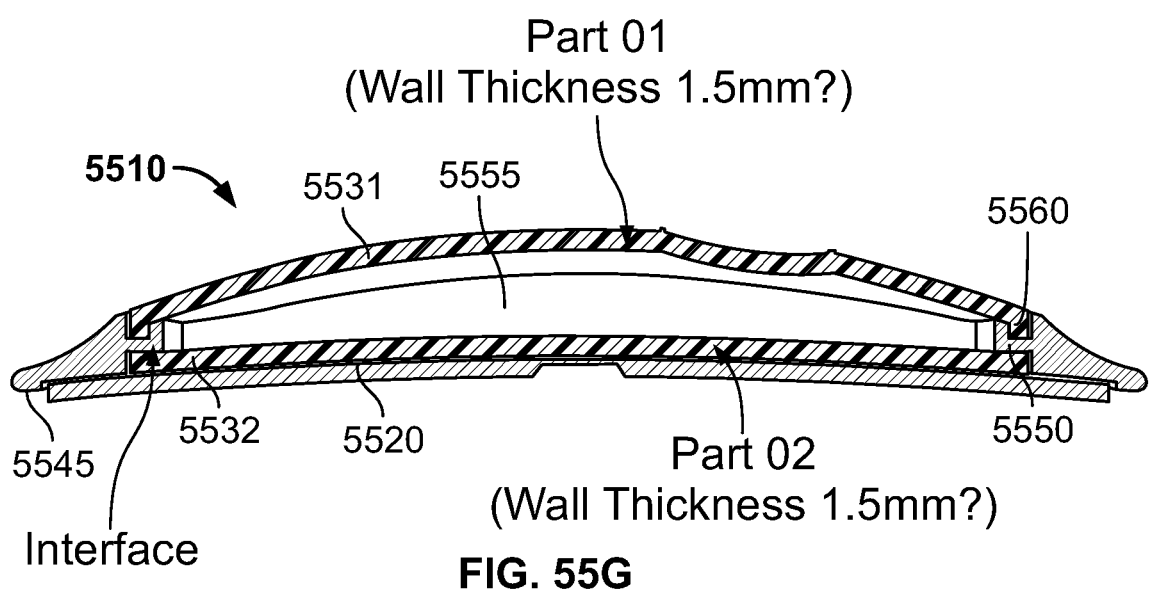
Figure 55H:
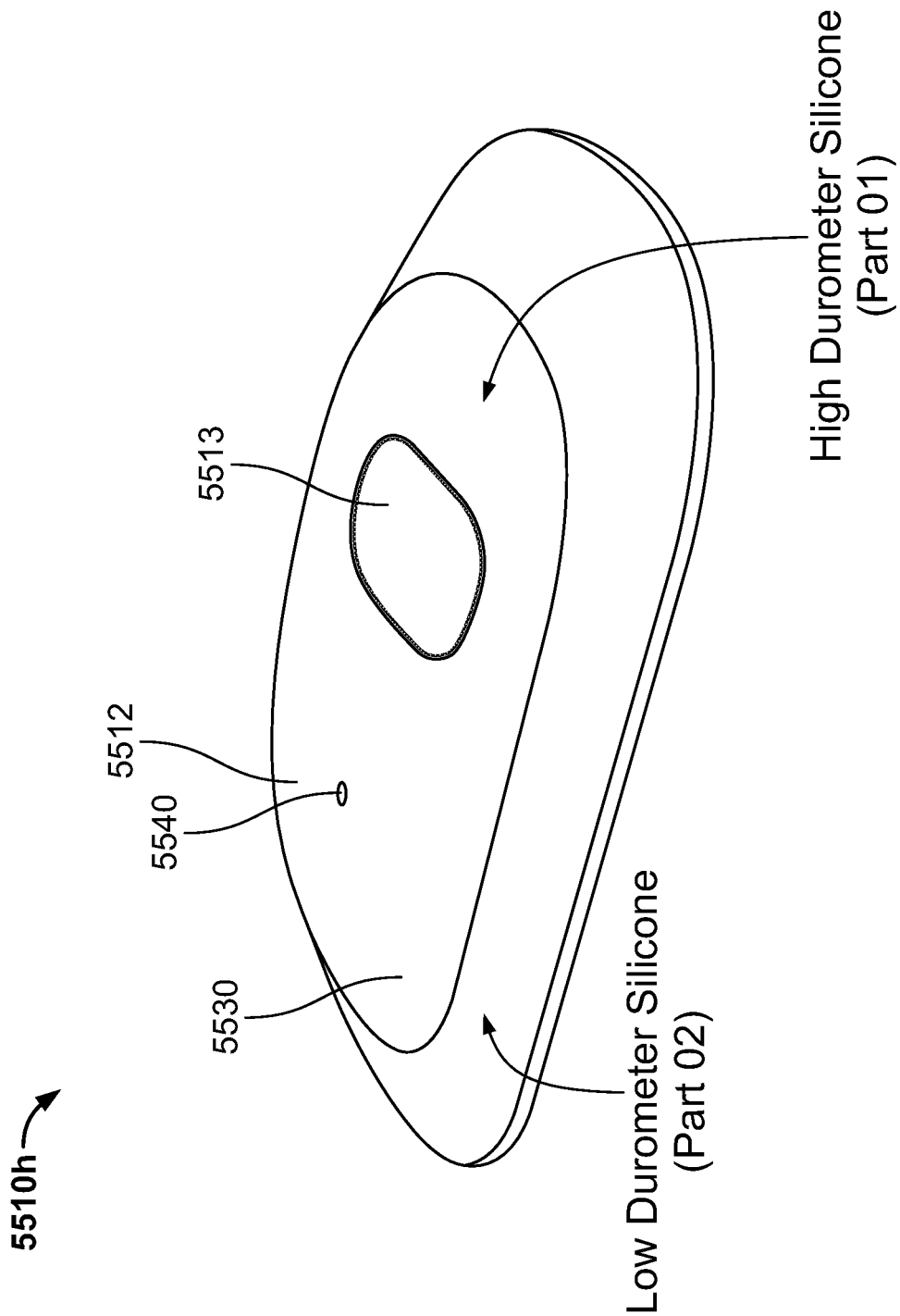
Figure 55I:
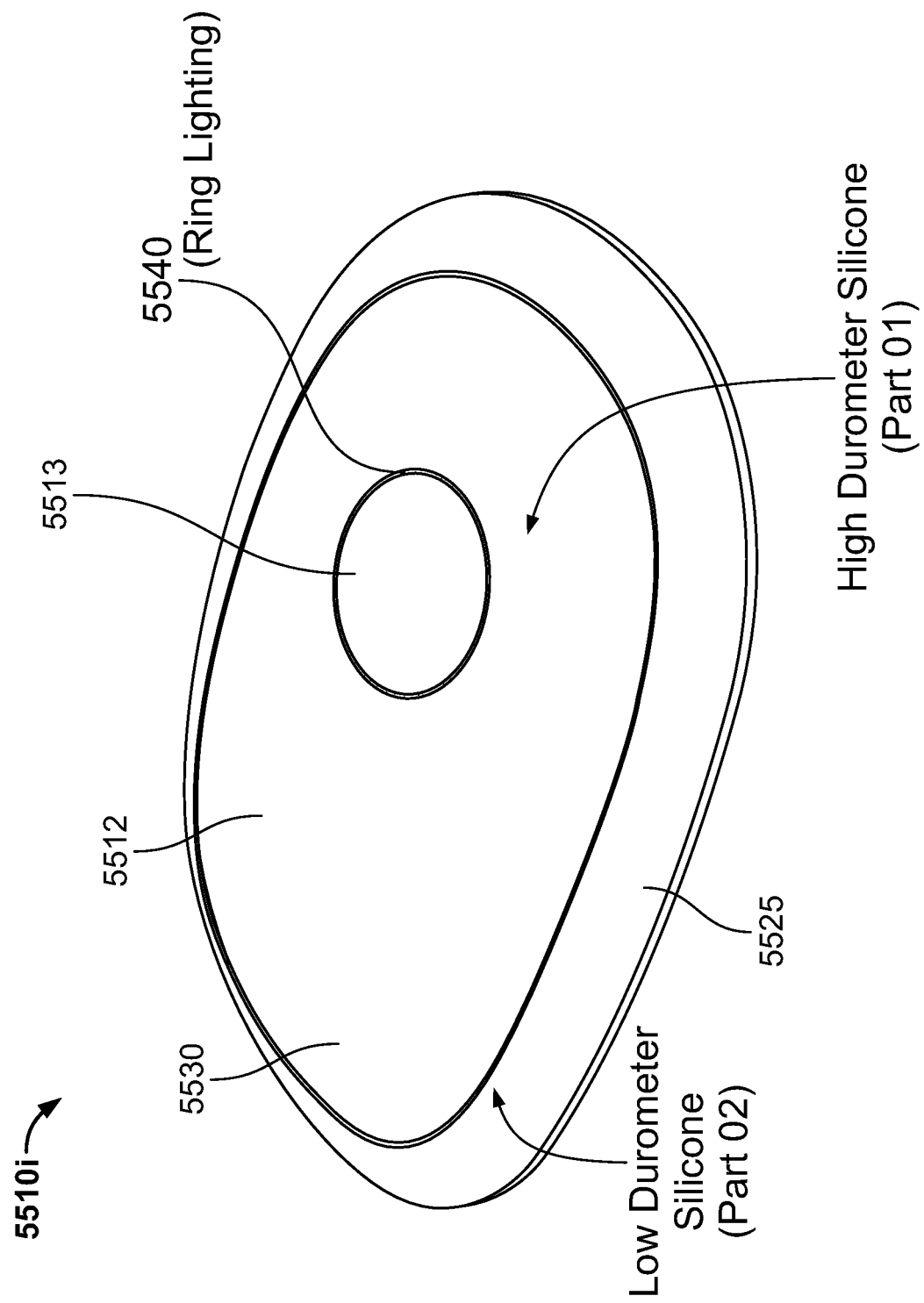
Figure 55L:
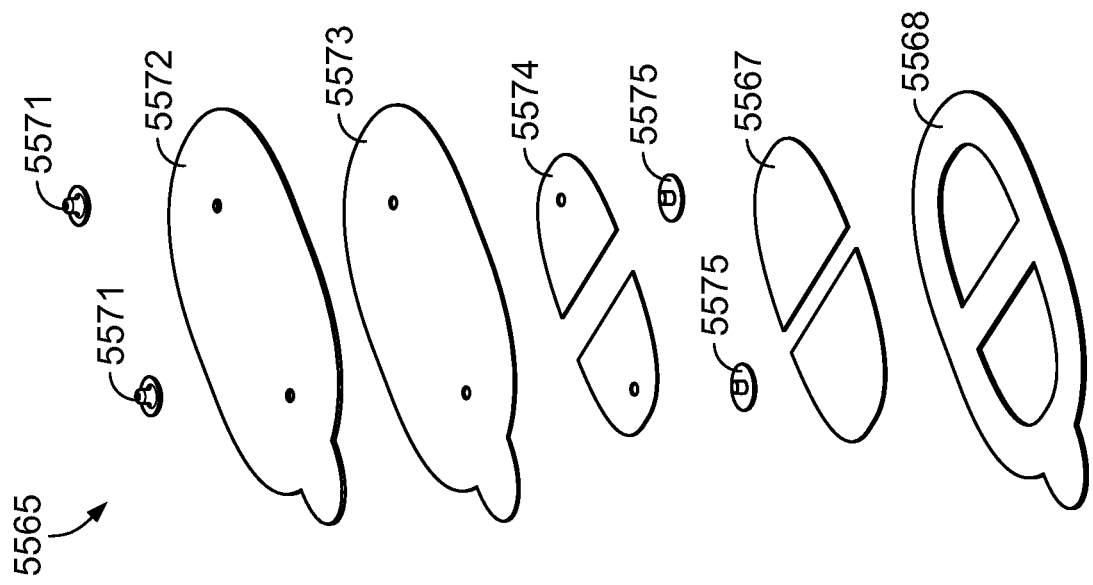
Figure 55K:
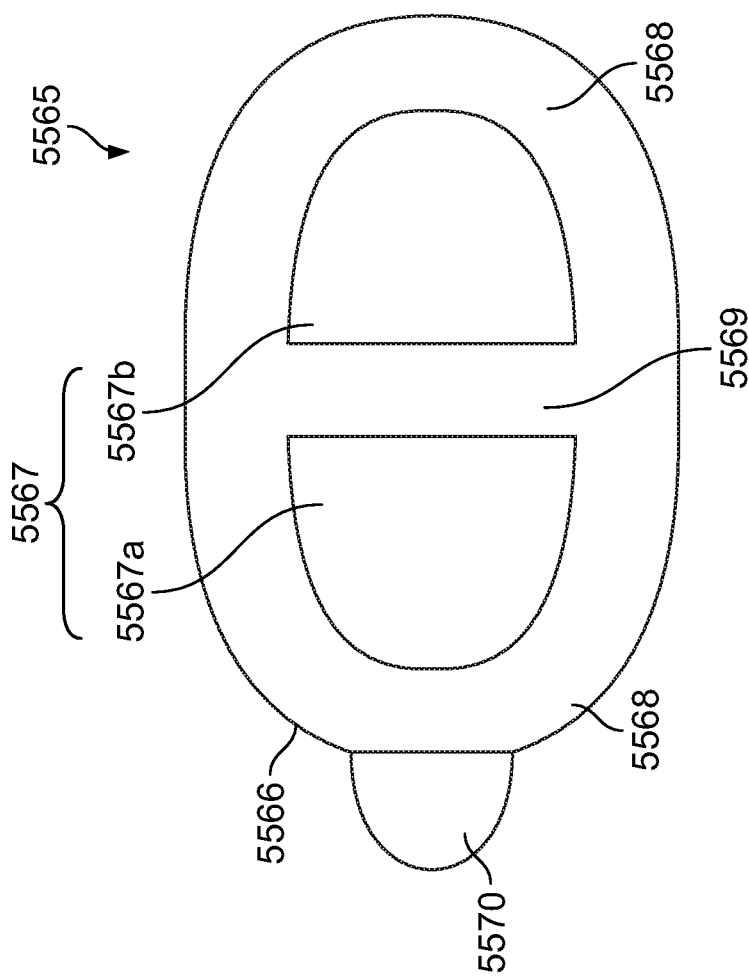
Figure 55M:
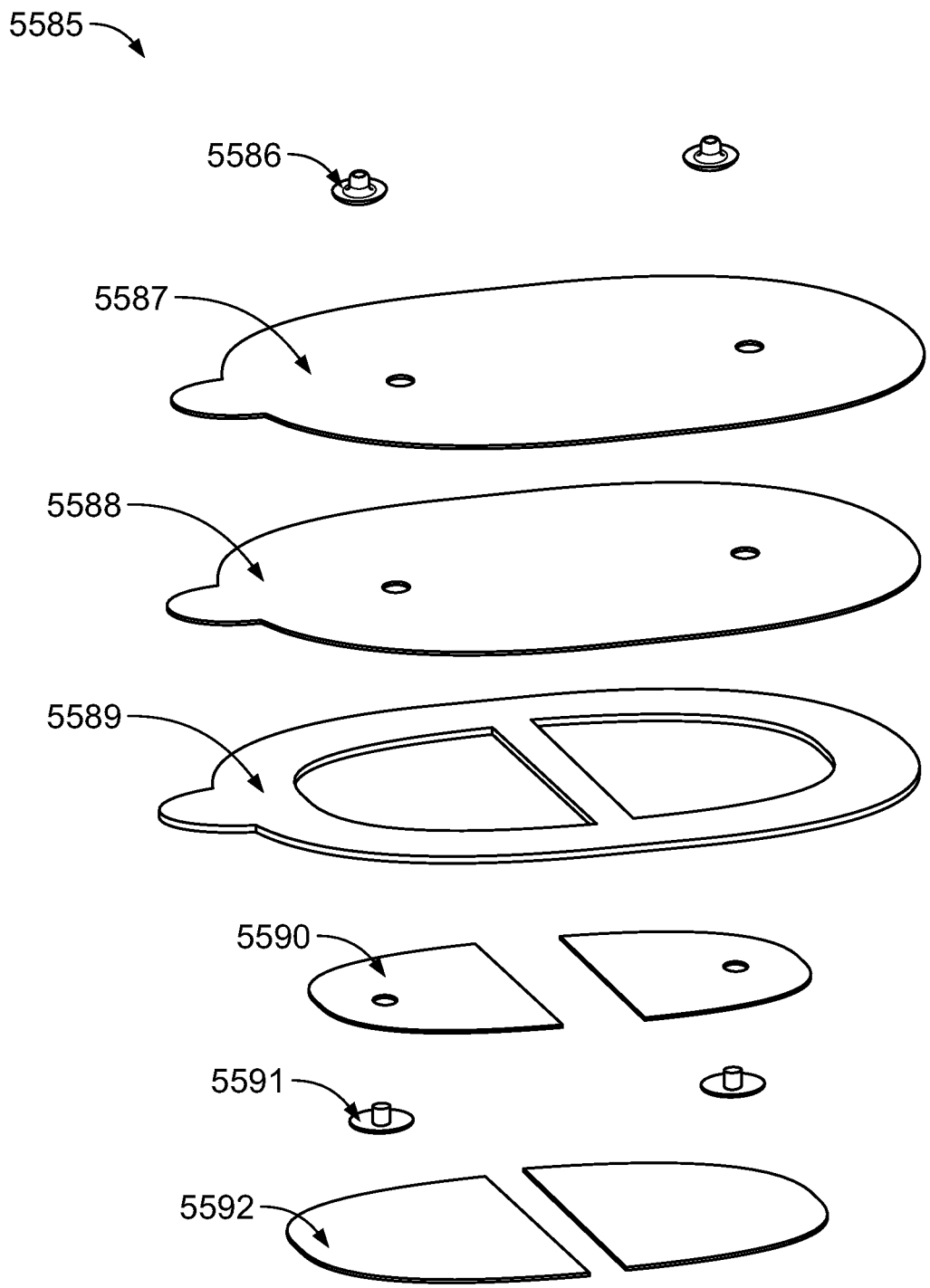
Figure 56:
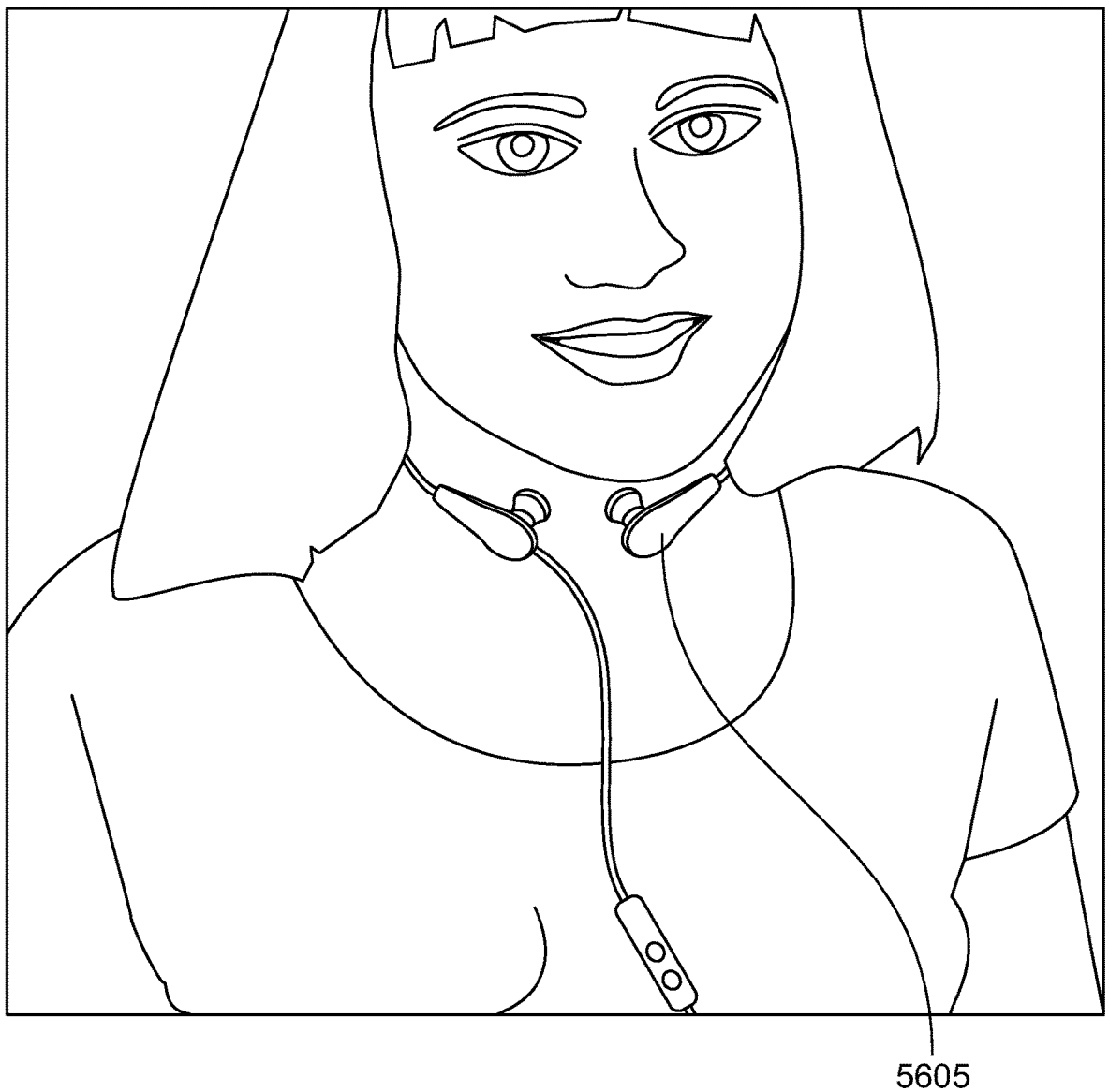
Figure 57:
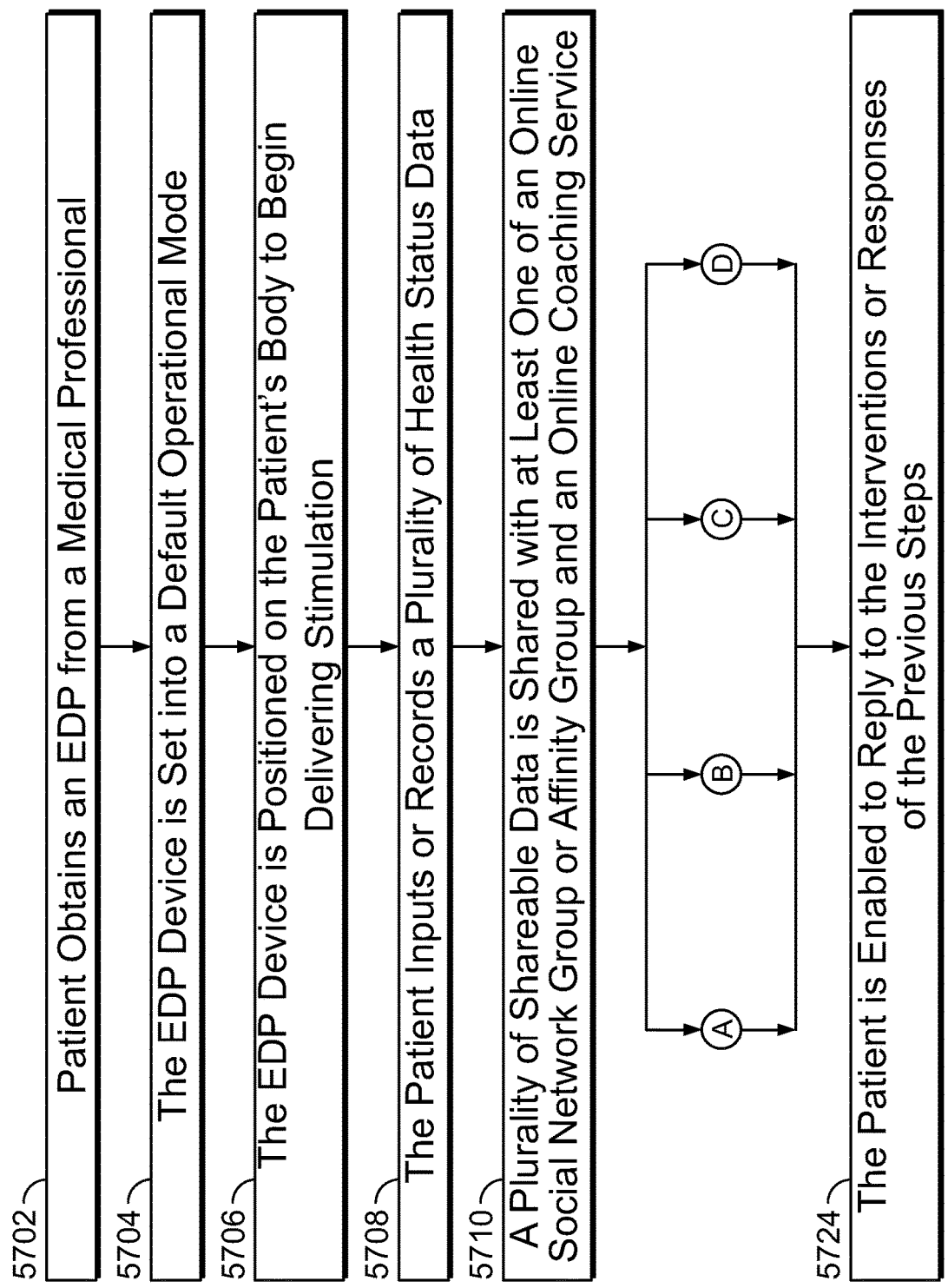
Figure 57:
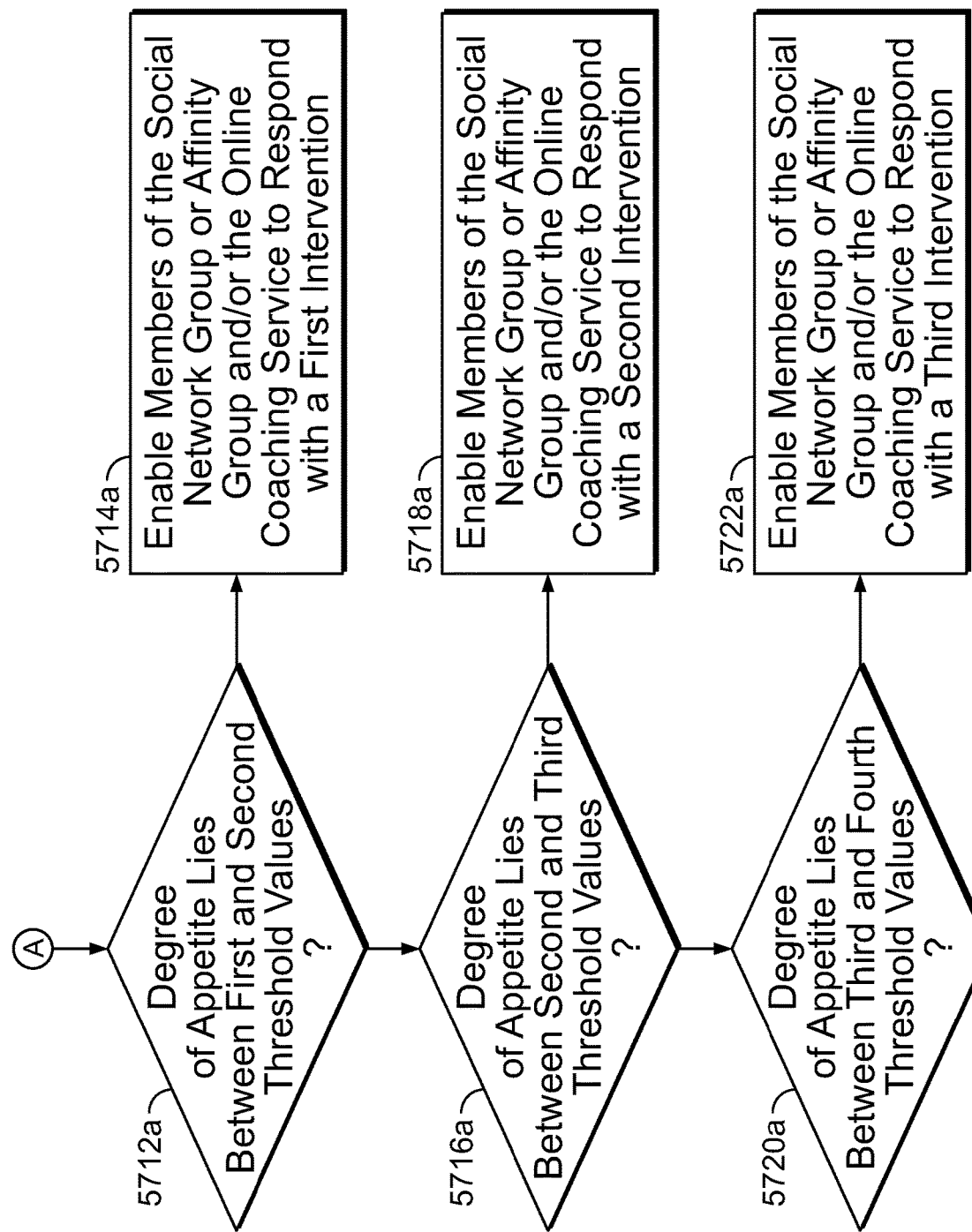
Figure 57:
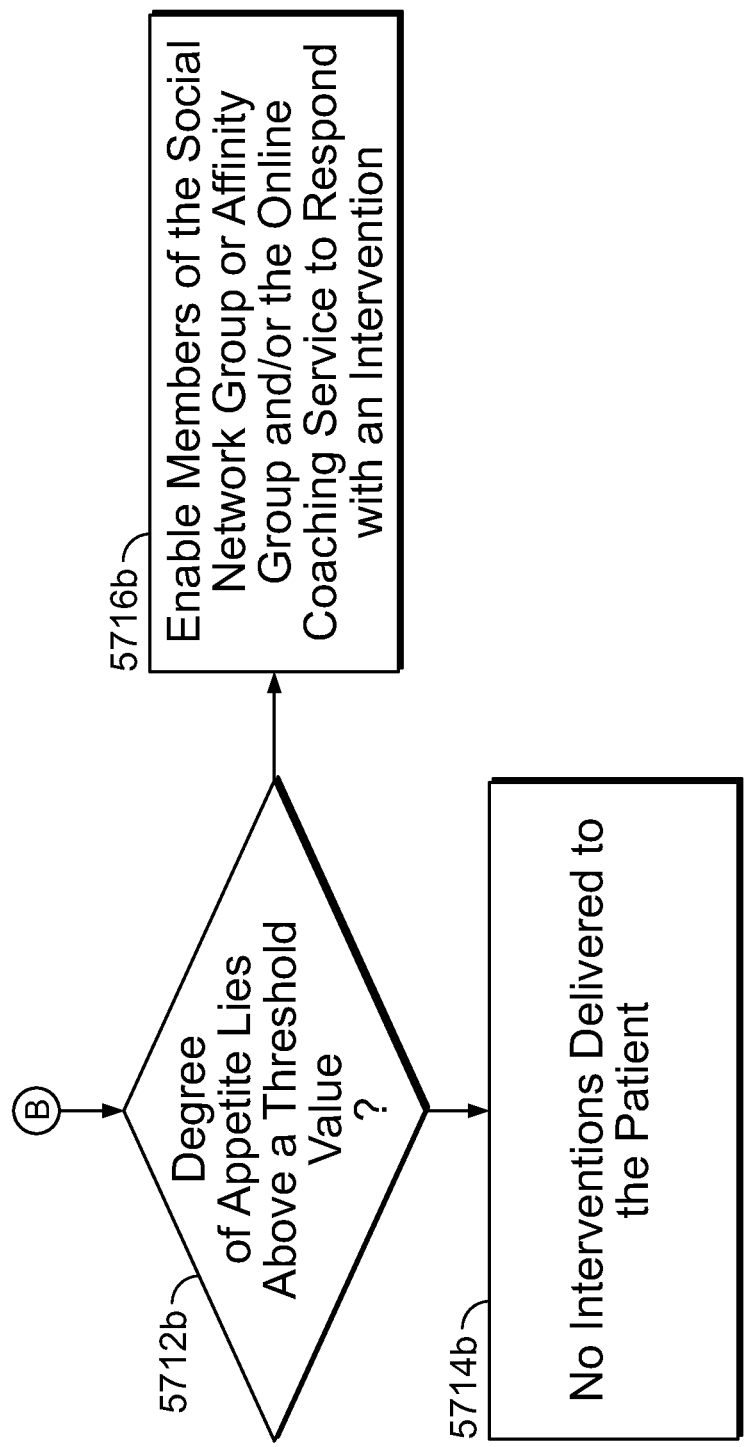
Figure 57:
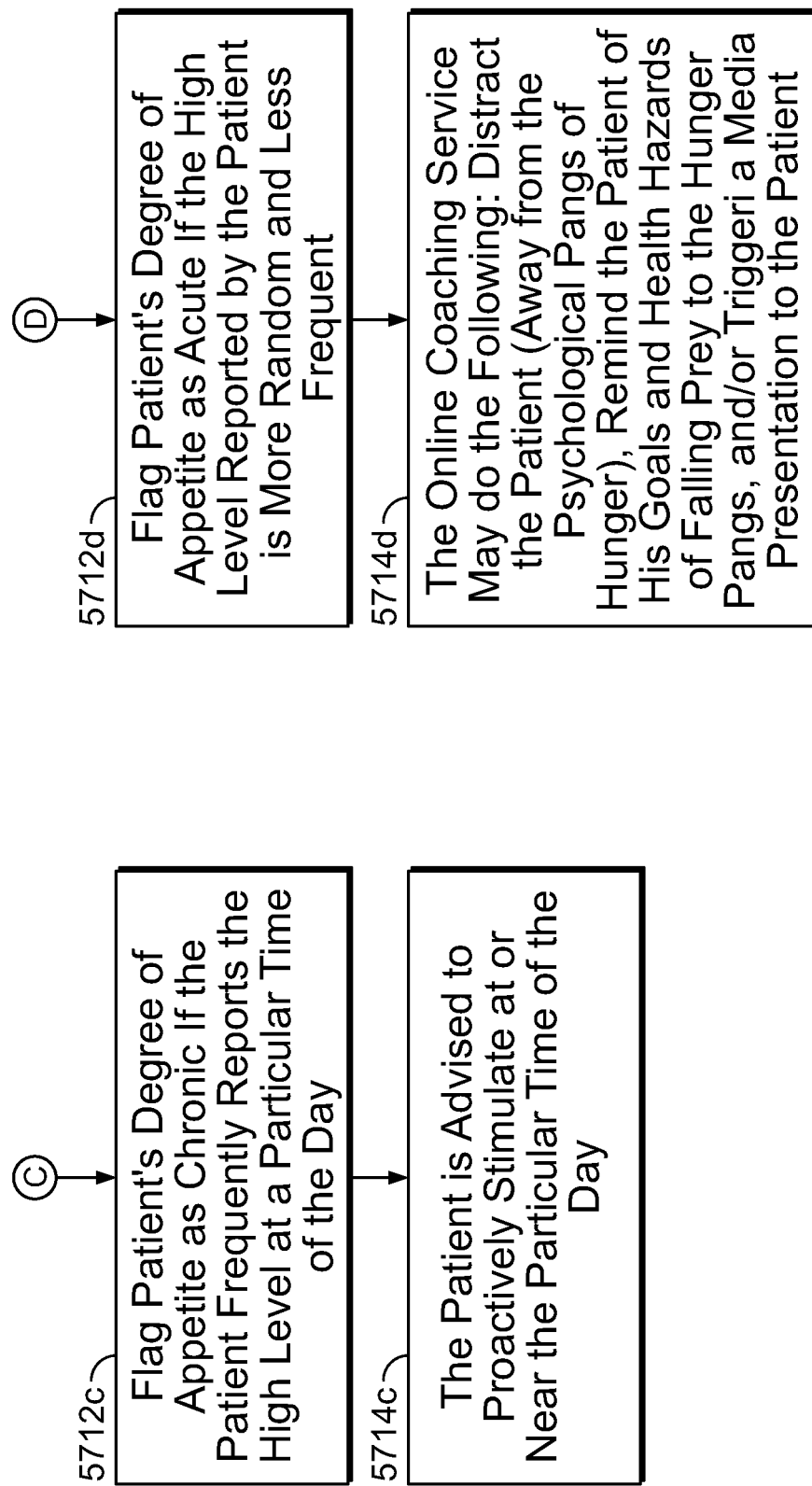
Figure 58:
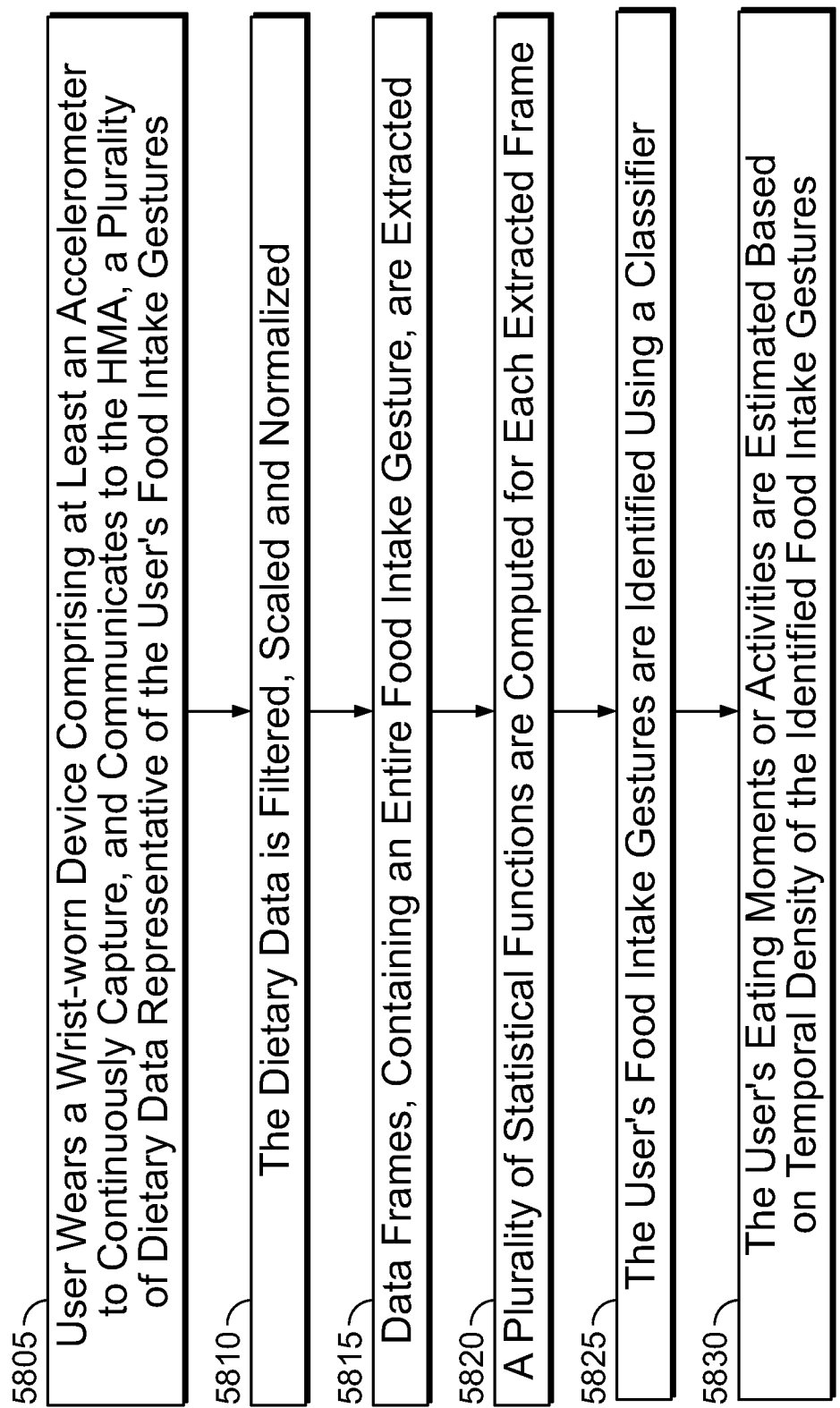
Figure 59A:
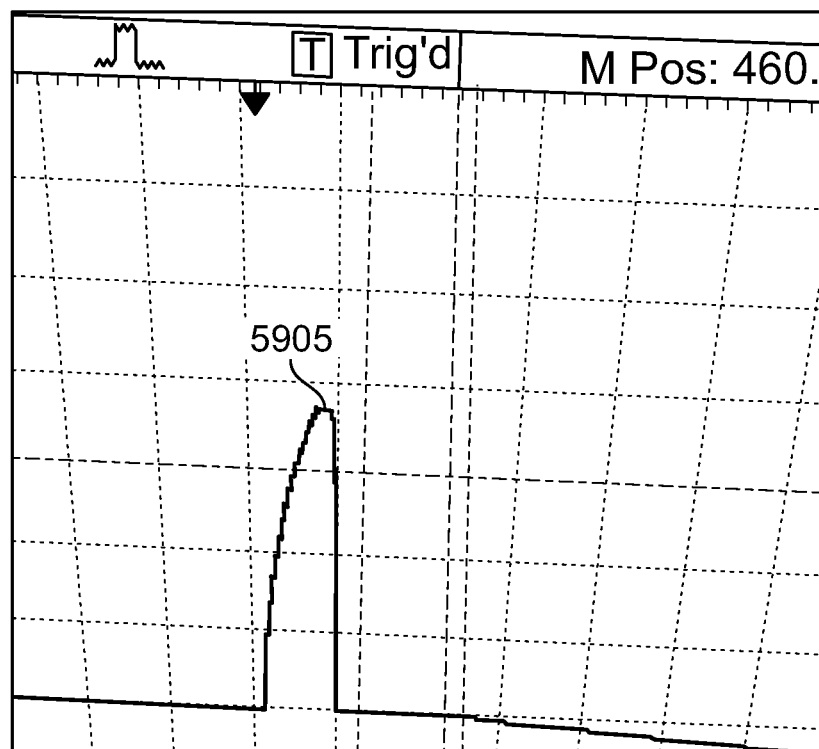
Figure 59B:
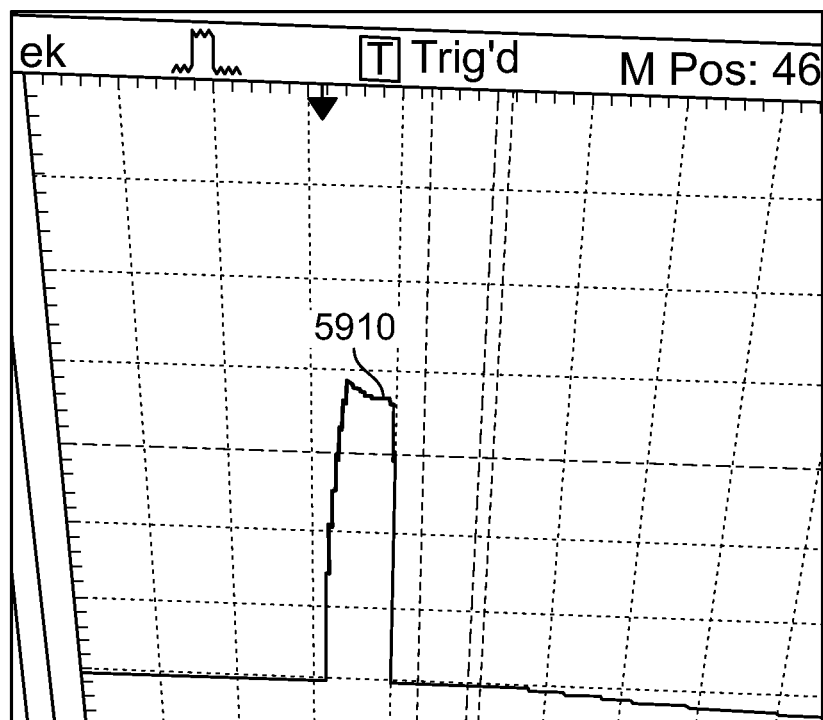
Figure 60:
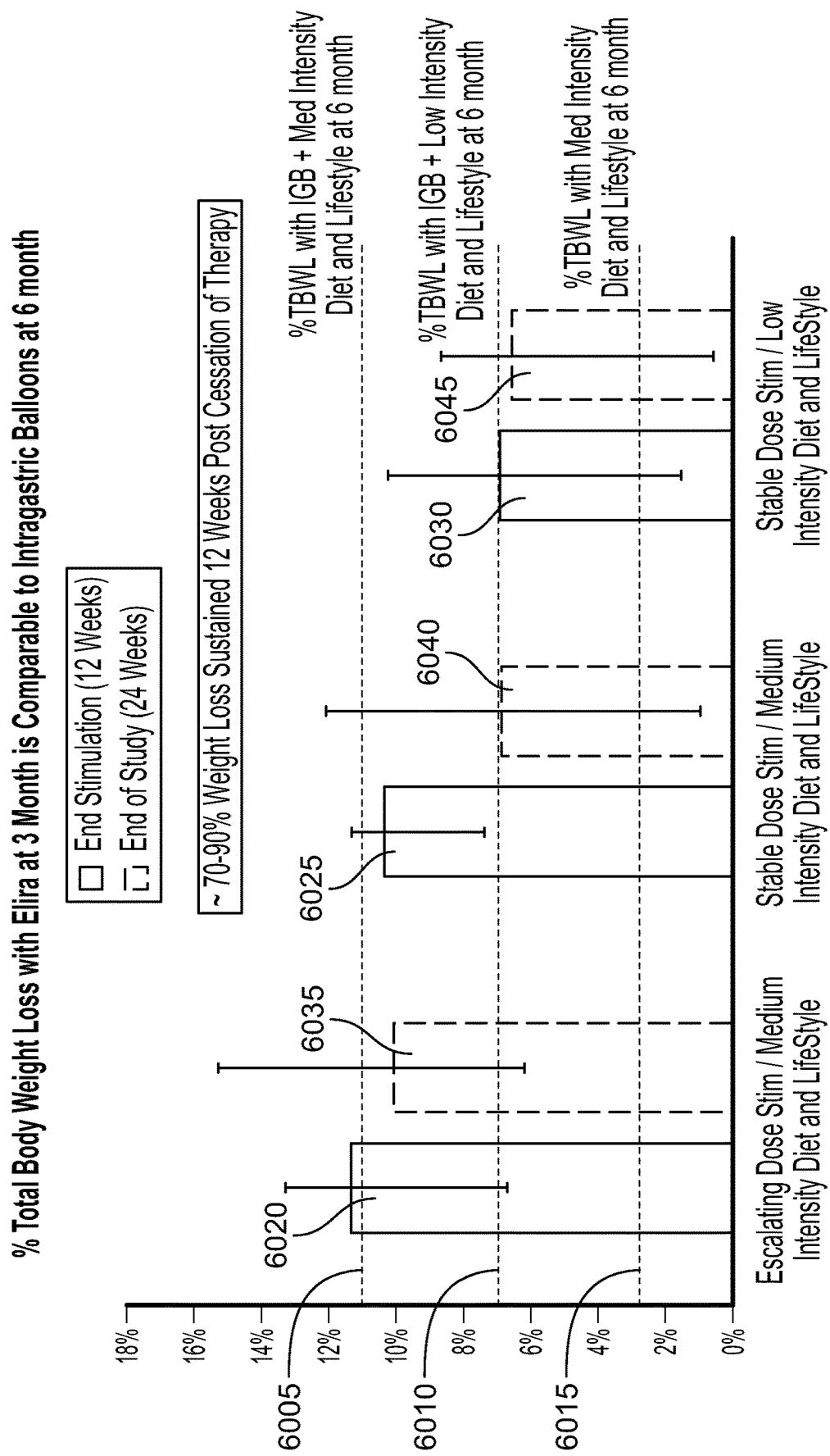
Figure 61:
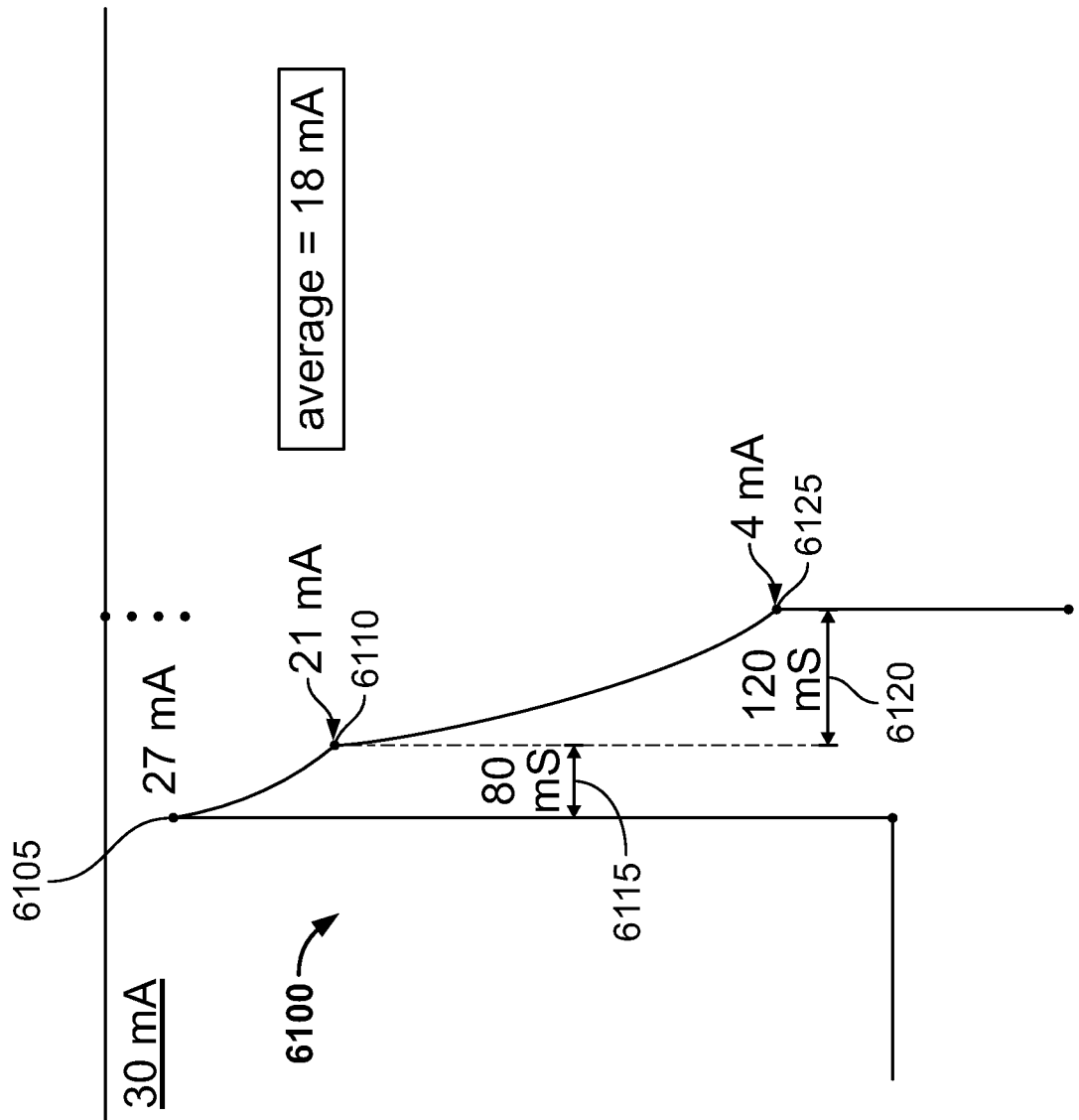
Figure 62:
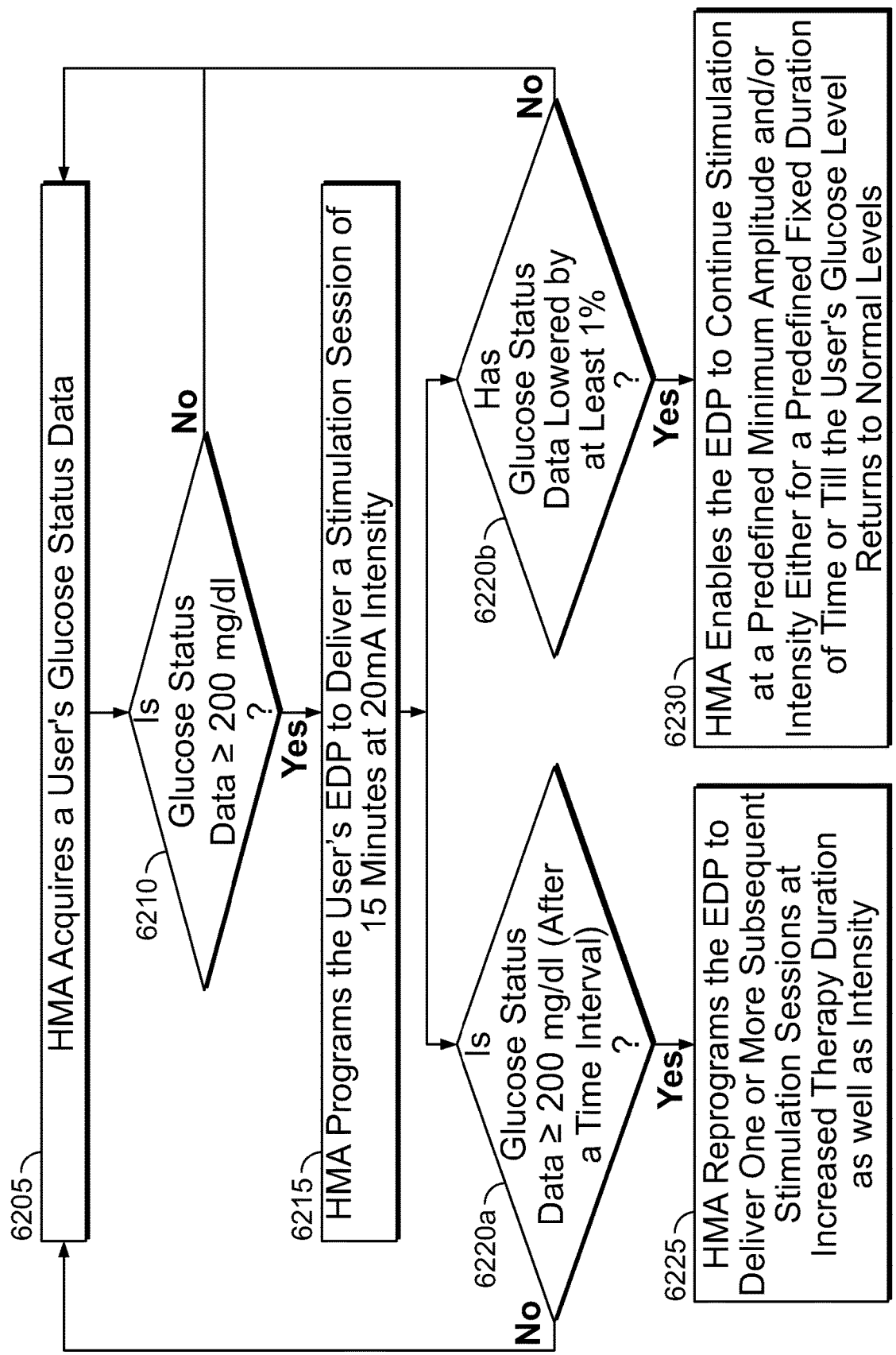
Figure 63:
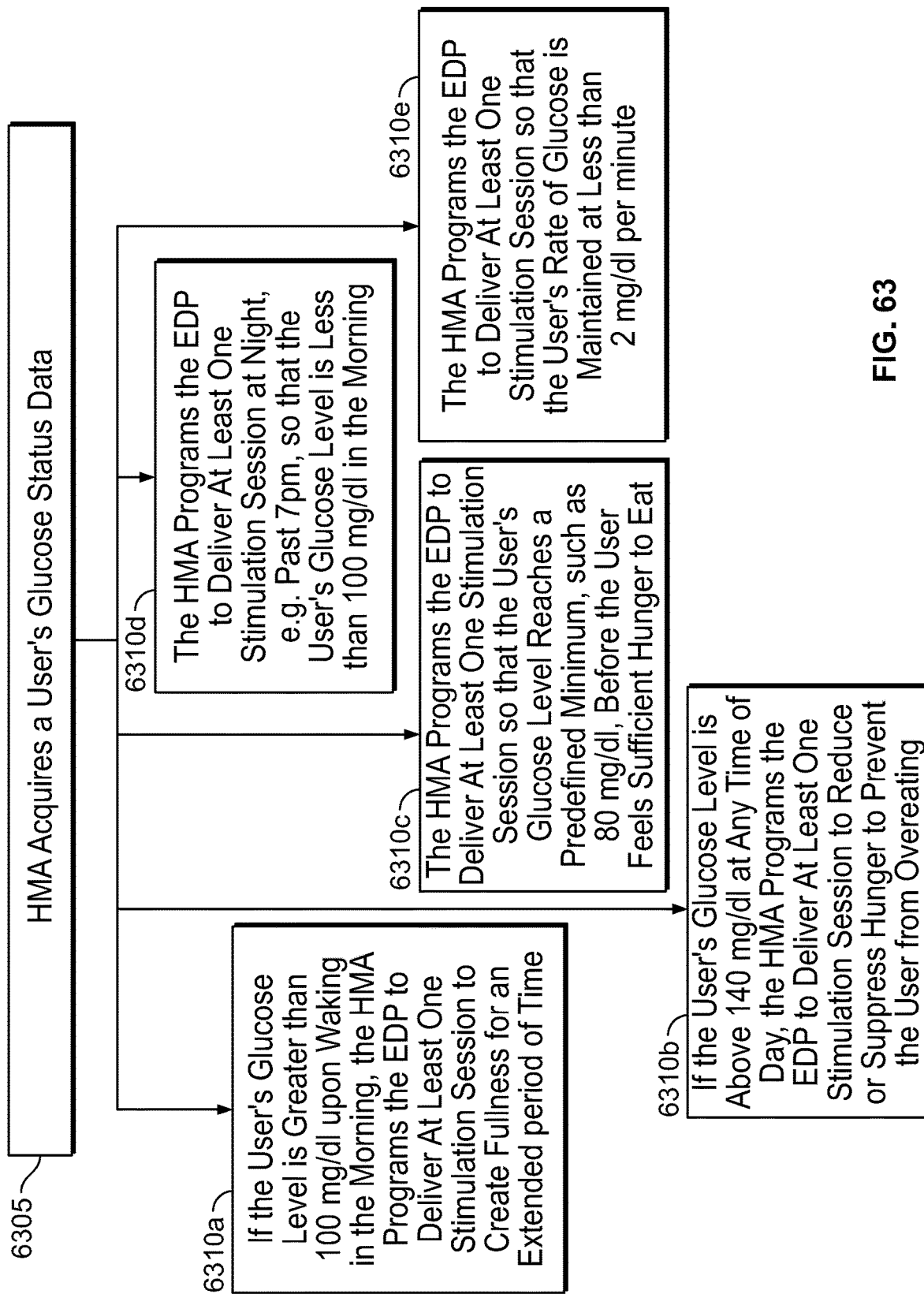
Figure 64:
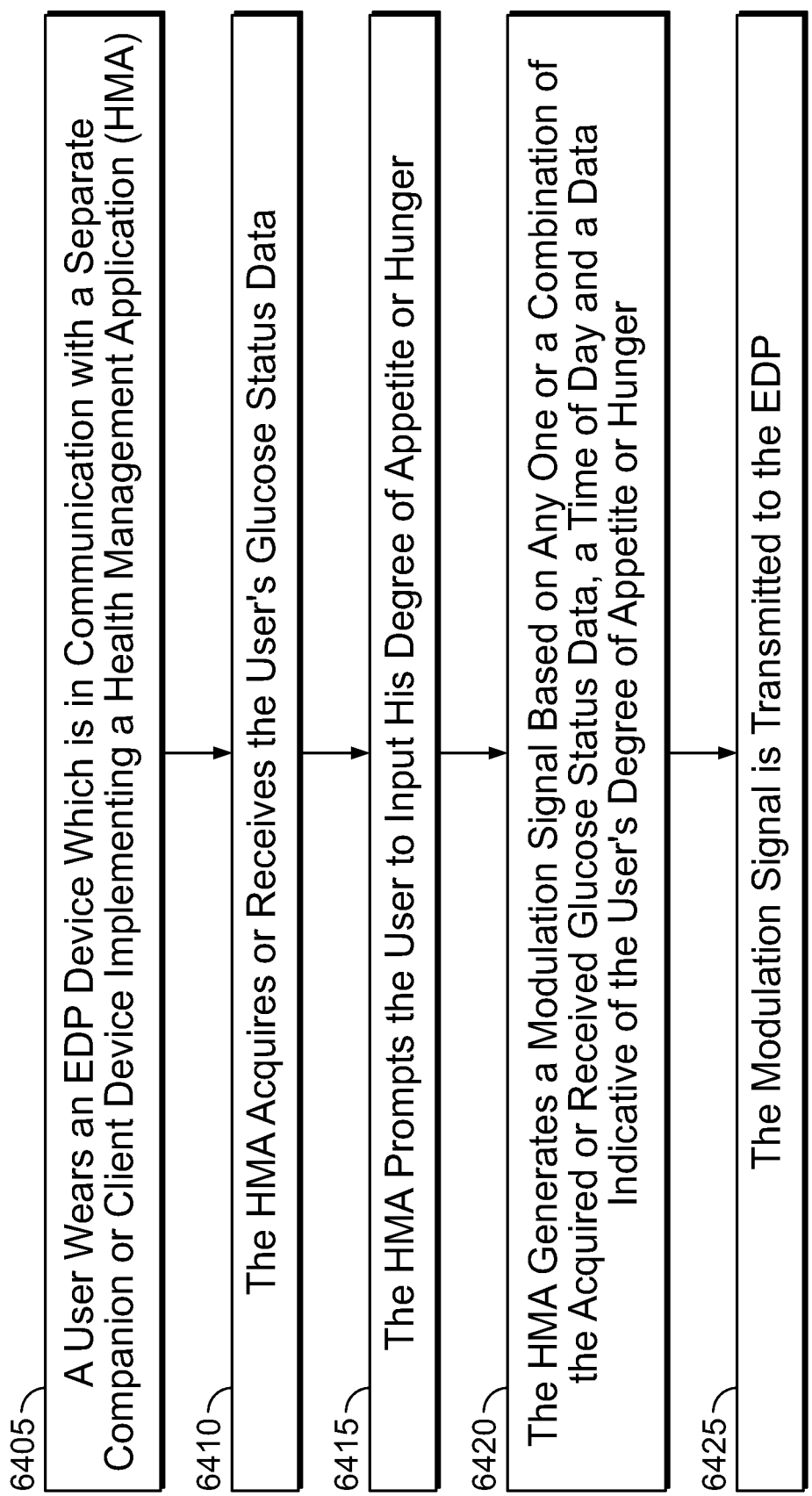
Figure 65:
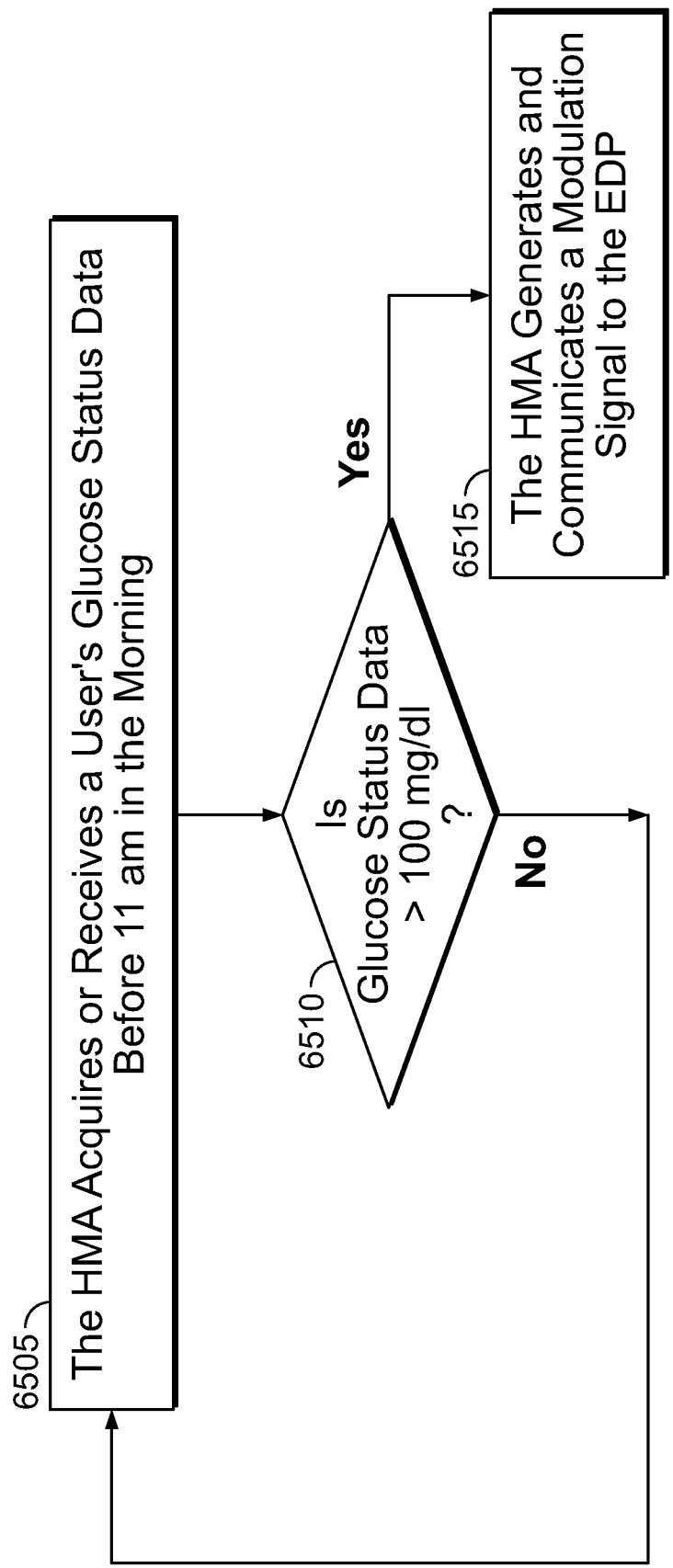
Figure 66:
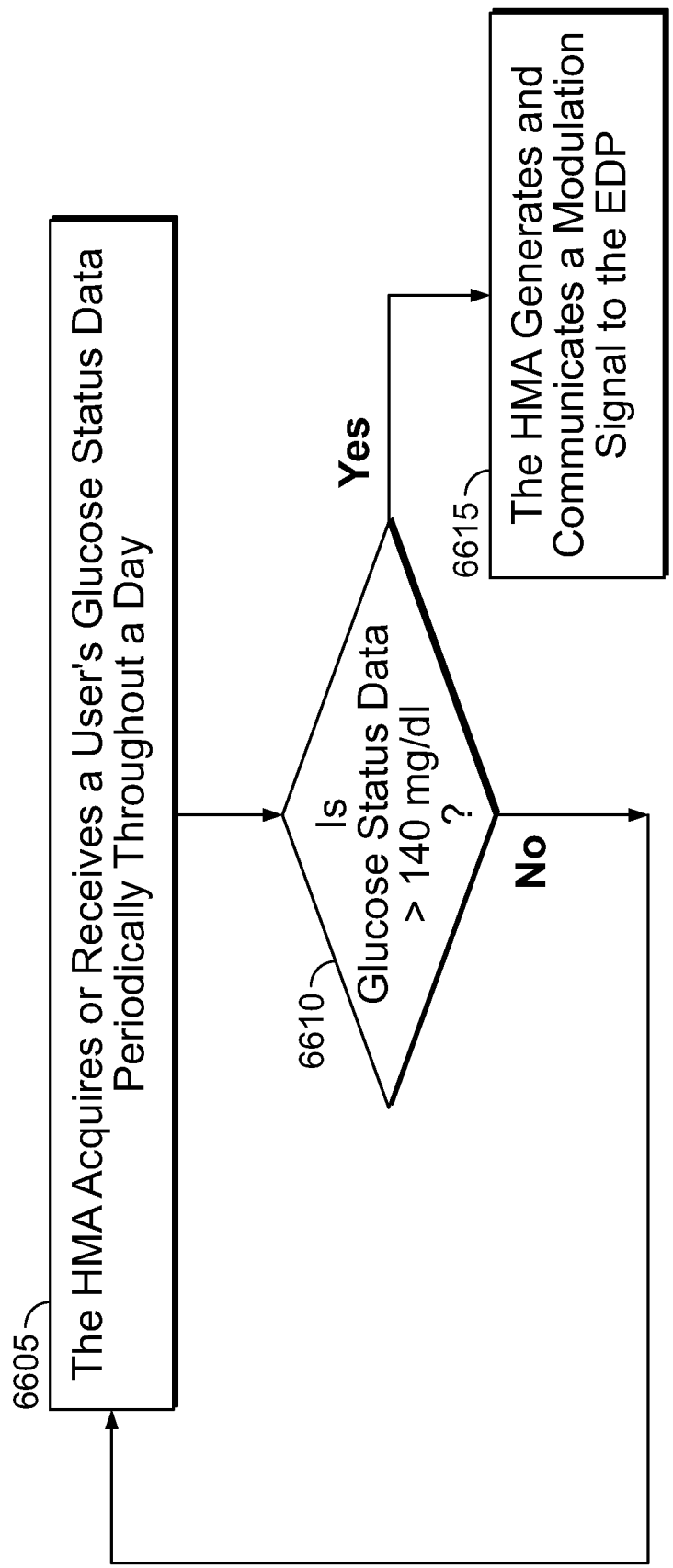
Figure 67:
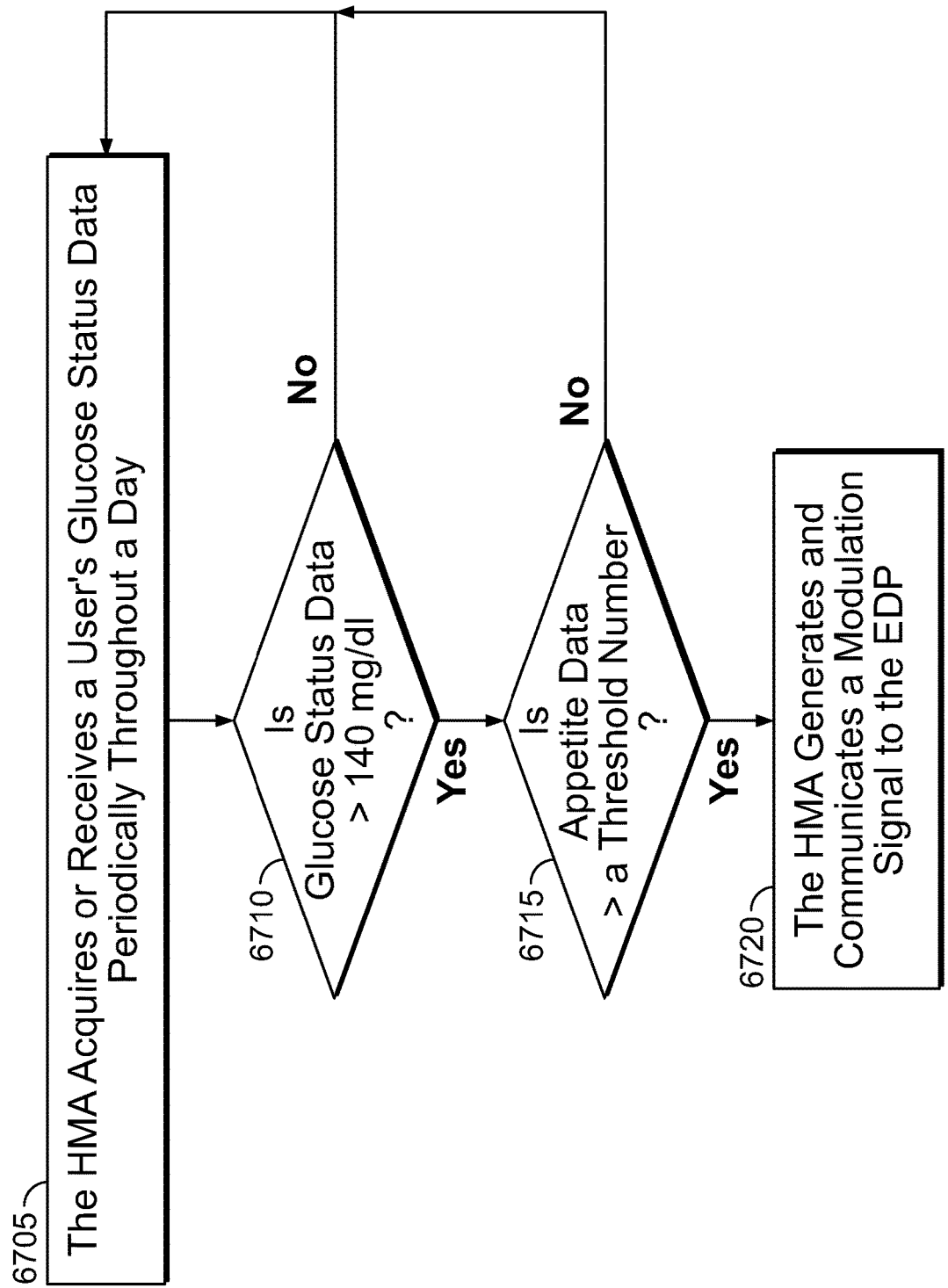
Figure 68:
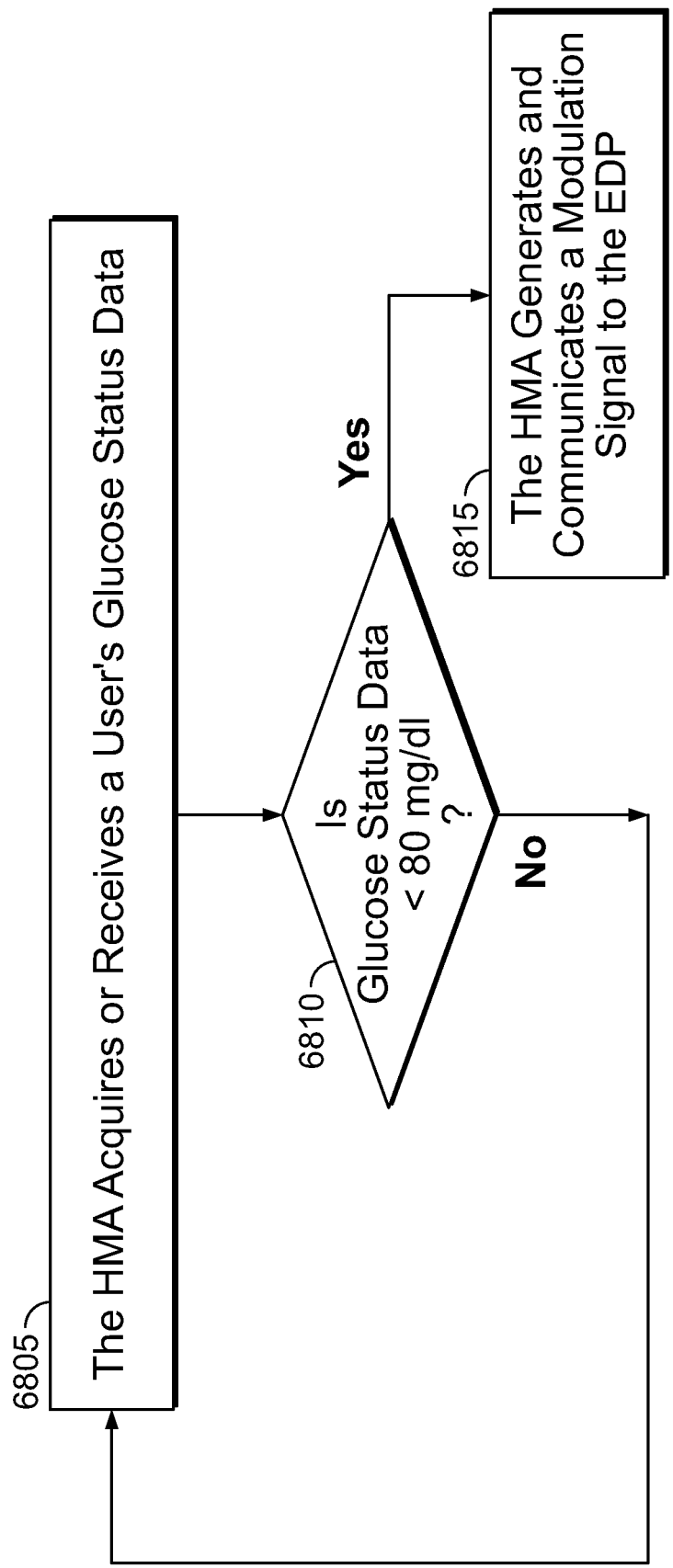
Figure 69:
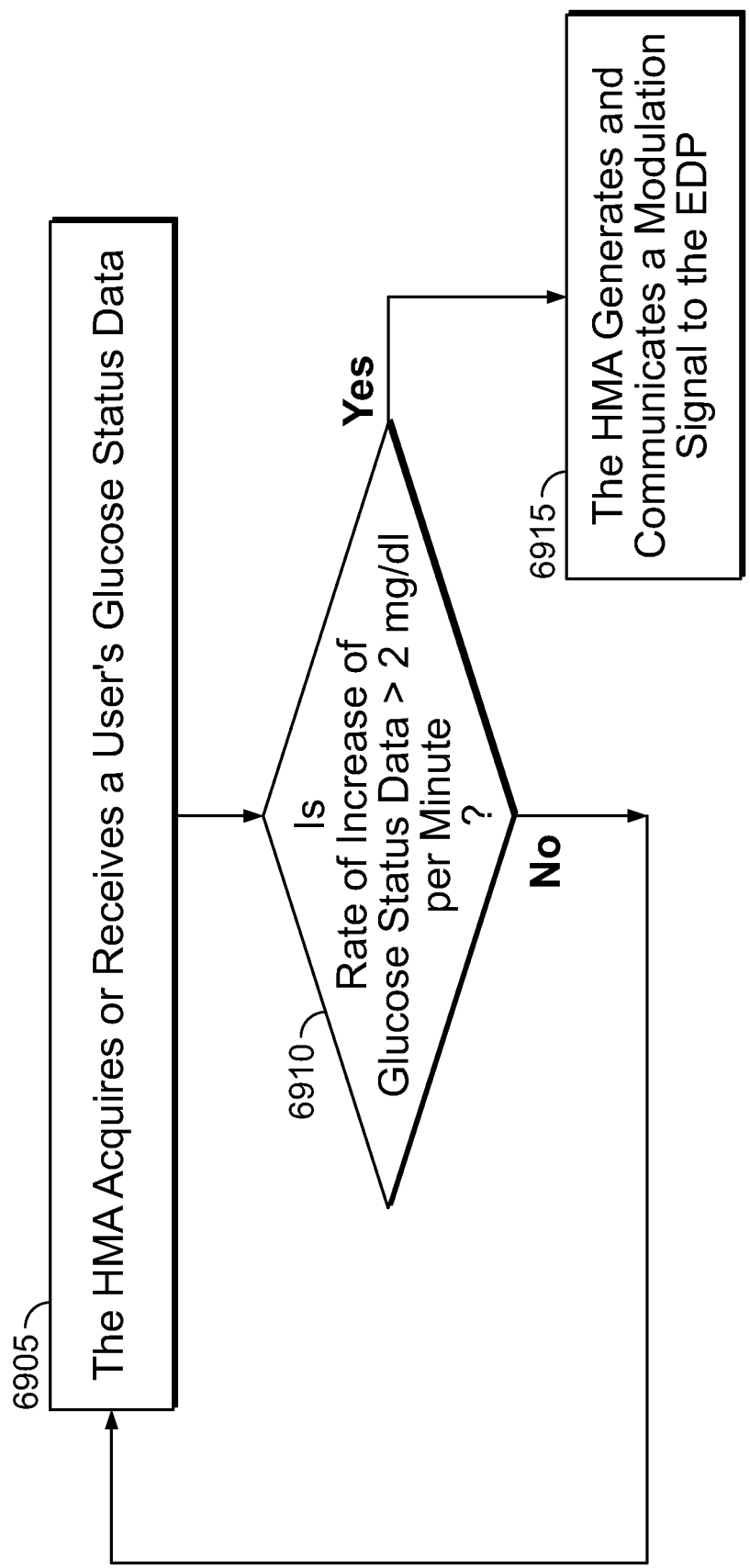
Figure 70:
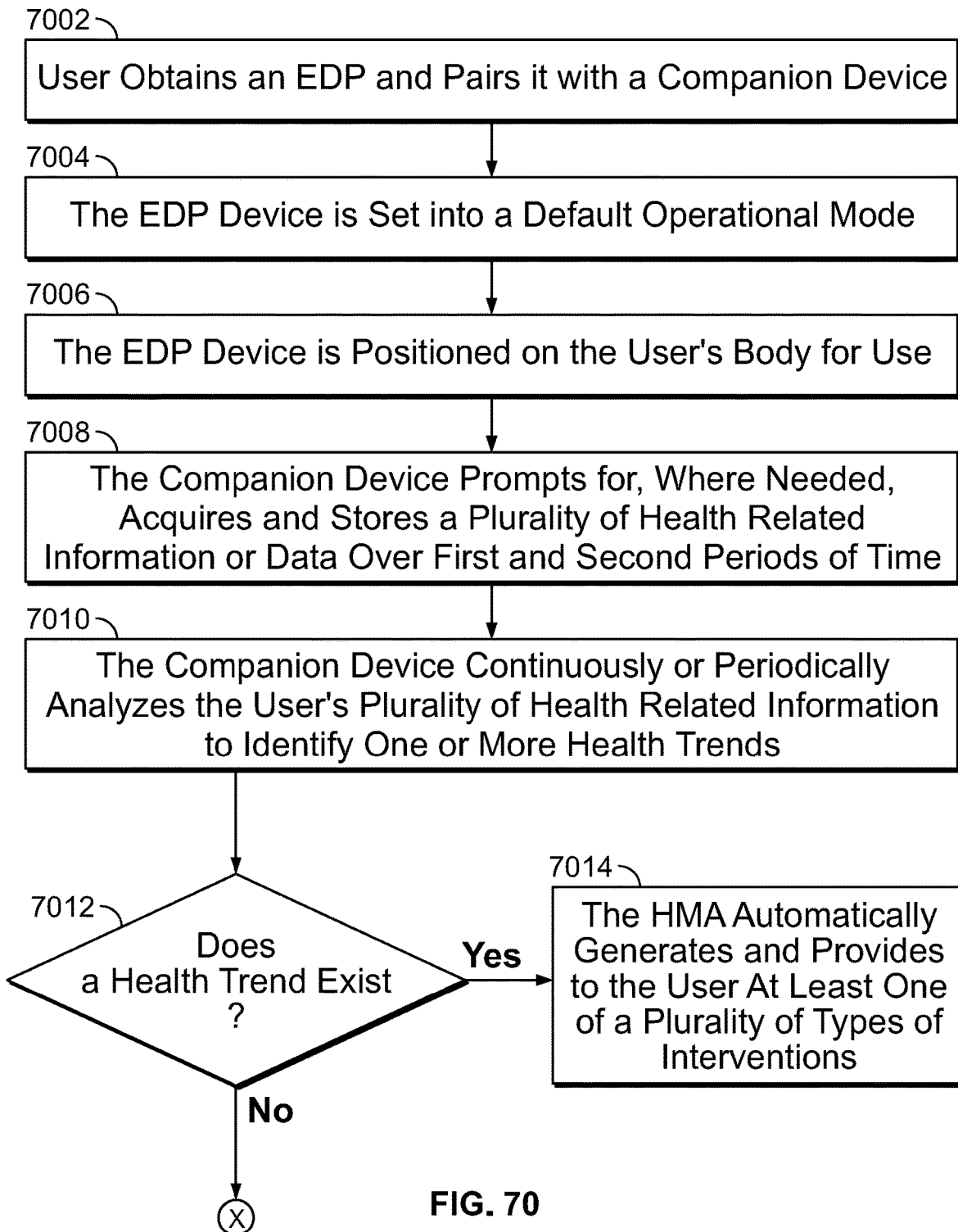
Figure 70:
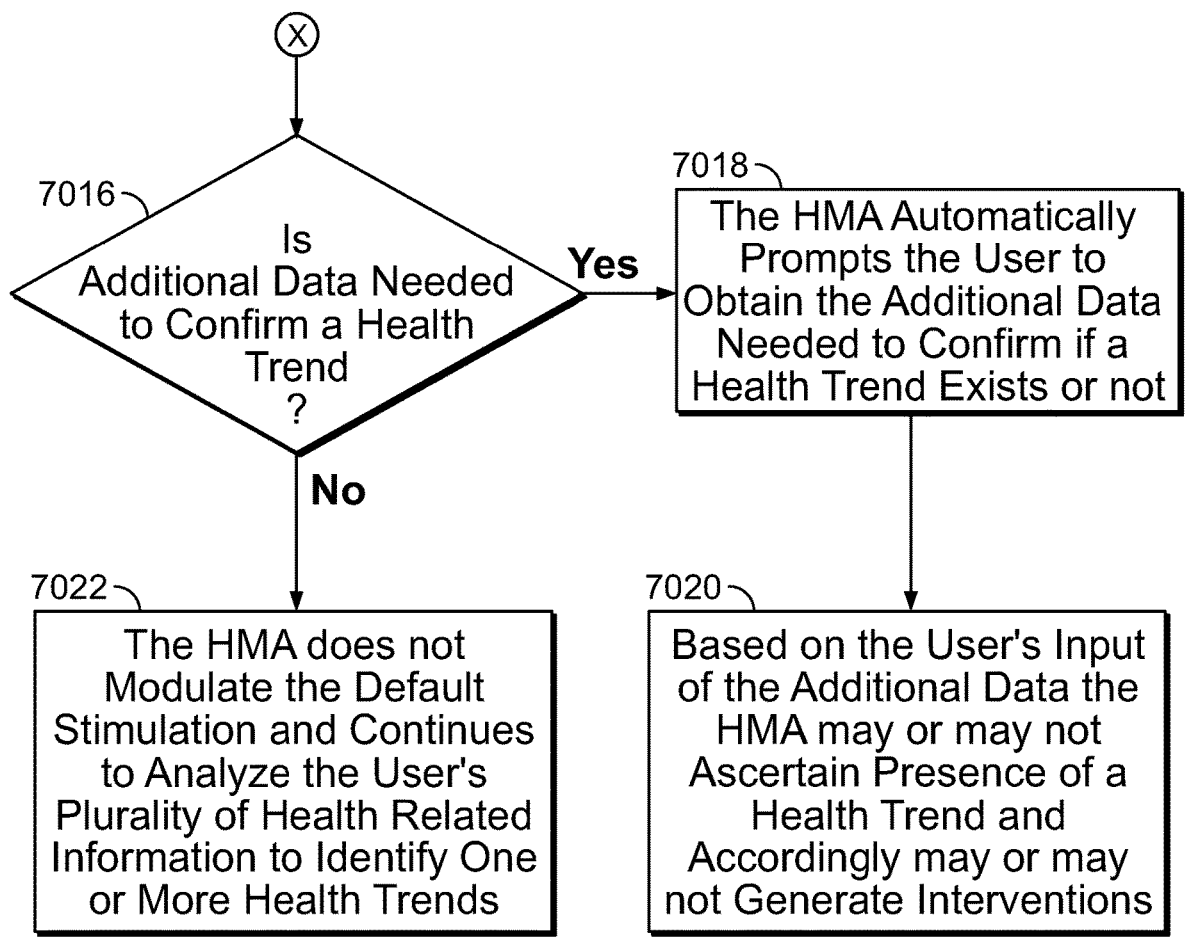
Figure 71:
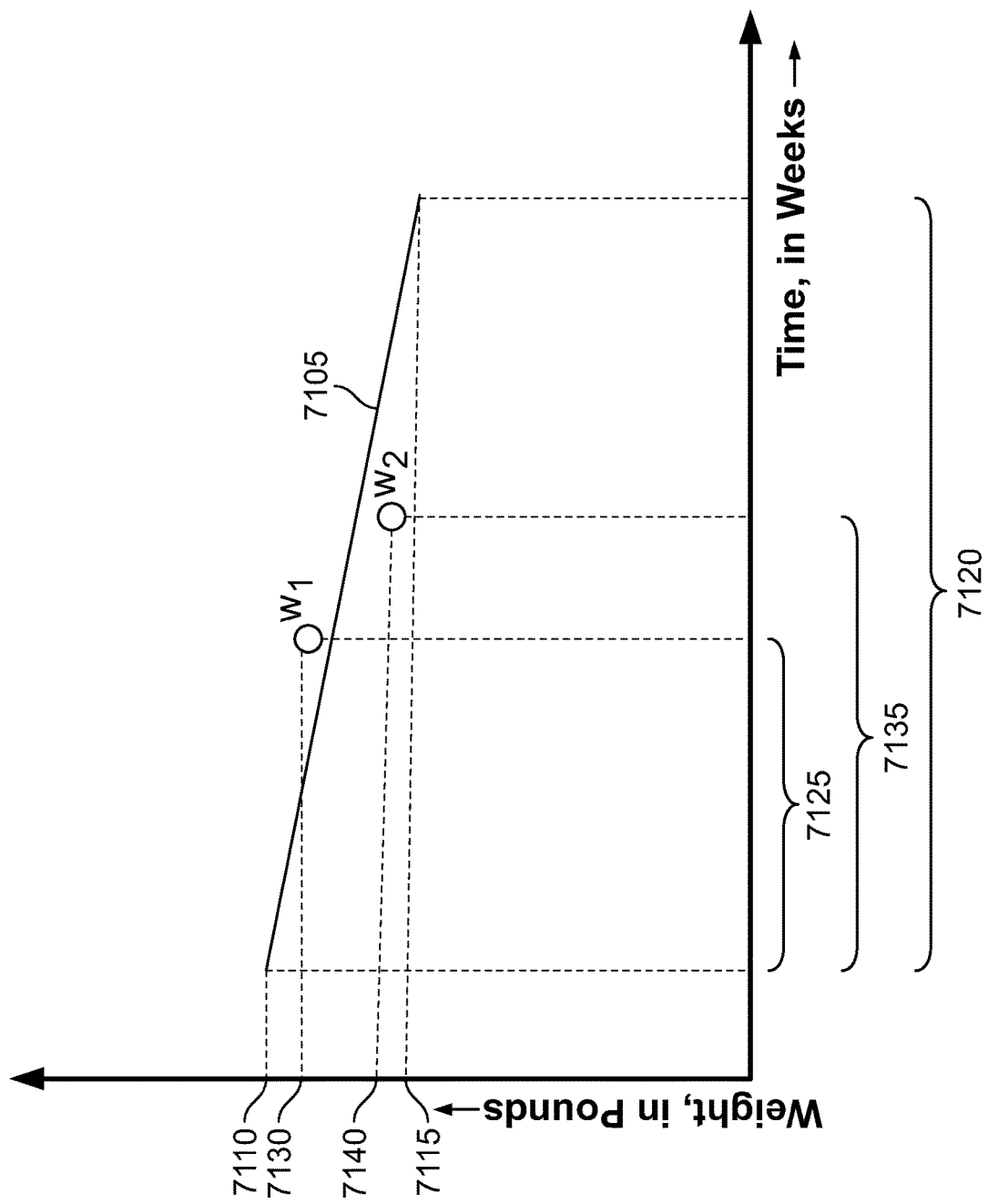
Figure 72B:
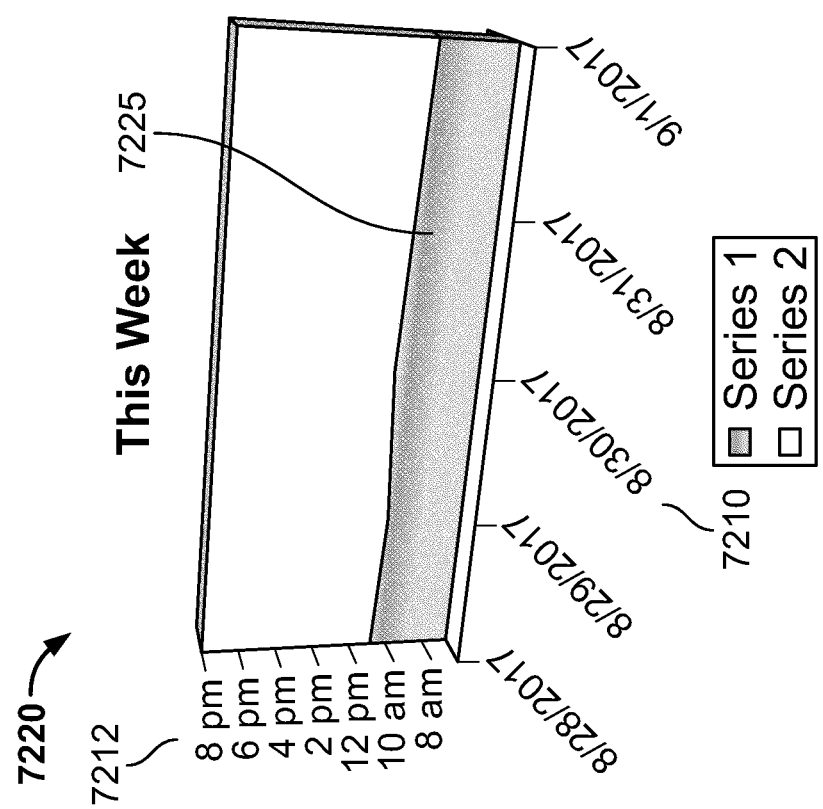
Figure 72A:
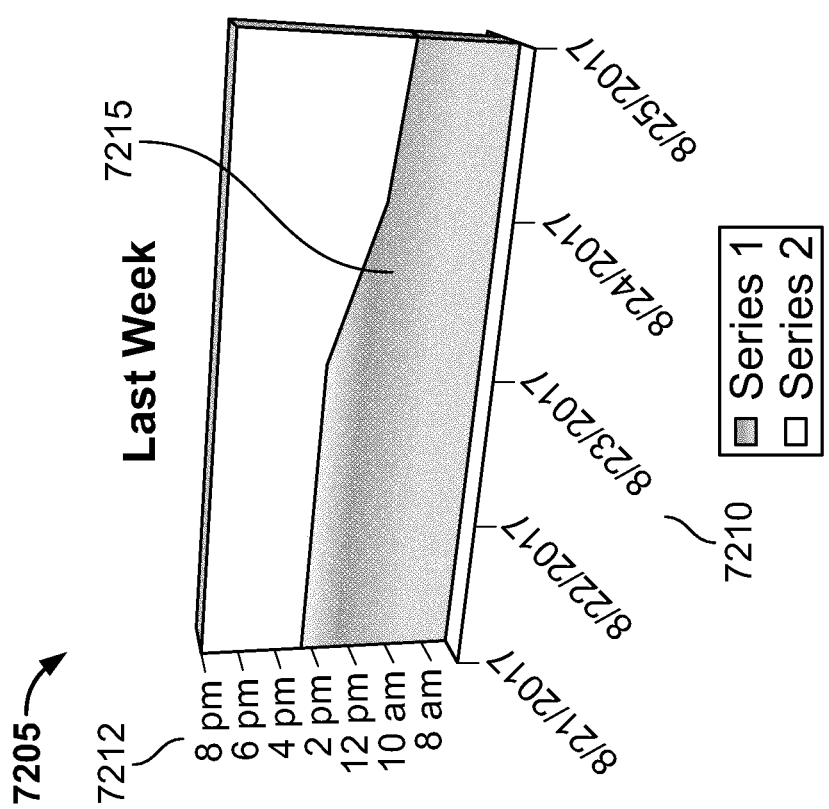
Figure 73:
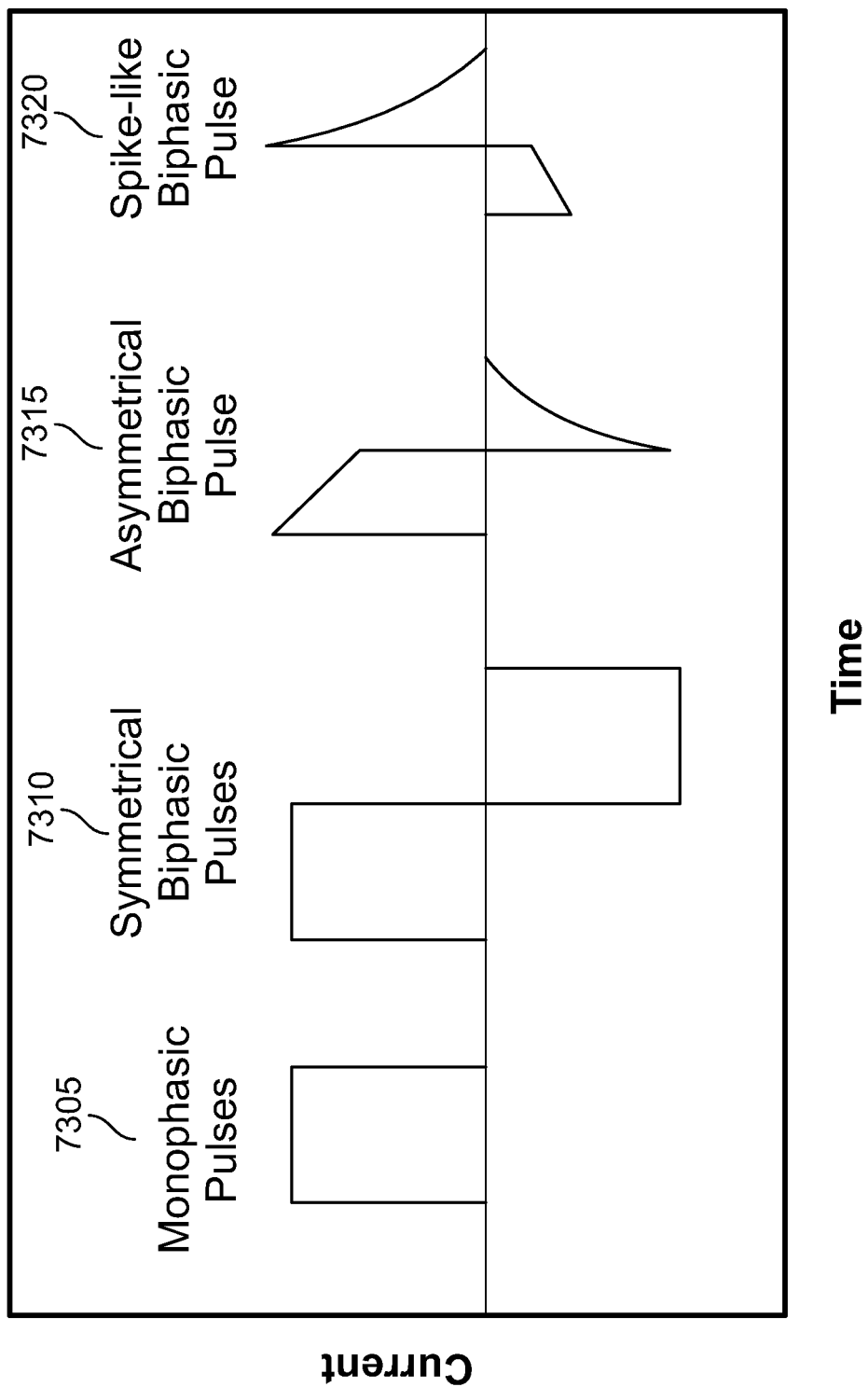
Figure 74A:
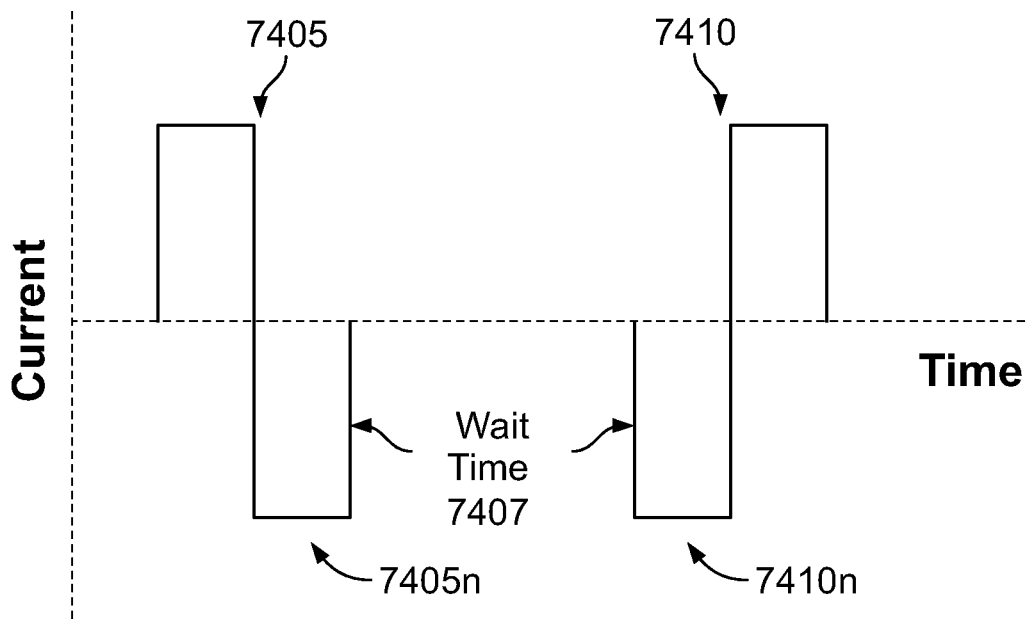
Figure 74B:
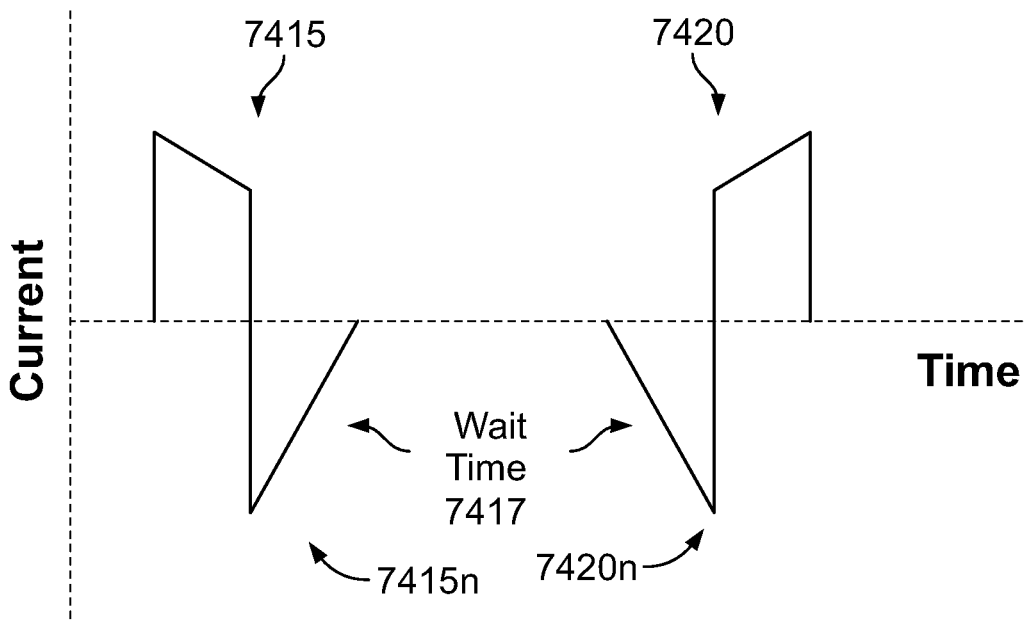
Figure 74C:
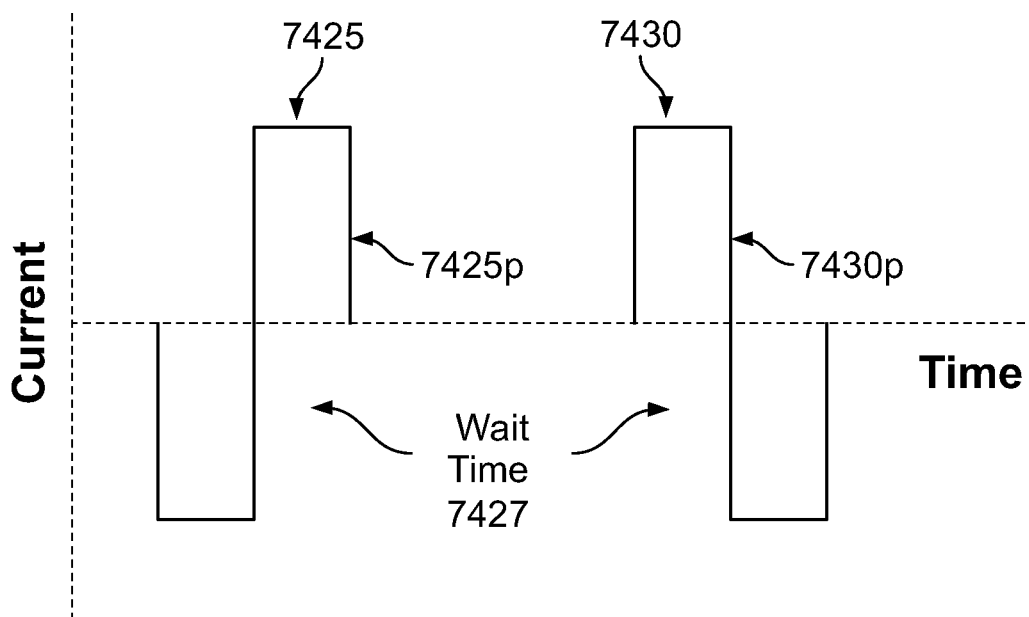
Figure 74D:
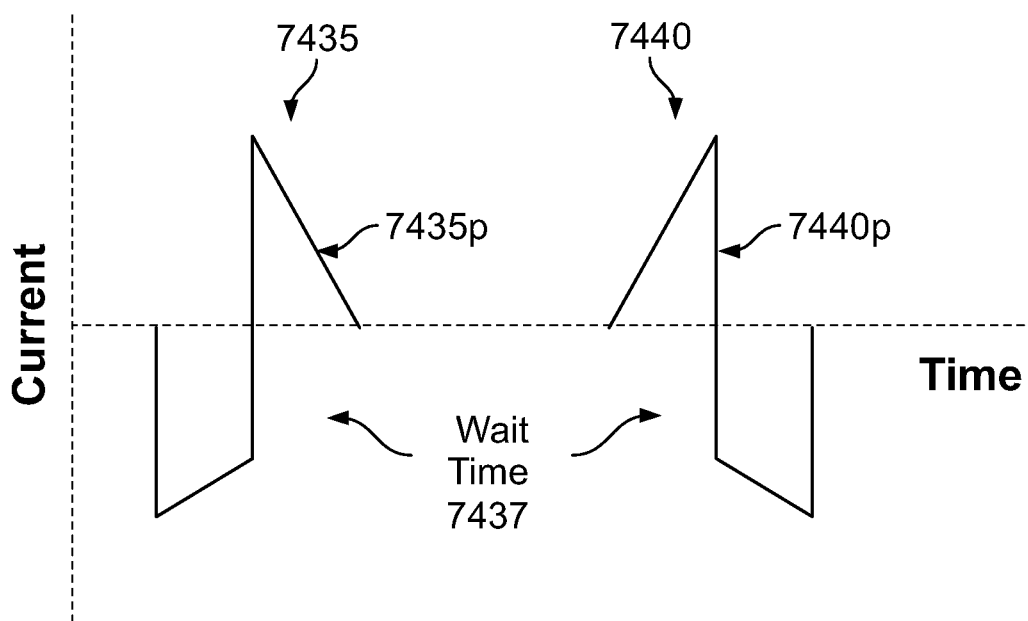
Figure 75A:
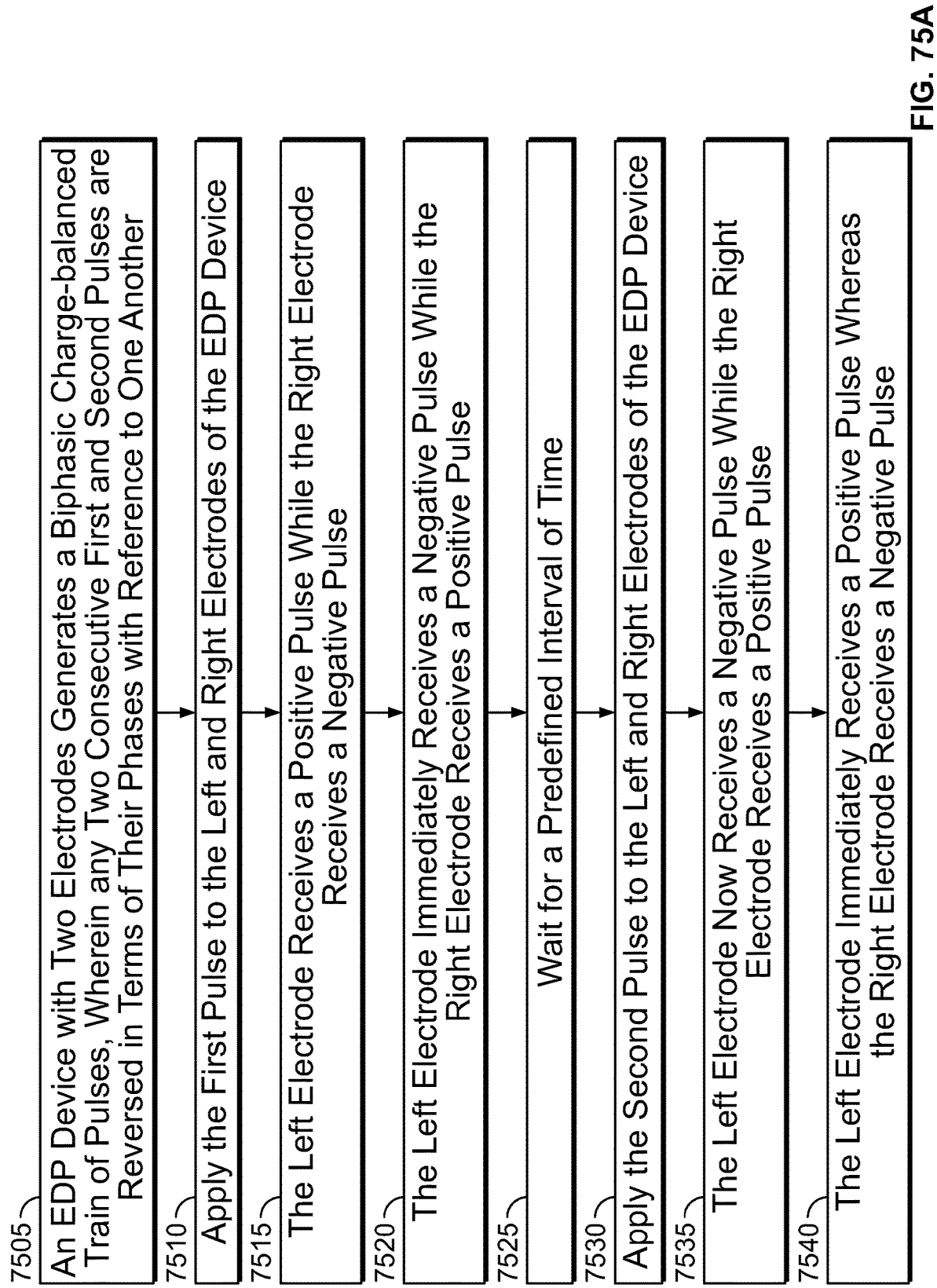
Figure 75B:
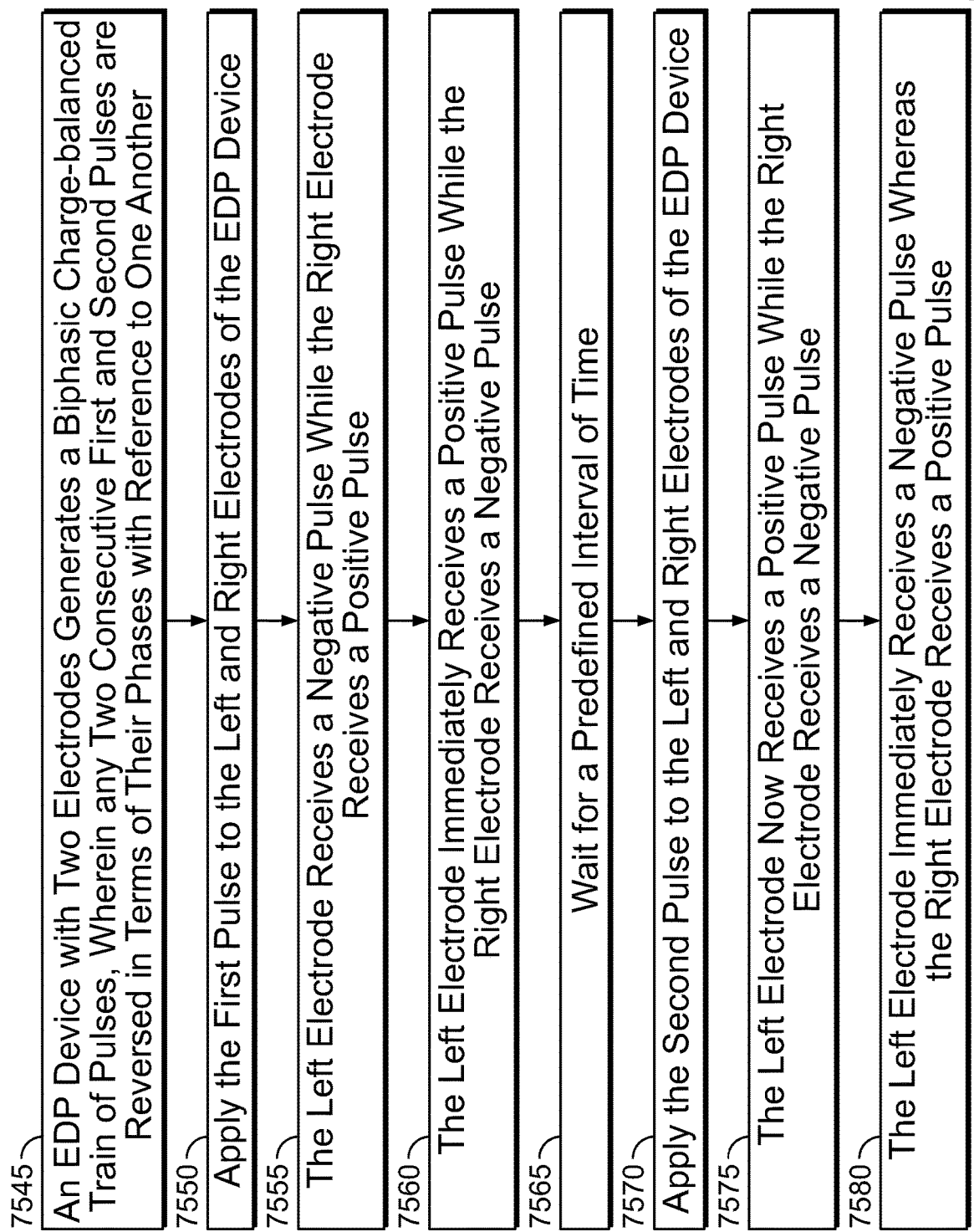
Figure 76:
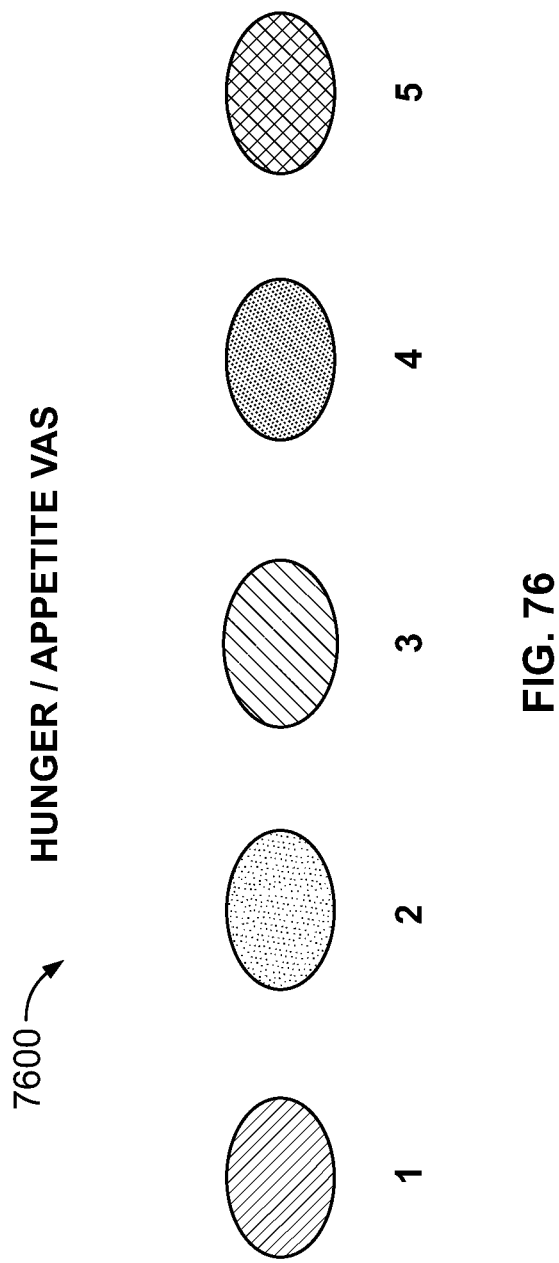

FIG. 51 is a depiction of a graphical user interface with a visual light bar;

FIG. 52 is a flow chart illustrating a method for enabling a TPM to prescribe, configure, manage, monitor and intervene with an EDP device-based stimulation therapy for a user, in accordance with some embodiments;

FIG. 53A is a horizontal bar graph illustrating a will power level corresponding to low or decreased levels of hunger;

FIG. 53B is the bar graph of FIG. 53A illustrating a will power level corresponding to high levels of hunger;

FIG. 54A is a vertical bar graph illustrating dietary will power of a user;

FIG. 54B is a vertical bar graph illustrating exercise will power of the user;

FIG. 55A is a top perspective view of an EDP device in accordance with an embodiment of the present specification;

FIG. 55B is another top perspective view of the EDP device in accordance with an embodiment of the present specification;

FIG. 55C is a bottom perspective view of the EDP device of FIG. 55A;

FIG. 55D is a bottom perspective view of the EDP device of FIG. 39A with hydrogel pads removed;

FIG. 55E is a side perspective view of the EDP device of FIG. 55A;

FIG. 55F is a first side perspective view of the EDP device of FIG. 55A with a portion of the housing cut away;

FIG. 55G is a second side perspective view of the EDP device of FIG. 55A with a portion of the housing cut away;

FIG. 55H is a top perspective view of an EDP device in accordance with some embodiments;

FIG. 55I is a top perspective view of another EDP device in accordance with some embodiments;

FIG. 55J is a top perspective view of yet another EDP device in accordance with some embodiments;

FIG. 55K shows a bottom view of a waterproof electrode pad assembly that utilizes two types of skin contacting adhesives, in accordance with some embodiments;

FIG. 55L is a disassembled or exploded view of the electrode pad assembly of FIG. 55K;

FIG. 55M is a disassembled or exploded view of electrode pad assembly employing either a foam pad with acrylic adhesive or a hydrocolloid adhesive;

FIG. 56 illustrates an exemplary use of a swallow detection device, in accordance with some embodiments;

FIG. 57 is a flow chart illustrating the steps involved in one embodiment of a method of using an electro-dermal patch device to elicit feedback, related to a medical condition of a patient, from at least one of a social network group (or affinity group) and an online coaching or concierge service;

FIG. 58 is a flow chart of a plurality of exemplary steps of an eating moment recognition method, in accordance with some embodiments;

FIG. 59A illustrates a first pulse waveform, in accordance with an embodiment;

FIG. 59B illustrates a second pulse waveform, in accordance with an embodiment;

FIG. 60 shows a graph comparing the % Total Body Weight Loss (% TBWL) achieved using the EDP devices of the present specification for 3 months against the % TBWL achieved using an Intragastric Balloon for 6 months;

FIG. 61 illustrates a third pulse waveform, in accordance with an embodiment of the present specification;

FIG. 62 is a flowchart illustrating steps of example use cases of titrating stimulation therapy based at least on a user's glucose status data, in accordance with embodiments of the present specification;

FIG. 63 is a flowchart illustrating steps of additional example use cases of titrating stimulation therapy based at least on a user's glucose status data, in accordance with embodiments of the present specification;

FIG. 64 is a flowchart illustrating steps of an example use case of titrating stimulation therapy based at least on a user's glucose status data, in accordance with an embodiment of the present specification;

FIG. 65 is a flowchart illustrating steps of yet another example use case of titrating stimulation therapy based at least on a user's glucose status data, in accordance with an embodiment of the present specification;

FIG. 66 is a flowchart illustrating steps of yet another example use case of titrating stimulation therapy based at least on a user's glucose status data, in accordance with an embodiment of the present specification;

FIG. 67 is a flowchart illustrating steps of yet another example use case of titrating stimulation therapy based at least on a user's glucose status data, in accordance with an embodiment of the present specification;

FIG. 68 is a flowchart illustrating steps of yet another example use case of titrating stimulation therapy based at least on a user's glucose status data, in accordance with an embodiment of the present specification;

FIG. 69 is a flowchart illustrating steps of still another example use case of titrating stimulation therapy based at least on a user's glucose status data, in accordance with an embodiment of the present specification;

FIG. 70 is a flow chart illustrating a plurality of steps involved in an embodiment of a method of using an EDP device to automatically generate one or more interventions based on identified health trends of a user;

FIG. 71 is a linearly sloping weight trend with reference to a user's target weight loss goal, in accordance with an embodiment of the present specification;

FIG. 72A illustrates a first heat map plotted with icons or dots indicative of appetite data for a first period of time, in accordance with an embodiment of the present specification;

FIG. 72B illustrates a second heat map plotted with icons or dots indicative of appetite data for a second period of time, in accordance with an embodiment of the present specification;

FIG. 73 illustrates a plurality of waveforms or pulses including symmetric and asymmetric, biphasic, charge-balanced waveforms generated by the EDP device, in accordance with embodiments of the present specification;

FIG. 74A illustrates a train of symmetric biphasic charge-balanced pulses, in accordance with embodiments of the present specification;

FIG. 74B illustrates a train of asymmetric biphasic charge-balanced pulses, in accordance with embodiments of the present specification;

FIG. 74C illustrates another train of symmetric biphasic charge-balanced pulses, in accordance with embodiments of the present specification;

FIG. 74D illustrates another train of asymmetric biphasic charge-balanced pulses, in accordance with embodiments of the present specification;

FIG. 75A is a flowchart illustrating a plurality of steps for generating a train of biphasic pulses, in accordance with embodiments of the present specification;

FIG. 75B is a flowchart illustrating a plurality of steps for generating a train of biphasic pulses, in accordance with alternate embodiments of the present specification; and FIG. 76 illustrates a VAS configured as a color spectrum for assessing an intensity of hunger or appetite, in accordance with an embodiment of the present specification.

DETAILED DESCRIPTION

The present specification is directed toward systems and methods of modulating a patient's appetite, hunger, satiety level, satiation level, or fullness level by delivering electrical stimulation to a predetermined area of the user's anatomy in a manner that is convenient, easy to use, and amenable to increased patient compliance. More particularly, the present specification relates to electrical stimulation devices comprising low profile, wearable, disposable skin patches that are configured for placement on a patient's front, lateral and/or back T2 to T12 and/or C5-T1 dermatomes, easy to self-administer, programmable and monitorable using a mobile handheld device, and programmed to stimulate, from the external surface of the patient's epidermal layer through a range of 0.1 mm to 10 mm of the dermis or through a range of 0.1 mm to 20 mm of the dermis, nerves located proximate to the front, lateral and/or back T2 to T12 and/or C5-T1 dermatomes in a manner that enables modulation of a patient's appetite, hunger, satiety level, satiation level or fullness level, and that avoids nausea, dyspepsia and minimizes habituation. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein. The present specification further relates to a low profile, wearable, disposable skin patch that is capable of integrating with, and being controlled by, a plurality of different hardware devices or software applications depending on the type, extent, nature and scope of the appetite, hunger, satiety level, satiation level or fullness level modulation desired, including immediate, large weight loss or long term weight maintenance.

An electrical neuro-stimulation device, in the form of an electro-dermal patch (EDP) is disclosed that, in various embodiments, is configured as a discrete, disposable and waterproof adhesive patch or pad for placement on a user's skin, particularly on the regions encompassing the front, lateral and/or back T2-T12 dermatomes and/or C5-T1 dermatomes. In various embodiments, the EDP is wireless and incorporates flexible circuits and elastomeric overmolding, making the device waterproof and flexible enough to be able to mold to body contours for greater comfort and permanent wearability. In some embodiments, the EDP device also modulates ghrelin production.

In accordance with various aspects of the present specification, the resultant benefits of modulating appetite, hunger, satiety level, satiation level or fullness level include treating conditions associated with persons who are overweight or those with metabolic syndrome, treating obesity and T2DM prevention or management. In accordance with various aspects of the present specification, the electro-dermal patch device treats people having a BMI (Body Mass Index) of 25 or greater (overweight being 25-30, obese being 30 and above, and morbid obesity being above 35). In embodiments of the present specification, the electro-dermal patch device is wearable and can be controlled and programmed by the patient, allowing the patient to administer therapy and eliminating the need for frequent patient visits to a medical professional. In embodiments, the electro-dermal patch device is designed to be placed on the front, lateral and/or back thoracic dermatomes and/or C5-T1 dermatomes of the patient. Therefore, the patient is able to place the electro-dermal patch device on him or herself, without the assistance of a medical professional.

In embodiments, the electro-dermal patch device is wirelessly coupled to a companion device (e.g. smartphone, watch, glove, wristband or tablet) which can be used to program the electro-dermal patch device, allowing the patient to self-administer therapy on-demand. In some embodiments, all therapy provided by the electro-dermal patch device is coupled with a storage or recording (for keeping a log of the therapy) and patient compliance reminders. The benefits provided by having a wearable and self-administered electro-dermal patch device include, among others, greater patient independence and improved patient compliance to stimulation protocols, with resultant increased dietary compliance and overall efficacy, and the ability to modify stimulation parameters based on real-time feedback provided to the electro-dermal patch device by the patient and other devices. In some embodiments, the electro-dermal patch device is driven by an algorithm derived from patient input data and monitored data (e.g. exercise monitored by a separate device). Adjustments to the algorithm, and therefore stimulation, are made both manually by the patient and automatically by the device itself or the companion device. In some embodiments, the electro-dermal patch device is driven by an algorithm derived from patient input data and monitored data (e.g. exercise monitored by a separate device). In some embodiments, the algorithm is also derived from monitored parameters, such as leptin (for ghrelin suppression), glucagon-like peptide 1 (GLP-1), hemoglobin A1C, and blood glucose levels (for diabetes treatment), lipids, and triglycerides. These parameters are measured at baseline and over time during treatment and are used as inputs to titrate therapy. Adjustments to the algorithm, and therefore stimulation, are made either manually by the patient or automatically by the electro-dermal patch device itself or the companion device or both. In accordance with some aspects of the present specification, a medical professional can flexibly program the electro-dermal patch and still direct the patient, only allowing the patient to adjust device parameters (for greater patient independence) but within restricted bounds or predetermined parameters.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

For purposes of the present specification, the terms "trigger" and "triggering" do not necessarily imply immediately triggering stimulation. "Trigger" and "triggering" are defined as initiating or starting the execution of a protocol that will result in stimulation over a predefined period.

The term "modulating" refers to any form of regulation, manipulation or control to change a given variable from one state to another state.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

The terms "patient", "individual", "person", and "user" are used interchangeably throughout this specification and refer to the person that is receiving treatment or stimulation from the devices and methods of the present specification.

The term "hunger" is defined as a physical sensation indicative of a person's physical need for food and may be related to low levels of glucose in the person's blood and/or concentrations of ghrelin and/or hunger-inducing gut hormones.

The term "appetite" is defined as a desire for food, possibly prompted by an emotional, psychological, and/or sensory reaction to the look, taste, or smell of food.

The term "satiation" is defined as a sensation of fullness that results in cessation of eating.

The term "fullness" is defined as a sensation of an adequate amount of food present in the stomach. It should be appreciated that the term "fullness" refers to a psychological or perceptive sensation by the patient, which may be objectively measured using the scales described herein. The term "physiological fullness" shall refer to a physical measurement of the actual contents of a person's stomach.

The term "satiety" is defined as a sense of fullness that prolongs the time between meals (the more satiety, the longer duration between two meals). It is intended to refer to a patient's perception of a sense of fullness that prolongs the time between meals.

The phrase "change in satiety" is defined as an alteration in the patient's perception of gastric fullness or emptiness.

The term "dietary compliance" is defined as a patient's ability to adhere to a prescribed regimen of caloric intake, whether defined in terms of total permissible calories or a type or amount of nutritional intake, or some combination thereof, in order to achieve a targeted daily, weekly, or monthly calorie consumption and/or a targeted type or amount of nutritional intake.

The phrase "weight maintenance" means adjusting an appetite or hunger suppression/decrease goal in order to maintain a certain amount of weight loss that has already been achieved and to now avoid gaining weight. In some embodiments, weight loss maintenance entails engaging in a surgical procedure (such as various bariatric surgeries), applying the EDP of the present specification and using appetite or hunger suppression/decrease in order to maintain the weight loss achieved by surgery.

The term "microbiota" is defined as an ensemble of microorganisms that reside in a previously established environment, such as the stomach or gastrointestinal system. The term "gut microbiota" or "gut flora is the name given to the microbiota living in a person's intestine.

The term "glycemic index (GI)" is defined as a number associated with a particular type of food that indicates the food's effect on a person's blood glucose (also called blood sugar) level. A value of 100 represents the standard, an equivalent amount of pure glucose. The glycemic index is calculated by determining the incremental area under the blood glucose response curve of a specific portion of a test food expressed as a percent of the response to the same amount of carbohydrate from a standard food taken by the same subject.

The term "glycemic load (GL)" is defined as the glycemic index multiplied by grams of carbohydrate per serving size. GL is based on a specific quantity and carbohydrate content of a test food and calculated by multiplying the weighted mean of the dietary glycemic index by the percentage of total energy from the test food. When the test food contains quantifiable carbohydrates, the GL=GI(%)×grams of carbohydrate per serving.

The terms "epidermal layer" and "epidermis" are used interchangeably throughout this specification and refer to the outermost, protective, nonvascular layer of a person's skin, covering the dermis and shall be construed to cover all variants of the word "epidermal".

The term "power source" is used to represent any energy providing device, including a lithium-ion battery, a betavoltaic battery, a solar cell, nickel-cadmium battery, a fuel cell, a mobile phone, or remote charging station.

The term "controller" is used to denote a processing unit configured to control the initiation of stimulation, termination of stimulation, and type and/or extent of stimulation and shall include the terms "control unit", "processing unit", "microcontroller", "microprocessor", or "processor".

The term "pulse generator" means a device configured to generate electrical pulses in accordance with instructions from a controller. It should be appreciated that the pulse generator and controller can be integrated into a single device or multiple devices.

The term "electrode" is used to refer to a conducting material that is capable of receiving electrical pulses and communicating them to another surface.

The term "modulation" or "modulating" means any form of regulation, manipulation or control to change a given variable from one state to another state.

Any increases or decreases in levels or rates are determined by the following formula [(New Level or Rate)−(Old Level or Rate)]/(Old Level or Rate).

The phrase "at least one of x, y, and z" means that only one of x or y or z need to be true or present in order to satisfy that limitation.

The term "dermatome" refers to an area of skin that is primarily innervated and/or supplied by a specific spinal nerve.

The term "meridian" refers to low resistance fluid channels where various chemical and physical transports take place and are individual pathways which exist among the subcutaneous tissues and serve as channels for the flow of interstitial microscopic fluid throughout the body.

The term "big data" refers to voluminous amount of structured, semi-structure and unstructured data that has the potential to be mined and analyzed for patterns and information.

The term "bolus" refers to a discrete, single dosage of stimulation that is given in one instance in contrast to "constant stimulation" that refers to a certain intensity of stimulation that is delivered over a certain period of time at a constant rate.

The term "gastric emptying time" is defined as the time it takes to empty a predefined percentage of the patient's stomach contents, such as 25%, 50%, 75%, or 95%. Measures of gastric emptying time are established assuming the same composition of a known bolus of food. Therefore, where one is comparing a post-prandial time to empty 50% of the patient's stomach contents with stimulation to a post-prandial time to empty 50% of the patient's stomach contents without applying stimulation sessions, the comparison presumes a situation where the patient has consumed the exact same composition of food and liquid.

The term "direct electrical stimulation" of a given anatomical structure shall mean encompassing the anatomical structure in an electrical field generated by the electrical stimulation.

The term "meal" refers to any of the regular occasions in a day when an amount of solid or liquid food is eaten, such as breakfast, lunch, or dinner, and including various snacks therebetween.

The term "gastric retention" refers to a measure of how much content is left in the stomach after a predefined period of gastric activity.

The terms "server", "server(s)" and "at least one server" refer to one or more servers, including a cloud configuration where a specific individual server may not be identifiable.

The term "interneuron" is defined as a broad class of neurons found in the human body. Interneurons create neural circuits, enabling communication between sensory or motor neurons and the central nervous system (CNS).

The term "metabolic or health state" of a patient refers to at least one or any sub-set or combination of the following therapeutic parameters that define the physiology of the patient: an amount or rate of antral motility, gastric motility, gastric emptying time, gastric retention, gastric accommodation or distention, appetite or hunger level; satiety, satiation or fullness levels; compliance with a target daily caloric intake or dietary compliance; quality of sleep; glucagon-like peptide 1 (GLP-1), leptin, serotonin, peptide YY, beta-endorphin levels, resting metabolic rate, cholecystokinin; total body weight; total weight loss, excess weight loss; well-being level; pre and post-prandial ghrelin level; acyl-ghrelin; total ghrelin; triglycerides, cholesterol, lipopolysaccharides, motilin-related peptide or plasma motilin level peak value; degree of glycemia, glycemia peak; glucose level of a non-diabetic or a non-pre-diabetic patient, postprandial plasma glucose concentration of a pre-diabetic and diabetic patient, glycemic control, fasting blood or plasma glucose; hemoglobin A1C; glucose homeostasis, HOMA-IR (Homeostasis Model Assessment—estimated Insulin Resistance); fasting plasma insulin level; degree of insulin resistance; gut microbiota; metabolism rate (such as RMR or BMR); perception of gastric fullness or emptiness; exercise output, defined as the amount of calories burned in a given time period or steps taken in a given time period; hepatic gluconeogenesis; prolactin level; dopamine level; and/or plasma cytokeratin 18 (CK-18).

The term "real-time" refers to the concurrence in time between two events. For example, if a dietary intervention is described as being provided in "real-time" relative to the acquisition of appetite data, it means that the dietary intervention occurs within 24 hours, preferably 12 hours, preferably 6 hours, preferably 1 hour, or any increment therein, of acquiring appetite data. This is contrast to patient diaries that acquire data over the course of weeks and then, modifying therapy based on long term data collection.

Electro-Dermal Patch System

Figure 1A:
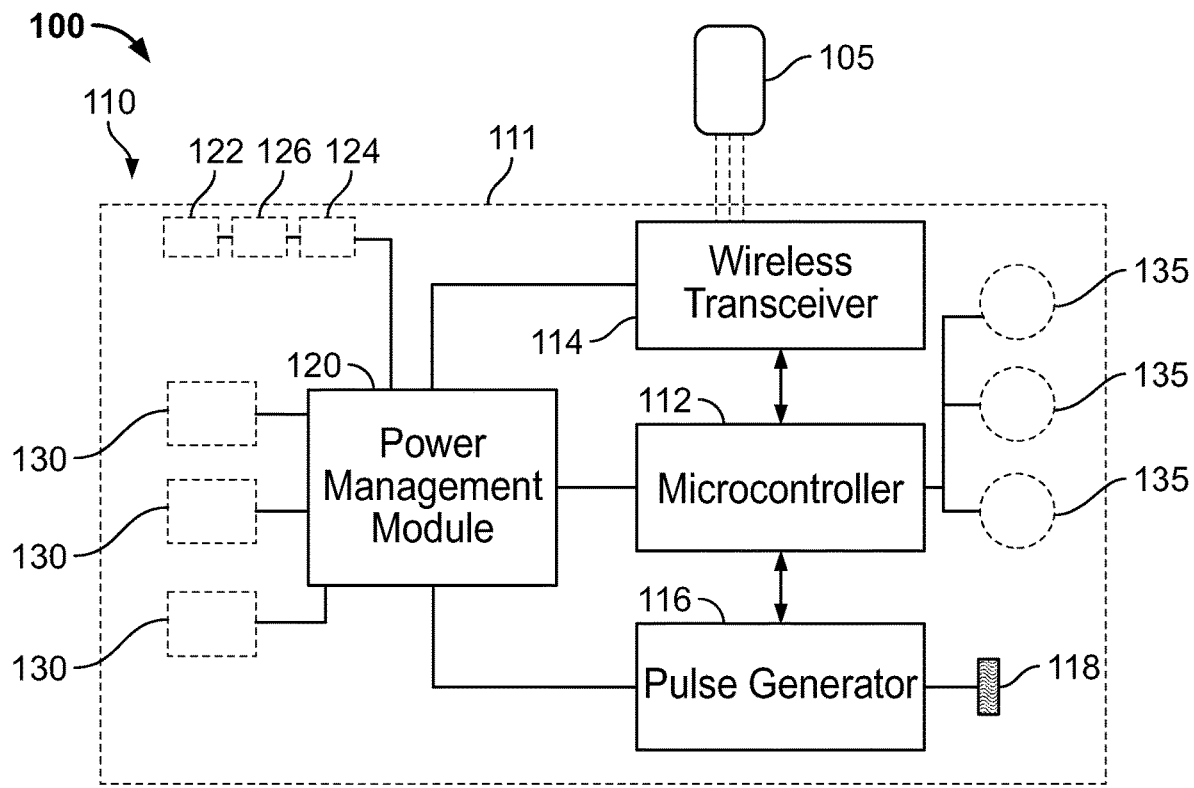
FIG. 1A is a block diagram of a system for stimulating nerves and nerve endings in body tissue, in accordance with various embodiments of the present specification.

FIG. 1A is a block diagram illustration of a system 100 for stimulating or modulating nerves and nerve endings in body tissues, in accordance with an embodiment of the present specification. The system 100 comprises an electro-dermal patch (EDP) device 110 in data communication with a companion device 105. In various embodiments, the companion device 105 is further capable of being in data communication with a remote patient care facility, data server and/or patient care personnel. The companion device 105, comprising a computer readable medium and processor, can be any type of computing and communication device, including a computer, server, mobile phone, gateway, laptop, desktop computer, netbook, personal data assistant, remote control device or any other device capable of accessing a cellular, Internet, TCP/IP, Ethernet, Bluetooth, wired, or wireless network.

The electro-dermal patch device 110, in various embodiments, has a housing 111 comprising a microprocessor or microcontroller 112 electronically connected to a transceiver 114 to wirelessly communicate with the companion device 105, a pulse generator 116 to generate a plurality of electrical pulses for application through one or more electrodes 118 and a power management module 120, such as a lithium-ion battery, a betavoltaic battery, a solar cell, nickel-cadmium battery, or a fuel cell. In some embodiments, the power management module 120 comprises a battery having a voltage in a range of 1.5 V to 4.5 V (for a single battery). The voltage depends on the chemistry of the battery being used. In other embodiments, the power management module 120 includes a plurality of batteries stacked in series to increase the voltage supply, wherein per battery voltage ranges from 1.5 V to 4.5 V. The power management module 120 has one or more additional receptor slots 130 to enable snap on or clip on attachment of a disposable electronic assembly that includes a battery for providing additional backup charge to the electro-dermal patch device 110.

Optionally, the housing 111 also comprises one or more actuators 122 such as push buttons or switches to switch the device 110 on/off and to enable user control or settings of a plurality of stimulation therapy protocols such as for, but not limited to, toggling stimulation up or down, one or more visual indicators 124, such as LEDs (Light Emitting Diodes), and one or more tactile and audio indicators 126, such as a vibrator, buzzer or beeper to provide feedback to a user, such as about the on/off state of the electro-dermal patch device 110, commencement or conclusion of therapy, battery charge/discharge, and/or malfunction of the electro-dermal patch device 110, among other information. In one embodiment, the one or more actuators 122 includes a touch sensitive screen that enables (using an accelerometer) the user to finger-tap to control and adjust stimulation therapy protocols while the electro-dermal patch device 110 is still worn by the user. Still further embodiments may include (additionally or alternatively) control interfaces on the EDP such as, but not limited to, a slider on the surface of the EDP, an infrared interface wherein communication between the EDP 110 and the companion device 105 is achieved by transmission of infrared radiation, a magnetic interface wherein an external magnet or electro-magnet activates a reed switch or GMR (giant magnetoresistance) device or sensor positioned on the EDP 110, or an audible (speaker) command input interface.

Figure 21B:
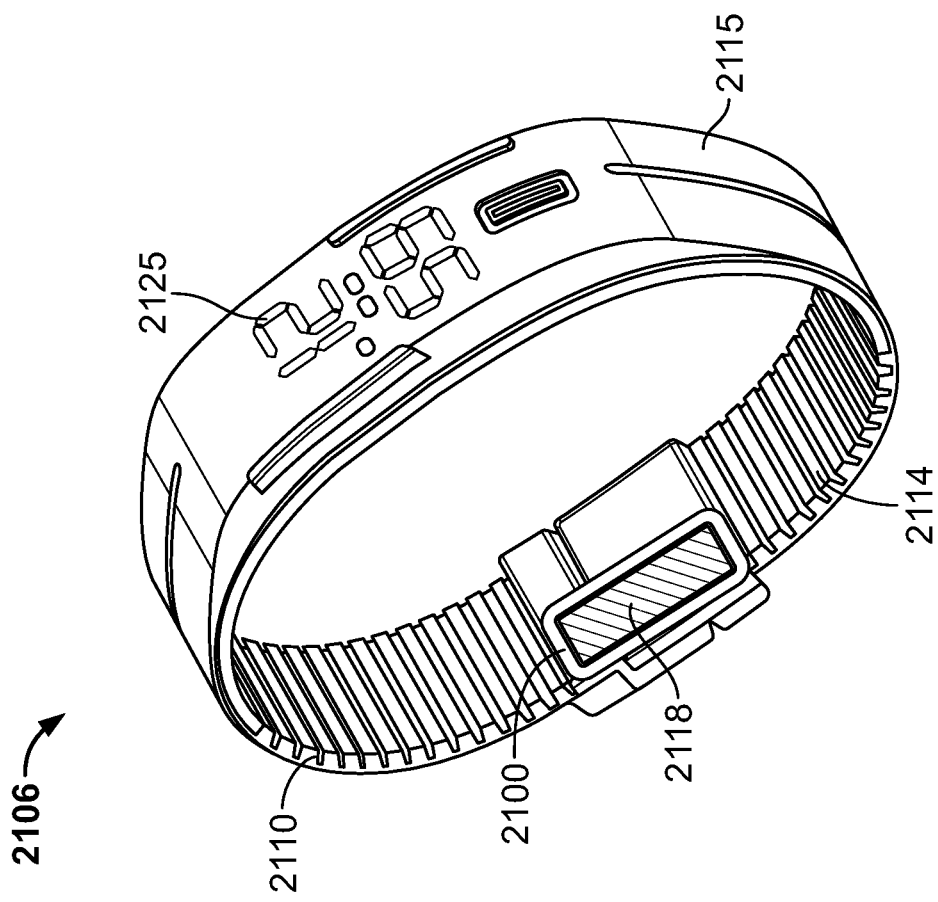
FIG. 21B is a perspective view of a wristwatch incorporating an EDP device of the present specification, in accordance with an embodiment.
Figure 21A:
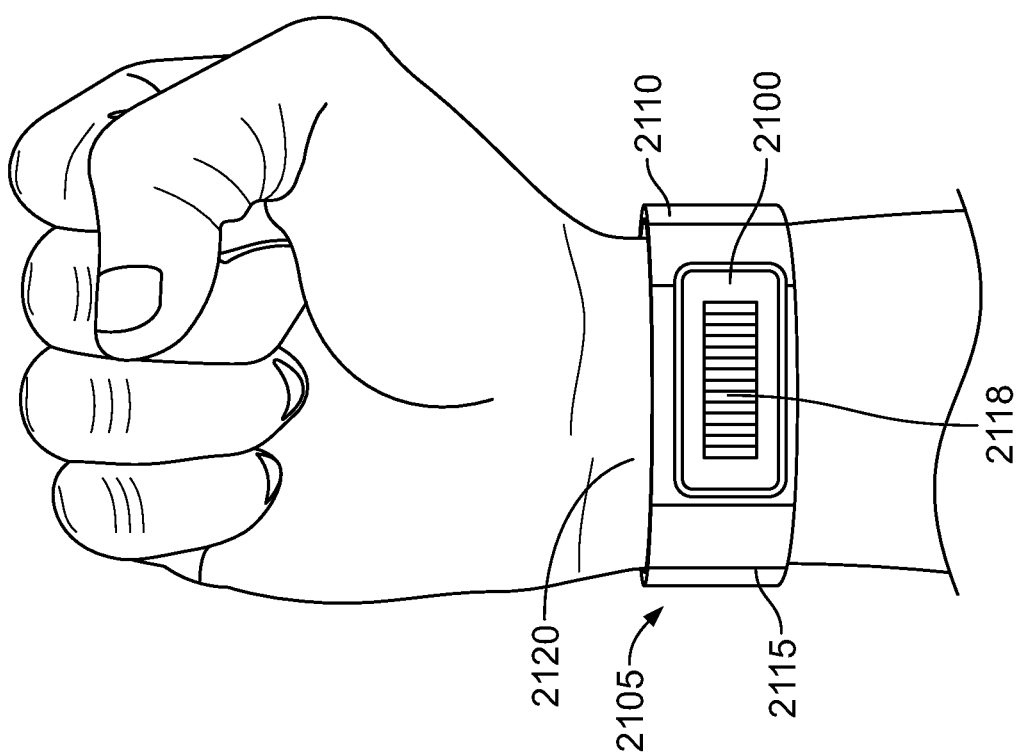
FIG. 21A is a perspective view of a band incorporating an EDP (electro-dermal patch) device of the present specification, in accordance with an embodiment.

In various embodiments, the EDP 110 is programmable and controlled directly, that is without the companion device 105, such as, but not limited to, by actuating one or more buttons (actuators 122) to enable user control or settings of a plurality of stimulation therapy protocols and parameters (for example, a pre-defined number of presses of a button may correspond to a predefined functional setting of the EDP); by issuing predefined voice based commands to an audible (speaker) command input interface of the EDP or via an Intelligent Personal Assistant (IPA) system (described with reference to FIG. 48A through C) that may be in direct communication with the EDP 110; or by issuing commands through pre-defined physical body movements, such as (for example) haptic motions of the wrist or hand, when the user is wearing the EDP 110 configured as a wristwatch or wristband (such as the band 2105 of FIG. 21A or the wristwatch 2106 of FIG. 21B and that also includes an accelerometer or inclinometer to detect, capture and acquire the user's haptic motions).

It should also be appreciated that, in one embodiment, the EDP comprises no such on/off actuators or stimulation toggling actuators and is entirely controlled by an external device, as described below.

In various embodiments, the housing 111 is sealed so that it is waterproof or water-resistant. In some embodiments, the housing 111 is hermetically sealed to be airtight. In various embodiments, the housing 111 is molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or poly-lactide (PL/DLA) co-polymers, PLLA-polyglycolic acid (PGA) co-polymers, and photocrosslinkable polymers. In some embodiments, the housing 111 is of transparent polymeric material to allow visibility of the contained electronic components and circuitry.

In various embodiments, the microprocessor 112 is in electronic communication with one or more sensors 135 to generate data representative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and/or UV radiation exposure and absorption. In certain cases, the data representative of the various physiological parameters are the signal or signals themselves generated by the one or more sensors 135 and in certain other cases the data is calculated by the microprocessor 112 based on the signal or signals generated by the one or more sensors 135. Methods for generating data representative of various physiological parameters and sensors to be used therefor are well known to persons of ordinary skill in the art.

Table 1 provides several examples of well-known parameters and the sensor used to measure the parameter. The types of data listed in Table 1 are intended to be examples of the types of data that can be generated by the one or more sensors 135. It is to be understood that other types of data relating to other parameters can be generated by the electro-dermal patch device 110 without departing from the scope of the present specification. It is further understood that the sensors may be located in the housing 111, as shown in FIG. 1A, or remotely positioned from the housing 111 and configured to be electronic communication, via the wireless transceiver 114, with the microcontroller 112.

TABLE 1

| Parameter | Sensor |
| --- | --- |
| Heart Rate/Pulse Rate | EKG (2 Electrodes)/BVP (LED Emitter and Optical Sensor) |
| Beat-to-Beat Variability | EKG (2 Electrodes) |
| EKG Skin Surface Potential | EKG (3-10 Electrodes) |
| Respiration Rate | Chest Volume Change (Strain Gauge) |
| Skin Temperature | Surface Temperature Probe (Thermistors) |
| Core Temperature | Esophageal or Rectal Probe (Thermistors) |
| Heat Flow | Heat Flux (Thermopile) |
| Galvanic Skin Response | Skin Conductance (2 Electrodes) |
| EMG Skin Surface Potential | EMG (3 Electrodes) |
| EEG Skin Surface Potential | EEG (Multiple Electrodes) |
| EOG Eye Movement | Thin Film Piezoelectric Sensors |
| Blood Pressure | Electronic Sphygmomanometer |
| Body Fat | Body Impedance (2 Active Electrodes) |

TABLE 1-continued

| Parameter | Sensor |
| --- | --- |
| Activity | Accelerometer |
| Oxygen Consumption | Oxygen Uptake (Electro-chemical) |
| Glucose Level | Electro-chemical sensors, Optical techniques, Aqueous techniques (tears, saliva, and sweat), and Iontophoresis techniques. |
| Body Position | Mercury Switch Array, Accelerometer |
| Muscle Pressure | Thin Film Piezoelectric Sensors |
| UV Radiation | UV Sensitive Photo Cells |
| Blood oxygen saturation | Pulse oximeter |

The microprocessor 112 is programmed to summarize and analyze the data representative of the physiological parameters of the individual. For example, the microprocessor 112 can be programmed to calculate an average, minimum or maximum heart rate or respiration rate over a defined period of time, such as ten minutes. The electro-dermal patch device 110 is also able to derive information relating to the individual's physiological state based on the data representative of one or more physiological parameters. The microprocessor 112 is programmed to derive such information using known methods based on the data representative of one or more physiological parameters. Table 2 provides examples of the type of information that can be derived, and indicates some of the types of data that can be used therefor.

TABLE 2

| Derived Information | Data Used |
| --- | --- |
| Activity level | Heart rate, pulse rate, respiration rate, heat flow, activity, oxygen consumption |
| Basal metabolic rate | Heart rate, pulse rate, respiration rate, heat flow, activity, oxygen consumption, glucose level |
| Basal temperature | Skin temperature, core temperature |
| Calories burned | Heart rate, pulse rate, respiration rate, heat flow, activity, oxygen consumption |
| Maximum oxygen consumption rate | EKG, heart rate, pulse rate, respiration rate, heat flow, blood pressure, activity, oxygen consumption |
| Relaxation Level | EKG, beat-to-beat variability, heart rate, pulse rate, respiration rate, skin temperature, heat flow, galvanic skin response, EMG, EEG, blood pressure, activity, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |

Additionally, the electro-dermal patch device 110 may also generate data indicative of various contextual parameters relating to the environment surrounding the individual. For example, the electro-dermal patch device 110 can generate data representative of the air quality, sound level/quality, light quality or ambient temperature near the individual, or the global positioning of the individual. The electro-dermal patch device 110 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

In one embodiment, the electro-dermal patch device 110 includes at least one or a combination of the following three sensors 135: 1) an impedance or bio-impedance sensor to determine electrode integrity, i.e. whether the electrode is functioning properly or damaged, to detect and confirm contact integrity of the one or more electrodes 118 with tissues to be stimulated, or to estimate body fat or Body Mass Index (BMI) and accordingly modify or manage stimulation therapy. In another embodiment, a first impedance or bio-impedance sensor is used to detect and confirm contact integrity of the one or more electrodes 118 with tissues to be stimulated and a second impedance or bio-impedance sensor is used to estimate body fat or Body Mass Index (BMI), 2) an accelerometer or inclinometer to monitor user activity such as walking, running, exercises, distance covered, sleep quality, including sleep duration, detection and monitoring, sensing user input to the electro-dermal patch device 110, 3) a neural activity monitor to detect presence of neural activity as well as an amount of neural activity (firing rate).

In one embodiment, the electro-dermal patch device 110 only includes one or a combination of the following three sensors 135, and no other sensors: 1) an impedance or bio-impedance sensor to determine electrode integrity, i.e. whether the electrode is functioning properly or damaged, to detect and confirm contact integrity of the one or more electrodes 118 with tissues to be stimulated, or to estimate body fat or Body Mass Index (BMI) and accordingly modify or manage stimulation therapy. In another embodiment, a first impedance or bio-impedance sensor is used to detect and confirm contact integrity of the one or more electrodes 118 with tissues to be stimulated and a second impedance or bio-impedance sensor is used to estimate body fat or Body Mass Index (BMI), 2) an accelerometer or inclinometer to monitor user activity such as walking, running, exercises, distance covered, sleep quality, including sleep duration, detection and monitoring, sensing user input to the electro-dermal patch device 110, 3) a neural activity monitor to detect presence of neural activity as well as an amount of neural activity (firing rate). With respect to confirming contact integrity, it should be appreciated that, in one embodiment, sufficient contact integrity of the one or more electrodes 118 is defined in terms of achieving a predefined amount of electrode impedance with the patient's epidermal layer, such as in the range of 200 to 1000 ohms, as measured by the impedance sensor.

The neural sensor is used to generate a plurality of feedback such as, but not limited to, an indication that the electro-dermal patch device 110 is placed in the right location or area, an indication that the electro-dermal patch device 110 is increasing neural-activity in line with, and in accordance with, a stimulation protocol or an indication that the neural response rate is too slow or insufficient and, therefore, the stimulation protocol needs to be modified. Such plurality of feedback generated by the neural sensor is provided to the user through a Health Management software application running on the user's hand-held computing device such as a smartphone, PDA, tablet that, in various embodiments, functions as the companion device 105. In some embodiments, the neural sensor connects to at least one of the one or more stimulation electrodes 118 while in some alternate embodiments, the neural sensor connects to at least one additional sensing electrode in addition to the one or more stimulation electrodes 118. In some embodiments, the electro-dermal patch device 110 also integrally includes a glucose sensor to monitor the user's blood glucose level. In some embodiments, the glucose sensor is configured as a standalone third party device in wireless communication with the Health Management application of the present specification.

In some embodiments, the electrodes 118 are in the housing 111, while in other embodiments, the electrodes 118 are removably connectable to the housing 111. In one embodiment, the electrodes 118 are configured to be partially or wholly positioned in the housing 111 and extend outward to be in electrical communication with a hydrogel pad (for example, as described with reference to FIGS. 4D-4S). In another embodiment, the electrodes 118 are configured to be snap-on electrodes where the electrodes 118 are removably connectable to an exterior surface of the housing 111. This allows for the electrode 118 and/or hydrogel pad to be removed and replaced with a new electrode 118 and hydrogel pad, thereby reusing the electrical dermal patch device 110 with the new electrode and hydrogel pad and minimizing the cost of electrodes that fail after just a few days of use. In yet another embodiment, the electrodes 118 are configured to be removably connectable to the exterior surface of the housing 111 using at least one magnet. Use of magnet(s) requires the user to use minimal force or effort to re-attach the electrodes 118 to the housing 111 as compared to a snap-on configuration.

Figure 1B:
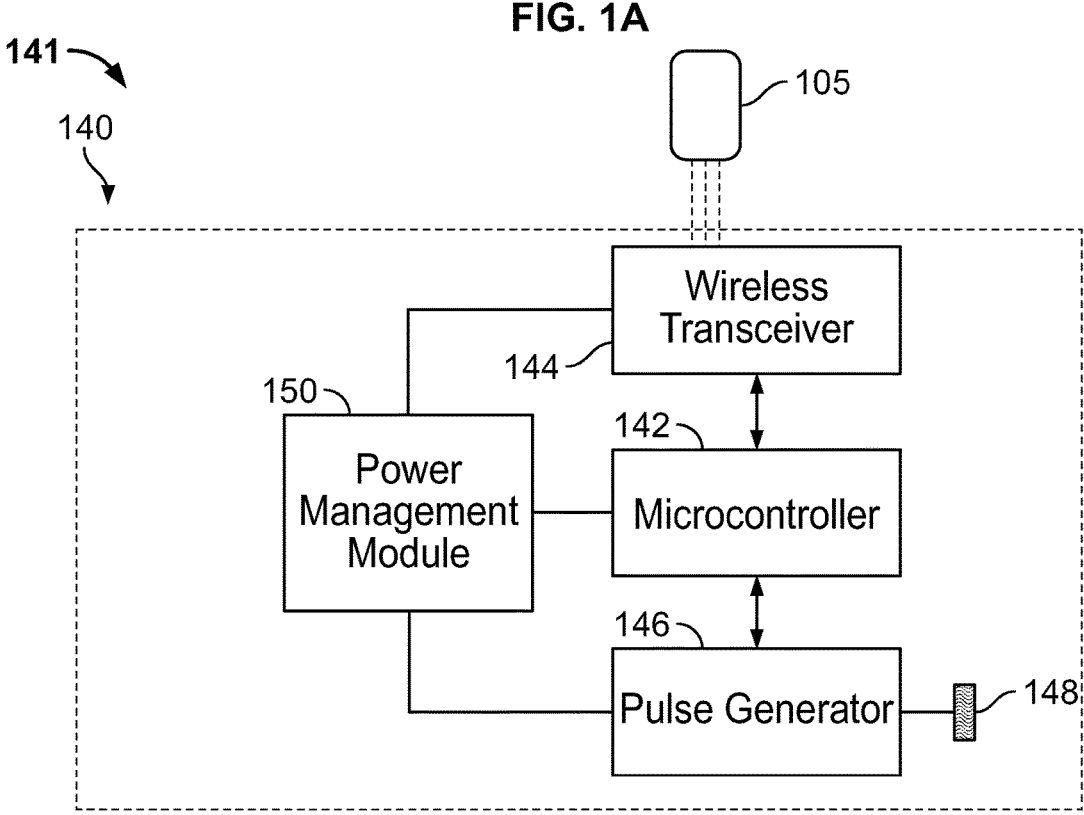
FIG. 1B is a block diagram of a system for stimulating or modulating nerves and nerve endings in body tissues, in accordance with another embodiment of the present specification.

FIG. 1B is a block diagram illustration of a system 141 for stimulating or modulating nerves and nerve endings in body tissues, in accordance with another embodiment of the present specification. In some embodiments, referring to FIG. 1B, the electro-dermal patch device (EDP) 140 includes a microcontroller 142, wireless transceiver 144, a power management module 150, such as a lithium-ion battery, a betavoltaic battery, a solar cell, nickel-cadmium battery, or a fuel cell, a pulse generator 146, and at least one electrode 148, and includes no other physical inputs or sensors on the EDP 140 itself. The remaining inputs are on the companion device 105 and are actuated through the wireless coupling of the companion device 105 and EDP 140.

In some embodiments, rather than including a physical on/off switch, the EDP 140 depicted in FIG. 1B is always using at least a minimum amount of power such that an 'off' state refers to a low power state. While no stimulation is being provided, there is, at a minimum, a periodic 'wake-up' of the EDP 140 to check for communication from the companion device 105. The 'wake-up' places the device in an 'on' state and, in some embodiments, includes no stimulation wherein the EDP 140 runs diagnostics for reporting to the companion device 105. Therefore, while in the 'off' state, the EDP 140 is constantly using a very low amount of power, is not providing stimulation, and is either awaiting a signal from the companion device or is performing diagnostics or other non-stimulation activities requiring very little power. In some embodiments, the energy usage is less than 5 µA average current or in the range of 0.1 µA to 5 µA average current while in the 'off' state and greater than 10 µA average current while in the 'on' state. In some embodiments, the energy usage is at least 1 µA greater while in the 'on' state than while in the 'off' state. Once the EDP 140 receives a signal from the companion device 105 to initiate stimulation, it enters the 'on' state and uses an amount of energy associated with the level of stimulation. In another embodiment, the EDP 140 uses no energy while in an 'off' state and must be awakened, or switched to an 'on' state, by a signal from the companion device.

Figure 1C:
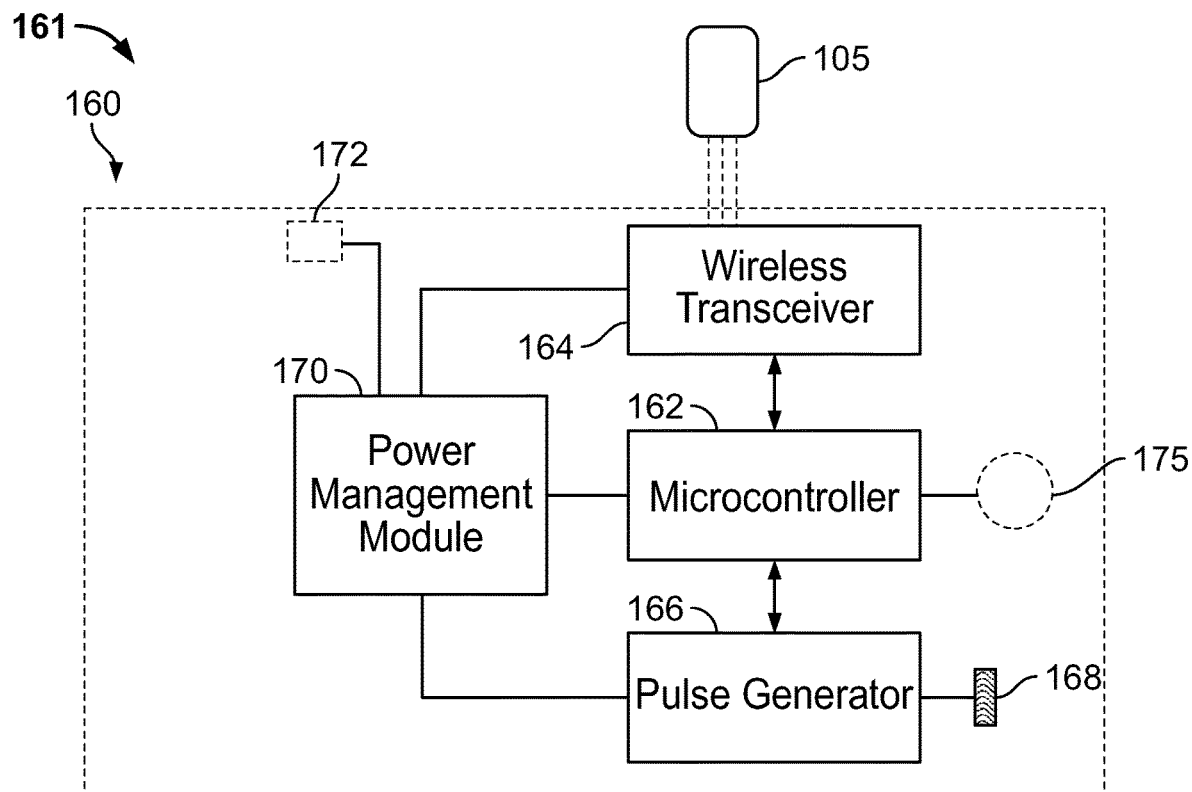
FIG. 1C is a block diagram of a system for stimulating or modulating nerves and nerve endings in body tissues, in accordance with yet another embodiment of the present specification.

FIG. 1C is a block diagram illustration of a system 161 for stimulating or modulating nerves and nerve endings in body tissues, in accordance with yet another embodiment of the present specification. In some embodiments, referring to FIG. 1C, the electro-dermal patch device (EDP) 160 includes a microcontroller 162, wireless transceiver 164, a power management module 170, such as a lithium-ion battery, a betavoltaic battery, a solar cell, nickel-cadmium battery, or a fuel cell, a pulse generator 166, one electrode 168, an optional single actuator 172 to turn the EDP 160 on or off, one sensor 175 for sensing a physiological parameter of the patient, and includes no other physical inputs on the EDP 160 itself. In one embodiment, the sensor 175 is a neural sensor. The remaining inputs are on the companion device 105 and are actuated through the wireless coupling of the companion device 105 and EDP 160.

In accordance with various aspects of the present specification, each component (power management module, microprocessor or microcontroller, pulse generator, transceiver, and one or more electrodes) of the electro-dermal patch may be positioned in a separate housing, in a separate device, or otherwise physically remote from each other. For example, as described with reference to FIG. 1A, the electro-dermal patch device 110 comprises a power management module 120, microprocessor or microcontroller 112, pulse generator 116, transceiver 114, and one or more electrodes 118 in a housing 111, where the one or more electrodes 118 are in physical communication with a hydrogel pad.

Figure 1D:
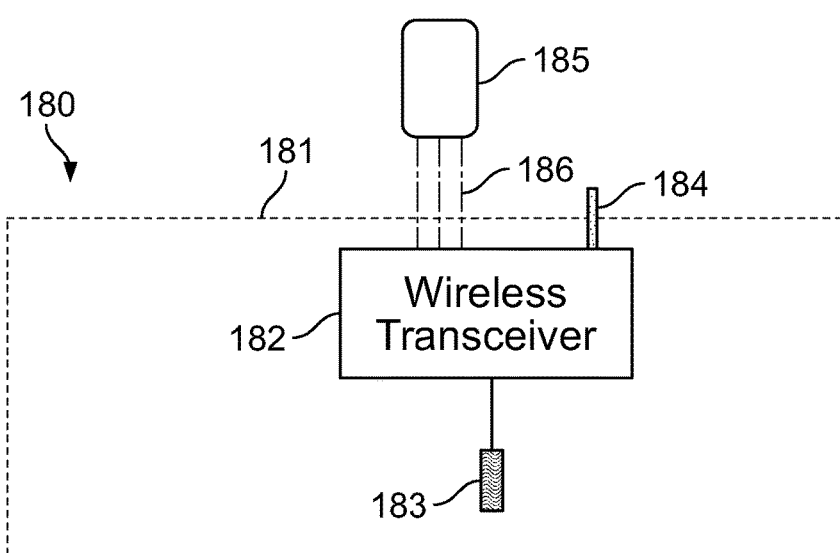
FIG. 1D is a block diagram of a system for stimulating or modulating nerves and nerve endings in body tissues, in accordance with yet another embodiment of the present specification.

However, in a first alternative embodiment as shown in FIG. 1D, the electro-dermal patch device 180 comprises a transceiver 182 having an antenna 184 for receiving electrical pulse signals 186 and an electrode 183, which may or may not be in physical contact with a hydrogel pad. A housing 181 may be positioned around the transceiver 182 and electrode 183 or a substrate carrier may be used to support a low-profile transceiver and/or electrode circuit without any additional housing structure. In this embodiment, an external device 185 comprises the power source, controller, and pulse generator adapted to generate a plurality of electrical pulses, as described earlier with reference to FIGS. 1A through 1C. The external device 185 may be a watch, mobile phone, a sensor pod configured to attach to the patient using a strap or band, or other wearable device. The external device 185 wirelessly transmits the electrical pulses 186 to the transceiver 182 which, in turn, transmits the electrical pulses to the electrode 183 and, thereafter, to the patient's epidermal layer through the hydrogel pad.

Figure 1E:
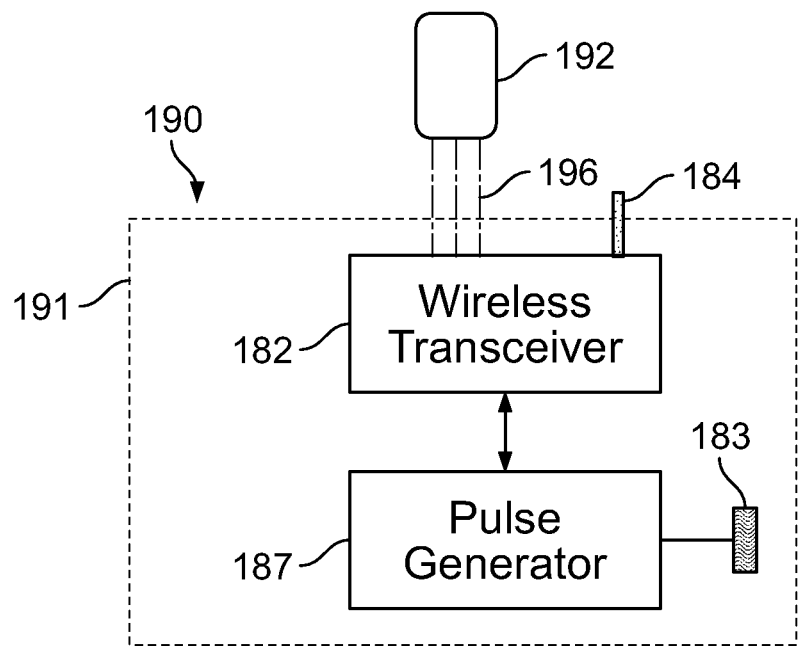
FIG. 1E is a block diagram of a system for stimulating or modulating nerves and nerve endings in body tissues, in accordance with still another embodiment of the present specification.

In a second alternative embodiment, as shown in FIG. 1E, the EDP device 190 comprises a transceiver 182 having an antenna 184 for receiving signals 196, a pulse generator 187, and an electrode 183 in physical communication with a hydrogel pad. A housing 191 may be positioned around the transceiver 182, pulse generator 187, and electrode 183. In this embodiment, an external device 192 comprises the power source and controller adapted to generate an electrical signal, power signal, or data signal 196 that is wirelessly transmitted to transceiver 182 and, in turn, to the pulse generator 187 and used by the pulse generator 187 to generate a plurality of electrical pulses. The external device 192 may be a watch, mobile phone, a sensor pod configured to attach to the patient using a strap or band, or other wearable device. The electrical pulses are communicated to the electrode 183 and, thereafter, to the patient's epidermal layer through an optional hydrogel pad.

Figure 1F:
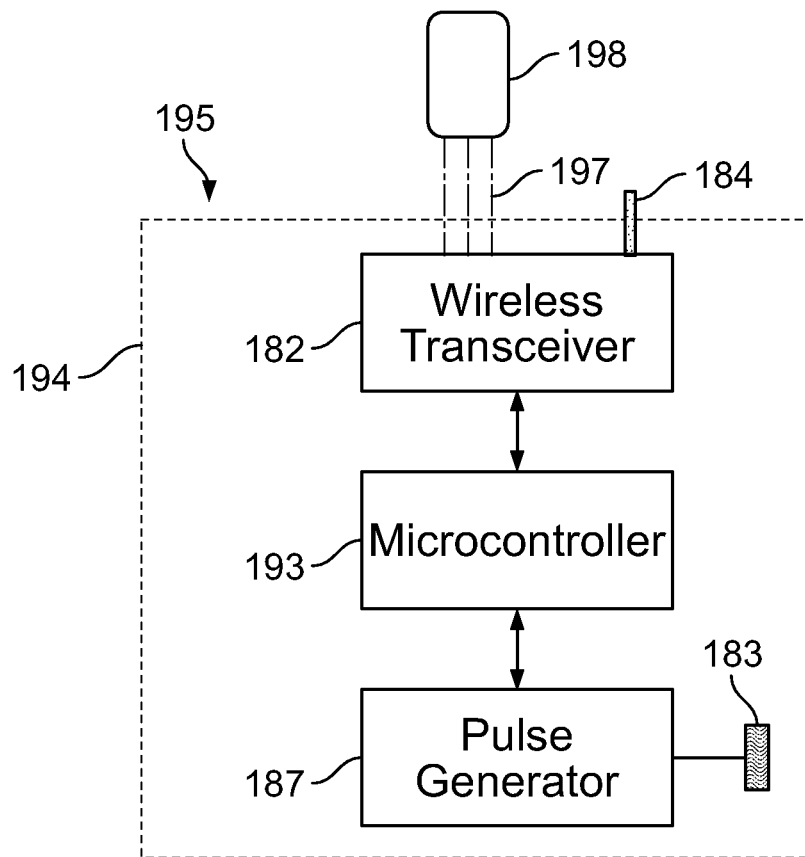
FIG. 1F is a block diagram of a system for stimulating or modulating nerves and nerve endings in body tissues, in accordance with yet another embodiment of the present specification.

In a third alternative embodiment, as shown in FIG. 1F, the EDP device 195 comprises a transceiver 182 having an antenna 184 for receiving power signals 197, a microprocessor or microcontroller 193, a pulse generator 187, and an electrode 183 in physical communication with a hydrogel pad. A housing 194 may be positioned around the transceiver 182, microcontroller 193, pulse generator 187, and electrode 183. In this embodiment, an external device 198 comprises a power source and transceiver adapted to generate the power signal 197 that is wirelessly transmitted to the transceiver 182 of the EDP device 195 and, in turn, to the microcontroller 193 and pulse generator 187 which generates a plurality of electrical pulses. The external device 198 may be a watch, mobile phone, a sensor pod configured to attach to the patient using a strap or band, or other wearable device. The electrical pulses are communicated to the electrode 183 and, thereafter, to the patient's epidermal layer through an optional hydrogel pad.

In a fourth alternative embodiment, each of the power source, controller, pulse generator, transceiver, electrode, and hydrogel pad are combined altogether in a single housing. In a fifth alternative embodiment, the controller, pulse generator, and/or transceiver are combined together in a first housing while the electrode, power source, and/or hydrogel pad are in a disposable second housing, thereby allowing the electrode, power source, and hydrogel to be disposed of when exhausted. Accordingly, the controller, pulse generator, and/or transceiver could be reused and connected to a second electrode, power source, and/or hydrogel pad, yielding a refreshed device.

It should be appreciated that each of the above embodiments can be implemented without a transceiver, replacing the wireless communication with a wired connection between the external device and the electro-dermal patch. It should also be appreciated that, for each embodiment, signal processing to determine data indicative of a physiological condition can be done at the sensor level, i.e. in the impedance or other sensor, at the controller level in the EDP device, or at the external device level using a mobile application software or other program.

Electro-Dermal Patch (EDP) Device Configurations

Prior art TENS (Transcutaneous Electrical Neurostimulation) or electrostimulation devices worn externally are not well suited for extended wear (such as, for more than a few hours). The stimulation therapy of the present specification requires a wearable device that is attached to the user's skin during waking hours so as to enable a plurality of specific treatment protocols to the user, automatically over time. In order for this to be feasible, the EDP device of the present specification must possess a high level of extended wearability that is not compromised by either the device falling off or by causing skin irritation or itching.

Thus, in accordance with an aspect of the present specification, the electro-dermal patch device 110 is configured as a wearable and disposable skin patch that is adhesively attached to the user's skin. Optionally, the EDP includes at least one or a pair of removable and replaceable conductive hydrogel, hydrocolloid or foam pads and have an adhesive base surface covered by a tab (described with reference to FIG. 2D) such that, when the tab is removed, the base surface can be adhered to the user's skin. Alternatively, the conductive hydrogel, hydrocolloid (contains gel-like components in an adhesive compound laminated onto a flexible, water-resistant outer layer) or foam pads (as described with respect to FIG. 55M) are a permanent part of the electrodermal patch device 110 and the entire assembly is disposed of once the battery depletes. The hydrogel pads provide electrical conductivity from the EDP device to a user's skin surface. Hydrogel consists of a water based absorbing polymer and a water based electrolyte. Electrical current is transmitted to the skin via the electrolyte in the hydrogel. In various embodiments, both the hydrogel and the electrolyte within meet the requirements of biocompatibility as defined by ISO 10993-5,10, which is incorporated herein by reference. In some embodiments, the EDP device uses 'foam electrodes' (or foam pads comprising polyethylene acrylic foam adhesive) with either dry or wet conductive gels applied to the center of the electrode assembly. The foam is placed along the perimeter of the electrode assembly and provides adhesion to the skin. The gel is the conductive medium between the electrode metal and the skin. The 'foam electrodes' are impervious to water since the foam is closed cell and acts as a barrier to water ingress to the conductive gel.

In accordance with an aspect of the present specification, the electro-dermal patch device 110 is configured to be worn for prolonged usage, such as for at least 1, 2, 3, 4, 5, 6, 7, 8, 9, 10, 11, 12, 13, 14 days continuously or up to 3 months continuously or any increment therein, and removed solely for the purpose of recharging and/or optionally changing the replaceable conductive hydrogel pads. In accordance with another aspect of the present specification, the electro-dermal patch device 110 provides stimulation therapy while at the same time minimizing skin irritation and related side effects such as erythema (redness), scaling, pruritus (itching), stripping of stratum corneum, adhesive irritation, bacterial infection related to occlusion (folliculitis), irritant contact dermatitis and intertrigo. It should be noted that obese people with belly rolls are particularly susceptible to intertrigo (Intertriginous dermatitis or Candida Albicans) which causes abdominal rashes and irritation. Therefore, the EDP device of the present specification uses electrodes that are suited for prolonged stimulation without promoting the aforementioned skin problems.

In some embodiments, the electrical dermal patch is adapted to be continuously worn by a patient for at least 3 days and comprises a housing comprising a controller in electrical communication with a pulse generator and at least two electrodes adapted to be adhered to the patient's skin and in electrical communication with the pulse generator. The controller comprises programmatic instructions that, when executed and transmitted to the pulse generator, cause the pulse generator to generate and transmit to the at least two electrodes a first set of electrical stimulation pulses and a second set of electrical stimulation pulses. Each of the at least two electrodes comprise a hypoallergenic conductive gel with at least one adhesive surface.

In other embodiments, the electrical dermal patch is adapted to be continuously worn by a patient for at least 3 days and comprises a housing comprising a controller in electrical communication with a pulse generator and at least two electrodes adapted to be adhered to the patient's skin, positioned in a same plane parallel to the patient's skin, separated by a distance of 0.05 cm² to 0.4 cm². and in electrical communication with the pulse generator, wherein the controller comprises programmatic instructions that, when executed and transmitted to the pulse generator, cause the pulse generator to generate and transmit to the at least two electrodes a first set of electrical stimulation pulses and a second set of electrical stimulation pulses and wherein each of the at least two electrodes comprise a hypoallergenic conductive gel with at least one adhesive surface, wherein the hypoallergenic conductive gel does not comprise imidazolidinyl urea or diazolidinyl urea and wherein the at least one adhesive surface is adapted to adhere to the patient's skin and have a total skin contact surface area in a range of 2 cm² to 4 cm².

In one embodiment, a method of using the above described electrical dermal patch comprises programming the controller such that each of the electrical stimulation pulses comprises a pulse width in a range of 10 μsec to 10 msec, a pulse amplitude in a range of 100 μA to 100 mA, and a pulse frequency in a range of 1 Hz and 100 Hz and evaluating if the patient experiences a change in appetite as a result of an application of said first set of electrical stimulation pulses or said second set of electrical stimulation pulses to the patient's skin, wherein the patient does not experience erythema, scaling, pruritus, folliculitis, or intertrigo at a point where said two electrodes adhere to the patient's skin.

Accordingly, in some embodiments, the EDP device uses self-adhesive electrodes or electrode pads having a contact surface (for contact to the user's skin) made of a hypoallergenic conductive gel with at least one adhesive surface and that has enough adhesive properties to stay attached to the user's skin for at least 12 hours. In embodiments, the hypoallergenic conductive gel is made from a hydrogel not containing known allergens such as imidazolidinyl urea or diazolidinyl urea. In embodiments, the gel is tested and approved as non-allergenic using IgE skin tests, specifically that the conductive gel registers either a negative IgE skin test or below a threshold value to thereby be considered as not triggering an allergic reaction. In some embodiments, the hydrogel is made from a modified carboxymethylcellulose polymer with propylene glycol.

The adhesive of the pads is preferably biocompatible to prevent skin irritation due to prolonged usage of the patch. Loctite®, manufactured by Henkel, is a non-limiting example of a medical or biocompatible adhesive. The adhesive of the pads provides sufficient attachment integrity of the EDP to the user's skin. In various embodiments, the EDP has an average minimum 'peel strength' in a range of 1.0 to 2.1 Newton and preferably 1.5 Newton on living skin, allowing the EDP to be adhered to the skin for at least 8 hours of intensive activity, such as exercise. In one embodiment, the EDP device uses the KM30B hydrogel, manufactured by Katecho Inc., having a 'peel strength' in a range of 1 to 2.5 Newton. Persons of ordinary skill in the art would appreciate that 'peel strength' is the force required to remove or peel off the EDP, having adhesive pads, from the user's skin and is a measure of the attachment integrity of the EDP. 'Peel strength' is typically quantified by pulling the device from a flexible end or edge at an angle of 90 degrees from the skin surface at a peel rate that ranges from 100 to 500 mm/minute. In alternate embodiments, placement of the electro-dermal patch device 110 is accomplished using a band, strap or a belt (for example, at the user's abdomen, trunk, arm or wrist regions) without any adhesive. In embodiments, the band, strap or belt is of a flexible or elastic material such as, but not limited to, Lycra or Spandex and holds the electro-dermal patch device 110 at a target location/region (such as the abdomen, trunk, arm or wrist) by virtue of its elasticity. In some embodiments, the band, strap or belt is additionally or alternately held in place using conventional fastening means such as, but not limited to, Velcro, clasps, or buckle fastening. In still other embodiments, the electro-dermal patch device 110 is incorporated into a form fitting garment such as a tight undershirt (for example, a Body Glove, Lycra or Spandex undershirt) which when worn by the user positions the incorporated electro-dermal patch device 110 at the desired dermatome. In embodiments, the electro-dermal patch device 110 is either directly attached to the form fitting garment or is incorporated in the garment as woven-in circuitry. It should be appreciated that the term "adhered" is intended to encompass all forms of achieving device-to-skin contact, including adhesives, bands, straps, or belts.

In accordance with some embodiments, the one or more electrodes 118 enable the electro-dermal patch device 110 to provide electrical stimulation therapy, from the external surface of the patient's epidermal layer through a range of 0.1 mm to 10 mm or a range of 0.1 mm to 20 mm of the dermis, to a user. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20, 21, 22, 23, 24, or 25 mm or any increment therein. An embodiment of the present specification uses two electrodes disposed within hydrogel, foam or hydrocolloidal pads (also referred to, generically, as electrode pads). The electrode pads are disposed on the surface of the skin of the user to pass electrical pulses through the skin and stimulate nerves and nerve endings in body tissues under the skin in the region of the electrodes.

Figure 2B:
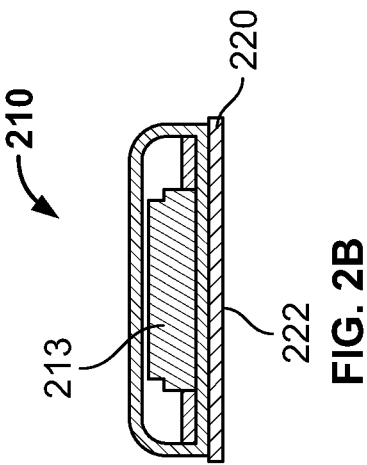
FIG. 2B is a front perspective view of the electro-dermal patch device of FIG. 2A.
Figure 2C:
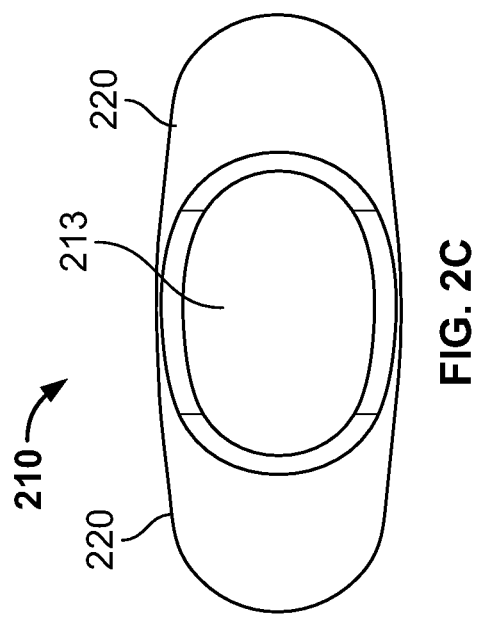
FIG. 2C is a top perspective view of the electro-dermal patch device of FIG. 2A.
Figure 2A:
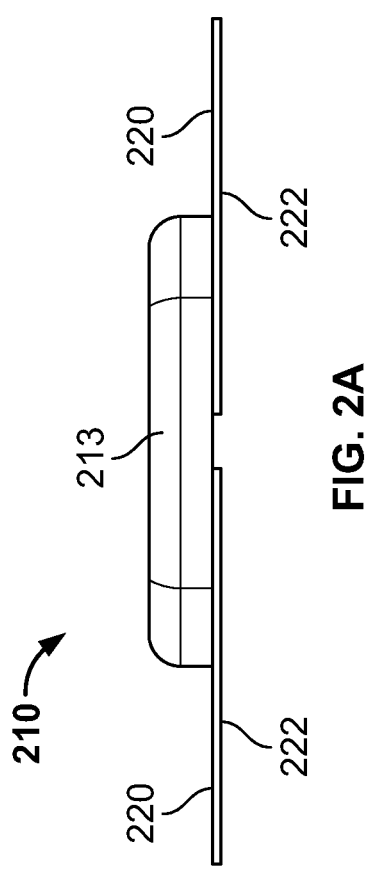
FIG. 2A is a side perspective view of an electro-dermal patch (EDP) device, in accordance with some embodiments of the present specification.

FIGS. 2A, 2B and 2C are respectively side, front and top perspective views of an electro-dermal patch device 210, in accordance with an embodiment, having a pair of conductive hydrogel pads 220 and a device housing 213. The housing 213 includes the microcontroller, pulse generator, wireless transceiver, and power management module of the system described with reference to FIG. 1A. The electrodes extend from the housing 213 and into the pads 220 for placement proximate the skin surface of a patient. In one embodiment, the pads 220 have at least one and preferably two electrodes (not shown) disposed or printed on a lower surface 222 of the pads 220. In some embodiments, the pads 220 have two electrodes, each disposed or printed in opposing halves of the lower surface 222. In embodiments, a distance between the two electrodes is less than 20 mm, preferably less than 15 mm, preferably less than 10 mm, preferably less than 5 mm. In one embodiment, the distance between the two electrodes is about 4 mm. The pads 220, when adhered to a user's skin, enable the electrodes to be in direct contact with the outer surface of the skin. It should be appreciated that while the electrodes touch the skin surface, the housing 213 remains above the skin surface. In some embodiments, the housing 213 remains within a range of 2 to 4 mm, and preferably 2 mm above the skin surface. In various embodiments, the electrodes can be in the form of typical gel-based skin electrodes, gel-less skin electrodes, or skin puncturing or skin abrading electrodes in order to reduce skin-electrode impedance. In various embodiments, the electrode surface area ranges from 0.1 inches² to 10 inches, 0.001 inches² to 0.1 inches, or 0.001 inches² to 10 inches². In some embodiments, the total surface area taken up by the base of the two electrodes is less than 10 in² and preferably less than 5 in². In some embodiments, the total surface area taken up by the two electrodes is less that 10 in², preferably less than 8 in², and more preferably, 7 in² or less.

Figure 2D:
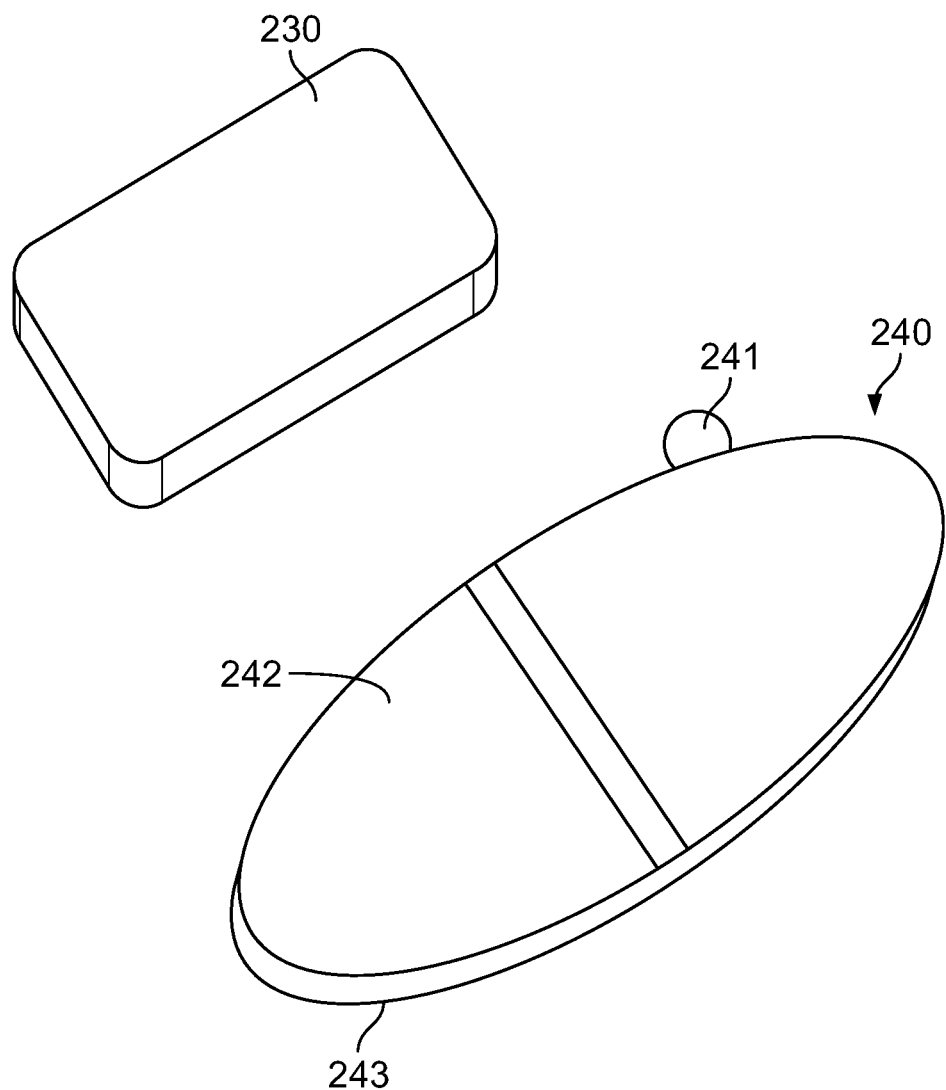
FIG. 2D is an oblique perspective view of an electro-dermal patch with hydrogel removed and a replacement hydrogel with liners, in accordance with one embodiment of the present specification.

In some embodiments, hydrogel pads 220 of the electro-dermal patch device of the present specification are replaceable, enabling re-attachability of new conductive pads and therefore new adhesion surfaces to the EDP device. FIG. 2D is an oblique perspective view of an electro-dermal patch 230 with hydrogel removed and a replacement hydrogel 240 with liners 242, 243, in accordance with one embodiment of the present specification In accordance with an aspect of the present specification, used hydrogel pads can be peeled off the EDP device by pulling on a removal tab 241. In one embodiment, the removal tab 241 is made from a white polyester film. On one side of this film there is an acrylic adhesive. When building the hydrogel and removal tab assembly, the acrylic side is placed facing the hydrogel on both the top and bottom. The replacement pad 240 is a custom shaped hydrogel, sandwiched between two pieces of transparent release liners 242, 243, in accordance with an embodiment. An EDP-facing release liner 242 is peeled away. The second piece of release liner 243, facing a skin surface, is used to handle and locate the hydrogel 240 accurately onto the bottom of the EDP 230. Light finger pressure is applied through the second release liner 243 to insure good contact to the EDP 230. The second liner 243 is then peeled away thus exposing the working surface of the hydrogel.

In an alternate embodiment, referring again to FIGS. 2A-2C, the housing 213 is detachable from the hydrogel pads 220 and can be snap-connected to the hydrogel pads 220. In yet another embodiment, the hydrogel pads 220 can be detachably connected to the housing 213 using at least one magnet. Use of magnet(s) requires the user to use minimal force or effort to detach and re-connect the hydrogel pads 220 and the housing 213 as compared to a snap-on configuration.

The skin patches or pads 220 can have different shapes and sizes for different body types and areas of stimulation. In some embodiments, the patches or pads are irregularly shaped. In various embodiments, the patches or pads 220 are rectangular having a length of about 2 inches, a breadth of about 1 inches and a thickness of about 0.2 inches. In another embodiment, the patches or pads 220 are rectangular having a length of about 3 to 5 inches, a breadth of about 0.5 to 2.5 inches and a thickness of about 0.10-0.30 inches. In various other embodiments, the patches or pads 220 are round or circular having a diameter of about 2 to 4 inches and a thickness of about 0.10 to 0.30 inches. In still other embodiments, the patches or pads 220 are square having sides of about 2 to 4 inches and a thickness of about 0.10 to 0.30 inches. The patches or pads 220 can have other sizes and shapes such as, but not limited to, elliptical or triangular. In other embodiments, the electrode/pad combination may have a shape including any one of irregular, rectangular, circular, square, elliptical, and triangular and wherein, at its widest, would between 0.25 to 5 inches in width, at its tallest would be between 0.25 to 5 inches in height, and at its thickest would be between 0.25 to 5 inches in thickness. In another embodiment, the device would comprise two of such electrode/pad combinations placed side by side.

Figure 3A:
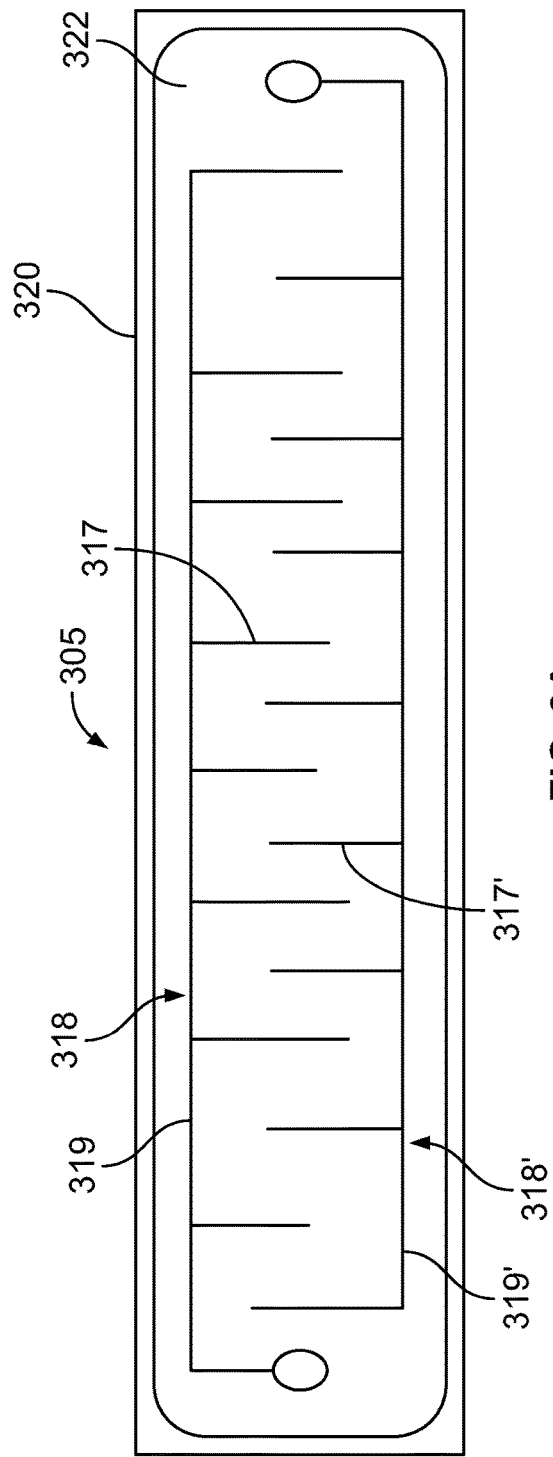
FIG. 3A illustrates a first pattern of electrodes, in accordance with certain embodiments.
Figure 3B:
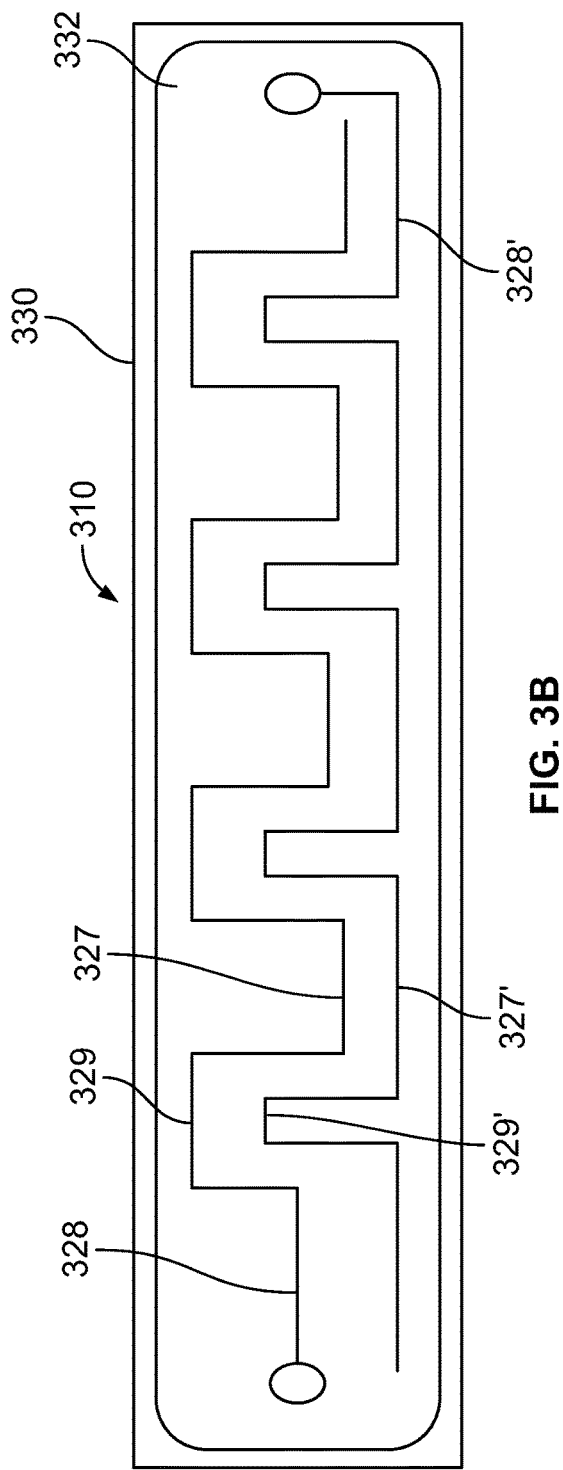
FIG. 3B illustrates a second pattern of electrodes, in accordance with certain embodiments.

In accordance with various embodiments, the electrodes are disposed or printed on the lower surface 222 of the pads 220 in the form of a plurality of patterns or geometries. FIGS. 3A and 3B illustrate, respectively, a first pattern 305 and a second pattern 310 of first 318, 318' and second electrodes 328, 328'. Referring to FIG. 3A, in one embodiment, the electrodes 318, 318' each have a 'comb' like pattern comprising an elongate 'backbone' 319, 319' with a plurality of 'teeth' 317, 317' extending perpendicularly therefrom. The two electrodes 318, 318' are positioned facing one another such that the 'teeth' 317 of a first electrode 318 are configured to alternate between the 'teeth' 317' of a second electrode 318'. Referring to FIG. 3B, in one embodiment, the electrodes 328, 328' each have a 'square wave' pattern comprising a plurality of peaks 329, 329' and valleys 327, 327'. In one embodiment, the peaks 329 of a first electrode 328 are wider than the peaks 329' of a second electrode 328' such that the peaks 329' of the second electrode 328' fit within the peaks 329 of the first electrode 328. Referring to FIGS. 3A and 3B simultaneously, the patterns 305, 310 are printed on the lower adhesive surface 322, 332 of skin patches or pads 320, 330. Persons of ordinary skill in the art should appreciate that the first and second patterns 305, 310 are only exemplary. In some embodiments, the skin patches or pads 320, 330 are transparent such that the pattern of electrodes 318, 318', 328, 328' are visible to the user through the patches or pads 320, 330.

In accordance with various embodiments, the electrical field generated by the electrodes, such as the electrodes 318, 318', 328, 328', is shallow and widely distributed to spread over a sufficiently large area of application of a stimulation therapy. The characteristics of the electrical field generated depend at least upon: a distance between the electrodes and the pattern or geometry of the electrodes on the patch or pad. In accordance with an embodiment, the distance between the two electrodes 318, 318' and 328, 328' is fixed along the entire length of the electrodes 318, 318', 328, 328'. In one embodiment, the electrical field generated by the electrodes is distributed along an area of attachment of the electro-dermal patch device and penetrates a depth of up to 20 mm from the skin surface. In other words, in various embodiments, the electrical field generated by the EDP device has a width and length equal to the width and length of the device footprint and a depth sufficient to target neural tissue within 20 mm of the surface of the skin.

FIG. 4A shows an electro-dermal patch device 410 configured to provide electrical stimulation therapy, from the external surface of the patient's epidermal layer through 10 mm or 20 mm of the dermis, in accordance with some embodiments. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein. The electro-dermal patch device 410 includes a housing 413, an electrode pad or skin patch (removed to enhance visibility of electrode 411) for placing on the user's skin surface, and an electrode 411 in the form of an insulated fine wire 415 with bared distal tip 416 extending from a bottom surface of the housing 413. When the electro-dermal patch device 410 is placed on a patient, the electrode 411 is disposed completely within the pad or skin patch and does not pierce, or directly contact, the skin of the patient. The housing 413 includes the microcontroller, pulse generator, wireless transceiver, and power management module of the system described with reference to FIGS. 1A through 1C.

FIGS. 4B and 4C are side and bottom perspective views respectively, of another embodiment of an electro-dermal patch device 420 of the present specification. The electro-dermal patch device 420 depicted in FIGS. 4B and 4C differs from the electro-dermal patch devices 210, 410 shown in FIGS. 2A-2C and FIG. 4A respectively, in that all of the components of electro-dermal patch device 420 are positioned in a single patch such that electro-dermal patch device 420 has a flat profile in contrast with electro-dermal patch devices 210, 410 having a profile with a centrally raised housing 213, 413. The lower profile of electro-dermal patch device 420 facilitates ease of use and placement by a patient. In various embodiments, the electro-dermal patch device 420 has a width w of 2 inches or less, a length l of 5 inches or less, and a height h of 1.5 inches, preferably 0.35 inches or less. In some embodiments, the electro-dermal patch device of the present specification has a height h of less than 1 inch, preferably less than ¾ inch, and more preferably, ½ inch or less.

In various embodiments, the electro-dermal patch device 420 has a weight of 5 ounces or less.

In various embodiments, the electro-dermal patch device 420 has an ingress protection rating (IPX) of at least IPX7, allowing the patient to take showers and swim for at least 30 minutes while the electro-dermal patch device 420 is positioned on the body without water damage to the electro-dermal patch device 420. In some embodiments, the hydrogel (of the electro-dermal patch) is surrounded along the perimeter with a closed cell foam to prevent water ingress to the hydrogel and adhesion reduction in a long shower and/or a 30 minute swim. In various alternate embodiments, the EDP device 420 has an ingress protection rating (IP) ranging from IP3 to IP5 and preferably a waterproof rating of IP4 (that is, protection from water splashing from any direction for 5 minutes) per IEC standard 60529. The electro-dermal patch device 420 is composed of a flexible, rubber or silicone material with sufficient structural strength to remain on the body once positioned while still flexible enough to be peeled back by its edges. The electro-dermal patch device 420 is storable when not in use. In other embodiments, the electro-dermal patch device 420 has an ingress protection rating (IPX) of at least IPX1, IPX2, IPX3, IPX4, IPX5, or IPX6, as known to persons of ordinary skill in the art.

Referring to FIG. 4C, in various embodiments, the bottom surface of the electro-dermal patch device 420 includes at least one electrode 428 having a specific configuration and able to provide enough electrical current to stimulate dermatomes at various rates and pulses. In one embodiment, the electro-dermal patch device 420 includes two electrodes 428, 428' having a pattern similar to that described with reference to FIG. 3B. In various embodiments, the electro-dermal patch device 420 is configured ergonomically to have as low a profile as possible and uniform in shape while still providing strong adhesive properties lasting for at least four weeks during normal usage. In the embodiment depicted in FIGS. 4B and 4C, the electro-dermal patch device 420 includes no visible or tactile user interface and all communication with the electro-dermal patch device 420 is achieved wirelessly using a companion device as described further below.

In some embodiments, the electro-dermal patch device 420 includes a disposable battery which provides operating power for at least 90 days of usage. In one embodiment, the electro-dermal patch device electronic circuitry, in combination with the electrodes, is used to sense skin placement and to turn therapy on and off automatically as further described below. As described with reference to FIGS. 4B and 4C, the electro-dermal patch device electronic core and adhesive pad with electrodes are all combined in one flat component configured to provide therapy for at least 3 months. Alternatively, as described with reference to FIGS. 2A-2D and 4A, the electro-dermal patch device electronic core is located within a housing separate from the pad and, in some embodiments, is easily replaceable by the patient or a medical professional.

Figure 4D:
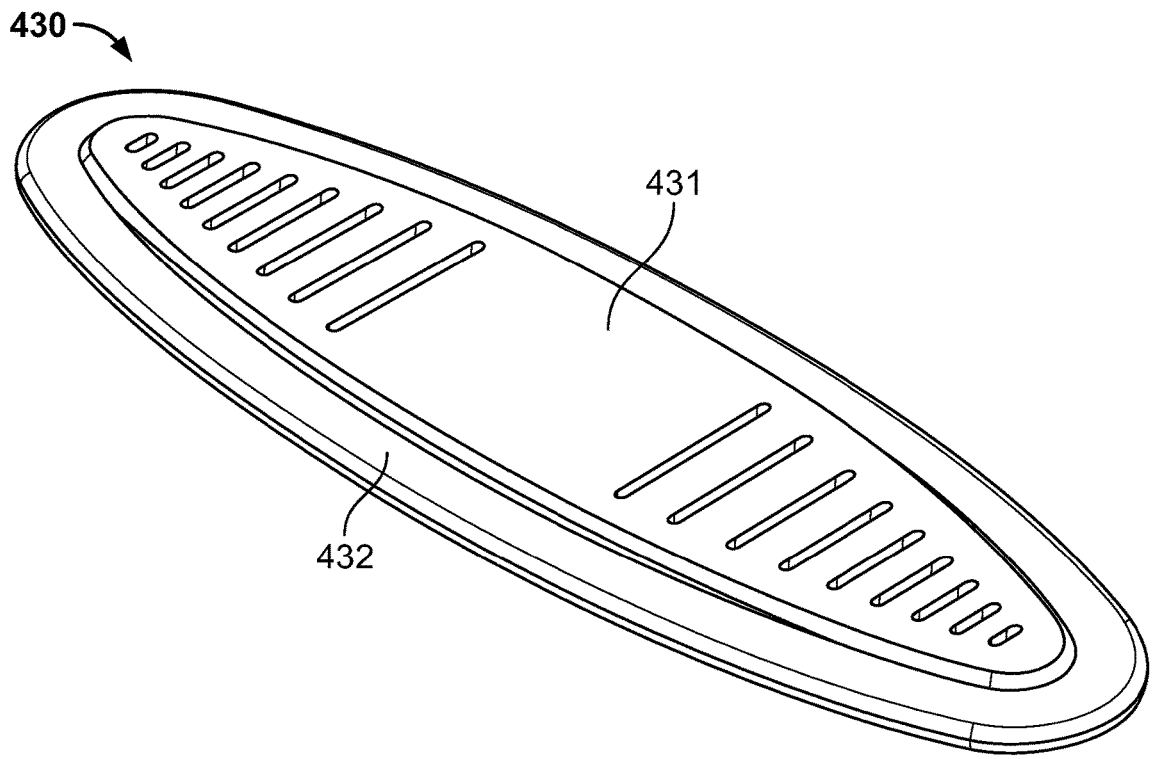
FIG. 4D is an oblique, top perspective view of an electro-dermal patch device, in accordance with another embodiment of the present specification.

FIG. 4D is an oblique, top perspective view of an electro-dermal patch device 430, in accordance with another embodiment of the present specification. The electro-dermal patch 430 comprises a controller assembly 431 and an electrode assembly 432. In one embodiment, the controller assembly 431 is reusable and detachable from a disposable electrode assembly 432. It should be appreciated that while the electrode assembly 432 touches the skin surface, the controller assembly 431 remains above the skin surface. In some embodiments, the controller assembly 431 remains within a range of 2 mm to 4 mm above the skin surface, and preferably within 2 mm above the skin surface. In some embodiments, the EDP 430 has an elliptical or surfboard-like shape as seen in FIG. 4D. The surfboard shape allows for better adhesion to, and better movement with, a patient's skin surface. In an embodiment, the elliptical or surfboard-like shape of the EDP 430 has a short axis or dimension in a range of 0.1 to 0.6 inches, preferably around 0.33 inches, and a long axis or dimension in a range of 2 to 8 inches, preferably around 5.365 inches, or any increment therein. In various embodiments, the elliptical shape of the EDP 430 may require the user to orient the device in such a way that the short dimension of the EDP traverses a smallest radius of the skin topography at a desired body location.

Figure 4E:
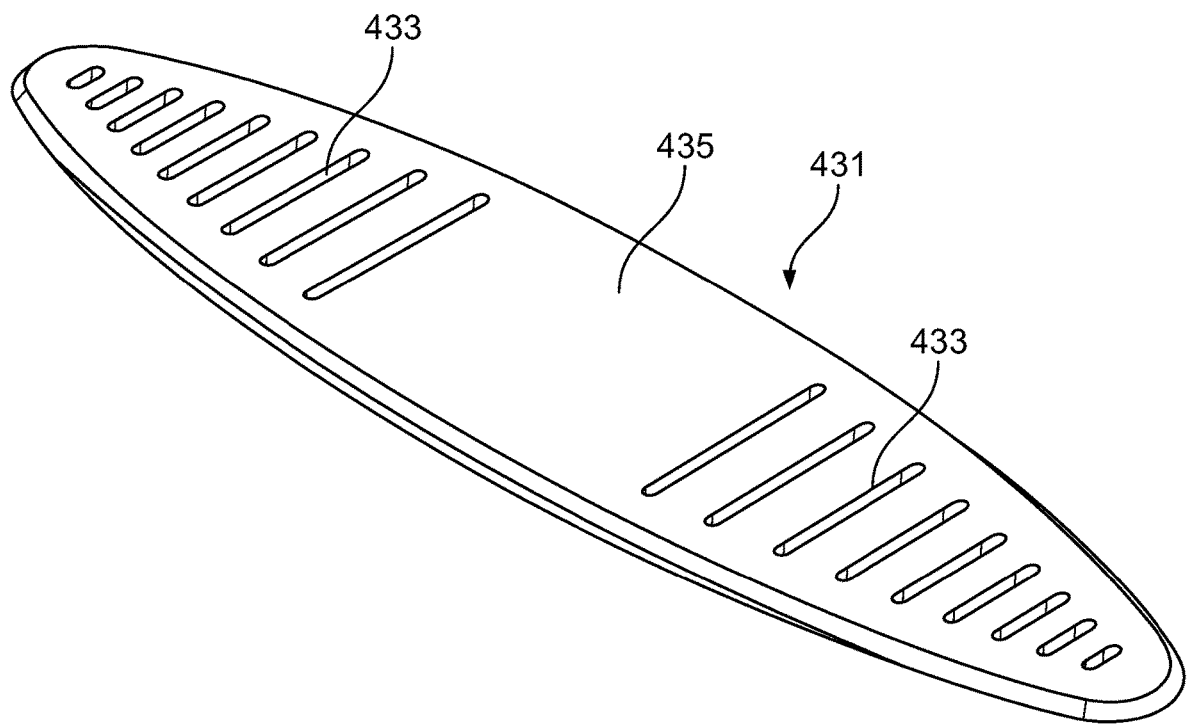
FIG. 4E is an oblique, top perspective view of the controller assembly of the electro-dermal patch device of FIG. 4D.

FIG. 4E is an oblique, top perspective view of the controller assembly 431 of the electro-dermal patch device of FIG. 4D. The controller assembly 431 is flexible and comprises a flexible circuit with carrier and electrode contacts, discrete electrical components, a rechargeable battery, and a flexible overmold 435. In a less preferred embodiment, the controller assembly comprises a rigid housing in place of the overmold. In some embodiments, the overmold 435 comprises a low durometer material with its geometry defined via a single shot injection mold process wherein there is one durometer throughout the entire overmold 435.

In various embodiments, materials for the overmold 435 include a thermoplastic elastomer, or (TPE), such as, for example, Monprene manufactured by Teknor Apex as an ultra-soft TPE gel. TPEs are processed like any other thermoplastic material but typically have low elastic moduli, thus making the assembly flexible. In various embodiments, the TPE used as material for the overmold 435 has hardness in a range of 30 to 70, preferably 45-65, and more preferably 50 to 60 on the sub-zero shore (00) scale and a tensile modulus (indicative of flexural properties) in a range of 15 to 55 psi, preferably 30 to 45 psi. For example, Monprene Ultra Soft Gel grade CP-32053G (manufactured by Teknor Apex) has a hardness measure of 53 on the subzero shore (00) scale and a tensile modulus of about 37 psi. Viscosity of the Monprene Ultra Soft Gel ranges from 30 to 65 on the subzero shore (00) scale. The EDP device of the present specification, taken as a whole, has a measurement on the flexural modulus scale per ASTM D-747 in a range of 10 psi to 35 psi, preferably 15 to 25 psi. Such overmolding material applies to all other embodiments disclosed herein, whether in a single shot or dual shot molding embodiment.

In other embodiments, thermoset material is used to create the overmold 435 and facilitate the manufacture of the controller assembly 431 because low durometer thermoset materials, such as liquid silicone rubber (LSR), have a low viscosity at room temperature prior to cure. This may make the filling of the injection mold cavity less stressful on the flexible circuit during processing.

In some embodiments, the overmold 435 includes a plurality of slots 433. The slots 433 impart increased flexibility to the controller assembly 431 and provide tooling access so that the flexible circuit within can be accurately held in place during the overmolding process. The slots 433 also act as windows to the flexible circuit within. In some embodiments, the controller assembly 431 further includes light emitting diodes (LEDs) which, through the window-like slots 433, visually communicate to the user product function and/or product status.

Figure 4F:
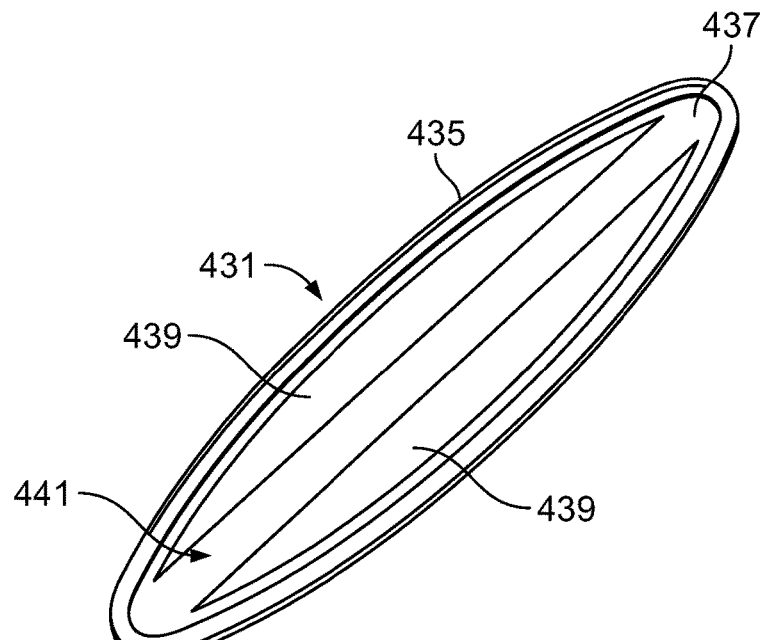
FIG. 4F is an oblique, bottom perspective view of the controller assembly of the electro-dermal patch device of FIG. 4D.

FIG. 4F is an oblique, bottom perspective view of the controller assembly 431 of the electro-dermal patch device of FIG. 4D. Visible on the underside of the controller assembly 431 is a flexible circuit 441 with an edge of the overmold 435 around its periphery. In various embodiments, the flexible circuit 441 provides three functions. One, the flexible circuit 441 contains and carries the discrete electrical components and battery. Two, the flexible circuit provides electrical contacts 439 used for connecting to a hydrogel of the electro-dermal patch. Three, the flexible circuit provides a recharge path, if desired, for a rechargeable battery. In some embodiments, a flexible circuit carrier 437 for the circuitry is comprised of a single or multilayer polyimide/copper laminate processed by masking and etching of a copper substrate to create the circuit. In some embodiments, discrete components of the controller assembly 431 are either surface mounted or "thru hole" mounted comparable to the process used in the manufacture of rigid printed circuit boards.

In various embodiments, the electrode contacts 439 are gold-plated copper pads created as part of an etching and plating process of the flexible circuit 441. Flexible circuit 441 is comprised of a single or multilayer polyimide/copper laminate where each layer of copper has circuitry traces masked in such a way that when acid is applied, any exposed copper is etched away leaving the masked areas in place. Subsequently, the masking material is removed with a solvent thus exposing the remaining copper creating the circuit. The electrode contacts 439 are then gold plated to ensure connection to the hydrogel of the EDP. The creating of electrical contacts in this way has three advantages. One, it occurs at the processing stage and is embedded in the cost of the flexible circuit 441 and therefore does not require an additional process to handle and attach a discrete connector to both the controller assembly 431 and an electrode. Two, it eliminates the tight tolerances required of typical electrical connections. Three, it reduces the cost of the electrode by not requiring the electrode to have a connector at all since the electrical contacts on the controller assembly 431 come in direct contact with a hydrogel of the electrode assembly.

Figure 4G:
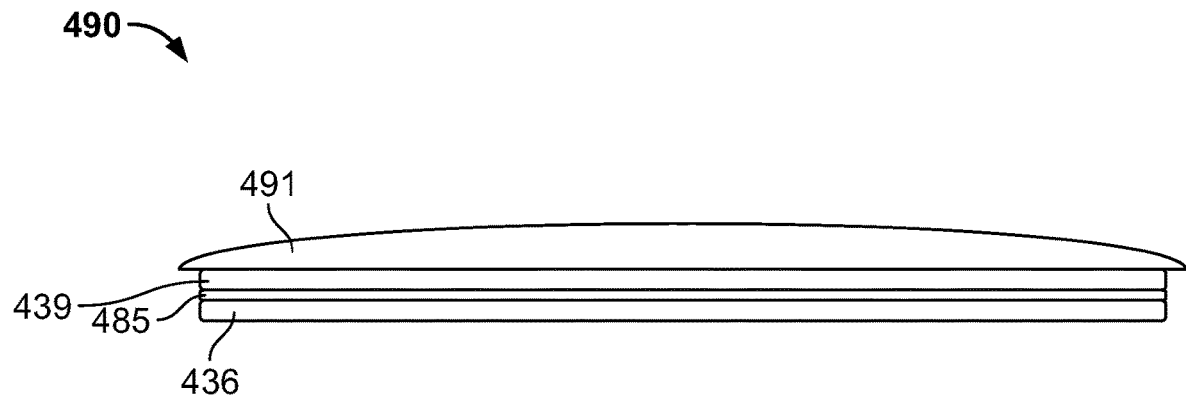
FIG. 4G is a side perspective cross-sectional view of an electro-dermal patch device comprising a capacitance type connection (dielectric material) between the electrode contacts and a hydrogel of the electrode assembly, in accordance with one embodiment of the present specification.

In another embodiment, as depicted in cross-sectional FIG. 4G, the electro-dermal patch device (EDP) 490 includes a housing 491 and a capacitance type connection between the electrode contacts 439 and a hydrogel 436 of the electrode assembly, comprising a very thin dielectric material 485 laminated over either the hydrogel 436 or the electrode contacts 439. In various embodiments, a thickness of the dielectric laminate ranges from 0.001 inches for a single layer of dielectric material, 0.003 inches of two layers of dielectric material to no greater than 0.005 inches of three layers of dielectric material. The dielectric material 485 creates a DC blocking capacitor that is used in an output stage circuit. There are three advantages to this alternate connection. One, the exposed metal electrode contacts 439 on the underside of the controller assembly would not need to be of a non-oxidizing type, such as gold, since they would not be reliant on an intimate conductor/conductor contact to maintain electrical connection. Two, circuitry impedance of a drive circuit would be much more predictable since the connection to the hydrogel may not be a variable resistance upon subsequent usages. Three, the need of maintaining physical contact (and electrical short) between the two metal contacts is eliminated, thus improving reliability/robustness of the connection.

Figure 4H:
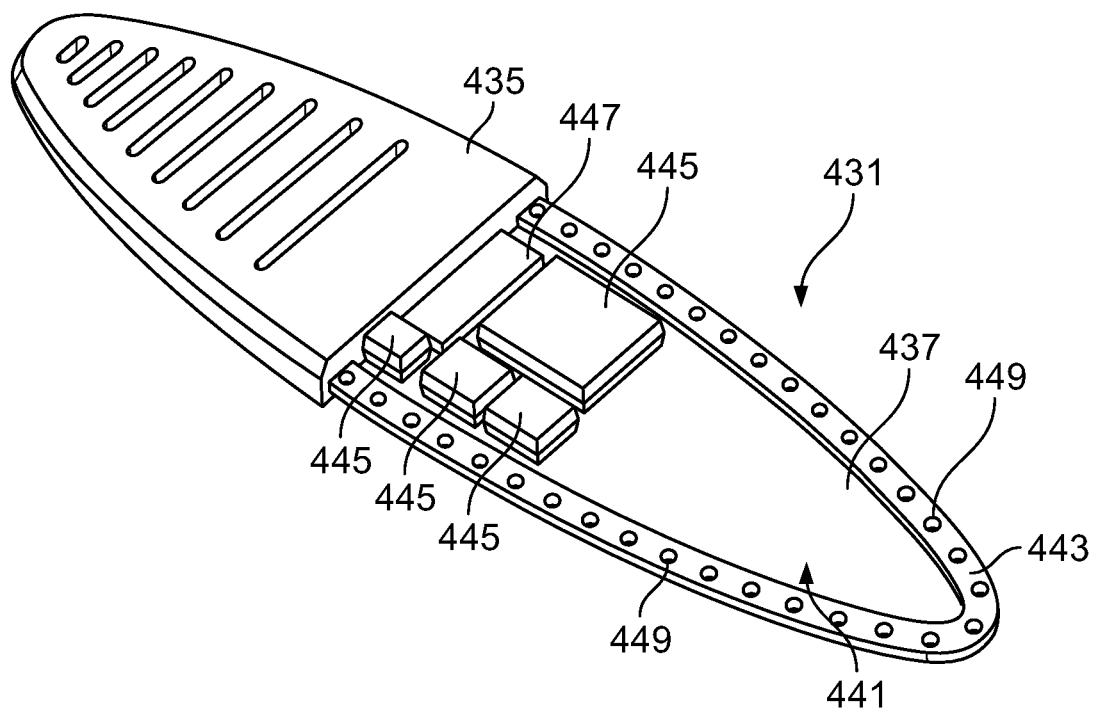
FIG. 4H is an oblique, top perspective view of the controller assembly of the electro-dermal patch device of FIG. 4D with a portion of the overmold cut away to expose additional components of the controller assembly.

FIG. 4H is an oblique, top perspective view of the controller assembly 431 of the electro-dermal patch device of FIG. 4D with a portion of the overmold 435 cut away to expose additional components of the controller assembly 431. In some embodiments, a flexible circuit 441 comprises a flexible circuit carrier 437 with a plurality of discrete components 445 and at least one battery 447 surface mount soldered to exposed conductor pads. In some embodiments, a flexible circuit anchor 443 is laminated to the perimeter of the flexible circuit carrier 437. In various embodiments, the anchor 443 comprises a layer of polyimide or another semi-rigid material. Perforation holes 449 along the anchor 443 perimeter length are included so that the overmold 435 material can aggressively attach to the flexible circuit 441, thus making a robust/reusable controller assembly 431. In various embodiments, the battery 447 is that of a flat technology to which most battery chemistries conform. In some embodiments, the battery 447 is rechargeable. In various embodiments, the controller assembly 431 has a typical footprint area of 1.5 inches$^2$ for a physical aspect ratio of the width to the length of the flexible circuit carrier 437 of about 1:1.

Figure 4I:
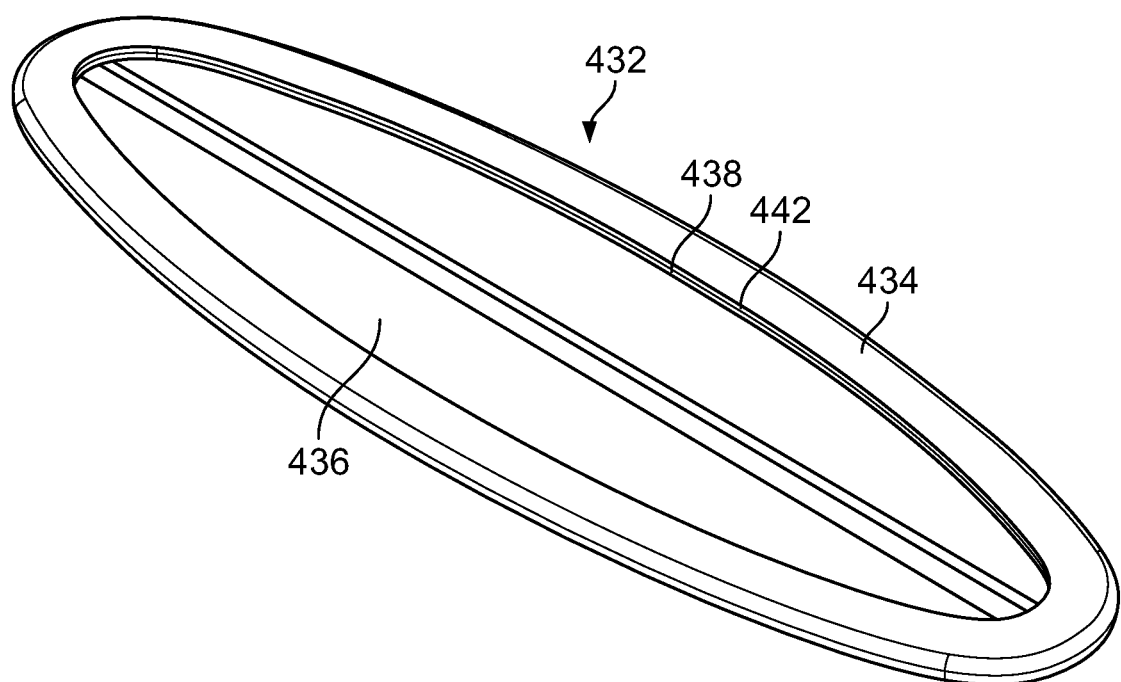
FIG. 4I is an oblique, top perspective view of the electrode assembly of the electro-dermal patch device of FIG. 4D.

FIG. 4I is an oblique, top perspective view of the electrode assembly 432 of the electro-dermal patch device of FIG. 4D. In various embodiments, the electrode assembly 432 is flexible and comprises a hydrogel 436, hydrogel carrier 438, release liner 442, and electrode bezel 434. The electrode contact surface is below the hydrogel 436 surface and therefore not shown. The electrode surface is in physical contact, and in electrical communication with, the hydrogel 436 which is contained in a polymer coating (carrier). The electrode bezel 434 is designed to keep the carrier 438 and hydrogel 436 in place. A release liner 442 is on the base of the carrier 438 surface and serves to protect the adhesive coating of the carrier 438 surface until a user is ready to use the EDP. At that point, the release liner 442 is removed and the carrier 438 and adhesive are exposed.

Once the EDP is fully assembled, the electrode contacts 439 depicted in FIG. 4F are in physical contact with the hydrogel 436 depicted in FIG. 4I to allow for transmission of electrical stimuli from the EDP to the skin surface of a patient. The hydrogel carrier 438 and release liner 442 allow for simple separation of the controller assembly from the electrode assembly 432 so that a reusable controller assembly can be joined with a new electrode assembly.

Figure 4J:
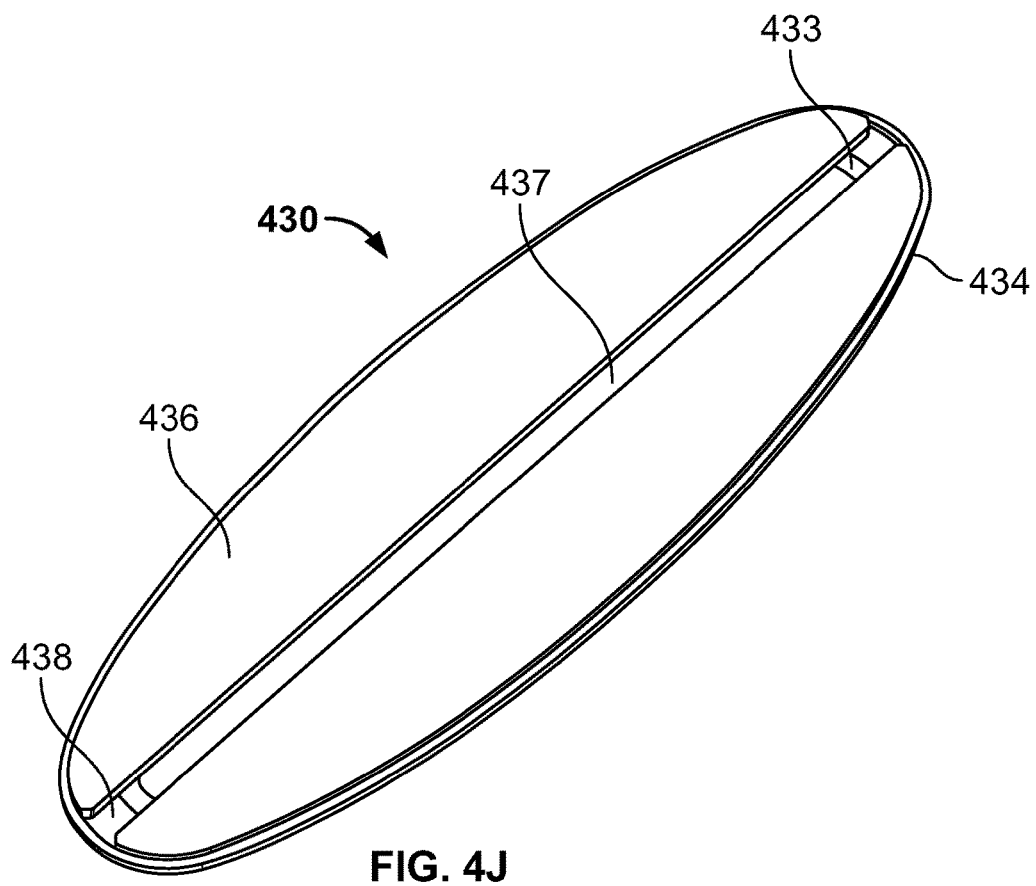
FIG. 4J is an oblique, bottom perspective view of the electro-dermal patch device of FIG. 4D.

FIG. 4J is an oblique, bottom perspective view of the electro-dermal patch device 430 of FIG. 4D. Visible are the overmold 433 and flexible circuit carrier 437 of the controller assembly and the hydrogel 436, hydrogel carrier 438, and electrode bezel 434 of the electrode assembly.

Figure 4K:
FIG. 4K is a side perspective view of the electro-dermal patch device of FIG. 4D.

FIG. 4K is a side perspective view of the electro-dermal patch device 430 of FIG. 4D. In various embodiments, the EDP 430 has a thickness, or height h from a patient's skin surface, in a range of 0.075 to 0.25 inches. In one embodiment, the EDP 430 has a thickness, or height h from a patient's skin surface of 0.156 inches.

Figure 4L:
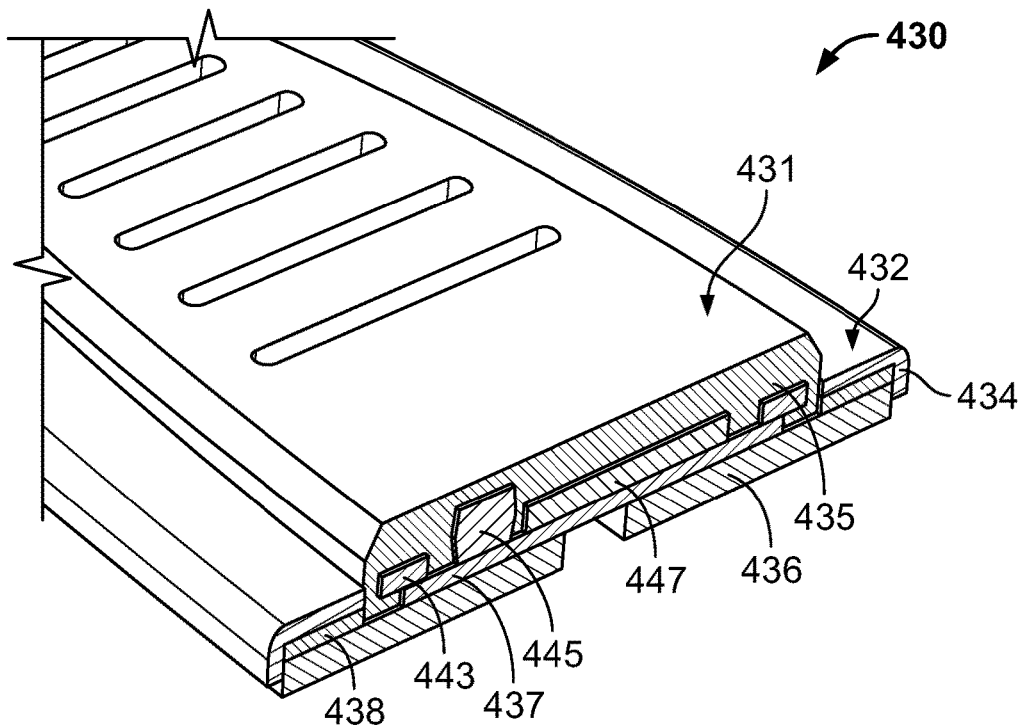
FIG. 4L is an oblique, top perspective, short axis cross-sectional view of the electro-dermal patch device of FIG. 4D.
Figure 4M:
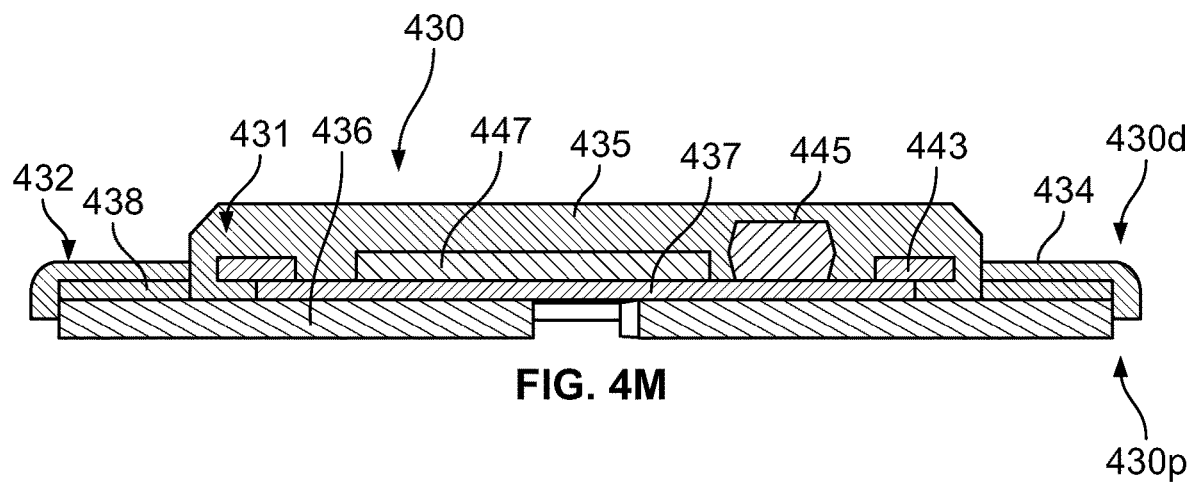
FIG. 4M is a front perspective cross-sectional view of the electro-dermal patch device of FIG. 4D.

FIGS. 4L and 4M are oblique, top perspective, short axis and front perspective, cross-sectional views respectively, of the electro-dermal patch device 430 of FIG. 4D. Visible are the overmold 435, discrete component 445, battery 447, flexible circuit carrier 437, and circuit carrier anchor 443 of the controller assembly 431 and the hydrogel 436, hydrogel carrier 438, and electrode bezel 434 of the electrode assembly 432. The controller assembly 431 is configured to detachably connect to the electrode assembly 432 such that the overmold 435 sits within an area defined by the electrode bezel 434 and the electrode contacts (439 in FIG. 4F) are in physical contact with the hydrogel 436. Using a patient's skin surface as a point of reference, the overmold 435 of the controller assembly 431 and the electrode bezel 434 of the electrode assembly 432 comprise a distal or outer surface 430d of the EDP 430. The hydrogel 436 comprises a proximal or inner, skin facing surface 430p of the EDP. The discrete component 445, battery 447, flexible circuit carrier 437, and circuit carrier anchor 443 are positioned within the controller assembly 431 in a central portion of the EDP 430. The hydrogel carrier 438 is positioned between the electrode bezel 434 and hydrogel 436 of the electrode assembly 432 about a periphery of the EDP 430.

Figure 4N:
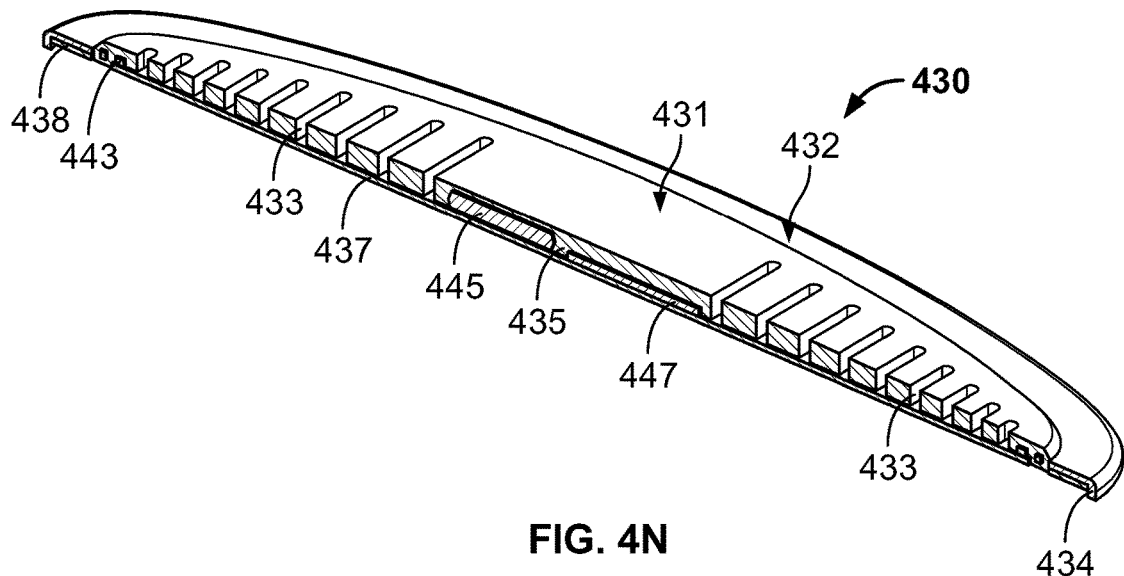
FIG. 4N is an oblique, top perspective, long axis cross-sectional view of the electro-dermal patch device of FIG. 4D.
Figure 4O:
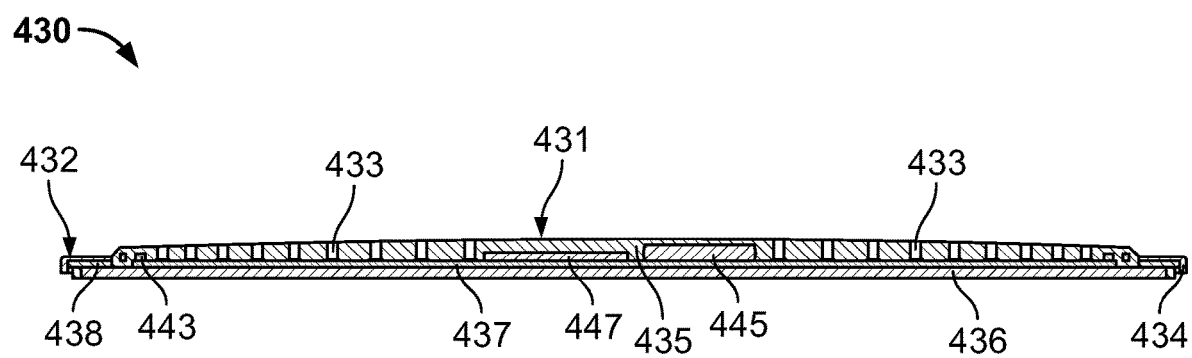
FIG. 4O is a side perspective cross-sectional view of the electro-dermal patch device of FIG. 4D.

FIGS. 4N and 4O are oblique, top perspective, long axis and side perspective, cross-sectional views respectively, of the electro-dermal patch device 430 of FIG. 4D. Visible are the overmold 435, discrete component 445, battery 447, flexible circuit carrier 437, circuit carrier anchor 443, and slots 433 of the controller assembly 431 and the hydrogel 436 (seen in FIG. 4O), hydrogel carrier 438, and electrode bezel 434 of the electrode assembly 432.

In accordance with various embodiments, the electrodes, such as the electrode contacts 439 of FIG. 4F, are disposed or printed on the lower surface of the pads of the EDP device 430 of FIG. 4D in the form of a plurality of patterns or geometries. FIGS. 4P through 4S illustrate, respectively, a first pattern 450, a second pattern 455, a third pattern 460 and a fourth pattern 465 of corresponding first 451, 452, second 456, 457, third 461, 462 and fourth electrodes 466, 467. In embodiments, a distance between the electrode, such as electrodes 439 of FIG. 4F or electrodes of first, second, third and fourth electrode patterns of FIGS. 4P through 4S, is less than 20 mm, preferably less than 15 mm, preferably less than 10 mm, preferably less than 5 mm. In one embodiment, the distance between the electrodes is about 4 mm.

Figure 4P:
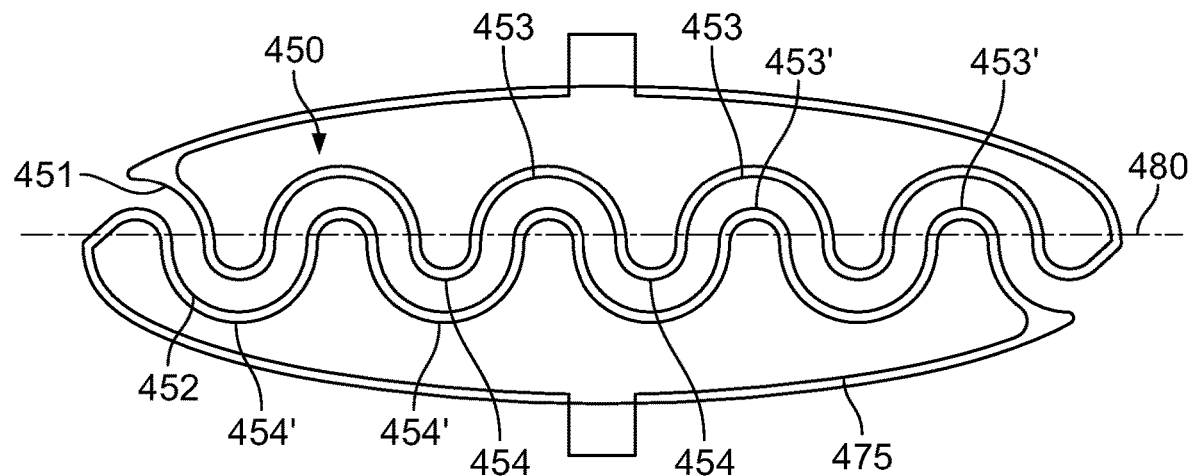
FIG. 4P illustrates a first pattern of electrodes of the electro-dermal patch device of FIG. 4D, in accordance with an embodiment.
Figure 4Q:
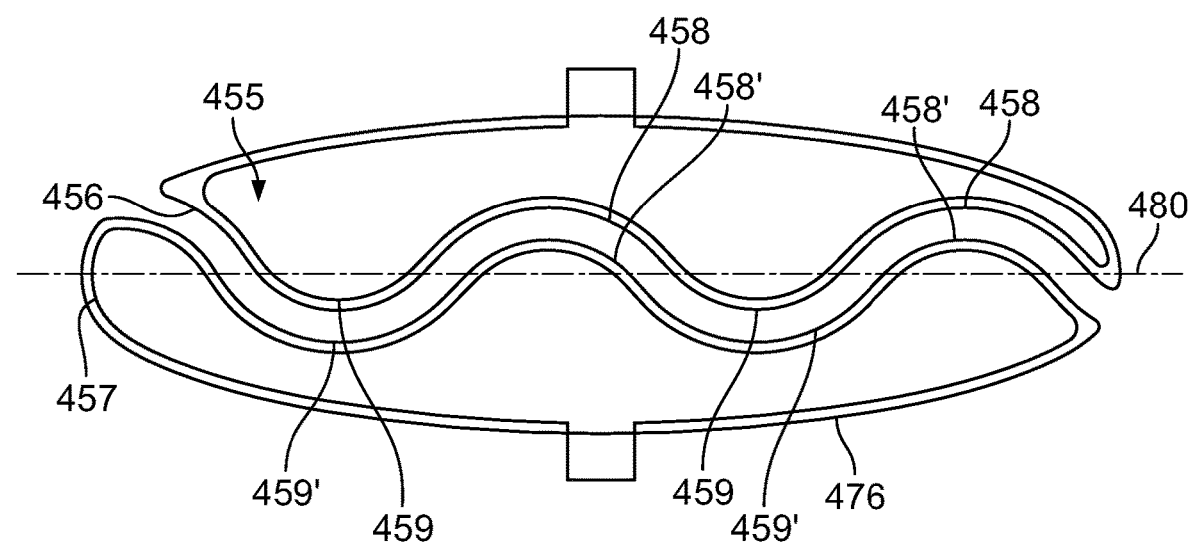
FIG. 4Q illustrates a second pattern of electrodes of the electro-dermal patch device of FIG. 4D, in accordance with an embodiment.

Referring to FIG. 4P, in one embodiment, the electrodes 451, 452 each have an approximate 'sine wave' pattern 450 and extend along a long axis 480 of a substantially elliptical pad 475, for example. The pattern 450 comprises a plurality of peaks 453, 453' and valleys 454, 454'. In one embodiment, the peaks 453 of a first electrode 451 are wider than the peaks 453' of a second electrode 452 such that the peaks 453' of the second electrode 452 fit within the peaks 453 of the first electrode 451. Referring to FIG. 4Q, in another embodiment, the electrodes 456, 457 each have an approximate 'sine wave' pattern 455 also extending along the long axis 480 of the pad 476. The 'sine wave' pattern 455 differs from the pattern 450 of FIG. 4P in that the pattern 455 has a longer 'period' (wherein 'period' is a distance between consecutive peaks and valleys measured along the long axis 480) relative to the pattern 450. As a result, the pattern 455 comprises a plurality of peaks 458, 458' and valleys 459, 459' that are fewer in number relative to the number of peaks 453, 453' and valleys 454, 454' of pattern 450.

Figure 4R:
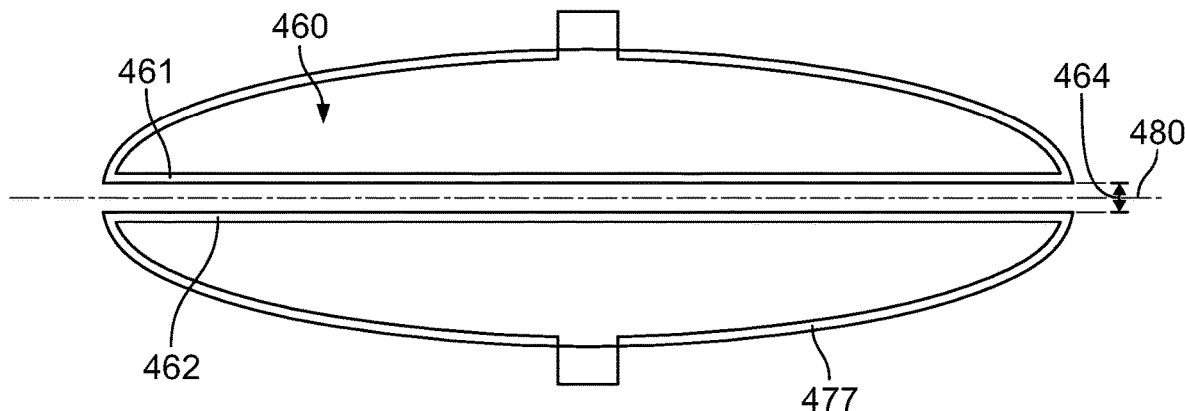
FIG. 4R illustrates a third pattern of electrodes of the electro-dermal patch device of FIG. 4D, in accordance with an embodiment.
Figure 4S:
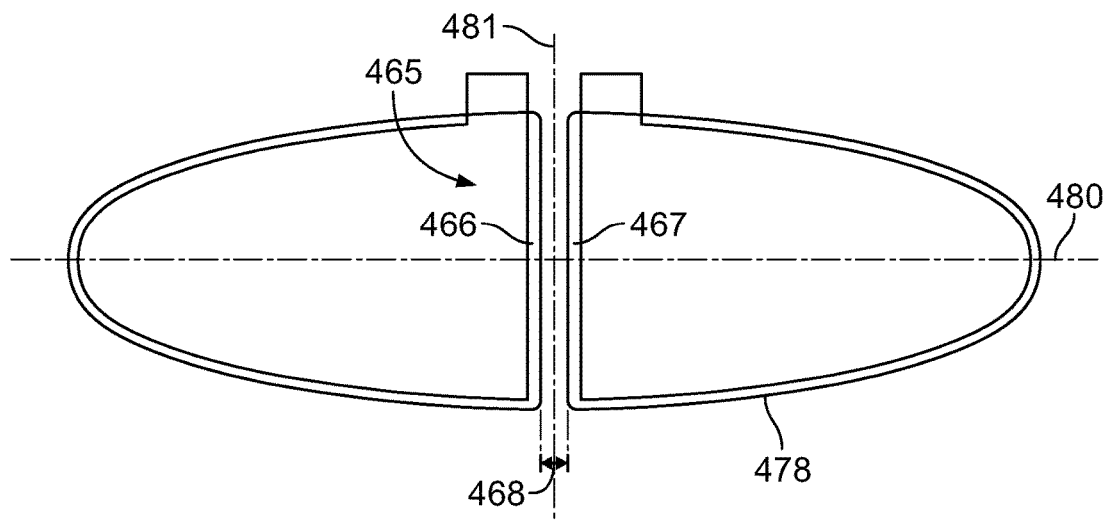
FIG. 4S illustrates a fourth pattern of electrodes of the electro-dermal patch device of FIG. 4D, in accordance with an embodiment.

Referring now to FIG. 4R, in one embodiment, the electrodes 461, 462 each have a linear pattern 460 and extend along the long axis 480 of the pad 477. In accordance with an embodiment, a gap 464 between the electrodes 461, 462 is maintained or remains constant along the long axis 480. Referring to FIG. 4S, in one embodiment, the electrodes 466, 467 each have a linear pattern 465 and extend along a short axis 481 of the pad 478, wherein the axes 480, 481 are substantially perpendicular to each other. In accordance with an embodiment, a gap 468 between the electrodes 466, 467 is maintained or remains constant along the short axis 481.

Figure 5A:
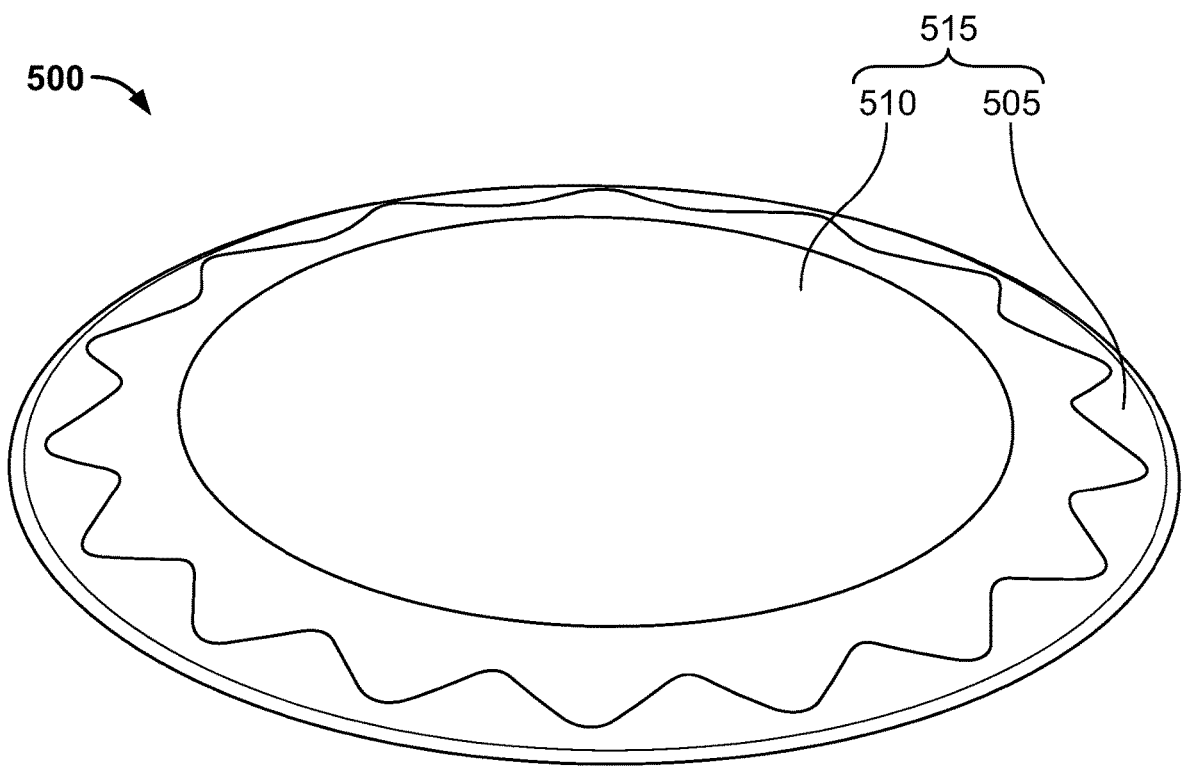
FIG. 5A is an oblique, top perspective view of an electro-dermal patch device in accordance with some embodiments.
Figure 5B:
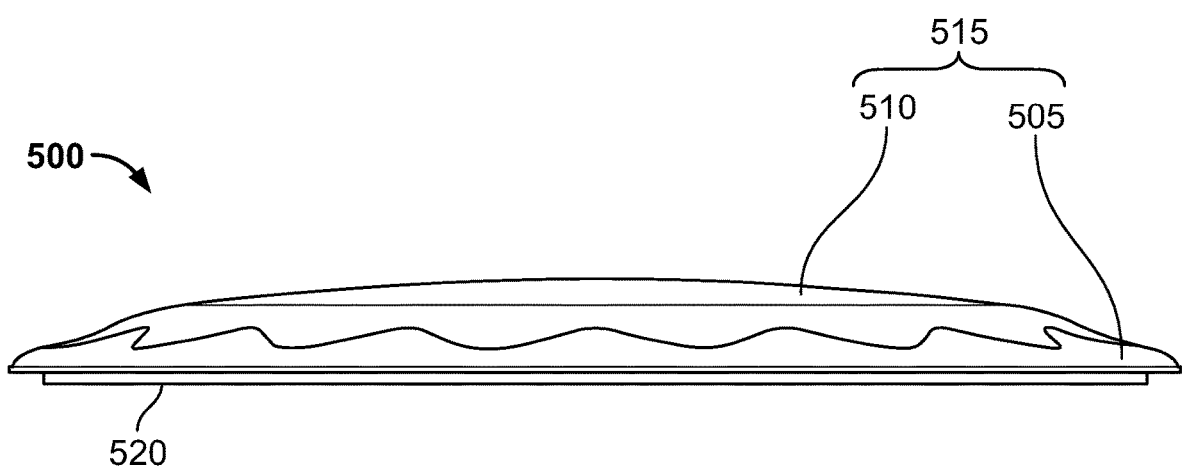
FIG. 5B is a side perspective view of the EDP device of FIG. 5A.
Figure 5C:
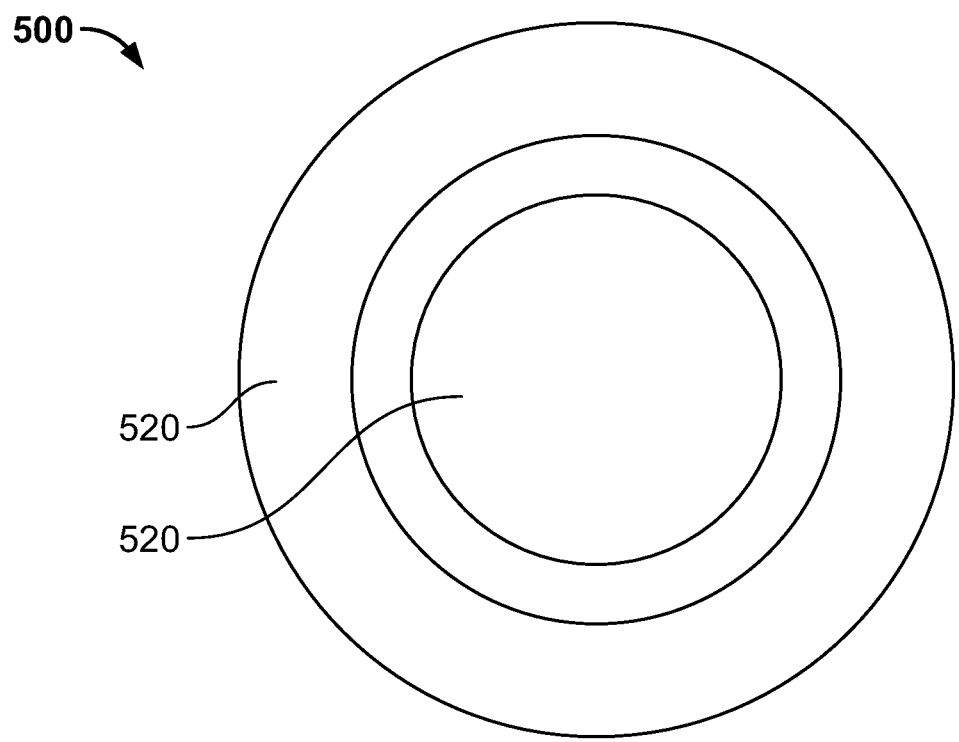
FIG. 5C is a bottom view of the EDP device of FIG. 5A.

FIG. 5A is an oblique, top perspective view of an electro-dermal patch device 500 in accordance with another embodiment of the present specification. The EDP device 500 is overmolded and configured in a round, circular or "sand dollar" like shape. The overmold 515 includes a first overmold portion 505 forming a perimeter of the EDP device 500 and a second overmold portion 510 forming a central portion of the EDP device 500. While described in reference to the "sand dollar" configuration depicted in FIG. 5A, a "two-shot" overmold process (comprising first and second overmold portions) is not specific to the sand dollar shape and can be applied to create any shape of EDP. FIG. 5B is a side perspective view of the EDP device 500 showing hydrogel pads 520. The hydrogel pads 520, that in some embodiments are concentric ring shaped, are also shown in FIG. 5C which is a bottom view of the EDP device 500. As shown in FIG. 5B, the overmold 515, comprising the first and second overmold portions 505, 510, envelopes the full surface area or footprint of the hydrogel pads 520, in accordance with an aspect of the present specification.

Figure 5D:
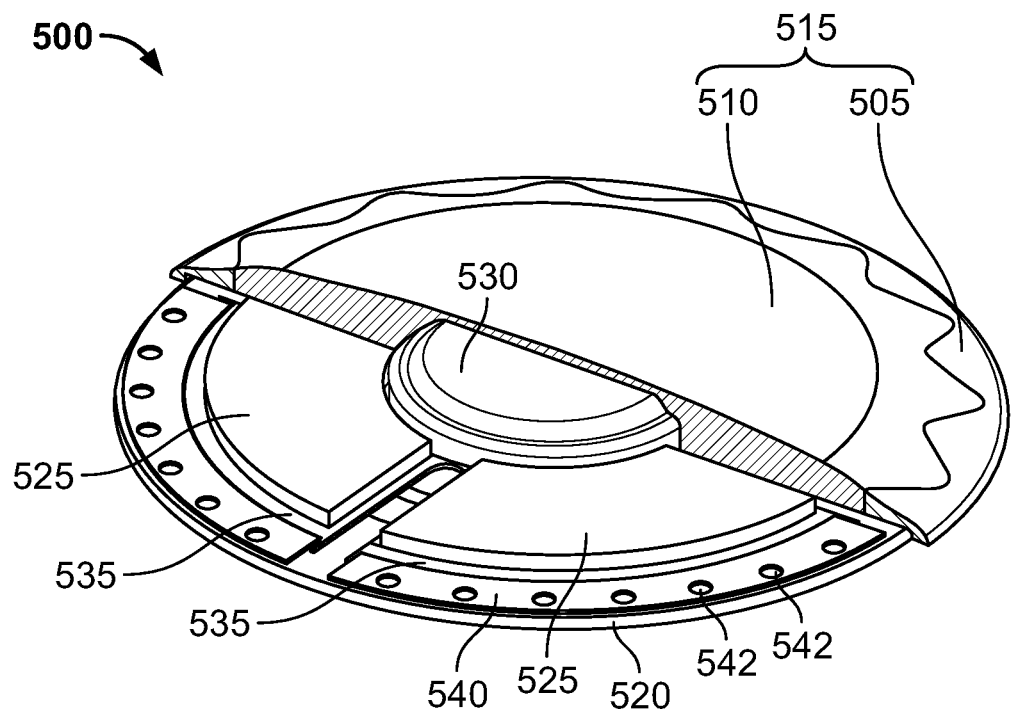
FIG. 5D is an oblique, top perspective view of the EDP device of FIG. 5A with a portion of an overmold removed.

FIG. 5D is an oblique, top perspective view of the EDP device 500 with a portion of the overmold 515 (of FIG. 5A) removed to reveal internal components of the EDP device. FIG. 5E is a side cross-sectional view while FIG. 5F is a top perspective view of the EDP device 500 with the entire overmold 515 (of FIG. 5A) removed.

Referring now to FIGS. 5D through 5F, the first and second overmold portions 505, 510 encompass a flexible circuit carrier 525 supporting a housing 530 that includes a flexible circuit having a plurality of discrete electronic components (such as those described with reference to FIG. 1A) including a rechargeable battery. The housing 530 is in electrical communication with electrode contacts 535 that are in physical contact with the hydrogel pads 520. It should be appreciated that while the electrode contacts 535 in physical contact with the hydrogel pads 520 touch the skin surface, the housing 530 remains above the skin surface. In some embodiments, the housing 530 remains within a range of 2 to 4 mm above the skin surface, and preferably within 2 mm above the skin surface. In some embodiments, a flexible circuit anchor 540 is laminated to the perimeter of the electrode contacts 535. In various embodiments, the anchor 540 comprises a layer of polyimide or another semi-rigid material. Perforation holes 542 along the anchor 540 perimeter length are included so that the material of the overmold portions 505, 510 can seep therein and attach thereto to fully envelope the electrode contacts 535 as well as the hydrogel pads 520. Since the overmold portions 505, 510 together envelop the hydrogel pads 520, this allows for the flexible circuit to provide electrical contacts for connecting to the hydrogel thus keeping the cost of the hydrogel based electrodes low by eliminating the need for tight tolerance discrete electrical connectors.

Referring back to FIG. 5A, in some embodiments, the overmold portions 505, 510 comprise low durometer materials with their geometry defined via a two shot injection mold process. In various embodiments, materials for the overmold 505, 510 include a thermoplastic elastomer (TPE) such as, for example, Monprene (manufactured by Teknor Apex) as an ultra-soft TPE gel. TPEs are processed like any other thermoplastic material but typically have low elastic moduli, thus making the assembly flexible. A first shot injection mold forms the overmold portion 505 as a narrow cross-sectional hoop or perimeter of the EDP device 500 while a second shot injection mold forms the overmold portion 510.

In various embodiments, the TPE used as material for the overmold portions 505, 510 has hardness in a range of 30 to 70, preferably 45-65, and more preferably 50 to 60 on the sub-zero shore (00) scale and a tensile modulus (indicative of flexural properties) in a range of 15 to 55 psi, preferably 30 to 45 psi. For example, Monprene Ultra Soft Gel grade CP-32053G (manufactured by Teknor Apex) has a hardness measure of 53 on the subzero shore (00) scale and a tensile modulus of about 37 psi. Viscosity of the Monprene Ultra Soft Gel ranges from 30 to 65 on the subzero shore (00) scale. It should be appreciated that the use of low durometer materials, such as Monprene gel, along with the built-in flex joints of the flexible circuit enable the EDP device assembly to be quite supple and achieve a measurement on the flexural modulus scale per ASTM D-747 in a range of 10 psi to 35 psi, preferably 15 to 25 psi.

In accordance with aspects of the present specification, the flex joints exist between rigid or inflexible inseparable assemblies within the EDP device. In one embodiment, the battery and the flexible circuit are inseparable assemblies. Therefore, a flexible joint exists between these two assemblies. In various embodiments, flex joints between rigid inseparable assemblies are obtained by designing both first shot and second shot tooling (for the two shot injection molding process) such that in the fully fabricated EDP device, soft overmold material resides between the rigid assemblies. Also, the joints are oriented within the body of the EDP device, such that when the EDP device is placed on the patient's body, in a way that will properly stimulate the intended dermatomes, the flex joints are perpendicular to the curved contour of the patient's body at that location, thereby enabling flexing of the EDP device to conform to the patient's body curvature.

In one embodiment, the overmold portion 505 utilizes a higher durometer TPE compared to the overmold portion 510. The overmold 505 is of a slightly higher durometer material (than of the overmold portion 510) since although the perimeter of the device needs to be flexible it also needs to provide tensile integrity such that induced stretching via rough handling of the EDP will not result in damage to the encompassed electronic circuitry. The higher durometer material which is used to create the narrow cross sectional hoop 505 along the perimeter is a modified TPE manufactured by Kraton Corporation, grade G-7970, in accordance with an embodiment. This TPE grade is a block polymer in which the elastomeric portion of the molecule is a saturated olefin polymer. The higher durometer material ranges from 35 to 45 Shore A, in various embodiments, with the lower durometer material being below 35 Shore A.

In various embodiments, the electro-dermal patch device 500 has an ingress protection rating (IPX) of at least IPX7, allowing the patient to take showers and swim for at least 30 minutes while the electro-dermal patch device 500 is positioned on the body without water damage to the electro-dermal patch device 500. In various alternate embodiments, the EDP device 500 has an ingress protection rating (IP) ranging from IP3 to IP5 and preferably a waterproof rating of IP4 (that is, protection from water splashing from any direction for 5 minutes) per IEC standard 60529.

In various embodiments, the flexible overmold, such as the overmold 435 of FIG. 4E and the overmold 515 of FIG. 5A, is also non-toxic to safeguard against any incidental contact with the skin.

In various embodiments, the housing 530 has a typical footprint area of 1.5 inches$^2$ for a physical aspect ratio of the width to the length of the flexible circuit carrier 525 of about 1:1.

In one embodiment, the electro-dermal patch device (EDP) comprises a print-on-the-skin circuit designed to be printed directly onto the epidermis of a patient. The printable EDP comprises film electrodes having a thickness sufficient to withstand the currents required for the electrical stimulation protocols of the current specification without degrading. The printable EDP comprises a wireless transceiver (for communication with a companion device), microcontroller, power management module or battery, pulse generator, and at least one electrode. In some embodiments, the printable EDP further includes at least one sensor.

In another embodiment, the electro-dermal patch device (EDP) comprises a highly flexible membrane, or 'flex-circuit', configured to adhere to the patient's epidermis. The 'flex-circuit' is configured to be applied and adhere to the patient's skin much like a conventional tattoo. The 'flex-circuit' comprises a curved, or 'S' shaped circuit. The curved shape allows the 'flex-circuit' to move with the patient's skin without being damaged. The 'flex-circuit' EDP comprises a wireless transceiver (for communication with a companion device), microcontroller, power management module or battery, pulse generator, and at least one electrode. In some embodiments, the 'flex-circuit' EDP further includes at least one sensor.

In yet another embodiment, the electro-dermal patch device (EDP) comprises a combination of a printed circuit board, for example grade FR-4, and a flex circuit, for example Kapton®, with a connector.

In various embodiments, the dimensions and/or form factor of the electro-dermal patch device of the present specification has any one or a combination of the following attributes: at least one dimension of length or width measuring less than 1.26 inches; a volume in a range of 0.1 inches$^3$ to 0.5 inches$^3$; a weight in a range of 10 grams to 80 grams; a physical aspect ratio of width to thickness in a range of 1:1 to 6:1; a maximum height or thickness of the EDP of 1 inch, preferably less than ¾ inch, and more preferably, ½ inch or less; a footprint of the EDP device in a range of 3.5 inches$^2$ (1:1 aspect ratio) to 6 inches$^2$ (6:1 aspect ratio); an electrical aspect ratio in a range of 1:1 to 1.5:1. In various embodiments, a ratio of EDP electrode surface area to EDP weight is selected to keep the size of the electrode equal to or smaller than the skin contacting foot print of the EDP device. In some embodiments, the ratio of EDP electrode surface area to EDP weight is in a range of 0.1 to 0.8 square inches per gram weight of the EDP device, preferably between 0.2 and 0.5 in$^2$/gram.

In some embodiments, a substantially rectangular shaped EDP (such as that of FIGS. 4B, 4C) has a width of 1.25 inches, a length of 4.0 inches and a height of 0.15 inches. In some embodiments, a circular shaped EDP (such as that of FIGS. 5A through 5F) has a radius of 1.125 inches and a height of 0.15 inches.

It should be appreciated that, while different physical configurations may exist for the electrical dermal patch, it is important that the device deliver enough electrical stimulation in a reasonably sized patch structure, namely one that is not so large that it would be uncomfortable to wear. To that end, in one embodiment, a preferred electrical dermal patch comprises an electrode that is removably attached to the surface of the housing. The contact surface area of such electrode is preferably less than 10 in$^2$, more preferably less than 8 in$^2$, and still preferably 7 in$^2$ or less and within a range of 0.1 in$^2$ to 10 in$^2$, or, more preferably, 0.5 in$^2$ to 4 in$^2$ and the programmable current ranges from 100 µA to 500 mA, or, more preferably, 2 mA to 50 mA. In these embodiments, the current density of the electrical dermal patch is in a range of 10 µA/in$^2$ to 5000 mA/in$^2$, more preferably 25 µA/in$^2$ to 1000 mA/in$^2$, and even more preferably 0.5 mA/in$^2$ to 100 mA/in$^2$. The total contact surface area of the electrical dermal patch in this configuration is equal to the contact surface area of its electrode(s).

In another embodiment, a preferred electrical dermal patch comprises an electrode that is at least partially affixed within the housing and not removably attached to a surface of the housing. The contact surface area of such electrode is preferably less than 10 in$^2$, more preferably less than 8 in$^2$, and still preferably 7 in$^2$ or less and within a range of 0.1 in$^2$ to 10 in$^2$, or, more preferably, 0.5 in$^2$ to 4 in$^2$ and the programmable current ranges from 100 µA to 500 mA, or, more preferably, 2 mA to 50 mA. In these embodiments, the current density of the electrical dermal patch is in a range of 10 µA/in$^2$ to 5000 mA/in$^2$, more preferably 25 µA/in$^2$ to 1000 mA/in$^2$, and even more preferably 0.5 mA/in$^2$ to 100 mA/in$^2$. The total contact surface area of the electrical dermal patch in this configuration is equal to the contact surface area of its electrode(s) plus a small additional amount for peripheral portions of the housing, which typically will not amount to more than an additional 5-10% more contact surface area relative to the electrode(s) surface area.

It should be appreciated that, in either configuration, one, two, three or more electrodes may be attached to the housing, or integrated into the housing, each having the characteristics described above, without departing from the scope of this invention.

FIGS. 55A and 55B are top perspective views while FIG. 55C is a bottom view of an electro-dermal patch device 5510, in accordance with an embodiment, having a pair of removable and replaceable conductive hydrogel, hydrocolloidal or foam pads 5520 (FIG. 55C) and a substantially rectangular shaped patch housing 5535. In an embodiment, the housing approximates an oval shape or a curvilinear rectangle. The patch housing 5535 includes a microcontroller, pulse generator, wireless transceiver, and power management module, such as those described with reference to FIG. 1A. The electrodes extend from the housing 5535 and into the pads 5520 for placement proximate the skin surface of a patient. It should be appreciated that while the electrode pads 5520 touch the skin surface, the housing 5535 remains above the skin surface. In some embodiments, the housing 5535 remains within a range of 2 mm to 4 mm, and preferably within 2 mm above the skin surface. In one embodiment, the pads 5520 have two electrodes 5518 disposed or printed on a lower surface 5522 of the pads 5520. The lower surface 5522 is adhesive—covered by a tab—such that, when the tab is removed the base surface 5522 can be adhered to the skin. The peel strength of the adhesively adhered pads 5520 is in a range of 1.0 to 2.1 Newton, allowing the device to be adhered to the skin for at least 8 hours of intensive activity, such as exercise. The pads 5520, when adhered to a user's skin, enable the electrodes to be in direct contact with the outer surface of the skin. As illustrated in FIG. 55C, in embodiments, pads 5520 have each of the two electrodes 5518 disposed or printed in opposing halves of the lower surface 5522. In embodiments, a distance 'D' between the two electrodes 5518 is less than 20 mm, preferably less than 15 mm, preferably less than 10 mm, preferably less than 5 mm. In one embodiment, distance 'D' between the two electrodes is about 4 mm. In an embodiment, each of the printed electrodes 5518 has a surface area in a range of 0.01 in$^2$ to 10 in$^2$, preferably 1.7 in$^2$ that is divided by a depression or spine 5503 having a width 'W' in a range of 1 to 12 mm, preferably 6 mm. In some embodiments, the total surface area taken up by the base of the two electrodes 5518 is preferably less than 10 in$^2$, more preferably less than 8 in$^2$, and still preferably 7 in$^2$ or less or within a range of 0.1 in$^2$ to 10 in$^2$. In accordance with some embodiments, the skin contact surface area of each one of the two electrodes 5518 is 3 cm$^2$±0.5 cm$^2$, the distance 'D' is about 0.2 cm±0.1 cm and an area between the two electrodes is 0.2 cm$^2$±0.1 cm$^2$ and preferably in a range of 0.05 cm$^2$ to 0.4 cm$^2$. In accordance with some embodiments, the total skin contact surface area of the two electrodes 5518 is in a range of 2 cm$^2$ to 4 cm$^2$.

In accordance with an embodiment, the housing 5535 includes a first portion 5525 forming a perimeter or outer border of the EDP device 5510 and a second portion 5530 forming a central portion of the EDP device 5510. In various embodiments, the system electronics described with reference to FIG. 1A are enclosed substantially within the second portion 5530. In some embodiments, the top surface 5512 of the second portion 5530 includes a button 5513 that can be actuated, such as by pressing or switching, to enable the EDP device 5510 to be toggled between an activated or deactivated state and/or to provide feedback to the patient when pressed while the EDP device 5510 is in activated state. In some embodiments, button 5513 may provide different functionality depending on the number of times the button is pressed or depending upon the position of the switch. For example, with the EDP device 5510 in activated state and adhered to the patient's skin, pressing or switch button 5513 may provide a tactile feedback, such as a vibratory or audio feedback, indicating tissue and electrode contact integrity and electrode integrity.

In an embodiment, an overall length of the EDP device 5510 along a longitudinal axis 5501 is less than 200 mm, preferably less than 100 mm, preferably approximately 76 mm, while an overall width along an axis 5502 (wherein axis 5502 is substantially perpendicular to the longitudinal axis 5501) is less than 200 mm, preferably less than 100 mm, preferably less than 50 mm, and preferably approximately 46 mm. In an embodiment, a width of the second portion 5530 along the axis 5502 is 32 mm to allow for a 7 mm thickness of the first portion 5525 that forms the perimeter or outer border of the EDP device 5510. In one embodiment, the button 5513 has a first dimension of 11 mm along the longitudinal axis 5501 and a second dimension of 16 mm along the axis 5502.

In some embodiments, visual feedback may additionally or alternatively be generated via LEDs in accordance with various configurations. Also, in some embodiments, instead of a separate button 5513 the entire top surface 5512 is configured to function as an actuatable button. In one embodiment, FIG. 55H shows an EDP device 5510*h* with button 5513 and a visual indicator 5540, comprising at least one LED, positioned on the top surface 5512 of the second portion 5530. In another embodiment, FIG. 55I shows an EDP device 5510*i* having the first portion 5525 surrounding the perimeter of the central second portion 5530. In this embodiment, button 5513 is positioned on the top surface 5512 of the second portion 5530 while the visual indicator 5540 comprises a perimeter or rim of the button 5513 which is visually lit using at least one LED enclosed within the second portion 5530. In yet another embodiment, FIG. 55J shows an EDP device 5510*j* having the first portion 5525 surrounding the perimeter of the central second portion 5530. In this embodiment, the entire top surface 5512 of the second portion is configured to function as an actuatable button 5513. Visual indicators 5540, comprising one or more LEDs, are also positioned on the top surface 5512. It should be appreciated that the visual indicator 5540 of the embodiments of FIGS. 55H, 55I and 55J generate visual feedback such as, but not limited to, a red light indicating that the patient's health parameter such as the will power levels, scores, reserves or conservation is very low (at or below a predefined minimum will power threshold), a yellow light indicating that the patient's will power reserve is in a medium zone, and a green light indicating that the patient's will power reserve is robust or high (above a predefined will power threshold). Instead of will power, the visual indicator 5540 can be used to generate feedback corresponding to any health parameter such as, but not limited to, target weight, dietary compliance, hunger level, exercise or activity level. Additionally, the visual indicator 5540 may also be used to indicate the active or inactive state of the EDP device in lieu of or in addition to the feedback generated through the button 5513. Still further, the visual indicator may be used to communicate a battery level of the EDP.

Referring back to FIGS. 55A through 55C, in various embodiments the hydrogel pads 5520 are replaceable, enabling attachment of new conductive pads and therefore new adhesion surfaces to the EDP device 5510. FIG. 55D is a bottom perspective view of the EDP device 5510 with the hydrogel pads removed. Two electrode contacts 5519 in electrical communication with the housing 5535 (FIG. 55A, B) are visible on the bottom surface 5542, of the second portion 5530. In accordance with an aspect, a ridge or rim portion 5545, around the circumference, perimeter or outer border 5543 of the bottom surface 5542 of the first portion 5525 (FIG. 55A, B), forms a nest, recess or hollow to enable the hydrogel electrode pads 5520 (FIG. 55C) to be snapped therein such that they are flush with ridge or rim portion 5545. This allows the electrodes to be less noticeable while enabling patients to easily match electrode or hydrogel pads to the EDP device via snaps or pin configurations corresponding to the electrode contacts 5519. In an embodiment, the ridge or rim portion 5545 has a thickness of 2 mm. FIG. 55E is a side perspective view of the EDP device 5510 with the hydrogel pads 5520 tucked in or snapped into place within the nest formed by the first portion 5525 at the bottom of the EDP device 5510.

In accordance with an aspect, in some embodiments the electrode pads 5520 (FIG. 55C) include two types of skin contacting adhesives (in contrast to electrode pads 5520 which use only hydrogel as an adhesive) which cause the electrodes to be substantially waterproof. FIG. 55K shows a bottom view of a waterproof electrode pad assembly 5565 while FIG. 55L shows a disassembled, breakaway view of the electrode pad 5565. As shown in FIG. 55K, a bottom surface 5566 of the electrode pad 5565 has a first skin contacting adhesive 5567 and a second skin contacting adhesive 5568 along the periphery of the bottom surface 5566 of the pad as well as along a mid-rib 5569 (that is, between the two electrodes 5518 shown in FIG. 55C) forming first skin contacting adhesive areas 5567a, 5567b. In various embodiments, the first skin contacting adhesive 5567 is hydrogel which is used as a primary adhesive to the skin as well as a conductive medium through which electric current flows from the EDP device to the patient's skin. The second skin contacting (secondary) adhesive 5568 is an acrylic-based pressure sensitive adhesive that uses an adhesive coated non-woven polyester fabric (such as Hypafix manufactured by Smith and Nephew) or adhesive-coated polyethylene acrylic foam (such as MDFT4532 manufactured by Coating and Converting Technologies). Electrode pads 5565 can be peeled off the EDP device by pulling on a removal tab 5570.

Referring now to FIG. 55L, the electrode pad assembly 5565 comprises a pair of snaps 5571 at the top followed by a thermoplastic polymer or PET (Polyethylene Terephthalate) layer 5572, a double-sided tape layer 5573, a carbon loaded vinyl layer 5574, snap eyelets 5575, first skin contacting adhesive or hydrogel 5567 and second skin contacting acrylic based adhesive 5568.

The acrylic adhesive 5568 is not soluble in water thus making it impervious to water. The hydrogel 5567 is not impervious to water. When the hydrogel 5567 comes in contact with water (human sweat or a shower), it absorbs the water and becomes less adherent to the skin while still remaining electrically conductive. With the use of the secondary acrylic adhesive 5568 adhesion to the skin remains unchanged in the presence of water. The use of secondary adhesive 5568 allows the user to keep the electrode pad assembly 5565 as well as the EDP device on their skin during strenuous activity where the user might sweat or shower and, as a result, reduce adherence of the primary adhesive or hydrogel 5567.

FIG. 55M is a disassembled or exploded view of electrode pad assembly employing either a foam pad with acrylic adhesive or a hydrocolloid adhesive. Referring now to FIG. 55M, the electrode pad assembly 5585 comprises a pair of snaps or romefast studs 5586 at the top following be a thermoplastic polymer or PET (Polyethylene Terephthalate) layer 5587, a double-sided tape layer 5588, a first adhesive layer 5589, a carbon loaded vinyl layer 5590, snap or romefast eyelets 5591, and a second skin contacting adhesive or hydrogel layer 5592.

In some embodiments, PET layer 5587 has a thickness or 0.005 inches.

In some embodiments, first adhesive layer 5589 is comprised of a foam with acrylic adhesive. In some embodiments, first adhesive layer 5589 is 0.032 inches thick. In embodiments where first adhesive layer 5589 is a foam, acrylic layer, second adhesive or hydrogel layer 5592 is 0.032 inches thick.

In some embodiments, first adhesive layer 5589 is comprised of a hydrocolloid adhesive. In embodiments where first adhesive layer 5589 is a hydrocolloid adhesive layer, second adhesive or hydrogel layer is 0.020 inches thick. In an embodiment, the surface area of the hydrocolloid layer is a maximum of 8 in$^2$. In embodiments, the hydrocolloid adhesive is designed such that it is waterproof and sweatproof and will stay on during intensive exercise. In embodiments, the hydrocolloid adhesive is designed to adhere to the skin for a time period ranging from at least 8 hours to several days.

FIGS. 55F and 55G are side perspective views with a portion of the housing 5535 cut away to expose an assembly of the EDP device 5510, in accordance with an embodiment also showing how each portion of the housing is connected. Referring now to FIGS. 55F, 55G, in accordance with an aspect, the central second portion 5530 is manufactured as a clamshell comprising a first top or upper part 5531 and a second bottom or lower part 5532 that define a space 5555 therebetween to house or accommodate the system electronics described with respect to FIG. 1A. The first portion 5525 is manufactured with a flange, collar or rib 5550 that runs along the inner circumference of the first portion 5525. Similarly, the first part 5531 also has a flange, collar or rib 5560 extending vertically downwards and running along the inner circumference of the first part 5531. During assembly, the flange 5550 is sandwiched between and used to connect the first and second parts 5531, 5532 of the clamshell-like central second portion 5530. In various embodiments, the flange 5550 is L-shaped that locks with the vertically extending flange 5560 to enable retention of the first portion 5525 by the second portion 5530 and form the assembly of the EDP device 5510. Also visible is the ridge or rim portion 5545 that defines the nest therebetween to accommodate the hydrogel pads 5520 (or the waterproof electrode pads 5565 of FIGS. 55K, 55L in some embodiments).

The EDP device assembly formed by connecting the first portion 5525 by the clamshell-like second portion 5530 has a plurality of advantages, such as but not limited to: simplicity of assembling the EDP device; reliable fit of the first and second portions 5525 and 5530; ease of accommodating one or more LEDs within the space 5555 to generate light around the rim of the button 5513 (as shown in FIG. 55I), which, in some embodiments, is the entire top surface 5512 (as shown in FIG. 55J); enabling a plurality of different colored first portions or skirts 5525 to be easily changed and reassembled with the second portion 5530; allowing internal components within the space 5555 (comprising system electronics of FIG. 1A, for example) to be recycled or replaced; and effectively protecting the internal components from damage.

Referring back to FIGS. 55A, 55B and 55F, in some embodiments the central second portion 5530 is made of hard plastic while the first skirt-like portion 5525 is made from relatively more flexible and soft materials such as silicone, rubber, LSR (Liquid Silicone Rubber) or any other flexible polymer known to persons of ordinary skill in the art. In other embodiments, materials for both the first as well as the second portions 5525, 5530 comprise silicone, rubber or LSR of similar or different durometer ratings. In one embodiment, material for the first portion 5525 is a low durometer silicone while material for the second portion 5530 is a relatively high durometer silicone. In some embodiments, materials for the housing 5535 include a thermoplastic elastomer, or (TPE), such as, for example, Monprene manufactured by Teknor Apex as an ultra-soft TPE gel. TPEs are processed like any other thermoplastic material but typically have low elastic moduli, thus making the assembly flexible. In various embodiments, the TPE used as material for the housing 5535 has hardness in a range of 30 to 70, preferably 45-65, and more preferably 50 to 60 on the sub-zero shore (00) scale and a tensile modulus (indicative of flexural properties) in a range of 15 to 55 psi, preferably 30 to 45 psi. For example, Monprene Ultra Soft Gel grade CP-32053G (manufactured by Teknor Apex) has a hardness measure of 53 on the subzero shore (00) scale and a tensile modulus of about 37 psi. Viscosity of the Monprene Ultra Soft Gel ranges from 30 to 65 on the subzero shore (00) scale. The EDP device of the present specification, taken as a whole, has a measurement on the flexural modulus scale per ASTM D-747 in a range of 10 psi to 35 psi, preferably 15 to 25 psi.

In various embodiments, the dimensions and/or form factor of the electro-dermal patch device 5510 has any one or a combination of the following attributes: at least one dimension of length or width measuring less than 1.26 inches; a volume in a range of 0.1 inches$^3$ to 0.5 inches$^3$; a weight in a range of 10 grams to 80 grams; a physical aspect ratio of width to thickness in a range of 1:1 to 6:1; a height h of less than 1 inch, preferably less than ¾ inch, and more preferably, ½ inch or less; a footprint of the EDP device in a range of 3.5 inches$^2$ (1:1 aspect ratio) to 6 inches$^2$ (6:1 aspect ratio); an electrical aspect ratio in a range of 1:1 to 1.5:1. In various embodiments, a ratio of EDP electrode surface area to EDP weight is selected to keep the size of the electrode equal to or smaller than the skin contacting foot print of the EDP device. In some embodiments, the ratio of EDP electrode surface area to EDP weight is in a range of 0.1 to 0.8 square inches per gram weight of the EDP device, preferably between 0.2 and 0.5 in$^2$/gram.

Companion Device/Control

Referring back to FIG. 1A, the electro-dermal patch device 110 is in data communication with and controlled by the companion device 105 in accordance with an aspect of the present specification. The companion device 105 is further capable of being in data communication with a remote patient care facility and/or patient care personnel. The companion device 105 is in data communication with the electro-dermal patch device 110 through a direct link to drive therapy. In accordance with a preferred embodiment, the companion device 105 is a hand-held computing device such as a watch, wristband, smartphone, tablet, or PDA that controls the electro-dermal patch device 110 through a wireless connection, such as Bluetooth, WiFi or any other private/public cellular or TCP/IP network such as the Internet. In some embodiments, the companion device is physically separated from and external to the EDP, hence referred to as a separate or external device. In some embodiments, the companion device may be a wearable activity monitor that tracks heart rates, movement, and other physiological data. In some embodiments, the EDP may be integrated into a wearable activity monitor and communicate with an external device, such as a smartphone, that is executing a software application in data communication with the wearable activity monitor.

In embodiments the companion device 105 may be in data communication, simultaneously, with the EDP device as well as other devices or equipment. For example, the companion device 105 configured as a smartphone may be in data communication with a car or a car audio system while also being in communication with at least one EDP device. Accordingly, when in the user is in the car, the car functions as the master while the smartphone (companion device) functions as the slave whereas between the smartphone and the EDP device, the smartphone is the master and the EDP is the slave.

The companion device 105 is configured to monitor and record ('learn') a patient's appetite patterns and monitor and record, learn, and modify the stimulation parameters of the stimulation protocols delivered by the electro-dermal patch device 110. In some embodiments, all therapy provided by the electro-dermal patch device 110 is coupled with recording (keeping a log of the therapy) and patient compliance reminders provided by the companion device 105. FIG. 6A shows the electro-dermal patch device 610 of the present specification, configured as a skin patch and placed at a lateral thoracic dermatome, in accordance with an embodiment, and being wirelessly controlled by a smartphone 605, for example.

With reference to FIG. 1A, in accordance with an aspect, the companion device 105, which is a hand-held computing device (such as a smartphone, tablet, PDA) in various embodiments, runs or implements a Health Management software application. The Health Management application activates, deactivates and controls the electro-dermal patch device 110 to provide a plurality of stimulation therapies or protocols in accordance with various embodiments. In some embodiments, this is enabled by pairing or syncing the hand-held computing device (wirelessly or through a wired connection) with the electro-dermal patch device 110. In some embodiments, the Health Management application pairs or syncs and controls more than one electro-dermal patch device 110 worn by the user for treating a combination of conditions.

In still further embodiments, the Health Management application is capable of also communicating (via pairing or syncing) with a third party device (including a third party application software on an external device), with physiological sensors, configured to be worn on the human body, such as around the wrist, in order to monitor, acquire, record, and/or transmit the physiological data, to receive and integrate exercise and weight loss information, along with one or more electro-dermal patch devices 110 of the present specification. In various embodiments, the third party device includes a glucose sensor.

In embodiments where the Health Management application pairs or syncs with a plurality of electro-dermal patch devices 110 it is desired that the user be able to ascertain that the Health Management application has successfully paired or synced with each of the plurality of electro-dermal patch devices. In some embodiments, an electro-dermal patch device and the companion device (running the Health Management application) flash a similar color (using LEDs) to indicate successful pairing or syncing. Thus, each of the plurality of electro-dermal patch devices flash a color in tandem with the companion device, one after another for example or simultaneously, indicating successful pairing or syncing with each of the electro-dermal patch device. In some embodiments, the companion device (running the Health Management application) displays a unique identification (ID) of an electro-dermal patch device indicating successful pairing or syncing with the electro-dermal patch device. Thus, the unique IDs of each of the plurality of electro-dermal patch devices are displayed by the companion device indicating successful pairing or syncing with each of the electro-dermal patch device.

In accordance with an aspect of the present specification, cervical auscultation is used to detect pharyngeal swallow and therefore determine if the user is indulging in an eating activity. FIG. 56 illustrates a swallow detection device 5605 configured to be worn by a user around her neck, in accordance with some embodiments. The Health Management application is capable of also communicating (via pairing or syncing) with the swallow detection device 5605 in order to monitor, acquire, record, and analyze swallowing sounds while the user is engaged in eating. In an embodiment, the swallow detection device 5605 comprises an accelerometer to detect signals associated with swallowing sounds and noise associated with laryngeal elevation and carotid pulse. The detected signals are transmitted to the Health Management application (on the companion device, such as a smartphone) for acoustic processing and analysis. The analysis, for example, differentiates between a dry (not associated with eating) and a wet (associated with eating) swallow by considering at least the repetitiveness of a plurality of swallow events, time elapsed between the plurality of swallow events and the overall duration encompassing the plurality of swallow events. Thus, in some embodiments prolonged occurrence of a plurality of swallow events may be considered as consumption of a meal. In various embodiments, the swallow detection sensor 4005 is configured to be worn or adhered to the user's skin so as to cover an optimal site for swallow detection. In embodiments, the optimal site comprises any one of: a) a lateral border of the trachea immediately inferior to the cricoid cartilage, b) a center of the cricoid cartilage and the midpoint between the site over the center of the cricoid cartilage and c) a site immediately superior to the jugular notch.

In various alternate embodiments, impedance and/or acoustic detection of gastric sounds, at the level of the user's stomach, are utilized to determine an eating event.

In accordance with another embodiment of the present specification, an eating activity or eating moment of the user is determined automatically using an inertial sensor, such as an accelerometer or inclinometer, for automated dietary monitoring. In various embodiments, the accelerometer or inclinometer is included in a wrist-band or wristwatch, such as the band 2105 of FIG. 21A or the wristwatch 2106 of FIG. 21B, to detect, capture and acquire a plurality of dietary data related to physical body movements, such as (for example) haptic motions of the wrist or hand, of the user involved in food intake gestures (also referred to as the hand-to-mouth gestures). The plurality of dietary data is communicated to the Health Management application that implements an eating moment recognition method to process and analyze the plurality of dietary data and identify when the user is eating. In accordance with an embodiment, the eating moment recognition method a) performs eating gesture detection on the plurality of dietary data captured by the accelerometer incorporated within the wristband or wristwatch/smartwatch of the user, and b) clusters these eating gestures across a time dimension to identify eating moments or activities.

In embodiments where the Health Management application is in communication with an Intelligent Personal Assistant (IPA), as discussed later in this specification, identification or determination of an eating moment or activity (by the eating moment recognition method) by the HMA is communicated to the IPA that may deliver auditory prompts to user enquiring if the user is indeed eating and if yes, then cautioning the user if the eating event is unscheduled or not in line with a meal regimen being followed by the user. In some embodiments, the eating moment recognition method is implemented directly by the IPA device such that dietary data from the wristwatch or band is communicated directly to the IPA device (in communication with the wristwatch or band) for detecting eating events or activities.

FIG. 58 is a flow chart of a plurality of exemplary steps of the eating moment recognition method, implemented by the HMA, in accordance with some embodiments. At step 5805, a user wears a wrist-worn device, such as a wristband or wristwatch/smartwatch, comprising at least an accelerometer that continuously captures, and communicates to the HMA, a plurality of dietary data representative of the user's food intake gestures. The HMA receives and stores the plurality of dietary data from the accelerometer. At step 5810, the plurality of dietary data is filtered using a filter such as, but not limited to, an exponentially-weighted moving average and thereafter scaling the resulting filtered data to unit norm (such as, for example, 12 normalization). At step 5815, data frames are extracted, from the resulting filtered and normalized data of step 5810, using a sliding window approach with a predefined overlap, such as, say, 50% overlap. It should be appreciated that a frame size is chosen so that the extracted frames contain an entire food intake gesture. The gesture duration is based on factors, such as the user's eating styles and whether he is multitasking (e.g., reading a book, socializing with friends) while eating or drinking. In various embodiments, the frame size ranges from a duration of 2 to 10 seconds. In an embodiment, the frame size is chosen to be of 6 seconds duration.

At step 5820, a plurality of statistical functions are computed for each extracted frame. In one embodiment five statistical functions are computed comprising the frame's mean, variance, skewness, kurtosis and root mean square. These frame-level features result in 5-dimensional feature vectors for each axis of the accelerometer, in accordance with an embodiment.

At step 5825, the user's food intake gestures (defined as the arm and hand gestures involved in bringing food to the mouth from a resting position on a table, for instance, and then lowering the arm and hand back to the original resting position) are identified using a classifier such as, but not limited to, the Random Forest learning algorithm or the Scikit-learn Python package.

Thereafter, at step 5830, the user's eating moments or activities are estimated based on temporal density of the identified food intake gestures. When a predefined minimum number of identified food intake gestures are within a predefined temporal distance of each other, then such an event is construed as an eating moment or activity. In embodiments, a density-based clustering algorithm, such as DBSCAN (Density-based spatial clustering of applications with noise), is used to identify high food intake gesture densities as clusters in the time domain. In an embodiment, the centroids of these clusters are identified as eating moment occurrences.

In accordance with another aspect of the present specification, the accelerometer or inclinometer included in the wrist-band or wristwatch, such as the band 2105 of FIG. 21A or the wristwatch 2106 of FIG. 21B, is used to detect, capture and acquire a plurality of gesture data corresponding to a plurality of pre-defined haptic motions of the wrist of the user. In embodiments, the plurality of pre-defined haptic motions of the wrist are indicative of a plurality of user-initiated commands and/or inputs to the HMA.

Accordingly, the eating moment recognition method of FIG. 58 is configured to detect and interpret the plurality of pre-defined haptic motions of the wrist of the user. For example, a number (say three or more) of repetitive circular motions of the hand—using wrist as a pivot—may be detected and interpreted by the eating moment recognition method to be indicative of the user wanting to trigger a standard or pre-programmed stimulation session (pre or post prandial) or to trigger a hunger or appetite scale to record an unscheduled hunger event and consequently trigger a rescue stimulation session. In some embodiments, the direction of such repetitive circular motions of the hand may be further differentiated to indicate differing commands and/or inputs by the user. For example, in one embodiment, a clockwise rotatory motion of the hand—using the wrist as the pivot—may be detected and interpreted to be indicative of the user wanting to trigger a standard or pre-programmed stimulation session (pre or post prandial) while an anti-clockwise rotatory motion may be indicative of the user wanting to trigger a hunger or appetite scale to record an unscheduled hunger event and consequently trigger a rescue stimulation session.

Let us say that the user rotates his hand anti-clockwise, with wrist as pivot, causing the hunger VAS bar scale to be triggered on his wrist-band or wristwatch. Next, in some embodiments, the user may move his hand up-and-down in a vertical plane, with the wrist as a pivot, to input and record the intensity of hunger he is experiencing. For example, the number of times the user moves his hand up-and-down may be indicative of a level of hunger the user wants to input. Thus, on a hunger scale of 1 to 5, one up-and-down movement of the hand may indicate a level 1 hunger intensity while 5 successive up-and-down movements of the hand may correspondingly indicate a level 5 hunger intensity. In alternate embodiments, the user may move his hand side-to-side in a horizontal plane, with the wrist as a pivot, to input and record the intensity of hunger he is experiencing. Thus, the number of times the user moves his hand side-to-side may be indicative of the level of hunger the user wants to input.

In accordance with still another aspect of the present specification, the wrist-band or wristwatch includes a touch-sensitive display screen configured to accept and subsequently interpret the user's taps and/or swipes. In a non-limiting example, the user may trigger the hunger VAS bar scale by rotating his hand anti-clockwise, with wrist as pivot. Next, the user may use a specific number of taps or swipes on the display screen of his wrist-band or wristwatch to input and record the intensity of hunger he is experiencing. Thus, on a hunger scale of 1 to 5, a single tap or swipe would indicate a level 1 of hunger intensity while a series of 5 taps or swipes would indicate a level 5 of hunger intensity. It should be appreciated that in embodiments, any one or a combination of the plurality of haptic motions of the hand (using wrist as a pivot) and taps or swipes on the display screen (of the wrist-band or wristwatch) may be used to enable the user to issue commands and/or inputs to the HMA.

In yet further embodiments, the Health Management application is capable of also detecting and communicating with a plurality of wireless proximity sensor tags. The plurality of proximity tags are located at potential areas of meal sourcing and/or consumption such as, but not limited to, refrigerator, pantry, kitchen, and dining room to detect the user's proximity at these areas. If the user's presence, at these areas, is detected the HMA may prompt and caution the user with reference to out-of-plan meal consumption, for example.

In accordance with aspects of the present specification, multiple electro-dermal patch (EDP) devices along with a plurality of additional devices when paired or synced with at least one companion device of a user—constitute a health or therapeutic network or eco-system for the user. Similarly, health or therapeutic networks or eco-systems of a plurality of users are networked together to form a large or wide-area health or therapeutic eco-system (stylized as an Internet of Things). In embodiments, additional devices comprise devices such as, but not limited to, third party devices (with physiological sensors) configured to be worn on the human body such as around the wrist, a glucose sensor, an IPA (Intelligent Personal Assistant) system (as described in detail later in the specification), proximity sensor tags, a swallow detection device (such as device 5605 of FIG. 56), Bluetooth activated locks, and kitchen appliances (such as a refrigerator). In embodiments, the health or therapeutic network or eco-system allows connecting any wire or wirelessly syncable additional devices. In some embodiments, the health or therapeutic network or eco-system allows a subset of the additional devices to be preferentially synced such as, for example, the third party devices (with physiological sensors).

In some embodiments, multiple electro-dermal patch (EDP) devices 110 are networked together with a single companion device 105 to aggregate data feedback from the EDP devices 110. The aggregated data is then used to modify stimulation parameters and develop more precise stimulation algorithms. In various embodiments, the companion device 105 enables social networking with friends and family, provides voice recognition and voice feedback, and includes anti-hacking data protection for HIPAA compliance. In some embodiments, the wireless connection (for pairing or syncing) is optionally compliant with HIPAA and other regulatory body requirements and laws relating to OUS (Outside United States) countries for patient data privacy. In various embodiments, the wireless connection is encrypted to prevent hacking of the device to retrieve patient data and/or inappropriately stimulate the patient and/or destroy the device.

Figure 6B:
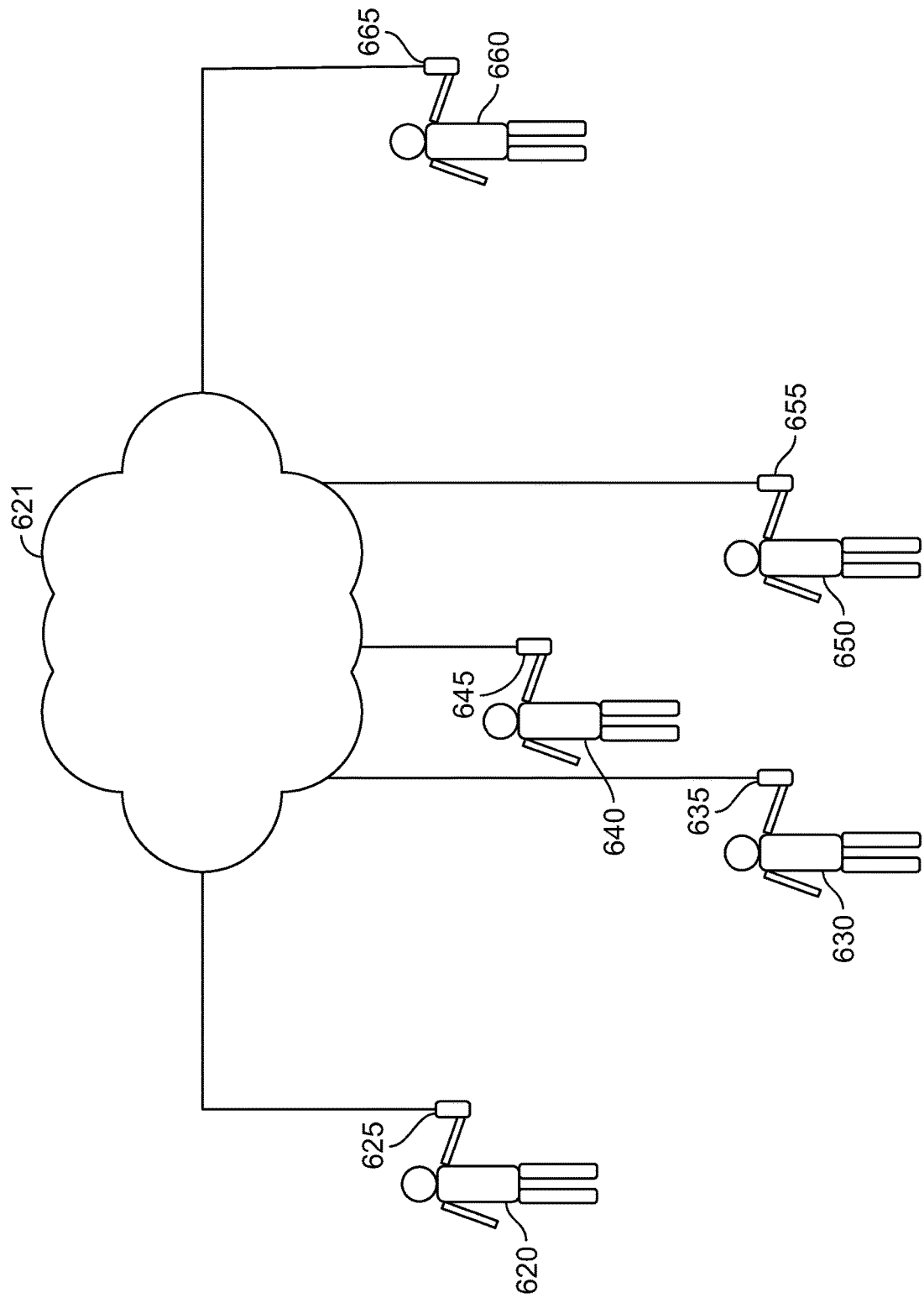
FIG. 6B is a schematic diagram of a plurality of electro-dermal patch users with companion devices shared over a common network connection, in accordance with one embodiment of the present specification.

In various embodiments, as shown in FIG. 6B, using a companion device 625, 635, 645, 655, 665 multiple EDP users 620, 630, 640, 650, 660 can network with one another and communicate regarding their therapy over a shared network connection 621, such as a cloud based connection, which can lead to improved patient compliance to stimulation protocols, with resultant increased dietary compliance. For example, networked EDP users could share and exchange experiences, progress, dietary ideas, and success stories. In some embodiments, networked exchanges are automatically input into companion devices, resulting in changes to therapy provided by the EDP devices. For example, in one embodiment, aggregated dosing data is used to reset baseline default dosing settings to provide different dietary recommendations. Traditionally, small group clinical studies are performed to obtain data used for creating dosing strategies. By networking EDP users through companion devices, larger amounts of aggregated user settings can be obtained automatically, for example, via a cloud based connection, and used to automatically fine tune dosing settings. In some embodiments, EDP users have the ability, over a network connection, to share data among friends and family who are also users. In some embodiments, EDP users can be segmented into diet clubs based on their connected friends and/or based on the type of diet they have chosen. Therefore, in various embodiments, users can connect with friends and also connect into "groups" defined around the type of diet plan, i.e. Atkins, Mediterranean, and intermittent fasting, they are following. Further, in some embodiments, users connected to a group, for example, Weight Watchers, can receive "group therapy" support in the form of input, as needed or at periodic intervals, from a moderator or therapist. In embodiments, the "groups" also enable communication between EDP devices, between users, and between users and a moderator or therapist. Such interconnectivity among friends, groups, and moderators/therapists provides a larger support network for EDP users and promotes user compliance.

Figure 6C:
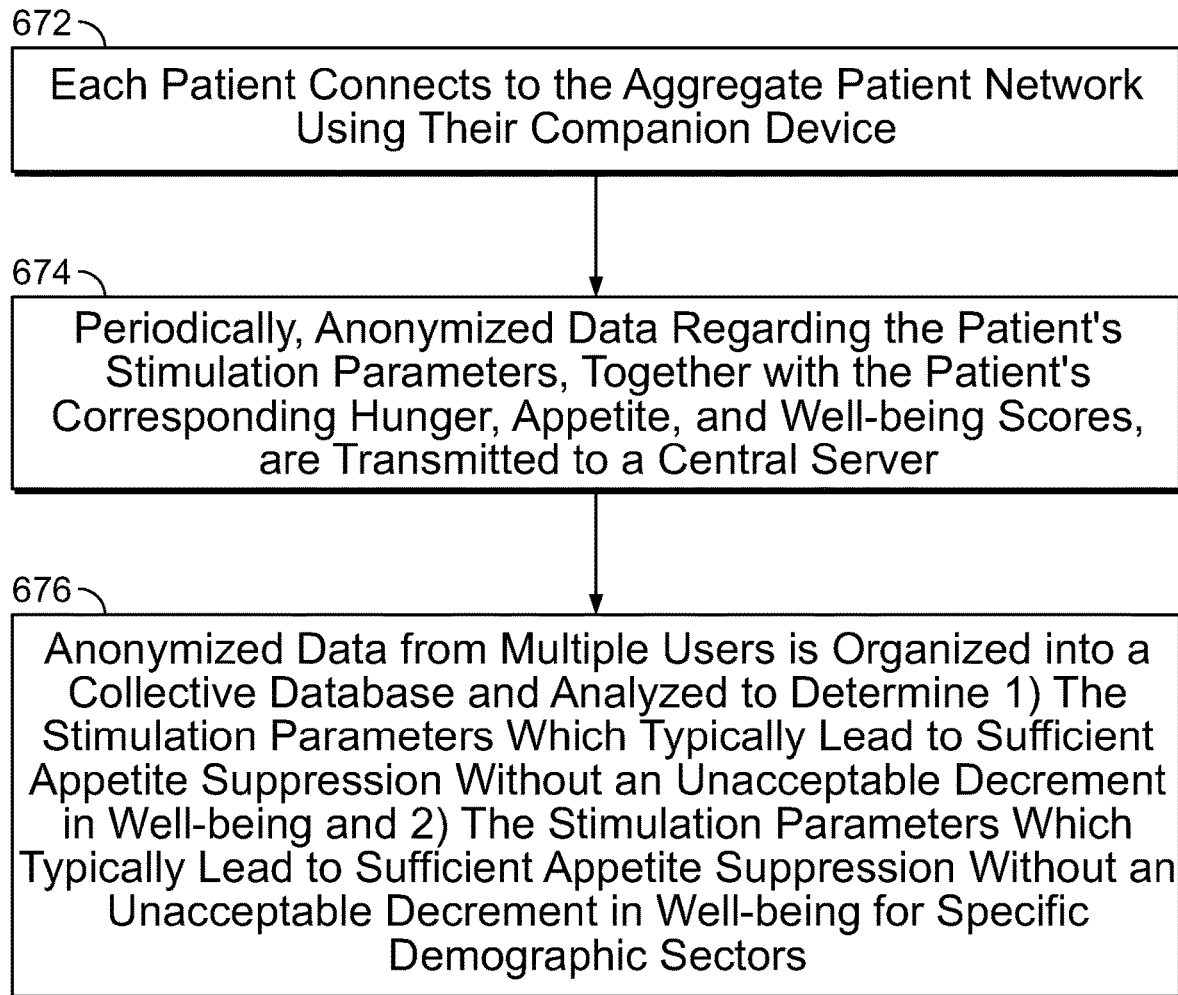
FIG. 6C is a flow chart listing the steps in one embodiment of a method of aggregating, organizing, and analyzing stimulation parameters and patient hunger, appetite, and well-being scores for a plurality of patients, each having an EDP device with linked companion device connected to an aggregate patient network.

In some embodiments, an EDP user network functions as a dosing settings and dietary information exchange. For example, in an aggregate patient data network, multiple different patients have an EDP communicating with a personal companion device. FIG. 6C is a flow chart listing the steps in one embodiment of a method of aggregating, organizing, and analyzing stimulation parameters and patient hunger, appetite, and well-being scores for a plurality of patients, each having an EDP device with linked companion device connected to an aggregate patient network. At step 672, each patient connects to the aggregate patient network using their companion device. At step 674, periodically, e.g. several times a day, once a day, 2-6 times a week, or any such increment, anonymized data regarding the patient's stimulation parameters including, but not limited to, stimulation pulse width, pulse amplitude, pulse frequency, pulse shape, duty cycle, session duration, and session frequency, together with the patient's corresponding hunger, appetite, and well-being scores (the hunger, appetite, and well-being scores being collectively referred to as patient status data), are transmitted to a central server, or set of servers.

At the central server, at step 676, the anonymized data from multiple users are organized into a collective database and analyzed to determine 1) the stimulation parameters including, but not limited to, stimulation pulse width, pulse amplitude, pulse frequency, pulse shape, duty cycle, session duration, and session frequency, which typically lead to sufficient appetite suppression without an unacceptable decrement in well-being and 2) the stimulation parameters including, but not limited to, stimulation pulse width, pulse amplitude, pulse frequency, pulse shape, duty cycle, session duration, and session frequency, which typically lead to sufficient appetite suppression without an unacceptable decrement in well-being for specific demographic sectors. In some embodiments, patient status data such as the hunger and appetite scores are aggregated into a composite score, also referred to as a satiety score. In some embodiments, exercise scores reflective of calories expended are also factored into the composite or satiety score. The user can share her composite score (along with treatment or stimulation settings that led to the composite score) with friends and family via social networking (and/or with an online coaching or concierge service), to illicit advice, encouragement and compare progress with fellow dieters.

It should be appreciated that while in some embodiments data regarding the patients' stimulation parameters is anonymized, in some embodiments the data may not be anonymized if the patients sign away their respective privacy rights.

In various embodiments, hunger and appetite scores across demographic profiles are analyzed to determine what stimulation settings achieve optimum appetite and hunger levels or scores for a given age, gender, race, body fat, BMI, ethnicity, weight loss goal, or bacterial microbiome profile. Thus, for a given user, once the optimum stimulation settings are identified, it is then determined how stimulation settings for the given user must be modified, titrated or personalized in order to match those optimum stimulation settings, and a modulation signal is transmitted in order to establish those new (optimum) stimulation settings. In various embodiments, the electrical stimulation dosing settings are titrated and personalized from one user and/or user group to another user and/or user group based on optimum stimulation settings tracked, analyzed and determined across various group demographic profiles.

In various embodiments, the EDP device, and the electrical stimulation it delivers, is configurable and re-configurable for different therapies and for different aspects within a specific therapy. For example, regarding weight loss and management, the patient and/or companion device can configure the EDP to deliver electrical stimulation in an effort to promote active weight loss in the patient and then, once a target weight is achieved, reconfigure the EDP to deliver electrical stimulation to maintain the patient at the target weight. This can be accomplished via one or more applications downloaded to the companion device. FIG. 6D is a flow chart illustrating the steps involved in using one or more downloadable applications to configure and reconfigure stimulation provided by an electro-dermal patch (EDP) device, in accordance with one embodiment of the present specification. At step 680, a patient obtains an EDP from a medical professional. At step 681, the patient pairs a companion device with the EDP and with a separate physiological monitoring device with physiological sensors, configured to be worn on the human body, such as around the wrist, in order to monitor, acquire, record, and/or transmit physiological data to the companion device, wherein the companion device is adapted to create and modify stimulation parameters based on the monitored physiological data. At step 682, the patient then downloads, from an online marketplace, a first application designed to configure the EDP to achieve a first objective associated with a specific therapy, for example, weight loss for weight management. The patient positions the EDP on his body at step 683. The first application, at step 684, configures the EDP for the first objective by establishing certain baseline stimulation parameters designed to achieve said first objective and by titrating or fine-tuning said stimulation parameters based on patient diary input into the companion device and/or physiological data transmitted to the companion device by the separate monitoring device. After the first objective has been achieved, at step 685, the patient then downloads a second application, from an online marketplace, designed to reconfigure the EDP to achieve a second objective associated with the specific therapy, for example, maintaining weight for weight management.

In various embodiments, one or both of the first and second applications is available from the online marketplace for a fee. Additionally, both the first and second applications may be separate and distinct applications which reside on the companion device, are separately obtained by accessing the on-line application marketplace associated with the companion device, and are activated, and executed, by clicking on separate and distinct icons from the companion device's home screen. In another embodiment, the first application may be downloaded from the on-line application marketplace associated with the companion device and may be activated, and executed, by clicking on separate and distinct icons from the companion device's home screen while the second application, and all subsequent applications responsible for modulating the EDP's stimulation parameters, are downloaded by accessing a marketplace of such applications through the first application. Specifically, the first application provides a gateway to a database, or library, of additional applications which may provide for different stimulation parameters based on inputs, weights, and other criteria that differ from the first application, or each other.

The second application, at step 686, then configures the EDP for the second objective by establishing certain baseline stimulation parameters designed to achieve said second objective and by titrating or fine-tuning said stimulation parameters based on patient diary input into the companion device and/or physiological data transmitted to the companion device by the separate monitoring device. In one embodiment, for weight management, the stimulation parameters for the first objective (weight loss) are more focused on patient diary record of well-being and hunger as inputs to titrate therapy while the stimulation parameters for the second objective (weight maintenance) are more focused on daily body weight as an input to titrate therapy. While weight management has been used to describe the method above for modifying therapy provided by the EDP, in various embodiments, the method of using one or more online applications to configure and reconfigure the stimulation parameters of the EDP can be used on any condition receptive to electrical stimulation therapy.

In various embodiments, the EDP and companion device are open source to allow for the creation of applications for the devices designed to enact therapy methods similar to the one described above. In another embodiment, a single master application downloadable to a companion device is responsible for controlling the EDP and setting initial stimulation parameters. This master application may come with the EDP upon initial purchase or may be separately purchasable or downloadable for free from an online marketplace. In various embodiments, further software upgrades, such as in-application or "in-app" purchases, can be obtained, for a fee, within the master application and used to fine-tune therapy. In various embodiments, such software upgrades include, for example, new diet plans, new exercise plans, and improved fitness tracking, among others. In various embodiments, these software upgrades are created by third parties or by the creator of the master application. In some embodiments, new applications or software upgrades to a master application reconfigure the EDP to provide electrical stimulation targeting different conditions. For example, in various embodiments, applications or upgrades reconfigure baseline EDP stimulation parameters to treat other conditions including, but not limited to, dysmenorrhea, back pain, urinary incontinence, and peripheral neuropathy, including diabetic peripheral neuropathy. In some embodiments, the electrical components of the device are the same and the patient uses a different, disposable electrode patch portion and repositions the device on his or her body. These applications and upgrades modify the algorithms used by the companion device to change the stimulation parameters for the EDP to treat the different conditions. For example, in one embodiment, a patient initially uses the EDP for weight management in a method similar to that described above. She then downloads a fee based online application to the companion device which then reconfigures the EDP stimulation to treat her dysmenorrhea. She can then use her initial application to return the EDP back to weight management settings. She could continually download new applications and upgrades and reconfigure the EDP to treat a plurality of different conditions and go back and forth between different conditions. It would be preferred that, for the non-weight loss applications, such as urinary incontinence, back pain, dysmenorrhea and peripheral neuropathy, including diabetic peripheral neuropathy, a completely different application be downloaded while for new or different weight loss plans, it would be preferred to download additional applications through the first downloaded weight loss application itself, thereby avoiding having multiple different and distinct weight loss applications on the companion device's home screen.

Because the presently disclosed embodiments are directed to medical treatments, it is imperative that patient specific data, such as data representing specific stimulation settings and patient status data, are stored, transmitted, and verified in a manner that is secure and subject to authentication. In one embodiment, data transmissions between the EDP, the companion device, and any remote server(s) are subject to verification and authentication, such as by using checksums, private and public keys, and other forms of verification known in the art. If, at any time, one or more of the data transmissions fail to be properly verified or authenticated, any new or modulated stimulation settings associated with such data transmissions are discarded or otherwise set aside and only a previous stimulation setting associated with a fully verified and/or authenticated complete set of data transmissions is used. Alternatively, the system may lock the use of any stimulation setting until such data transmissions can be fully verified, along with any new or modulated stimulation settings associated therewith.

Figure 6E:
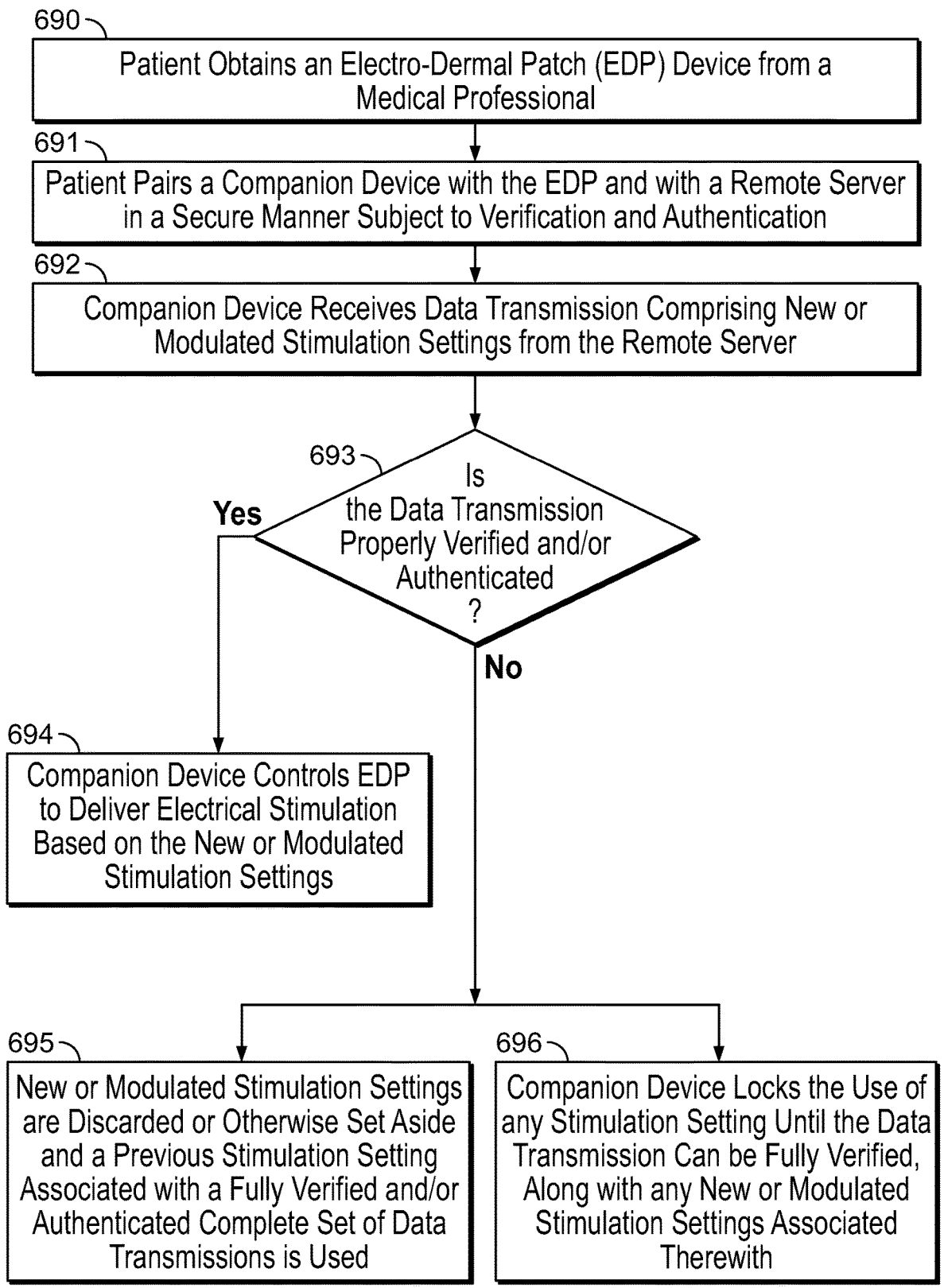
FIG. 6E is a flow chart illustrating the steps involved in a method of a companion device verifying and/or authenticating data transmission received from a remote server, in accordance with some embodiments of the present specification.

FIG. 6E is a flow chart illustrating the steps involved in a method of a companion device verifying and/or authenticating data transmission received from a remote server, in accordance with some embodiments of the present specification. At step 690, a patient obtains an electro-dermal patch (EDP) device from a medical professional. The patient pairs a companion device with the EDP and with a remote server, in a secure manner subject to verification and authentication, at step 691. At step 692, the companion device receives a data transmission comprising new or modulated stimulation settings from the remote server. The companion device then checks if the data transmission is properly verified and/or authenticated at step 693. In one embodiment, if the data transmission is properly verified and/or authenticated, the companion device controls the EDP to deliver electrical stimulation based on the new or modulated stimulation settings at step 694. In one embodiment, if the data transmission is not properly verified and/or authenticated, the new or modulated stimulation settings are discarded or otherwise set aside and a previous stimulation setting associated with a fully verified and/or authenticated complete set of data transmissions is used at step 695. In another embodiment, if the data transmission is not properly verified and/or authenticated, the companion device locks the use of any stimulation setting until the data transmission can be fully verified, along with any new or modulated stimulation settings associated therewith at step 696.

In another embodiment, communications between an EDP, companion device and any remote server(s) may comprise an indication, such as a packet header, identifier, tag, or other representation, of whether the specific EDP involved in the data transmissions is a device that has been sold subject to FDA regulatory approval or whether it is a device that has not been sold subject to FDA regulatory approval. Depending on such an identifier (indicative of government regulatory governance, or some extent thereof), different data processing may occur. For example, if the companion device or remote server(s) determine the EDP in question is subject to FDA approval (based on an identifier being stored in a memory within the EDP), it may cause a different or higher level of encryption, authentication, and/or verification to be applied to the stored data or to data transmissions. In one case, all data transmissions to and from the EDP, between the EDP and companion device, and/or between the companion device and remote server(s) are encrypted, authenticated, and anonymized subject to verification. In another case, only data transmissions containing patient-specific stimulation settings or patient status data are encrypted, authenticated, and/or subject to verification while all other data transmissions are not encrypted.

If, on the other hand, the companion device or remote server(s) determines the EDP in question is not subject to FDA approval (based on an identifier being stored in a memory within the EDP), it may cause a lower level of encryption, authentication, and/or verification to be applied to the stored data or to data transmissions relative to the FDA case. In one embodiment, no data transmissions to and from the EDP, between the EDP and companion device, and/or between the companion device and remote server(s) are encrypted, authenticated, and subject to verification. In another case, only data transmissions containing patient-specific stimulation settings or patient status data are authenticated and/or subject to verification and no data transmissions are encrypted.

Figure 6F:
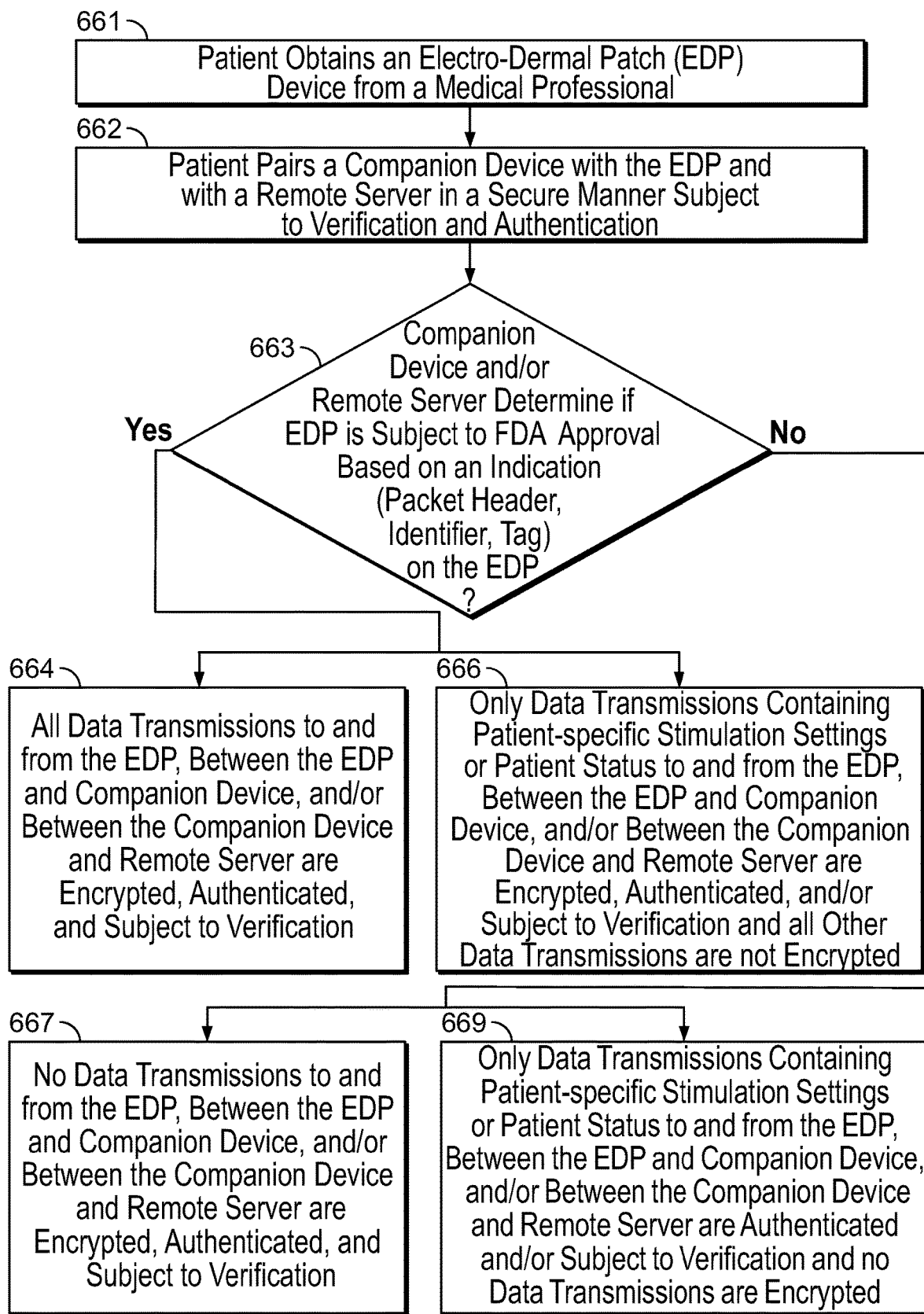
FIG. 6F is a flow chart illustrating the steps involved in a method of encrypting, authenticating, and/or verifying data transmissions between an EDP, companion device, and remote server based on FDA approval status of the EDP, in accordance with some embodiments of the present specification.

FIG. 6F is a flow chart illustrating the steps involved in a method of encrypting, authenticating, and/or verifying data transmissions between an EDP, companion device, and remote server based on FDA approval status of the EDP, in accordance with some embodiments of the present specification. At step 661, a patient obtains an electro-dermal patch (EDP) device from a medical professional. The patient pairs a companion device with the EDP and with a remote server, in a secure manner subject to verification and authentication, at step 662. At step 663, the companion device and/or remote server determine if the EDP is subject to FDA approval based on an indication (packet header, identifier, tag) on the EDP. In one embodiment, if it is determined that the EDP is subject to FDA approval, then all data transmissions to and from the EDP, between the EDP and companion device, and/or between the companion device and remote server are encrypted, authenticated, and subject to verification at step 664. In another embodiment, at step 666, if it is determined that the EDP is subject to FDA approval, only data transmissions containing patient-specific stimulation settings or patient status to and from the EDP, between the EDP and companion device, and/or between the companion device and remote server are encrypted, authenticated, and/or subject to verification and all other data transmissions are not encrypted. In another embodiment, if it is determined that the EDP is not subject to FDA approval, then no data transmissions to and from the EDP, between the EDP and companion device, and/or between the companion device and remote server are encrypted, authenticated, and subject to verification at step 667. In another embodiment, at step 669, if it is determined that the EDP is not subject to FDA approval, only data transmissions containing patient-specific stimulation settings or patient status to and from the EDP, between the EDP and companion device, and/or between the companion device and remote server are authenticated and/or subject to verification and no data transmissions are encrypted.

In accordance with an aspect of the present specification, patient status data and, if needed, stimulation setting, parameters and protocols are transmitted to insurance companies to support medical treatments, such as bariatric surgeries, or other insurance claims, or for other general insurance data needs. In some embodiments, such data transmission may be subjected to encryption, authentication and verification as described at step 666.

The Health Management Application (hereinafter also referred to as 'HMA') of the present specification comprises a plurality of programmatic instructions and algorithms and implements a plurality of GUIs (Graphical User Interface) to enable a plurality of functions, non-limiting examples of which are described henceforth.

Referring back to FIG. 1A, in various embodiments, the HMA enables confirming linkup to the electro-dermal patch device 110 and displaying battery life of the electro-dermal patch device 110. In embodiments, the EDP device 110 goes into a sleep mode or state periodically, when not stimulating for example, to conserve power. In the sleep mode or 'off' state the EDP device 110 uses a minimum amount of power. As a result of being in the low power state, a Bluetooth connection between the EDP device and the associated companion device (the hand-held computing device 105) may be lost or the pairing or synchronization between the EDP device and the companion device may be lost. Also, the Bluetooth connection may be lost if a distance between the EDP device and the companion device increases beyond a certain limit. To ensure appropriate connection between the EDP device and the companion device, the HMA enables generating an audio, visual and/or tactile (such as, vibratory) alarm if the Bluetooth connection between the EDP device and the companion device deteriorates and the EDP device is not detectable.

The HMA enables generating an audio and/or visual indicator on the hand-held computing device 105 indicating that a) the electro-dermal patch device 110 has been properly placed on the user's body by, for example, confirming sufficient electrode and tissue contact or integrity, b) the one or more electrodes 118 is aged or compromised (ascertained by, for example, impedance measurements) and needs to be replaced. In some embodiments, electrode and tissue contact integrity and electrode integrity, i.e. whether the electrode is functioning properly or damaged, are checked through at least one sensor, such as an impedance or bio-impedance sensor of the electro-dermal patch device 110. In other embodiments, an acoustic sensor, capable of sensing specific acoustic signals unique to an area of the human body, is used to determine if the electro-dermal patch device 110 has been properly positioned on the user's body. In various embodiments, sufficient electrode and tissue contact or integrity is defined as achieving electrode impedance in a range of 200 ohms to 1000 ohms. In one embodiment, pulse amplitude is automatically adjusted by virtue of there being a constant current source (from one or more batteries). A constant current source circuit automatically adjusts the pulse to maintain a programmed amplitude in the event of electrode-tissue interface impedance changes. This automatic adjustment may be programmed to occur for voltages ranging from 0.1V to 500V. Accordingly, the pulse amplitude is automatically modulated in order to maintain a constant current source. In other words, the stimulation pulse amplitude or intensity is adapted automatically as a function of electrode-tissue interface impedance changes. In some embodiments, the pulse intensity varies as a directly proportional function of the electrode-tissue interface impedance changes. In some embodiments, the pulse intensity varies as a directly inverse proportional function of the electrode-tissue interface impedance changes.

The HMA also enables analyzing sensed neural activity prior to the commencement of a stimulation therapy to assess and indicate to the user that the electro-dermal patch device 110 has been placed at an appropriate location, such as the T2-T12 and/or C5-T1 dermatomes for eating disorders. In various embodiments, the accuracy or appropriateness of the electro-dermal patch device location is assessed through the neural activity monitor of the electro-dermal patch device 110. In various embodiments, neural activity sensing or monitoring is accomplished by using a sense amplifier circuit to measure neural activity and output a representative signal to the microcontroller or microprocessor of the electro-dermal patch device 110. The microcontroller algorithmically processes the data to determine if there is neural activity. In some embodiments, the sense amplifier circuit measures neural activity signals directly using the same electrodes used for stimulation. In other embodiments, the sense amplifier circuit measures neural activity signals separately using different electrodes than those used for stimulation. In still other embodiments, the sense amplifier circuit measures neural activity signals using both the same electrodes used for stimulation and different electrodes than those used for stimulation. In various embodiments, the sense amplifier circuit incorporates a gain in a range of 1 to 100,000,000 and all values in between, and incorporates a bandpass filter of 0.1 Hz to 10,000 Hz and all combinations in between. These functions are accomplished using conventional analog circuity known in the art, such as operational amplifier circuits and transistor circuits. In one embodiment, a process used by the microprocessor to process the sensed neural activity comprises counting the number of events within a predetermined time period. In other embodiments, the process is modified to add moving averages in the form of finite impulse response (FIR) or infinite impulse response (IIR) digital filters.

The HMA enables the user to self-administer therapy, including the ability to stimulate multiple times per day or per week, thereby accelerating treatment effect and efficacy. In various embodiments, the self-administration is on-demand and is actuated via a button on the companion device 105 used to trigger the electro-dermal patch device 110. Triggering the electro-dermal patch device 110 is defined as triggering a protocol that may result in stimulation over a predefined period and does not necessarily indicate electrical stimulation begins immediately. The companion device 105 and/or electro-dermal patch device 110 include pre-programmed restrictions which prevent the patient from over-stimulating. In addition, the companion device 105 and/or electro-dermal patch device 110 include triggers which prompt the patient to stimulate based upon time of day, historical trends in appetite, caloric intake, and exercise data.

The HMA also enables analyzing sensed neural activity during a stimulation therapy to assess effectiveness of the stimulation. Depending upon the effectiveness, the Health Management application may automatically recommend and/or implement adjustments or modifications to a plurality of stimulation parameters. In some embodiments, the recommended adjustments to the plurality of stimulation parameters must be accepted or authorized for implementation by at least one of the user (that is, the patient) and/or the remote patient care facility or personnel. In various embodiments, neural activity is sensed using a sense amplifier circuit as described above.

The HMA enables the user to input his current weight per day through a GUI screen and provides real-time or near real-time integration of feedback from patient parameters such as, but not limited to, exercise and fitness, diet, hunger, appetite, and well-being, recorded in a patient daily diary, from the patient and obtaining real-time or near real-time integration of feedback, such as steps taken as an indicator of calories burned, from other wearable devices, for example, a device, with physiological sensors, configured to be worn on the human body, such as around the wrist, in order to monitor, acquire, record, and/or transmit the physiological data, allowing for frequent adjustability and customization of therapy as needed. The integration of feedback from the patient and from other devices allows for modification of therapy, as needed, to suppress appetite and treat conditions such as obesity, over-weight, and/or metabolic syndrome. In accordance with various aspects of the present specification, the electro-dermal patch device enables treating people with BMI (Body Mass Index) of 25 or greater (overweight being 25-30, obese being 30 and above, with morbid obesity being above 35).

The HMA enables providing recording, storage and display of all stimulation parameters and other real-time inputs, such as diary and exercise monitoring, to provide the physician and patient real-time records and treatment profiles. The information stored includes a combination of inputs from the stimulation device and from other sources of information, for example, from a device, with physiological sensors, configured to be worn on the human body, such as around the wrist, in order to monitor, acquire, record, and/or transmit the physiological data. In accordance with an aspect, the HMA enables the patient to record her daily diary parameters (such as, hunger, appetite, well-being, exercise) using emoticons displayed to the patient on a touch-screen display, for example, of the companion device. In an example, to record an intensity of hunger the patient may be visually presented or prompted with a plurality of bear emoticons showing varying levels of empty stomach. In other words, a bear emoticon with an empty stomach may be indicative of a high level of hunger or appetite whereas a bear emoticon with a more full stomach may be indicative of a low level of hunger or appetite. On a scale of 0 to 5 or 0 to 10, the lowest level of hunger or appetite (corresponding to 0) may be indicated with a bear emoticon with a completely full stomach, the highest level of hunger or appetite (corresponding to 5 or 10) may be indicated with a bear emoticon with a completely empty stomach whereas the intermediate levels of hunger or appetite may be indicated with bear emoticons having correspondingly varying degrees of full or empty stomach. Thus, the patient is visually presented or prompted with a plurality of icons or emoticons wherein each of the plurality of icons is representative of a different degree of hunger or appetite.

The HMA enables communication with one or more third party service providers for user activated or automated ordering of accessories, such as electrode patches for example, standard meals, such as Jenny Craig, or fitness coaching services. HMA's enablement of communication with one or more third party service providers also allows for sourcing and paying for online services and/or for advertising.

The HMA enables presenting GUI screens to enable the user to provide inputs such as, but not limited to, eating information and activities information. In various embodiments, eating information comprises standard regular eating and meals profile or routine of the user such as the number of meals per day typically consumed and the types and amounts of food eaten at each of the meals per day. For example, in some embodiments, the standard regular eating and meals profile of the user comprises at least the number and timing of meals per day (such as three daily meals; breakfast at 8:00 am, lunch at noon and dinner at 6:00 pm). The user is enabled to manually adjust the timings of the meals. The standard regular eating and meals profile is typically input only once by the user as it represents the general eating habit of the user and is likely to be modified by the user over long periods of time. In some embodiments, the standard regular eating and meals profile is representative of a standard diet plan such as, but not limited to, Mediterranean, Intermittent Fasting, Jenny Craig, Weight Watchers, SlimFast and Custom Plan.

In various embodiments, eating information additionally or alternatively comprises real time actual eating and meals profile of the user such as the time of consumption of a meal in a day and the type and amount of food eaten at the meal. In other words, each time the user consumes a meal he (in real time) records the occurrence of the meal event, which is automatically time stamped by the application, as well as the type and amount of food eaten. If the meal being consumed and the type and amount of food are in line with the user's standard regular eating profile, he may simply select the meal and types and amounts of food from the pre-stored eating profile of the user.

In various embodiments, the HMA in communication with a swallow detection device, such as the device 5605 of FIG. 56, detects if the user is engaged in an eating event. In alternate embodiments, the user's eating event, activity or moment is determined automatically using an inertial sensor, such as an accelerometer, for automated dietary monitoring. In embodiments, the accelerometer is included in a wristband or wristwatch, such as the band 2105 of FIG. 21A or the wristwatch 2106 of FIG. 21B, to detect, capture and acquire a plurality of dietary data related to physical body movements of the user involved in food intake gestures. The plurality of dietary data is communicated to the Health Management application that implements an eating moment recognition method (FIG. 58) to process and analyze the plurality of dietary data and automatically identify when the user is eating.

Detection of the eating event causes the HMA to perform any one or a combination of the following actions: prompt the user to input the type and amount of meal being consumed, provide the user with healthier food options (such as via an Intelligent Personal Assistant system described later with reference to FIGS. 48A through 48C), automatically time stamp the meal consumption event, automatically determine if the meal consumption is or is not in line with the user's standard regular eating profile, advise the user to avoid having the meal if the meal consumption is not in line with the user's standard regular eating profile (that is, is an out of schedule or plan eating event), automatically trigger a stimulation session during meal consumption and/or post-prandial, that is after the user has finished consuming the meal.

In accordance with an aspect of the present specification, the real time eating and meals profile is utilized to calculate the actual amount of calories consumed by the user in a day. On the other hand, the standard regular eating and meals routine of the user is utilized to calculate a forecasted or expected amount of calories likely to be consumed by the user in a day. A difference between the daily, weekly or monthly expected and actual calories consumption value may prompt a plurality of recommendations from the Health Management application to the user.

In accordance with some aspects of the present specification, it is advantageous to also assess the quality of meal or diet consumed along with the amount of calories consumed as a result of the meal or diet in a day. In some embodiments, the quality of a meal or diet is determined based on a mix of macronutrients such as carbohydrates (also referred to as "carbs"), proteins and fats present in the meal or diet. Thus, the user's standard diet plan may propose an acceptable ratio for each macronutrient. For example, the Zone Diet (by Barry Sears, PhD) proposes a meal of 40% carbs, 30% protein and 30% fats, the Atkins Diet proposes a meal of 5% carbs, 25% protein and 75% fats, while the Ketogenic Diet proposes a meal of 10% carbs, 45% protein and 45% fats. Thus, for a user who is endeavoring to follow a standard diet plan or a custom diet plan designed around a specific ratio of macronutrients, the expected ratio of macronutrients and the expected calories likely to be consumed in a day are known and pre-stored by the Health Management application.

In various embodiments, the actual or real time eating and meals profile of the user is indicative of the time of consumption of a meal in a day as well as the type and amount of food eaten at the meal. The type and amount of food eaten enables calculating the calories consumed as well as a ratio of macronutrients, that is, carbs, protein and fats consumed. It should be appreciated that while in some embodiments, the Health Management application calculates the ratio of all three macronutrients, (carbs, proteins and fats) consumed in a meal, in various alternate embodiments, an amount and effect of any one or two macronutrients may be monitored and calculated. For example, in some embodiments, the Health Management application is focused on monitoring and determining the effect of carbohydrates consumed compared to an acceptable amount of carbohydrates allowed based on the standard diet plan being followed by the user.

Thus, in accordance with an aspect, carbohydrate containing foods are rated on a scale called the glycemic index (GI) and the glycemic index is used to calculate a glycemic load (GL) associated with the food consumed. The GI ranks carbohydrate containing foods based on their effect on blood sugar levels over a period of time. Carbohydrate containing foods are compared with glucose or white bread as a reference food, which is given a GI score of 100. The GI compares foods that have the same amount of carbohydrate, gram for gram. Carbohydrates that break down quickly during digestion have a higher glycemic index (say, GI more than 70). These high GI carbohydrates, such as a baked potato, release their glucose into the blood quickly. Carbohydrates that break down slowly, such as oats, release glucose gradually into the bloodstream. They have low glycemic indexes (say, GI of approximately less than 55). The blood glucose response is slower and flatter. Low GI foods prolong digestion due to their slow break down and may help with satiety.

The glycemic index compares the potential of foods containing the same amount of carbohydrate to raise blood glucose. However, the amount of carbohydrate consumed also affects blood glucose levels and insulin responses. The glycemic load (GL) takes into account both the GI of the food and the amount of carbohydrate in a portion or serving consumed. GL is based on the idea that a high GI food consumed in small quantities would give the same effect on blood glucose levels as larger quantities of a low GI food. GL is calculated by multiplying the GI by the amount of carbohydrates (in grams) in a serving of food.

Thus, in accordance with another aspect of the present specification, the real time eating and meals profile is utilized to calculate the ratio of macronutrients, that is, carbs, proteins and fats, consumed in a day or at least the glycemic load (GL) associated with the meals profile. On the other hand, the standard regular eating and meals routine of the user is utilized to calculate a forecasted, allowed or expected ratio of the macronutrients consumed by the user in a day or at least the allowable glycemic load. A difference between the daily, weekly or monthly expected and actual macronutrient ratio or a difference between the daily, weekly or monthly expected and actual glycemic load may prompt a plurality of recommendations from the Health Management application to the user.

Activities information relates to how much and when a person moves around and/or exercises during the day and utilizes both data input by the user and data sensed by the one or more sensors 135. The data input by the user may include details regarding the user's daily activities, for example the fact that the user worked at a desk from 9 a.m. to 5 p.m. and then took an aerobics class from 6:30 p.m. to 7:30 p.m. Relevant data sensed by the sensors 135 may include heart rate, movement as sensed by an accelerometer, heat flow, respiration rate, calories burned, and galvanic skin response (GSR). Accordingly, calories burned or spent (calories expenditure) maybe calculated in a variety of manners, including: the multiplication of the type of exercise input by the user by the duration of exercise input by the user; sensed motion multiplied by time of motion multiplied by a filter constant; and sensed heat flux multiplied by time multiplied by a filter constant or on the basis of metabolic equivalents (METs). In some embodiments, the user's RMR (Resting Metabolic Rate) or BMR (Basal Metabolic Rate) is also calculated to estimate the amount of calories consumed by the user which is then used to calculate a daily caloric balance. As known to persons of ordinary skill in the art, RMR or BMR is the rate at which you burn energy or calories when resting and is a function of at least the user's age, gender, height and weight. This helps fulfill the basic requirements of the body to function optimally.

The amount of calories actually consumed by the individual is compared to the amount of calories expended or burned by the individual for daily, weekly or monthly periods and is referred to hereinafter as energy balance of the user. A positive or surplus energy balance is representative of more actual calories consumed in comparison to the calories expended and is considered to be indicative of a potential weight gain scenario for the user over a period of time. A negative energy balance is representative of less actual calories consumed in comparison to the calories expended and is considered to be indicative of a potential weight loss scenario for the user over a period of time.

Continuing with various non-limiting examples of the plurality of functions of the HMA, in various embodiments the HMA also enables presenting GUI screens to enable the user to record his hunger or appetite profile. Hunger or appetite profile includes data such as the time of day when the user feels hungry and the intensity of hunger felt. In some embodiments, the intensity of hunger is recorded by the user by selecting from a scale of, for example, 1 to 5, where 1 is indicative of light hunger and 5 is indicative of very high hunger intensity. In various embodiments, the hunger profile includes only those times when the user feels hungry but should ideally not consume a meal. This may include, for example, times that do not match the user's standard regular eating and meals profile or routine.

The HMA further enables providing daily feedback from the electro-dermal patch device to the patient on dietary compliance, calories burned and displaying diet plans.

The HMA also enables receiving, processing and analyzing glucose data generated by a glucose sensor, included as one of the sensors 135 or configured as a third party device in wireless communication with the HMA, in some embodiments. In various embodiments, the glucose data is analyzed to detect conditions such as a hyperglycemic rush, resulting from, for example, a large carbohydrate meal, and titrate stimulation to treat or manage a condition where there is a surplus of insulin secretion that may trigger hunger in non-diabetic users.

The HMA enables generating and displaying a plurality of charts or graphs representative of the user's standard regular eating and meals profile, actual eating and meals profile, energy balance information, weight trend including a rate of weight loss or gain, glucose data trend and hunger profile over a period of time such as daily, weekly or monthly.

The HMA enables managing and generating prompts (audio—including actual phone calls, visual and/or tactile) with respect to a plurality of compliance aspects such as, but not limited to: stimulation therapy compliance—prompts the user if the user forgets to apply or wear the electro-dermal patch device and/or disables a recommended duration or frequency of stimulation therapy; prompts the user with respect to a stimulation protocol that a scheduled stimulation is going to begin in the next T minutes, 10 or 15 minutes for example, and presenting the user with an option to disable the scheduled stimulation which if not disabled allows the scheduled stimulation to begin after T minutes; dietary compliance or guidance—the user either selects a predefined standard dietary plan (from a drop down list of multiple predefined dietary plans, such as but not limited to Mediterranean Zone diet, Atkins diet, or Jenny Craig) or inputs a customized plan as part of the standard regular eating and meals routine. The user also records details of the actual meals taken and time of meals. Audio, visual and/or tactile alert(s) may be generated, for example, if the user is not in compliance with the selected dietary plan. The compliance prompts are intended to encourage patient compliance and, in some embodiments, include composite scores and displays for overall patient progress.

The HMA enables recommending and/or implementing modification to stimulation patterns or protocols when receiving an input from the user that the user is encountering a feeling of nausea, dyspepsia, heartburn, or sensation at the stimulation site during and/or after stimulation.

The HMA further enables assessing stimulation habituation, nausea and/or dyspepsia scenarios in the user and accordingly modifying the stimulation patterns or protocols. In various embodiments, these events are input into the electro-dermal patch device or companion device by the patient. For example, in one embodiment, the patient can input, via a GUI on one or both devices, nausea events, dyspepsia events or hunger events. The microprocessor then algorithmically processes these events and accordingly modifies stimulation.

The HMA enables the remote patient care facility and/or patient care personnel to access (via cellular and/or private or public wired or wireless networks such as the Internet) a plurality of user's health related information such as the user's hunger profile, standard eating and meals profile, actual eating and meals profile, energy balance, weight trends, glucose data and stimulation induced nausea, dyspepsia, habituation events. In some embodiments, the Health Management application periodically transmits the user's health related information apart from enabling the remote patient care facility and/or patient care personnel to access such information in real time or on demand, if required. In various embodiments, the user's authorization is needed to allow such access to the user's health related information.

The HMA also enables detecting removal of the electro-dermal patch device—the impedance or bio-impedance electrode enables the Health Management application to regularly or continuously monitor electrode and skin contact impedance. This allows the Health Management application to detect whether the electro-dermal patch device has been removed or worn by the user. In some embodiments, where the electro-dermal patch device is configured for use as a 24/7 wearable device, detection of removal of the electro-dermal patch device corresponds to missing of the user's health related information. However, in other embodiments, where the electro-dermal patch device is configured for use on as-needed or on-demand basis, any missing user health related information is treated as non-occurrence of any stimulation event.

The HMA also enables providing unique electrical stimulation characteristics and 'footprints', based on electrode design and stimulation parameters, allowing the patient to use a variety of methodologies for stimulation.

In still a further non-limiting example, the HMA enables providing a weight loss graph along with the patient's pictures corresponding to various milestones on the weight loss graph.

In still a further non-limiting example, the HMA enables; enables bariatric surgeons, doctors, dieticians or medical personnel to tell new patients about their medical practice.

In still a further non-limiting example, the HMA enables patients to keep time intervals between meals and fluids. For example, the HMA may notify users when enough time has passed after drinking to eat and vice versa.

In still further non-limiting examples, the HMA enables patients to view their medical personnel and request an appointment with the office; enables setting of daily reminders for prescribed vitamins and supplements; enables patients to pose queries to their dietician; enables communicating schedules of weight loss seminars and support groups, to the patients; enables medical personnel to communicate healthy recipes with the patients to support their continued weight loss success; enables bariatric surgery patients to stay on track with reminders and a pre-populated checklist—Psych Eval, Insurance Pre-approval, Physician Supervised Diet; enables medical personnel as well as patients to journalize daily thoughts and progress notes; enables information exchange with third party applications; enables patients to track their water intake along with food consumed; enables automatic tracking of calories, protein, fat and carbohydrates consumed by patients; enables scanning of barcodes of package food to allow patients to see the nutritional information, and have it logged automatically to the feed consumed daily diary; enables physicians or medical personnel to enter specific goals for their patients; enables physicians to share their patient status data, with approval from their patients, with the fellow practice/department physicians to solicit better recommendations for the patients; enables instilling weight management habits in the patients since monitoring of food/calories intake leads to better dietary compliance; enables physicians, dieticians and other medical personnel to send out push notifications to their patients to keep the patients engaged and motivated towards their health goals.

It should be appreciated that in various embodiments, the user's plurality of health related information is utilized by the Health Management application to suggest and/or implement a plurality of recommendations comprising stimulation patterns or protocols, medication (such as an amount of insulin intake, for example), dietary and/or activities plans. For example, if the user's actual calories consumption is found to be higher than the expected calories consumption, consistently over a period of time, the Health Management application may recommend any one or a combination of: a specific standard diet plan to the user; a change from a first standard diet plan to a second standard diet plan or prescribe customization of an existing standard diet plan that the user may be following; recommend or change an existing stimulation protocol to suppress the user's appetite and/or suggest to the user to increase his activity levels such as walking, exercising.

In some embodiments, the plurality of recommendations is auto generated by the Health Management application and presented to the user for his authorization for implementation. In some embodiments, the plurality of recommendations auto generated by the Health Management application are presented to the remote patient care facility and/or personnel for authorization or approval and thereafter either implemented or presented again to the user for a final authorization for implementation. In some embodiments, the Health Management application receives a plurality of recommendations prescribed by the remote patient care facility and/or personnel based on the user's plurality of health related information.

In various embodiments, the user is presented, on one or more GUIs, a plurality of recommendations, which are auto generated by the Health Management application as well as those received as prescriptions or recommendations from the remote patient care facility or personnel, the reasons for each of the plurality of recommendations, authorizations/approvals or disapprovals against each of the plurality of recommendations as received from the remote patient care facility or personnel, and annotations or notes from the remote patient care facility or personnel describing reasons for approving or disapproving each of the plurality of recommendations that were generated by the Health Management application. The user then reviews and authorizes/approves or disapproves implementation of each of the plurality of recommendations. In some embodiments, however, authorizations to implement the plurality of recommendations may not be required from the user and/or the remote patient care facility or personnel. For example, in one embodiment wherein the electro-dermal patch device is worn 24 hours per day, the number of stimulation sessions per a specified time period is automatically titrated up or down based on the recommendations. In another embodiment, the duration of stimulation is automatically titrated up or down based on the recommendations. In other embodiments, other stimulation parameters are changed automatically based on the recommendations.

In various embodiments, the companion device includes a 'diary' for the patient to input, track, record, and display patient parameters. FIG. 7 is a screen shot of a companion device depicting a diary widget 705, in accordance with one embodiment of the present specification. The diary widget 705 includes icons enabling the patient to input and view entries in the diary. The diary widget 705 includes a quick entry buttons icon 706 which, when pressed, causes the companion device to display buttons for making diary entries. The diary widget 705 also includes a list view of diary entries icon 707 which, when pressed, causes the companion device to display the diary in a list format. The diary widget 705 also includes a calendar view of diary entries icon 708 which, when pressed, causes the companion device to display the diary in a calendar format.

FIG. 8 is a screen shot of a companion device depicting a list view of diary entries 805, in accordance with one embodiment of the present specification. The list view of diary entries 805 is accessed by pressing the list view of diary entries icon 707 as shown on FIG. 7. In various embodiments, the list view of diary entries 805 displays entries input by the patient for instances such as stimulation sessions 806 and patient parameters, for example, hunger 807 and appetite 808. The stimulation session entry 806 displays the time 816 of the entry and details 826 of the stimulation session. Each patient parameter entry 807, 808 displays the time 817, 818 of the entry, the type of parameter 837, 838, and a score with description 827, 828 associated with the entry. The list view of diary entries 805 also displays the date 803 and the name of the diary 802 being viewed.

Figure 9:
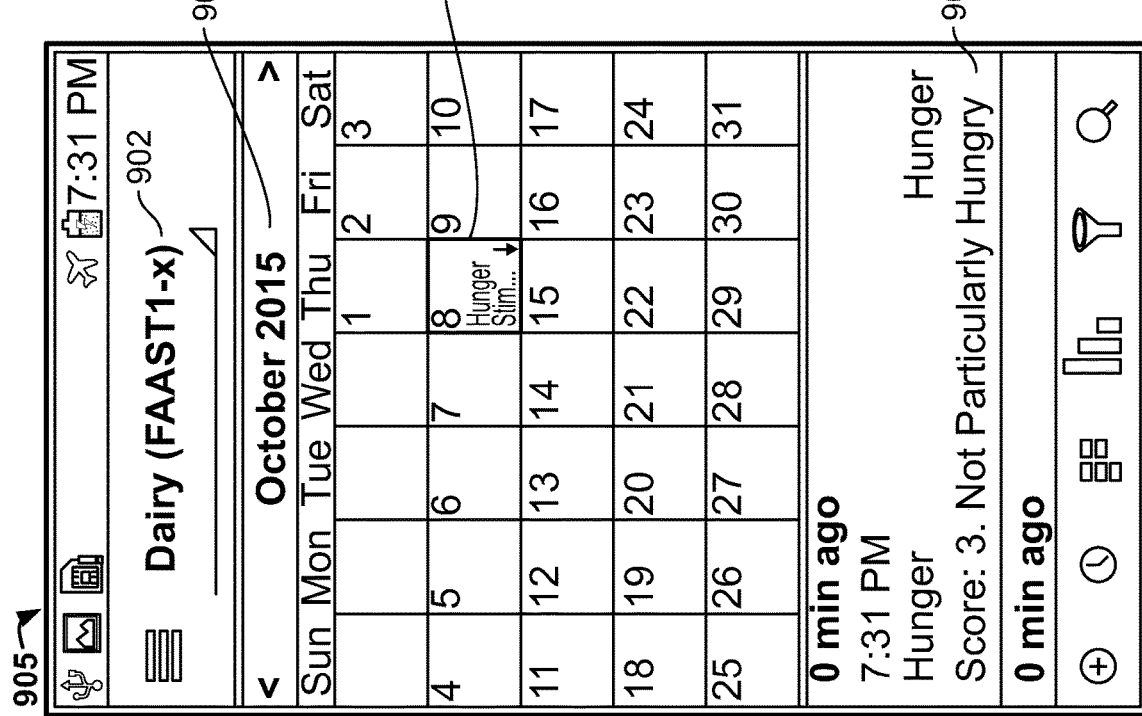
FIG. 9 is a screen shot of a companion device depicting a calendar view of diary entries, in accordance with one embodiment of the present specification.

FIG. 9 is a screen shot of a companion device depicting a calendar view of diary entries 905, in accordance with one embodiment of the present specification. The calendar view of diary entries 905 is accessed by pressing the calendar view of diary entries icon 708 as shown on FIG. 7. The calendar view of diary entries 905 displays the days 906 of the month being viewed. Pressing on an individual day displays the diary entries for that day as a list 907. The patient can scroll through the list 907 to view entries. The calendar view of diary entries 905 also displays the month and year 903 and the name of the diary 902 being viewed.

Figure 10:
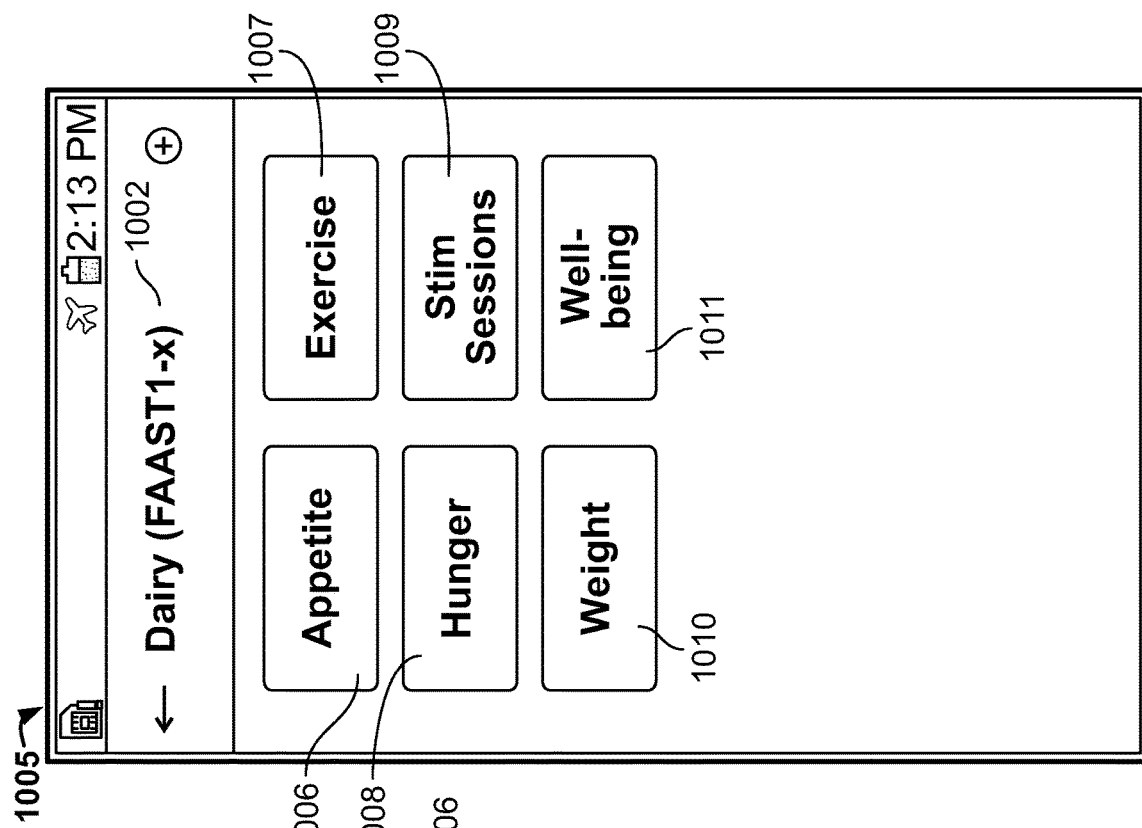
FIG. 10 is a screen shot of a companion device depicting a quick entry buttons view, in accordance with one embodiment of the present specification.

FIG. 10 is a screen shot of a companion device depicting a quick entry buttons view 1005, in accordance with one embodiment of the present specification. The quick entry buttons view 1005 is accessed by pressing the quick entry buttons icon 706 as shown on FIG. 7. In one embodiment, the quick entry buttons view 1005 includes six quick entry buttons: appetite 1006, exercise 1007, hunger 1008, stim (that is, stimulation) sessions 1009, weight 1010, and well-being 1011. The quick entry buttons depicted in FIG. 10 are exemplary only and not intended to be limiting. In other embodiments, fewer or additional quick entry buttons are included on the quick entry buttons view. Pressing on any one of the quick entry buttons 1006, 1007, 1008, 1009, 1010, 1011 causes the companion device to display an entry screen for the chosen button. The quick entry button view 1005 also displays the name of the diary 1002 being viewed.

FIG. 11 is a screen shot of a companion device depicting an appetite entry screen 1105, in accordance with one embodiment of the present specification. The appetite entry screen 1105 allows the user to enter the type 1106 and item 1107 of patient parameter, in this case appetite, and a score 1108 associated with the parameter. The score 1108 has a numerical value 1109 and a description 1110 associated therewith to help the patient determine which score best fits the current parameter. In some embodiments, for appetite, the description relates to how much the patient ate compared to the amount recommended by the patient's diet. In some embodiments, the score ranges from 1 to 5. The appetite entry screen 1105 also displays the time and date 1103 the entry is being entered and the name of the diary 1102. The patient can save the entry by pressing the disk icon 1101 or cancel the entry by pressing the X icon 1104.

FIG. 12 is a screen shot of a companion device depicting an exercise entry screen 1205, in accordance with one embodiment of the present specification. The exercise entry screen 1205 allows the user to enter the type 1206 and item 1207 of patient parameter, in this case exercise, and a score 1208 associated with the parameter. The score 1208 has a numerical value 1209 and a description 1210 associated therewith to help the patient determine which score best fits the current parameter. In some embodiments, for exercise, the description relates to how many steps the patient took per day. In some embodiments, the score ranges from 1 to 5. The exercise entry screen 1205 also displays the time and date 1203 the entry is being entered and the name of the diary 1202. The patient can save the entry by pressing the disk icon 1201 or cancel the entry by pressing the X icon 1204.

FIG. 13 is a screen shot of a companion device depicting a hunger entry screen 1305, in accordance with one embodiment of the present specification. The hunger entry screen 1305 allows the user to enter the type 1306 and item 1307 of patient parameter, in this case hunger, and a score 1308 associated with the parameter. The score 1308 has a numerical value 1309 and a description 1310 associated therewith to help the patient determine which score best fits the current parameter. In some embodiments, for hunger, the description relates to the level of hunger the patient is experiencing. In some embodiments, the score ranges from 1 to 5. The hunger entry screen 1305 also displays the time and date 1303 the entry is being entered and the name of the diary 1302. The patient can save the entry by pressing the disk icon 1301 or cancel the entry by pressing the X icon 1304.

FIG. 14 is a screen shot of a companion device depicting a stimulation session entry screen 1405, in accordance with one embodiment of the present specification. The stimulation session entry screen 1405 allows the user to enter the type 1406 and item 1407 of session, in this case a stimulation session, and a level 1408 associated with the session. The level 1408 has a numerical value 1409 and a description 1410 associated therewith to help the patient determine which level best represents what was applied during the current session. In some embodiments, for stimulation session, the description relates to how often stimulation was delivered per day and for how long the stimulation was applied during each session. In some embodiments, the level ranges from 1 to 4. The stimulation session entry screen 1405 also displays the time and date 1403 the entry is being entered and the name of the diary 1402. The patient can save the entry by pressing the disk icon 1401 or cancel the entry by pressing the X icon 1404.

Figures 15, 16:
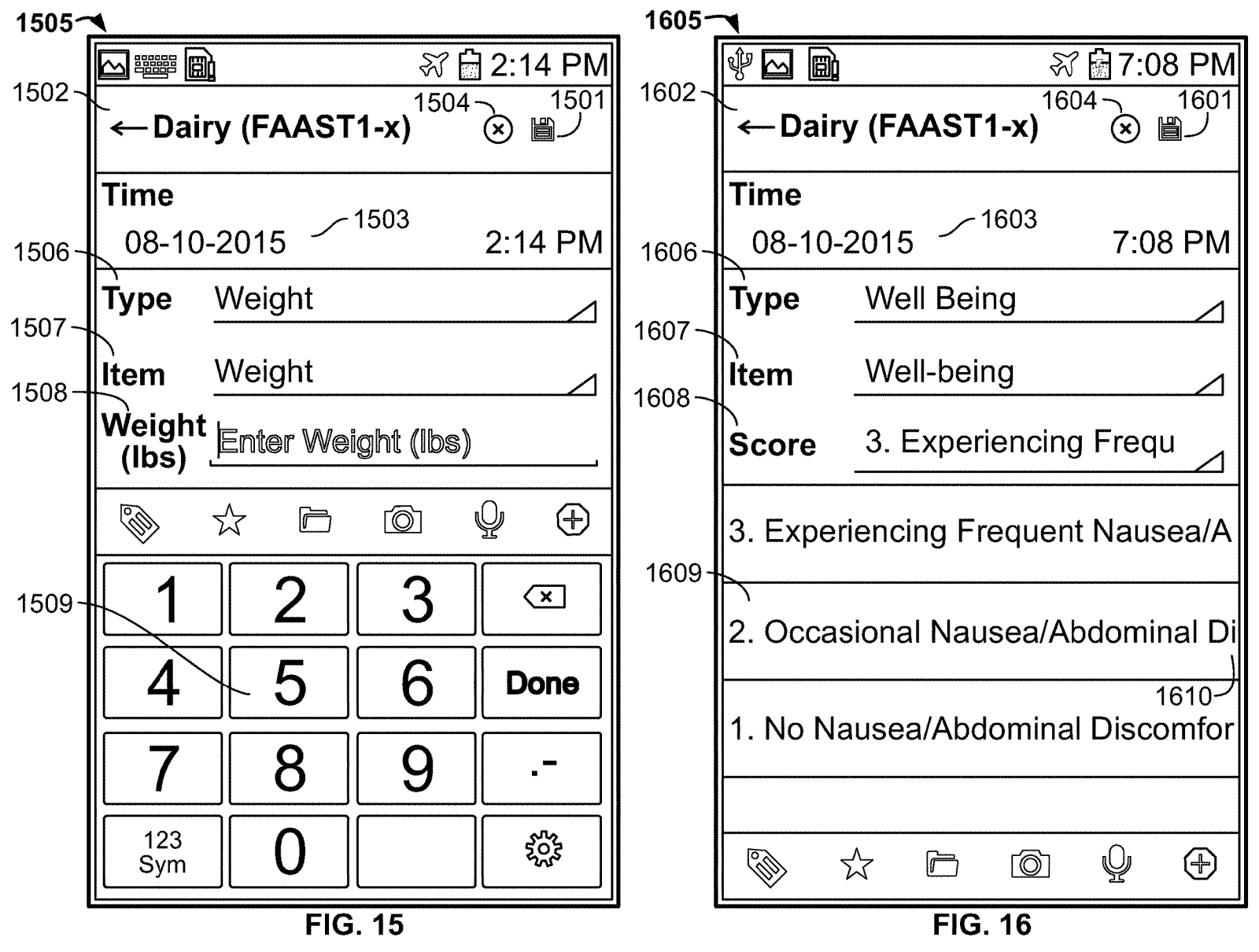

FIG. 15 is a screen shot of a companion device depicting a weight entry screen 1505, in accordance with one embodiment of the present specification. The weight entry screen 1505 allows the user to enter the type 1506 and item 1507 of patient parameter, in this case weight, and a weight in pounds 1508 associated with the parameter. The weight entry screen 1505 includes a numeric keypad 1509 for the patient to use to enter the weight. The weight entry screen 1505 also displays the time and date 1503 the entry is being entered and the name of the diary 1502. The patient can save the entry by pressing the disk icon 1501 or cancel the entry by pressing the X icon 1504.

FIG. 16 is a screen shot of a companion device depicting a well-being entry screen 1605, in accordance with one embodiment of the present specification. The well-being entry screen 1605 allows the user to enter the type 1606 and item 1607 of patient parameter, in this well-being, and a score 1608 associated with the parameter. The score 1608 has a numerical value 1609 and a description 1610 associated therewith to help the patient determine which score best fits the current parameter. In some embodiments, for well-being, the description relates to a level of nausea, dyspepsia and/or abdominal discomfort the patient is experiencing. In some embodiments, the score ranges from 1 to 3. The well-being entry screen 1605 also displays the time and date 1603 the entry is being entered and the name of the diary 1602. The patient can save the entry by pressing the disk icon 1601 or cancel the entry by pressing the 'X' icon 1604.

It should be appreciated that, in some embodiments, the HMA incorporates GUIs that present scales, surveys, or questionnaires designed to quantitatively assess one or more of a person's appetite, hunger, level of satiety, level of satiation, level of fullness, level of well-being, level of nausea, feelings of pain, level of dyspepsia, perception of food, and changes thereto.

For example, SNAQ (Simplified Nutritional Appetite Questionnaire) is an appetite assessment tool that predicts weight loss. SNAQ includes questions that rank, on a scale of 1 to 5, the strength of appetite, feelings of fullness after eating, taste of food and number of meals eaten each day. A SNAQ score of less than or equal to 14 predicts high likelihood of at least 5% weight loss within six months. The Ghrelin Hunger Scale (G-scale) is a two dimensional scale wherein a first scale of 1 to 7 on the y-axis is used to assess the feeling of hunger/fullness and a second scale of 1 to 7 on the x-axis is used to assess the time elapsed since a last meal (breakfast, lunch, snack, or dinner).

In general, each such scale is a form of a visual analog scale (VAS). A VAS is question-based assessment mechanism, where a visual measure is associated with each question and where answering the question requires selecting a quantifiable position within that visual measure, indicative of a particular level or degree. The scale is typically composed of lines (of varying length) with words anchored at each end, describing the extremes (that is, 'I am not hungry at all' on the left to 'I have never been more hungry' on the right). Patients are asked to make a mark across the line corresponding to their feelings. Quantification of the measurement is done by measuring the distance from the left end of the line to the mark. In some embodiments, VAS may be used to assess sensations of pain (due to stimulation, for example), hunger, appetite, satiation, fullness, satiety, overall quality of life, degree of nausea, degree of well-being, degree of dyspepsia, perception of food, food aversions, and perceptions of dietary compliance. In accordance with some aspects of the present specification, the users are provided with GUIs to activate VAS based light or progress bars to enable the users to record parameters such as the level of hunger, appetite and well-being.

FIG. 35A illustrates a VAS questionnaire 3505 for assessing hunger sensations or appetite. The questionnaire 3505 presents a patient with a leading question, such as, "how hungry do you feel?" while the two extremities 3506, 3507 of the scale line 3508 are anchored with words that describe the feeling of least and maximum hunger. In one embodiment the two extremities 3506, 3507 are described as "I am not hungry at all" and "I have never been more hungry", respectively.

FIG. 35B illustrates a VAS questionnaire 3510 for assessing a feeling of fullness. The questionnaire 3510 presents the patient with a leading question, such as, "how full do you feel?" while the two extremities 3511, 3512 of the scale line 3513 are anchored with words that describe the feeling of least and maximum fullness. In one embodiment the two extremities 3511, 3512 are described as "Not at all full" and "Totally full", respectively.

FIG. 35C illustrates a VAS questionnaire 3515 for assessing a feeling of satiation. The questionnaire 3515 presents the patient with a leading question, such as, "how satisfied do you feel?" while the two extremities 3516, 3517 of the scale line 3518 are anchored with words that describe the feeling of least and maximum satiation. In one embodiment the two extremities 3516, 3517 are described as "I am completely empty" and "I cannot eat another bite", respectively.

FIG. 35D illustrates a VAS questionnaire 3520 for assessing a feeling of satiety. The questionnaire 3520 presents the patient with a leading question, such as, "how much do you think you can eat?" while the two extremities 3521, 3522 of the scale line 3523 are anchored with words that describe the feeling of least and maximum satiety. In one embodiment, the two extremities 3521, 3522 are described as "A lot" and "Nothing at all", respectively.

Persons of ordinary skill in the art should appreciate that the leading question and anchoring words at the two extremities of the scale, for each questionnaire of FIG. 35A through 35D, may be linguistically modified in alternate embodiments without departing from the assessment objective or the feeling to be assessed. For example, in an alternate embodiment the questionnaire 3520 the leading question is "How strong is your desire to eat now?" while the two extremities 3521, 3522 are described as "Extremely" and "Not at all". Additionally, other intermediate language may be used between the two extremes.

In various alternate embodiments, GUIs showing VAS questionnaires can be designed to assess aspects such as, but not limited to, health-related overall quality of life, degree of nausea, degree of pain felt, degree of well-being, and degree of dyspepsia. For example, in one embodiment, to assess nausea levels a VAS questionnaire may present a leading question, such as, "Do you feel nauseous?" while the two extremities of the scale are described as "A lot" and "Not at all". In another embodiment, to assess health-related overall quality of life or degree of well-being a VAS questionnaire may present a leading question, such as, "How satisfied are you with your health as whole?" with the two extremities of the scale being described as "completely dissatisfied" and "completely satisfied". In yet another embodiment, to assess degree of dyspepsia a VAS questionnaire may present a leading question, such as, "Has your ability to eat or drink (including when, what, and how much) been disturbed by your stomach problems in the last 2 weeks?" with the two extremities of the scale being described as "Extremely" and "Not at all". In still another embodiment, to assess bowel movements, a VAS questionnaire may present a plurality of leading questions to assess timing of bowel movement, whether the bowel movements are emergencies or not, frequency and/or amount of defecation.

In some embodiments, as described above, the VAS is configured as a questionnaire with each question representative of a quantifiable position (or number such as, for example, 1,2,3,4 or 5 on a VAS scale ranging from 1 to 5) within the visual measure that is indicative of a particular level, intensity or degree. In some alternate embodiments, the VAS is configured as a spectrum of colors wherein each color of the spectrum is quantifiable (optionally, in the form of a number) to indicate a particular level, intensity or degree. FIG. 76 illustrates a hunger or appetite VAS scale 7600 configured as a color spectrum wherein each color, when chosen by the user, is quantified into a number and representative of an intensity of hunger or appetite. As an example, the scale 7600 ranges from light green, dark green, yellow, orange to red positions corresponding to an intensity ranging from 1 to 5 such that light green (quantifiable as 1) represents a lowest intensity of hunger/appetite whereas red (quantifiable as 5) represents a highest intensity of hunger/appetite. The scale may vary in different embodiments, for example instead of the color spectrum representing the scale of 1 to 5 a color spectrum may represent a scale of 1 to 10. Thus, a VAS can be displayed as a questionnaire, number and/or color spectrum, in various embodiments.

In various embodiments, the HMA presents GUIs to enable the user to record daily diary recordings of: timing, duration and amplitude of planned or scheduled stimulation sessions; timing, duration and amplitude of on-demand or rescue boluses (as described later in this specification); amount and type of calories consumed per day; hunger based on, for example, an aggregation of rescue boluses and/or VAS hunger scale entries whenever the user is hungry; user's weight; calories burned based on, for example, steps taken; daily quality of life and/or nausea/dyspepsia entry on VAS.

As discussed earlier, the Health Management application is capable of communicating (via pairing or syncing) with a third party device (including a third party application software on an external device), with physiological sensors, configured to be worn on the human body, such as around the wrist (as a smart watch, for example), or the feet (as smart shoes, for example, that utilize a plurality of sensors, to track and record physiological data associated with running such as, but not limited to, cadence, steps taken, calories burned, duration of run, pace, heart rate), in order to monitor, acquire, record, and/or transmit the physiological data, to receive and integrate exercise or calories expended and weight loss information, along with one or more electrodermal patch devices of the present specification.

In some embodiments, the third party device enables diet monitoring (in terms of amount and type or quality of calories consumed) and communicates dietary information to the HMA for display to the user on his companion device, for example. In various embodiments, the user's dietary information (received from a third party device and/or application) alone or in tandem with the user's daily diary information is/are used to titrate stimulation therapy. In embodiments, the third party device is a WIFI or Bluetooth enabled bathroom weighing scale to capture daily weight and automatically input this data into the user's daily diary. In embodiments, the third party device is an exercise monitoring wearable device, such as a smart watch, that communicates exercise or fitness information (such as, but not limited to, steps taken, heart rate) to the HMA for display on the user's companion device. The exercise or fitness information is utilized by the HMA to also titrate stimulation therapy.

It should be appreciated that the third party device, whether it is a third party application software on an external device or a second external device entirely (such as, but not limited to, a watch, a pair of smart shoes, a diabetes wearable pump, or another medical device), is enabled to obtain information from the EDP device of the present specification, either directly from the EDP device, directly from the Health Management application, or directly from a server in data communication with the EDP device or the Heath Management application of the present specification. In some embodiments, the user's daily diary information such as, but not limited to, appetite score can be displayed on the user's third party device such as the smart watch. Consequently, the third party application or the second external device can display any information gathered by the EDP device and/or Health Management application, including patient diary inputs, the patient's level of hunger, the patient's level of wellbeing, the patient's level of appetite, the stimulation settings, or an aggregate/composite weight management performance score which aggregates any of the data tracked by the third party device with any of the data tracked by the EDP device and/or Health Management application to yield a single composite score.

In some embodiments, the HMA prompts the user to click her selfie or photo—indicative of the user's input of her health status comprising current body outline, contour, shape and size. In some embodiments, the selfie is body part specific such as that of the face, torso and/or butt). In embodiments, the user's selfie is processed and stored, by the HMA, as an avatar or graphical representation of the user. In embodiments, the HMA prompts the user to click and input her selfie at predetermined intervals of time, such as every day, alternate days, twice or thrice a week, for example, during the course of the stimulation treatment. If the user's health goal is to lose weight, the evolving avatars, selfies or photo records (during the course of the stimulation therapy), periodically acquired and stored by the HMA, are analyzed to determine if the user's body outline is changing compared to an ideal or target body outline, shape (at the user's target weight goal, for example) and/or compared to the body outline at the beginning or during earlier periods of the therapy. The user's evolved body outline, shape and size is displayed with a comparison to the user's body outline prior to commencement of the stimulation therapy and/or against an ideal or target body outline and shape. Such a comparative display serves to provide to the user an evolving long term health performance record. In various embodiments, the user can have her evolved avatar printed on her clothes and displayed as a display picture on her communication networks or channels such as, but not limited to, social media networks, affinity groups, Facebook, and WhatsApp.

In various embodiments, the Health Management application of the present specification interrogates the user (using GUIs of VAS questionnaires, for example or through voice-based inputs using an Intelligent Personal Assistant as described later in the specification) at the end of each day, at a time convenient and chosen by the user, about his daily well-being. In some embodiments, VAS questionnaires are directed towards at least, but not limited to, the user's satisfaction with his hunger/appetite management for the day, dietary compliance for the day and overall well-being level for the day. The HMA also automatically downloads health or fitness related information from third party devices each day, and preferably at the end of the day. In some embodiments, the HMA prompts the user to record his weight at least once in a week (or more frequently, such as daily, in alternate embodiments). In embodiments, the HMA generates automated feedback or advice based on a plurality of user's aggregated health related information such as, but not limited to, the daily inputs recorded for the VAS questionnaires, daily fitness related information (such as, steps taken for example) from third party devices, general compliance such as wearing the EDP device to stimulate as per scheduled protocol, daily rescue boluses and the daily or weekly weight measurements. In some embodiments, the automated feedback is delivered to the user through an Intelligent Personal Assistant (IPA) as described later in this specification.

In some embodiments, the Health Management application of the present specification may be directly installed or implemented on a third party device, such as a wristwatch, via a download from a remote server. In such embodiments, the Health Management application is configured for compatibility and use on such third party devices. Accordingly, apart from displaying any information gathered by the EDP device and/or Health Management application, the third party device can also be used by the user to manage titration or setting of stimulation parameters, including patient diary inputs. Such embodiment would obviate a need for a separate companion device.

The third party device, in various embodiments, may track one or any combination of the following patient related data: heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and/or UV radiation exposure and absorption or any other parameter listed in Tables 1 and Table 2 above, data representative of the air quality, sound level/quality, light quality or ambient temperature near the patient, or the global positioning of the patient, patient's weight, food consumed, type and amount of activity or exercise (such as steps take, swimming, running).

In accordance with an aspect of the present specification, the HMA is enabled for communicating or interfacing with and operating or driving an Intelligent Personal Assistant (hereinafter also referred to as IPA) system. In embodiments, the IPA system is capable of accepting and processing a user's voice based inputs and performing a plurality of tasks or services, based on the user's voice based inputs or commands, including providing to the user voice based outputs such as, but not limited to, alerts, reminders, information or prompts. In accordance with various aspects of the present specification, the IPA system is designed to simulate a conversation with one or more human users via auditory methods. The IPA system may also be referred to as a chat robot, chatter robot, chatterbot, chatbot or chat bot, Artificial Conversational Entities (ACEs), Artificial Intelligence Agent (AIA), talk bot, and/or chatterbox. In some embodiments, the IPA system comprises an IPA device running an IPA software application. In some embodiments, the IPA system is implemented as a client-server architecture wherein the IPA device (client) is in communication with an IPA server. In such embodiments, the IPA software application is implemented as a client component residing on the IPA device and a server component residing on the IPA server. Alternately, the IPA software application may be implemented only on the IPA server side.

In various embodiments, the IPA device is a hand-held or portable computing device capable of accepting voice based inputs (using one or more microphones), generating voice based outputs (using one or more speakers) and capable of accessing a cellular, Internet, TCP/IP, Ethernet, Bluetooth, wired, or wireless network. Examples of such portable computing devices include, but are not limited to, smartphones, tablets, speakers, or PDAs.

Figure 48A:
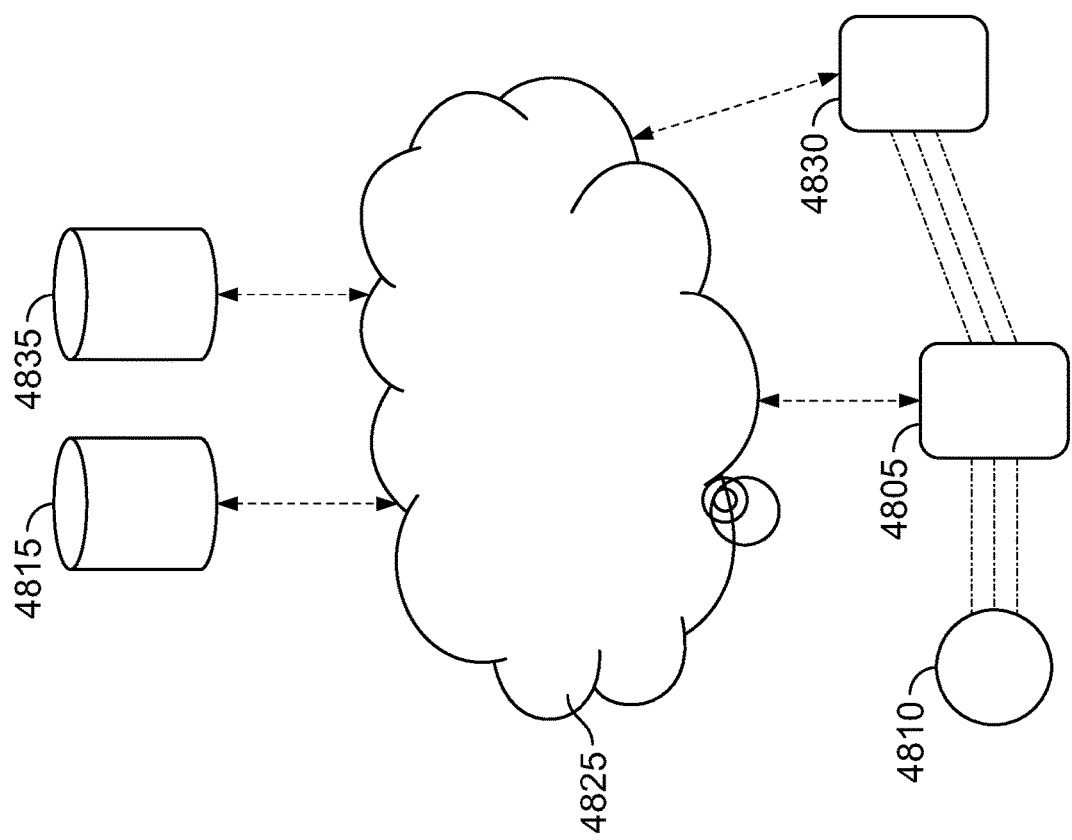

FIG. 48A is a block diagram illustration of the HMA, of the present specification, integrated and in communication with an IPA system, in accordance with an exemplary embodiment. In this embodiment, the HMA is implemented, as a client side software component, on a companion device 4805 (similar to the companion device 105 of FIG. 1A) which is in data communication with at least one EDP device 4810 of the present specification. The companion device 4805 is also in communication, via network 4825, with a health management server 4815, that implements a server side software component of the HMA, and optionally a remote patient care facility and/or patient care personnel. The network 4825 is a cellular, Internet, TCP/IP, Ethernet, Bluetooth, wired, or wireless network. In accordance with an embodiment, the companion device 4805, and therefore the HMA client component, is further in data communication with an IPA device 4830 that implements a client side software component of the IPA software application. The IPA device 4830 is also in communication, via the network 4825, with an IPA server 4835 that implements a server side software component of the IPA software application. It should be appreciated that the companion device 4805 may be in data communication with the at least one EDP device 4810 and the IPA device 4830 through a direct wired or wireless link such as WiFi or Bluetooth, via pairing or syncing for example, or through the network 4825. Similarly, the health management server 4815 and the IPA server 4835 are also capable of being in data communication with each other through network 4825. Thus, in this embodiment, the IPA system comprises a standalone IPA device 4830 separate from the companion device 4805. In other words, the IPA and HMA software applications are installed or implemented on separate devices.

FIG. 48B is a block diagram illustration of the HMA, of the present specification, integrated and in communication with the IPA system, in accordance with another exemplary embodiment. In this embodiment, the HMA as well as the IPA software application are installed or implemented, as client side software components, on the companion device 4805 which is in data communication with at least one EDP device 4810 of the present specification. The client side HMA and IPA software components, on the companion device 4805, are in data communication with each other. The IPA software component, on the companion device 4805, may or may not be in direct communication with the at least one EDP device 4810. The companion device 4805 is also in communication, via network 4825, with the health management server 4815 that implements the server side software component of the HMA, the IPA server 4835 that implements the server side software component of the IPA software application and optionally a remote patient care facility and/or patient care personnel. The network 4825 is a cellular, Internet, TCP/IP, Ethernet, Bluetooth, wired, or wireless network. Also, the health management server 4815 and the IPA server 4835 are capable of being in data communication with each other through network 4825.

Thus, in this embodiment, the IPA system does not comprise a standalone IPA device 4830 separate from the companion device 4805. In other words, the IPA and HMA software applications are installed or implemented on the same client side devices, that is, the companion device 4805.

During operation the HMA communicates with the IPA system to enable voice based interfacing with the user. Thus, the voice enabled interface of the IPA system augments or replaces the plurality of GUIs and associated functionalities implemented by the HMA of the present specification. Referring now to FIGS. 48A and 48B, in various embodiments, the user's voice based inputs, commands, instructions and/or queries (collectively also referred to as 'inputs') are received by the client side IPA software component—residing on the companion device 4805 (along with the client side HMA software component) or separately on the IPA device 4830. The client side IPA software component, in some embodiments, may stream the user's voice based inputs to the IPA server 4835, via network 4825, for further processing and thereafter communication to the HMA server 4815 and/or the client side HMA software component residing on the companion device 4805. In other embodiments, the client side IPA software component may itself process the user's voice based inputs and thereafter communicate with the HMA server 4815 and/or the client side HMA software component residing on the companion device 4805.

In accordance with various aspects, the IPA system processes the user's voice based inputs to derive input programmatic instructions that are communicated to the HMA for a plurality of health management related actions associated with the EDP device 4810 of the present specification. Similarly, output programmatic instructions associated with a plurality of prompts, alerts, reminders, instructions or status reports (collectively also referred to as 'outputs') generated by the HMA are communicated by the companion device 4805 and/or the HMA server 4815 to the IPA device 4830 and/or the IPA server 4835. In accordance with various aspects, the IPA system processes these output programmatic instructions to convert them into voice based outputs that are communicated to the user as information and/or for further user actions.

In accordance with some embodiments, the HMA shares, with the IPA system, a plurality of the user's (and/or social network aggregated) health related information such as the user's hunger profile, standard eating and meals profile, actual eating and meals profile, energy balance, weight trends, glucose data and stimulation induced nausea, dyspepsia, habituation events. In some embodiments, the HMA periodically transmits the user's health related information apart from enabling the IPA system to access such information in real time or on demand, if required. In various embodiments, the user's authorization is needed to allow such access to the user's health related information.

The HMA in communication with the IPA system enables receiving from and providing to the user, voice based inputs and outputs associated with a plurality of functions enabled by the HMA, non-limiting examples of which are described henceforth.

The HMA in communication with the IPA system, enables voice based communication to the user that the HMA (companion device 4805) is successfully linked (via pairing or syncing, for example) with the EDP device 4810 including announcements related to battery life of the EDP device 4810.

The HMA in communication with the IPA system, enables voice based communication to the user indicating that a) the EDP device 4810 has been properly placed on the user's body, b) the one or more electrodes of the EDP device 4810 is aged and needs to be replaced.

The HMA in communication with the IPA system, enables voice based communication to the user indicating whether the EDP device 4810 has been placed at an appropriate location, such as the T2-T12 and/or C5-T1 dermatomes for eating disorders.

The HMA in communication with the IPA system, enables voice based communication by the user to the HMA that the user needs to administer stimulation therapy on-demand. Additionally, the HMA in communication with the IPA system enables voice based instructions or commands by the user to select, set and/or modify a plurality of stimulation parameters, settings or protocol therapies.

The HMA in communication with the IPA system, enables voice based communication prompting the user to stimulate based upon time of day, historical trends in appetite, caloric intake, and exercise data.

The HMA in communication with the IPA system, enables voice based communication to the user regarding effectiveness of a stimulation during a stimulation therapy. This includes announcing to the user, recommended adjustments or modifications to a plurality of stimulation parameters. In some embodiments, the recommended adjustments to the plurality of stimulation parameters must be accepted or authorized for implementation by the user through voice based acceptances.

The HMA in communication with the IPA system, enables voice based notification to the user when enough time has passed after drinking to eat and vice versa.

The HMA in communication with the IPA system enables voice based user inputs regarding his current weight per day. Voice based communication to the user includes current stimulation parameters and other real-time inputs, such as diary and exercise monitoring.

The HMA in communication with the IPA system enables voice based user inputs such as, but not limited to, eating information and activities information. The eating information includes standard regular eating and meals profile of the user (representing the general eating habit of the user) as well as real time actual eating and meals profile of the user such as the actual time of consumption of a meal in a day and the actual type and amount of food eaten at the meal.

The HMA in communication with the IPA system enables voice based communication to the user regarding the difference between the user's daily, weekly or monthly expected and actual calories consumption value including a plurality of recommendations (by the HMA) resulting from the calculated difference. Voice enabled user communication also includes announcing the amount of extra macronutrients, such as carbs, protein and fats, and/or glycemic load consumed compared to an acceptable amount of macronutrients allowed based on a standard diet plan being followed by the user, including the effect such extra consumption will have on the user's weight loss goal, for example.

The HMA in communication with the IPA system enables voice based user inputs regarding activities information such as how much and when the user moves around and/or exercises during the day.

The HMA in communication with the IPA system enables voice based communication to the user if he is at a positive or negative energy balance. Such communication may be triggered by the user's voice based queries asking for his energy balance status for the day or for his average weekly or monthly energy balance. The HMA in communication with the IPA system also enables voice based reporting to the user (based on the user's voice based queries, for example) regarding the user's standard regular eating and meals profile, actual eating and meals profile, weight trend including a rate of weight loss or gain, glucose data trend and hunger profile over a period of time such as daily, weekly or monthly.

The HMA in communication with the IPA system enables voice based user inputs regarding his hunger or appetite profile.

The HMA in communication with the IPA system enables voice based communication with one or more third party service providers for user activated or automated ordering of accessories, such as electrode patches for example; standard meals, such as Jenny Craig, or fitness coaching services. HMA's enablement of communication with one or more third party service providers, via the IPA system, also allows for sourcing and paying for online services and/or for advertising.

The HMA in communication with the IPA system enables voice based feedback to the user on dietary compliance, calories burned, diet plans and detected conditions such as a hyperglycemic rush. The HMA in communication with the IPA system also enables voice based prompts to the user with respect to a plurality of compliance aspects such as, but not limited to: stimulation therapy compliance—generating voice based prompts if the user forgets to apply the electrodermal patch device and/or disables a recommended duration or frequency of stimulation therapy; generating voice based prompts to the user with respect to a stimulation protocol that a scheduled stimulation is going to begin in the next T minutes, 10 minutes for example, and asking the user with an option to disable the scheduled stimulation which if not disabled allows the scheduled stimulation to begin after T minutes; dietary compliance or guidance—the user either selects, using interactive voice based inputs, a predefined standard dietary plan or inputs a customized plan as part of the standard regular eating and meals routine. The user also records, using interactive voice based inputs, details of the actual meals taken and time of meals. Voice based alert(s) may be generated, for example, if the user is not in compliance with the selected dietary plan. The voice enabled compliance prompts are intended to encourage user compliance and, in some embodiments, include announcing composite scores and overall patient progress.

With reference to FIG. 48A, for example, the IPA device 4830 may include a sensor to detect proximity of the EDP device 4810. The IPA device 4830 may be, for example, stationed in the user's kitchen. When the user, wearing the EDP device 4810, enters the kitchen the IPA device 4830 detects the user's presence and, in real-time or near real-time, communicates the user's presence in the kitchen to the companion device 4805. The HMA, on the companion device 4805, processes the user's visit to the kitchen (assuming the user's visit to the kitchen is likely to lead to an eating event based on the user's past eating records) in light of at least the user's current energy balance and standard diet plan to determine if the user should or should not eat. If the user's energy balance is positive and/or the user's consumption of a meal, as a result of the visit to the kitchen, is unscheduled and not in line with the standard diet plan—the HMA generates an alert. The alert, in some embodiments, is communicated to the IPA system as a result of which the IPA device 4830, in the kitchen, provides a voice based alert to the user dissuading him from consuming an unscheduled meal. In alternate embodiments, the HMA alert results in triggering the EDP device 4810 to start a therapeutic stimulation or a short and low amplitude cautionary stimulation pulse.

However, if the user visits the kitchen near meal time, the IPA device 4830, in the kitchen, may ask the user what he is eating or planning to eat. Depending on the user's response, the IPA system may breakdown the potential amount and types of calories for the food the user is eating or about to eat and recommend healthier food options to the user besides providing advice on the amount of serving of the food that the user may consume, for example. In various other embodiments, the IPA system integrates the user's hunger level, profile and timing with the IPA system's knowledge of the user's kitchen inventory to proactively advice the user on what to eat and make recommendations (such as, how much of what food to eat, and what to avoid) knowing that the user is hungry or likely to be hungry around a certain time. Such IPA system based proactive recommendations on food consumption, starting of a therapeutic stimulation or a short and low amplitude cautionary stimulation pulse could be triggered based on various combinations of events such as, but not limited to, the user leaving the house or based on a certain time of day when the user feels out-of-time snacking pangs, for example.

In accordance with another aspect, the IPA system responds differently depending at least upon the time of day when the user verbally conveys to the IPA system that he is hungry. For example, if the user indicates hunger at a mealtime, the HMA in communication with the IPA system may recommend healthy recipes and/or offer to order food from various restaurants. However, if the user indicates hunger past standard or scheduled mealtimes the HMA in communication with the IPA system may send a signal to Bluetooth activated locks that would lock pantry or terminate functionality of kitchen appliances (using wireless communication).

The HMA in communication with the IPA system enables voice based user inputs related to feeling of nausea, dyspepsia, heartburn, or sensation at the stimulation site during and/or after stimulation.

The HMA in communication with the IPA system enables voice based alerts to the user in case of removal of the EDP device 4810 from the user's body.

In embodiments where the Health Management application implements an eating moment recognition method (FIG. 58) and is also in communication with the IPA system, identification or determination of an eating moment or activity by the HMA is communicated to the IPA system that may consequently deliver auditory prompts to the user enquiring if the user is indeed eating and if yes, then cautioning the user if the eating event is unscheduled or not in line with a meal regimen being followed by the user, for example. In some embodiments, the eating moment recognition method is implemented directly by the IPA device which may be in direct communication with the EDP device 4810. In some embodiments, the EDP device 4810 is configured as a band or wristwatch (such as the band 2105 of FIG. 21A or the wristwatch 2106 of FIG. 21B) and includes an accelerometer to detect, capture and acquire a plurality of dietary data related to physical body movements, such as (for example) haptic motions of the wrist or hand, of the user involved in food intake gestures. In such embodiments, dietary data from the EDP device (wristwatch or band) is communicated directly to the IPA device (in communication with the wristwatch or band) for detecting eating events or activities to issue appropriate auditory prompts or conversation to the user.

In still further non-limiting examples, the HMA in communication with the IPA system enables: voice based setting, by the user, of daily reminders for prescribed vitamins and supplements; enables users to pose voice based queries to their dietician; enables voice based announcements of schedules of weight loss seminars and support groups, to the user; enables medical personnel to communicate healthy recipes with the user to support their continued weight loss success; enables bariatric surgery patients to stay on track with voice enabled reminders and review of pre-populated checklist—Psych Eval, Insurance Pre-approval, Physician Supervised Diet; enables medical personnel as well as users to dictate daily thoughts and progress notes; enables or disables information exchange with third party applications by allowing the user to provide voice enabled commands; enables the user to receive voice based status reports related to tracked calories, protein, fat and carbohydrates consumed by the user; enables scanning of barcodes of package food to allow users to listen to the nutritional information, and have it logged automatically to the feed consumed daily diary by issuing voice based commands; enables instilling weight management habits in the patients since voice enabled prompts related to food/calories intake leads to better dietary compliance; enables physicians, dieticians and other medical personnel to send out voice based push notifications to their users to keep the users engaged and motivated towards their health goals.

As discussed earlier in this specification, the user's plurality of health related information is utilized by the HMA to suggest and/or implement a plurality of recommendations comprising stimulation patterns or protocols, medication (such as an amount of insulin intake, for example), dietary and/or activities plans. In some embodiments, the plurality of recommendations are announced to the user for his voice enabled authorization for implementation.

In yet further non-limiting examples, the HMA in communication with the IPA system enables delivering voice based prompts to the user and receiving voice based user inputs related to the user's daily 'diary' for tracking and recording the user's parameters. For example, instead of presenting GUI screens of FIGS. 8 through 13 to the user to track and record the user's parameters related to appetite, exercise, hunger, stimulation sessions, weight and well-being, the HMA in communication with the IPA system enables voice based prompts to be delivered to the user for each of the user parameter and allows the user to track and record these parameters via voice based inputs, commands or instructions. For example, in some embodiments, the HMA in communication with the IPA system enables a voice recognition verbal/auditory numeric or intensity scale, which may be, for example, a huger scale, to allow the user to record hunger level (appetite, exercise or any other daily 'diary' based parameter, for example) and hunger event/episode (including date and time of the hunger event) and use that as a trigger to initiate or titrate therapy. In embodiments, the verbal/auditory hunger scale may be a 1 to 10 analog numeric hunger scale or an analog intensity hunger scale where descriptors such as "not hungry", "somewhat hungry" and "extremely hungry" are spoken to the user to choose from in order to indicate/input the user's current state of hunger. In embodiments, the verbal/auditory scale is activated by a verbal input or command (to the IPA system) such as, but not limited to, "I'm hungry".

Following is an exemplary, non-limiting, simulated interaction that may occur using the IPA system: Patient: I'm hungry IPA system: how hungry are you on a scale of 1 to 10

Patient: Not very . . . I'd say 5/10

IPA system: Thanks, your scheduled meal is only in 45 minutes so let's see if you can hang on until then [hunger event is recorded]

But if the patient responds Very, I'm at a 6/10

IPA system: hang in there, I'm going to give you a mild rescue session [A 15 minutes stimulation therapy at 10 mA is automatically initiated], following which:

IPA system: I think that will help—your next meal is only 60 minutes away, just let me know if you need more help, I'm by your side.

Instead, if the patient says: I'm very hungry . . . 8/10

IPA system: hang in there, I'm going to give you a full rescue session [A 15 minutes stimulation therapy at 20 mA is automatically initiated]

The aforementioned voice based interaction illustrates how the HMA in communication with the IPA system enables voice based input of a daily 'diary' parameter by the user and based on at least the level (on a verbal/auditory scale) and time of input of the parameter how the user's stimulation, including rescue sessions, may be triggered and/or titrated.

Following is another exemplary, non-limiting, simulated interaction that may occur using the IPA system:

Patient: my hunger today was pretty intense around mid morning

IPA system: sorry to hear that. I notice that you didn't use your stimulation rescue button during that time. Why don't you activate your rescue button at 10:00 am tomorrow? By the way you are doing really well with your weight loss and have lost just over 8 pounds so far, better than the average for other users. Nice job!!

In various embodiments, the HMA in communication with the IPA system also enables voice based dietary coaching depending upon the user's verbal input of his daily 'diary' parameter.

Figure 48C:
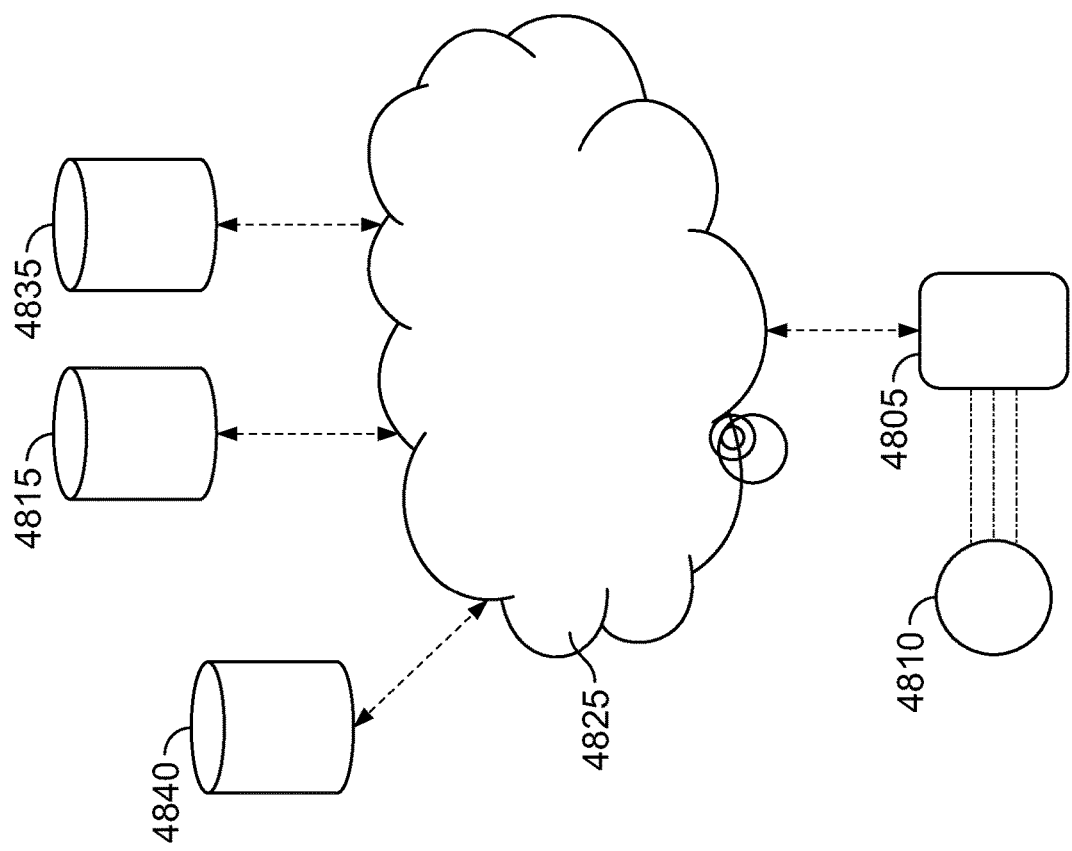

FIG. 48C is a block diagram illustration of the HMA, of the present specification, in communication with the IPA system as well as a Big Data database server, in accordance with an exemplary embodiment. In this embodiment, the HMA as well as the IPA software application are installed or implemented, as client side software components, on the companion device 4805 which is in data communication with at least one EDP device 4810 of the present specification. The client side HMA and IPA software components, on the companion device 4805, are in data communication with each other. The IPA software component, on the companion device 4805, may or may not be in direct communication with the at least one EDP device 4810. The companion device 4805 is also in communication, via network 4825, with the health management server 4815 that implements the server side software component of the HMA, the IPA server 4835 that implements the server side software component of the IPA software application and optionally a remote patient care facility and/or patient care personnel. The network 4825 is a cellular, Internet, TCP/IP, Ethernet, Bluetooth, wired, or wireless network. Also, the health management server 4815 and the IPA server 4835 are capable of being in data communication with each other through network 4825. In accordance with an aspect of the present specification, the server side software component of the HMA, apart from being in communication with the IPA system, is also in communication with a Big Data database server 4840 through the network 4825. The Big Data database server 4840, via network 4825, is in communication with the EDP device 4810 and the companion device 4805 to store a plurality of health related data of the user. In various embodiments, the Big Data database server 4840, via network 4825, is in communication with a plurality of networks or groups of a plurality of users each using an EDP device (such as device 4810) and a corresponding companion device (such as device 4805). Thus, in various embodiments, the Big Data database server 4840 is able to access and store a plurality of aggregated health related data of a plurality of networks or groups of users (hereinafter referred to as users' "health related data"). In various embodiments, the health related data also includes attributes data such as, but not limited to, date of birth, work address, home address, social security number, gender, height, occupation, income, present and past ailments and medications, history of ailments in the family. The Big Data database server 4840, via network 4825, is also in communication with a plurality of generic data sources or databases such as, but not limited to, those associated with news, weather and climate forecasts, demographics, genome, geographical maps, electronic health records, GPS, merchant or shopping transaction records such as supermarkets or shop checkouts data, public holidays, festivals, and other data. Thus, in various embodiments, the Big Data database server 4840 is able to store a plurality of data (hereinafter referred to as "general data") by accessing a plurality of generic data sources.

In one embodiment the server side software component of the HMA also implements a Big Data analytics engine that mines the Big Data database server 4840 to analyze a plurality of users' health related data (including attributes data) as well as general data, generate a plurality of patterns and correlations from the users' health related data and general data, predict what effects such patterns and correlations may have on a specific user, and eventually generates and implements a plurality of predictive stimulation therapy regimens or outcomes corresponding to the predicted effects. In various embodiments, the Big Data analytics engine is an artificial intelligence program implementing one or more of a case based reasoning (constituting a process of solving new problems based on the solutions of similar past problems), fuzzy logic (constituting a process of solving problems based on degrees of truth rather than the usual true or false Boolean logic) and/or rule based reasoning (constituting a process of solving problems based on a plurality of pre-defined rules or criterion).

In some embodiments, the Big Data analytics engine analyzes a plurality of users' historical (of the past pre-defined period of time such as weeks, months or years) as well as current (of a given day) health related data (such as, but not limited to, historical and current daily 'diary' entries, caloric intake, and exercise trend) to predict onset of a hunger event and proactively trigger or recommend a stimulation session (for example, a rescue session) prior to the predicted or forecasted hunger event.

In some embodiments, the Big Data analytics engine mines the general data and identifies a plurality of adverse factors that are likely to contribute to an EDP user's failure to achieve his goal, such as a weight loss goal. For example, historical shopping data may suggest increased buying of less healthy or high calorie eateries such as savory or gourmet foods and carbonated soft drinks at and around festive season such as Christmas or around holidays such as Thanksgiving. If the EDP user has a high positive energy balance and the festive season is approaching, the HMA, via the IPA system, will automatically generate an alert prompting the user to be careful and not indulge in unhealthy eating during a certain high risk period of time such as a few days before and after Christmas, for example. Similar alerts are automatically generated when the user's birthday approaches.

In some embodiments, the Big Data analytics engine may associate general data with the user's health and attributes data. For example, if the user's GPS coordinates are known additional general data can be associated with the user such as, but not limited to, weather, time zone, venue and venue categories (for example, at home, work, a bar, a restaurant, a concert hall). If the user's GPS coordinates indicate presence of the user in a bar or a restaurant, the HMA may automatically alert the user with regards to potential over indulgence. In another embodiment, if historical trends suggest a correlation of the user's spike in positive energy balance following visits to the bar or the restaurant, then the HMA may automatically schedule a preventive stimulation session on the user's next visit to the bar or restaurant, in order to suppress appetite. In another example, the Big Data analytics engine may access the user's OpenTable (an online restaurant-reservation service) reservation or the user's Calendar appointment for a visit to a bar or a restaurant. Accordingly, the HMA may automatically alert the user with regards to potential over indulgence prior to the user's visit to the bar or restaurant and event trigger or recommend a rescue session prior to the user's visit to the bar or restaurant.

In another example, considering people with the same gene as that of the user and the same level of sunlight exposure available as in the location of the user, the user may have a high likelihood of deficiency in Vitamin D. This correlation may be further accentuated if the user's exercise regimen is largely limited to indoor workouts. Accordingly, the HMA may automatically recommend the user for periodic tests for Vitamin D and encourage the user to include ample outdoor exercise or workouts.

In still other embodiments, the Big Data analytics engine may identify a statistically significant trend, where the user feels more tired on days following intense exercise. In the same example, the system may find that the user's sleep is more fragmented on nights following intense exercise. In one embodiment, if the correlation between intense exercise, fragmented sleep and depleted energy on the following day is strong enough, and no other significant correlations are made despite adequate data sources and types, intense exercise or workout is flagged as a potential contributing factor to negative well-being. In another embodiment, the user-specific trend can be compared to aggregate data, in order to reinforce the validity of the user-specific correlation. For example, the Big Data analytics engine may go on to find that a substantial portion of the general population also experiences fragmented sleep on nights following intense workouts. Accordingly, the HMA may, via the IPA system, alert the user when the user's exercise intensity on a particular day is high and suggest a moderated exercising regimen.

Electro-Dermal Patch Device Placement

In various embodiments, the electro-dermal patch device (such as the electro-dermal patch device 110 of FIG. 1A through 1C) of the present specification is placed at or near an 'area of interest' on the user's body to provide stimulation therapies for a plurality of conditions or treatments.

In various embodiments, the 'area of interest' comprises a dermatome. As understood by persons of ordinary skill in the art, a dermatome is an area of skin supplied by sensory neurons that arise from a spinal nerve ganglion. There are 8 cervical nerves (C1 being an exception with no dermatome), 12 thoracic nerves, 5 lumbar nerves and 5 sacral nerves. Each of these nerves relays sensation from a particular region of skin to the brain.

In some embodiments, the 'area of interest' comprises a thoracic dermatome, such as the user's front or lateral T2 to T12 dermatomes. In other embodiments, the 'area of interest' comprises a dermatome, such as the user's front (anterior) and/or back (posterior) C5-T1 dermatomes in the hand and arm along with the front (anterior) C5-T1 dermatomes on the upper chest region (hereinafter together referred to as 'hand dermatomes'). In various embodiments, the 'area of interest' expressly excludes the back (posterior) C5-T1 dermatomes of the upper chest region since the back portions are inaccessible to the user and therefore would need a medical practitioner to apply the devices of the present specification. In still other embodiments, the 'area of interest' comprises epidermis regions for stimulating a median nerve in the hand, and more specifically, in the wrist region.

In some embodiments, however, the 'area of interest' includes the back (posterior) T2-T12 and/or C5-T1 dermatomes. In such embodiments, the EDP device of the present specification is configured to be positioned on the back dermatomes by the user with ease and with minimal or no help from a third party such as a medical practitioner. Accordingly, in some embodiments, the EDP device is incorporated into a tight undershirt which when worn by the user simply positions the incorporated EDP device at the desired back dermatome. In some embodiments, the user is enabled to position the EDP device on the desired back dermatome using an elastic band, strap or belt encircling his trunk, wherein the elastic band, strap or belt incorporates the EDP device of the present specification.

In some embodiments, the 'area of interest' comprises at least one of the patient's T2 front, lateral and/or back thoracic dermatome, T3 front, lateral and/or back thoracic dermatome, T4 front, lateral and/or back thoracic dermatome, T5 front, lateral and/or back thoracic dermatome, T6 front, lateral and/or back thoracic dermatome, T7 front, lateral and/or back thoracic dermatome, T8 front, lateral and/or back thoracic dermatome, T9 front, lateral and/or back thoracic dermatome, or T10 front, lateral and/or back thoracic dermatome. In some embodiments, the 'area of interest' comprises at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, and T10 frontal and lateral thoracic dermatome and does not include any one of the patient's T2 posterior thoracic dermatome, T3 posterior thoracic dermatome, T4 posterior thoracic dermatome, T5 posterior thoracic dermatome, T6 posterior thoracic dermatome, T7 posterior thoracic dermatome, T8 posterior thoracic dermatome, T9 posterior thoracic dermatome, and T10 posterior thoracic dermatome.

In some embodiments, the 'area of interest' comprises at least one of the patient's C8 anterior or posterior dermatome located on the patient's hand, wrist, elbow, and fingers, C8 anterior or posterior dermatome located on the patient's arm, C8 dermatome located on the patient's upper trunk, T1 anterior or posterior dermatome located on the patient's arm, T1 anterior or posterior dermatome located on the patient's wrist, elbow, and hand, and T1 anterior or posterior dermatome located on the patient's upper trunk.

In some embodiments, the 'area of interest' comprises at least one of the patient's C5, C6, C7, C8, T1, T2, T3, T4, T5, T6, T7, T8, T9, T10, T11, and T12 frontal, lateral and/or back dermatomes.

In some embodiments, the 'area of interest' comprises at least one of the patient's C5, C6, C7, C8, T1, T2, T3, T4, T5, T6, T7, T8, T9, T10, T11, and T12 frontal and lateral dermatomes and does not include any portion of the patient's C5, C6, C7, C8, T1, T2, T3, T4, T5, T6, T7, T8, T9, T10, T11, and T12 posterior dermatomes.

In alternate yet less preferred embodiments, the 'area of interest' comprises one or more meridians.

Figure 17A:
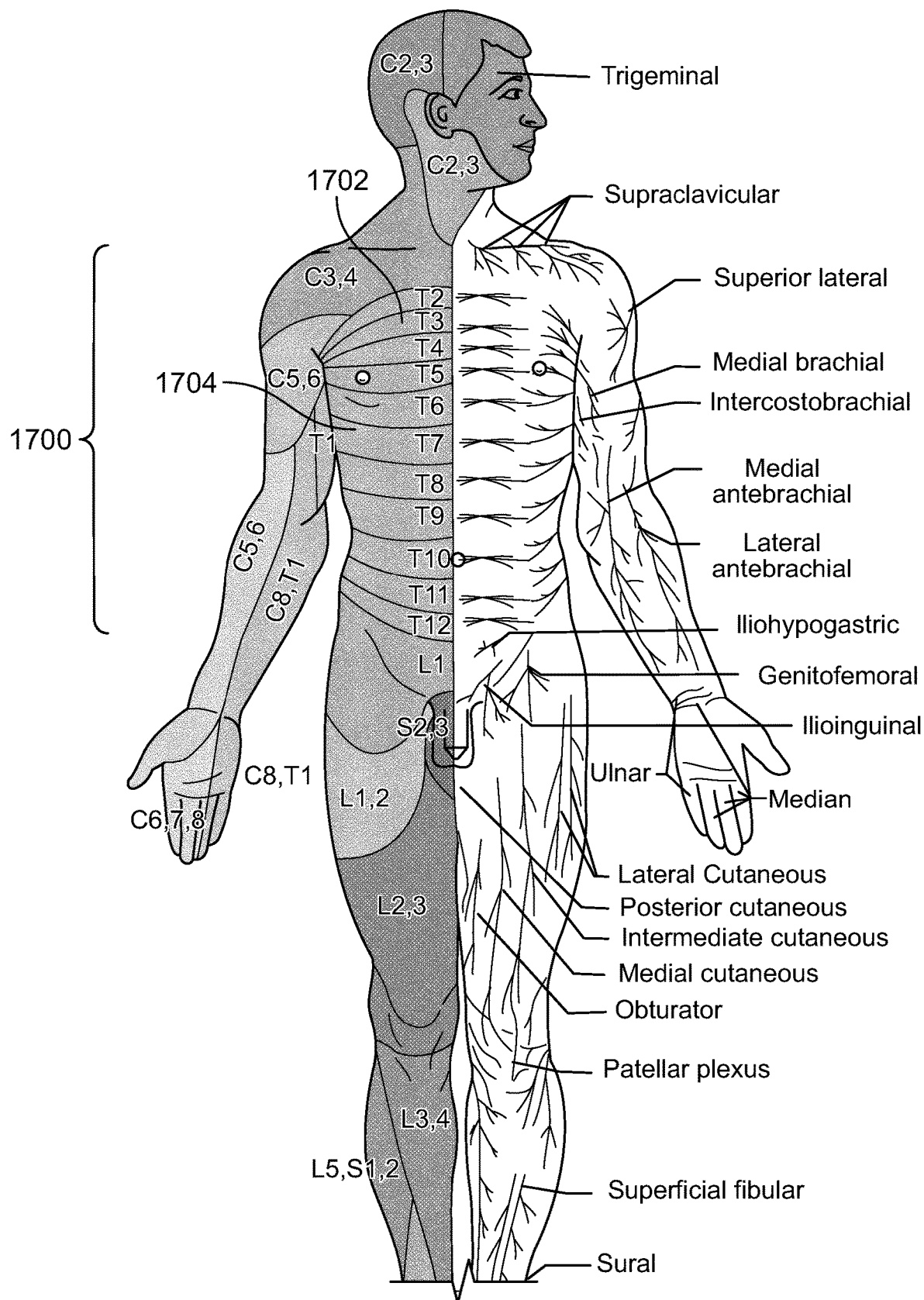
FIG. 17A is an illustration depicting the distribution of the front and lateral T2-T12 dermatomes across a thorax and abdomen of a human body.

FIG. 17A is an illustration depicting the distribution 1700 of the front and lateral, or frontal, T2-T12 dermatomes across a thorax and abdomen, that is trunk, of a human body. The frontal dermatome is defined as the front and lateral thoracic dermatome which expressly do not include the back or spinal roots of said patient. In various embodiments, the electro-dermal patch devices of the present specification are positioned on the surface of the epidermis on the front portion 1702 or lateral portion 1704 of the T2-T12 dermatomes. The electrode(s) positioned in the pads or skin patches of the electro-dermal patch device then provide electrical stimulation to the epidermis of the targeted dermatome(s). The T2 to T12 dermatomes are anatomically identifiable as follows:

T2—At the apex of the axilla.
T3—Intersection of the midclavicular line and the third intercostal space.
T4—Intersection of the midclavicular line and the fourth intercostal space, located at the level of the nipples.
T5—Intersection of the midclavicular line and the fifth intercostal space, horizontally located midway between the level of the nipples and the level of the xiphoid process.
T6—Intersection of the midclavicular line and the horizontal level of the xiphoid process.
T7—Intersection of the midclavicular line and the horizontal level at one quarter the distance between the level of the xiphoid process and the level of the umbilicus.
T8—Intersection of the midclavicular line and the horizontal level at one half the distance between the level of the xiphoid process and the level of the umbilicus.
T9—Intersection of the midclavicular line and the horizontal level at three quarters of the distance between the level of the xiphoid process and the level of the umbilicus.
T10—Intersection of the midclavicular line, at the horizontal level of the umbilicus.
T11—Intersection of the midclavicular line, at the horizontal level midway between the level of the umbilicus and the inguinal ligament.
T12—Intersection of the midclavicular line and the midpoint of the inguinal ligament.

Figure 17B:
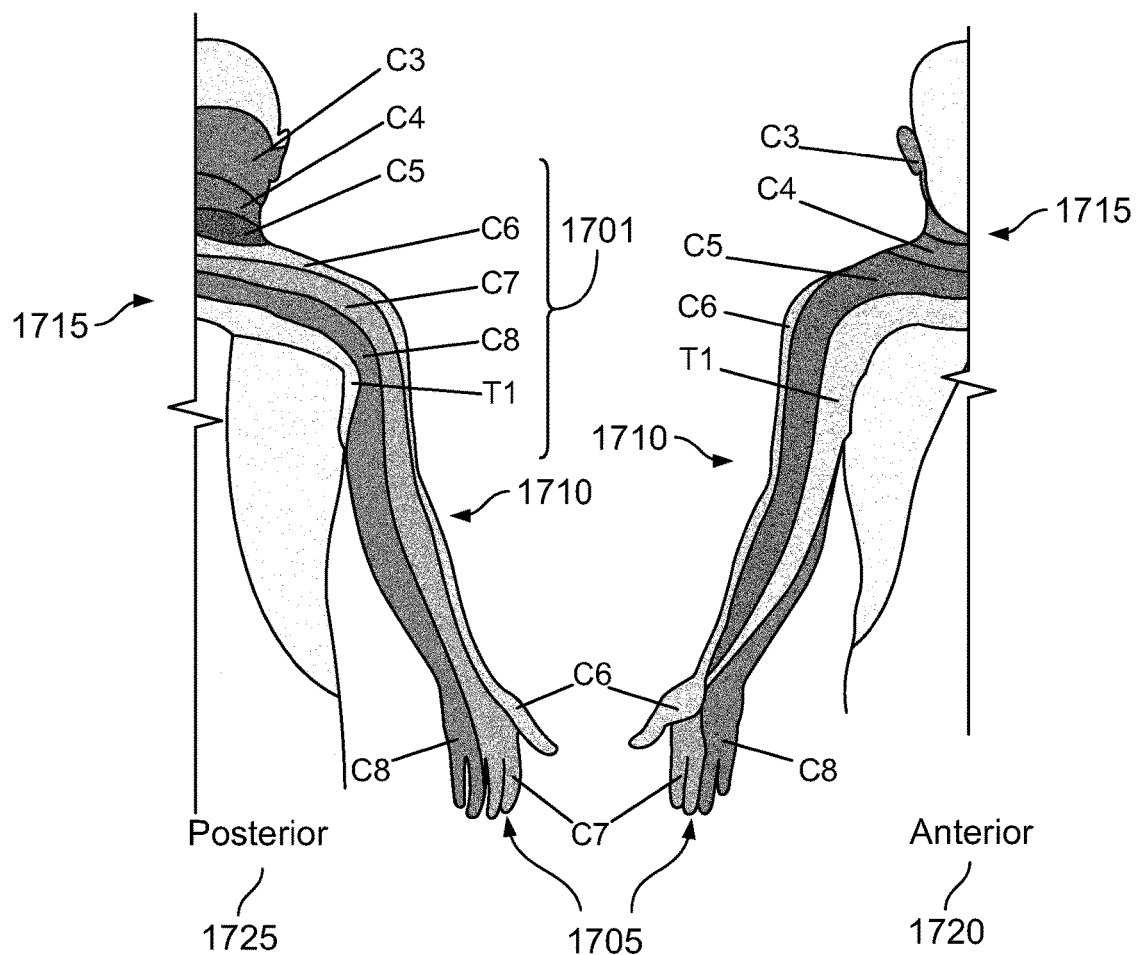
FIG. 17B is an illustration depicting the distribution of the anterior and posterior C5-T1 dermatomes across a hand, arm and upper chest regions of a human body.
Figure 17C:
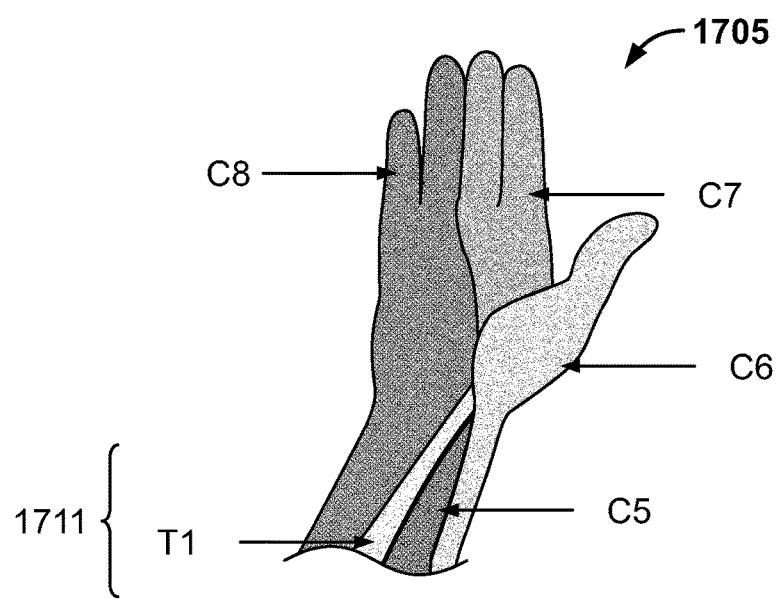
FIG. 17C is an illustration depicting the distribution of the C5-T1 dermatomes across the ventral side of the hand and lower arm of the human body.

FIG. 17B is an illustration depicting the distribution 1701 of the front and back, C5-T1 dermatomes across the hand 1705, arm 1710 and upper chest 1715 regions of a human body. In various embodiments, the electro-dermal patch devices of the present specification are positioned on the surface of the epidermis on the front portion 1720 and/or back portion 1725 of the C5-T1 dermatomes on the hand 1705 and arm 1710 along with the front (anterior) C5-T1 dermatomes on the upper chest 1715. FIG. 17C is an illustration depicting the distribution of the C5-T1 dermatomes across the hand 1705 and lower arm 1711 regions. In various embodiments, the electro-dermal patch devices of the present specification are positioned on the surface of the epidermis on the front (palm) and/or back side of the hand 1705 targeting the C6-C8 dermatomes or on the front and/or back side of the lower arm 1711 (such as at a wrist region, for example) targeting the C5 and T1 dermatomes. The electrode(s) positioned in the pads or skin patches of the device then provide electrical stimulation to the epidermis of the targeted dermatome(s).

The C5-T1 dermatomes are anatomically identifiable as follows:
C5—On the lateral (radial) side of the antecubital fossa, just proximally to the elbow.
C6—On the dorsal surface of the proximal phalanx of the thumb.
C7—On the dorsal surface of the proximal phalanx of the middle finger.
C8—On the dorsal surface of the proximal phalanx of the little finger.
T1—On the medial (ulnar) side of the antecubital fossa, just proximally to the medial epicondyle of the humerus.

Figure 17D:
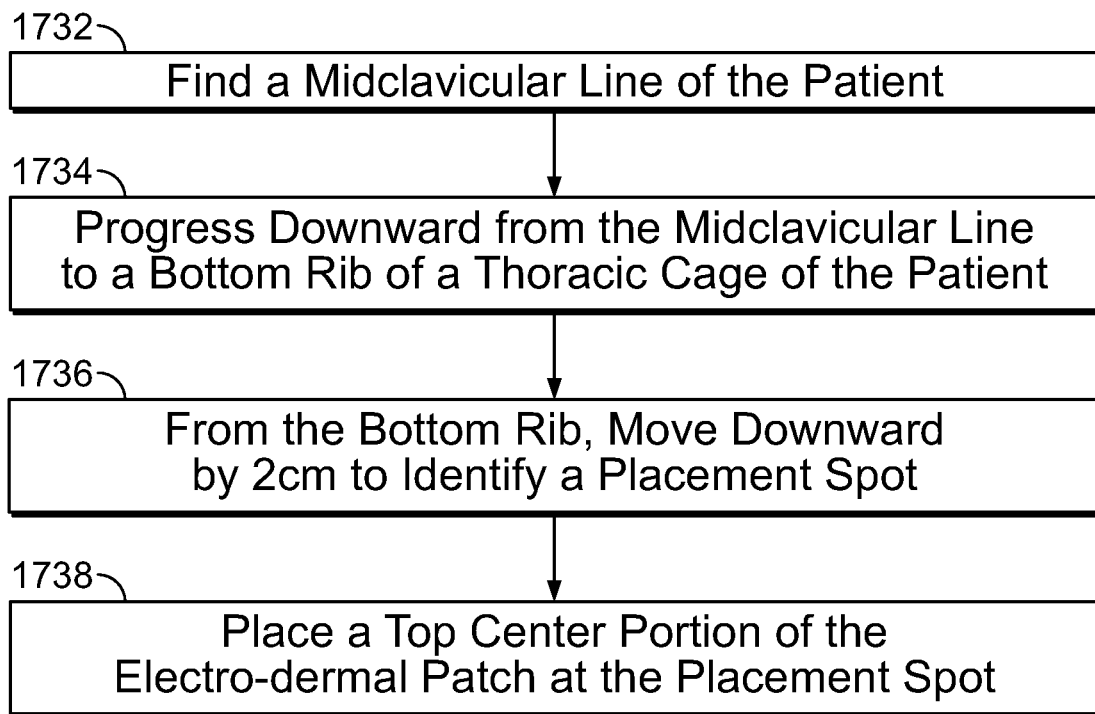
FIG. 17D is a flow chart listing the steps involved in one method of identifying a proper placement location for an electro-dermal patch on a front thoracic surface of a patient, in accordance with one embodiment of the present specification.
Figure 17E:
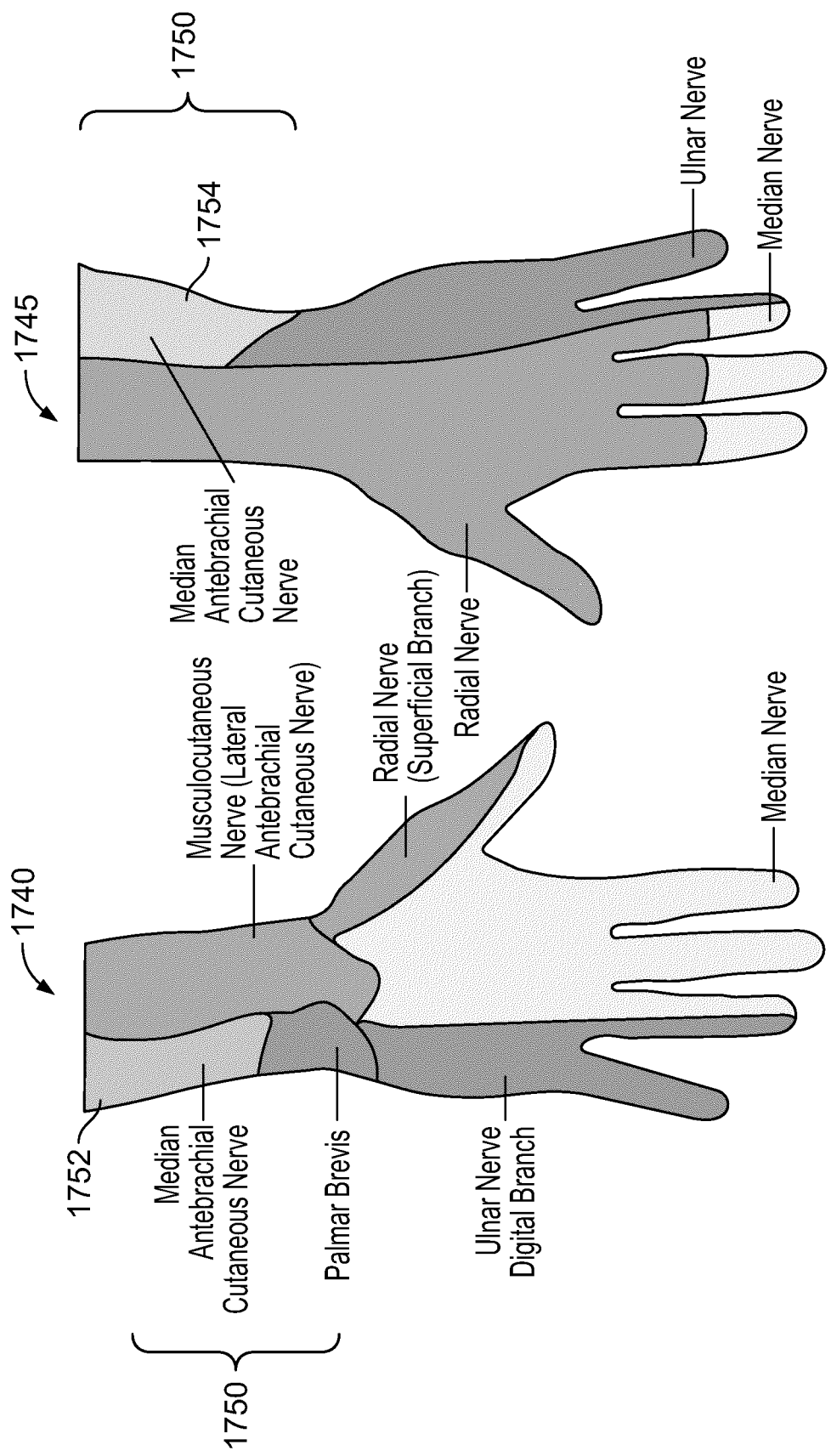
FIG. 17E is an illustration depicting region on a front and back side of the hand of the human body innervated by a median nerve.

As shown in FIG. 17E, in some embodiments, the electro-dermal patch devices of the present specification are positioned on the surface of the epidermis on the front 1740 and/or back side 1745 of the wrist region 1750 targeting the median nerve. The electrode(s) positioned in the pads or skin patches of the device then provide electrical stimulation to the epidermis of the targeted median nerve. In the hand, the median nerve supplies motor innervation to the 1st and 2nd lumbrical muscles. It also supplies the muscles of the thenar eminence by a recurrent thenar branch. The median nerve innervates the skin of the palmar side of the index, the thumb and middle finger, half the ring finger, and the nail bed. The lateral part of the palm is supplied by the palmar cutaneous branch of the median nerve, which leaves the nerve proximal to the wrist creases. Thus, in some embodiments, the epidermis region 1752 on the front side 1740 and/or the epidermis region 1754 on the back side 1745 of the wrist region 1750 are electrically stimulated to target the median nerve to cause satiety, weight loss and/or metabolic improvement.

It should be appreciated that in some embodiments the hand dermatomes, such as the C5-T1 dermatomes, as well as the epidermis regions related to stimulation of the median nerve in the wrist region are stimulated using conductive metal electrodes (such as, but not limited to, of Gold) without any adhesive skin patches. In such embodiments, the conductive metal electrodes are positioned on an appropriate epidermis (with user applied conductive gel, in some embodiments) to deliver electrical stimulation pulses without any skin patch. In an embodiment, the conductive metal electrodes stimulate dermatomes C8 and T1 at the location of the Median nerve under the wrist (ventral side). In one embodiment, the electrodes are on opposing sides of the nerve.

FIG. 17D is a flow chart listing the steps involved in one method of identifying a proper placement location for an electro-dermal patch on a front thoracic surface of a patient, in accordance with one embodiment of the present specification. At step 1732, the patient, a physician, or anyone placing the EDP device on the patient, finds a midclavicular line of the patient. The person applying the device then progresses downward from the midclavicular line to a bottom rib of a thoracic cage of the patient at step 1734. From the bottom rib, at step 1736, the person applying the device moves downward by 2 cm to identify a placement spot. At step 1738, the person applying the device places a top center portion of the electro-dermal patch at the placement spot.

Referring back to FIG. 1A, in various embodiments, at least one thoracic dermatome, from T2 to T12 and/or 'arm dermatome' or 'hand dermatome' C5-T1, is stimulated by the electro-dermal patch device 110 to provide electrical stimulation therapy, from the external surface of the patient's epidermal layer through 10 mm or 20 mm of the dermis, wherein the one or more electrodes 118 are configured to be positioned in skin patches or pads as described with reference to FIGS. 2A through 2C, FIGS. 3A, 3B, and 4A through 4C.

The prior art has focused on one of three different approaches: 1) stimulating the back, near the spinal root, 2) providing percutaneous electrical stimulation, which requires an electrode to be implanted, or 3) stimulating using conventional acupuncture meridians. However, the electro-dermal patch device 110 of the present specification provides electrical stimulation, from the external surface of the patient's epidermal layer through 10 mm or 20 mm of the dermis, and targets front, lateral or back thoracic dermatomes and/or front or back 'hand dermatomes' (excluding the back C5-T1 dermatomes in the upper back region), in accordance with various embodiments, having nerves that are closer to the skin surface. The electro-dermal patch device 110 of the present specification generates an electrical field, defined as voltage over distance, which penetrates to a shallower depth compared to stimulation encountered in the prior art. This allows the electro-dermal patch device 110 to have relatively smaller electrodes 118, lowers the current density and therefore the device requires less power than prior art devices to affect target tissues. The electrical field generated by the EDP device 110 is a function of at least the electrode geometry, electrode-tissue interface impedance, and the stimulating current amplitude. Providing an integrated device design and targeting the front, lateral or back thoracic dermatomes and/or C5-T1 dermatomes allows the patient to apply the electro-dermal patch device and stimulation independently. Prior art devices, particularly those stimulating the back (posterior side), require a medical professional for application.

In some embodiments, the electro-dermal patch device 110 stimulates areas in the T6 and/or T7 dermatome. In some embodiments, the electro-dermal patch device 110 stimulates areas in at least one of T6 through T10 dermatomes. In some embodiments, the electro-dermal patch device 110 stimulates areas in the C8 and/or T1 dermatome on the hand of a patient. In still other embodiments, the electro-dermal patch device 110 stimulates areas in the T6, T7, C8 and/or T1 dermatomes.

In one embodiment, as shown in FIG. 18A, the electro-dermal patch device 1800 stimulates the T6 dermatome, including meridians. In another embodiment, as shown in FIG. 18B, the electro-dermal patch device 1810 stimulates the T7 dermatome. In yet another embodiment, as shown in FIG. 18C, the electro-dermal patch device 1820 stimulates both the T6 and T7 dermatomes. In some embodiments, referring to FIG. 18A, an electro-dermal patch device 1800 delivers, through one or more electrodes disposed in a pad or skin patch, electrical stimulation 1802 above a rib (T6) and electrical stimulation 1804 below the rib (T6) to stimulate an intercostal nerve 1805 and the T6 dermatome. In one embodiment, the EDP device 1800 is positioned 2 cm below the margin or edge of the rib cage (on at least one of either side of the abdomen) to stimulate the T6 dermatome. In other embodiments, referring to FIG. 18B, an electro-dermal patch device 1810 delivers, through one or more electrodes disposed in a pad or skin patch, electrical stimulation 1812 above a rib (T7) and electrical stimulation 1814 below the rib (T7) to stimulate an intercostal nerve 1815 and the T7 dermatome. In one embodiment, the EDP device 1810 is positioned 2-6 cm (preferably 3.5 to 4.5 cm) below the margin or edge of the rib cage (on at least one of either side of the abdomen) to stimulate the T7 dermatome. In yet other embodiments, referring to FIG. 18C, an electro-dermal patch device 1820 delivers, through one or more electrodes disposed in a pad or skin patch, electrical stimulation 1822 below a rib (T6) and above a rib (T7) and electrical stimulation 1824 below a rib (T7) to stimulate intercostal nerves 1825, 1835 and the T6 and T7 dermatomes. In one embodiment, the EDP device 1820 is positioned 2.5 cm to 3.5 cm below the margin or edge of the rib cage (on at least one of either side of the abdomen) to stimulate both the T6 and T7 dermatomes.

In one embodiment, the electro-dermal patch device 1800 is positioned on a very specific portion of the patient's T6 dermatome. Specifically, the EDP device 1800 is positioned on the left upper quadrant along the mid-clavicular line, 2 cm below the ribcage at a 90 degree angle towards the abdominal wall at a depth of approximately 0.5-1 cm. In other words, the EDP device 1800 is positioned at the intersection of two lines drawn on a standing patient: a first line vertically down from a mid-clavicle and a second line horizontally across from the xyphoid process. The first and second lines would form an angle of 90 degrees on the right side and left side of the anterior trunk of the patient.

In accordance with an aspect of the present specification, the T6 dermatome is stimulated to treat conditions such as obesity, over-weight, eating disorders, metabolic syndrome and/or for appetite suppression. In accordance with another aspect of the present specification, the T7 dermatome is stimulated to treat T2DM (Type 2 Diabetes Mellitus). In accordance with yet another aspect of the present specification, any one of T6 through T10 dermatome is stimulated to treat T2DM. In accordance with yet another aspect of the present specification, up to two dermatomes, such as T6 and T7, are simultaneously or alternatingly stimulated to treat multiple conditions (e.g., appetite suppression and T2DM). In accordance with still another aspect of the present specification, any two dermatomes, from T6 through T10 dermatomes, are simultaneously or alternatingly stimulated. In accordance with another aspect of the present specification, the C8 or T1 dermatome is stimulated to treat conditions such as obesity, over-weight, eating disorders, metabolic syndrome and/or for appetite suppression. In accordance with yet another aspect of the present specification, up to two dermatomes, such as C8 and T1, are simultaneously or alternatingly stimulated. In still further embodiments, T6, C8 and/or T1 dermatome is stimulated to treat conditions such as obesity, over-weight, eating disorders, metabolic syndrome and/or for appetite suppression, while the T7 dermatome is stimulated to treat T2DM (Type 2 Diabetes Mellitus). In still additional embodiments, multiple dermatomes are simultaneously stimulated, for example any one or any combination of T6, T7, C8 and/or T1 dermatomes are stimulated simultaneously.

Figure 19D:
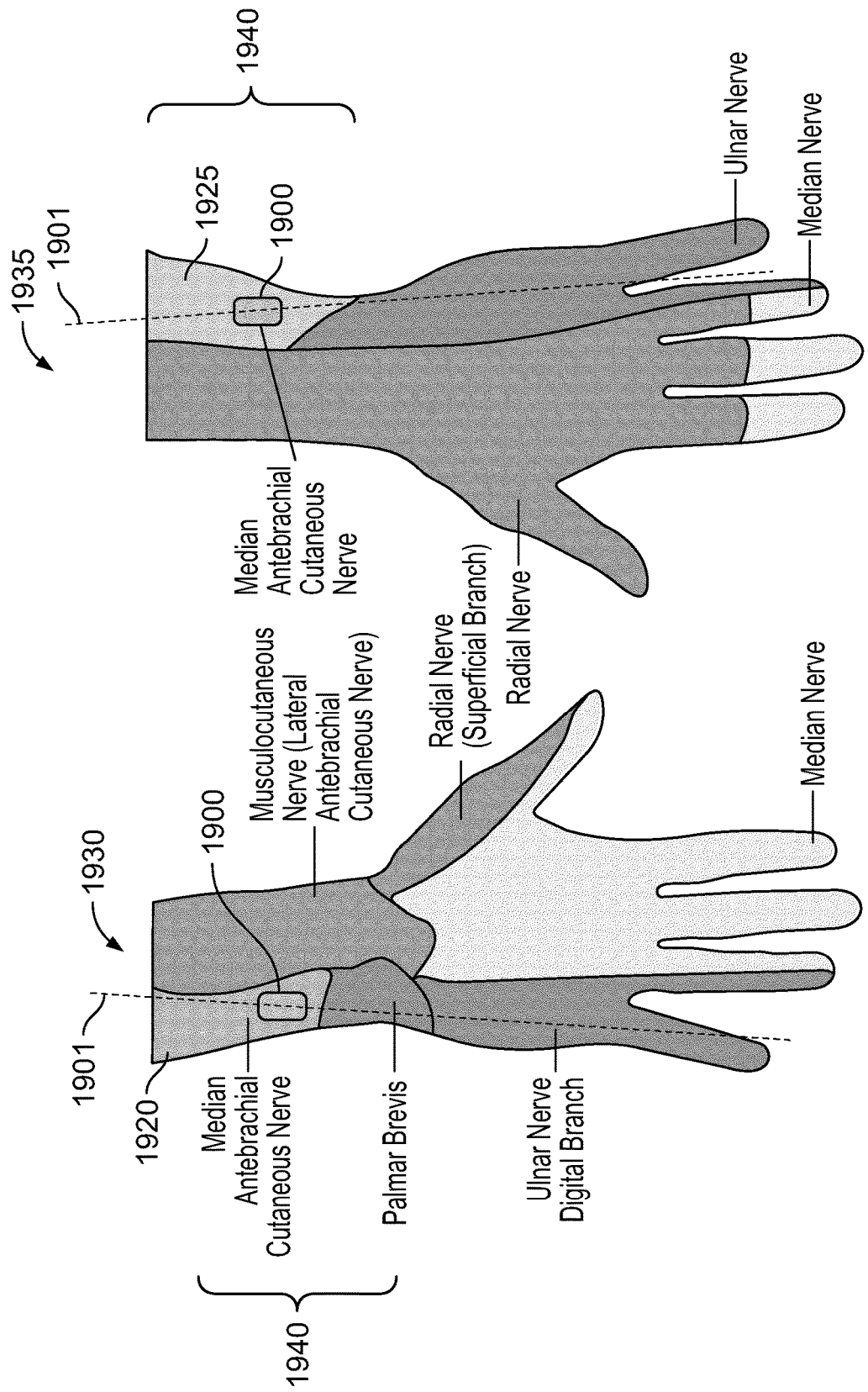
FIG. 19D illustrates median nerve stimulation position of the ventral and dorsal side of the user's lower arm or wrist regions using an electro-dermal patch, in accordance with certain embodiments.

In some embodiments, the electro-dermal patch device 110 stimulates areas in the C8 and/or T1 dermatome on the hand of a patient. In still other embodiments, the electro-dermal device 110 stimulates the median nerve at the wrist region. In one embodiment, as shown in FIG. 19A, the electro-dermal patch device 1900, through one or more electrodes disposed in a pad or skin patch, stimulates the C8 dermatome on the front (palm) or ventral side 1905 of the hand 1910. In another embodiment, as shown in FIG. 19B, the electro-dermal patch device 1900, through one or more electrodes disposed in a pad or skin patch, stimulates the C8 dermatome on the back or dorsal side 1906 of the hand 1910. In yet another embodiment, as shown in FIG. 19C, the electro-dermal patch device 1900, through one or more electrodes disposed in a pad or skin patch, stimulates both the C8 and T1 dermatomes by being placed on the front or ventral side of the lower arm or wrist region 1915. In some embodiments, as shown in FIG. 19D, the electro-dermal patch device 1900, through one or more electrodes disposed in a pad or skin patch, stimulates the epidermis region 1920 on the front side 1930 and/or the epidermis region 1925 on the back side 1935 of the wrist region 1940 to target the median nerve.

It should be appreciated that, in various embodiments, the electro-dermal patch device 1900 is placed in-line with the patient's fingers, such that a longitudinal axis 1901 of the electro-dermal patch device 1900 is approximately in the direction of the fingers. However, in various alternate embodiments the electro-dermal patch device may not be placed in-line with the patient's fingers. In various embodiments, the electro-dermal patch device 1900 is placed on a non-dominant hand of the patient. In some embodiments, the electro-dermal patch device 1900 is preferably placed on the back or dorsal side of the hand (as shown in FIG. 19B) as the patient's palm (ventral side) comes into contact with many surfaces in daily routine that may cause damage to the electro-dermal patch device 1900.

In accordance with an aspect, the electro-dermal patch device 1900 is sufficiently flexible so that it conforms to the contour of the user's hand 1910 and does not interfere in free movement of the hand 1910. Referring back to FIG. 1A, to enable sufficient flexibility of the electro-dermal patch device 110 (that is, electro-dermal patch device 1800 configured as a skin patch as shown in FIGS. 19A through 19C) the underlying electronics such as the microcontroller 112, transceiver 114, the pulse generator 116 and the power management module 120 including the receptor slots 130 are mounted on flexible plastic substrates, such as polyimide, PEEK (Polyether Ether Ketone) or transparent conductive polyester film—to form flex circuits. Alternatively, the underlying electronics are substantially miniature so that their rigid substrate, in some embodiments, do not need to flex over their small area. In some embodiments, the power management module 120 including the receptor slots 130, the actuators 122 and the indicators 124, 126 are physically separated or at a distance from the electronic circuitry such as the microcontroller 112, transceiver 114, and the pulse generator 116 to enable increased flexibility. In various embodiments, the housing 111 of the electro-dermal patch device 110 is of a flexible material such as silicone, rubber or any other flexible polymer known to persons of ordinary skill in the art.

Figure 20B:
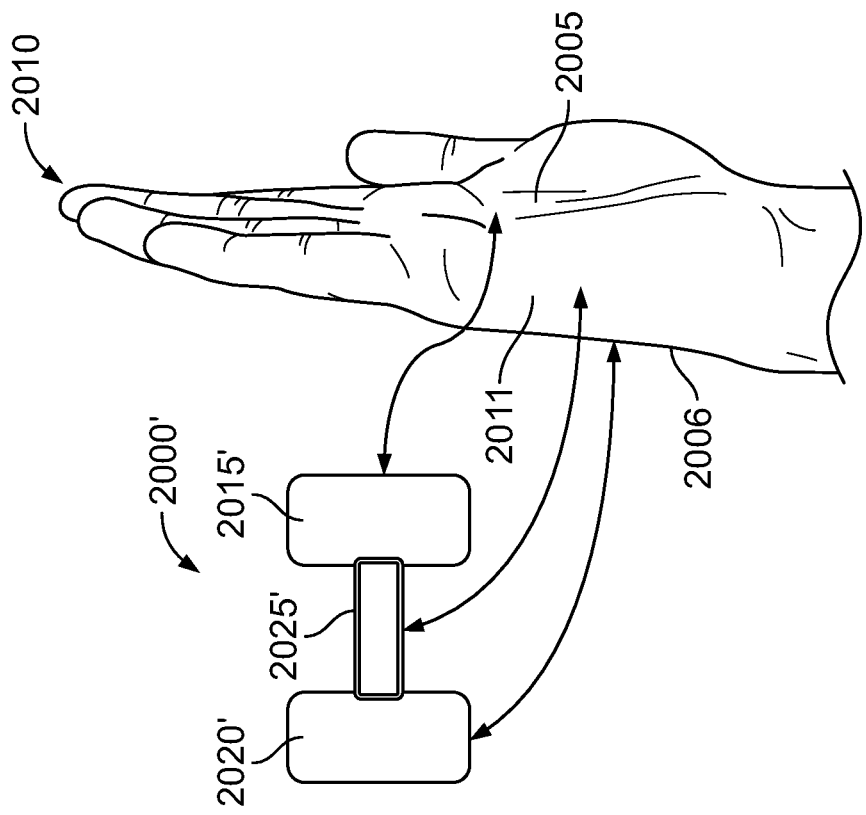
FIG. 20B illustrates another embodiment of an electro-dermal patch device of the present specification wrapped around the edge of the user's hand for stimulating the C8 dermatome.
Figure 20A:
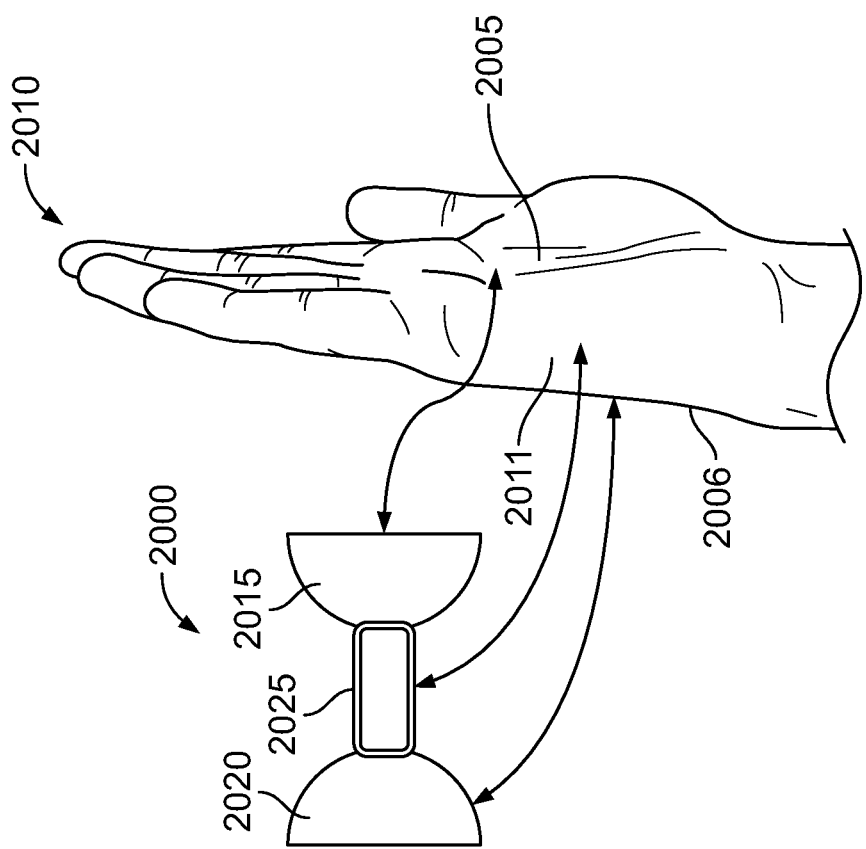
FIG. 20A illustrates an embodiment of an electro-dermal patch device of the present specification wrapped around the edge of the user's hand for stimulating the C8 dermatome.

In some embodiments, the electro-dermal patch device, through one or more electrodes disposed in a pad or skin patch, is configured to stimulate the C8 dermatome on the front (palm side) or ventral side as well as the back or dorsal side of the user's hand. In one embodiment, as shown in FIG. 20A, the electro-dermal patch device 2000 comprises a first patch portion 2015, a second patch portion 2020 and a third patch portion or bridge 2025 connecting the first and second patch portions 2015, 2020. In some embodiments, the first and second patch portions 2015, 2020 are substantially semi-circular shaped that are connected by a substantially rectangular bridge 2025 such that the electro-dermal patch device 2000 forms an approximate 'hourglass' shape. In another embodiment, as shown in FIG. 20B, the first and second patch portions 2015', 2020' are substantially rectangular that are connected by a substantially rectangular bridge 2025' such that the electro-dermal patch device 2000' forms an approximate 'H' shape. In various embodiments, the bridge 2025, 2025' is narrow (that is, the width is substantially less than the length of the bridge) to increase flexibility of this segment of the electro-dermal patch device 2000, 2000'. It should be appreciated that the 'hourglass' and 'H' shaped configurations of FIGS. 20A, 20B are non-limiting examples of the various shapes that the electro-dermal patch device may have in various embodiments.

In some embodiments, all three patch portions 2015, 2020 and 2025 are adhesive. However, in alternate embodiments only the first and second patch portions 2015, 2020 are adhesive while the bridge portion 2025 is non-adhesive to improve comfort, wearability tolerance and overall flexibility of the patches 2000, 2000'. The non-adhesive bridge portion 2025 may be configured into a thinner portion relative to the adhesive first and second adhesive patch portions 2015, 2020.

During use, the electro-dermal patch devices 2000, 2000' respectively wrap around the edge 2011 of the hand 2010 such that the first patch portion 2015 adheres to or lies on the front (palm) or ventral side 2005, the second patch portion 2020 adheres to or lies on the back or dorsal side 2006 while the bridge 2025 wraps around the edge 2011 of the hand 2010. In accordance with an aspect of the present specification, a first electrode is disposed in the first patch portion 2015 to stimulate the C8 dermatome on the ventral side 2005 and a second electrode is disposed in the second patch portion 2020 to stimulate the C8 dermatome on the dorsal side 2006 of the hand 2010.

In some embodiments, the electro-dermal patch devices 2000, 2000' are configured such that the underlying electronic circuitry including the power management module are disposed on one of the first or second patch portions 2015, 2020. Thus, referring to FIGS. 1A, 20A, 20B the electro-dermal patch device 110 is configured or disposed as patches 2000, 2000' of FIGS. 20A, 20B such that the microcontroller 112, transceiver 114, pulse generator 116, the power management module 120 including the receptor slots 130, actuators 122 and the indicators 124, 126 are located on either the first or the second patch portions 2015, 2020. In one embodiment, the microcontroller 112, transceiver 114, pulse generator 116, the power management module 120 including the receptor slots 130, actuators 122 and the indicators 124, 126 are located on the second patch portion 2020 i.e., the patch portion that adheres to the back or dorsal side 2006 of the hand 2010 to avoid damage to the electronic components from daily use.

In other embodiments, the electro-dermal patch devices 2000, 2000' are configured such that the underlying circuitry and the power management module are distributed between the first and second patch portions 2015, 2020. Thus, referring to FIGS. 1A, 20A, 20B the electro-dermal patch device 110 is configured or disposed as patches 2000, 2000' of FIGS. 20A, 20B such that the microcontroller 112, transceiver 114, pulse generator 116 the power management module 120 including the receptor slots 130, actuators 122 and the indicators 124, 126 are distributed and therefore physically separated between the first and second patch portions 2015, 2020 to improve flexibility of the electro-dermal patch devices 2000, 2000'. In one embodiment, the microcontroller 112, transceiver 114, pulse generator 116, actuators 122 and the indicators 124, 126 are located on, say, the first patch portion 2015 (that adheres to the ventral or palm side 2005 of the hand 2010) whereas the power management module 120 including the receptor slots 130 is located on the second patch portion 2020 (that adheres to the dorsal or back side 2006 of the hand 2010). In another embodiment, the microcontroller 112, transceiver 114, pulse generator 116, actuators 122 and the indicators 124, 126 are located on, say, the second patch portion 2020 (that adheres to the dorsal or back side 2006 of the hand 2010) whereas the power management module 120 including the receptor slots 130 is located on the first patch portion 2015 (that adheres to the ventral or palm side 2005 of the hand 2010).

Continuing to refer to FIGS. 1A, 20A, 20B, in one embodiment, the first and second electrodes 118 as well as the sensors 135 are disposed on the first patch portion 2015 i.e., the patch portion that adheres to the front (palm) or ventral side 2005 of the hand 2010. In another embodiment, the first and second electrodes 118 are disposed on the first patch portion 2015 while the sensors 135 are located on the second patch portion 2020. In yet another embodiment, the first and second electrodes 118 are disposed on the second patch portion 2020 while the sensors 135 are located on the first patch portion 2020. In still further embodiments, the first and second electrodes 118 are respectively disposed on the first and second patch portions 2015, 2020 while the sensors 135 are located on either the first or the second patch portion 2015, 2020. It should be noted that while in various embodiments, the electro-dermal patch devices of FIGS. 19A, 19B, 19C, 19D, 20A and 20B have been illustrated as being placed at locations on the hand of the user, in various alternate embodiments these electro-dermal patch devices may be placed at other points to stimulate the C5-C8 and/or T1 dermatomes on the user's arms or upper chest regions as well. It should further be appreciated that in some embodiments the hand dermatomes, such as the C5-T1 dermatomes, as well as the epidermis regions related to stimulation of the median nerve in the wrist region are stimulated using conductive metal electrodes (such as, but not limited to, of Gold) without any adhesive skin patches. In other words, the electrodes are not disposed in an adhesive skin patch. In such embodiments, the conductive metal electrodes are positioned on an appropriate epidermis (with user applied conductive gel, in some embodiments) to deliver electrical stimulation pulses without any skin patch. In an embodiment, the conductive metal electrodes stimulate dermatomes C8 and T1 at the location of the Median nerve under the wrist (ventral side). In one embodiment, the electrodes are positioned on opposing sides of the Median nerve.

In accordance with another aspect, the EDP device 110, 140 or 160 of FIGS. 1A through 1C is configured as a wearable gear to stimulate areas in the C8 and/or T1 dermatome on the hand of the patient. Accordingly, in some embodiments, the EDP device of the present specification is configured as a wristband or wristwatch, as shown in FIGS. 21A and 21B, respectively. It should be noted that as a wristband or wristwatch, the EDP device may not include an adhesive and the contact integrity with the user's skin may be less compared to stick-on patch configurations of the EDP device. Referring now to FIG. 21A, the wristband 2105 comprises a flexible band or strap 2110 that is worn to wrap around the wrist of the patient. The flexible band 2110 has an inner surface (not visible) that, when worn, interfaces with the skin of the patient and an outer surface 2115. The band 2110 is strapped around the wrist and held in place using conventional fastening means such as, but not limited to, Velcro, clasps, or buckle fastening. In accordance with an embodiment, the EDP device 2100, which may be similar to the EDP device 110, 140 or 160 of FIGS. 1A through 1C, is incorporated within the flexible band 2110 such that the inner surface of the flexible band 2110 exposes the one or more electrodes 2118 to touch the external surface of the patient's epidermal layer when the wristband 2105 is worn around the wrist. To enable visibility and for illustration purposes, the EDP device 2100 and the one or more electrodes 2118 have been shown exposed, in FIG. 21A, through the outer surface 2115. It should however be appreciated that the EDP device 2100, in various embodiments, lies embedded within and between the inner and outer surfaces of the flexible band 2110 while allowing only the one or more electrodes 2118 to be exposed through the inner surface of the band to allow contact with the patient's skin. In various embodiments, the EDP device 2100 is located within the band 2110 such that when worn, the one or more electrodes 2118 stimulate both the C8 and T1 dermatomes by touching or contacting the front or ventral side of the wrist region 2120. In a preferred embodiment, the EDP device 2100 is located within the band 2110 such that when worn, the one or more electrodes 2118 touch or contact the ulnar region (where dermatomes C8 and T1 meet) of the front or ventral side of the wrist region 2120.

In various alternate embodiments, the EDP device 2100 is configured in the form of an armband (instead of the wristband 2105). This embodiment is similar to the wristband 2105 in terms of the overall structure and design, however the flexible band 2110 is sized to be worn anywhere on the arm of the patient such that the one or more electrodes 2118 stimulate the C8 dermatome of the patient.

In another alternate embodiment, the EDP device is configured in the form of a wristwatch 2106 as shown in FIG. 21B. Referring to FIG. 21B, the wristwatch 2106 comprises a flexible band 2110 that is worn to wrap around the wrist of the patient. The flexible band 2110 has an inner surface 2114 that, when worn, interfaces with the skin of the patient and an outer surface 2115. The band 2110 is strapped around the wrist and held in place using conventional fastening means such as, but not limited to, Velcro, clasps, or buckle fastening. In accordance with an embodiment, the EDP device 2100, which may be similar to the EDP device 110, 140 or 160 of FIGS. 1A through 1C, is incorporated within the flexible band 2110 such that the inner surface 2114 of the flexible band 2110 exposes the one or more electrodes 2118 that touch the external surface of the patient's epidermal layer when the wristwatch 2106 is worn around the wrist. In various embodiments, the EDP device 2100 is located within the band 2110 such that when worn, the one or more electrodes 2118 stimulate both the C8 and T1 dermatomes by touching or contacting the front or ventral side of the wrist region. A dial 2125, which, in some embodiments, comprises a GUI (Graphical User Interface) attached to the band 2110, is located on the dorsal side of the wrist when the wristwatch 2106 is worn by the patient. In a preferred embodiment, the EDP device 2100 is located within the band 2110 such that when worn, the one or more electrodes 2118 touch or contact the ulnar region (where dermatomes C8 and T1 meet) of the front or ventral side of the wrist region.

In some embodiments, the flexible band 2110 can be removed from the dial 2125 and replaced with another similar flexible band. In still other embodiments, the flexible band 2110 is detachable from the dial 2125 and worn at the wrist, arm or hand separate from the dial 2125. In such embodiments, the EDP device 2100 located within the flexible band 2110 is in wireless data communication with a smartphone (functioning as a companion device) of the user. In still other embodiments, the EDP device 2100 configured to be worn on the wrist, arm or band, such as in FIG. 21A, is in data communication with the wristwatch 2106 of FIG. 21B that, alternatively, may not include the EDP device therein. In some embodiments, wrist mounted EDP device configurations, such as those described with reference to FIGS. 21A, 21B, operate at pulse amplitudes ranging from 5 mA to 10 mA.

In various embodiments, the hand dermatomes, such as the C5-T1 dermatomes, as well as the epidermis regions related to stimulation of the median nerve in the wrist region are stimulated using conductive metal electrodes 2118 (such as, but not limited to, an embodiment where gold is used as the conductive metal) without the use of adhesive skin patches. In other words, the electrodes 2118 are not disposed in an adhesive skin patch. As discussed with reference to FIGS. 21A, 21B, the conductive metal electrodes 2118 are positioned on an appropriate epidermis (with user applied conductive gel, in some embodiments) to deliver electrical stimulation pulses without a skin patch. In an embodiment, the conductive metal electrodes 2118 stimulate dermatomes C8 and T1 at the location of the Median nerve under the wrist (ventral side).

In other embodiments, the EDP device of the present specification is configured in the form of hand gloves that may be one (for wearing in one hand only) or a pair of gloves (for wearing in both hands). FIGS. 22A, 22B, 22C and 22D respectively show first, second, third and fourth embodiments of hand gloves 2201, 2202, 2203, 2204 comprising at least one EDP device 2200a through 2200j together referenced as EDP device 2200. The gloves 2201, 2202, 2203, 2204 when worn, have an inner surface (not visible) that interface with the skin of the patient's hands, both on the ventral as well as the dorsal sides, and an outer surface 2215. In accordance with an embodiment, the at least one EDP device 2200 (2200a through 2200j), which may be similar to the EDP device 110, 140 or 160 of FIGS. 1A through 1C, is incorporated within the gloves 2201, 2202, 2203, 2204 such that the inner surface (of the gloves) exposes the one or more electrodes 2218 that touch the external surface of the patient's epidermal layer when the gloves are worn. To enable visibility and for illustration purposes, the EDP device 2200 and the one or more corresponding electrodes 2218 have been shown exposed, in FIGS. 22A through 22D, through the outer surface 2215. It should however be appreciated that the EDP device 2200, in various embodiments, lies on the inner surface of the gloves while allowing only the one or more electrodes 2218 to be exposed through the inner surface to allow contact with the patient's skin.

Figure 22A:
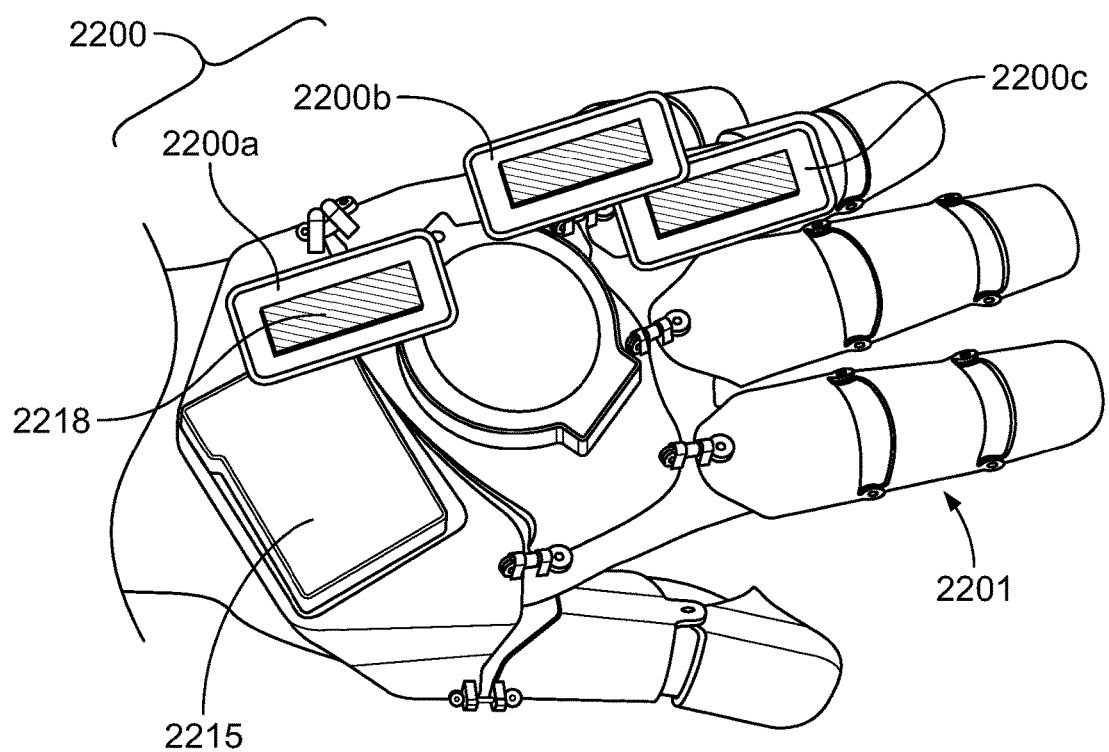
FIG. 22A illustrates a first embodiment of a hand glove incorporating one or more EDP devices of the present specification.
Figure 22B:
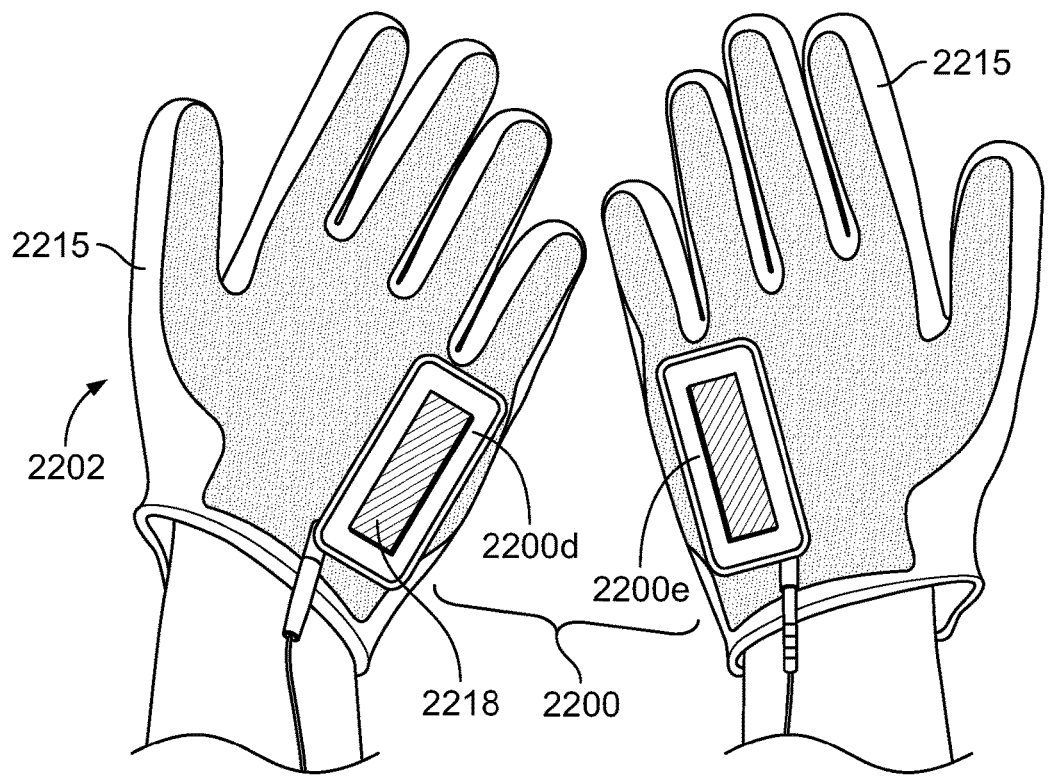
FIG. 22B illustrates a second embodiment of a pair of hand gloves incorporating one or more EDP devices of the present specification.
Figure 22C:
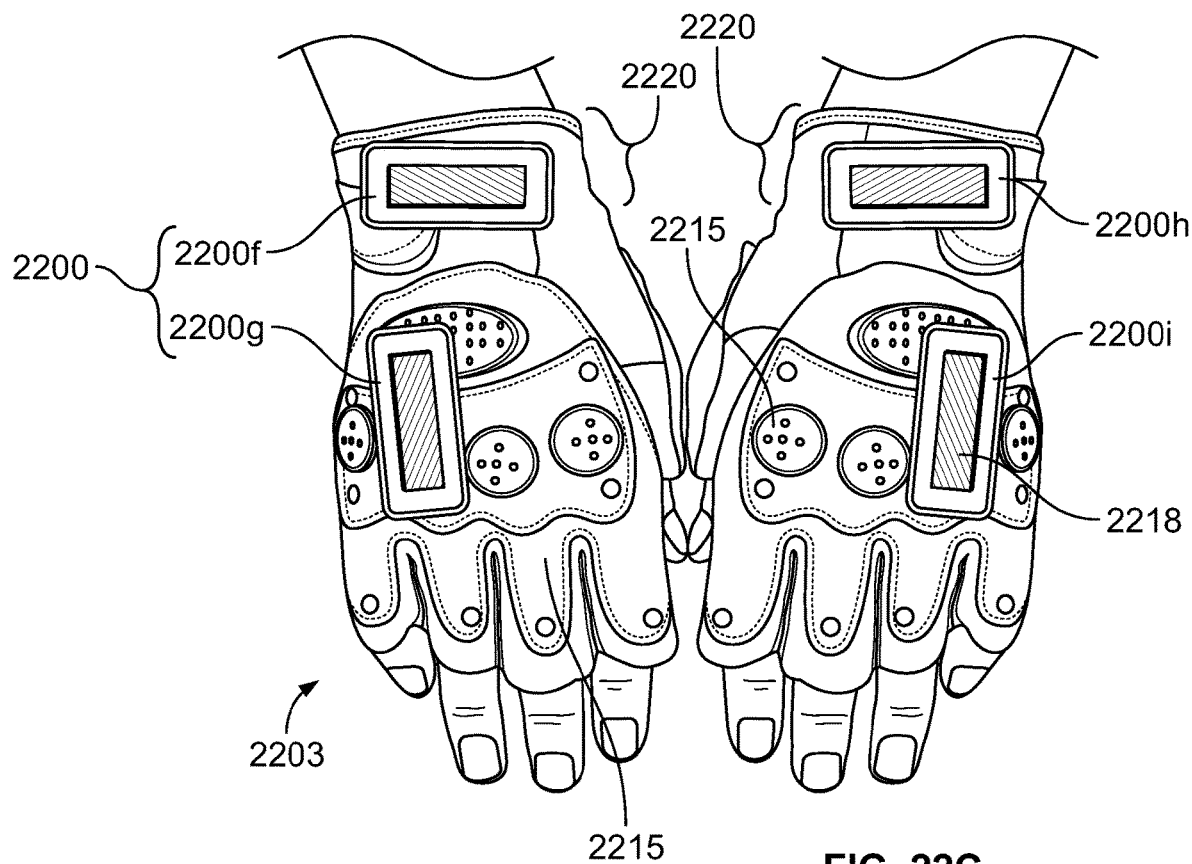
FIG. 22C illustrates a third embodiment of a pair of hand gloves incorporating one or more EDP devices of the present specification.
Figure 22D:
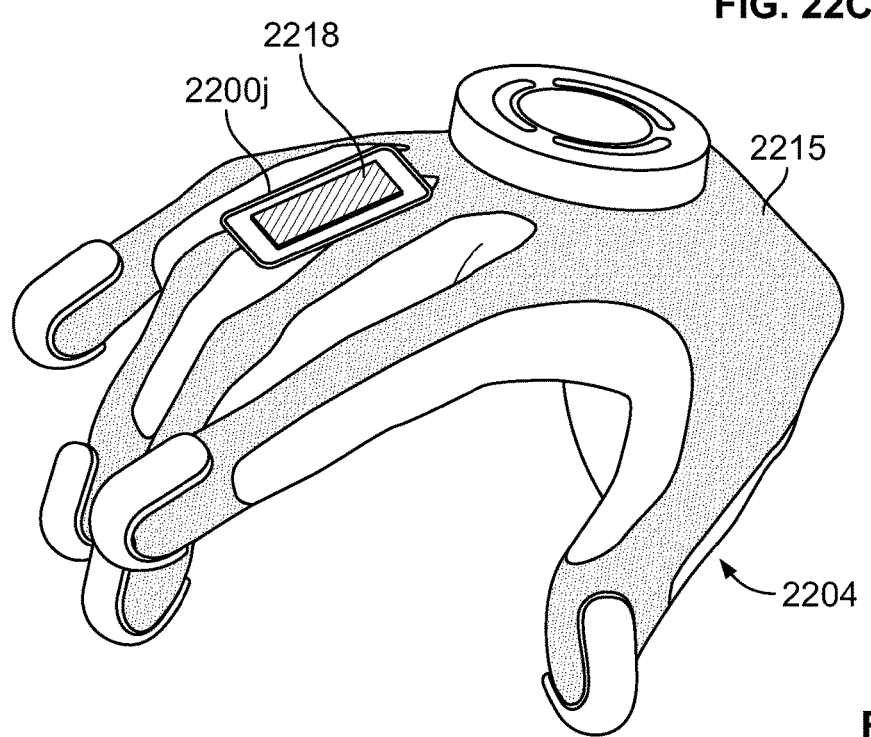
FIG. 22D illustrates a fourth embodiment of a hand glove incorporating at least one EDP device of the present specification.

FIGS. 22A through 22D illustrate a plurality of locations of one or more EDP devices 2200a through 2200j for stimulating the C5-C8 and/or T1 dermatomes of the patient's hands. While FIGS. 22A through 22D show the plurality of locations of one or more EDP devices 2200 (2200a through 2200j) on the dorsal side of the patient's hands, it should be appreciated that one or more EDP devices 2200 can alternatively or additionally be located on the ventral side of the patient's hands to stimulate the C8 and/or T1 dermatomes. Thus, in various embodiments one or more EDP devices 2200 are located such that their corresponding electrodes stimulate C5-C8 and/or T1 dermatomes on the dorsal and/or ventral sides of the patient's one or both hands. To stimulate both the C8 and T1 dermatomes, in one embodiment, at least one EDP device 2200 is located such that the corresponding electrodes 2218 contact the ulnar region of the patient's wrist as shown in FIG. 22C where the gloves 2203 extend over the wrist region 2220.

Figure 23:
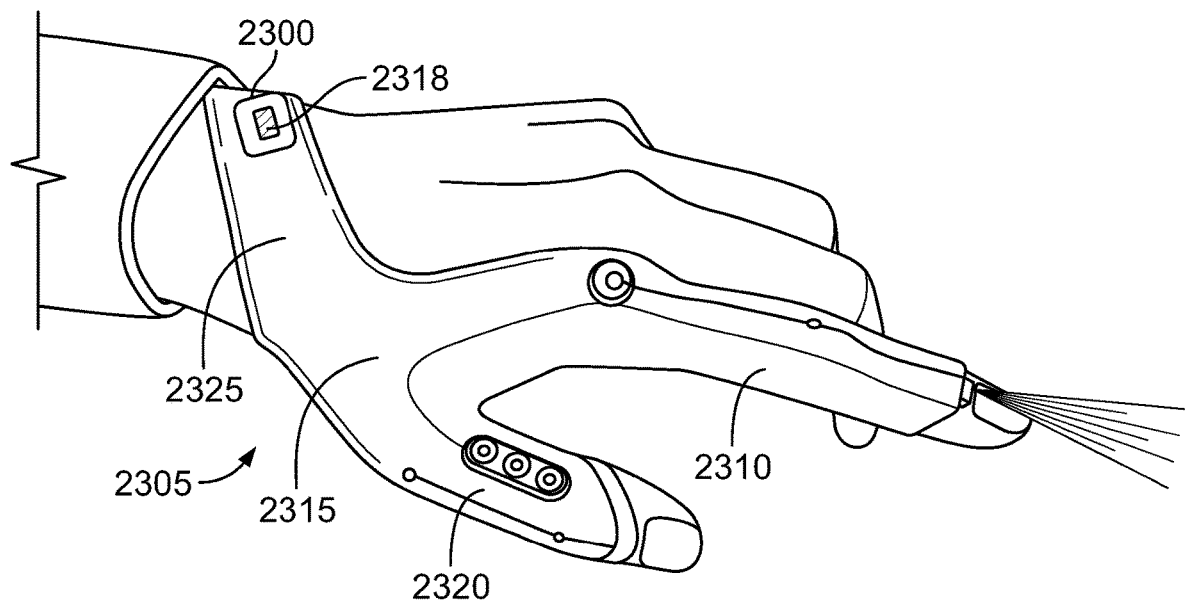
FIG. 23 is a perspective view of hand gear incorporating at least one EDP device of the present specification, in accordance with an embodiment.

FIG. 23 shows another embodiment where the EDP device is configured in the form of a hand gear 2305. The hand gear 2305 resembles a partial glove comprising an index finger wrap portion 2310, a thumb wrap portion 2320 and a wrist wrap portion 2325. The hand gear 2305 has an outer surface 2315 and an inner surface (not visible) that interfaces with the patient's skin when worn. In various embodiments, at least one EDP device 2300 (which may be similar to the EDP device 110, 140 or 160 of FIGS. 1A through 1C) is located on the inner surface of the hand gear 2305 such that one or more electrodes 2318 are exposed to contact the surface of the epidermal layer of the patient. To enable visibility and for illustration purposes, the EDP device 2300 and the one or more electrodes 2318 have been shown exposed, in FIG. 23, through the outer surface 2315. It should however be appreciated that the EDP device 2300, in various embodiments, lies on the inner surface of the hand gear 2305 enabling only the one or more electrodes 2318 to be exposed through to allow contact with the patient's skin. In accordance with various embodiments, the at least one EDP device 2300 is located at the wrist wrap portion 2325 to stimulate the C8 dermatome on the dorsal side of the wrist and/or to stimulate both the C8 and T1 dermatomes on the ventral side of the wrist. To stimulate both the C8 and T1 dermatomes, the EDP device is located such that its corresponding electrodes stimulate the ulnar region on the ventral side of the patient's wrist.

Figure 24:
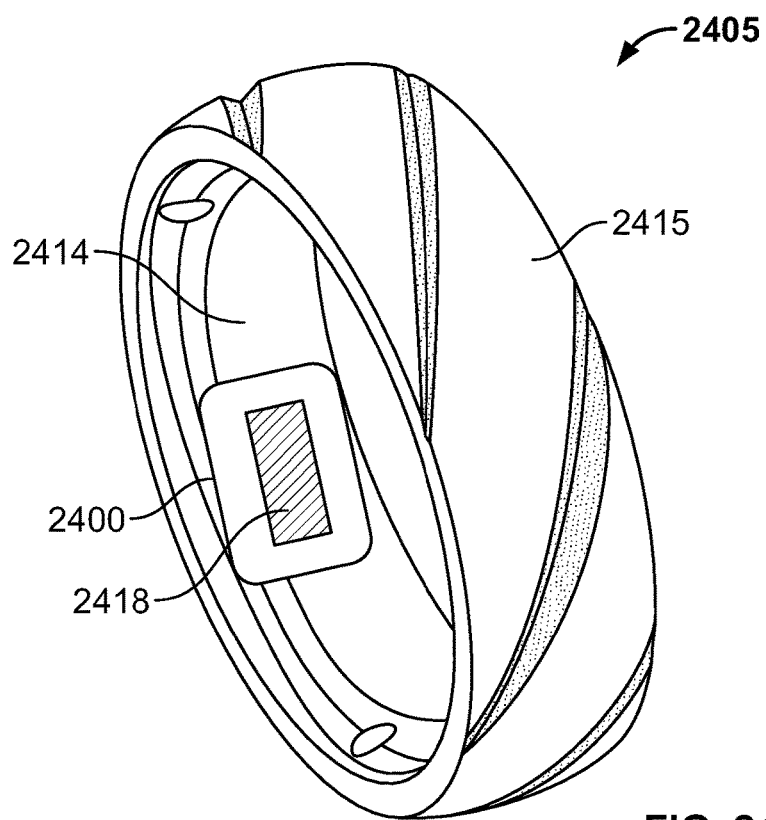
FIG. 24 is a perspective view of a finger ring incorporating an EDP device of the present specification, in accordance with an embodiment.

FIG. 24 shows another embodiment where the EDP device is configured in the form of a ring 2405 sized to be worn on the patient's little finger or pinky and/or the ring finger. The ring 2405 has an inner surface 2414 that interfaces with the patient's skin when worn and an outer surface 2415. In various embodiments, at least one EDP device 2400 (which may be similar to the EDP device 110, 140 or 160 of FIGS. 1A through 1C) is located on the inner surface 2414 (or alternatively embedded within the ring 2405 to lie between the inner and outer surfaces 2414, 2415) such that one or more electrodes 2418 are exposed to contact the surface of the epidermal layer of the patient, when the ring 2405 is worn. The one or more electrodes 2418 stimulate the C8 dermatome when the ring 2405 is worn on the little or ring finger by the patient. It should be appreciated that the one or more electrodes 2418 may contact the patient's skin (on the little or ring finger) anywhere along the circumference of the little or ring finger to stimulate the C8 dermatome.

Figure 25:
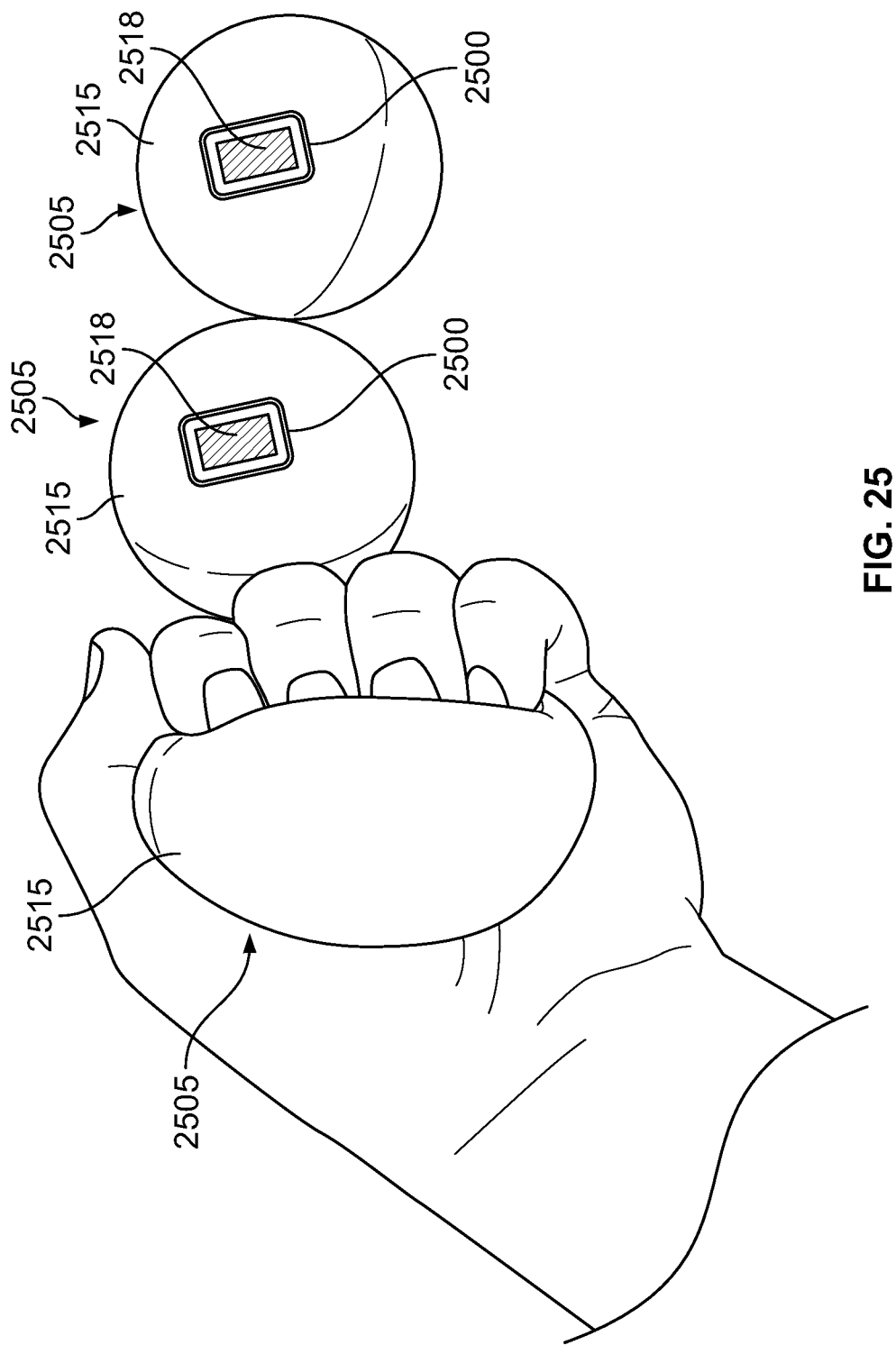
FIG. 25 illustrates a squeezable ball incorporating an EDP device of the present specification, in accordance with an embodiment.

FIG. 25 shows yet another embodiment where the EDP device is configured in the form of a squeezable toy or unit 2505 sized to be held within the hand of the patient. The squeezable toy 2505 may take any form such as, but not limited to, a ball (as shown in FIG. 25), a cylinder, an egg shaped toy or any other squeezable toy that can be held within the patient's hand and squeezed or compressed. As shown in FIG. 25, the squeezable toy 2505 has an outer surface 2515 that contacts the patient's skin when the toy 2505 is held in the hand by the patient. In various embodiments, at least one EDP device 2500 is located on the outer surface 2515 such that one or more electrodes 2518 of the EDP device contact the patient's skin when the toy 2505 is held in hand by the patient. Alternatively, the at least one EDP device 2500 may be placed within the toy 2505 such that one or more electrodes 2518 of the EDP device are exposed through the outer surface 2515 of the toy 2505 for contact with the patient's skin when the toy 2505 is held in hand by the patient. In accordance with an aspect of the present specification, the toy 2505 is held in the hand by the patient. The one or more electrodes 2518 contact the C8 dermatome of the patient's palm or ventral side of the hand. In one embodiment, the region exposing the electrodes 2518 on the toy 2505 is marked or tattooed indicating that the patient should hold the toy 2505 such that the mark/tattoo contacts the regions corresponding to the C8 dermatome.

In some embodiments, the one or more electrodes 2518 deliver stimulation when the toy 2505 is squeezed or compressed by the patient but switch off the stimulation when the toy 2505 is relaxed or uncompressed by the patient. Thus, repeated compression and relaxation of the squeezable toy 2505 results in repeated cycles of stimulation and non-stimulation of the C8 dermatome. In other embodiments, the one or more electrodes 2518 initiate stimulation when the toy 2505 is squeezed the first time and thereafter continue stimulation according to a pre-programmed stimulation protocol while the patient holds the toy 2505 in his hand. In still other embodiments, the one or more electrodes 2518 initiate a pre-programmed stimulation protocol when the toy 2505 is held in the hand by the patient (without being compressed or squeezed). Thereafter, the patient may continue to squeeze the toy 2505 periodically without affecting the application of the stimulation protocol.

Figure 26:
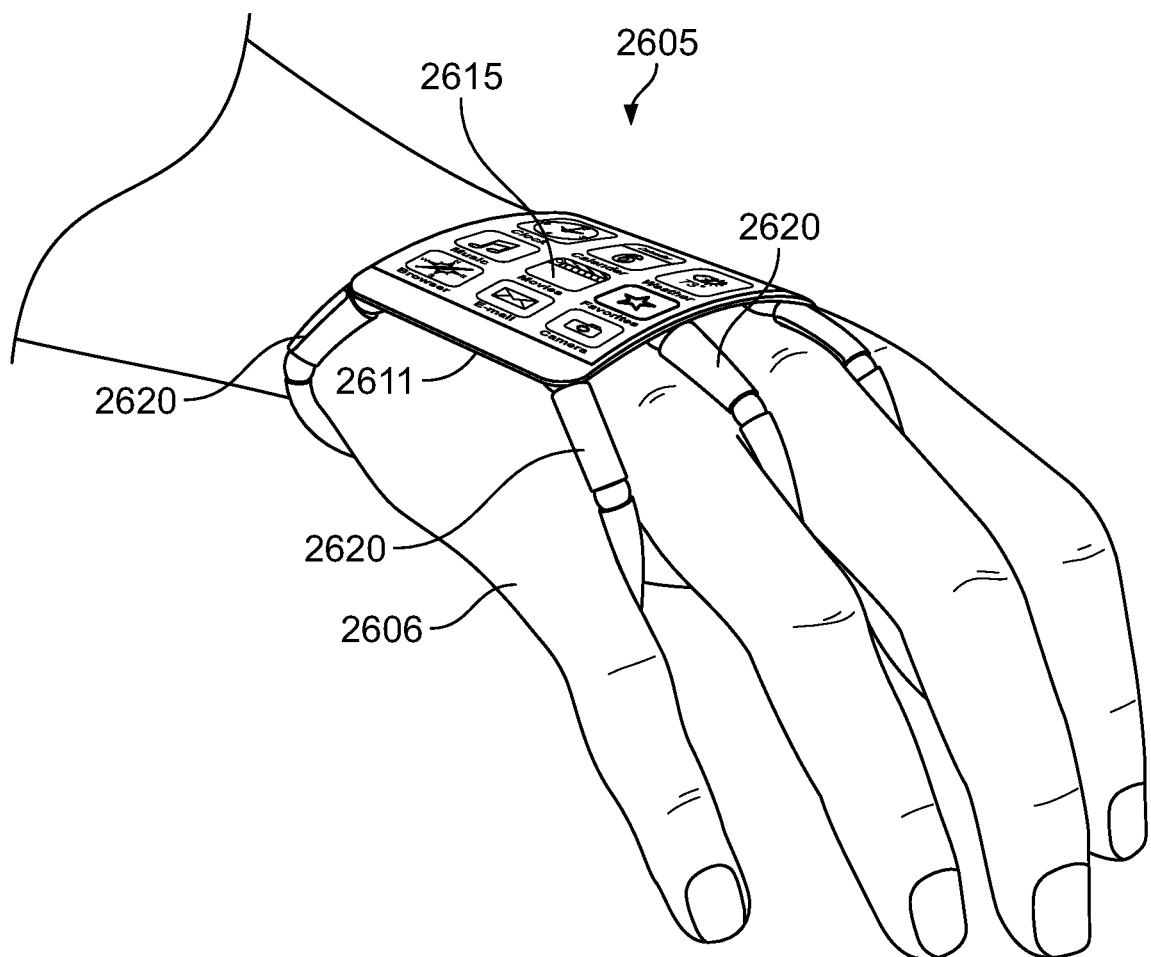
FIG. 26 illustrates hand gear incorporating an EDP device of the present specification, in accordance with an embodiment.

FIG. 26 shows still another embodiment where the EDP device is configured in the form of a hand or palm gear 2605. The hand gear 2605 comprises a housing 2611 having an upper or outer surface 2615 that includes a GUI display, for example, and a lower or inner surface (not visible) that touches the patient's skin on the dorsal side of the patient's hand 2606 when worn. A plurality of arms 2620 extend from the housing 2611 to enable the hand gear 2605 to be worn and held on the patient's hand 2606 as shown in FIG. 26. In various embodiments, the EDP device (not visible) is positioned within the housing 2611 such that the one or more electrodes of the EDP device are exposed through the lower or inner surface of the housing 2611 to enable contact with the patient's skin (on the dorsal side of the patient's hand 2606) when worn. In accordance with an embodiment, the one or more electrodes stimulate the C8 dermatome on the patient's dorsal side of the hand 2606.

Thus, in accordance with some aspects of the present specification, electrical stimulation from the external surface of the patient's epidermal layer through 10 mm or 20 mm of the dermis (using the electro-dermal patch device 110 of FIG. 1A) provides for a non-invasive treatment of appetite suppression, ghrelin production modulation, eating disorders, excessive weight or over-weight, obesity, metabolic syndrome and diabetes. In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein.

Mechanisms of Action

The therapeutic objectives of the presently disclosed embodiments may be effectuated by one or more of the following mechanisms of action. In a first mechanism of action, the pain of hunger is negated, operating under one or more predefined stimulation parameters. Small diameter nerve fibers carry pain stimuli through a theoretical "gate mechanism" but larger diameter nerve fibers can inhibit the transmission of pain stimuli by the smaller nerves, in effect blocking or closing this theoretical gate. It is believed that by stimulating the large nerve fibers, the gate can be closed to block the pain and thereby block any sensation of hunger. In a second mechanism of action, the production of endorphins, which are natural pain relieving hormones produced by the body, may be upregulated or increased, operating under one or more predefined stimulation parameters, again thereby blocking any sensation of hunger.

In a third mechanism of action, the present embodiments, operating under one or more stimulation parameters, causes a somato-somatic, somato-autonomic and/or a somato-visceral reflex with resulting afferent central as well as efferent visceral effects. In various embodiments, electrical stimulation from the external surface of the patient's epidermal layer through the dermis of the dermatomes disclosed herein creates a somatovisceral reflex with sensory nerves that connect specifically to the stomach as an efferent pathway. As a consequence of this stimulation, the stomach slows down its emptying process and increases the feeling of fullness, satiety or satiation, which translates into a reduction in appetite. Similarly, in various embodiments, electrical stimulation from the external surface of the patient's epidermal layer through the dermis of certain dermatomes, such as the T7 dermatome, also creates a somatovisceral reflex with sensory nerve endings to dermatome T7 as an afferent pathway and branches of the sensory nerves which stimulate the pancreatic gland as an efferent pathway.

In a fourth mechanism of action, the present application discloses a method of modifying an individual's perception of food, or otherwise undermining their association of positive feelings with food, and thereby increasing his or her aversion to or negative association with food intake comprising: providing an electrical dermal patch adapted to adhere to the patient's epidermal layer, wherein said electrical dermal patch comprises a controller, at least one electrode adapted to be in electrical contact with said patient's epidermal layer, and a pulse generator in electrical communication with the controller and said at least one electrode, defining a plurality of stimulation parameters, and programming the pulse generator to generate a plurality of electrical pulses using said plurality of stimulation parameters, wherein said plurality of stimulation parameters are defined such that, after applying at least one stimulation to the patient's epidermal layer, the patient has an increased aversion to food intake. In this regard, the stimulation parameters may be defined such that a) the stimulation is painful, b) the stimulation is coordinated with, and automatically triggered during, the person's actual food intake times, such times being programmed into the controller or pulse generator either directly or from an external device and automatically triggering a stimulation at the appropriate times, c) the stimulation is coordinated with, and automatically triggered during, times of day other than the person's actual food intake times, such times being programmed into the controller or pulse generator either directly or from an external device and automatically triggering a stimulation at such times, and d) the stimulation is manually triggered at any given time by the patient, either directly via an interface on the EDP or via the external device, as the patient may require. The benefit of this method is that it achieves, in addition to the physiological effects of appetite modulation, the psychological effect of associating a negative sensation (electrical stimulation) with food intake, thereby undermining the otherwise positive associations the individual has with food and, therefore, one of the key psychological impetuses for compulsive eating. In this regard, the present invention achieves an aversion to food intake, in addition to a decrease in appetite.

In accordance with an aspect, the fourth mechanism of action is agnostic of the dermatome of placement for the EDP device. In some embodiments, the user's negative association with food or the user's dissociation of positive feelings towards food is influenced and enhanced by timing the stimulation around meal consumption—such as substantially prior, during and/or after meals. In various embodiments, the EDP device stimulation influences non-specific dermatomes, cranial nerves, cervical and lumbosacral dermatomes in order to work through this mechanism.

In a fifth mechanism of action, the presently disclosed embodiments selectively cause electrical central nervous stimulation over electrical spinal stimulation. Electrical stimulation in the perceptive range is central (sensory) and in the non-perceptive range is spinal (autonomic). Electrical stimulation above a sensation reaction threshold results in selective central stimulation while electrical stimulation below the sensation reaction threshold results in selective spinal stimulation. Therefore, determining the sensation reaction threshold in a patient allows for the adjustment of electrical stimulation parameters for selective central or spinal stimulation to modulate the patient's appetite level.

Figure 27A:
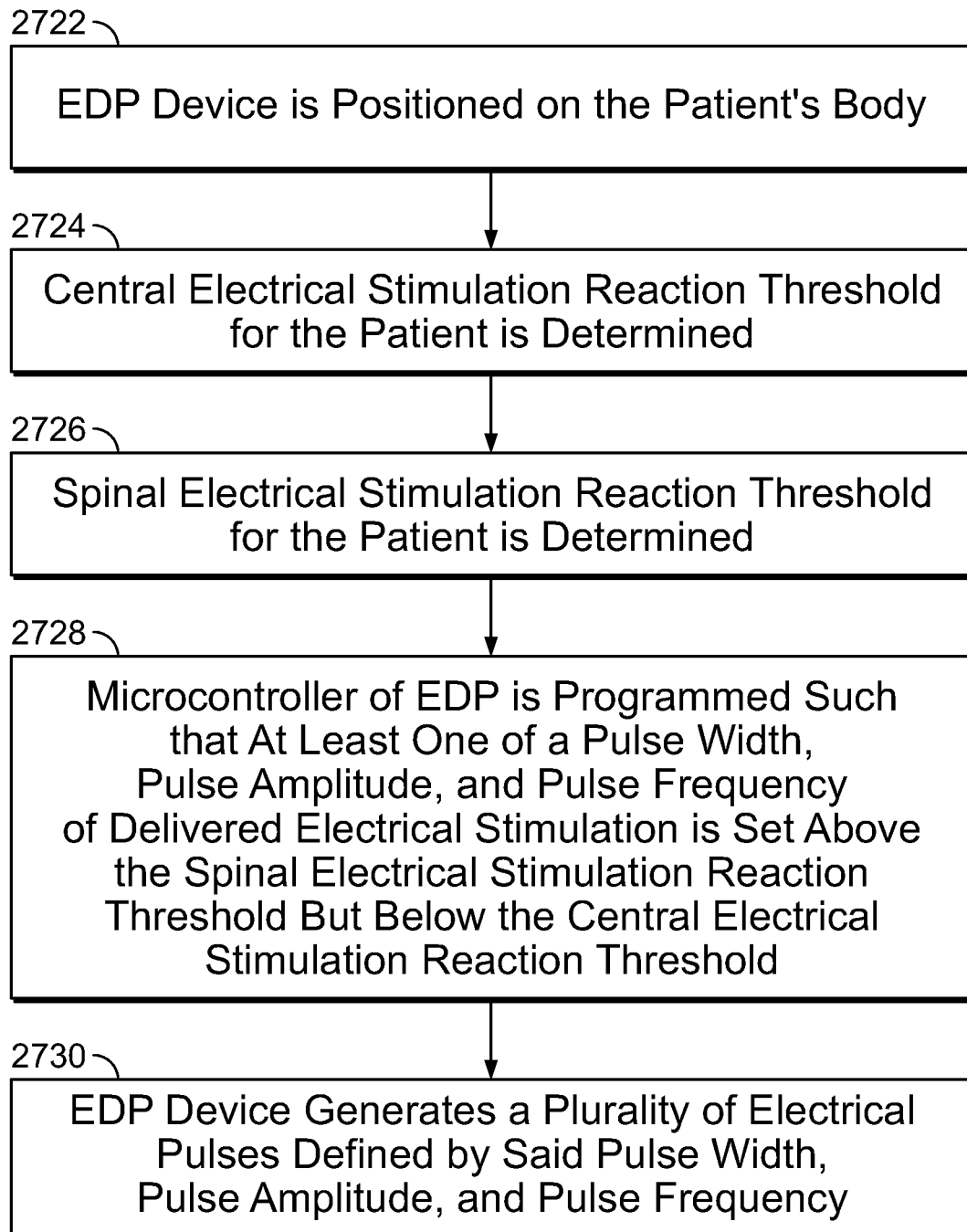
FIG. 27A is a flow chart illustrating the steps involved in a method of determining stimulation reaction thresholds and using an electro-dermal patch (EDP) device to suppress appetite in a patient, in various embodiments of the present specification.

FIG. 27A is a flow chart illustrating the steps involved in one embodiment of a method of determining stimulation reaction thresholds and using an electro-dermal patch (EDP) device to suppress appetite in a patient. At step 2722, the EDP device is positioned on the patient's body. At step 2724, a central electrical stimulation reaction threshold for the patient is determined. Then, at step 2726, a spinal electrical stimulation reaction threshold for the patient is determined. A microcontroller of the EDP device is then programmed, at step 2728, such that at least one of a pulse width, pulse amplitude, and pulse frequency of delivered electrical stimulation is set above the spinal electrical stimulation reaction threshold but below the central electrical stimulation reaction threshold. At step 2730, the EDP device then generates a plurality of electrical pulses defined by the pulse width, pulse amplitude, and pulse frequency set at step 2728.

Figure 27B:
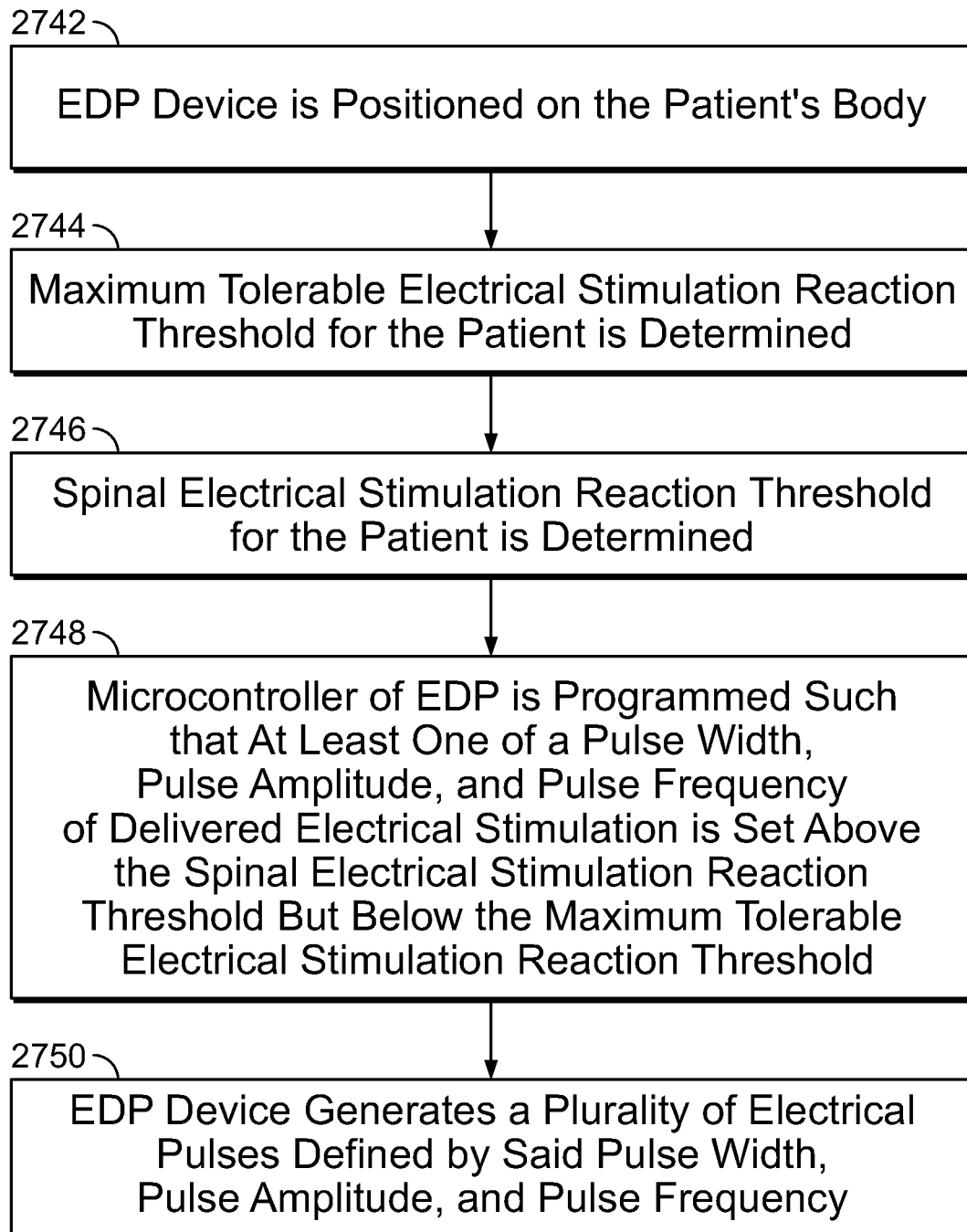
FIG. 27B is a flow chart illustrating the steps involved in a method of determining stimulation reaction thresholds and using an electro-dermal patch (EDP) device to suppress appetite in a patient, in various embodiments of the present specification.

FIG. 27B is a flow chart illustrating the steps involved in another embodiment of a method of determining stimulation reaction thresholds and using an electro-dermal patch (EDP) device to suppress appetite in a patient. At step 2742, the EDP device is positioned on the patient's body. At step 2744, a maximum tolerable electrical stimulation reaction threshold, which can be measured as a pain sensation, for the patient is determined. Then, at step 2746, a spinal electrical stimulation reaction threshold for the patient is determined. A microcontroller of the EDP device is then programmed, at step 2748, such that at least one of a pulse width, pulse amplitude, and pulse frequency of delivered electrical stimulation is set above the spinal electrical stimulation reaction threshold but below the maximum tolerable electrical stimulation reaction threshold. At step 2750, the EDP then generates a plurality of electrical pulses defined by the pulse width, pulse amplitude, and pulse frequency set at step 2748.

In a sixth mechanism of action, the electro-dermal patch (EDP) devices of the present specification stimulate specific dermatomes as described above to modulate ghrelin and suppress appetite. The gastric mucosa plays a role in ghrelin-induced gastric contractions. Intrinsic primary afferent neurons (IPAN), which comprise multi-axonal interneurons, may be involved in passing signals from the mucosa to the myenteric plexus. Ghrelin may stimulate and modulate gastric contractions through cholinergic, adrenergic, serotonergic, and/or opioidergic actions and/or via nitric oxide synthase in the myenteric plexus. The stimulatory effects of ghrelin on gastric motility are mediated by the direct stimulation of the intrinsic enteric neural pathway and capsaicin-sensitive afferent neurons. There exists a close interaction between ghrelin and enteric neurotransmission, involving the stimulation of the excitatory neural system and/or the suppression of the inhibitory neural system via ghrelin receptors, under stimulation of the intrinsic neural pathways. Ghrelin secretion during fasting is induced by adrenergic agents (locally released norepinephrine), released by neurons acting directly on B1 receptors on ghrelin secreting cells of the stomach, resulting in fasting-induced elevation in plasma ghrelin levels.

Stimulation at certain dermatomes, such as dermatome T6, causes a somato-visceral arc reflex which causes inhibition of the B1 adrenergic neurons that produce ghrelin. This results in a decrease in ghrelin levels. This decrease in ghrelin causes activity in the enteric nervous system and intrinsic primary afferent neurons contained in the gastric mucosa (necessary as a final step in ghrelin's action on gastric and antral motility).

Therefore, in various embodiments of the present specification, the EDP devices are believed to suppress appetite via the following mechanism. To begin, an EDP device delivers electrical stimulation to the cutaneous nerves at dermatome T6 (or any of the other dermatomes described in the present specification), activating the somato-visceral reflex described above. In some embodiments, the EDP device delivers electrical stimulation to the cutaneous nerves at dermatomes T5-T10. Stimulation of the B1 adrenergic plexus (neurons), which are inhibitory in nature, results in decreased production of fasting ghrelin. This leads to decreased activity in the enteric nervous system and in intrinsic primary afferent neurons (responsible for the final steps necessary for ghrelin action on gastrointestinal motility). The decreased plasma ghrelin levels result in appetite suppression as well as decreased gastric motility and decreased gastric emptying time.

In a seventh mechanism of action, the electro-dermal patch (EDP) device embodiments of the present specification use electrical stimulation to effect a reduction in antral or gastric activity resulting in a feeling of satiety over increased periods of time between meals. In one embodiment, through the application of the right stimulation parameters, antral motility may be modulated faster than gastric emptying time. Specifically, a greater than 10% change in antral motility may be achieved after applying one electrical stimulation session while gastric emptying times only increase by more than 10% after at least 2 sessions, with no changes after just 1 session. In one embodiment, a greater than 10% change in antral motility may be achieved after applying one electrical stimulation session while gastric emptying times only increase by more than 10% after at least 2 sessions, with each session on a different day and all sessions occurring within one week. In one embodiment, a greater than 10% change in antral motility may be achieved after applying one electrical stimulation session while gastric emptying times only increase by more than 10% after at least 3 sessions, with each session on a different day and all sessions occurring within one week.

In another mechanism of action, the electro-dermal patch (EDP) device embodiments of the present specification use electrical stimulation to effect a reduction in antral activity resulting in reduction in gastric motility and slowing of gastric emptying. Somatic stimulation of the T2-T12 and/or C5-T1 dermatomes, using the electro-dermal patch device of the present specification, affects modulation of the gastrointestinal phasic pressure activity resulting in reduction in antral motility and an increase in plasma beta-endorphin levels. Thus, somatic stimulation causes reduced post-prandial antral phasic pressure activity, slowing of gastric emptying and therefore a feeling of satiety over increased periods of time between meals.

Figure 47A:
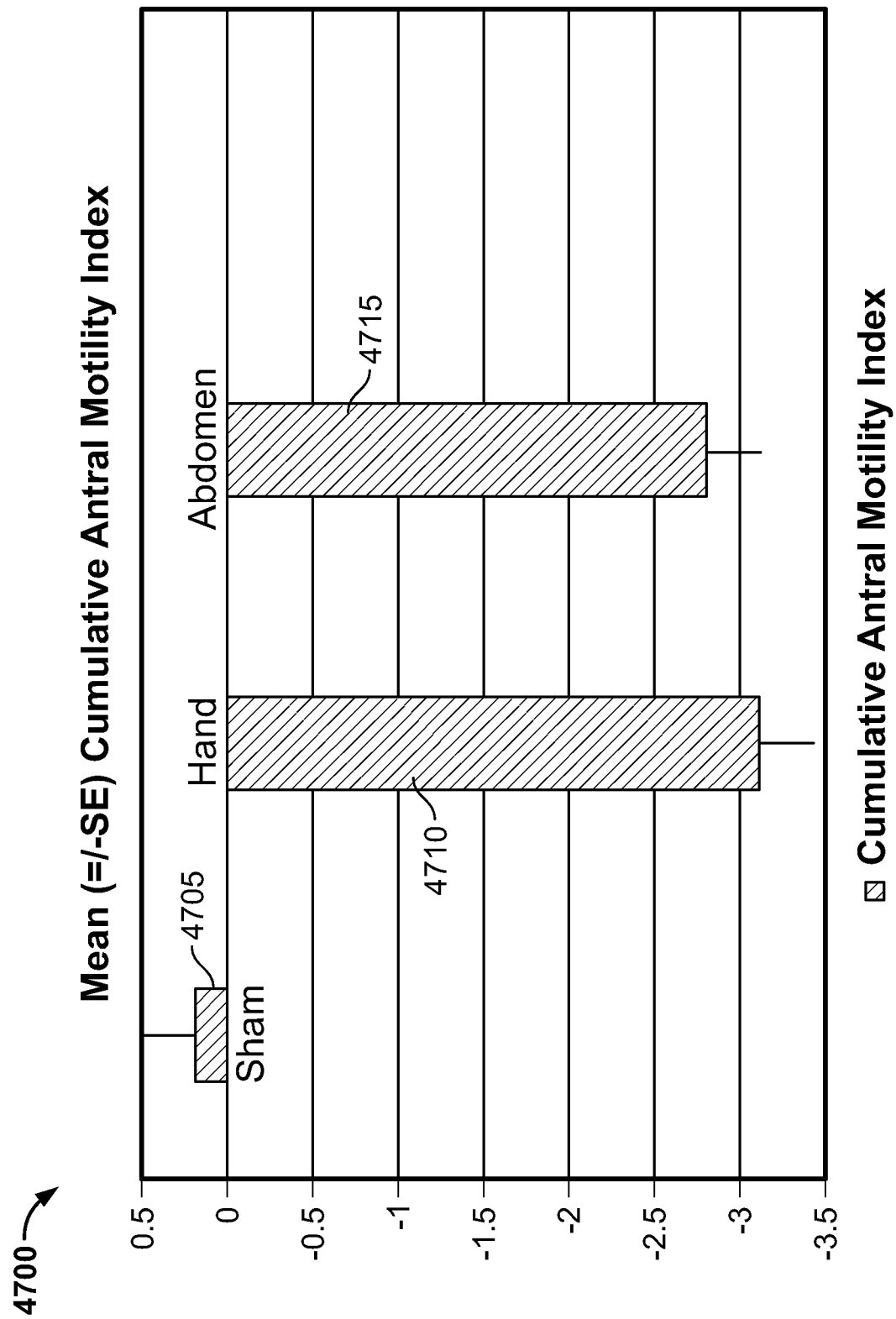
Figure 47B:
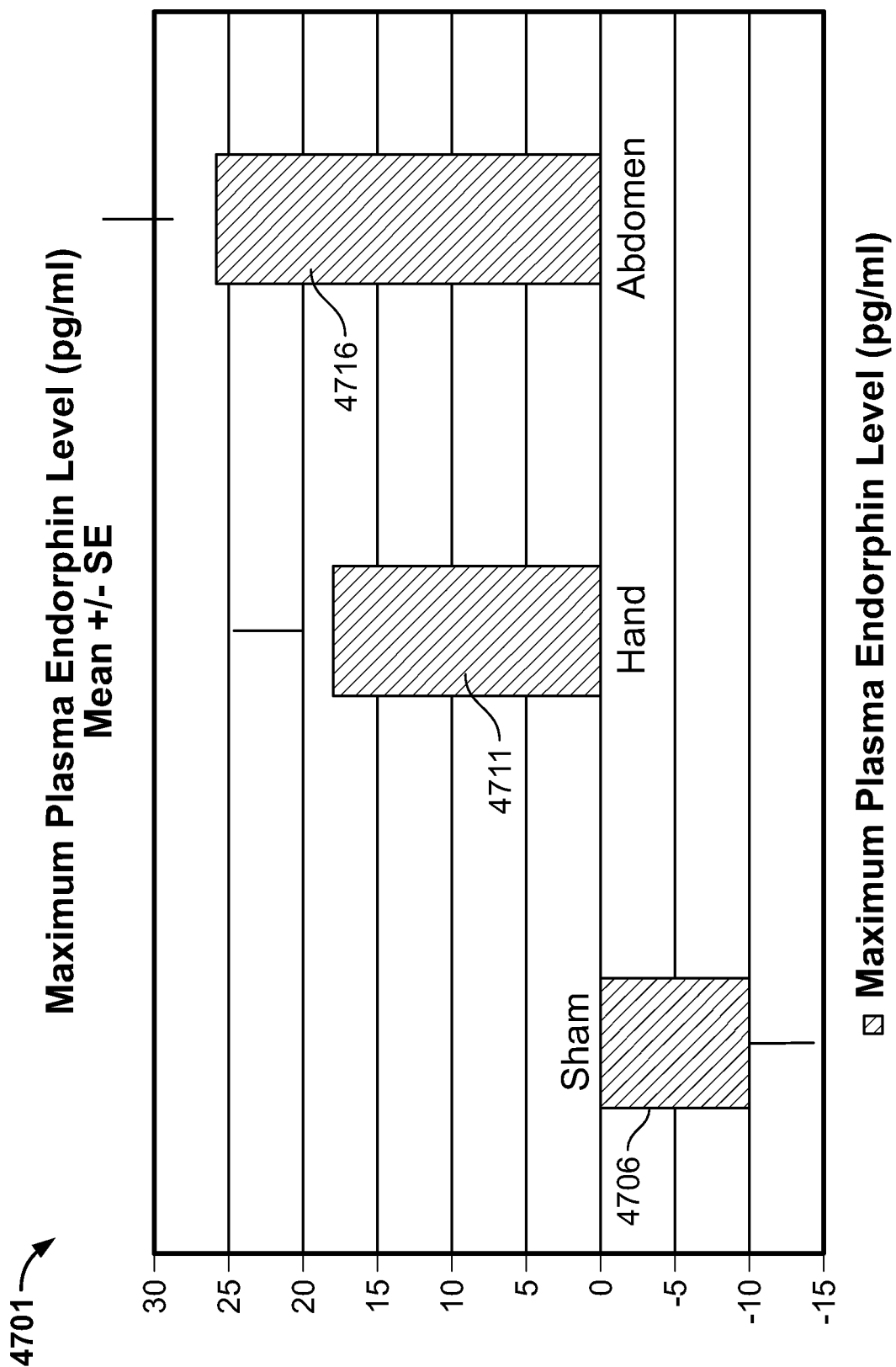

FIG. 47A is a chart 4700 illustrating mean cumulative changes (in 20 minutes increments) of antral motility indices during sham stimulation sessions 4705, stimulation sessions 4710 targeted to hand dermatomes C8 and/or T1 and stimulation sessions 4715 targeted to thoracic dermatomes T2-T12. Note the effect on antral motility of the hand and abdomen stimulation sessions. FIG. 47B is a chart 4701 illustrating maximum plasma endorphin levels in pg/ml related to sham stimulation sessions 4706, stimulation sessions 4711 targeted to hand dermatomes C5-C8 and/or T1 and stimulation sessions 4716 targeted to thoracic dermatomes T2-T12. Note the increase in endorphin levels as a result of the hand and abdomen stimulation sessions. In additional mechanisms of action, the electro-dermal patch (EDP) devices of the present specification use electrical stimulation to modulate gut microbiota to improve the ratio of favorable to unfavorable gut bacteria, modulate secretions of a plurality of hormones such as serotonin, glucagon-like peptide 1 (GLP1), and leptin, reduce serum levels of lipopolysaccharide (LPS), improve metabolic inflammation and insulin resistance, modulate resting metabolic rate (RMR) and by improving glucose homeostasis. The specific therapeutic objectives related to each of the above listed hormones and other physiological markers are further discussed below.

It should be appreciated that delayed gastric emptying causes improved post prandial glycemia and improved insulin sensitivity. Delayed gastric emptying causes food to remain in stomach for longer leading to decreased ghrelin production and therefore hunger attenuation. Thus, delayed gastric emptying delays the ghrelin cycle thereby overcoming the ghrelin induced 'urge to eat' effect, by ghrelin level diminution, on a daily basis.

In an eighth mechanism of action, the electro-dermal patch (EDP) devices of the present specification use electrical stimulation to effect an impairment in gastric distention/accommodation resulting in improved satiety, satiation and weight loss. The plurality of stimulation parameters are selected to cause at least one of: a therapeutically sufficient amount of delay in the patient's gastric emptying time, a therapeutically sufficient amount of increase in the patient's gastric retention, and/or a therapeutically sufficient amount of impairment in the patient's gastric distention/accommodation.

In a ninth mechanism of action, the electro-dermal patch (EDP) devices of the present specification use electrical stimulation to effect a reduction in plasma motilin resulting in a reduction in gastric motility and improved satiety, satiation and weight loss.

In a tenth mechanism of action, the electro-dermal patch (EDP) devices of the present specification use electrical stimulation to inhibit nitric oxide synthase around eating events (pre-eating/pre-prandial, during eating and post-eating/post-prandial) so as to maintain or increase gastric muscle tone, impair gastric accommodation/distention and increase gastric retention.

In some embodiments, one can measure the effects of eliciting somatovisceral reflexes through selective dermatomal stimulation in order to effect changes in antral pressure, antral motility, gastric emptying, satiation, satiety, ghrelin production, ghrelin circulation, GLP1, glycemia (Hemoglobin A1c), insulin, appetite, and weight (weight loss).

In accordance with some aspects of the present specification, the mechanisms of action related to abdominal cutaneous dermatomal stimulation (targeting T2-T1 and preferably T5-T10 dermatomes) involve activating somato-visceral reflexes that relay at the level of the spinal cord. Abdominal cutaneous dermatomal stimulation causes somatic and visceral afferents to converge on the same neurons on lamina 5 of the dorsal horn of the spinal cord, and depolarize one another and exert reciprocal pre-synaptic inhibition. This inhibition causes antral motility to decrease in both amplitude and frequency resulting in delayed gastric emptying, the feeling of satiation and satiety. This inhibition also produces a decrease in the production and circulation of stomach ghrelin. The summation of these effects causes appetite suppression and weight loss. In some embodiments, dermatomes T2-T12 and preferably, T5-T10, are selected for somatic electrical stimulation because these are the spinal levels from which outflow from the upper gut arises.

In accordance with some aspects, electrical stimulation of dermatomes C5-T1 and preferably, dermatomes C8-T1, are utilized to cause the same effect as stimulating dermatomes T2-T12 and preferably dermatomes T5-T10. When dermatomes C5-T1 and preferably dermatomes C8-T1 are electrically stimulated it elicits a centrally relaying somatovisceral reflex. Somatic afferent stimulation influence (in an inhibitory manner) efferents to the viscera if the entry and exit of the afferent and efferent limbs are separated by at most 2 spinal levels. Dermatomes C5-T1 and preferably dermatomes C8-T1 are only separated by one spinal level. The stimulation therapy of the present specification leverages this phenomenon to cause a stimulation of the somatovisceral reflex system resulting in inhibitory outcomes, and specifically, inhibition of upper gastro-intestinal motility. The similarity in response between stimulation of dermatomes T2-T12 and preferably T5-T10 (for example, on the trunk of the body) and dermatomes C5-T1 and preferably dermatomes C8-T1 (for example, on the wrist) demonstrates a dominance of central over spinal relay. This is further demonstrated by similar increases in beta endorphin levels whether electrical stimulation was performed at the abdominal or hand level. A further indication that dermatomal electrical stimulation of dermatomes T2-T12 and C5-T1, preferably T5-T10 and C8-T1, are inhibitory in nature is that plasma levels of norepinephrine, epinephrine, and dopamine are not altered. Also, heart rate, systolic and diastolic blood pressure are not altered when these dermatomes are electrically stimulated.

Conventional approaches to neuro-stimulation of the gastro-intestinal system to induce satiety or weight loss have typically focused on the parasympathetic nervous system (vagal nerve). The present specification is, however, directed towards electrical stimulation of the somatovisceral system to achieve satiety, appetite suppression, weight loss and improvement in glycemia. In other words, the mechanisms of action, in accordance with various aspects of the present specification, use external dermatomal stimulation to activate inhibitory pathways via the nervous system in order to a) slow antral motility (both amplitude and frequency) b) delay or slow down gastric emptying c) decrease appetite and cause weight loss d) decrease ghrelin e) increase insulin f) improve glycemia (Hemoglobin A1c) g) increase gastric retention/distention and h) reduce plasma motilin.

Stimulation of the somatovisceral system via transcutaneous electrical neurostimulation of targeted dermatomes is further enhanced by targeting stimulation sessions to coincide with specific pre- and post-prandial "metabolic windows". The pre-prandial window relates to the body's secretion of ghrelin just prior to anticipated eating. In some embodiments, approximately a 60 minute pre-prandial window is referred to as the "ghrelin window". Following a meal, there is a period of post-prandial digestive activity lasting up to about 2 hours, which is referred to as the "antral motility window". In various embodiments, the EDP system of the present specification enables timing stimulation within or around the ghrelin window (decreasing ghrelin and thereby reducing appetite) and/or the antral motility window (decreasing antral motility and thereby causing delayed gastric emptying and a feeling of satiety). These stimulation sessions can be triggered directly by patients (manually), triggered by a preset schedule (entered by the user, for example) or automatically triggered with reference to a detection of an eating event by a swallow detection device, such as the device 5605 of FIG. 56, for example, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B. In still additional embodiments, the stimulation sessions are triggered automatically by sensors configured to detect hunger or eating events/signals such as, but not limited to, gut sounds, expansion of stretch receptors.

The inhibitory mechanism of action, via the somatovisceral system, is enabled by the wearable EDP device of the present specification making it possible to time neurostimulation sessions to coincide with specific metabolic windows that occur around meal time throughout the day and week.

In a yet another mechanism of action, the electro-dermal patch (EDP) device(s) of the present specification may use superficial electrical stimulation of epidermal (cutaneous) nociceptor free ending nerves which use the myelinated A-delta fibers to transmit signals to the spinal cord (afferent pathway). The EDP device and HMA system of the present specification optimize electrical stimulation of these superficial nerves in the skin causing increased tactile sensitivity (for example, tingling) however, a) without causing pain, that is without breaching the pain threshold which in some embodiments is measured as a score on a VAS pain scale, and b) without causing involuntary skeletal muscle contractions or fasciculations (involuntary rapid flickering of muscles).

In accordance with still another mechanism of action, abdominal cutaneous dermatomal stimulation of T6-T7 dermatomes, using the electro-dermal patch (EDP) device(s) of the present specification, induces improved beta cell function of the pancreas.

Method of Use of the EDP of the Present Specification for the Treatment of Neurodegenerative Diseases As discussed throughout the specification, transcutaneous electrical neurostimulation of certain dermatomes results in a reduction of gastric emptying time and prolongs gastric retention. Using neurostimulation to reduce gastric emptying time, optionally in conjunction with direct neuromodulatory action on the sensory afferents may reduce insulin resistance and improve neurologic function in patients suffering from neurodegenerative diseases, such as Alzheimer's disease (AD), since AD, diabetes and obesity are linked by a common dependence on insulin signaling pathways in the central nervous system. Insulin resistance is a key factor to the development of AD pathology as insulin regulates not only energy homeostasis, but also synaptic plasticity and memory function.

Obesity is a key risk factor for developing insulin resistance. A higher level of fasting insulin resistance, measured with the homeostatic model assessment of insulin resistance (HOMA-IR) is associated with a decline in cognitive ability. Delayed gastric emptying via transcutaneous electrical stimulation of key dermatomes decreases fasting insulin resistance by at least 0.1% after a plurality of stimulation sessions. Transcutaneous electrical stimulation of dermatomes T6 and T7, among other dermatomes and according to the disclosed embodiments, may result in an increase in delayed gastric emptying time by 25% in overweight patients (BMI>25), a decrease of HOMA-IR by 0.5-1, an improvement in fasting insulin levels (part of the calculation used to determine HOMA-IR) by at least 15%, and a decrease in hemoglobin A1c (HbA1c) by 0.5, which is 50% of the effect seem with GLP-1 receptor agonists. Accordingly, in one embodiment, a plurality of transcutaneous electrical stimulation sessions results in a therapeutic endpoint that is within 30-70% of a therapeutically effective dose of glucagon-like peptide (GLP-1) receptor agonists.

Positive therapeutic results may also be achieved by applying transcutaneous electrical stimulation, in accordance with the disclosed embodiments, to treat Parkinson's disease (PD). Lowering HOMA-IR via stimulation of key dermatomes, such as dermatomes T6, would reduce extracellular accumulation of Aβ in plaques, the deposition of which is a key pathologic driver of AD. In addition, patients may see an increase in cerebral blood flow. Patients may see an increase of 15% in regional glucose metabolism. PD patients treated with transcutaneous electrical stimulation will show an improvement in "motor" and "non-motor" disease measures including cognition. Motor symptoms include bradykinesia, tremor, rigidity, and gait and postural disturbances and are typically measured by the Unified Parkinson's Disease Rating Scale (UPDRS part III) or Movement Disorder Society sponsored revision of the Unified Parkinson's Disease Rating Scale (the MDS-UPDRS-III).

Positive therapeutic results may also be achieved by applying transcutaneous electrical stimulation, in accordance with the disclosed embodiments, to treat Alzheimer's disease (AD). Cognitive gains in patients with AD can be assessed by multiple methods (in addition to formal neuropsychological testing). The Mini Mental Status Exam (MMSE) is one of the most widely used and validated bedside instruments for mental status evaluation. The Mattis Dementia Rating Scale (DRS), which yields a total DRS score, is a reliable and clinically useful measure of mental status in patients with AD. A score cutoff of less than 120 can be used to identify dementia. The DRS-2 is the more recent version of the DRS and is a frequently used assessment of cognitive status among older adults in both a clinical and research setting. Transcutaneous electrical stimulation, in accordance with the embodiments disclosed herein, would exhibit an average improvement in the treatment group of at least 2.5 points in the DRS-2 over 1 year, compared with deterioration in control patients.

Alternative scales which are appropriate tools to monitor dementia progression include the Severe Impairment Battery (SIB), the modified 19-item AD Cooperative Study—Activities of Daily Living Inventory (ADCS-ADL19), the Clinician's Interview-Based Impression of Change Plus Caregiver Input (CIBIC-Plus), the Neuropsychiatric Inventory, and the Behavioral Rating Scale for Geriatric Patients (BGP Care Dependency Subscale). Additional testing which may show benefit comes from the Montreal Cognitive Assessment (MoCA), which is a brief cognitive assessment capable of identifying specific memory deficits. Finally, the Wechsler Memory Scale (WMS-IV) is an effective tool for evaluating cognition via tests of orientation, time estimation, mental control, clock drawing, incidental recall, inhibition, and verbal reproduction. Transcutaneous electrical stimulation, in accordance with the embodiments disclosed herein, would exhibit an improvement in the treatment group as measured using any of the aforementioned scales.

By using electrical neurostimulation of certain key dermatomes, patients may see a combination of improved insulin resistance as measured by HOMA-IR, modification of amyloid burden, regional brain glucose metabolism, and direct action by sensory afferent stimulation, resulting in improvement of cognitive function.

Stimulation Patterns/Protocols to Drive Therapy

As discussed earlier, the user's plurality of health related information, such as the user's hunger profile, standard eating and meals profile, actual eating and meals profile, energy balance, weight trends, glucose data, stimulation induced nausea, dyspepsia and habituation events, are used by the Health Management application to suggest and/or implement a plurality of recommendations comprising stimulation patterns or protocols, medication (such as an amount of insulin intake, for example), dietary and/or activities plans. It should be appreciated that this integrated system provides users with a degree of independence and encourages patient compliance. Notwithstanding the above, however, the present application does apply to having physicians set or modify the stimulation protocols, either directly programming the EDP, programming the EDP through the companion device, or remotely communicating a desired protocol from a remote server or third party computing device to either the EDP directly or via the companion device.

In various embodiments, recommendations related to stimulation patterns or protocols comprise driving, setting, customizing or adjusting a plurality of stimulation parameters such as, but not limited to, the number of stimulation sessions per day; duration of each stimulation; time or moment of application of the stimulation sessions; intensity of stimulations, stimulation pulse shape, frequency, width and amplitude; stimulation duty cycle; stimulation continuity profile; minimum and maximum overall duration or course of stimulation treatment in days, weeks or months. Following are exemplary standard setting ranges for some of the stimulation parameters:

Pulse Width: 10 μsec to 10 msec

Pulse Amplitude: 100 μA to 500 mA, less than 60 mA, 100 μA to 100 mA, 100 μA to 500 mA, 1 mA to 30 mA, 15 mA to 30 mA, 5 mA to 45 mA, and any increment therein in the aforementioned ranges Pulse Frequency: 1 Hz to 10,000 Hz, preferably 1 Hz to 100 Hz and preferably 1 Hz to 100 Hz with no other frequencies greater than 100 Hz included in the stimulation signal Pulse Shape: Monophasic, biphasic, sinusoidal Duty Cycle: 1% to 100% calculated on a weekly basis Stimulation Session Duration: 1min to 120 min or 50 ms to 120 min or substantially continuously Number of Stimulation Sessions/Day: 1 to 24

Number of Sessions/Week: 1 to 168 or 1 to substantially continuously

Daily Pre-Prandial Stimulations: half hour to an hour prior to each meal every day, as most patients typically report hunger peaking just prior to meals Burst Mode (a burst of programmable pulses at a rate): 0.1 Hz to 100 Hz Ramp Up/Down Mode (the time it takes to go from no stimulation to a peak or steady state (Ramp Up) and the time it takes to go from peak or steady state stimulation to no stimulation (Ramp Down)): 0.1 sec to 60 sec Modulated Mode: Range between 1%-100% amplitude, modulating up/down over a period of 0.1 sec-60 sec; modulation can be linear or sinusoidal; that is, in "modulated mode" the amplitude varies between 1% and 100% of a target amplitude (such as 10 mA) and this amplitude variation occurs over a period of 0.1 seconds to 60 seconds Electrode impedance (the electrode-tissue interface impedance): 100 ohms to 5 kilo-ohms, 10 ohms to 5 kilo-ohms, 200 ohms to 1000 ohms, 500 ohms to 1000 ohms, or 1 kilo-ohms to 100 kilo-ohms In embodiments, a duty cycle of stimulation is optimized or adjusted such that the EDP device remains in sleep mode between consecutive stimulation sessions that correspond to an active mode of the EDP device. In various embodiments, the sleep mode corresponds to an average current of less than 10 µA while the active mode corresponds to an average current range of 2 to 30 mA.

In some embodiments, the electro-dermal patch device provides electrical stimulation having the following parameters which are adjustable by the patient using the companion device:

Monophasic pulse shape with an active charge balancing phase
Pulse Width: 25 µsec to 400 µsec in steps of 25 µsec
Pulse Amplitude: 1 mA to 50 mA in steps of 1 mA
Pulse Frequency: from 1 Hz, 5 Hz, 10 Hz, 15 Hz, 20 Hz, 25 Hz, 30 Hz, 40 Hz, 50 Hz, 60 Hz, 70 Hz, 80 Hz, 90 Hz, 100 Hz, 150 Hz, 200 Hz
Stimulation Session Duration: from 5 min to 60 min in steps of 5 min In some embodiments, the electro-dermal patch device provides electrical stimulation having the following parameters which are adjustable by the patient using the companion device:

Pulse Width: 100 µsec to 500 msec, preferably 10 µsec to 100 msec
Pulse Amplitude: 1 µA to 1 mA
Pulse Frequency: 0.1 Hz to 1 kHz
Stimulation Session Duration: 1 min to 24 hr
Number of Stimulation Sessions/Day: 1 to 24
Number of Sessions/Week: 1 to substantially continuously In various embodiments, the plurality of stimulation parameters are chosen or set to cause at least one of: a therapeutically sufficient amount of delay in the patient's gastric emptying time, a therapeutically sufficient amount of increase in the patient's gastric retention, a therapeutically sufficient amount of impairment in the patient's gastric distention/accommodation, a therapeutically sufficient amount of reduction in the patient's plasma motilin.

In one embodiment, the electrical pulses, whether in a single waveform or multiple waveforms, only have a frequency of up to 200 Hz and no greater. In other words, the system does not deliver any electrical pulse that has a frequency in excess of 200 Hz. In another embodiment, the electrical pulses are delivered in a single waveform and do not take the form of multiple waveforms integrated or combined together.

In various embodiments, the electro-dermal patch device, being wearable, enables providing electrical stimulation more frequently than one day per week. Also, the stimulation parameters and protocols are programmed to be therapeutically effective without triggering habituation, nausea and/or dyspepsia. Accordingly, in some embodiments, the amount of electrical stimulation delivered is equal to or greater than energy equivalent of 30 minutes per day at an amplitude of 20 mA (or equals, say, 10 mA hours=10 mA×60 minutes of energy equivalent) but less than 240 mA hours per day (that is less than, say, 12 hours at 20 mA, 6 hours at 40 mA or 24 hours at 10 mA), with the delivered amount including every energy increment between the minimum and maximum amounts. In other embodiments, a minimum amount of electrical stimulation delivered is an energy equivalent of 5 minutes per day at 10 mA, whereas a maximum amount of electrical stimulation delivered is an energy equivalent of 12 hours per day at 30 mA, with the delivered amount including every energy increment between the minimum and maximum amounts. In accordance with some embodiments, a weekly minimum amount of electrical stimulation delivered is an energy equivalent of 30 minutes per day at 10 mA delivered 3 days per week (which for a patient's minimum estimated skin resistance of 400 Ohms is equal to about 5 Joules per session or 15 Joules per week), whereas a weekly maximum amount of electrical stimulation delivered is an energy equivalent of 24 hours per day at 30 mA delivered 7 days per week (which for a patient's maximum estimated skin resistance of 1000 Ohms is equal to about 44,000 Joules per week), with the delivered amount including every energy increment between the minimum and maximum amounts. In an alternate embodiment, the weekly maximum amount of electrical stimulation delivered is an energy equivalent of 12 hours per day at 45 mA delivered 7 days per week. In another embodiment, a weekly minimum amount of electrical stimulation delivered is 60 Joules with two stimulation sessions of 30 Joules per stimulation at 20 mA, whereas a weekly maximum amount of electrical stimulation delivered is 13,000 Joules with 12 hours of stimulation at 20 mA for 7 days, with the delivered amount including every energy increment between the minimum and maximum amounts. It should be appreciated that any of the aforementioned maximums may be combined with any of the aforementioned minimums, with the delivered amount including every energy increment between the minimum and maximum amounts.

Table Z illustrates the energies delivered to a patient for stimulation therapy ranging from 30 minutes per day to 12 hours per day, at programmed parameters of pulse amplitude of 20 mA, pulse width of 200 µSec, frequency of 20 Hz wherein the patient's skin resistance is estimated to be 650 Ohms (skin resistance ranges from 400 to 1000 Ohms) in accordance with an embodiment.

TABLE Z

| Parameters | Value | Unit |
| --- | --- | --- |
| Current (I) | 20 | mA |
| Pulse Width (w) | 200 | µSec |
| Frequency (F) | 20 | Hz |
| Resistance (R) (estimated) | 650 | Ohms |
| Pulse Power (P = I² × R) | 0.26 | Watts |
| Pulse Duty Cycle (D = w × 20) | 0.004 | |
| Power Second (J = P × D × F) | 0.0208 | W-sec (Joules) |
| Stimulation energy for various time intervals | | |
| Time Interval (T$_1$) | 30 | minutes |
| Energy delivered (E = J × T$_1$) | 37.44 | Joules/30 Minutes |
| Time Interval (T$_2$) | 12 | Hours |
| Energy delivered (E = J × T$_2$) | 898.56 | Joules/12 Hours |

In some embodiments, the electro-dermal patch device provides a constant basal rate of electrical stimulation having the following parameters which are adjustable by the patient using the companion device. In some embodiments, the electro-dermal patch device provides electrical stimulation timed around meals and having the following parameters which are adjustable by the patient using the companion device:

Daily Pre-Prandial Stimulations: at least one minute to two hours prior to each meal (breakfast, lunch and dinner) every day, as most patients typically report hunger peaking just prior to meals.

Daily During Meal or Post-Prandial Stimulations: during consumption of each meal immediately or at least one minute to 120 minutes after consumption of each meal.

In accordance with aspects of the present specification, stimulation sessions are timed to coincide with pre- and post-prandial "metabolic windows". The pre-prandial window relates to the body's secretion of ghrelin just prior to anticipated or scheduled eating. It should be appreciated that an individual has a ghrelin profile comprising a plurality of peaks or maximum levels of ghrelin plasma concentration and a plurality of valleys or minimum levels of ghrelin plasma concentration distributed over a time span of 24 hours. The plurality of peaks or maximum levels of ghrelin plasma concentration typically correspond to anticipated or scheduled meal timings—such as breakfast, lunch and dinner. In accordance with various aspects of the present specification, a pre-prandial window begins with an increase or surge in ghrelin plasma concentration and reaches a zenith with peaking of ghrelin plasma concentration near anticipated or scheduled meal timings. In some embodiments, approximately a 60 minute pre-prandial window is referred to as a "ghrelin window". In various embodiments, a stimulation session is timed to occur within the ghrelin window, wherein the stimulation session is initiated when the ghrelin plasma concentration is within range of the maximum acceptable level of ghrelin plasma concentration. Stimulation during the ghrelin window results in decreasing ghrelin plasma concentration and thereby reduced appetite or readiness to eat.

The post-prandial window relates to the body's incrementally decreasing secretion of ghrelin during and/or after consumption of a meal. In accordance with various aspects of the present specification, the post-prandial window begins during and/or after culmination of consumption of a meal and reaches a nadir corresponding to minimum levels of ghrelin plasma concentration. Thus, in some embodiments, following a meal there is a period of post-prandial digestive activity lasting about 1 hour to 2 hours, which is referred to as an "antral motility window". In various embodiments, a stimulation session is timed to occur within the antral motility window, wherein the stimulation session is terminated when the ghrelin plasma concentration is within range of the minimum acceptable level of ghrelin plasma concentration. Stimulation during the antral motility window results in decreasing antral motility thereby causing delayed gastric emptying and a feeling of satiety.

In an embodiment, a baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these pre-prandial and post-prandial stimulation sessions are triggered manually by the user (in response to scheduled prompts, for example). In some alternate embodiments, the pre-prandial and post-prandial stimulation sessions are automatically triggered based on pre-stored meal time schedule or calendar, daily diary inputs (such as, but not limited to, weight), historic record of hunger events and/or other eating related events (such as, for example, unscheduled eating events). In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B. In further alternate embodiments, the baseline stimulation scheme or protocol is pre-programmed by either factory setting or by the physician while the user can only schedule timing of mealtimes.

It should be appreciated that any initial, baseline or default stimulation parameters, which are implemented upon starting the device and without the benefit of any user input regarding their appetite, hunger, satiety level, satiation level, fullness level, well-being status, nausea status or other information, may be universally fixed for all persons or may be based upon any one or a combination of the following parameters of the person: age, gender, ethnicity, weight, body mass index, body fat percentage, and/or race. Therefore, stimulation dosing may be initially based on categorizing the individual into one or more template groups and choosing a corresponding protocol. For example, one may classify individuals into various groups (a BMI greater than 40, a BMI of 35 to 39, a BMI of 30 to 34, and a BMI of 25 to 29) and apply a standard or baseline stimulation scheme for all individuals within that classification. The same could apply to a combination of age and gender for example (females 65 and over, females 55 to 64, females 45 to 54, females 35 to 44, females 25 to 34, females 24 and under, males 65 and over, males 55 to 64, males 45 to 54, males 35 to 44, males 25 to 34, males 24 and under). Additionally, the initial stimulation settings may be based on any parameters indicative of the patient's extent of appetite, or hunger, satiety level, satiation level, or fullness level.

It should further be appreciated that any selected stimulation parameters may be titrated for a given patient. Specifically, they may be adjusted upward or downward based on the amount of stimulation felt by the patient and/or immediately reported feelings of pain, nausea, or other discomfort.

In some embodiments, the stimulation continuity profile may be, for each stimulation session duration the stimulation profile applied, continuous; intermittent including short intervals of Y seconds of no stimulation; step-up stimulation wherein the stimulation amplitude and/or frequency increases at a predefined rate from commencement to completion of a stimulation session duration; or step-down stimulation wherein the stimulation amplitude and/or frequency decreases at a predefined rate from commencement to completion of a stimulation session duration. In some embodiments, the stimulation continuity profile may vary on a day to day basis. For example, for a treatment duration of, say, 4 weeks the stimulation profile applied may be at least one of continuous wherein the number and/or intensity of stimulation does not vary throughout the treatment; step-up stimulation wherein the intensity and number of sessions per day increase at a predefined rate on a daily or weekly basis; step-down stimulation wherein the intensity and number of sessions per day decrease at a predefined rate on a daily or weekly basis.

In accordance with an aspect, the stimulation energy delivered to the patient, in each stimulation session, can be increased or decreased by modifying either of the stimulation pulse amplitude or the stimulation pulse width. In an embodiment, both the pulse width and pulse amplitude may be modified.

In one embodiment, the stimulation pulse width is changed while the pulse amplitude is kept constant. For example, the pulse width may be modified within a range of, say, 50 μsec to 400 μsec in steps of 25 μsec while the pulse amplitude ranges from 10 mA to 200 mA, or any increment thereof. In an embodiment, the pulse amplitude is fixed at, for example, 50 mA (assuming a 500 ohm load). The waveform shape is chosen to be monophasic with charge balancing. In the embodiment where pulse width may be increased while the pulse amplitude is fixed, the number of nausea episodes may increase.

In another embodiment, the stimulation pulse amplitude is changed while the pulse width is kept constant. For example, the pulse amplitude may be modified within a range of, say, 100 μA to 500 mA while the pulse width is fixed at, say, 100 μsec. The waveform shape may remain monophasic with charge balancing.

It should be noted herein that the pulse amplitude range may be electrode dependent. In an embodiment, the electrode-skin interface impedance (function of electrode design and skin type) determines this range, as well as the target nerves for stimulation (or inhibition).

In accordance with an aspect of the present specification, the target or full pulse amplitude for a stimulation session is not delivered or reached immediately or instantly at the start of the stimulation session rather, in various embodiments, the pulse amplitude is gradually increased or ramped up to reach the target pulse amplitude over a predefined period of time. For example, the baseline pulse amplitude of 20 mA, in a stimulation session, is reached gradually over a predefined period of time (such as, say, 1 minute) starting from zero or very low pulse amplitude such as, say, 5 mA. This is advantageous in that an immediate or instant delivery of 20 mA pulse amplitude may startle and cause discomfort to the user whereas a gradual pulse amplitude ramp-up profile of the present specification will enable the user to get accustomed to the electrical energy to be delivered and prevent any shock or alarm due to an initial spike of pulse amplitude exposure.

In some embodiments, the time or moment of application of stimulation sessions may be, for example, 't' minutes before meals such as breakfast, lunch, snack, dinner, wherein T is within a range of 1 min to 150 min; right before going to bed; at the onset of hunger and/or right before an expected hunger event based on the user's recorded hunger profile.

In accordance with an embodiment, a stimulation scheme or protocol is set at 3 daily stimulation sessions of 30 minutes each (3×30 minutes per day) timed post-prandial (that is, for example, after breakfast, lunch and dinner).

In accordance with aspects of the present specification, the EDP device delivers stimulation therapy over prolonged periods of time while at the same time ensuring minimization of skin irritation or rashes.

When the user's skin is exposed to electrical stimulation each electrical pulse not only induces a nerve conduction reaction but also drives a chemical reduction-oxidation (redox) reaction. The redox reaction generates ions which, if left to build up, negatively affects the pH of local tissue, creates acidity, and causes skin irritation.

FIG. 73 shows a first waveform 7305 which is a mono-phasic waveform, a second waveform 7310 representing a symmetrical, biphasic, charge-balanced waveform, a third waveform 7315 indicative of an asymmetrical, biphasic, charge-balanced waveform and a fourth waveform 7320 illustrating a spike-like biphasic waveform or pulse. Consider the mono-phasic pulse 7305, such as a square wave with a positive wave that goes up and back down to a baseline. If such a wave is applied, it will induce a nerve reaction but it will also drive a redox reaction in one direction, generating an increased number of ions over time. Now consider changing that mono-phasic pulse 7305 to biphasic (for example, waveform 7310 or 7315), such as a square wave that is positive, which then becomes negative and then returns back to baseline. In this case, one is inducing a nerve reaction with each wave, however, by changing the wave phase, the redox reaction is reversed. Accordingly, while the positive wave may drive the redox reaction forward, the negative wave drives the redox reaction in reverse, thereby reducing the generation of ions.

The symmetrical, biphasic, charge-balanced waveform starts at a baseline, rapidly increases to a peak current with a first current ramp slope greater than one and approaching an undefined, vertical value, plateaus at that peak current for a period of time, T1, rapidly decreases to baseline with a second current ramp slope less than negative one and approaching an undefined, vertical value, rapidly decreases to a negative current value at the same second current ramp slope or a negative first current ramp slope, plateaus at that current for a period of time T2, and rapidly increases to baseline with a negative second current ramp slope or the first current ramp slope. The asymmetrical, biphasic, charge-balanced waveform starts at a baseline, rapidly increases to a peak current with a first current ramp slope greater than one, plateaus at a peak current and decays thereafter for a period of time, T1, rapidly decreases to baseline with a second current ramp slope less than negative one, rapidly decreases to a negative current value at a third current ramp slope less than negative one, plateaus at that current, and rapidly increases to baseline with a positive fourth current ramp slope, where the first, second, third, and fourth current ramp slopes are all different or where at least one of the first and third and the second and fourth current ramp slopes are different.

In various embodiments, the stimulation sessions of the present specification comprise charge-balanced, biphasic symmetrical or asymmetrical waveform or current pulses 7310, 7315. In other words, in various embodiments, the EDP device generates pulse to pulse flipped symmetrical or asymmetrical, biphasic, charge-balanced waveform or pulses 7310, 7315. The waveform is driven by an algorithm that stops at predefined time interval (for example after every 5 minutes, and allows the skin to rest from 1 to 2 minutes) and then continues until a prescribed therapy time. The predefined time interval can also be a randomized value, in various embodiments, so as to not create skin fatigue. In embodiments, the waveform is further characterized by a rapid attainment of a peak amplitude followed by an almost instantaneous drop in the amplitude.

While the negative wave in the waveforms 7310, 7315 will reverse the redox reaction, the reduction or elimination of ions will not be at 100%. It will be more in a range of 90%. In some embodiments, ion generation is further reduced by at least one of: 1) generating a biphasic pulse—such as the symmetric or asymmetric waveforms 7310, 7315; and, optionally, 2) following a first pulse with a second pulse, wherein the second pulse is same as the first pulse except that the phase of the second pulse is reversed with respect to the first pulse.

FIG. 74A illustrates first and second consecutive symmetric biphasic pulses 7405, 7410 where the phase or polarity of the second pulse 7410 is reversed with reference to the first pulse 7405 and there is a predefined time interval or wait time 7407 between the pulses 7405, 7410.

FIG. 74B illustrates first and second consecutive asymmetric biphasic pulses 7415, 7420 where the phase or polarity of the second pulse 7420 is reversed with reference to the first pulse 7415 and there is optionally a predefined time interval or wait time 7417 between the pulse 7415, 7420. In each of the cases of FIGS. 74A, 74B, the negative pulse 7405n, 7415n of the respective first biphasic pulses 7405, 7415 reverses most of the redox reaction and the negative pulse 7410n, 7420n of the respective second biphasic pulses 7410, 7420 continues the reversal, extending the reaction further and thereby making sure that more of the redox reaction is reversed before creating more ions.

In some embodiments, an amplitude of the first phase, the second phase, the third phase, and the fourth phase are equal and a pulse width of the first phase, the second phase, the third phase, and the fourth phase are equal.

In some embodiments, the predefined time interval is in a range of 1 minute to 10 minutes.

Therefore, by applying the train of pulses of FIG. 74A or 74B to two electrodes, left and right, of an EDP device of the present specification: a) a positive pulse is applied to the left electrode while a negative pulse is applied to the right electrode; b) a negative pulse is immediately applied to the left electrode, while a positive pulse is applied to the right electrode; c) there is preferably a wait time between pulses where no stimulation is occurring; d) a negative pulse is then applied to the left electrode while a positive pulse is applied to the right electrode; and e) a positive pulse is applied to the left electrode while a negative pulse is applied to the right electrode. It should be appreciated that the term phase refers to a portion of the waveform having a consistent polarity, either positive or negative, and the term polarity refers to the negative or positive stimulation state of the pulse.

FIG. 74C illustrates, in accordance with alternate embodiments, first and second consecutive symmetric biphasic pulses 7425, 7430 where the phase or polarity of the second pulse 7430 is reversed with reference to the first pulse 7425 and there is a predefined time interval or wait time 7427 between the pulse 7425, 7430. As shown in FIG. 74C, the positive pulse 7425p of the first biphasic pulse 7425 is followed by a positive pulse 7430p of the second biphasic pulse 7430.

FIG. 74D illustrates, in accordance with alternate embodiments, first and second consecutive asymmetric biphasic pulses 7435, 7440 where the phase or polarity of the second pulse 7440 is reversed with reference to the first pulse 7435 and there is optionally a predefined time interval or wait time 7437 between the pulse 7435, 7440. As shown in FIG. 74D, the positive pulse 7435p of the first biphasic pulse 7435 is followed by the positive pulse 7440p of the second biphasic pulse 7440. In each of the cases of FIGS. 74C, 74D, the positive pulse 7425p, 7435p of the respective first biphasic pulses 7425, 7435 reverses most of the redox reaction and the positive pulse 7430p, 7440p of the respective second biphasic pulses 7430, 7440 continues the reversal, extending the reaction further and thereby making sure that more of the redox reaction is reversed before creating more ions.

In some embodiments, an amplitude of the first phase and the fourth phase are equal, a pulse width of the first phase and the fourth phase are equal, an amplitude of the second phase and the third phase are equal, wherein a pulse width of the second phase and the third phase are equal, and wherein at least one of the amplitude and the pulse width of the first phase is different from the amplitude and pulse width of the second phase.

In some embodiments, the first phase is defined by a waveform characterized by a first period and a second period, wherein the first period comprises a first 10 μs of the waveform and the second period comprises a remainder of the waveform and wherein said waveform is defined by a maximum amplitude during the first period and an amplitude less than said maximum amplitude during the second period.

In some embodiments, at least one of the first phase, second phase, third phase, and fourth phase is defined by a waveform characterized by a first period, a second period, and a third period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a maximum amplitude and the second and third periods are defined by a remainder amplitude less than said maximum amplitude.

By applying the train of pulses of FIG. 74C or 74D to two electrodes, left and right, of an EDP device of the present specification: a) a negative pulse is applied to the left electrode while a positive pulse is applied to the right electrode; b) a positive pulse is immediately applied to the left electrode, while a negative pulse is applied to the right electrode; c) there is preferably a wait time between pulses where no stimulation is occurring; d) a positive pulse is then applied to the left electrode while a negative pulse is applied to the right electrode; and e) a negative pulse is applied to the left electrode while a positive pulse is applied to the right electrode. It should be appreciated that the term phase refers to a portion of the waveform having a consistent polarity, either positive or negative, and the term polarity refers to the negative or positive stimulation state of the pulse.

FIG. 75A is a flowchart illustrating a plurality of steps of generating a train of biphasic pulses, in accordance with embodiments of the present specification. At step 7505, an EDP device with two electrodes, left and right, generates a biphasic charge-balanced train of pulses (such as the train of pulses of FIGS. 74A, 74B). The pulses are symmetric or asymmetric in various embodiments. Also, the train of pulses is characterized in that any two consecutive first and second pulses (of the train of pulses) are reversed in terms of their phases with reference to one another.

At step 7510, the first pulse is applied to the left and right electrodes of the EDP device. At step 7515, the left electrode receives a positive pulse while the right electrode receives a negative pulse. At step 7520, the left electrode immediately receives a negative pulse while the right electrode receives a positive pulse. At step 7525, there is a predefined wait time before the second pulse, consecutively following the first pulse, is received at the electrodes. At an end of the wait time, at step 7530, the second pulse is applied to the left and right electrodes of the EDP device. At step 7535, the left electrode now receives a negative pulse while the right electrode receives a positive pulse. Finally, at step 7540, the left electrode immediately receives a positive pulse whereas the right electrode receives a negative pulse.

Thus, in some embodiments, the first electrical pulse is defined by a first phase having a first polarity and a second phase having a second polarity that is opposite the first polarity, wherein the second electrical pulse follows the first electrical pulse and is defined by a third phase having a third polarity and a fourth phase having a fourth polarity that is opposite the third polarity, and wherein the second polarity is equal to the third polarity. In some embodiments, the first polarity is positive, the second polarity is negative, the third polarity is negative, and the fourth polarity is positive.

FIG. 75B is a flowchart illustrating a plurality of steps of generating a train of biphasic pulses, in accordance with embodiments of the present specification. At step 7545, an EDP device with two electrodes, left and right, generates a biphasic charge-balanced train of pulses (such as the train of pulses of FIGS. 74C, 74D). The pulses are symmetric or asymmetric in various embodiments. Also, the train of pulses is characterized in that any two consecutive first and second pulses (of the train of pulses) are reversed in terms of their phases with reference to one another.

At step 7550, the first pulse is applied to the left and right electrodes of the EDP device. At step 7555, the left electrode receives a negative pulse while the right electrode receives a positive pulse. At step 7560, the left electrode immediately receives a positive pulse while the right electrode receives a negative pulse. At step 7565, there is a predefined wait time before the second pulse, consecutively following the first pulse, is received at the electrodes. At an end of the wait time, at step 7570, the second pulse is applied to the left and right electrodes of the EDP device. At step 7575, the left electrode now receives a positive pulse while the right electrode receives a negative pulse. Finally, at step 7580, the left electrode immediately receives a negative pulse whereas the right electrode receives a positive pulse.

Thus, in some embodiments, the first electrical pulse is defined by a first phase having a first polarity and a second phase having a second polarity that is opposite the first polarity, wherein the second electrical pulse follows the first electrical pulse and is defined by a third phase having a third polarity and a fourth phase having a fourth polarity that is opposite the third polarity, and wherein the second polarity is equal to the third polarity. In some embodiments, the first polarity is negative, the second polarity is positive, the third polarity is positive, and the fourth polarity is negative.

As shown in FIG. 61, in an embodiment, each of the 3 daily stimulation sessions delivered has a pulse waveform 6100 with the following characteristics or parameters:

Maximum Compliance Voltage: 45 Volts (can range from 40 Volts to 60 Volts in various embodiments)
Pulse Amplitude: 30 mA (can be any one of 20 mA, 30 mA or 40 mA in various embodiments)
Pulse Width: 200 μsec
Pulse Frequency: 30 Hz (can be any one of 20 Hz, 30 Hz or 40 Hz in various embodiments)
Waveform: biphasic (charge balanced)

With the EDP electrodes impedance ranging from 300 ohms to 1000 ohms and due to the patient's skin resistance, the waveform 6100 immediately attains a peak amplitude value 6105 at the beginning. The peak amplitude value 6105 ranges from 25 mA to 30 mA, in some embodiments, and ranges from 20 mA to 50 mA in other embodiments. The peak amplitude value 6105 deteriorates almost instantaneously to a first amplitude value 6110 in a first time period 6115. In embodiments, the first amplitude value 6110 ranges from 20 mA to 22 mA and the first time period 6115 is 80 μsec. Thereafter, the waveform 6100 deteriorates even further during a second time period 6120 to attain a second amplitude value 6125. In embodiments, the second time period 6120 is 120 μsec and the second amplitude value 6125 ranges from 4 mA to 8 mA. Essentially, the waveform 6100 behaves as a waveform equivalent to one with an average amplitude of 18 mA across the first and second time periods. In the embodiment, the sum of the first and second time periods 6115, 6120 is 200 μsec. Also, while in the present embodiment the first time period 6115 is about 40% (that is, 80 μsec) of the total pulse width (that is, 200 μsec) in other embodiments the first time period may range from 5% to 95%, where the maximum and minimum may be any increment therein, of the pulse width.

It should be appreciated that the quick deterioration of the peak amplitude value 6105 to the first amplitude value 6110 in the first time period 6115 and to the second amplitude value 6125 in the remaining second time period 6120 imparts a sharp tingling perception or feel to the waveform in the beginning that reduces subsequently. In some embodiments, the waveform may attain the peak amplitude value 6105 immediately and then quickly deteriorate to the lower amplitude value of 6125 (without first deteriorating to the first amplitude value 6110). While in one embodiment, of FIG. 61, the pulse waveform has a pulse amplitude of 30 mA and a frequency of 30 Hz, in alternate embodiments the pulse amplitude may be 20 mA or 40 mA and the frequency may be 20 Hz or 40 Hz. In one preferred embodiment, the waveform 6100 is characterized by a peak amplitude of 40 mA, a pulse frequency of 30 Hz and a pulse width of 200 μsec.

The sharp tingling feeling is characteristic of the stimulation therapy of the present specification, compared to prior art TENS devices, and is attributable to the waveform parameters, such as those of the waveform 6100, an upper compliance voltage limit of 45 Volts coupled with low skin impedance of below 1000 ohms for the electrodes of the EDP device of the present specification. Prior art TENS devices tend to use high voltages such as those at or above 80 Volts. It should be appreciated, that capping or limiting the voltage at 45 Volts for the EDP device of the present specification coupled with the waveform 6100 enables a unique stimulation footprint and a unique patient sensation that avoids the vibrations and muscle spasm typically generated by conventional and prior art TENS units operating at similar amplitudes.

In another embodiment, the waveform 6100 is characterized by: a maximum compliance voltage in a range of 40 volts to 60 volts, a peak amplitude value 6105 in a range of 20 to 50 mA, a first time period 6115 of 10 μs while the second time period 6120 comprising a remainder of the waveform, average amplitude across the first and second time periods is in a range of 10 mA to 30 mA.

In yet another embodiment, the waveform is characterized by a first time period, a second time period, and a third time period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a peak or maximum amplitude and the second and third periods are defined by a remainder amplitude less than the maximum amplitude. In this embodiment, the peak or maximum amplitude is in a range of 20 mA to 50 mA. In this embodiment, in the second period, a decay of the remainder amplitude is defined by a first negative slope having a first magnitude and, in the third period, a decay of the remainder amplitude is defined by a second negative slope having a second magnitude, wherein the first magnitude is less than the second magnitude. In this embodiment, an average of the peak or maximum amplitude and the remainder amplitude is in a range of 10 mA to 30 mA.

In various embodiments, any two consecutive stimulation pulses, having waveforms described with reference to embodiments above and FIG. 61, are separated by a predefined time interval. In some embodiments, the predefined time interval is in a range of 1 minute to 10 minutes. In other embodiments, the predefined time interval is randomized and is at least 1 minute.

It should further be appreciated that, in contrast to certain prior art approaches, the waveform is preferably a single waveform and not a multiplexed, integrated, or otherwise combined set of multiple waveforms in different frequency ranges, particularly waveforms greater than 500 Hz.

In one embodiment, the EDP has a predefined voltage limit, for example in a range of 40 to 60 volts or any increment therein. This voltage limit has the effect of quickly degrading an initial 30 mA pulse down to a lower amperage, for example 18 mA.

In accordance with an aspect of the present specification, the user as well as the remote patient care facility or personnel are able to control and adjust the plurality of stimulation parameters through the Health Management application and/or by the user via actuators 122 such as buttons or switches of FIG. 1A. In some embodiments, the remote patient care facility or personnel is authorized to control and adjust all stimulation parameters while the user is enabled to control and adjust a subset of the stimulation parameters with or without authorization/approval of the remote patient care facility or personnel. For example, the user may be allowed to change the number of stimulation sessions per day from, for example, 2 sessions per day to 1 session per day; stimulation session duration from, for example, 30 minutes to 15 minutes; and/or stimulation pulse amplitude from, for example, 20 mA to 150 µA. In one embodiment, the maximum change is limited to a predefined amount or multiple of the prior settings.

It should be noted that changing the pulse width is a less energy efficient approach as it requires the fixed voltage to be larger than typically needed. Energy efficiency considerations involve varying both the pulse width and pulse amplitude to find the minimum combination that will cause neural activation. In some embodiments, patients may use sensory feedback to modify stimulation or as a mechanism to choose. For example, in using a larger amplitude, the patient may experience more irritation or a tingly sensation and can thus use the discomfort as a means of modifying therapy. In some embodiments, battery life may also dictate the choice of whether to increase pulse width, pulse amplitude or both.

In a preferred embodiment, the user is able to increase the stimulation pulse amplitude from a minimal default amplitude setting of, say, 100 µA to a 'sensory threshold' corresponding to amplitude where the user can just feel the stimulation. The user may then save the 'sensory threshold' setting and continue stimulation at this setting. The sensory perception varies from person to person and therefore in various embodiments the 'sensory threshold' ranges from about 5 mA to 10 mA on the lower side and from about 20 mA to 30 mA on the higher side.

In some embodiments, a stimulation protocol includes alternating stimulation sessions between a first session having a low pulse frequency, for example, less than 50 Hz, followed by a second session having a high pulse frequency, for example, greater than 50 Hz.

In still further embodiments, the user may be able to control and adjust the subset of stimulation parameters within the standard settings ranges, such as those described above, or within a narrower band of range or constrained range within the standard settings ranges. For example, the user may be allowed to modify the stimulation pulse width, amplitude and frequency by no more than +/−50% from the original, default or standard setting. In another example, the user may be allowed to modify all stimulation parameters by +/−10% (from the original, default or standard setting) except for allowing the amplitude to decrease unbounded in order to address safety and/or comfort reasons User modification of the stimulation parameters beyond the constrained range may require authorization from the remote patient care facility or personnel. In some embodiments, the range within which the user is able to control and adjust the subset of stimulation parameters is set by the remote patient care facility or personnel. Also, in some embodiments, the user may be allowed to control and adjust stimulation parameters within a first range at the onset of therapy, but as therapy progresses (for example, after 2 to 3 weeks) the user is allowed to control and adjust stimulation parameters within a second range wherein the second range is narrower, limited or constrained compared to the first range.

It should be appreciated that the type and number of stimulation parameters that the user is allowed to control and adjust can vary in multiple embodiments.

In accordance with an aspect of the present specification, the Health Management software application provides a plurality of pre-configured default or standard stimulation protocols to drive therapy for a plurality of conditions such as obesity, over-weight, eating disorders, metabolic syndrome or appetite suppression and T2DM, as examples.

Example Stimulation Protocols for Treating Conditions of Obesity, Over-Weight, Eating Disorders, Metabolic Syndrome or Appetite Suppression and/or T2DM In various embodiments, a standard stimulation protocol, for stimulating the T6, C8 and/or T1 dermatome for treating conditions of obesity, over-weight, eating disorders, metabolic syndrome or for appetite suppression and the T7 dermatome for treating T2DM, may comprise a plurality of pre-configured standard settings such as at least three setting options, for example mild, optimal, intense. For example, an embodiment of a standard optimal stimulation protocol comprises two 30 minute sessions a day, 30 to 45 minutes before lunch and right before bed or after a specific time, say, after 8 or 9 pm, at an intensity that doesn't bother patient, but can still be felt by them, such as at a frequency of 20 Hz and at a 'sensory threshold' amplitude of 10 mA. A standard mild stimulation protocol comprises one 20 minute session a day, 30 to 45 minutes before lunch or right before bed or after a specific time, say, after 8 or 9 pm, at a frequency of 20 Hz and at a 'sensory threshold' amplitude of 5 to 35 mA. A standard intense stimulation protocol comprises three 30 minute sessions a day, 30 to 45 minutes before lunch, right before bed and also after a specific time, say, after 8 or 9 pm, at a frequency of 40 Hz and at a 'sensory threshold' amplitude of 10 mA. In some embodiments, a latency effect is encountered with stimulation wherein the stimulation is provided for a specific amount of time and the effect is not witnessed until a certain amount of time has passed and/or the effect remains for a certain amount of time post stimulation. For example, in one embodiment, ghrelin remains suppressed for at least several weeks post stimulation.

It should be noted that, in various embodiments, the stimulation parameters and protocols enable treatment of conditions of obesity, over-weight, eating disorders, metabolic syndrome or appetite suppression and/or T2DM without causing painful, uncomfortable or uncontrollable sensations to the user (that is, without reaching a painful threshold of sensation).

In one preferred embodiment a standard or baseline stimulation scheme or protocol (also referred to as 'default operational mode') is set at, for example, 3 daily stimulation sessions of 30 minutes each having a pulse amplitude of 20 mA. Each of the three daily stimulation sessions is initiated 30 to 60 minutes and preferably 45 minutes prior to mealtimes, such as, breakfast, lunch and dinner, for example. In various embodiments, the remote patient care facility or personnel set times for the meals that, in some embodiments, may be in accordance with a diet plan. Thus, the HMA application is pre-set at the standard or baseline stimulation protocol to begin stimulation in absence of any initial health related data of the user. As the therapy progresses, the Health Management application recommends and periodically adjusts the baseline stimulation protocol or pattern based on the user's health related information. In another preferred embodiment, the baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these post-prandial stimulation sessions are triggered manually by the user. In some alternate embodiments, the pre-prandial and post-prandial stimulation sessions are automatically triggered based on pre-stored meal time schedule. In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B.

It should be appreciated that, in some embodiments, the standard optimal stimulation protocol (out of the three options of mild, optimal and intense) is set at the baseline stimulation protocol which is the default protocol set for most users. In still alternate embodiments, the standard baseline stimulation protocol is the only pre-configured setting available to users instead of multiple stimulation options, such as the three options of mild, optimal and intense. However, the baseline stimulation protocol is programmable, adjustable or modifiable. That is, in various embodiments, the remote patient care facility or personnel can modify the baseline stimulation parameters to a higher level of stimulation, longer duration and/or more times daily.

It should be appreciated that the default or base stimulation protocol may be set through a number of different mechanisms. First, a biomarker may be used to define a threshold which, if met, would indicate a proper a default or baseline stimulation setting. In one embodiment, the biomarker may be pain level, heart rate values, skin impedance values, degree of pupil dilation, blood pressure values, salivary cortisol values, or EKG values. Pain level may be determined by a visual analog scale and having a patient either verbally state or input into a computing device a level on a visual analog scale that equates to the amount of pain being experienced by the patient. Heart rate and blood pressure may be determined from conventional heart rate monitors, which may be incorporated into a watch or patch, or blood pressure monitors. Pupil dilation may be measured visually or using a camera. EKG values may be determined from conventional EKG devices. Skin impedance values may be determined from impedance sensors incorporated into the EDP.

The biomarker may be used to determine when a patient is receiving a sufficient amount of stimulation. For example, in one embodiment, if the measured heart rate increases by at least 5%, but no more than 20%, over a period of five minutes after stimulation initiates, the provided stimulation is sufficient. If the measured heart rate does not increase by at least 5%, then the provided stimulation is not sufficient. If the measured heart rate increases by more than 20%, preferably 15% and more preferably 10%, then the provided stimulation is too excessive.

For example, in one embodiment, if the measured pain level, using a VAS scale, exceeds 5, but is less than 8, over a period of five minutes after stimulation initiates, the provided stimulation is sufficient. If the measured pain level does not exceed 5, then the provided stimulation is not sufficient. If the measured pain level exceeds 8, then the provided stimulation is too excessive.

For example, in one embodiment, if the measured blood pressure increases by at least 5%, but no more than 20%, over a period of five minutes after stimulation initiates, the provided stimulation is sufficient. If the measured blood pressure does not increase by at least 5%, then the provided stimulation is not sufficient. If the measured blood pressure increases by more than 20%, preferably 15% and more preferably 10%, then the provided stimulation is too excessive.

For example, in one embodiment, if the measured skin impedance increases by at least 5%, but no more than 20%, over a period of five minutes after stimulation initiates, the provided stimulation is sufficient. If the measured skin impedance does not increase by at least 5%, then the provided stimulation is not sufficient. If the measured skin impedance increases by more than 20%, preferably 15% and more preferably 10%, then the provided stimulation is too excessive.

For example, in one embodiment, if the measured degree of pupil dilation increases by at least 5%, but no more than 20%, over a period of five minutes after stimulation initiates, the provided stimulation is sufficient. If the degree of pupil dilation does not increase by at least 5%, then the provided stimulation is not sufficient. If the degree of pupil dilation increases by more than 20%, preferably 15% and more preferably 10%, then the provided stimulation is too excessive.

For example, in one embodiment, if the measured EKG values increase by at least 5%, but no more than 20%, over a period of five minutes after stimulation initiates, the provided stimulation is sufficient. If the EKG values do not increase by at least 5%, then the provided stimulation is not sufficient. If the EKG values increase by more than 20%, preferably 15% and more preferably 10%, then the provided stimulation is too excessive.

For example, in one embodiment, if the measured salivary cortisol values increase by at least 5%, but no more than 20%, over a period of five minutes after stimulation initiates, the provided stimulation is sufficient. If the salivary cortisol values do not increase by at least 5%, then the provided stimulation is not sufficient. If the salivary cortisol values increase by more than 20%, preferably 15% and more preferably 10%, then the provided stimulation is too excessive.

Operationally, a patient would first be subjected to a stimulation having a low range of stimulation values, such as a pulse amplitude of 20 mA, a pulse width of 120 μsec, and a pulse frequency of 30 Hz. If one or more of the aforementioned biomarkers do not achieve the requisite threshold, the patient would be subjected to a stimulation having a medium range of stimulation values, such as a pulse amplitude of 30 mA, a pulse width of 120 μsec, and a pulse frequency of 30 Hz. If one or more of the aforementioned biomarkers do not achieve the requisite threshold, the patient would be subjected to a stimulation having a high range of stimulation values, such as a pulse amplitude of 40 mA, a pulse width of 120 μsec, and a pulse frequency of 30 Hz.

In another embodiment, the process could be reversed. Operationally, a patient would first be subjected to a stimulation having a high range of stimulation values, such as a pulse amplitude of 40 mA, a pulse width of 120 μsec, and a pulse frequency of 30 Hz. If one or more of the aforementioned biomarkers exceeds the requisite threshold, the patient would be subjected to a stimulation having a medium range of stimulation values, such as a pulse amplitude of 30 mA, a pulse width of 120 μsec, and a pulse frequency of 30 Hz. If one or more of the aforementioned biomarkers still exceed the requisite threshold, the patient would be subjected to a stimulation having a low range of stimulation values, such as a pulse amplitude of 20 mA, a pulse width of 120 μsec, and a pulse frequency of 30 Hz.

Some embodiments additionally comprise a custom setting option that allows the user to adjust or set the subset of stimulation parameters, which he is allowed to control, within constrained ranges. It should be appreciated that the number of pre-configured settings (such as mild, optimal, intense) may vary across various embodiments. Also, the stimulation protocol, with its mild, optimal and intense configurations, is only exemplary and may vary across various embodiments and for targeting specific conditions such as only appetite suppression or T2DM. For example, a stimulation protocol directed towards ghrelin modulation, and therefore appetite modulation, may include a stimulation pulse width of 200 μsec, pulse amplitude corresponding to the user's 'sensory threshold' such as 20 mA, pulse frequency of 20 Hz, stimulation session duration of 30 minutes and one session per day for 4 weeks. Another example stimulation protocol directed towards appetite suppression may include a 15 minutes stimulation session, using a current frequency of 6 Hz of 0.1 milliseconds (ms) duration starting at intensities of 1 to 20 milliampere (mA) until the intensity reaches the user's 'sensory threshold'.

In accordance with an aspect of the present specification, the Health Management application recommends and periodically adjusts the stimulation protocols or patterns based on the user's health related information, such as the user's hunger profile, standard eating and meals profile, actual eating and meals profile, energy balance, weight trends, glucose data and stimulation induced nausea, dyspepsia, habituation events. For example, if the user's energy balance is positive by about 5% beyond a pre-defined positive energy balance threshold at a certain calories consumption schedule per day, as dictated by the user's standard regular eating and meals profile, and the user is also found to be over-weight or obese, the Health Management application may suggest commencing with the optimal stimulation protocol for two weeks along with an activities regiment comprising, for example, daily or weekly goals of walking, exercising, running, swimming directed towards increasing the user's calories expenditure. The Health Management application monitors compliance of the user to the recommended optimal stimulation protocol and the activities regimen throughout the two weeks. The user's resulting energy balance and compliance profile is recorded and displayed to the user in the form of charts, graphs, tables or any other visual format as would be advantageously evident to persons of ordinary skill in the art. At the commencement or throughout the duration of the therapy, the Health Management application may also recommend a standard or customized dietary plan to the user as part of a holistic approach to improving effectiveness of the stimulation therapy. For example, Table 3 shows a 1200 Kcal/day customized diet plan (from a plurality of such diet plans pre-stored within the Health Management application) recommended by the Health Management application:

TABLE 3

| Mean values of carbohydrates 51%; proteins 23%; fats 26% | |
|---|---|
| Meal | Contents |
| Breakfast | Skimmed milk 200 cc or 2 natural skimmed yoghourts<br>Bread 50 g or 2 toasts of "biscotti" type bread |
| Mid-morning | Fruit (one piece, 100 g of apple, pear, orange, melon or kiwi) |
| Meal and dinner | Main course to choose from:<br>Vegetables 200 g: spinach, chard, eggplant, watercress, endive, lettuce, cauliflower, mushroom, leek, asparagus, escarole, cabbage, cucumber, peppers, tomatoes, alternating cooked or in a salad, or 150 g of green beans, beet, carrot, artichoke or Brussels sprouts<br>Vegetable soup<br>Skimmed broth (free consumption)<br>Andalusian gazpacho, provided it is prepare without bread and a small amount of oil, remembering not to exceed the ration of oil for the whole day<br>Pasta, semolina, rice or tapioca soup (15 g dry)<br>Second course to choose from:<br>White fish 120 g<br>Chicken, turkey, rabbit, veal meat 100 g<br>Eggs, one unit<br>Tomatoes and lettuce salad (or any other raw vegetable) 150 g only once a day<br>Dessert, to choose from:<br>Fruit (one piece, 100 g of apple, pear, orange, kiwi, melon or 200 g of watermelon)<br>Bread 25 g |

TABLE 3-continued

Mean values of carbohydrates 51%; proteins 23%; fats 26%

| Meal | Contents |
|---|---|
| Afternoon snack | 200 cc of skimmed milk, just milk or with coffee or tea |
| Oil for all day | 30 cc (2 soup spoons) |

If the user's energy balance and/or weight trend shows improvement, for example the energy balance reduces up to or below the positive energy balance threshold and/or the rate of weight reduction is within pre-defined acceptable limits, the Health Management application may recommend the user to shift to the mild stimulation protocol for the next two weeks. For example, if the rate of weight reduction or loss exceeds or is above a pre-defined threshold, for example X % over Y %, the Health Management application may recommend or automatically titrate therapy from a current optimal stimulation protocol to the mild stimulation protocol. On the other hand, if the user's energy balance and/or weight trend deteriorates or remains same as at the commencement of the stimulation therapy due the user's non-compliance to the activities regimen (as a result of which the user is not burning a requisite amount of calories), for example if the user's energy balance is found to be positive by about M %, wherein M %>L % and/or the rate of weight reduction is below the pre-defined acceptable limits or there is no significant weight reduction, the Health Management application may recommend the user to shift to the intense stimulation protocol for the next two weeks.

In accordance with aspects of the present specification, the Health Management Application continuously monitors and analyzes the user's plurality of health related information or data to identify emerging health trends and consequently, based on identified health trends or patterns, automatically (as opposed to manually by the user and/or by the TPM) determines and generates one or more interventions in real-time, within a predefined period of time, time-frame or time-window of identifying a health trend and/or at a future time window at which the identified health trend or pattern is expected to occur.

In embodiments, the HMA is programmed to identify health trends with reference to any one or a combination of any two or more of the user's plurality of health related information, such as the user's hunger profile, standard eating and meals profile, actual eating and meals profile (including caloric intake), energy balance, weight data and trends, glucose data, will power levels, daily or periodic scores related to hunger, appetite, and well-being ('diary' inputs), exercise or caloric expenditure, daily or periodic composite scores, stimulation induced nausea, dyspepsia and habituation events. The user's plurality of health related information or data also includes physiological data from a separate device, with physiological sensors, configured to be worn on the human body, such as around the wrist.

Appetite data, which is indicative of a degree of appetite being experienced by the patient, is stored in a database in association with a time of day and a calendar day. The system accesses the database to obtain the appetite data and process it to generate appetite graphs, tables, charts, or other visual displays. The system further accesses the database to obtain the appetite data and process it to develop an appetite pattern that determines, for future time windows, a likely appetite level of the patient. The system saves the appetite pattern, comprising a plurality of appetite levels for particular time windows on a given calendar day, and further uses that appetite pattern to trigger interventions based on such predicted appetite levels. An exemplary database therefore comprises an actual historical log of appetite levels, saved in association with a time of day, a time window, and/or a calendar day and a predicted future pattern of appetite levels associated with a time of day, a time window, and/or a calendar day.

FIG. 70 is a flow chart illustrating a plurality of steps involved in an embodiment of a method of using an EDP device to automatically generate one or more interventions based on identified health trends of a user. At step 7002, the user obtains an electro-dermal patch (EDP) device and pairs the EDP device with a companion device (running the HMA of the present specification), such as a smartphone, and a separate device, for example, a device, with physiological sensors, configured to be worn on the human body, such as around the wrist, in order to monitor, acquire, record, and/or transmit the physiological data. In some embodiments, pairing with the separate device can be done anytime within a treatment cycle. At step 7004, the device is set into a default operational mode. In some embodiments, the default operational mode includes the following stimulation parameters: a pulse width in a range of 10 μsec to 10 msec, a pulse amplitude in a range of 100 μA to 100 mA, and a pulse frequency in a range of 1 Hz and 100 Hz. In some embodiments, the default operational mode is set, for most patients, at 3 daily stimulation sessions of 30 minutes each to be initiated 30 to 60 minutes and preferably 45 minutes prior to or following an end of mealtimes, such as, breakfast, lunch and dinner, for example. In some embodiments, the default operational mode includes the stimulation parameters and parameter ranges listed with respect to FIG. 27C and includes daily stimulation. The EDP device is positioned on the user's body at step 7006 for use.

At step 7008, the companion device, executing the HMA, prompts for, where needed, acquires and stores the plurality of health related information or data over a first predefined period of time, immediately following wearing or use of the EDP for the first time, and a second period of time subsequent to the first predefined period of time. In embodiments, the first predefined period of time is referred to as the 'learning period' during which the HMA attempts to acquire enough data points related to one or more of the health related information or data that is deemed to be sufficient to identify one or more health trends or patterns. The 'learning period' is the time-frame immediately following use of the EDP by the user for the first time. In various embodiments, the 'learning period' is in a range of one day to one month. The second period of time following the 'learning period' is typically continuous (as opposed to be being predefined and time-bound as the 'learning period') till an end of a therapy and/or attainment of one or more objectives of the therapy.

As discussed earlier in the specification, the HMA is programmed to periodically prompt the user for providing his 'daily diary' inputs or any other health related information for which user's explicit or manual input may be necessary such as, for example, glucose data in scenarios where the glucose data is determined by the user using a third-party glucometer that may not be in data communication with the companion device. In accordance with aspects of the present specification, the HMA implements a notification protocol during the 'learning period' that triggers the HMA to generate notification or prompts for the user, to input or provide relevant health related information such as appetite or hunger data, at predefined time intervals. In embodiments, the HMA prioritizes assessment of the user's hunger or appetite profile, during the 'learning period', to subsequently identify related trends or patterns.

In embodiments, the HMA prompts the user to input data indicative of the user's degree of appetite or hunger (and/or other 'daily diary' parameters such as exercise and well-being) via a microphone or a display of the client or companion device. In various embodiments, the user is prompted at associated predefined times and his inputs are subsequently received and time-stamped using any one of the following: visual prompts comprising, generating on a touch-enabled display of the companion device, a light bar VAS, VAS configured as a questionnaire, numbers, color spectrum (as illustrated in FIG. 76) or a plurality of icons, emojis or emoticons and enabling the user to provide finger-based inputs (identifying a value on the VAS or identifying an emoji that is visually representative of the user's degree of appetite) of his degree or intensity of appetite/hunger or haptic inputs such as, for example, specific number of finger-tapping of the display screen by the user being indicative of a degree of appetite or hunger (for example, five finger-taps on the display screen would mean an appetite or hunger score of 5 on a scale of 10), by shaking motion of the companion device wherein an extent of said moving is indicative of the patient's degree of appetite (for example, seven shakes of the companion device would mean an appetite or hunger score of 7 on a scale of 10) or through pre-defined physical body movements, such as (for example) haptic motions of the wrist or hand, when the user is wearing a wristwatch or wristband (that includes an accelerometer or inclinometer to detect, capture and acquire the user's haptic motions); vibratory prompts (through the companion device and/or the EDP device) wherein the user can subsequently provide his inputs through any of the haptic motions as discussed above or by actuating buttons on the EDP device; auditory prompts wherein the HMA in communication with the IPA system, the companion device or the EDP device enables delivering voice based prompts to the user and receiving voice based user inputs through the IPA system, the companion device or the EDP device; by actuating a button on the EDP device itself or on a remote toggle switch configured to be worn around the user's neck or placed on his wrist in the form of a wristwatch or wristband; or by activating a light source (such as one or more LEDs) on the EDP device. Thus, the prompt triggered by the HMA is in a form of at least one of an audio message, video message, text message, and graphical message.

In some embodiments, the user is auditorily prompted an appetite scale and the user's time stamped inputs are received through at least one of a finger-based input, haptic input, or vocal input.

In embodiments, the notification protocol triggers the prompts at a first rate or frequency during the 'learning period' (first period of time) and at a second rate or frequency during the second period of time (that is, after the 'learning period') wherein the second rate is less than the first rate. The goal is to intensively barrage the user with input requests for appetite/hunger to establish a pattern during the learning period—that is, gain enough data to generate customized or personalized interventions and therapy. In one embodiment, an interval between notifications is at least 1 hour and the first rate of notifications is more than 1 time a day and less than 24 times a day. In some embodiments, the frequency of notifications may decrease at an end of the 'learning period' or when the HMA establishes a trend or pattern. In alternate embodiments, the frequency of notifications may remain unchanged.

Optionally, in embodiments, the notification option and the notification protocol may or may not be activated by the user on his companion device. In embodiments, the notification option and the notification protocol for the 'learning period' is active by default and may be deactivated by the user. In some embodiments, the user is allowed to control/modify the first rate or frequency of notifications—with a constraint that the user cannot decrease the frequency of notifications to less than one time per day.

At step 7010, the companion device, executing the HMA, continuously or periodically analyzes the user's plurality of health related information or data, over a predefined period of time, to identify one or more health patterns or trends. In some embodiments, a health trend may be derived by creating or generating a topographical map descriptive of the user's one or more health related information or data and determining trends from the map.

At step 7012, the HMA determines if a health trend or pattern exists or is confirmed. If a health trend exists or is confirmed, then at step 7014, the HMA prospectively automatically generates and provides to the user at least one of a plurality of types of interventions based on a prediction of what appetite level a patient will likely have in a given future time window. More specifically, once a pattern has been determined, the HMA has a degree of confidence that in a future time window, the patient's appetite will be less than, equal to, or greater than a predefined appetite threshold. Based upon such a determination, an intervention may be triggered, where the level and type of intervention is based on the degree to which the patient's appetite is less than, equal to, or greater than the predefined threshold. Such interventions include:

Coaching based intervention—providing online coaching or advice (including graphics, audio, video and/or text messages) on how to manage appetite (for example). In some embodiments, the coaching based intervention generates at least one of a visual display or auditory communication indicative of advice related to the patient's degree of appetite, wherein the advice provides guidance regarding the user's administration of medicine, selection of food, timing of meals, eating of food, abstaining from food, engaging in exercise, selection of a diet plan, or degree of compliance with a diet. Such a coaching-based intervention would be triggered if the patient's appetite is predicted to be greater than the predefined threshold value in a given time window. Alternatively, such a coaching based intervention would be triggered in real-time relative to the acquisition of the patient's appetite data, if such appetite data was above a predefined threshold.

Social network based intervention—allowing pre-recorded or real-time graphics, audio, video and/or text messages to be communicated to the user from members of the user's affinity group or social network. In embodiments, the social network based intervention enables the HMA to connect to a social network (of which the user is a member) and receive from the social network at least one of visual displays of advice related to the user's degree of appetite, auditory communications of advice related to the user's degree of appetite, automated messages, pre-recorded messages from connected individuals on the social network, and real-time messages from connected individuals on the social network. In embodiments, the advice provides guidance regarding the user's administration of medicine, selection of food, timing of meals, eating of food, abstaining from food, engaging in exercise, selection of a diet plan, or degree of compliance with a diet. Such a social networking-based intervention would be triggered if the patient's appetite is predicted to be greater than the predefined threshold value in a given time window. Alternatively, such a social networking-based intervention would be triggered in real-time relative to the acquisition of the patient's appetite data, if such appetite data was above a predefined threshold.

Rescue session based intervention—providing at least one rescue session to the user at a time of day. Such a rescue session-based intervention would be triggered if the patient's appetite is predicted to be greater than the predefined threshold value in a given time window. Alternatively, such a rescue session-based intervention would be triggered in real-time relative to the acquisition of the patient's appetite data, if such appetite data was above a predefined threshold.

Stimulation titration based intervention—modifying, adjusting or titrating the default stimulation parameters and protocols. Specifically, the system modifies at least one of a timing, intensity, pulse width, pulse amplitude, and pulse frequency of the electrical stimulation. In embodiments, the stimulation titration based intervention also includes determining at least one of a plurality of times of day when electrical stimulation is needed, a plurality of times of day when electrical stimulation is not needed, and a change to one or more scheduled electrical stimulations. In some embodiments, the health trend may be positive leading to an automatic moderation or down-modulation of the stimulation parameters, protocols or patterns. In some embodiments, the health trend may be negative leading to an automatic immoderation or up-modulation of the stimulation parameters, protocols or patterns. A stimulation increased titration-based intervention would be triggered if the patient's appetite is predicted to be greater than the predefined threshold value in a given time window. A stimulation decreased titration-based intervention would be triggered if the patient's appetite is predicted to be less than the predefined threshold value in a given time window. Alternatively, such a stimulation increased titration-based intervention would be triggered in real-time relative to the acquisition of the patient's appetite data, if such appetite data was above a predefined threshold. Alternatively, such a stimulation decreased titration-based intervention would be triggered in real-time relative to the acquisition of the patient's appetite data, if such appetite data was below a predefined threshold.

Data display based intervention—in some embodiments, causing an appetite pattern or the user's historical degree of appetite to be displayed on the companion or client device, wherein the appetite pattern is in a form of a heat map or graph having a time of day on a first axis, a calendar day on a second axis, and an icon representing a degree of the user' appetite plotted on the graph in relation to the time of day and calendar day. At least one of a size, shape, color, or pattern of the icon is indicative of the patient's degree of appetite or an amount of change in the user's degree of appetite over a plurality of days. It should be appreciated that the user's appetite pattern or historical degree of appetite may be displayed in a form of at least one of a heat map, topographical map, chart, table, and graph. Such a data display-based intervention would be triggered if the patient's appetite is predicted to be greater than the predefined threshold value in a given time window. Alternatively, such a data display-based intervention would be triggered in real-time relative to the acquisition of the patient's appetite data, if such appetite data was above a predefined threshold.

In some embodiments, the intervention is directed towards displaying data indicative of a degree of the user's appetite superimposed on data indicative of at least one of: a plurality of electrical stimulations applied to the user automatically, a plurality of electrical stimulations requested by, and applied to, the user, exercise performed by the user, calories consumed by the user, meals consumed by the user, and medication taken by the user.

In some embodiments, the superimposed data is represented by a first icon and a second icon plotted on a chart with a calendar day on one axis and a time of day on a second axis and wherein at least one of a color and a size of the first icon is indicative of the user's degree of appetite and wherein at least one of a color and size of the second icon is indicative of at least one of an intensity of the plurality of electrical stimulations applied to the user automatically, an intensity of the plurality of electrical stimulations requested by, and applied to, the user, an amount of exercise performed by the user, an amount of calories consumed by the user, a timing of the meals, and an amount of medication taken by the user.

In other embodiments, the superimposed data is represented by a first icon and a second icon plotted on a chart with a calendar day on one axis and a time of day on a second axis and wherein at least one of a color and a size of the first icon is indicative of a change in the user's degree of appetite and wherein at least one of a color and size of the second icon is indicative of a change in at least one of an intensity of the plurality of electrical stimulations applied to the user automatically, an intensity of the plurality of electrical stimulations requested by, and applied to, the user, an amount of exercise performed by the user, an amount of calories consumed by the user, a timing of the meals, and an amount of medication taken by the user.

In accordance with some embodiments, the intervention is directed towards displaying data of the user's historical degree of appetite on the companion device, wherein the data is represented by icons plotted on a first heat map with calendar days on one axis and a time of day on a second axis and wherein a color of the icons is indicative of the patient's degree of appetite and where the data is represented by icons plotted on a second heat map with calendar days of the month on one axis and a time of day on a second axis and wherein a color of the icons is indicative of the user's degree of appetite, wherein the first heat map represents data taken over a first time period and a second heat map represents data taken over a second time period, and wherein a difference in the patient's degree of appetite between the first heat map and second heat map is represented by a value.

FIG. 72A shows a first heat map 7205 plotted with a first set of icons or dots 7215 representing a user's appetite data over a first time period, such as a first week. The first heat map 7205 has calendar days 7210 on the x-axis and time of day 7212 on the y-axis. FIG. 72B shows a second heat map 7220 plotted with a second set of icons or dots 7225 representing the user's appetite data over a second time period, such as a second week immediately following the first week. The second heat map 7220 also has calendar days 7210 on the x-axis and time of day 7212 on the y-axis. A color of the first and second set of icons or dots 7215, 7225 represents the user's degree of appetite. For example, in some embodiments, the color of the icons or dots may range from white, gray, black, green, yellow, orange to red wherein white representing a lowest intensity or degree of appetite, red representing a highest degree of appetite and other colors, between white and red, representing progressive degrees of appetite. When the first and second heat maps 7205, 7220 are displayed to the user they indicate a change (increase or decrease) in the user's appetite between the first and second time periods. Thus, based on one or more interventions the user's heat map may evolve from the first map 7205 to the second map 7220 (of diminishing red dots and expanding green dots) indicating an efficacy of the overall treatment provided by the EDP.

It should be appreciated that appetite or hunger data represented on heat maps, such as the map 7205 or 7220, is actionable because interventions, such as titration of stimulation therapy, can be determined, timed and prescribed depending on appetite/hunger intensity and time of day and day of month. In some embodiments, the stimulation therapy can be scaled proportionately to the numerical appetite or hunger inputs. For example, if the user enters an appetite or hunger score of 8 (on a hunger scale of 0 to 10) it may result into an immediate intervention in the form of a rescue stimulation session, for example, along with automated coaching advice and/or peer support (in the form of messages from individuals who are members of the affinity group of which the user is also a member). In another example, if the user's weekly or monthly heat map reveals hotspots (high intensity appetite or hunger data) concentrated around certain times of the day, the stimulation therapy can be adjusted accordingly and targeted at vulnerable times of day. In embodiments, the interventions aim to focus on shifting the user's orange and red hotspots at certain times of day in a week to green dots at the same times of day in subsequent weeks.

It should be appreciated that, in some embodiments, the color of the icons or dots 7215, 7225 directly represents a color on a color spectrum based VAS (such as the VAS 7600 of FIG. 76) that is used to receive the user's inputs regarding an intensity of his appetite or hunger.

In other embodiments, the heat maps can also be used for research purposes. For example, to compare the efficacy of different weight loss treatments: sleeve gastrectomy vs lap band, low fat diet vs high protein diet, and to anticipate weight regain by monitoring post-surgery (or post weight loss) patients so as to observe their hunger related state and look for increases in hunger scores. In still another example, there may also be benefits for diabetic patients in titrating their medication in advance of anticipated hotspots. Using heat maps, the HMA can establish a correlation between hunger hotspots and glucometer scores. Since, hunger/appetite is a precursor to eating so being able to quantify and time appetite/hunger allows the patient or therapist to anticipate and act preemptively.

In accordance with still other embodiments, the intervention is directed towards receiving a weight trend of the user and an appetite pattern and determines a composite score of the user, wherein the composite score is a function of the user's historical degrees of appetite and weight trend. In one embodiment, the intervention causes the composite score to be displayed on the client device. In another embodiment, the intervention causes the client device to transmit the composite score to an online affinity or social network group, wherein the user is a member of the online affinity or social network group. In one embodiment, the intervention causes the daily or weekly composite scores to be displayed as icons or dots on heat maps.

In accordance with yet another embodiment, the intervention is directed towards plotting and displaying a composite score as icons or dots on heat maps, such as the map 7205 or 7220. In such embodiments, the composite score is daily or weekly appetite/hunger average or total.

It should be appreciated that the HMA automatically generates and provides at least one of the plurality of types of interventions based on at least the identified health trend or pattern—without any manual intervention from the user and/or a TPM. It should also be appreciated that at least one of the plurality of types of interventions is generated and provided to the user in any one of: in real-time with reference to identification of a health trend or pattern; within a predefined time-window such as within 72 hours, preferably within 24 hours, preferably within 12 hours, preferably within 2 hours of determining the health trend; or at a future time window at which the health trend is expected to occur or recur. The determination of a health trend, and more specifically an appetite pattern, is based on obtaining a sufficient amount of data, within a predefined range, for a given time window. In particular, the system analyzes acquired appetite data, each data element having a time stamp associated therewith, to determine a) how many data points are within a given time window and b) whether the data is clustered around a particular value or too distributed across a range of values to constitute a pattern. In one embodiment, data is considered to be sufficiently clustered if a majority of data elements are within a predefined deviation from an average appetite value in a given time window. In one embodiment, data is considered to be sufficiently clustered if a majority of data elements are outside a predefined deviation from an average appetite value in a given time window. A time window represents a range of time in a given day, such as from 11 am to 1 pm or 5 pm to 8 pm. In one embodiment, preferably the time windows are no less than 1 hour and no more than 6 hours.

In a first non-limiting example of steps 7012 and 7014, the HMA monitoring or tracking the plurality of health related information or data of the user may determine that the user's hunger level is above a predefined threshold level for 'N', say 3, number of consecutive occurrences, events, times or days—such as for 'N' consecutive meal events or for one or more meal events spread over 'N' consecutive days. Therefore, the HMA may flag the repeat consecutive occurrences of such high hunger levels as being indicative of a health trend. Consequently, the HMA automatically generates and provides at least one of the plurality of types of interventions for the corresponding future time windows within which the pattern occurs.

In a second non-limiting example of steps 7012 and 7014, the HMA monitoring or tracking the plurality of health related information or data of the user may determine that the user's appetite level is above a predefined threshold at a specific times of day, say at lunch time, for at least 'W' days, say 2 days, in a row. Additionally, the user's well-being level may be found to be at or above a predefined threshold level (representative of stagnant sub-optimal or deteriorating well-being) for the specific times of day and for at least 'W' days in a row. Based on the repeat consecutive occurrences of high appetite levels as well as stagnant sub-optimal or deteriorating well-being, the HMA may conclude that a health trend exists and, based on that, may automatically generate and provide at least one of the plurality of types of interventions for the corresponding future time windows within which the pattern occurs.

In a third non-limiting example of steps 7012 and 7014, the HMA monitoring or tracking the plurality of health related information or data of the user may determine that the user's weight loss is below a target range for 'Z' days, say 5 days, in a row. At the same time, the user's appetite level is found to be slightly above a predefined threshold level and the user's well-being level is also found to be at or above a predefined threshold level (representative of stagnant sub-optimal or deteriorating well-being) for 'Z' days consecutively. As a result, the HMA may conclude that a health trend exists and, based on that, may automatically generate and provide at least one of the plurality of types of interventions for the corresponding future time windows within which the pattern occurs.

In a fourth non-limiting example of steps 7012 and 7014, the HMA monitoring or tracking the plurality of health related information or data of the user may determine that the user reports 'T', e.g. 3, or more entries of hunger levels above a predefined threshold level within a same or similar predefined time-frame or time-window on 'V' different days, where the 'V' different days are at least 3 and where each of the days are separated by 1 to 2 days. Suppose the user reports hunger above a threshold level within a time-window ranging from ±15 minutes to ±3 hours of a time, say 6:45 am (or any other time, such as breakfast, lunch or dinner). In other words, the user reports hunger above a threshold level at 6:45 am, 7 am and 6:30 am on 'V', e.g. 3, respective different days. Such repeat occurrence of high hunger level within the same time-window is determined as a potential health trend. Consequently, the HMA may automatically generate and provide at least one of the plurality of types of interventions for the corresponding future time windows within which the pattern occurs. It should be appreciated, that if the high hunger level events are sporadic (for example, the user reports hunger above a threshold level at 6:45 am, 2 pm and 9 pm), that is not within a same or similar predefined time-frame or time-window, these are not recognized as patterns or health trends by the HMA.

In a fifth non-limiting example of steps 7012 and 7014, the HMA monitoring or tracking the plurality of health related information or data of the user may determine that the user's weight loss target over a period of targeted time is not being met. Let us say that the HMA determines that the user has not lost X pounds of weight by week Y (required to achieve or be on track for achieving a weight loss goal over a stipulated period of time) and may conclude this to be a health trend that would lead to the user missing his weight loss goal. Based on this determination, the HMA may automatically generate and provide at least one of the plurality of types of interventions for the corresponding future time windows within which the pattern occurs.

In a sixth non-limiting example of steps 7012 and 7014, the HMA monitoring or tracking the plurality of health related information or data of the user may validate the user's weight loss against a target linearly sloping weight trend or graph 7105 of FIG. 71. As shown in FIG. 71, the user's goal or target is to reduce his first weight 7110 to a second weight 7115 within a period of 'q' weeks 7120, wherein the second weight 7115 is less than the first weight 7110. Thus, the user's weight trend or graph 7105 is assumed to be downward sloping linearly over the 'q' weeks 7120. Now, if at any point in time, say at the end of 'r' weeks 7125 ('r' weeks is less than 'q' weeks) the user's weight may be $w_1$ 7130 that may lie above the required weight trend or graph 7105 at the end of the 'r' weeks 7125. In other words, the user is under-achieving his target weight loss. In such a situation, suppose the HMA determines a health trend related to hunger levels above a predefined threshold for 'N' consecutive days. At the same time, the HMA also determines a health trend related to well-being levels being at or above a predefined threshold (representative of stagnant sub-optimal or deteriorating well-being) for 'N' consecutive days. Since the user's weight $w_1$ 7130 lies above the required weight trend or graph 7105, the HMA may de-emphasize the well-being related health trend and emphasize or attach a higher weight or consideration to the hunger related health trend. Based on such a determination, the HMA may automatically generate and provide at least one of the plurality of types of interventions for the corresponding future time windows within which the pattern occurs.

However, if at any point in time, say at the end of 's' weeks 7135 ('s' weeks is less than 'q' weeks), the user's weight may be $w_2$ 7140 that may lie below the required weight trend or graph 7105 with reference to the end of 's' weeks 7135. In other words, the user is over-achieving his target weight loss. In such a situation, suppose the HMA determines a health trend related to hunger levels above a predefined threshold for 'N' consecutive days. At the same time, the HMA also determines a health trend related to well-being levels being at or above a predefined threshold (representative of stagnant sub-optimal or deteriorating well-being) for 'N' consecutive days. Since the user's weight $w_2$ 7140 lies below the required weight trend or graph 7105, the HMA may emphasize the well-being related health trend and de-emphasize or attach a lower weight or consideration to the hunger related health trend. Based on such a determination, the HMA may automatically generate and provide at least one of the plurality of types of interventions. In embodiments, the HMA may evaluate the user's weight to lie within a certain predefined range or band of the required weight trend or graph 7105. A deviation of the user's weight above or below the predefined band related to the weight graph 7105 is then used to weigh hunger trends vis-à-vis well-being trends to titrate stimulation.

In a seventh non-limiting example of steps 7012 and 7014, the HMA compares the user's most recent set of data (first set of appetite data) indicative of his degree of appetite in relation to historical data (second set of appetite data) indicative of the user's previous degree of appetite to determine to what extent the user's degree of appetite has changed (increased or decreased) over a predefined period for the same time of day. In embodiments, the HMA also generates a value indicative of the determined degree of change of appetite. Subsequently, the HMA determines and automatically generates at least one of the plurality of types of interventions based on the comparison of the first and second sets of appetite data.

In various embodiments, the type of intervention automatically generated for the user and/or a timing of providing the type of intervention to the user—depends on the amount of change (increase or decrease) of the user's most recent appetite data with respect to his historical appetite data over a predefined period for the same time of day. In some embodiments, if the amount of change is less than a predefined threshold value then a first type of intervention is automatically generated or triggered and delivered to the user while if the amount of change is more than the predefined threshold value then a second type of intervention is automatically generated or triggered and delivered to the user.

In an eighth non-limiting example of steps 7012 and 7014, the HMA determines an appetite pattern of the user based upon the inputted appetite data by determining a time window associated with each of the inputted appetite data and, for each time window, determining at least one of: if value ranges of all inputted appetite data associated with the time window are or, alternatively, are not within a predefined range around a value to constitute a pattern; and if a number of individual inputted appetite data values associated with the time window are sufficiently large or alternatively too low to constitute a pattern. In embodiments, the time window is in a range of 1 to 3 hours. Subsequently, the HMA determines and automatically generates at least one of the plurality of types of interventions if the value ranges of the inputted appetite data associated with the time window constitute a pattern.

In a ninth non-limiting example of steps 7012 and 7014, the HMA is configured to determine at least one of the following: prospectively predict the user's degree of appetite based upon an analysis of historical appetite data in relation to specific times of day; prospectively identify periods in which the patient's degree of appetite will exceed a threshold value based upon an analysis of historical appetite data in relation to specific times of day, wherein the periods correspond to particular times of day; and determine if the user's degree of appetite is expected to be greater than or less than a threshold value at a future time window.

Subsequently, the HMA determines and automatically generates at least one of the plurality of types of interventions in or before the future time window. For example, if the user's degree of appetite is expected to be less than the threshold value at the future time window, then the HMA does not generate any intervention during the future time window. However, if the user's degree of appetite is expected to be greater than the threshold value at the future time window, the HMA generates at least one of the plurality of types interventions during the future time window. In various embodiments, the HMA is configured to perform at least one of the following tasks based on a prospective prediction of the patient's degree of appetite: 1) modify parameters for a plurality of scheduled electrical stimulations, 2) add additional electrical stimulations, 3) remove electrical stimulations, 4) generate a notification, and 5) communicate a text-based message, video message, audio message, or graphic message to the user.

Referring back to FIG. 70, if a health trend is not determined or confirmed at step 7012 then, at step 7016, the HMA evaluates if additional information or data is required from the user in order to confirm an impending or ensuing health trend. If yes, then at step 7018, the HMA may automatically prompt the user for data inputs at specific points of time in the day to obtain the additional information or data needed to confirm or ascertain if a health trend exists or not. Optionally, the notification rate or frequency and timing may be modified by the HMA in order to get additional or missing health related data or obtain the data necessary to confirm a pattern. Optionally, the HMA may prompt or warn after a predefined period, such as one day, that the user is not providing enough data to establish an appetite pattern and that it will stimulate the user based on the predefined default stimulation or operational mode. In other words, according to aspects of the present specification, the notification rate or frequency is modified based on historical user inputs of health related information such as appetite or hunger. Thus, if user inputs in response to historical prompts regarding appetite, for example, are below a predefined threshold then the HMA may increase the rate or frequency of future prompts. Conversely, if the user inputs in response to historical prompts regarding appetite, for example, are above a predefined threshold then the HMA may increase the rate or frequency of future prompts. One of ordinary skill in the art would appreciate that the variation in prompt frequency may apply to hunger, satiety, satiation, fullness, caloric input, exercise input, among other variables.

Specifically, as data is gathered, the HMA evaluates the data to determine if there is a trend. For example, it may be determined that more data is needed if appetite data for a particular window, such as within 1 hour of conventional lunch time (noon), varies by more than 20%, as determined by a visual analog scale. In that case, it is unclear what the user's appetite is for key times of the day. In various embodiments, the HMA may also assume that, where the user does not provide, say, appetite/hunger data for example, then the appetite was below a threshold amount. Based on the user's input of the additional information or data, as a result of the prompt, the HMA may or may not ascertain presence of a health trend and accordingly may or may not generate one or more interventions, at step 7020.

By way of a non-limiting example of steps 6016, 7020, the HMA monitoring or tracking the plurality of health related information or data of the user may determine that the user's appetite level is above a predefined threshold at specific times of day, say at lunch time, for at least 'W' days, say 2 days, in a row. However, the user could not provide inputs related to his well-being levels for one or all of the 'W' days. In the absence of well-being related information or data, the HMA is unable to confirm the health trend related to heightened appetite. Therefore, the HMA (companion device) automatically prompts the user for his well-being levels and if the subsequently inputted well-being levels also show a deteriorating trend, the HMA may conclude that a heightened appetite related health trend does exist. Based on this conclusion, the HMA may automatically generate and provide at least one of the plurality of types of interventions for the corresponding future time windows within which the pattern occurs.

However, at step 7016, if the HMA determines that no additional information or data is required from the user in order to confirm a health trend then, at step 7022, the HMA does not generate any intervention and continues to continuously or periodically analyze the user's plurality of health related information to identify one or more health trends.

In accordance with an aspect, after generating and providing an intervention to the user, the HMA may query the user if he is satisfied with the intervention. If the user is not satisfied with the intervention, the user may be immediately prompted about his appetite or hunger data at that time and/or may be presented with a different intervention. For example, if the first intervention comprised coaching advice, the second intervention may comprise a modification of electrical stimulation parameters, prompted by a patient input that indicates the patient is not satisfied with the intervention.

Various embodiments also comprise triggering real-time stimulation based on the user's expressed request or need in addition to or in lieu of the standard stimulation protocol pre-configured settings (for example mild, optimal, intense) and/or in addition to or in lieu of the automatic stimulation modulation or titration based on identification or confirmation of one or more health trends. On-demand stimulations, also referred to hereinafter as "rescues" or "rescue sessions", are applied at the onset of unplanned or unscheduled hunger events and/or at a potential occurrences of hunger events as known from the user's hunger profile.

In various embodiments, the rescue sessions are initiated manually by the user in a plurality of ways, such as, but not limited to; by shaking motion of his smartphone that, in some embodiments, works as the companion device 105 of FIG. 1A; by issuing voice based commands to the Health Management Application (HMA) via an Intelligent Personal Assistant (IPA) system described with reference to FIG. 48A through C; by actuating a button on the EDP device itself or on a remote toggle switch configured to be worn around the user's neck or placed on his wrist in the form of a wristwatch or wristband; by issuing commands through pre-defined physical body movements, such as (for example) haptic motions of the wrist or hand, when the user is wearing a wristwatch or wristband (that includes an accelerometer or inclinometer to detect, capture and acquire the user's haptic motions). In other embodiments, the rescue sessions are automatically triggered, such as, by using the IPA system (configured as a Bluetooth speaker, for example) to sense the presence of the EDP device (worn by the user) within a food consumption area—for example, kitchen—as described earlier with reference to FIG. 48A through C. In some embodiments, the HMA, installed on the user's smartphone, utilizes the GPS sensor of the smartphone to determine if the user is in a restaurant, for example. If the user is found to be visiting a restaurant and it is not a meal time, the user is prompted for and delivered a rescue session. In still other embodiments, the rescue sessions are triggered by user action on a third party device (including a third party application software on an external device), with physiological sensors, configured to be worn on the human body, such as around the wrist, in order to monitor, acquire, record, and/or transmit the physiological data, to receive and integrate exercise and weight loss information.

In a preferred embodiment, demand for a rescue session is initiated by actuating a button on the user's smartphone that functions as the companion device 105 of FIG. 1A. In some embodiments, the button is physical such as a designated key on the smartphone while in other embodiments, the button is virtual such as a software-based icon on the smartphone. It is possible that the user may actuate the button multiple times, such as, by repeatedly pushing or clicking the button. To safeguard against such cases, repeated or multiple actuations are registered or counted as a single actuation if the repeated or multiple actuations occur within a predetermined time range (on the order of seconds or minutes) of each other. Actuating the button (such as by pressing the physical button or the software icon), in some embodiments, activates a light bar configured as a 0 to 10 point Visual Analog Scale (VAS) wherein 0 represents absence of any hunger and 10 represents the most intense level of hunger. FIG. 51 is a depiction of a graphical user interface with a visual light bar. It should be noted herein that while FIG. 51 is described in terms of a light bar having a scale from 0 to 10, any range may be employed, and any incremental iteration may correspond to any therapeutic length of time, in accordance with the present specification. For example, a range of 0 to 100 may be selected for the light bar to denote a patient's degree of hunger.

As shown in FIG. 51, the light bar VAS 5100 extends or progresses, from 0 at the far left 5102 of the scale to 10 at the far right 5104 of the scale depending upon how long the user presses the button. In other words, the longer the user presses the button, the longer the light bar extends. In an embodiment, the closer to 10 that the light bar progresses from 5102 to 5104, the darker it becomes. In an embodiment, the user may repeatedly press light bar 5100 on a touchscreen device until the appropriate degree of hunger is selected. In another embodiment, the user may slide the light bar 5100 from right to left or left to right, on a touchscreen device, to indicate the degree of hunger.

In accordance with an aspect, the length or extent of the light bar VAS is not only indicative of the level of hunger of a hunger event but is also indicative of the duration of a potential rescue session that may be triggered. In some embodiments, the length or extent of the light bar VAS is equal to the duration of the rescue session. Thus, a light bar VAS length representative of 7 (on the 0 to 10 VAS, for example) would trigger 7 minutes of rescue session therapy, a light bar VAS length representative of 8 would trigger 8 minutes of rescue session therapy and so on up to a maximum of 10 minutes of rescue session corresponding to a maximum light bar VAS length representative of 10. In accordance with an embodiment, a threshold or minimum actionable hunger level required to trigger any rescue session is set at 5 (that is, the midpoint of the light bar VAS). Thus, a light bar VAS length representative of 5 would trigger 5 minutes of rescue session therapy. However, light bar VAS lengths representative of hunger levels of less than 5, that is the levels of 0, 1, 2, 3 or 4, would register as low intensity hunger events but would not trigger a rescue session. In some embodiments, high levels of hunger on the light bar VAS (such as those greater than 6, for example) could trigger proportionally higher amplitude of rescue stimulation in conjunction or in lieu of longer rescue stimulation times.

It should be appreciated that the threshold or minimum actionable hunger level required to trigger any rescue session is set at 6, in alternate embodiments. In such alternate embodiments, light bar VAS lengths representative of hunger levels of less than 6, that is the levels of 0, 1, 2, 3, 4 or 5, would register as low intensity hunger events but would not trigger a rescue session.

In some embodiments, depending on the hunger intensity of the user any one of the following can happen: a) no stimulation because intensity level is below the threshold, b) hunger intensity level is above the threshold but below 8 that may trigger a rescue session of 15 minutes at 10 mA, c) hunger intensity level is above 8 that may trigger a rescue session of 15 minutes at 20 mA.

In some embodiments, the duration of the rescue session is proportional to the length or extent of the light bar VAS. For example, a VAS hunger intensity level of 7 (on a scale of 0 to 10) may trigger a proportionate rescue stimulus of, say, 10 minutes at 20 mA whereas a VAS hunger intensity level of 6 may trigger a proportionate rescue stimulus of, say, 5 minutes at 15 mA. A VAS hunger intensity level less than 6 (or less than 5, in alternate embodiments) may not trigger any rescue session.

In still other embodiments, the duration of the rescue session is proportional to the actual caloric intake (or caloric intensity) by the patient. Consider scenarios where the patient records caloric intake or consumption that exceeds planned consumption—for example, the actual caloric consumption of the patient at lunch is 800 calories instead of a planned 600 calories. Therefore, in such scenarios the patient is delivered a post-prandial rescue session which is proportionate to the caloric consumption of the patient.

While the user is allowed on-demand stimulations as well as customized stimulation protocols, in various embodiments the Health Management application is programmed to ensure (such as by continuous monitoring, limited or restricted control access to only the subset of stimulation parameters and/or restricting the user control access to only a constrained range within the standard settings ranges) that the user does not over or under stimulate, thereby resulting in habituation or ineffective stimulation. For example, the user may be allowed to add to the number of daily sessions, over and above those scheduled based on the standard protocol settings such as mild, optimal, intense or baseline stimulation protocol, but subject to some limitations or restrictions. For example, the user may have five additional "rescues" in the first month of the stimulation therapy, declining to 4 daily in the second month, and 3 daily in the third month of therapy. It should be appreciated that the limitations are critical to avoiding habituation over time. Also, the number of stimulation sessions may be restricted and then may decline and/or the stimulation intensity, such as the amplitude and frequency, may be allowed to be adjusted up or down by a set amount, for example by +/−10%. In some embodiments, the user is allowed up to 12 rescue sessions per day of short duration, say, 5 minutes.

In one embodiment, the user is allowed a daily total rescue budget of a maximum of, say, 60 minutes of rescue therapy that can be delivered in a minimum of 5 minutes and a maximum of 10 minutes boluses or rescue sessions—at an amplitude similar to the baseline stimulation protocol. Accordingly, the users are allowed a maximum of 12 rescue sessions of 5 minutes each (12×5 minutes) and a minimum of 6 rescue sessions of 10 minutes each (6×10 minutes) on a daily basis. Thus, in context of using the light bar VAS, the user can record an unlimited number of low level hunger events, but only a maximum budget of 60 minutes of actual rescue therapy, with no bolus shorter than 5 minutes. In an alternate embodiment, 60 minutes of rescue therapy can be delivered in 15 minutes of boluses or rescue sessions thereby allowing 4 rescue sessions of 15 minutes each (4×15 minutes). It should be appreciated that, in alternate embodiments, the daily total rescue budget may be defined in terms of minimum and maximum stimulation amplitude, frequency or number of rescue sessions within a stipulated period of time.

In another embodiment, the user is allowed a daily total rescue budget of a maximum of, for example, 90 minutes of rescue therapy that can be delivered in a minimum of 15 minutes boluses or rescue sessions—at an amplitude similar to the baseline stimulation protocol. Accordingly, the users are allowed a maximum of 6 rescue sessions of 15 minutes each (6×15 minutes) on a daily basis. In some embodiments, the daily total rescue budget of a maximum of 60 or 90 minutes can only be used between meals, such as, for example, more than 30 minutes prior or 90 minutes after a meal.

In one embodiment, the user is allowed a daily number of stimulations of, for example, 10 that can be delivered in default preprogrammed stimulations and/or real-time rescue sessions delivered in response to a patient's request. Before generating a rescue session, the system preferably analyzes the total number of stimulations delivered in a previous time period, such as 24 hours or less, and determines whether, and how many, stimulation sessions may be provided based on a combination of the number of pre-programmed stimulations and real-time rescue sessions being requested.

In embodiments, the daily total rescue budget is comprised of at least two components—a first component being the daily discretionary rescue budget and a second component being the daily automatic rescue budget. The daily discretionary rescue budget restricts the rescue sessions that the user is allowed to have according to his choice or discretion while the daily automatic rescue budget restricts the rescue sessions that the user is automatically delivered as a result of the user's history or pattern of unplanned or unscheduled hunger events. In some embodiments, the daily total rescue budget is set at, for example, 60 minutes while the daily discretionary and automatic rescue budgets are set at, for example, 30 minutes each. In alternate embodiments, the daily total rescue budget may be set at lesser or higher values and the daily discretionary and automatic rescue budgets may also comprise different percentages of the total rescue budget. In embodiments, where the daily total rescue budget is of a maximum of 90 minutes of rescue therapy, the daily discretionary and automatic rescue budgets are set at, for example, 45 minutes each.

In accordance with an aspect of the present specification, the hunger events, levels and the triggered "rescue sessions" are tracked (date and time stamped, including duration of each rescue session) and recorded (such as through the light bar VAS) to generate the user's individualized hunger profile or hunger map, over a predefined period of time and/or a predefined number of rescue sessions. In various embodiments, the predefined period of time ranges from a few days, say 5 to 7 days, to weeks, say 3 to 6 weeks. In various embodiments, the predefined number of rescue sessions ranges from 1 to 10 sessions. It should be appreciated that one or more threshold or filter conditions, such as but not limited to, the predefined period of time and/or number of rescue sessions are defined so as to achieve a sufficient level of confidence that the rescue sessions represent a pattern of hunger and not one-off random events.

The user's individualized hunger profile or map is dynamic and indicative of occurrences of events when the user actually feels hungry or is thinking about food and, in some embodiments, is representative of hunger spikes for the user. Therefore, in various embodiments, the user's individualized hunger profile is utilized to automatically customize, modify, drive and deliver stimulation therapy or protocol to target the user's hunger spikes. In other words, the variable number of daily rescue sessions are interpreted as the user's hunger or satiety level on a given day and used to create the user's individualized hunger map for that day, for example, showing the timing and/or intensity of hunger clusters. This hunger map is then be used to automatically titrate and time stimulation therapy. For example, in some embodiments, the threshold or filter conditions (to ascertain a pattern of hunger) may constitute or be defined as a minimum of, for example, 3 hunger events (each triggering a rescue session or bolus—that is, each of the 3 hunger event being of an intensity level greater than or equal to 5 on a 0 to 10 light bar VAS) recorded on 3 separate days in the same week and within, say, 60 minutes of the same time of day. Thus, meeting of the threshold or filter conditions may, for example, trigger an automatic 10 minutes rescue session or bolus at that time in subsequent week(s).

The user's individualized hunger profile or map represent a dynamic record of daily and weekly appetite trends and are therefore tracked and generated throughout the treatment cycle of the user. The dynamic hunger profile or map can be shown to the user daily and/or weekly and used as a measure or record of daily hunger intensity and distribution and, therefore, stimulation treatment progress over time. In some embodiments, the user's daily weight graph, as it evolves during a stimulation therapy, is overlaid or juxtaposed with the user's individualized hunger map to communicate treatment progress. The user's daily weight trend and hunger profile are utilized to titrate or trigger therapy as well as enable automated coaching so as to provide advice and encouragement to the user based on their performance and compliance. The user's individualized hunger profile or map is communicated to the user, affinity groups, physician, and an automated dietary coach or concierge service.

In some embodiments, the Health Management application continuously monitors, to titrate therapy accordingly, the user's glycemic indicator, such as, but not limited to, glucose level or glucose status data—in a closed loop configuration wherein glucose level, status data or data is obtained or received by the Health Management application by at least one of the following means: using a continuous glucose sensor integrated with the EDP as one of the sensors 135 of FIG. 1A, allowing the user to manually input glucose data using a VAS light bar at predetermined intervals (and/or as may be prompted by the HMA), allowing the user to verbally input glucose level at predetermined intervals via an IPA system (and/or as may be prompted by the IPA) in communication with the Health Management application, or using a third party device—whether it is a third party application software on an external device or a second external device entirely (such as, but not limited to, a watch, a pair of smart shoes, a diabetes wearable pump, or another medical device)—comprising a continuous glucose sensor alone or in combination with a plurality of physiological sensors and in communication with the HMA (via pairing or syncing). It should be appreciated that in some embodiments the HMA is installed or embedded on the third party device itself thereby obviating the need for a separate companion device.

Depending upon the received glucose data, a time of day and/or based on such historic glucose data as well as other current and/or historic health related information such as, but not limited to, the current and/or historic meal profile or the current and/or historic degree of appetite or hunger, the HMA may recommend (for user approval) or automatically commence (if pre-approved or pre-authorized by the user) a modified stimulation therapy (such as, modified timing, duration, number and/or intensity of stimulation sessions). For example, referring to a flow chart of FIG. 62, a user's glucose level or glucose status data is acquired by the HMA at step 6205. At step 6210, if it is determined that the user's glucose status data is higher than the normal, by a predefined glucose threshold, for example the glucose status data is equal to 200 mg/dl or higher, the HMA may program the EDP (in other words, the HMA generates and communicates a modulation signal to the EDP), at step 6215, to deliver a stimulation session of, e.g., 15 minutes duration at 20 mA intensity. If the glucose status data is not greater than 200 mg/dl, no stimulation session is delivered and the HMA continues to periodically and automatically monitor the user's glucose status data. In one exemplary scenario, at step 6220a, if after a predefined interval, e.g. an hour, it is determined that the user's glucose level is still high (e.g., greater than or equal to 200 mg/dl) the HMA, at step 6225, may re-program the EDP to deliver one or more subsequent stimulation sessions at increased therapy duration as well as intensity (for example). If, after the stimulation session and the predefined interval, the glucose status data is no longer greater than 200 mg/dl, the HMA does not reprogram the EDP to deliver one or more subsequent stimulation sessions but rather continues to periodically and automatically monitor the user's glucose status data.

In another exemplary scenario, at step 6220b, if after a predefined interval it is determined that the user's glucose level has lowered by at least 1% (compared to the glucose level before stimulation) the HMA, at step 6230, enables the EDP to continue stimulation at a predefined minimum amplitude and/or intensity either for a predefined fixed duration of time or until the user's glucose level returns to normal levels. If, after the stimulation session and the predefined interval, the user's glucose level has not lowered by at least 1% (compared to the glucose level before stimulation), the HMA does not enable the EDP to continue stimulation but rather continues to periodically and automatically monitor the user's glucose status data. In some embodiments, stimulation session(s) and titration of therapy protocols and/or patterns may be accompanied with cautionary alarms or feedback (audio, visual and/or tactile) to the user recommending the user to stop eating, for example when the glucose levels are observed to remain high for a period of time.

FIG. 63 is a flow chart illustrating a plurality of exemplary stimulation protocols followed once a user's glucose level or glucose status data is acquired by the HMA at step 6305. In one example protocol, at step 6310a, if the user's glucose level is greater than 100 mg/dl upon waking in the morning, the HMA may program the EDP to deliver at least one stimulation session to create fullness (equivalent to, say, a hunger level of less than 6 on a hunger scale of 0 to 10) for an extended period of time (in order to achieve a fasting state), wherein the extended period of time is at least 5 minutes. In another example protocol, at step 6310b, if the user's glucose level is above 140 mg/dl at any time of day, the HMA may program the EDP to deliver at least one stimulation session to reduce or suppress hunger to a level below 6 (on a hunger scale of 0 to 10) to prevent the user from overeating. In another example protocol, at step 6310c, the HMA may program the EDP to deliver at least one stimulation session so that the user's glucose level reaches a predefined minimum, such as 80 mg/dl, before the user feels sufficient hunger to eat. In yet another example protocol, at step 6310d, the HMA may program the EDP to deliver at least one stimulation session at night, e.g. past 7 pm, so that the user's glucose level is less than 100 mg/dl in the morning. In still another example protocol, at step 6310e, the HMA may program the EDP to deliver at least one stimulation session so that the user's rate of glucose is maintained at less than 2 mg/dl per minute.

FIG. 64 is a flowchart illustrating steps of a method of titrating stimulation therapy based on at least a glucose status data of a user, in accordance with an embodiment of the present specification. At step 6405, a user wears an EDP device of the present specification which is in communication with a separate companion or client device implementing a Health Management application (HMA) of the present specification. The EDP device is configured to generate a plurality of stimulation sessions comprising a plurality of electrical pulses defined by stimulation parameters such as, but not limited to, a session frequency, a session duration, a pulse width in a range of 10 μsec to 10 msec, a pulse amplitude in a range of 100 μA to 100 mA, and a pulse frequency in a range of 1 Hz and 100 Hz. At step 6410, the HMA acquires or receives the user's glucose status data or level using at least one of the following means: a) using a continuous glucose sensor integrated with the EDP as one of the sensors 135 of FIG. 1A to periodically and automatically monitor and record the user's glucose status data, b) by prompting the user, at predetermined intervals (and/or as may be prompted by the HMA), to input glucose status data by causing a VAS (visual analog scale) light bar to be displayed on the client device, c) allowing the user to verbally input glucose status data at predetermined intervals via an IPA system (and/or as may be prompted by the IPA) in communication with the Health Management application, or d) using a third party device, to periodically and automatically acquire the user's glucose status data and wirelessly communicate the glucose status data to the client device. The third part device may include a third party application software on an external device or a second external device entirely (such as, but not limited to, a watch, a pair of smart shoes, a diabetes wearable pump, or another medical device)—comprising a continuous glucose sensor alone or in combination with a plurality of physiological sensors and in communication with the HMA (via pairing or syncing).

It should be appreciated that the user's glucose status data acquired or received by the HMA is time stamped to associate a time of day to the monitored glucose status data. In some embodiments, the HMA acquires or receives the glucose status data at specific and predetermined times of day that are then associated with the acquired glucose status data and stored.

At step 6415, the HMA prompts the user to input his degree of appetite or hunger. In various embodiments, the user is prompted via an IPA system in communication with the HMA, through a microphone/speaker system of the client device and/or a display of the client device. The user may be prompted to input his degree of appetite at a predetermined schedule such as before and/or after scheduled or planned meals (like, breakfast, lunch and dinner), in association with a time of day when the user's glucose status data is acquired or received by the HMA and/or depending upon a need determined by the HMA based on an acquired or received glucose status data.

At step 6420, the HMA generates a modulation signal (to titrate stimulation protocols and/or parameters) based on any one or a combination of the acquired or received glucose status data, a time of day and a data indicative of the user's degree of appetite or hunger. At step 6425, the modulation signal is transmitted to the EDP. It should be appreciated that the modulation signal comprises a plurality of stimulation parameters and/or protocols that cause a glycemic indicator of the user to improve relative to the user's glycemic indicator prior to applying the modulation signal. In various embodiments, the glycemic indicator may include indicators such as, but not limited to, glucose level, a level of hemoglobin A1C, hepatic gluconeogenesis, a degree of insulin resistance, level of glucose homeostasis and a level of HOMA-IR (see section titled 'Therapeutic Objectives' of the specification for improvement objectives related to various glycemic indicators).

FIG. 65 is a flowchart illustrating steps of a use case of titrating stimulation based on at least a glucose status data of a user, in accordance with an embodiment of the present specification. At step 6505, the HMA acquires or receives a user's glucose status data before 11 am in the morning. The HMA examines, at step 6510, if the acquired or received glucose status data is greater than 100 mg/dl. If the glucose data is greater than 100 mg/dl then, at step 6515, the HMA generates and communicates a modulation signal to the EDP, wherein the modulation signal is configured to cause the electrical dermal patch to generate an electrical stimulation after 5 pm. It should be appreciated that the modulation signal comprises at least one of an increased second session frequency relative to a previous session frequency, an increased second session duration relative to a previous duration, an increased second pulse amplitude relative to a previous pulse amplitude, and an increased second pulse frequency relative to a previous pulse frequency. If the glucose status data is not greater than 100 mg/dl no modulation signal is generated and the HMA continues to periodically and automatically monitor the user's glucose status data.

FIG. 66 is a flowchart illustrating steps of another use case of titrating stimulation based on at least a glucose status data of a user, in accordance with an embodiment of the present specification. At step 6605, the HMA acquires or receives a user's glucose status data periodically throughout a day. The HMA examines, at step 6610, if the acquired or received glucose status data is greater than 140 mg/dl. If the glucose data is greater than 140 mg/dl then, at step 6615, the HMA generates and communicates a modulation signal to the EDP, wherein the modulation signal is configured to cause the electrical dermal patch to generate an electrical stimulation within two hours after determining the glucose level is greater than 140 mg/dl. If the glucose status data is not greater than 140 mg/dl no modulation signal is generated and the HMA continues to monitor the user's glucose status data throughout the day.

FIG. 67 is a flowchart illustrating steps of another use case of titrating stimulation based on at least a glucose status data of a user, in accordance with an embodiment of the present specification. At step 6705, the HMA acquires or receives a user's glucose status data periodically throughout a day. The HMA examines, at step 6710, if the acquired or received glucose status data is greater than 140 mg/dl. If the glucose data is greater than 140 mg/dl then, at step 6715, the HMA also examines data indicative of the user's degree of appetite or hunger. It should be appreciated that the HMA may examine a last stored degree of appetite (from the user's daily diary inputs) and/or prompt the user to acquire (immediately upon acquiring or receiving the glucose status data or at a predetermined later time or after a time interval) a current degree of appetite or hunger. If the glucose data is greater than 140 mg/dl and the degree of appetite is also greater than a predefined threshold or number then, at step 6720, the HMA generates and communicates a modulation signal to the EDP, wherein the modulation signal is configured to cause the electrical dermal patch to generate an electrical stimulation within a predefined time, such as two hours, after determining the glucose level is greater than 140 mg/dl and the user's degree of appetite is greater than the predefined number. If the glucose status data is not greater than 140 mg/dl and/or the user's degree of appetite is not greater than the predefined number, then no modulation signal is generated and the HMA continues to monitor the user's glucose status data throughout the day.

FIG. 68 is a flowchart illustrating steps of yet another use case of titrating stimulation based on at least a glucose status data of a user, in accordance with an embodiment of the present specification. At step 6805, the HMA acquires or receives a user's glucose status data. The HMA examines, at step 6810, if the acquired or received glucose status data is less than 80 mg/dl. If the glucose data is less than 80 mg/dl then, at step 6815, the HMA generates and communicates a modulation signal to the EDP. It should be appreciated that the modulation signal comprises at least one of a decreased second session frequency relative to a previous session frequency, a decreased second session duration relative to a previous duration, a decreased second pulse amplitude relative to a previous pulse amplitude, and a decreased second pulse frequency relative to a previous pulse frequency. If the glucose status data is not less than 80 mg/dl no modulation signal is generated and the HMA continues to monitor the user's glucose status data.

FIG. 69 is a flowchart illustrating steps of still another use case of titrating stimulation based on at least a glucose status data of a user, in accordance with an embodiment of the present specification. At step 6905, the HMA acquires or receives a user's glucose status data. The HMA examines, at step 6910, if a rate of increase in a glucose level of the patient is more than 2 mg/dl per minute. If the rate is more than 2 mg/dl per minute then, at step 6915, the HMA generates and communicates a modulation signal to the EDP. It should be appreciated that the modulation signal comprises at least one of an increased second session frequency relative to a previous session frequency, an increased second session duration relative to a previous duration, an increased second pulse amplitude relative to a previous pulse amplitude, and an increased second pulse frequency relative to a previous pulse frequency. If the rate is not more than 2 mg/dl per minute no modulation signal is generated and the HMA continues to monitor the user's glucose status data.

In some embodiments, the Health Management application is configured to be in communication with an insulin pump that the user may be using to infuse insulin while the electro-dermal patch device of the present specification uses a continuous glucose sensor, as one of the sensors 135 of FIG. 1A or as a standalone third party device in wireless communication with the HMA, to continuously monitor the user's glucose level in a closed loop configuration. Thus, for example if the user's glucose level is higher than the normal, by a predefined glucose threshold, the Health Management application may recommend commencing with the optimal or intense stimulation protocol along with a diet plan, such as that illustrated in Table 3, for a period of 2 weeks. In some embodiments, the HMA may be pre-configured or pre-authorized by the user to automatically trigger the optimal or intense stimulation protocol if the user's glucose level is found to be higher than the normal. In various embodiments, a predefined glucose threshold comprises a fasting blood sugar level greater than 80 mg %. The Health Management application continuously monitors the user's glucose levels during the therapy and allows the user to suppress postprandial glucose levels. When it is found that, due to the stimulation therapy, the user's glucose levels are gravitating towards normal levels the Health Management application communicates this information to the user's insulin pump to slow the insulin delivery/infusion. As discussed earlier, the stimulation protocol may be automatically adjusted to mild, optimal, intense or the stimulation therapy may be completely stopped depending upon the effect on the glucose levels of the user. It should be appreciated that while in some embodiments the HMA is pre-configured or pre-authorized by the user to automatically titrate stimulation therapy (that is, start, stop or adjust stimulation protocol) depending on the monitored glucose level, in alternate embodiments the HMA recommends a relevant stimulation therapy or protocol (for example, mild, optimal, intense or complete stop stimulation) to the user who then accepts the recommendations subsequent to which the accepted stimulation therapy or protocol is initiated.

In some embodiments, the electro-dermal patch device of the present specification is sized in the form of a skin patch that covers both of the T6 and T7 dermatomes. In alternate embodiments, the user may use a first electro-dermal patch on the T6 dermatome and a second electro-dermal patch on the T7 dermatome. In such cases, the Health Management application alternatingly stimulates the T6 and T7 dermatomes to treat conditions of obesity, over-weight, eating disorders, metabolic syndrome as well as T2DM. In some embodiments, the electro-dermal patch device of the present specification is sized to cover both of the C8 and T1 dermatomes (as shown in FIG. 19C). In alternate embodiments, the user may use a first electro-dermal patch device on the C8 dermatome and a second electro-dermal patch device on the T1 dermatome. In such cases, the Health Management application alternatingly stimulates the C8 and T1 dermatomes to treat conditions of obesity, over-weight, eating disorders, metabolic syndrome. In various embodiments, a plurality of electro-dermal patch devices of the present specification are used to cover T6, T7, C8 and/or T1 dermatomes that are simultaneously or alternatingly stimulated to conditions of obesity, over-weight, eating disorders, metabolic syndrome and/or T2DM.

It should be noted, that the various suggestions and recommendations auto generated by the Health Management application, for initial fresh stimulation protocols, patterns and parameter settings as well as those related to adjusting these stimulation protocols and settings may, in various embodiments, be implemented by the user only after an approval and advice from the remote patient care facility and/or personnel. In some embodiments, however, prior approval from the remote patient care facility or personnel may not be required. The Health Management application enables the user to set an option of prior approval or disable this option.

In some embodiments, the electro-dermal patch device is driven by stimulation algorithms having different stimulation parameters to treat conditions of obesity, over-weight, eating disorders, metabolic syndrome by first enabling the patient to lose excess weight and then maintain the weight loss. For example, in one embodiment, the patient is stimulated with a first stimulation algorithm to induce weight loss. Once the patient has reached a target weight, the stimulation algorithm is changed to a second stimulation algorithm to maintain the weight loss. In some embodiments, the total stimulation energy per day provided by the first algorithm to induce weight loss is greater than the total stimulation energy per day provided by the second algorithm to maintain weight loss.

Example Stimulation Protocols for Managing Habituation, Nausea, Dyspepsia, and Skin Irritation Habituation refers to a decrease in sensory perception of a stimulus after prolonged presentation of the stimulus. In various embodiments of the present specification, in order to overcome habituation, the stimulation intensity is designed to gradually increase or decrease throughout the entire therapy session, in contrast to prior art practices of requiring the patient to manually increase or decrease intensity periodically during the therapy session. The present specification also learns the manner and frequency of the manual adjustment of the desired stimulation intensity so as to customize the stimulation parameters that modify stimulation in order to combat habituation.

In accordance with an exemplary embodiment, the stimulation intensity (comprising the pulse amplitude and/or frequency) is increased or decreased arithmetically (that is, linearly) or geometrically (that is, exponentially) with time. It should be noted, that an increase in the stimulation intensity is always above the user's 'sensory threshold' (which is already determined prior to stimulation sessions) and a decrease in the stimulation therapy is constrained in that the stimulation intensity is not allowed to fall below the 'sensory threshold'. As an example, for geometric increase or decrease, the stimulation intensity is multiplied or divided by a fixed factor per unit time. For example, the stimulation intensity may be geometrically increased or decreased by a factor Z, wherein Z is say 1.004 as an example, for every minute of a therapy session. This equates to an approximately 27% increase or decrease in stimulation intensity over a 60 minute therapy session. In various embodiments, 'Z' comprises a 10% to 50% increase or decrease of any given parameter. In another embodiment, the stimulation intensity is linearly increased or decreased by a fixed amount, such as 0.5 mA, for every minute of the therapy session. In another embodiment, the rate of increase or decrease is adjusted to account for manual changes in the stimulation intensity. For example, if the user decreases the stimulation intensity in the middle of the therapy session, then the automatic rate of increase may be too high for this user and should be decreased for subsequent therapy sessions. Similarly, if the user increases the stimulation intensity in the middle of the therapy session, then the automatic rate of increase may be too low for this user and should be increased for subsequent therapy sessions. In this fashion, the automatic habituation compensation is adaptive and responsive to the user's physiology.

In further embodiments, the stimulation continuity profile may be a step-up or a step-down profile wherein the stimulation amplitude and/or frequency may increase or decrease on a per session basis and/or the number of stimulation sessions per day may increase or decrease throughout the duration of a stimulation therapy or course to combat habituation.

In various embodiments, if the user feels nausea or dyspepsia before, during and/or after stimulation sessions he may provide an input to the Health Management application that a nausea and/or dyspepsia event occurred which is then automatically time stamped and stored by the application to generate and display a dynamic well-being profile or map of the user.

In a preferred embodiment, a nausea and/or dyspepsia event—constituting the well-being parameter—is recorded by actuating a button on the user's smartphone that functions as the companion device 105 of FIG. 1A. In some embodiments, the button is physical such as a designated key on the smartphone while in other embodiments, the button is virtual such as a software-based icon on the smartphone. Actuating the button (such as by pressing the physical button or the software icon), in some embodiments, activates a light bar configured as a 0 to 10 point Visual Analog Scale (VAS) wherein 0 represents no nausea and/or dyspepsia (that is, the highest level of well-being) and 10 represents the most intense level of nausea and/or dyspepsia (that is, the worst level of well-being).

The light bar VAS extends or progresses depending upon how long the user presses the button. In other words, the longer the user presses the button, the longer the light bar extends. In accordance with an aspect, the length or extent of the light bar VAS is indicative of the level or intensity of nausea and/or dyspepsia experienced. In accordance with an embodiment, a threshold or minimum actionable nausea and/or dyspepsia level is set at 4 on the VAS. Thus, a light bar VAS length representative of a level of nausea and/or dyspepsia at or below 3 (that is, levels 1, 2 or 3) would not trigger any action. However, light bar VAS lengths representative of nausea and/or dyspepsia levels of 4 and above would register as high intensity, and therefore, actionable nausea and/or dyspepsia or negative well-being event.

As a result of occurrence of an actionable nausea and/or dyspepsia event, the Health Management application may modify an existing stimulation protocol, for example may recommend switching the current intense stimulation protocol to the mild stimulation protocol if, for example, the nausea and/or dyspepsia intensity ranges between 7 and 9. Additionally or alternatively, the stimulation continuity profile may be switched to the step-down profile. Still further, the Health Management application may recommend pausing the stimulation sessions for one or more days before restarting with a step-down stimulation protocol. In yet another embodiment, the Health Management application may recommend pausing the stimulation sessions as well as not allowing any rescue sessions for one or more days before restarting with a step-down stimulation protocol. For example, in one embodiment, any single nausea and/or dyspepsia event at an intensity of 10 on the VAS scale will immediately cause all subsequent therapy sessions to be stopped and the user prompted to call their physician. In another example, if the user records K number of nausea and/or dyspepsia events of intensity between 4 and 6, within L period of time the HMA may switch the stimulation continuity profile to the step-down profile. In another embodiment, for example, any cumulative actionable VAS score of 15 in the same week—that is, a score of a 4, and a 5 and a 6 would, in combination, cause the Health Management application to shut down therapy. In yet another embodiment, any actionable cumulative score in the same week greater than 10 would cause the Health Management application to reduce the baseline therapy sessions from 30 to 15 minutes each (that is, a total of 15 minutes×3 daily sessions=45 minutes per day rather than the baseline 30 minutes×3 daily sessions=90 minutes per day). In this embodiment, if the frequency of such actionable nausea and/or dyspepsia events continues, the therapy is terminated.

In various embodiments, modification of an existing stimulation protocol is affected at night when the user is in bed. In accordance with an aspect, the HMA enables the user to not only input and record a nausea and/or dyspepsia event but also input additional information such as how long the event lasted and presenting a GUI screen to the user, after a predefined period of time has elapsed since recordation of a nausea and/or dyspepsia event, to check and record if the user is still feeling the same way. If the user reports that he is still feeling the nausea and/or dyspepsia, even after the predefined period of time, the HMA prompts the user to meet or get in touch with his physician and also send a notification to the user's physician or remote care facility.

In accordance with an exemplary embodiment, the electro-dermal patch device of the present specification generates biphasic, symmetrical, rectangular pulses with regulated current. This pulse waveform is charge-balanced which prevents iontophoretic build-up under the electrodes that can lead to skin irritation and potential skin damage. In accordance with another exemplary embodiment, the EDP device generates biphasic, asymmetrical charge-balanced pulses with regulated current. Thus, in various embodiments, the EDP device generates pules to pulse flipped symmetrical or asymmetrical, biphasic, charge-balanced pulses. Regulated current pulses provide more stable stimulation than regulated voltage pulses, because the stimulation current is independent of the electrode-skin impedance, which typically changes during the course of a therapy session. In order to address a wide variety of skin types and electrode quality (due to repeat use and air exposure), the maximum output voltage is 100V and the maximum output current is 50 mA. Finally, the pulse pattern is continuous stimulation with randomly varying inter-pulse intervals such that the frequency of stimulation has a uniform probability distribution between 50 Hz and 150 Hz. Alternatively, the frequency of stimulation may have a Gaussian probability distribution between 50 Hz and 150 Hz, or some other probability distribution. The benefit of providing frequency stimulation with randomly varying inter-pulse intervals (versus frequency stimulation with constant inter-pulse intervals) is that the former type of stimulation may lead to less nerve habituation.

Still further embodiments may involve relocating the electro-dermal patch device from the first stimulation spot to a second spot and alternating between the first and second stimulation spots to avoid habituation, skin irritation, nausea and/or dyspepsia.

In accordance with some embodiments, stimulation sensation experienced by the user is modulated by modifying the waveform of the delivered pulses without modifying the pulse amplitude by more than 10%. Accordingly, in embodiments, the EDP device delivers electrical stimulation at, say, amplitude of 20 mA with biphasic current and a first waveform wherein the first waveform is a sloping waveform 5905 as shown in FIG. 59A. It should be appreciated that while the first waveform may provide a comfortable and therapeutically effective sensory stimulation to the user, this may not be therapeutically effective or be below "sensory threshold" for a different user. In accordance with aspects of the present specification, rather than substantially increasing the amplitude of stimulation—which may increase the risk of nausea, dyspepsia and/or habituation—the waveform of the electrical stimulation is modified to a second waveform wherein the second waveform is a square waveform 5910 as shown in FIG. 59B.

Accordingly, in one embodiment, a first pulse shape is modified to a second pulse shape in response to a determination that the stimulation comprising the first pulse shape is not sufficiently therapeutically effective. The first pulse shape is modified to the second pulse shape by modifying a slope function of the first pulse shape without modifying the overall pulse amplitude by more than 30%, preferably not more than 20%, and more preferably not more than 10%. In another embodiment, the first pulse shape is modified to the second pulse shape by increasing a rate of increase from a minimum pulse amplitude to a maximum pulse amplitude, increasing a rate of decrease from a maximum pulse amplitude to a minimum pulse amplitude, and/or lengthening a time at which the pulse remains at the maximum pulse amplitude.

For an exemplary test environment, Table W shows a plurality of skin impedance magnitudes obtained, using a MetroOhm AutoLab PGSTAT128N electrochemical workstation, by connecting two electrodes (of an embodiment of the EDP device of the present specification) in series with a patient's skin/abdomen impedance. Next, the electrode attached to the patient's abdomen was connected to a stimulator, of an embodiment of the EDP device of the present specification, programmed with asymmetric biphasic charge balanced waveform. As shown in Table X, using a frequency of 20 Hz and pulse width of 200 µs, the regulated current output was set to various values while the compliance voltage waveform was obtained on an oscilloscope.

TABLE W

| Frequency (kHz) | Impedance (kohm) |
| --- | --- |
| 1 | 5.5 |
| 2 | 3.6 |
| 3 | 2.8 |
| 4 | 2.3 |
| 5 | 2.0 |
| 6 | 1.7 |
| 7 | 1.6 |

TABLE W-continued

| Frequency (kHz) | Impedance (kohm) |
| --- | --- |
| 8 | 1.5 |
| 9 | 1.3 |
| 10 | 1.2 |

TABLE X

| Current (mA) | Voltage Peak (V) |
| --- | --- |
| 5 | 14 |
| 10 | 26 |
| 15 | 39 |
| 20 | 40 |
| 30 | 40 |

As seen in Table X, a maximum peak compliance voltage of approximately 40 volts was obtained around 16 mA of current. The waveform for the 20 mA setting is illustrated as the first waveform 5905 in FIG. 59A. Further increases in nominal current setting did not increase peak voltage past 40 Volts (since this was the maximum compliance voltage of the stimulator used). However, as the nominal current setting was increased, the leading voltage edge became steeper yielding a more 'square waveform' illustrated as the second waveform 5910 in FIG. 59B. This resulted in more charge being applied to the user (that is, area under the curve) and/or steeper initial upswing in current waveform minimizing the effects of accommodation—hence increased stimulation sensation to the user.

In some embodiments of the present specification, a flipped waveform is alternated every other pulse to ensure balanced charge while changing the leading edge time constant (that is, the slope). It should be noted that the 'sloping waveform' 5905 is characterized by a rate of increase from a minimum amplitude to a maximum amplitude that is less than that of the 'square waveform' 5910 and/or a rate of decrease from a maximum amplitude to a minimum amplitude that is less than that of the 'square waveform' 5910. Both waveforms 5905, 5910 have the same peak compliance voltage but different time constants for the rising phase and hence different stimulation levels perceived by the user. Thus, modifying the waveform from the first waveform to the second waveform increases the stimulation sensation to the user. In embodiments, the modulation or titration of the waveform may be affected in response to the user's input to the VAS hunger scale. In other words, if the user's VAS hunger scale, using stimulation with the first waveform, shows increased hunger or unchanged yet high hunger level after at least one stimulation session the stimulation waveform is modified to the second waveform either automatically (after the user's approval) or manually by the user. In various embodiments, the slope of the stimulation pulse waveform is gradually reduced from a substantially 'sloping' waveform to a less sloping or substantially 'square' waveform. In some embodiments, the waveform is modified from a 'sloping' waveform to a less sloping or 'square' waveform without modifying the pulse amplitude by more than 10%.

Placebo Stimulation Protocol for Psychological Treatment

In accordance with some aspects of the present specification, the HMA programs the EDP device to deliver placebo stimulation to the user in lieu of or in addition to actual stimulation sessions. Placebo stimulation refers to creating a perception of stimulation to modulate the psychology of the user without actually delivering an electrical stimulation treatment. In embodiments, placebo stimulation creates a psychological 'feeling' of receiving a stimulation treatment in the user—leading to a positive therapeutic effect (also referred to as the "placebo effect" or "placebo response").

In various embodiments, to create a placebo effect, the EDP device may do any one or a combination of the following: vibrate at an amplitude and/or frequency perceptible to the user, flash LEDs during a treatment session to create a feeling in the user that a therapy session is underway, generate auditory intonations or sounds, generate verbal messages to create an impression that a treatment is being delivered.

It should be appreciated that placebo stimulation sessions may be interleaved with actual electrical stimulation sessions, in various embodiments.

Incremental or Residual Therapy Benefits (Latency Effect), Therapy Vacation and Maintenance Therapy In accordance with aspects of the present specification, a user's stimulation therapy program or cycle, delivered using the EDP device embodiments of the present specification, comprises a plurality of phases or stages:

A first therapy phase is a period of time during which the user is delivered pre-programmed, customized and/or on-demand stimulation sessions. The first therapy phase is characterized by the fact that the user has a first (baseline) metabolic or health state at the beginning of the first therapy phase and a second metabolic or health state at the end of the first therapy phase. The first metabolic or health state may be defined by reference to the quantitative value of only one parameter of the patient's metabolic or health state, to the quantitative value of a subset of all parameters defining the metabolic or health state, or to the quantitative value of all parameters defining the metabolic or health state.

The first therapy phase is an active treatment period that may last for a period ranging from days, weeks to months to achieve the second metabolic or health state which is an improved or fully treated metabolic or health state compared to the first metabolic or health state of the user. In embodiments, achieving the second metabolic or health state comprises achieving one or more underlying therapeutic objectives that define a metabolic or health state such as, but not limited to, target weight loss and/or target glucose level. In embodiments, the end of the first therapy phase is marked by the user a) achieving at least one or any sub-set or combination of therapeutic objectives underlying the user's metabolic or health state (refer to the definition of "metabolic or health state" earlier in this specification), and/or b) completing a predetermined number of stimulation sessions (such as, three sessions over three separate days) over a predetermined therapeutic time period (such as, for example, 3 or 6 months).

A second therapy phase (that begins at the end of the first therapy phase) is a period of time during which the user is not delivered any stimulation but during which the user still continues to possess or enjoy incremental therapy or residual benefits (also referred to as 'latency effect') emanating from the treatment of the first therapy phase. In other words, although stimulation sessions are stopped and the user is on a therapy vacation, the user either continues to stay at the second metabolic or health state or the user's second metabolic or health state does not deteriorate and change by more than 15% during the second therapy phase. That is, the achieved at least one therapeutic objective (at the end of the first therapy phase) which defines the metabolic state does not degrade by more than 15%. In embodiments, the second therapy phase may extend over a period of days, weeks or months.

In some embodiments, the second therapy phase may extend an amount of time less than, equal to or greater than the first therapy phase or treatment period without degrading by more than 15%. For example, during the first therapy phase if the user is stimulated for a minimum amount of time, e.g. three times over three separate days for at least 15 minutes each time at 5 mA per session (or preferably, 30 minutes each time at 20 mA per session), then an improvement in a therapeutic objective such as, but not limited to, delay in gastric emptying (say, a 10% delay in gastric emptying post-stimulation therapy relative to the delay in gastric emptying prior to the stimulation therapy) continues for at least one day after terminating the stimulation.

FIG. 60 shows a graph comparing a therapeutic objective, such as % Total Body Weight Loss (% TBWL), achieved using the EDP devices of the present specification for 3 months against the % TBWL achieved using an Intragastric Balloon for 6 months. With reference to FIG. 60, a first % TBWL value 6005 is achieved using an Intragastric Balloon for 6 months with a first dietary regimen and a first lifestyle (that is, a certain intensity of exercising—for example), a second % TBWL value 6010 is achieved using the Intragastric Balloon for 6 months with a second dietary regimen and a second lifestyle, whereas a third % TBWL value 6015 is achieved using just the first dietary regimen and lifestyle (and without using the Intragastric Balloon).

The first bar graph 6020 illustrates the % TBWL value achieved using a first stimulation protocol lasting over 3 months and combined with the first dietary regimen and the first lifestyle, the second bar graph 6025 illustrates the % TBWL value achieved using a second stimulation protocol lasting over 3 months and combined with the first dietary regimen and the first lifestyle, whereas the third bar graph 6030 illustrates the % TBWL value achieved using the second stimulation protocol lasting over 3 months and combined with the second dietary regimen and the second lifestyle. In other words, the % TBWL values represented by the first, second and third bar graphs 6020, 6025, 6030 are achieved at the end of the 3 months period (the first therapy phase).

The fourth bar graph 6035 illustrates the % TBWL value retained at the end of 3 months after terminating stimulation (that is, at the end of the second therapy phase) in comparison to the first bar graph 6020 and associated % TBWL value achieved using the first stimulation protocol lasting over 3 months and combined with the first dietary regimen and the first lifestyle, the fifth bar graph 6040 illustrates the % TBWL value retained at the end of 3 months after terminating stimulation (that is, at the end of the second therapy phase) in comparison to the second bar graph 6025 and associated % TBWL value achieved using the second stimulation protocol lasting over 3 months and combined with the first dietary regimen and the first lifestyle, whereas the sixth bar graph 6045 illustrates the % TBWL value retained at the end of 3 months after terminating stimulation (that is, at the end of the second therapy phase) in comparison to the third bar graph 6030 and associated % TBWL value achieved using the second stimulation protocol lasting over 3 months and combined with the second dietary regimen and the second lifestyle.

As can be observed from FIG. 60, a) 70 to 90% of % TBWL value achieved during the first therapy phase was extended or retained during the second therapy phase, and b) the % TBWL values achieved using stimulation therapy was comparable to corresponding % TBWL values achieved using an Intragastric Balloon.

In various embodiments, an end of the second therapy phase is marked by the user's metabolic or health state returning to a third metabolic or health state wherein the third metabolic or health state is lower than the second metabolic or health state by more than 15%. In some embodiments, however, the third metabolic or health state may be equivalent to the user's first or baseline metabolic or health state.

Accordingly, in one embodiment, after a first phase of treatment using one of the aforementioned stimulation protocols, wherein the first phase lasts anywhere from 1 to 6 months, preferably 3, the patient loses a percent of total body weight in a range of 3% to 15%, preferably between 6% and 10%. After stimulation ceases and a second phase of time elapses (such as between 1 and 6 months, preferably 3), the percent of total body weight lost is in a range of 2% to 14%, preferably between 5% and 9%.

A third therapy phase (that begins at the end of the second therapy phase) is a period of time during which stimulation treatment is recommenced for the user as part of a maintenance therapy. An objective of the maintenance therapy is to ensure that the user either continues to stay or maintain the second metabolic or health state (if the user was at the second metabolic or health state at the end of the second therapy phase) or re-achieve and thereafter maintain the second metabolic or health state (if the user had fallen to the third metabolic or health state at the end of the second therapy phase). The maintenance therapy is characterized by a stimulation protocol that delivers a lower level of stimulation energy or intensity (such as, for example, fewer number of stimulation sessions per week and/or stimulation sessions at lower amplitudes) throughout the third therapy phase as compared to the level of stimulation energy or intensity delivered to the user during the first therapy phase. In embodiments, the third therapy phase may extend over a period of weeks or months.

It should be appreciated that the EDP based methods and systems of the present specification enable stimulation therapy to be delivered to the patient over extended period of time (ranging from weeks to months) with exceptionally high patient compliance to the therapy regimen while at the same time effectively avoiding and managing undesired affects such as habituation, nausea and/or dyspepsia. Owing to high therapy compliance over an extended therapy period, the patient's metabolic or health state is continuously reset to a better state throughout the first therapy phase—leading eventually to the second metabolic or health state. As a result, even when stimulation is stopped at the end of the first therapy phase, the patient continues to benefit therapeutically, during the second therapy phase, from the second metabolic or health state achieved due to a cumulative or latency effect (or a 'neurostimulation durability effect') of the stimulation therapy. Accordingly, the patient is enabled to take a vacation from therapy, during the second therapy phase, allowing the patient to further rid her body of any tendency to habituation to the stimulation while also taking a break from the daily routine of therapy.

Following the therapy vacation, that is during the third therapy phase, stimulation is recommenced but at lower levels of delivered energy in order to maintain the metabolic reset without risk of habituation. In various embodiments, over long term, maintenance therapy would proceed via a combination of therapy vacations and maintenance stimulation (at a lower level of stimulation intensity or energy).

Inputs to long term maintenance therapy would be from continuing patient diary (such as, but not limited to, daily weight, hunger, well-being).

In accordance with aspects of the present specification, the stimulation therapy program or cycle comprising the first, second and third therapy phases is managed, controlled and effectuated by the HMA via reminders, prompts and stimulation sessions in combination with subscription billing options. For example, in some embodiments, once at least one therapeutic goal, such as weight loss, has been achieved or a certain predetermined number of stimulation sessions have been completed over a predetermined therapeutic time period (for example, 3 to 6 months), the HMA a) automatically discontinues stimulation (in the second therapy phase) to allow the patient's body to rid of habituation effects, and b) requires the user to pay a renewal fee (perhaps lower than the fee required during the first therapy phase) to initiate maintenance therapy (in the third therapy phase).

Methods of Use

In accordance with various aspects of the present specification, the user is enabled to apply or use the electro-dermal patch device of the present specification with active, regular, periodic, none and/or minimal intervention, monitoring and management from a physician, dietician, weight loss clinician or a remote patient care facility (hereinafter referred to as a TPM (Third Party Manager) who will be responsible for prescribing the EDP device and monitoring therapy.

In some embodiments, the user visits his physician for just one session wherein, depending upon the user's medical condition, the physician may prescribe the electro-dermal patch device of the present specification to the user along with the stimulation configuration, from the external surface of the patient's epidermal layer through 10 mm or 20 mm of the dermis, of the electro-dermal patch device, as described with reference to FIG. 1A through 1C. In some embodiments, the user visits a TPM for a medical check-up or evaluation wherein, depending upon the user's medical condition, the TPM may prescribe the electro-dermal patch device of the present specification to the user along with the stimulation configuration, from the external surface of the patient's epidermal layer through 10 mm or 20 mm of the dermis, of the electro-dermal patch device, as described with reference to FIG. 1A through 1C.

In various embodiments, a stimulation depth through the patient's epidermal layer ranges from 0.1 mm to 0.5, 1, 2, 3, 4, 5, 6, 7, 8, 9, 10, 11, 12, 13, 14, 15, 16, 17, 18, 19, 20 mm or any increment therein.

In some embodiments, the user's need for the EDP device therapy is determined based on, at least, his current BMI for appetite modulation. For example, the EDP device therapy is recommended if the current BMI of the user lies above a BMI threshold ranging from 20 to 25, preferably greater than or equal to 25. Alternatively or additionally, the TPM may utilize the user's SNAQ score, for example, to assess if the user is anorexic or has poor appetite. If so, the TPM may not recommend EDP device therapy for the user. Similarly, if the user's BMI is below 20 then the EDP device therapy may not be considered ideal for the user. In other words, the TPM evaluates the user's medical condition to make sure that the user would benefit from the stimulation therapy and not be harmed.

During the session, the physician or the TPM then assists or instructs the user in identifying appropriate areas of stimulation, such as T6, C8 and/or T1 dermatomes for conditions of obesity, over-weight, eating disorders, metabolic syndrome and T7 for T2DM management, and also provides an orientation to the user regarding use and functions of the electro-dermal patch device. In various embodiments, the appropriate areas of stimulation may be identified, for example, by one or more temporary tattoos (such as a small dot) or an image of the user may be taken with a mark or icon locating the appropriate area on the user's body. FIG. 17D is a flow chart listing the steps involved in one method of identifying a proper placement location for an electro-dermal patch on a front thoracic surface of a user, in accordance with one embodiment of the present specification. At step 1732, with the user preferably standing, the TPM finds a midclavicular line of the user. The TPM then progresses downward from the midclavicular line to a bottom rib of a thoracic cage of the user at step 1734. From the bottom rib, at step 1736, the TPM moves downward by 2 cm to identify a placement spot. At step 1738, the TPM places a top center portion of the electro-dermal patch at the placement spot.

During the session, the physician or the TPM may further help the user to download the Health Management application on the user's computing device, such as his smartphone, tablet, PDA, laptop, computer and demonstrate pairing or syncing of the application to the user's computing device. The user may at this time or at a later time enable the Health Management application to be in communication with the physician or a remote patient care facility.

In alternate embodiments, the physician's or the TPM's intervention for initial set-up and use orientation of the electro-dermal patch device may not be required at all. In such embodiments, the user simply buys the electro-dermal patch device that comes along with a compact disk comprising detailed audio-visual tutorials demonstrating use, application download instructions, functions and identification of appropriate areas of stimulation. Additionally or alternatively, the audio-visual tutorials may be made accessible to the user via a dedicated website also hosting a web version of the Health Management application.

In some embodiments, the HMA also includes a device placement functionality to enable identification of the appropriate location on the user for placement of the EDP device. In one embodiment, where the HMA is installed on the user's smartphone (configured as the companion device), the device placement functionality operates by overlaying an image of where the identification mark or icon should be on the body of the user while the user's torso is being imaged by the user's smartphone. Thus, when the TPM activates the device placement functionality (such as by activating an icon on the user's smartphone), the TPM is instructed to stand at a pre-defined distance, such as 20 inches, from the user's torso and view the user's torso image by activating the camera of the smartphone. With the torso in view, overlay a mark, icon or dot on the image. The device placement functionality captures and stores the image with the overlay and the TPM then uses it to place a temporary tattoo on the user. When the device placement functionality or feature is activated again, the location of the tattoo can be compared with the overlay. Each time placement of the EDP device needs to be reviewed, the device placement functionality is activated—which will display the stored image with the overlay, preferably with the overlay relative to an outline of the nipple and belly button.

The HMA also enables the TPM to be associated with the user's EDP. To enable this association, in some embodiments, the TPM is presented with a GUI wherein the TPM inputs, for example, his unique code that associates the user, and therefore the user's EDP device, with the TPM. The TPM next pairs or syncs the user's computing device with the user's EDP device. Associating or linking the TPM and the user enables a plurality of functions such as, but not limited to, allowing the TPM to regularly receive and access, in real time or near real time, the user's health related information and progress reports related to various therapeutic objectives, to accordingly modulate or titrate stimulation protocols and parameters when needed; and enabling the TPM to deactivate and reactivate the EDP device remotely, when needed.

The TPM now configures, sets up or programs the stimulation protocols and parameters for therapy. In accordance with various embodiments, the TPM configures the stimulation therapy to be set at the standard or baseline stimulation protocol, in absence of any initial health related data of the user. As discussed earlier, in one embodiment the standard or baseline stimulation protocol (also referred to as 'default operational mode') is set at 3 daily stimulation sessions of 30 minutes each having a pulse amplitude of 20 mA. Each of the three daily stimulation sessions is initiated 30 to 60 minutes and preferably 45 minutes prior to mealtimes, such as, breakfast, lunch and dinner, for example. As the therapy progresses, the TPM periodically adjusts the baseline stimulation protocol or pattern based on the user's health related information and recommendations from the HMA.

In another preferred embodiment, the baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these post-prandial stimulation sessions are triggered manually by the user. In some alternate embodiments, the pre-prandial and post-prandial stimulation sessions are automatically triggered based on pre-stored meal time schedule. In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B.

The TPM also configures rescue protocols and parameters for allowable rescue sessions. The configurable rescue protocols and parameters include at least the number of rescue sessions allowed per day, duration, and intensity of stimulation. The TPM may also program rescue sessions based on triggers such as, but not limited to, the user's energy balance. For example, if the user's energy balance is positive and above a predefined threshold, one or more rescue sessions are triggered to occur in addition to the standard stimulation therapy or schedule.

In accordance with various embodiments, the TPM may alternatively or additionally program the stimulation protocols and parameters by allocating a total energy budget to the planned or scheduled therapy sessions (such as those part of the standard or baseline stimulation protocol) and to the rescue sessions (that is, unplanned on-demand sessions). In various embodiments, the total energy budget can be apportioned between the planned therapy sessions and the rescue sessions, subject to the daily total rescue budget (described earlier in the specification). In various embodiments, the total energy budget is measured in Joules. The TPM is allowed to distribute the allocated total energy budget over a period of time. In other words, the TPM programs the stimulation therapy by subjecting the user to a total amount of energy (in the form of stimulations) that is distributed over a period of time of therapy. The TPM has flexibility to program or distribute the allocated energy budget in any manner suitable for the user such as, for example, 40 mA stimulation for 23 hours or stimulation of 10 mA per day for 30 minutes a day. In accordance with various aspects, the TPM's flexibility to distribute the allocated total energy budget over a period of time is subject to the following constraints:

The user must necessarily receive a certain amount (also referred to as 'energy input') of the allocated total energy budget, per week. In various embodiments, a minimum energy input per week is 1 minute of 5 mA stimulation once per week and a maximum energy input per week constitutes 50 mA constant stimulation over 24 hour period. Thus, for an overall therapy cycle of 6 months or 180 days, the maximum energy input is 50 mA×24 hr per day×180 days.

The amount of energy delivered to the user in an allowed rescue session should not be greater than two times the amount of energy of a planned therapy session (such as a session of the standard or baseline stimulation protocol). In some embodiments, the amount of energy of an allowed rescue session should range from 5% to 200% of the amount of energy of a planned therapy session.

Preferably, a rescue session and a planned therapy session are separated by a predefined period of off-time. In some embodiments, the predefined period of off-time is defined such that for every Z minutes of stimulation in a session (rescue or planned therapy), at least 10%×Z minutes of off-time (that is, no stimulation) is necessary.

A rescue session and a planned therapy session, if occurring serially, should not result in an excessive amount of total energy input into the user that causes a breach of the allocated total energy budget for the entire therapy cycle. Thus, for example, if the user demands a rescue session just before a planned therapy session, the HMA is programmed or configured to choose between a) replacing the demanded rescue session with the scheduled or planned therapy session, that is the demanded rescue session is not allowed while continuing with the planned therapy session as scheduled, b) initiating the demanded rescue session and then moving onto the planned therapy session but truncating the planned session, if needed, to ensure that the allocated total energy budget for the entire therapy cycle is not breached or exceeded. If a rescue session overlaps with a planned therapy session then the planned therapy session is moved forward so that the two sessions are separated by at least the predefined period of off-time. Similarly, if a rescue session does not overlap with a planned therapy session, the rescue session may be allowed provided the sessions (rescue and planned) are separated by at least the predefined period of off-time.

In all cases, however, the total energy input into the user is not allowed to exceed the allocated total energy budget.

Once the TPM completes programming or configuration of the stimulation protocols and parameters, the HMA acknowledges that the configuration is successful and the EDP device also acknowledges successful configuration by, for example, vibratory, auditory and/or visual indications (such as flashing LEDs of a specific color). In some embodiments, the TPM may also prescribe a low calorie planned diet for the user. In various embodiments, a first planned therapy session is delivered to the user at the TPM's office or clinic to ensure that the stimulation parameters are conducive to the user. For example, a 30 or 60 minute session at baseline stimulation protocol is delivered to the user. If the user feels fine after the first session, the user is allowed to leave to continue the therapy at home. However, if the user reports inconvenience or deterioration in well-being, such as due to a feeling of nausea, the TPM reprograms the stimulation protocols and parameters by, for example, ramping down the intensity, duration, number of stimulation sessions per day and/or the total energy budget.

The user continues the TPM configured stimulation therapy at home. At home, the user may take off the EDP device for some time and may forget to put the EDP device on for his next planned therapy session. An impedance or bio-impedance sensor of the EDP device is used to detect and confirm contact integrity of the EDP device electrodes with tissues to be stimulated and therefore detect if the EDP device is being worn by the user. In some embodiments, if the impedance or bio-impedance measurement detects that the user is not wearing the EDP device, the EDP device and/or the companion device implementing the HMA, such as a smartphone, smart watch or smart band, generates vibratory, auditory and/or visual (such as flashing LEDs) alerts that are repeated at periodic intervals till the user wears the EDP device. When the EDP device has been worn by the user, as indicated by the impedance measurement, it is also determined if the user is or is not exposed to water such as, for example, during shower, while swimming or while traveling in rain. At least one of impedance, humidity and temperature sensor, included in the EDP device, is utilized to determine if the person and/or the EDP device is exposed to water. If the user and/or the EDP device are exposed to water, the EDP device is automatically switched off and all stimulation held off.

In accordance with an embodiment, the HMA generates vibratory, auditory and/or visual (such as flashing LEDs) alert or reminder, using the EDP device and/or the companion device (such as a smartphone, smart watch or smart band), at least 60 minutes prior to a scheduled stimulation session. This advance reminder allows the user requisite time to get to the EDP device and wear it—in case the EDP device was taken off by the user. Thus, in some embodiments, the alert or reminder is linked to the user's schedule of stimulation sessions and is programmed to remind the user, a requisite time (say, 60 minutes) ahead of a scheduled session, to ensure that the user wears her EDP device in time. Accordingly, in one embodiment, the smartphone comprises a plurality of programmatic instructions that automatically set an alarm for a predefined period of time, such as 120 minutes to 5 minutes and any increment therein, before the scheduled stimulation session. The alarm, which could be visual, auditory, and/or vibratory and which could be delivered via the smartphone or the EDP itself, communicates to the patient the need to put on the EDP in order to effectuate a stimulation session.

However, it is possible that the user's first stimulation session of the day is scheduled later than breakfast time, in which case the reminder may alert the patient after she has left for work that day (perhaps leaving the EDP device behind at home). To address such a scenario, in some embodiments, the first alert or reminder of the day is linked to the user's break-of-day that is programmed according to the user's waking-up schedule. For example, in an embodiment, the first alert or reminder of the day is linked to the user's alarm clock on her smartphone (companion device) to trigger a reminder (to wear the EDP device) within 0 to 60 minutes of the user's wake-up alarm going off. Thus, in some embodiments, while the first alert or reminder of the day is linked to the user's waking-up schedule, the remaining alerts or reminders of the day are linked to the user's schedule of stimulation sessions.

In accordance with another aspect, the EDP device is programmed to alert the user before commencing a stimulation session. In some embodiments, for example, the EDP device generates a low intensity stimulation or vibration, as preparatory signal to alert the user, before applying full therapy stimulation. This prevents the user from being surprised by a sudden onset of stimulation. In accordance with yet another aspect, the EDP device is switched off or deactivated if it senses an increase in the user's skin temperature above a threshold temperature within a predetermined period of time, thereby safeguarding the user from skin burns.

As the user continues to use the EDP device at home, the stimulation parameters and protocols, for both planned as well as rescue sessions, are modulated based on a plurality of health related information of the user generated as a result of the use of the EDP device. In accordance with an aspect, the TPM monitors the user's health related information and may periodically intervene by re-setting or reprogramming the EDP device and HMA. Thus, while the HMA is configured to automatically modulate or titrate stimulation based on the user's health related information, well-being scores and/or rescue sessions, in various embodiments the TPM may, remotely, at any time supersede and reprogram the HMA (with or without the user's consent). Additionally, in accordance with some aspects, the TPM's unique code allows the user to apply the stimulation therapy for only a predefined period of time, such as ranging from a few days to four weeks. At the end of the predefined period of time, the HMA may switch off the EDP device and therefore the therapy and prompt the user to contact his TPM for evaluation, modulation of the stimulation protocol and parameters (if needed), feedback and/or counseling before restarting the therapy.

In accordance with various embodiments, as discussed earlier in this specification, all time-stamped hunger entries or events (whether planned or unplanned), intensity levels and the triggered rescue sessions are tracked (date and time stamped, including duration of each rescue session) and recorded (such as through the light bar VAS) to generate the user's individualized hunger profile or hunger map. In some embodiments, the user's individualized hunger map is in the form of a scattergram or heat map. The scattergram maps and displays a plurality of icons or dots of different colors wherein each dot corresponds to a hunger event and the color of the dot represents the level of intensity of hunger recorded corresponding to the hunger event. If the rescue sessions or dots represent a pattern of hunger or hunger spikes, such as for example if a large number of high intensity hunger dots congregate at a particular time of day for a certain period of time (ranging from a few days, say 5 to 7 days, to weeks, say 3 to 6 weeks), the HMA and/or the TPM may customize, modify, drive and deliver stimulation therapy or protocol to target the user's hunger spikes.

In accordance with various embodiments, the TPM programs the HMA for a survey to be presented to and filled in by the user each day throughout the period of the therapy. The TPM programs the HMA to present the survey to the user depending upon the user's preferred or desired timings or time window during the day. For example, the user may desire the survey to be presented to him within a time window between 5 pm and midnight each day. Accordingly, the HMA notifies and presents the user with the survey within the desired time window. The user can take the survey or put the survey off for a later time. The user can also demand the survey at any time (outside the desired time window). In various embodiments, the survey enables the user to summarize, input and record health related information comprising at least his level of hunger, appetite, exercise, and well-being for the day. The scores representing levels of appetite, exercise, hunger, and well-being are recorded via respective light bar VAS or through the GUI screens of FIGS. 11, 12, 13 and 16 respectively. The user is also allowed to input and record the total calories consumed for the day. It should be appreciated that the survey ensures that the user is persuaded to regularly provide data related to, at least, his levels of hunger, appetite, exercise, well-being and calories consumed.

Thus, the survey acts as a safeguard against scenarios where the user may not be self-motivated to regularly record his health related information. In fact, it is possible that the user may not feel the need for rescue sessions and may not use up any of his daily total rescue budget. In such events, it will also not be possible to generate the user's individualized hunger map and determine stimulation modulation as therapy progresses. The necessity of recording hunger level, within the survey, safeguards against such scenarios where no rescue sessions are demanded by the user.

In accordance with various aspects, the HMA ensures that the user responds to the survey. Therefore, in some embodiments if the user does not respond to the survey he is continuously, repeatedly or periodically alerted to fill in the survey. The alerts may be vibratory, auditory and/or visual (such as flashing LEDs) generated by the EDP device and/or the user's smartphone (acting as a companion device). In some embodiments, the user is allowed to resolve the alerts only by responding to the survey. In some embodiments, if the user does not respond to the survey for a predefined period of time, such as 1, 2, 3, 4, 5, 6 or 7 or any number of days or increment therein, the EDP device is switched off or deactivated or the TPM can deactivate the EDP device remotely and is reactivated only by the TPM. The TPM can reset or reactivate the EDP device remotely, such as by remotely inputting or providing the user with a reactivation code, based on a conversation with the user.

It should be appreciated that the TPM's ability to remotely deactivate and reactivate the EDP device is also advantageous in scenarios where the user's recorded health related information (through the survey) indicates that the user is likely to suffer some harm (if the therapy is continued in its present state) such as, but not limited to, loss of too much weight, high levels of nausea that is recurring frequently.

The TPM is also allowed, by the HMA, to set or reconfigure various thresholds, ranges, protocols and parameters related to planned therapy sessions and rescue sessions as and when needed such as, during the initial set-up of the EDP device and/or during therapy based on the information provided by the user through the survey or based on the user's individualized hunger and/or well-being maps or profiles. For example, the TPM may configure and re-configure the thresholds for deciding when an unplanned hunger event is considered actionable and when a nausea and/or dyspepsia event is considered actionable. The TPM may also configure and re-configure as to what happens when actionable unplanned hunger and nausea (and/or dyspepsia) events occur. Thus, the TPM may program the HMA to ramp down stimulation if the user records a single nausea and/or dyspepsia event of intensity 9 followed by a certain number (say 2 to 3) of less nauseating events of intensity 6 or 7. The TPM may also program the HMA to ramp down stimulation to counter habituation or fatigue. Therefore, after a predefined period of time (say, 3 to 12 weeks—configurable by the TPM), the HMA may be configured to initiate an anti-habituation temporary ramp down (via, say, reduction of amplitude, frequency and/or duration of sessions). Alternatively, the TPM may configure the HMA to stop stimulation therapy for some time and restart thereafter.

Since the TPM is associated with the user's EDP device, through the unique code input by the TPM during initial setup or configuration of the EDP device for the user, the TPM receives the user's health related information regularly or periodically—that is daily, weekly or at any other periodicity customizable by the TPM. In various embodiments, the user's health related information may be sent and stored in a Cloud based datacenter and the TPM be notified or the information may be sent directly to the TPM. The user's health related information includes, at least, the user's weight, scores related to appetite, hunger, exercise, well-being (well-being profile including recorded nausea and/or dyspepsia events), values related to calories consumed, and individualized hunger profile (as a result of recorded unplanned hunger events and delivered rescue sessions). In some embodiments, the TPM additionally or alternatively receives a composite score related to and derived from any one or any combination of the user's health related information. In various embodiments, the TPM has the HMA installed on his smartphone and/or has an access to a web version of the HMA to be able to monitor the user and receive health related information. The HMA version installed on the TPM's smartphone, in various embodiments, is enabled for association and therefore data communication with a plurality of users.

In accordance with various aspects of the present specification, the TPM may intervene at various stages or phases of the therapy depending on the user's health related information, trends and/or the user's progress in context of the therapeutic objectives or end-points set to be achieved through the therapy. For example, if the user achieves a therapeutic objective, the TPM could extend the therapy (for example, if the user loses 10 pounds as per weight loss objective, the TPM may recommend continued therapy to lose another 10 pounds), end therapy altogether, extend a new therapy such as for weight maintenance. The new therapy may use a different stimulation protocol or may be the same as earlier but with a higher caloric diet, for example.

FIG. 52 is a flow chart illustrating a plurality of steps of a method for enabling a TPM to prescribe, configure, manage, monitor and intervene an EDP device based stimulation therapy for a user, in accordance with some embodiments. At step 5202, a user visits his TPM for a medical check-up or evaluation. The TPM recommends an EDP device of the present specification to the user based on the user's medical condition, such as for example obesity or over-weight. At step 5204, the TPM downloads the HMA on the user's smartphone (that works as a companion device). Thereafter, at step 5206, the TPM assists the user in identifying appropriate areas of stimulation (and therefore, placement of the EDP device on the user's body), such as T6, C8 and/or T1 dermatomes for conditions of obesity, over-weight, eating disorders, metabolic syndrome and T7 for T2DM management, and also provides an orientation to the user regarding use and functions of the electro-dermal patch device. The EDP device is positioned on the identified location on the user's body. Next, at step 5208, the TPM associates or links himself to the user, the user's EDP device and HMA, such as, by inputting his unique code into the user's HMA. Associating or linking the TPM and the user enables a plurality of functions such as, but not limited to, allowing the TPM to regularly receive and access, in real time or near real time, the user's health related information and progress reports related to various therapeutic objectives, to accordingly modulate or titrate stimulation protocols and parameters when needed; and enabling the TPM to deactivate and reactivate the EDP device remotely, when needed.

The TPM pairs or syncs the user's smartphone with the user's EDP device, at step 5210. Thereafter, at step 5212, the TPM configures or programs the stimulation protocols and parameters, including various associated thresholds, ranges, related to planned therapy sessions as well as unplanned on-demand rescue sessions. In one embodiment, the TPM configures the planned stimulation therapy to be set at standard or baseline stimulation protocol, in absence of any initial health related information of the user. At step 5214, the TPM also programs the user's HMA to generate and present to the user—a survey to illicit the user's health related information. The survey is programed to be presented to the user, daily, within a time window preferred by the user. The TPM may, optionally, also prescribe a low calorie planned diet for the user. The HMA, at step 5216, acknowledges that the configuration (by the TPM) is successful and the EDP device also acknowledges successful configuration by, for example, vibratory, auditory and/or visual indications or signals (such as flashing LEDs of a specific color).

At step 5218, the TPM delivers a first planned therapy session to the user in the presence of the TPM to ensure that the HMA or therapy configuration is conducive to the user. If the user feels fine after the first session, the user is allowed to leave to continue the therapy at home, at step 5220. However, if the user reports inconvenience or deterioration in well-being, such as due to a feeling of nausea, the TPM reprograms the stimulation protocols and parameters at step 5222. At home, the user continues with the stimulation therapy, at step 5224, and generates a plurality of health related information (such as, but not limited to, the user's weight, scores related to appetite, hunger, exercise, well-being (well-being profile including recorded nausea and/or dyspepsia events), values related to calories consumed, and individualized hunger profile (as a result of recorded unplanned hunger events and delivered rescue sessions)) during therapy. If and when needed, at step 5226, the TPM modulates the stimulation parameters and protocols, for both planned as well as rescue sessions, based on the plurality of user's health related information while the user is continuing with the stimulation therapy at home. The TPM also intervenes, by re-setting or reprogramming the EDP device and HMA and/or deactivating and reactivating the EDP device, when needed.

At step 5228, the user's stimulation is stopped, paused and/or the user prompted to revisit his TPM for re-evaluation of his medical condition or progress.

In accordance with some aspects of the present specification, a user has a plurality of options for purchasing the EDP device along with the TPM's services. In one embodiment, the user avails of the TPM's service at a first fee and purchases the EDP device for a first price. In some embodiments, the first fee and the first price are fixed one-time values valid for an entire treatment cycle of the user. In other embodiments, the user is allowed to pay a single one-time fixed price for a bundled deal comprising of the TPM's service and the EDP device price. In still other embodiments, the user purchases a bundled deal, comprising of the TPM's service and the EDP device price, at a price that is valid for a predefined period of time, say, for 1 week to 3 months, and recurs after the predefined period of time. In yet other embodiments, the first price is a one-time payable value while the first fee is valid for a predefined period of time, say, for 1 week to 3 months, and recurs after the predefined period of time. In accordance with an aspect, the TPM's fee schedule is enforced through his unique code that is valid only for the predefined period of time. For example, if the TPM's first fee is valid for a month of therapy, the TPM's unique code (input into the user's HMA) causes the HMA to deactivate the EDP device at the end of the month and prompts the user to meet the TPM. Based on the user's medical condition, the TPM may extend the therapy for another month (using another unique code) for an additional fee. The extended therapy may commence immediately or may restart after putting the user on hiatus. In still other embodiments, while the EDP device can be purchased for a one-time price, the TPM's fee is linked to achieving of specified goals. For example, the TPM's first fee includes an initial EDP therapy set-up and subsequent fees is due after the user achieves a weight loss goal of, say, 10 pounds. In other words, the TPM's fee is linked to the user achieving one or more therapeutic goals within a period of time.

In various embodiments, therapy provided by the electrodermal patch (EDP) devices of the present specification is driven or triggered by a plurality of variables. These variables can be entered by the patient or a medical professional into the companion device, sensed by a sensor on the EDP, transmitted to the companion device or EDP by a separate device, for example, a device, with physiological sensors, configured to be worn on the human body, such as around the wrist, in order to monitor, acquire, record, and/or transmit the physiological data, or can be acquired by a combination of any of the above means. In various embodiments, the variables are stored, preset, and/or measured or input on a regular, predetermined basis or time period. In some embodiments, the variables include primary variables which comprise primary drivers to any therapy regimen and secondary variables which comprise secondary indicators which may or may not affect the regimen. Some variables, such as weight in pounds, are entered into the patient diary based on their actual value while other variables, such as hunger, appetite and satiety, are given a score based on a predefined score value range or a scale such as the Visual Analogue Scale (VAS). The treatment algorithm of the companion device analyzes these scores in comparison to predefined limits and automatically modifies therapy accordingly. In some embodiments, the algorithm analyzes these scores on a daily basis. In other embodiments, the algorithm analyzes the scores every other day, every third day, every fourth day, every fifth day, every sixth day, or once per week. In various embodiments, the score values range from 0 to 100. In a preferred embodiment, the score values range from 1 to 10 and, more preferably, from 1 to 5 or 1 to 3, depending on the variable. In some embodiments, a high numerical score value indicates electrical stimulation therapy provided by the EDP is inadequate and additional stimulation is needed. A lower numerical score value indicates electrical stimulation therapy provided by the EDP is excessive and stimulation needs to be reduced. Conversely, in other embodiments, a high numerical score value indicates stimulation is excessive and needs to be reduced and a low numerical score value indicates stimulation is inadequate and needs to be increased. In some embodiments, a numerical score value proximate the middle of the score range indicates therapy is appropriate and can remain unchanged.

In one embodiment, the system uses one or more of the following triggers to initiate stimulation or modulate stimulation settings: a patient's glycemic level, metabolism levels, hemoglobin A1c, and/or blood sugar. Using integral physiological sensors or third party external devices which already measure metabolism, blood sugar, glycemic levels, or hemoglobin A1c, the companion device gathers such data, integrates it with existing patient status data, and generates a modulated stimulation setting, which may include a signal to initiate therapy, change therapy or cease therapy, based on an integrated patient status data profile. In one embodiment, a patient's increased blood sugar levels cause the stimulation settings to be modulated upward in order to increase the rate, frequency, or overall amount of stimulation. In one embodiment, a patient's decreased or normalized blood sugar levels (as a result of a delivered stimulation therapy, for example) cause the stimulation settings to be modulated downward in order to decrease the rate, frequency, or overall amount of stimulation. In one embodiment, a patient's decreased or normalized blood sugar levels (as a result of a delivered stimulation therapy, for example) cause the stimulation therapy to be ceased. In another embodiment, changes in the patient status data, including increases or decreases in metabolism, blood sugar, glycemic levels, or hemoglobin A1c, may cause the companion device to recommend moving the EDP to a different location on the patient's body to stimulate a different dermatome, such as from C8 on the hand to T1 or, for example, from T7 in the abdominal area to T6.

In some embodiments, therapy is driven by a set of three primary drivers. The primary drivers include: hunger, which is defined as the patient's desire to eat; appetite, defined as how much food the patient eats in relation to a diet plan (also considered caloric intake); and well-being, defined as simply how good the patient feels. In some embodiments, well-being is further subdivided specifically into feelings of nausea, dyspepsia, discomfort, energy level, and weakness/strength. Each of these primary drivers can be attributed a score which is entered into the companion device, as depicted in FIGS. 11, 13, and 16.

For example, for hunger, referring to FIG. 13, the patient can enter a hunger score from 1 to 5, wherein 1 indicates the patient is not hungry at all, 2 indicates the patient is almost never hungry, 3 indicates the patient is not particularly hungry, 4 indicates the patient is frequently hungry, and 5 indicates the patient is extremely hungry most of the time. In some embodiments, a hunger score having a higher numerical value indicates appetite suppression is inadequate and the patient requires greater stimulation. The treatment algorithm of the companion device recognizes the need for greater stimulation as indicated by the higher score and titrates therapy accordingly. For example, in one embodiment, if the patient enters a hunger score greater than 3 in the patient diary over a period of four to seven consecutive days within the first week, the algorithm uses the score to incrementally increase the duration of each stimulation session. If after three weeks the patient enters a hunger score greater than 3 in the patient diary for 3 consecutive days, the algorithm uses the score to increase the number of stimulation sessions per day. Conversely, a lower hunger score indicates stimulation needs to be decreased. For example, if the patient enters a hunger score of 1 for three consecutive days within the first week, stimulation sessions are decreased in duration and frequency. In other embodiments, the hunger score scale extends from 1 to 10.

In other embodiments, rather than a scale to determine the presence or absence of hunger, the system presents the patient with a scale configured to record changes in his hunger after stimulation. For example, in an embodiment, a hunger change score scale extends from 1 to 3 wherein 1 is indicative of no change, 2 is indicative of some change, and 3 is indicative of significant change in hunger after stimulation. If a patient reports a 1, no change in hunger after stimulation, stimulation parameters are increased.

For appetite, referring to FIG. 11, the patient can enter an appetite score from 1 to 5, wherein 1 indicates the patient ate substantially less than his diet, 2 indicates the patient ate a little less than his diet, 3 indicates the patient followed his diet, 4 indicates the patient somewhat exceeded his diet, and 5 indicates the patient substantially exceeded his diet. As with the hunger score discussed above, in some embodiments, an appetite score having a higher numerical value indicates appetite suppression is inadequate and the patient requires greater stimulation. The treatment algorithm of the companion device recognizes the need for greater stimulation as indicated by the higher score and titrates therapy accordingly. For example, in one embodiment, if the patient enters an appetite score greater than 3 in the patient diary over a period of four to seven consecutive days within the first week, the algorithm uses the score to incrementally increase the duration of each stimulation session. If after three weeks the patient enters an appetite score greater than 3 in the patient diary for 3 consecutive days, the algorithm uses the score to increase the number of stimulation sessions per day. Conversely, a lower appetite score indicates stimulation needs to be decreased. For example, if the patient enters an appetite score of 1 for three consecutive days within the first week, stimulation sessions are decreased in duration and frequency. In other embodiments, the appetite scale extends from 1 to 10.

As discussed earlier, in some embodiments the plurality of variables, such as hunger, appetite, satiation level, fullness, satiety, and feelings of pain, nausea, or dyspepsia, that drive or trigger therapy are alternately assessed on at least one of a plurality of scientific VAS scales. Graphs 36A through 38F represent exemplary data which the inventors believe are indicative of the therapeutic benefits of the present inventions. It should be appreciated that data may be collected and compared on a per patient basis, both before and after stimulation, on a sample group of patients, both before and after stimulation, or by using two separate groups of patients, one subjected to stimulation and the other not subjected to stimulation (as a control). Therefore the post-stimulation benefits would be achieved regardless of whether one were comparing it to the same population of users before stimulation or to a different population of users acting as a control group.

FIGS. 36A through 36I are a set of graphs illustrating effects of stimulation on a feeling of hunger as assessed on a VAS (Visual Analogue Scale) in accordance with some embodiments, while FIGS. 37A through 37I are a set of graphs illustrating effects of stimulation on a feeling of satiety as assessed on a VAS in accordance with some embodiments. Referring to FIGS. 36A through 36E, in accordance with an embodiment, a sample of 5 patients, having weight loss as an objective or goal, were assessed for their feeling of hunger (using VAS) at a first occasion, corresponding to a pre-stimulation scenario wherein the 5 patients were not subjected to stimulation therapy, and at a second occasion, corresponding to a post-stimulation scenario wherein the 5 patients were subjected to stimulation therapy using an EDP of the present specification.

In accordance with an embodiment, the 5 patients were assessed both pre- and post-stimulation using a VAS hunger questionnaire, such as the questionnaire of FIG. 35A, having a 100 mm VAS line. At the first occasion (pre-stimulation), each patient's responses or scores to the VAS hunger questionnaire were recorded at intervals of every 60 minutes starting from a first response or score 3606a through 3606e that, in one embodiment, is recorded just prior to a meal (such as breakfast) but without subjecting any of the patients to stimulation therapy. At the second occasion (post-stimulation), each patient's responses or scores to the VAS hunger questionnaire were again recorded at intervals of every 60 minutes starting from a first response or score 3607a through 3607e recorded just prior to the meal (such as breakfast) but after having treated each of the patients with stimulation therapy prior to, for example 30 minutes before, the meal. In accordance with an embodiment, the responses or scores related to the first occasion are recorded on a first day while those related to the second occasion are recorded on a second day, preferably at the same time of day and under the same eating or fasting conditions as the first day.

Figure 36A:
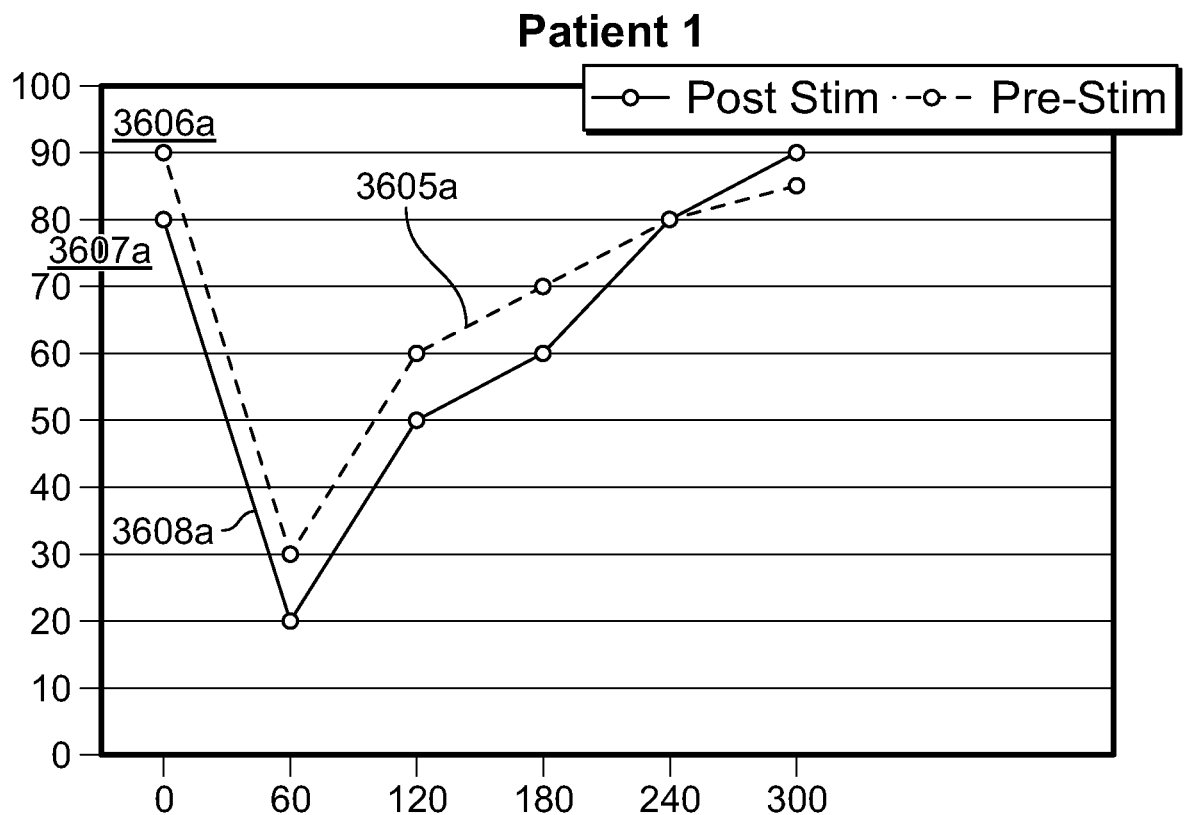
FIG. 36A is a graph illustrating pre-stimulation and post-stimulation hunger profiles of a first patient, in accordance with an embodiment.
Figure 36B:
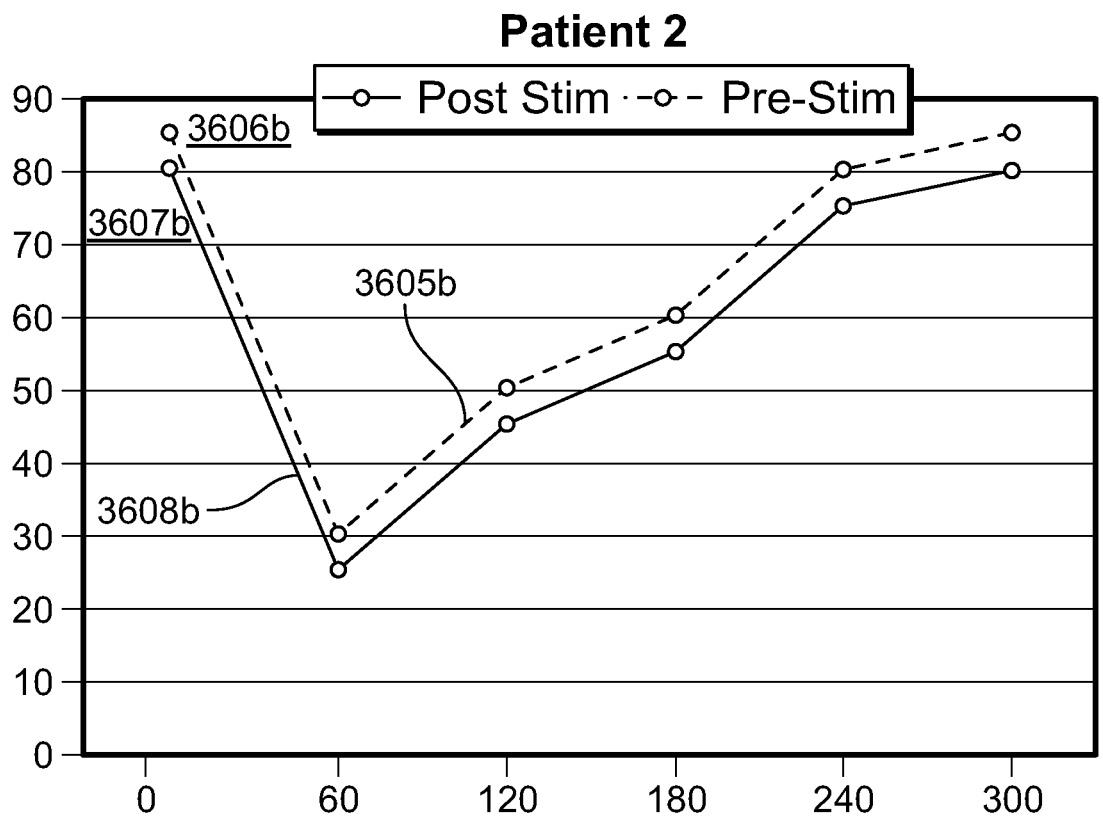
FIG. 36B is a graph illustrating pre-stimulation and post-stimulation hunger profiles of a second patient, in accordance with an embodiment.
Figure 36C:
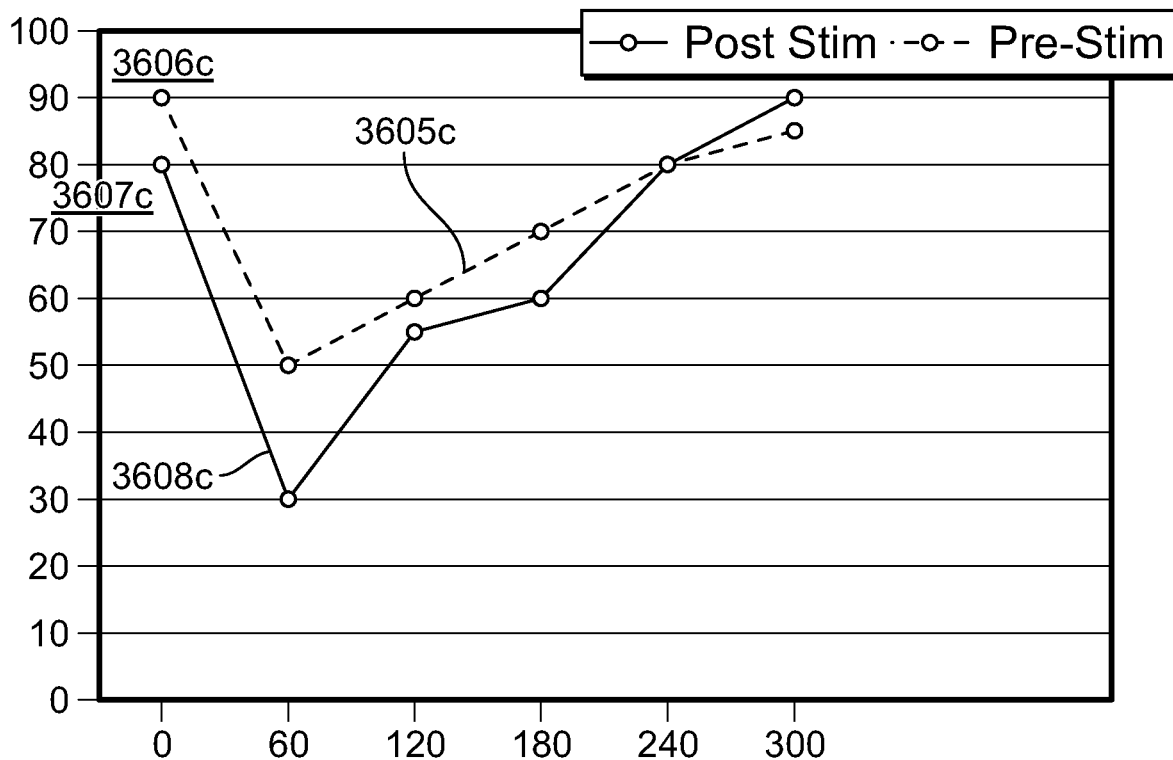
FIG. 36C is a graph illustrating pre-stimulation and post-stimulation hunger profiles of a third patient, in accordance with an embodiment.
Figure 36D:
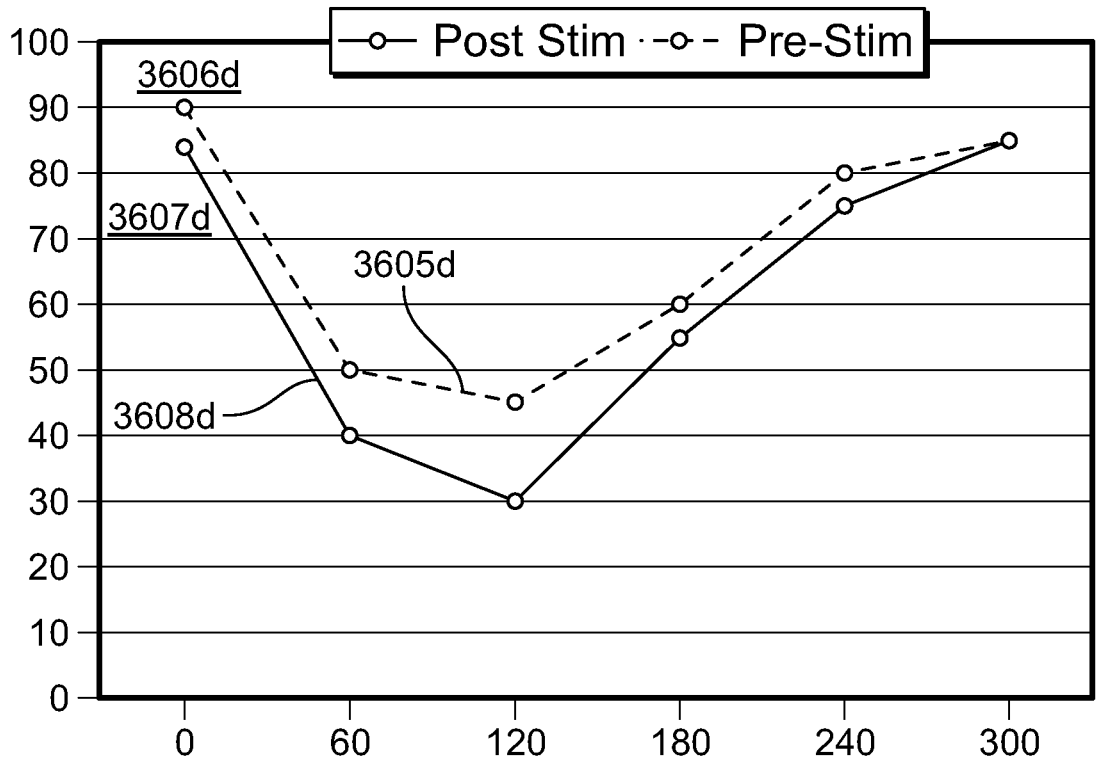
FIG. 36D is a graph illustrating pre-stimulation and post-stimulation hunger profiles of a fourth patient, in accordance with an embodiment.
Figure 36E:
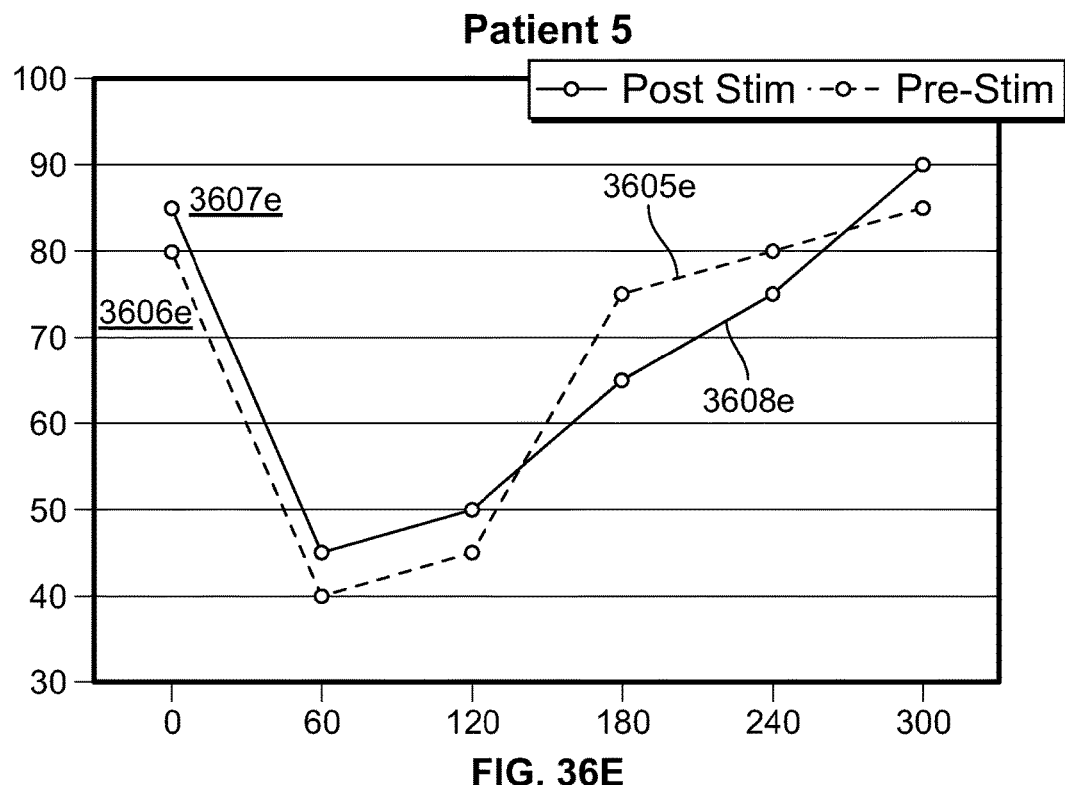
FIG. 36E is a graph illustrating pre-stimulation and post-stimulation hunger profiles of a fifth patient, in accordance with an embodiment.

As shown in FIG. 36A, the first patient's hunger responses or scores for the first occasion (that is, pre-stimulation) are recorded on a first day and plotted on a graph, whose x-axis represents time in minutes and y-axis represents VAS hunger responses or scores in millimeters, to generate a pre-stimulation hunger profile 3605a. Thereafter, the first patient is subjected to stimulation therapy, in accordance to embodiments of the present specification, and the hunger responses or scores for the second occasion (that is, post-stimulation) are also plotted on the graph to generate a post-stimulation hunger profile 3608a. Similarly, the second, third, fourth and fifth patients' responses or scores are recorded to generate the respective pre-stimulation hunger profiles 3605b, 3605c, 3605d, 3605e and the respective post-stimulation hunger profiles 3608b, 3608c, 3608d, 3608e as shown in FIGS. 36B through 36E. As can be observed from FIGS. 36A through 36E, the post-stimulation huger profiles 3608a, 3608b, 3608c, 3608d, 3608e reflect reduced hunger magnitude relative to the pre-stimulation hunger profiles 3605a, 3605b, 3605c, 3605d, 3605e. In some embodiments, the post-stimulation hunger profile of a patient reflects at least a 5% decrease in hunger magnitude relative to the patient's pre-stimulation hunger profile.

Figure 36F:
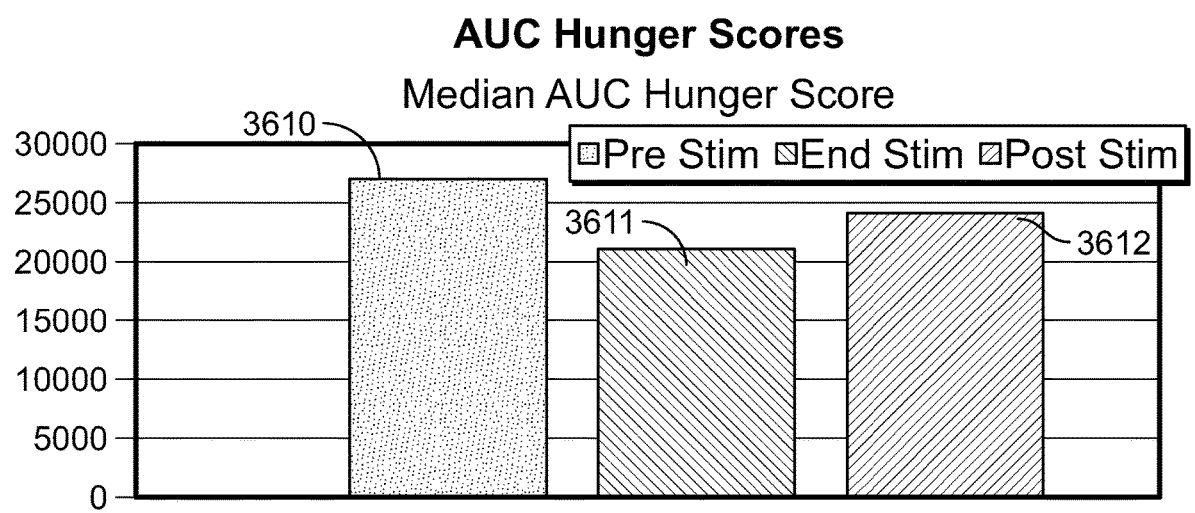
FIG. 36F is a graph illustrating median AUC (Area Under the Curve) hunger scores for pre-stimulation, end-of-stimulation and post-stimulation scenarios.

FIG. 36F shows a first bar 3610 representing a median area under curve (AUC) pre-stimulation hunger score. An AUC value is determined by calculating the area under the lines which define a given plotted profile. A second bar 3611 represents a median AUC end-of-stimulation hunger score derived from AUC values for end-of-stimulation hunger profiles (that is, the hunger profiles recorded starting immediately after the end of stimulation therapy) of the sample patients, and a third bar 3612 represents a median AUC post-stimulation hunger score derived from AUC values for post-stimulation hunger profiles of the sample patients. In various embodiments, end-of-stimulation is defined as the end of a period of stimulation lasting in a range from one session to a multitude of sessions over six months. In various embodiments, post-stimulation is defined as a time after the cessation of therapy and ranges from one day after cessation to six months after cessation. As shown in the figure, the median AUC hunger scores 3611, 3612 corresponding to end-of-stimulation and post-stimulation scenarios are reduced relative to the median AUC hunger score 3610 corresponding to the pre-stimulation scenario. In other words, the stimulation therapy of the present specification results in hunger suppression. In some embodiments, an area under the curve (AUC) of the post-stimulation hunger profile of a patient reflects at least a 5% decrease relative to the patient's AUC of the pre-stimulation hunger profile.

Figure 36G:
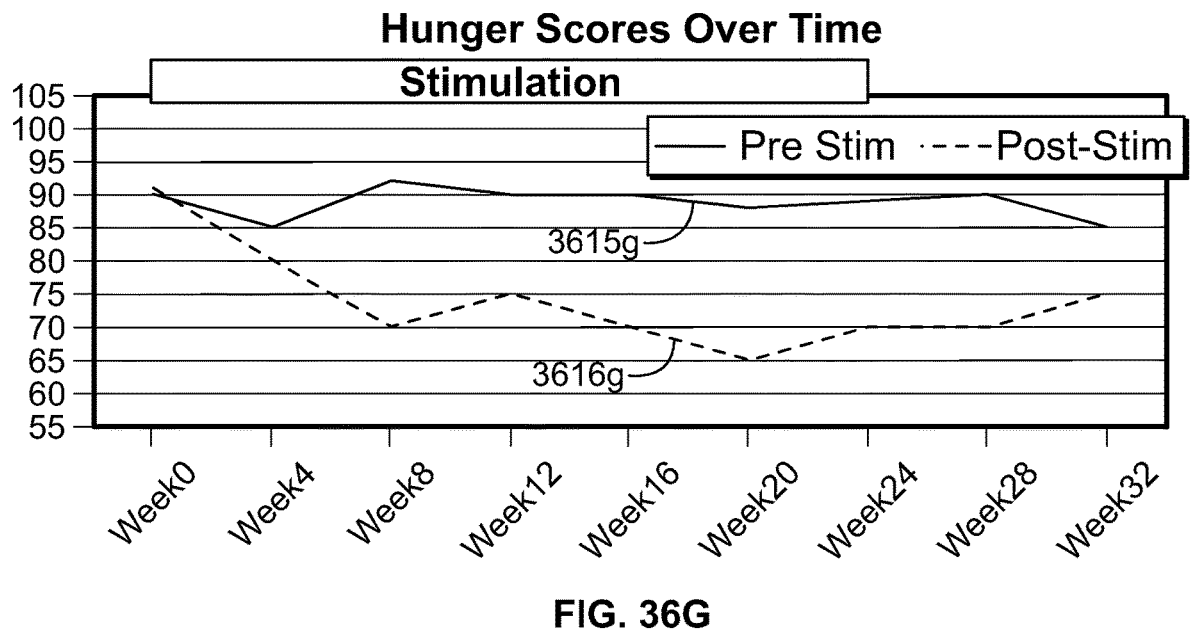
FIG. 36G is a graph illustrating pre-stimulation and post-stimulation hunger profiles over an extended period of time, in accordance with a first embodiment.
Figure 36H:
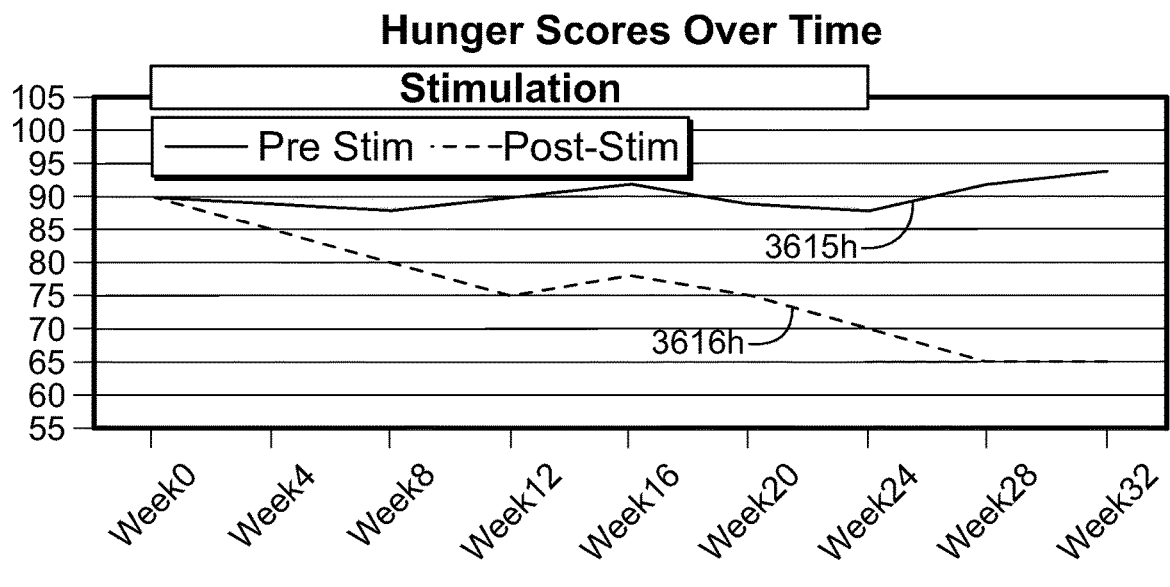
FIG. 36H is a graph illustrating pre-stimulation and post-stimulation hunger profiles over an extended period of time, in accordance with a second embodiment.

FIGS. 36G and 36H also illustrate reduced magnitude of hunger scores, for at least one patient, assessed post stimulation relative to those assessed pre-stimulation. FIGS. 36G and 36H are charts having x-axis representing time in weeks and y-axis representing hunger scores. FIG. 36G shows a pre-stimulation hunger profile 3615g relative to a post-stimulation hunger profile 3616g over extended period of times such as, in weeks and up to 32 weeks. Similarly, FIG. 36H also shows a pre-stimulation hunger profile 3615h relative to a post-stimulation hunger profile 3616h over the same extended period of times. As can be observed from the FIGS. 36G and 36H, the post-stimulation hunger profiles 3616g, 3616h show reduced hunger AUC and magnitude relative to the respective pre-stimulation hunger profiles 3615g, 3615h, even over extended periods of time.

Figure 36I:
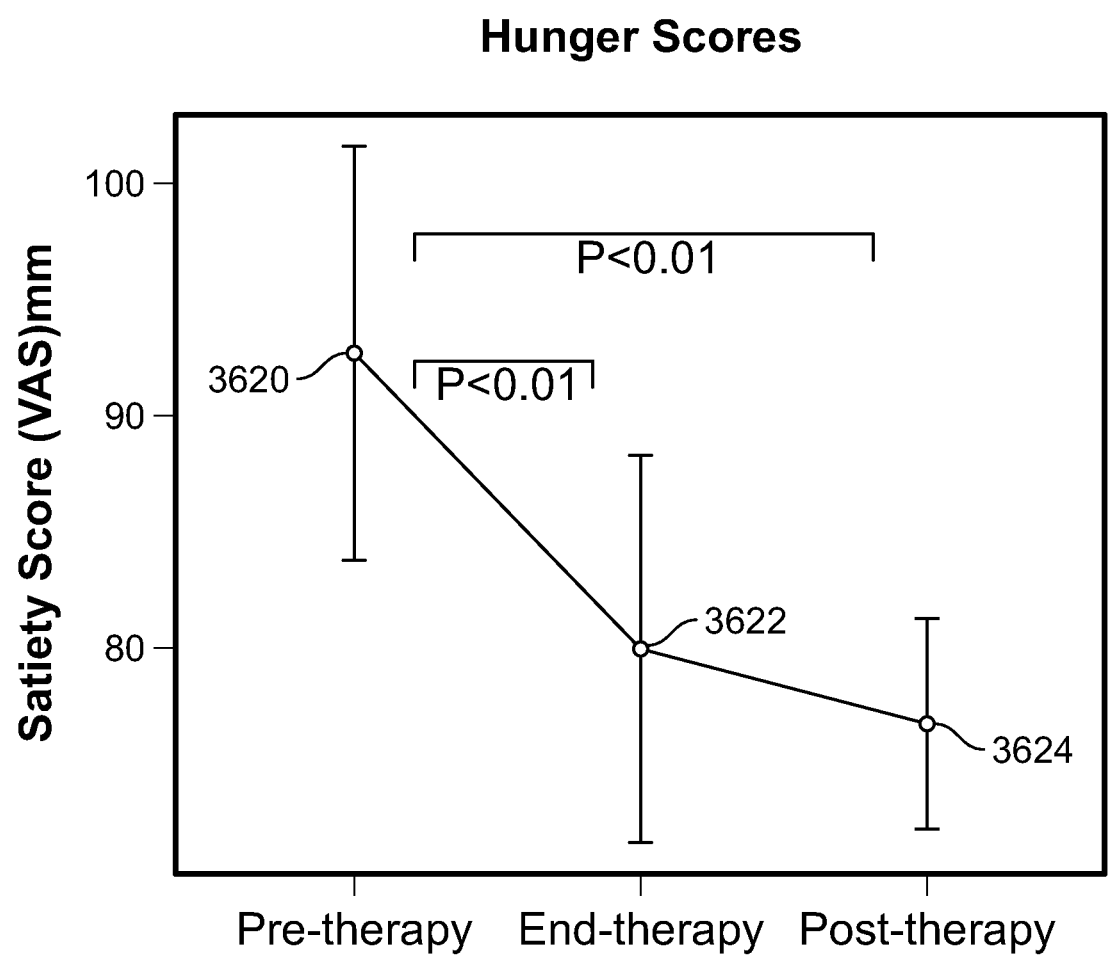
FIG. 36I is a graph illustrating hunger scores for pre-stimulation, end-of-stimulation and post-stimulation scenarios.

FIG. 36I is another graph showing a first median or average hunger score 3620 (assessed using the VAS hunger questionnaire, such as that of FIG. 35A) recorded on a first day prior to subjecting one or more patients to stimulation therapy (pre-stimulation scenario), a second median or average hunger score 3622 recorded at the end of subjecting one or more patients to stimulation therapy (end-of-stimulation scenario) and a third median or average hunger score 3624 recorded on a second day after having subjected one or more patients to stimulation therapy (post-stimulation scenario).

Referring now to FIGS. 37A through 37E, in accordance with an embodiment, a sample of 5 patients, having weight loss as an objective or goal, were assessed for their feeling of satiety (using VAS) at a first occasion, corresponding to a pre-stimulation scenario wherein the 5 patients were not subjected to stimulation therapy and at a second occasion, corresponding to a post-stimulation scenario wherein the 5 patient were subjected to stimulation therapy using an EDP of the present specification.

In accordance with an embodiment, the 5 patients were assessed both pre and post stimulation using a VAS satiety questionnaire, such as the questionnaire of FIG. 35D, having a 100 mm VAS line. At the first occasion (pre-stimulation), each patient's responses or scores to the VAS satiety questionnaire were recorded at intervals of every 60 minutes starting from a first response or score 3706a through 3706e that, in one embodiment, is recorded just prior to a meal (such as breakfast) but without subjecting any of the patients to stimulation therapy. At the second occasion (post-stimulation), each patient's responses or scores to the VAS satiety questionnaire were again recorded at intervals of every 60 minutes starting from a first response or score 3707a through 3707e recorded just prior to the meal (such as breakfast) but after having treated each of the patients with stimulation therapy prior to, for example 30 minutes before, the meal. In accordance with an embodiment, the responses or scores related to the first occasion are recorded on a first day while those related to the second occasion are recorded on a second day, preferably at the same time of day and under the same eating or fasting conditions as the first day.

Figure 37A:
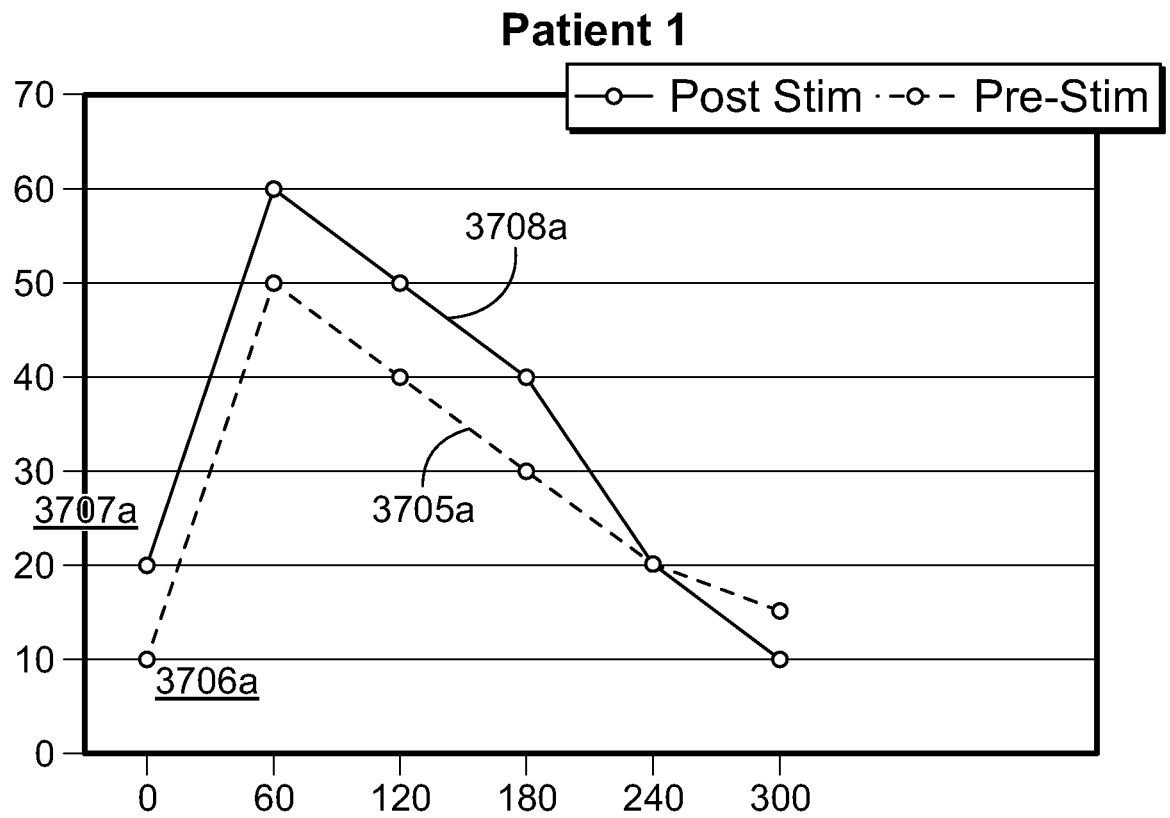
FIG. 37A is a graph illustrating pre-stimulation and post-stimulation satiety profiles of a first patient, in accordance with an embodiment.
Figure 37B:
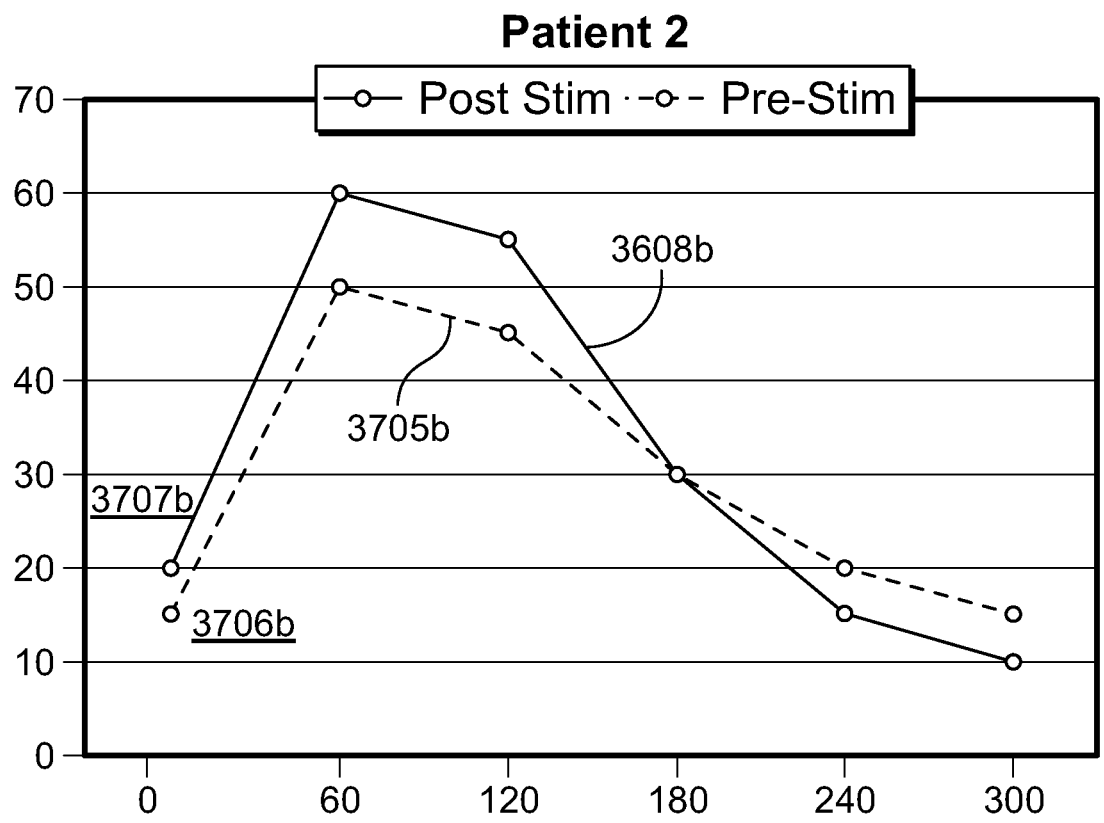
FIG. 37B is a graph illustrating pre-stimulation and post-stimulation satiety profiles of a second patient, in accordance with an embodiment.
Figure 37C:
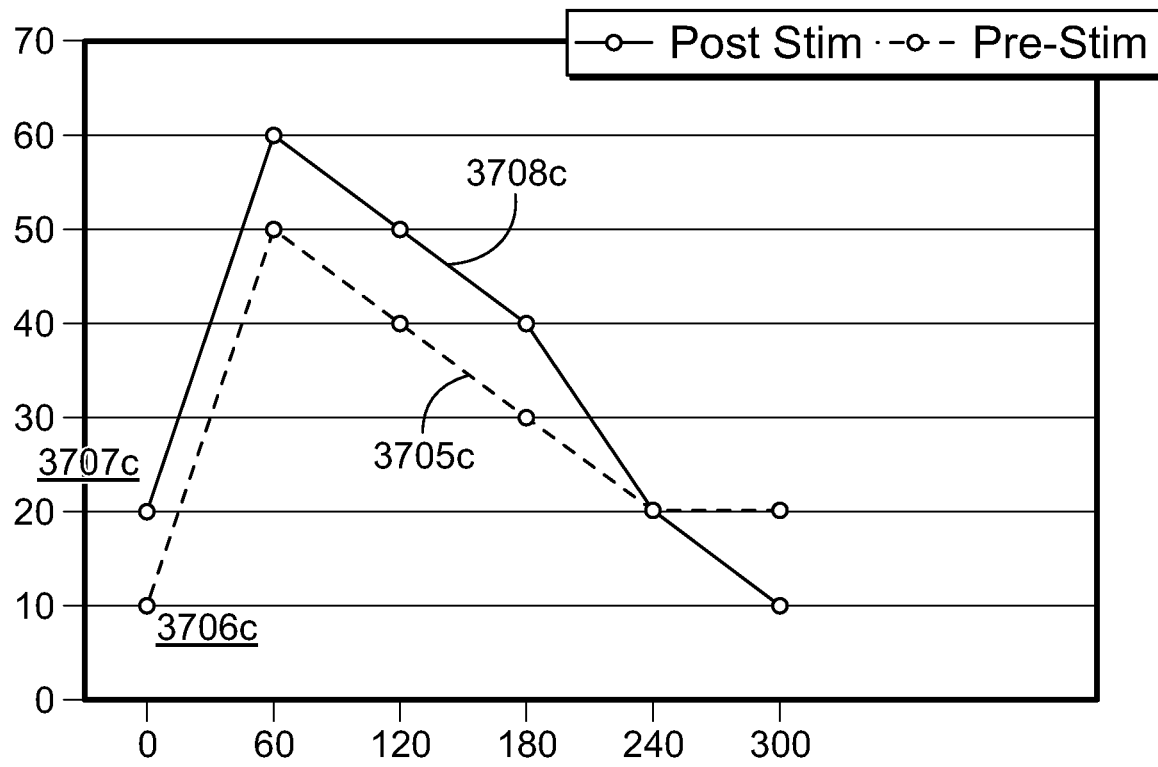
FIG. 37C is a graph illustrating pre-stimulation and post-stimulation satiety profiles of a third patient, in accordance with an embodiment.
Figure 37D:
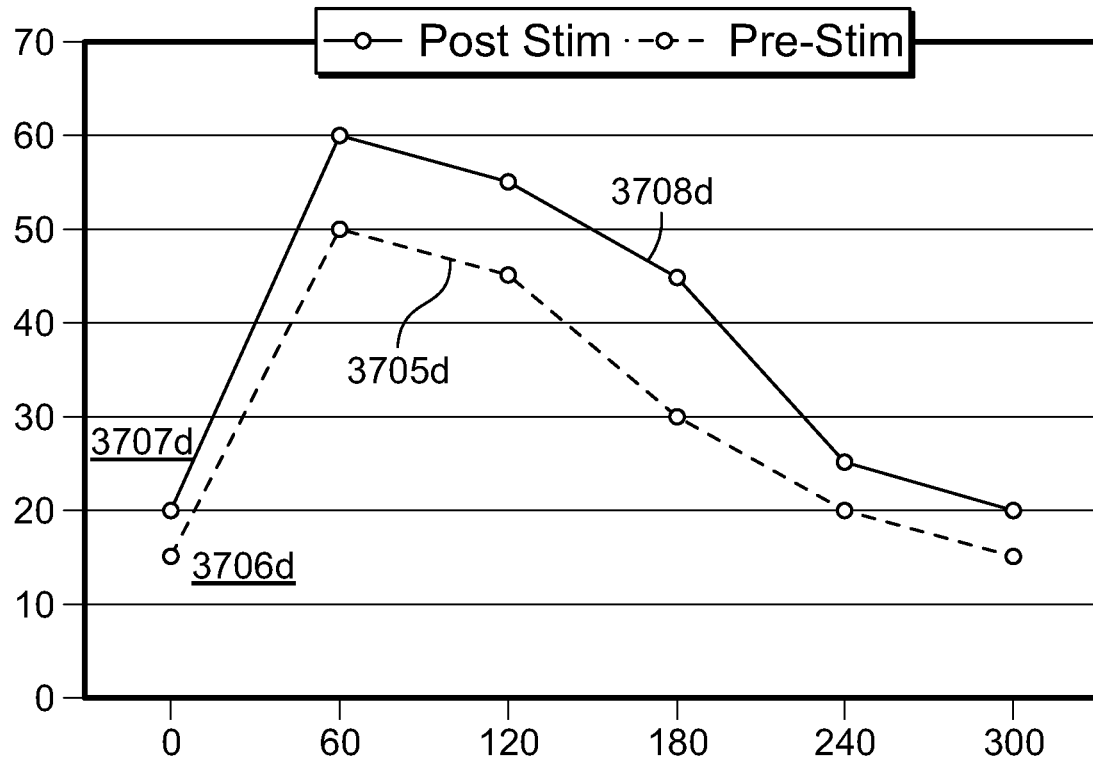
FIG. 37D is a graph illustrating pre-stimulation and post-stimulation satiety profiles of a fourth patient, in accordance with an embodiment.
Figure 37E:
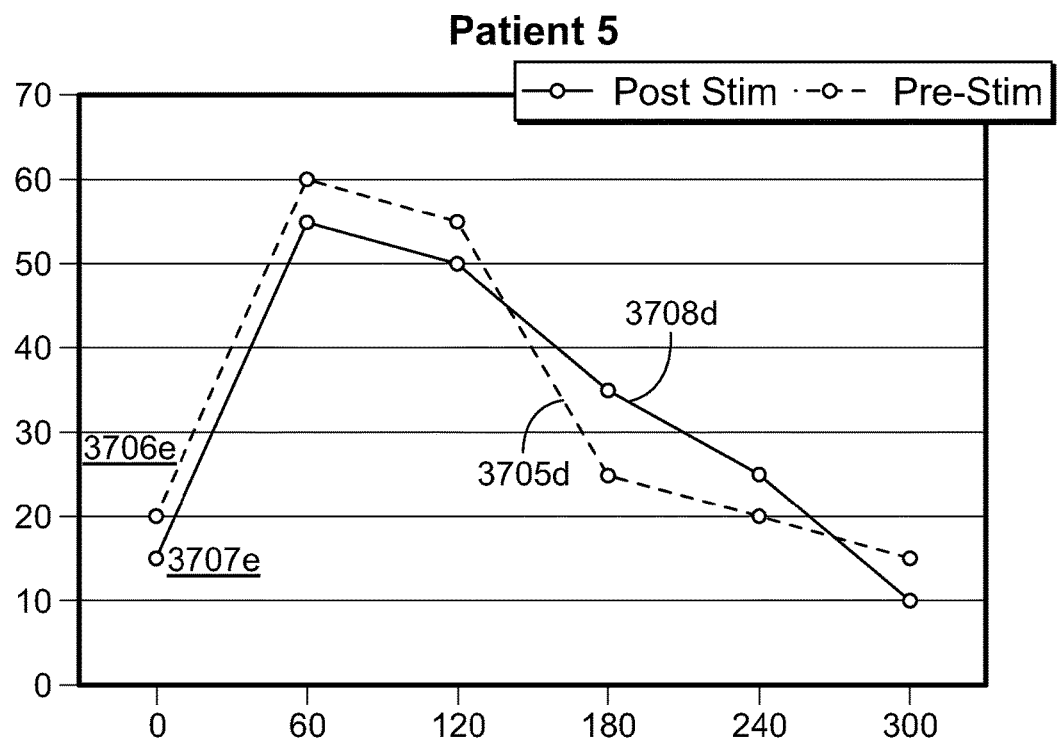
FIG. 37E is a graph illustrating pre-stimulation and post-stimulation satiety profiles of a fifth patient, in accordance with an embodiment.

As shown in FIG. 37A, the first patient's satiety responses or scores for the first occasion (that is, pre-stimulation) are recorded on a first day and plotted on a graph, whose x-axis represents time in minutes and y-axis represents VAS satiety responses or scores in millimeters, to generate a pre-stimulation satiety profile 3705a. Thereafter, the first patient is subjected to stimulation therapy, in accordance to embodiments of the present specification, and the satiety responses or scores for the second occasion (that is, post-stimulation) are also plotted on the graph to generate a post-stimulation satiety profile 3708a. Similarly, the second, third, fourth and fifth patients' responses or scores are recorded to generate the respective pre-stimulation satiety profiles 3705b, 3705c, 3705d, 3705e and the respective post-stimulation satiety profiles 3708b, 3708c, 3708d, 3708e as shown in FIGS. 37B through 37E. As can be observed from FIGS. 37A through 37E, the post-stimulation satiety profiles 3708a, 3708b, 3708c, 3708d, 3708e reflect reduced satiety magnitude relative to the pre-stimulation satiety profiles 3705a, 3705b, 3705c, 3705d, 3705e. In some embodiments, the post-stimulation satiety profile of a patient reflects at least a 5% increase in satiety magnitude relative to the patient's pre-stimulation satiety profile.

Figure 37F:
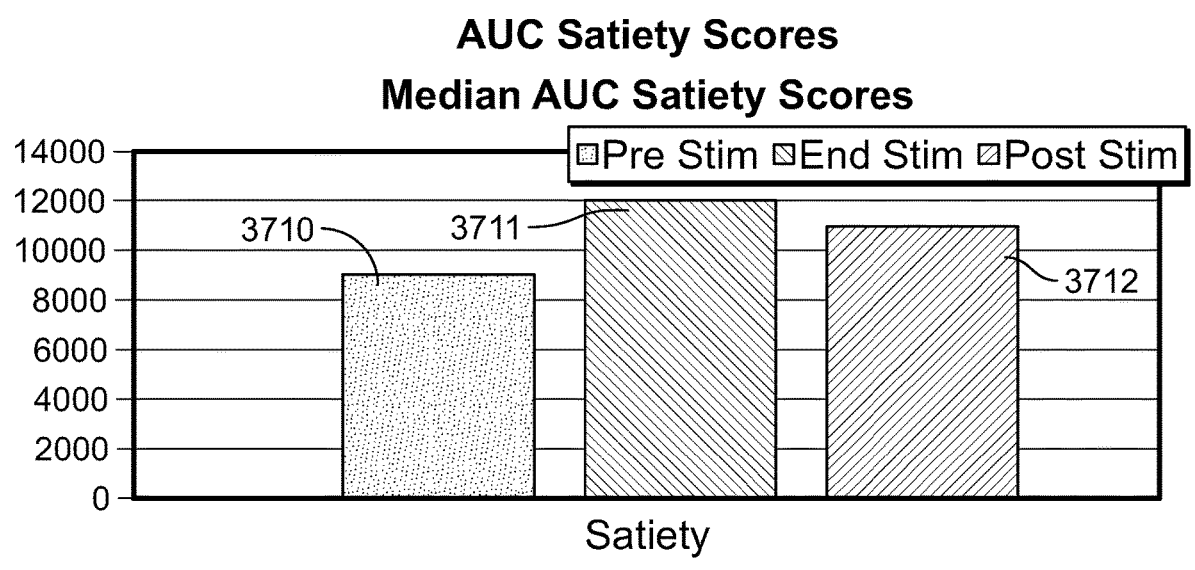
FIG. 37F is a graph illustrating median AUC (Area Under the Curve) satiety scores for pre-stimulation, end-of-stimulation and post-stimulation scenarios.

FIG. 37F shows a first bar 3710 representing a median AUC pre-stimulation satiety score derived from AUC values for pre-stimulation satiety profiles of at least one patient, a second bar 3711 representing a median AUC end-of-stimulation satiety score derived from AUC values for end-of-stimulation satiety profiles (that is, the satiety profiles recorded starting immediately after the end of stimulation therapy) of the at least one patient and third bar 3712 representing a median AUC post-stimulation satiety score derived from AUC values for post-stimulation satiety profiles of the at least one patient. In various embodiments, end-of-stimulation is defined as the end of a period of stimulation lasting in a range from one session to a multitude of sessions over six months. In various embodiments, post-stimulation is defined as a time after the cessation of therapy and ranges from one day after cessation to six months after cessation. As shown in the figure, the median AUC satiety scores 3711, 3712 corresponding to end-of-stimulation and post-stimulation scenarios are elevated or improved relative to the median AUC satiety score 3710 corresponding to the pre-stimulation scenario. In other words, the stimulation therapy of the present specification results in hunger suppression or improved satiety. In some embodiments, an area under the curve (AUC) of the post-stimulation satiety profile of a patient reflects at least a 5% increase relative to the patient's AUC of the pre-stimulation satiety profile.

Figure 37G:
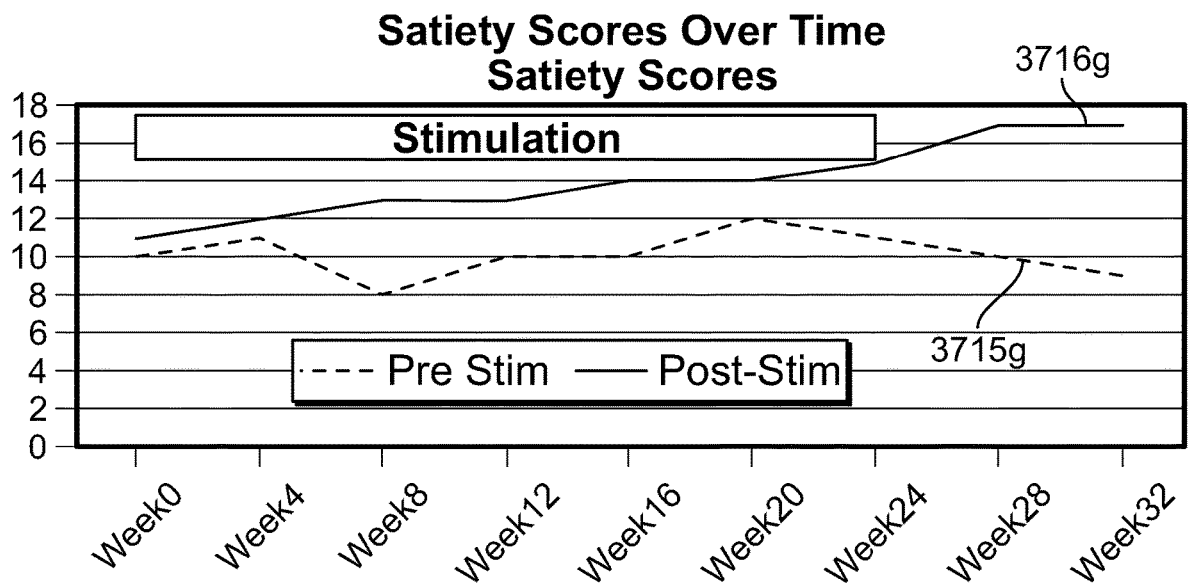
FIG. 37G is a graph illustrating pre-stimulation and post-stimulation satiety profiles over an extended period of time, in accordance with a first embodiment.
Figure 37H:
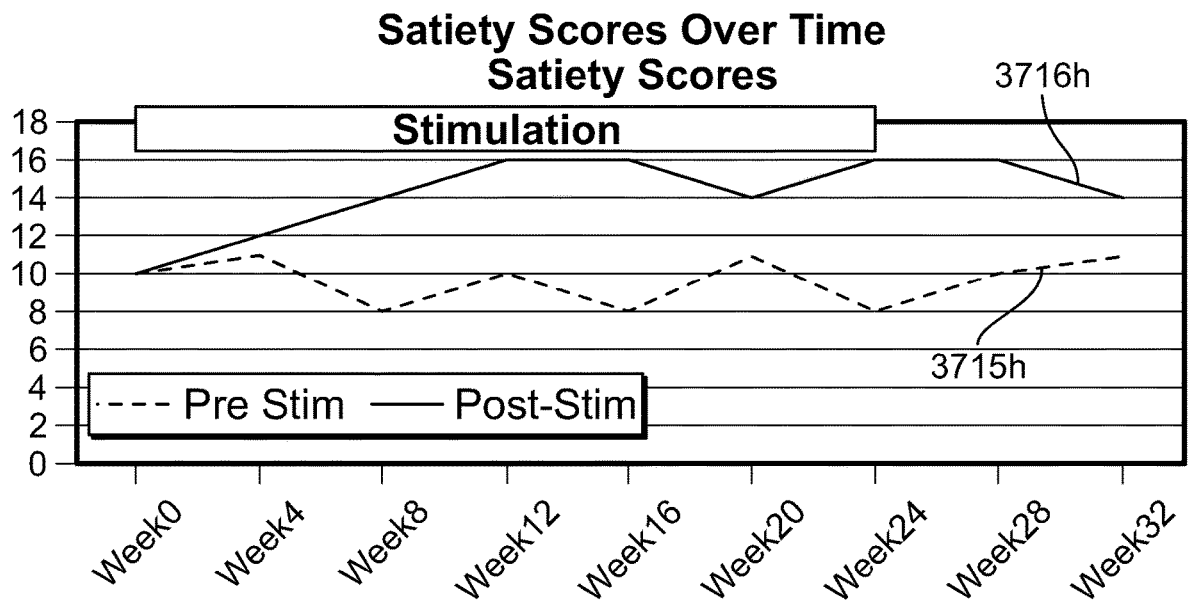
FIG. 37H is a graph illustrating pre-stimulation and post-stimulation satiety profiles over an extended period of time, in accordance with a second embodiment.

FIGS. 37G and 37H also illustrate reduced magnitude of satiety scores, for at least one patient, assessed post stimulation relative to those assessed pre-stimulation. FIGS. 37G and 37H are charts having x-axis representing time in weeks and y-axis representing satiety scores. FIG. 37G shows a pre-stimulation satiety profile 3715g relative to a post-stimulation satiety profile 3716g over extended period of times such as, in weeks and up to 32 weeks. Similarly, FIG. 37H also shows a pre-stimulation satiety profile 3715h relative to a post-stimulation satiety profile 3716h over the same extended periods of time. As can be observed from the FIGS. 37G and 37H, the post-stimulation satiety profiles 3716g, 3716h show improved or increased satiety AUC and magnitude relative to the respective pre-stimulation satiety profiles 3715g, 3715h, even over extended periods of time.

Figure 37I:
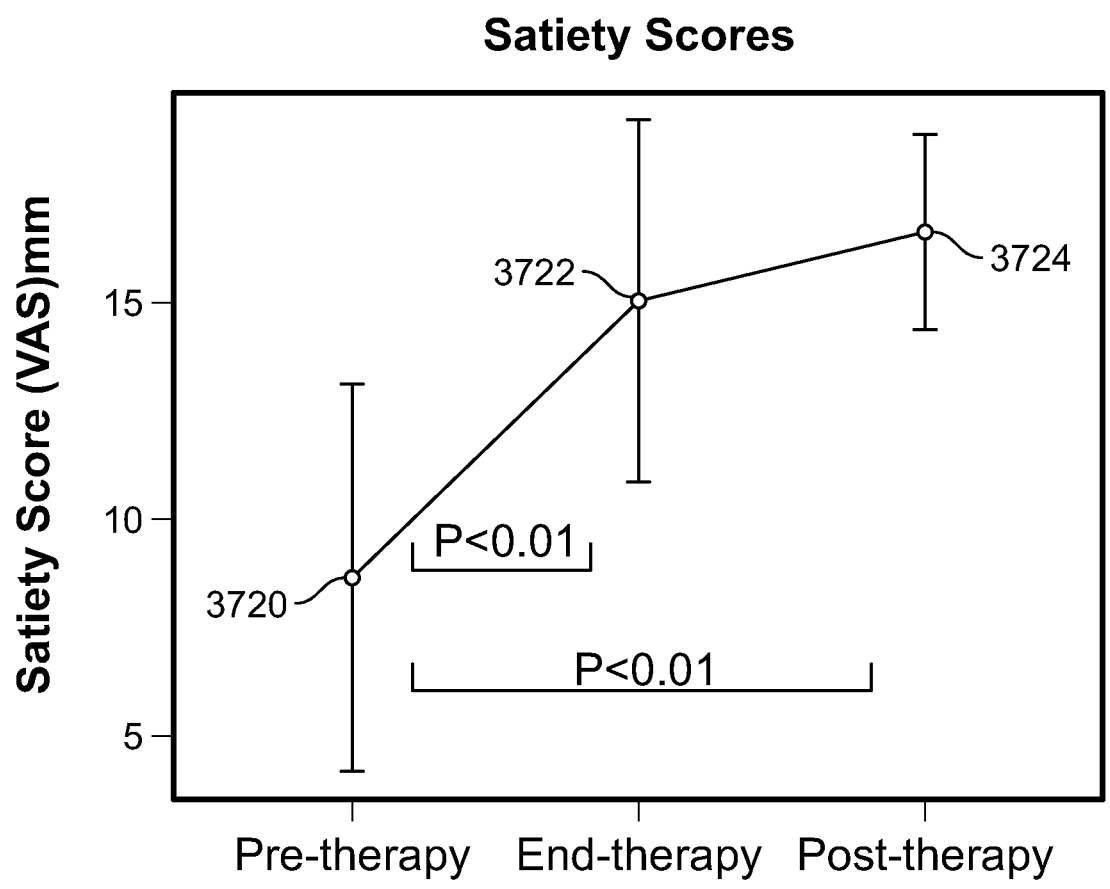
FIG. 37I is a graph illustrating satiety scores for pre-stimulation, end-of-stimulation and post-stimulation scenarios.

FIG. 37I is another graph showing a first median or average satiety score 3720 (assessed using the VAS hunger questionnaire, such as that of FIG. 35D) recorded on a first day prior to subjecting the at least one patient to stimulation therapy (pre-stimulation scenario), a second median or average satiety score 3722 recorded at the end of subjecting the at least one patient to stimulation therapy (end-of-stimulation scenario) and a third median or average satiety score 3724 recorded on a second day after having subjected the at least one patient to stimulation therapy (post-stimulation scenario).

It should be appreciated that while FIGS. 36A through 36I illustrate pre and post hunger levels and FIGS. 37A through 37I illustrate pre and post satiety levels, in various embodiments, various patient sensations such as satiation and fullness are also similarly assessed and recorded using VAS under pre and post stimulation scenarios. It should also be appreciated that the pre-stimulation levels of a patient sensations, such as hunger, appetite, satiety, satiation and fullness, are measured using a scale (such as a VAS) at pre-defined times of day over a first predefined period of time, and the post-stimulation levels of the patient sensations are measured, after stimulation is initiated, using the scale at the predefined times of day over a second predefined period of time, equal in duration to the first predefined period of time. In addition, in various embodiments, a patient's change in satiety, defined as an alteration in the patient's perception of gastric fullness or emptiness, is measured using a scale (such as a VAS) to determine efficacy of therapy provided by an EDP device. Further, in various embodiments, the results obtained by the VAS, not only for change in satiety but for all patient sensations, are used to modify stimulation provided by the EDP device.

For well-being, in one embodiment and referring to FIG. 16, the patient can enter a score from 1 to 3, wherein 1 indicates no nausea/abdominal discomfort, 2 indicates occasional nausea/abdominal discomfort, and 3 indicates the patient is experiencing frequent nausea/abdominal discomfort. In some embodiments, for well-being, a higher score indicates stimulation is too intense, causing the patient to experience nausea, and that a reduction in stimulation is needed. The treatment algorithm of the companion device recognizes the need for reduced stimulation as indicated by the higher score and titrates therapy accordingly. For example, in one embodiment, if the patient enters a well-being score of 3 in the patient diary for three consecutive days, the algorithm uses the score to incrementally reduce the number of stimulation sessions per day or week and/or the length of each stimulation session. In one embodiment, parameter modifications based on well-being scores supersede those based on hunger and/or appetite scores. These primary drivers are tracked to determine how best to modify stimulation on an on-going basis to provide the patient with the proper amount of stimulation such that the patient does not experience feelings of nausea, dyspepsia, does not experience low energy or weakness, and does not have too large an appetite or consume too much food. The tracking of these variables allows for automatic modification of stimulation parameters, based on predefined variable ranges and limits, to provide the patient with a therapeutic stimulation protocol without the need of constant management by the patient.

In some embodiments, therapy is further driven by a set of two secondary indicators. The secondary indicators include patient weight and calories expended/exercise. Weight can be entered in pounds and calories expended/exercises can be attributed a score which is entered into the companion device, as depicted in FIGS. 15 and 12. For example, for weight, referring to FIG. 15, the patient can enter his weight in pounds using a keypad on the companion device. In one embodiment, the patient enters his weight in the patient diary on a weekly basis. In other embodiments, the companion device is configured to communicate wirelessly with a wireless scale (i.e. bathroom scale) such that the patient's weight is automatically entered into the companion device when the patient weighs himself on the scale. This improves system accuracy by eliminating the possibility of the patient entering an incorrect weight. In addition, the system can track how often and when the patient weighs himself, send reminders, and titrate therapy based on the communicated weight. In another embodiment, the companion device is configured to communicate wirelessly with a separate body fat measuring device. As with the patient's weight, automatic transmission of calculated body fat to the companion device results in improved system accuracy, body fat measuring tracking and reminders, and therapy titration based on communicated body fat data. In various embodiments, the companion device is configured to communicate wirelessly with a separate device capable of measuring a plurality of physiological parameters, including, but not limited to, patient weight, body fat, lean mass, and body mass index (BMI). Data from these parameters is automatically input into a treatment algorithm of the companion device and is used to drive therapy by modifying electrical stimulation parameters.

For calories expended/exercise, referring to FIG. 12, the patient can enter an exercise score from 1 to 5, wherein 1 indicates the patient took more than 10,000 steps in a single day, 2 indicates the patient took 7,500-10,000 steps in a single day, 3 indicates the patient took 5,000-7,500 steps in a single day, 4 indicates the patient took 2,500-5,000 steps in a single day, and 5 indicates the patient took less than 2,500 steps in a single day. In some embodiments, the secondary indicators further include fitness input (from a separate device, for example, a device, with physiological sensors, configured to be worn on the human body, such as around the wrist, in order to monitor, acquire, record, and/or transmit the physiological data) and biological inputs (such as ghrelin levels).

Similar to the primary drivers, these secondary indicators can be tracked to determine how best to modify stimulation on an on-going basis to provide the patient with the proper amount of stimulation. In some embodiments, the secondary indicators possess less value compared to the primary drivers in determining how best to modify the EDP stimulation parameters. Although embodiments having three primary drivers and two secondary indicators have been discussed, additional embodiments having greater or fewer primary drivers and/or secondary indicators are possible and the variables presented are not intended to be limiting.

The EDP devices of the present specification can be used to enable a patient to comply with a dietary plan. In some embodiments, the system calculates, for example, via an application or software on the microprocessor of the EDP, the timing of food consumption by the patient, the total calories consumed, and the type of food consumed (i.e. glycemic index, carbohydrate profile, and protein profile). The system then, via an algorithm through said application or software, uses the calculated information to titrate electrical stimulation therapy. For example, if the patient eats outside his normal dietary time, eats too many calories based on his diet, and/or eats foods high in glycemic index or carbohydrate profile, the system recognizes this and increases any one or combination of stimulation amplitude, frequency, number of sessions, session length, or session timing.

Specifically, in various embodiments, the system calculates timing of consumption, total calories consumed, and type of food consumed, as described above, along with other parameters such as exercise and on-going weight loss, and, based on the calculations, performs the following therapy adjustments:

- If a patient consumes too many calories, based on his dietary plan, over a predetermined period (for example, 3 days), the stimulation duration, intensity, and/or number of sessions is increased.
- If a patient consumes too much food at a specific time of day each day over a predetermined period (for example, 3 days), the timing of stimulation is changed to prior to (for example, a half hour or 1 hour before) the overeating time and/or an additional stimulation session is added prior to the overeating time.
- If a patient consumes foods outside his dietary plan, for example, too many carbohydrates, over a predetermined period (for example, 3 days), the stimulation duration, intensity, session timing, and/or number of sessions is increased.
- If a patient stops exercising for a predetermined period (for example, 3 days), stimulation parameters are increased.
- If, following a course of treatment, the patient has lost a predetermined amount of target weight, the system algorithm decreases stimulation parameters, in some embodiments either by a physician or via a downloadable application.

For some patients, compliance becomes easier when the patient does not need to track the amount of calories in each piece of food consumed but rather is presented with a dietary plan with a listing of foods wherein the calorie profile of each item of food is already known. Therefore, in some embodiments, the system provides the patient with a number of breakfast, lunch, dinner, and optionally snack meal plans from which to choose. The calorie profile of each of these meal plans is pre-calculated. These calorie profiles are pre-programmed into the software or applications of the EDP device. Patients no longer need to track the calorie content of each item of food consumed but can simply report how well they are complying with the chosen meal plans. Further, in some embodiments, the EDP can be linked to a separate wearable device, for example, a device, with physiological sensors, configured to be worn on the human body, such as around the wrist, in order to monitor, acquire, record, and/or transmit physiological data, such as exercise data, to the EDP so that calories expended, as tracked by the separate device, are deducted from calories consumed, as per the specific meal plans, to provide the patient and system with calorie balance information.

In some embodiments, patients are instructed to follow a 1200 calorie/day diet plan. Based on the above, too many calories consumed above the baseline 1200 and/or the wrong calories consumed (for example, a bad glycemic index, too many sugars consumed, and/or too many carbohydrates consumed) will result in an increase in stimulation. If poor eating habits (for example, too many of the wrong calories) are concentrated at a particular time of day, the system adjusts to add a session just prior to the particular time to lower hunger and improve eating behavior.

In some embodiments, stimulation is programmed to begin before (for example, 1 week prior to) the patient starts on his dietary plan. Beginning stimulation before the patient changes to a new dietary plan reduces the patient's appetite before the change in eating and results in better compliance as patients are less likely to become disheartened if they stray from their diet due to high hunger levels. In other embodiments, patients only receive stimulation therapy and do not go on a dietary plan.

Figure 27C:
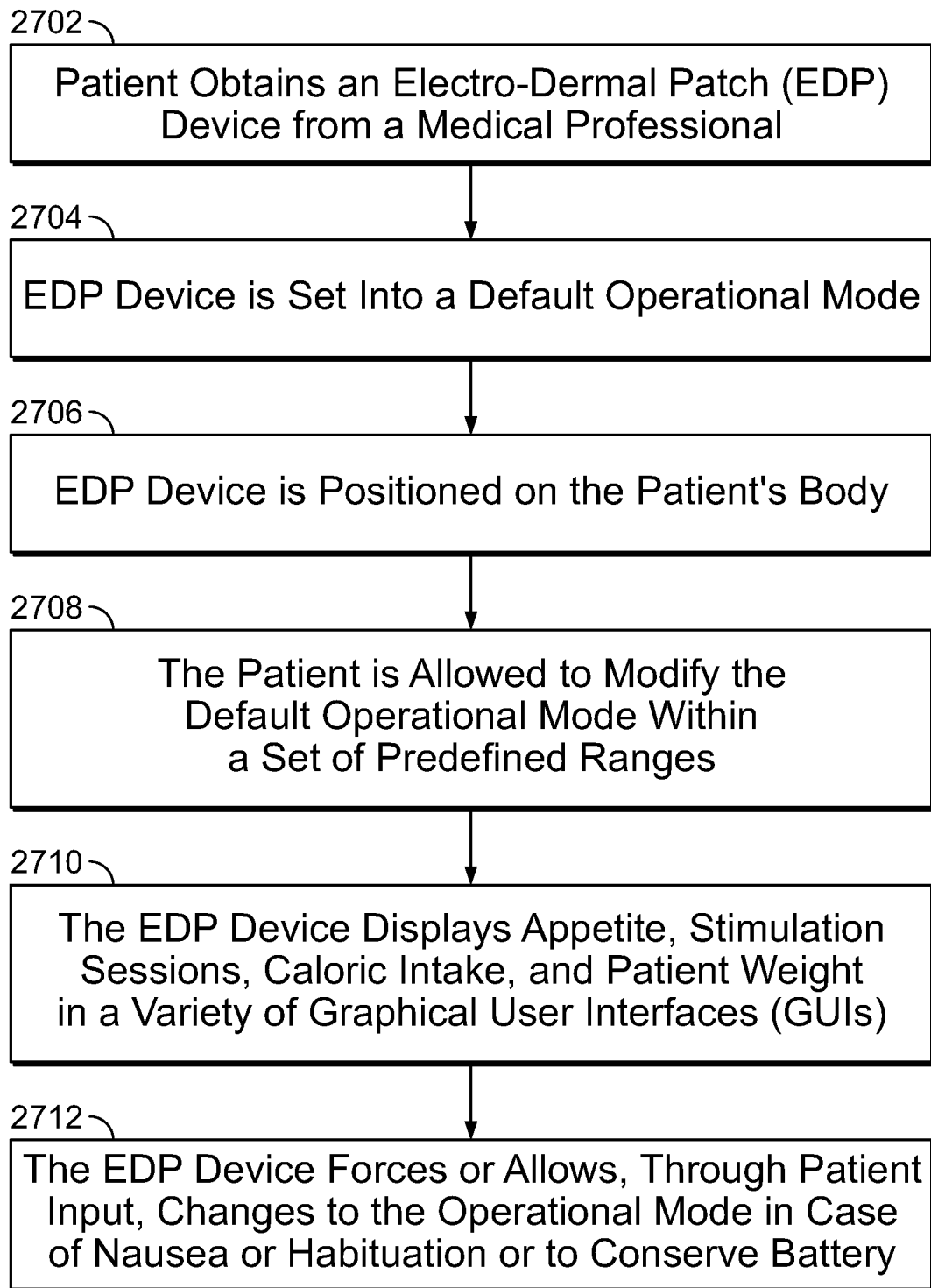
FIG. 27C is a flow chart illustrating the steps involved in a method of using an electro-dermal patch device to suppress appetite in a patient, in various embodiments of the present specification.

FIG. 27C is a flow chart illustrating the steps involved in one embodiment of a method of using an electro-dermal patch device to suppress appetite in a patient. At step 2702, a patient obtains an electro-dermal patch (EDP) device, in accordance with the devices disclosed in the present specification, from a medical professional.

The EDP device is set into a default operational mode, either by the patient or by the medical professional, at step 2704. In some embodiments, the default operational mode includes the following stimulation parameters and parameter ranges: pulse width in a range of 10 μsec to 10 msec; pulse amplitude in a range of 100 μA to 500 mA; pulse frequency in a range of 1 Hz to 10,000 Hz; pulse duty cycle in a range of 1% to 100%; session duration in a range of 1min to 120 min or substantially continuously; and 1 to 24 sessions per day. In a preferred embodiment, the default operational mode includes the following stimulation parameters: pulse width equal to 200 μsec; pulse amplitude equal to 5 mA; pulse frequency equal to 20 Hz; pulse duty cycle equaling 100%; session duration equaling 30 minutes; and 1 session per day. In another preferred embodiment, the default operational mode is set, for most patients, at 3 daily stimulation sessions of 30 minutes each having pulse amplitude of 20 mA. Each of the three daily stimulation sessions is initiated 30 to 60 minutes and preferably 45 minutes prior to meal-times, such as, breakfast, lunch and dinner, for example. In yet another preferred embodiment, the baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these post-prandial stimulation sessions are triggered manually by the user. In some alternate embodiments, the pre-prandial and post-prandial stimulation sessions are automatically triggered based on pre-stored meal time schedule. In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B.

Then, at step 2706, the EDP device is positioned on the patient's body, either by the patient or by the medical professional. The patient is allowed to modify the default operational mode within a set of predefined ranges at step 2708. The patient may modify the default operational mode based upon patient feedback or feedback provided by a separate wearable device, for example, a device, with physiological sensors, configured to be worn on the human body, such as around the wrist, in order to monitor, acquire, record, and/or transmit the physiological data. At step 2710, the EDP device displays appetite, stimulation sessions, caloric intake, and patient weight in a variety of graphical user interfaces (GUIs). Other parameters may also be listed, and the list in step 2710 is not intended to be limiting. The EDP device forces or allows, through patient input, changes to the operational mode in the case of nausea, dyspepsia or habituation or to conserve battery at step 2712. The EDP device forces the changes when feedback data provided by the device or another wearable device falls outside preset ranges indicating habituation is occurring. In some embodiments, habituation occurs when hunger returns over time despite electrical stimulation via the stimulation protocols disclosed in the present specification.

The return of hunger indicates a loss of appetite suppression due to habituation of the patient to the electrical stimulation. The patient may change the operational mode if he or she is experiencing nausea and/or dyspepsia.

Figure 28:
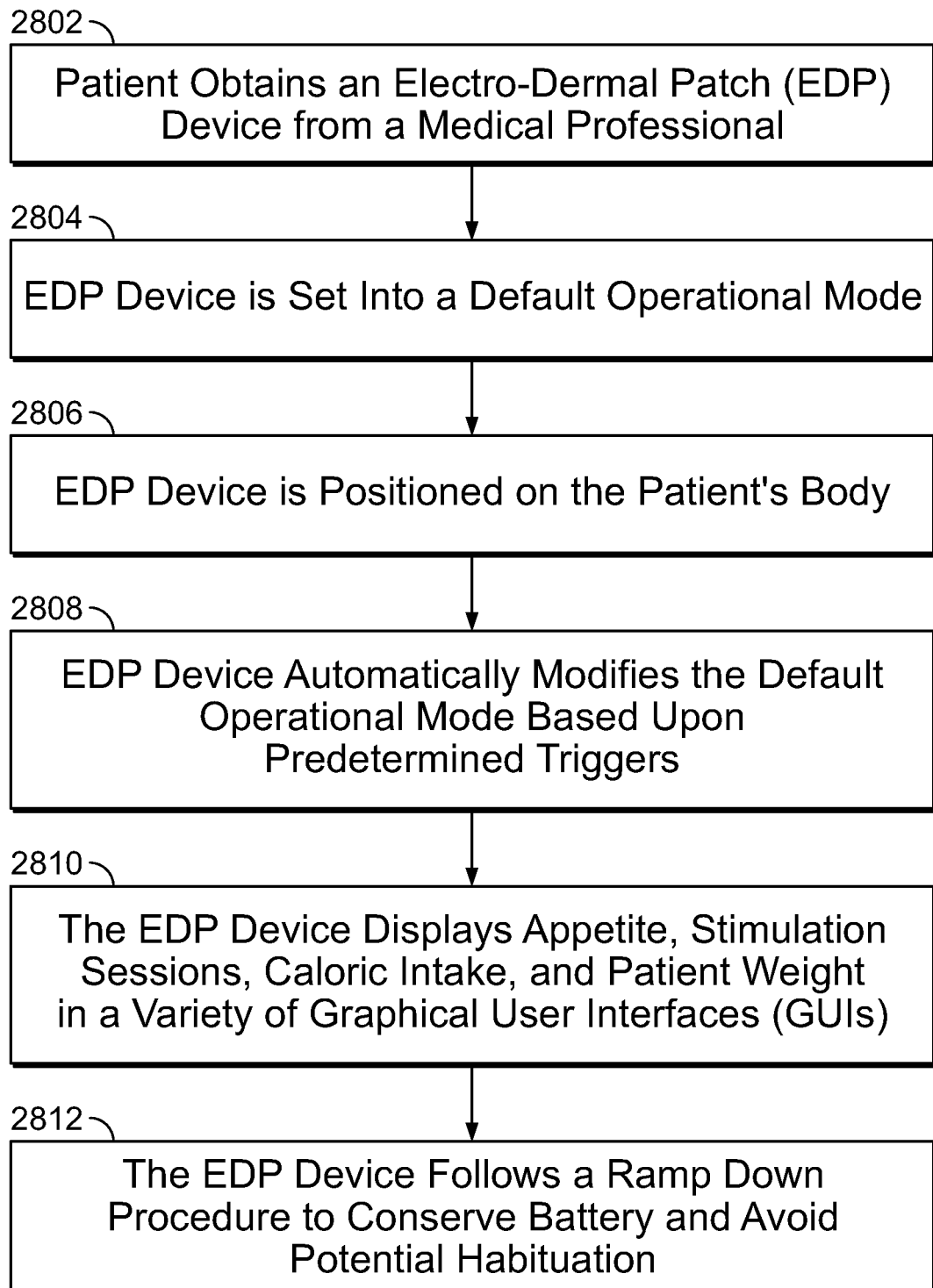
FIG. 28 is a flow chart illustrating the steps involved in a method of using an electro-dermal patch device to suppress appetite in a patient, in various embodiments of the present specification.

FIG. 28 is a flow chart illustrating the steps involved in another embodiment of a method of using an electro-dermal patch device to suppress appetite in a patient. At step 2802, a patient obtains an electro-dermal patch (EDP) device, in accordance with the devices disclosed in the present specification, from a medical professional. The EDP device is set into a default operational mode, either by the patient or by the medical professional, at step 2804. In various embodiments, the default operational mode includes the stimulation parameters and parameter ranges listed above with respect to FIG. 27C. Then, at step 2806, the EDP device is positioned on the patient's body, either by the patient or by the medical professional. The EDP device automatically modifies the default operational mode based upon predetermined triggers at step 2808. In various embodiments, the triggers include, but are not limited to, patient diary recording of appetite, hunger, and well-being, and data from a separate device, with physiological sensors, configured to be worn on the human body, such as around the wrist, in order to monitor, acquire, record, and/or transmit the physiological data, data transmitted to the companion device. For example, in one embodiment, the patient records an appetite diary entry with a score of 5, wherein the patient substantially exceeded his diet during his most recent meal, indicative of dietary non-compliance (that is, not conforming to a diet plan) or poor dietary compliance. In some embodiments, one or more scores of 5 on appetite triggers the companion device to automatically increase therapy parameters, for example, an increase in stimulation intensity, duration, or sessions.

In another embodiment, for example, the patient records a hunger diary entry with a score of 1, wherein the patient experienced no hunger at all at his most recent meal time. In some embodiments, one or more scores of 1 on hunger triggers the companion device to automatically decrease therapy parameters, for example, a decrease in stimulation intensity, duration, or sessions. At step 2810, the EDP device displays appetite, stimulation sessions, caloric intake, and patient weight in a variety of graphical user interfaces (GUIs). Other parameters may also be listed, and the list in step 2810 is not intended to be limiting. The EDP device then follows a ramp down procedure, wherein stimulation parameters are decreased sequentially, to conserve battery and avoid potential habituation at step 2812.

Figure 29:
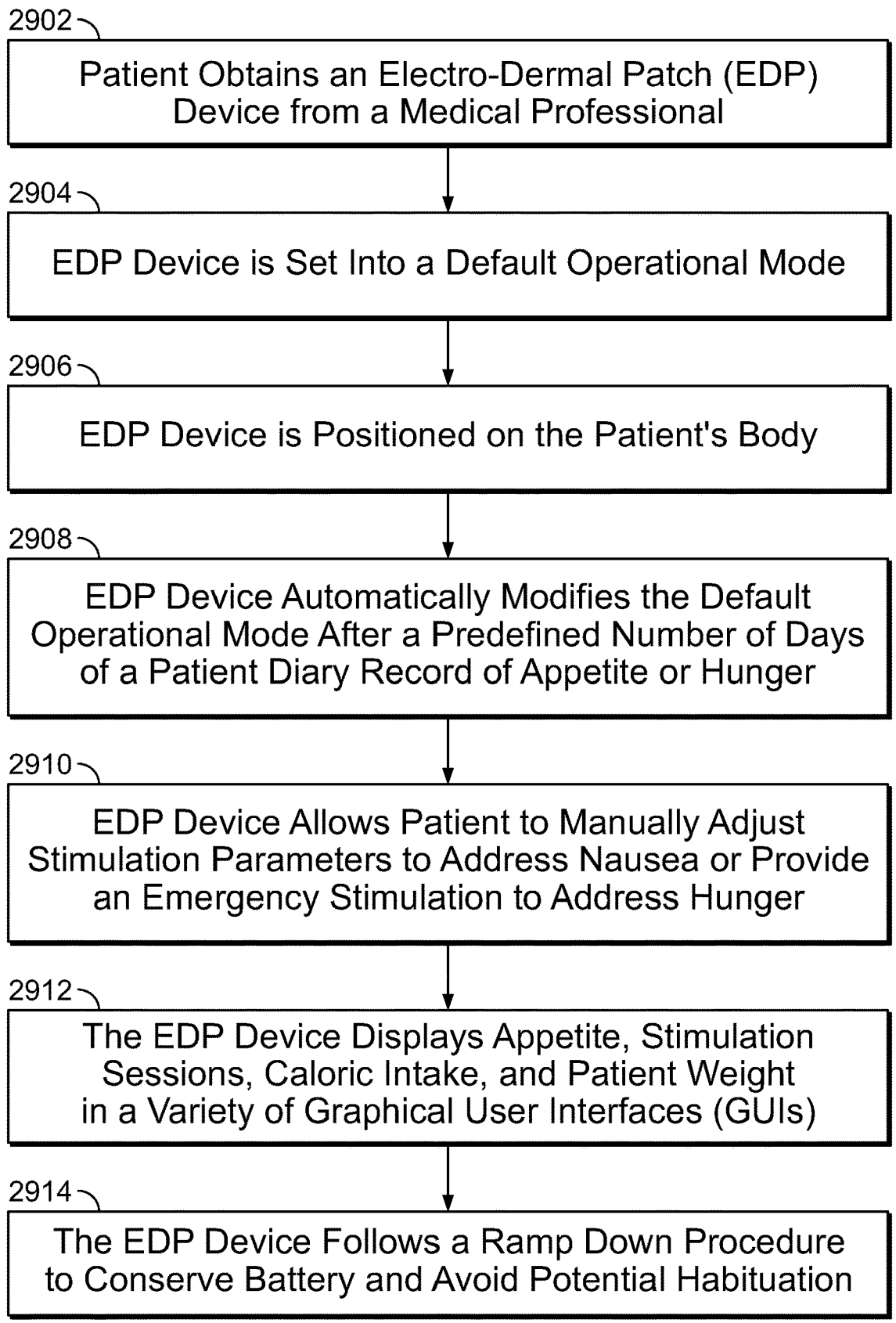
FIG. 29 is a flow chart illustrating the steps involved in a method of using an electro-dermal patch device to suppress appetite in a patient, in various embodiments of the present specification.

FIG. 29 is a flow chart illustrating the steps involved in another embodiment of a method of using an electro-dermal patch device to suppress appetite in a patient. At step 2902, a patient obtains an electro-dermal patch (EDP) device, in accordance with the devices disclosed in the present specification, from a medical professional. The EDP device is set into a default operational mode, either by the patient or by the medical professional, at step 2904. In various embodiments, the default operational mode includes the stimulation parameters and parameter ranges listed above with respect to FIG. 27C. Then, at step 2906, the EDP device is positioned on the patient's body, either by the patient or by the medical professional. The EFP device automatically modifies the default operational mode after a predefined number of days of a patient diary record of appetite or hunger at step 2908. In various embodiments, the predefined number of days is in a range of 1 to 7 days. In one embodiment, the predefined number of days is 3 days. In one embodiment, in combination with step 2908, the EDP device allows the patient to manually adjust stimulation parameters to address nausea, dyspepsia or provide an emergency stimulation to address hunger at step 2910. At step 2912, the EDP device displays appetite, stimulation sessions, caloric intake, and patient weight in a variety of graphical user interfaces (GUIs). Other parameters may also be listed, and the list in step 2912 is not intended to be limiting. The EDP device then follows a ramp down procedure, wherein stimulation parameters are decreased sequentially, to conserve battery and avoid potential habituation at step 2914.

Figure 30:
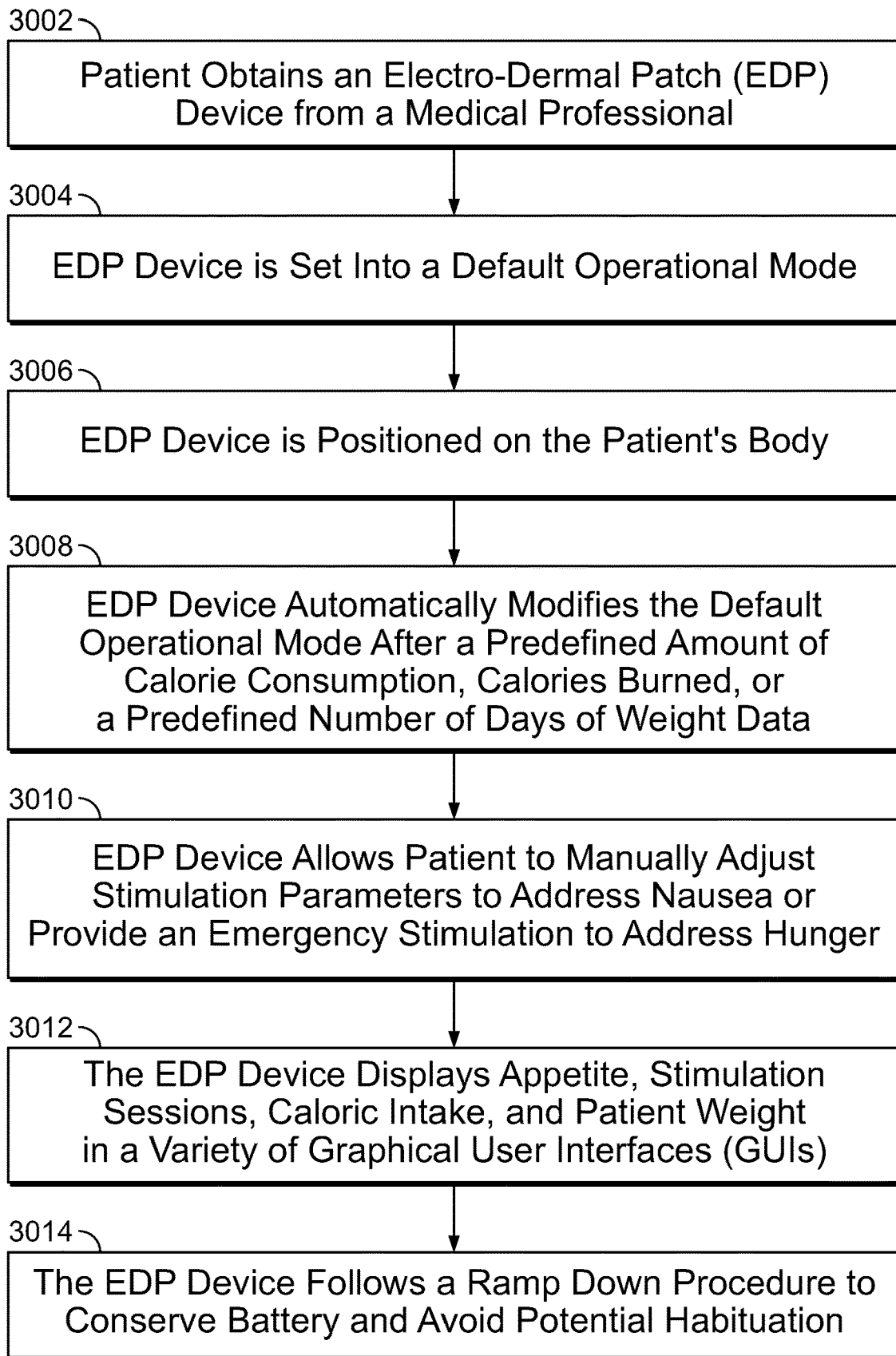
FIG. 30 is a flow chart illustrating the steps involved in a method of using an electro-dermal patch device to suppress appetite in a patient, in various embodiments of the present specification.

FIG. 30 is a flow chart illustrating the steps involved in another embodiment of a method of using an electro-dermal patch device to suppress appetite in a patient. At step 3002, a patient obtains an electro-dermal patch (EDP) device, in accordance with the devices disclosed in the present specification, from a medical professional. The EDP device is set into a default operational mode, either by the patient or by the medical professional, at step 3004. In various embodiments, the default operational mode includes the stimulation parameters and parameter ranges listed above with respect to FIG. 27C. Then, at step 3006, the EDP device is positioned on the patient's body, either by the patient or by the medical professional. The EFP device automatically modifies the default operational mode after a predefined amount of calorie consumption or calories burned, as determined by diary entries or information gathered from a separate device, or after a predefined number of days of weight data has been recorded at step 3008. In various embodiments, the predefined number of days is in a range of 1 to 7 days. In one embodiment, the predefined number of days is 3 days. In one embodiment, in combination with step 3008, the EDP device allows the patient to manually adjust stimulation parameters to address nausea, dyspepsia or provide an emergency stimulation to address hunger at step 3010. At step 3012, the EDP device displays appetite, stimulation sessions, caloric intake, and patient weight in a variety of graphical user interfaces (GUIs). Other parameters may also be listed, and the list in step 3012 is not intended to be limiting. The EDP device then follows a ramp down procedure, wherein stimulation parameters are decreased sequentially, to conserve battery and avoid potential habituation at step 3014.

Figure 31:
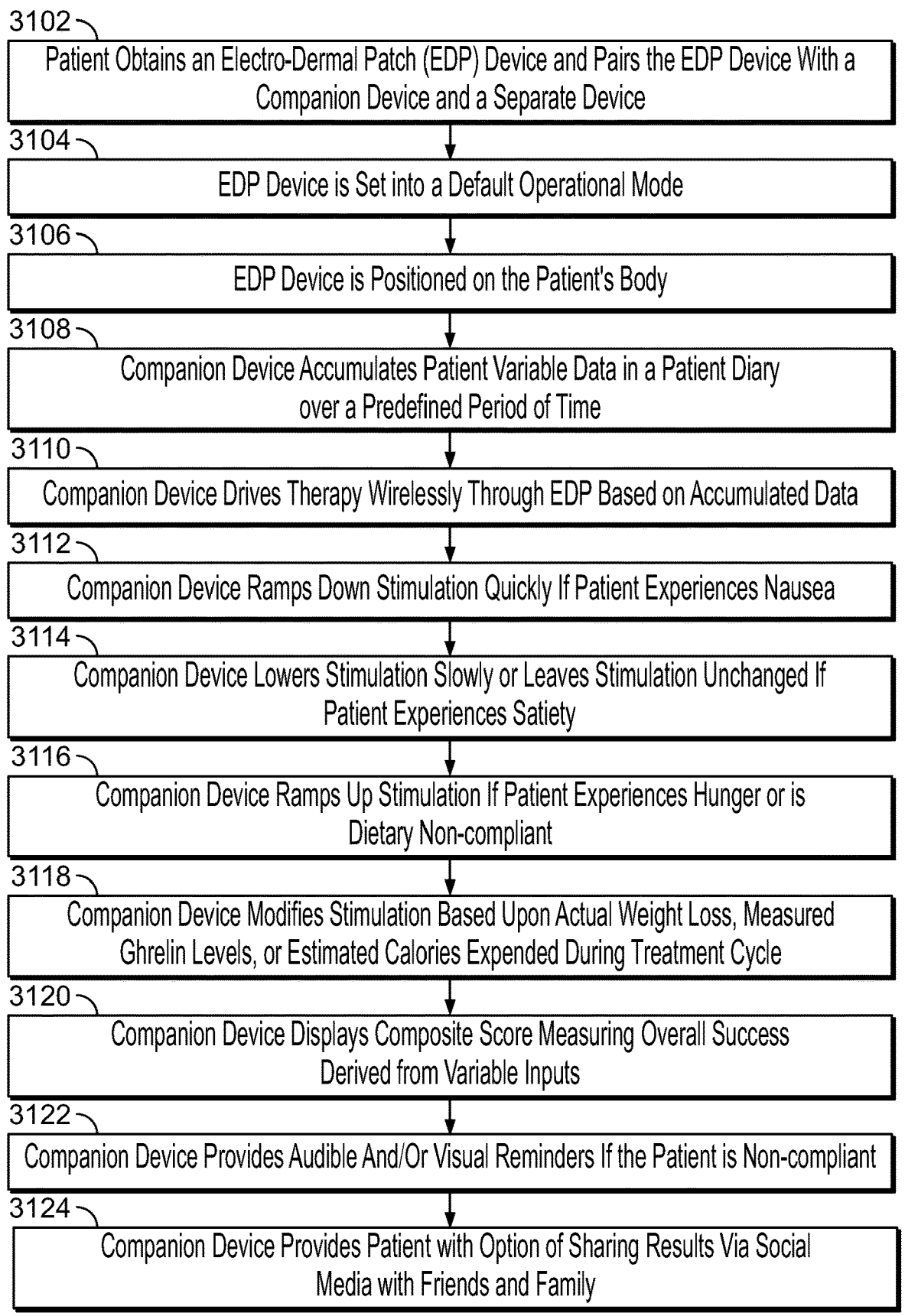
FIG. 31 is a flow chart illustrating the steps involved in a method of using an electro-dermal patch device to suppress appetite in a patient, in various embodiments of the present specification.

FIG. 31 is a flow chart illustrating the steps involved in yet another embodiment of a method of using an electro-dermal patch device to suppress appetite in a patient. At step 3102, the patient obtains an electro-dermal patch (EDP) device and pairs the EPD device with a companion device, such as a smartphone, and a separate device, for example, a device, with physiological sensors, configured to be worn on the human body, such as around the wrist, in order to monitor, acquire, record, and/or transmit the physiological data. In some embodiments, pairing with the separate device can be done anytime within a treatment cycle. In some embodiments, a treatment cycle lasts 3 months. At step 3104, the device is set into a default operational mode. In some embodiments, the default operational mode includes the stimulation parameters and parameter ranges listed above with respect to FIG. 27C and includes daily stimulation.

The EDP device is positioned on the patient's body at step 3106. At step 3108, the companion device accumulates patient variable data, including, but not limited to, appetite, hunger, well-being, weight, and calories expended/weight loss, in a patient diary over a predefined period of time. In some embodiments, the companion device accumulates data over a range of 1 to 7 days. In one embodiment, the companion device accumulates data for 3 days. Then, at step 3110, the companion device drives stimulation therapy wirelessly through the EDP device based on accumulated patient diary data over the treatment cycle. During the treatment cycle, if the patient experiences nausea and/or dyspepsia, the companion device ramps down stimulation parameters quickly at step 3112. During the treatment cycle, if the patient experiences satiety, defined as the absence of hunger coupled with good dietary compliance, the companion device slowly lowers stimulation to a minimum threshold, such as one 15 minute stimulation session every other day, to preserve battery and prevent habituation, or leaves stimulation unchanged at step 3114. During the treatment cycle, if the patient experiences hunger is dietary non-compliant, the companion device ramps up stimulation accordingly at step 3116. At step 3118, the companion device modifies stimulation based upon actual weight loss, measured ghrelin levels, or estimated calories expended during the treatment cycle. In one embodiment, the companion device uses a weight loss predictor algorithm based on caloric input versus caloric consumption. At step 3120, the companion device displays a composite score measuring overall success derived from the variable inputs. If the patient is non-compliant, the companion device will provide audible and/or visual reminders to the patient at step 3122. Optionally, at step 3124, the companion device provides the patient with the option of sharing his results via social media with designated friends and family.

In an alternate embodiment, the companion device first accumulates patient diary data before the EDP device is set into the default operation mode. Referring to FIG. 31, in this alternate embodiment, step 3108 is performed prior to step 3104. The remaining steps proceed in the same order.

In other embodiments, a patient is provided with manual options of operating the EDP device. The patient may operate the device at low, medium, and high settings, based on the patient variable data. For example, in one embodiment, a patient starts the EDP device at a high setting but begins to experience nausea and/or dyspepsia. The patient then resets the EDP device to the medium setting, and then to the low setting. Eventually, the patient experiences hunger and resets the EDP device to the medium setting. In some embodiments, this protocol is driven by a therapy intensity scale, such as 1 to 5 or 1 to 10, or a graphic on the display of the companion device. In some embodiments, manual operation using low, medium, and high settings is coupled with the protocols described with reference to FIGS. 27C-31 to establish baseline EDP device settings.

Figure 32:
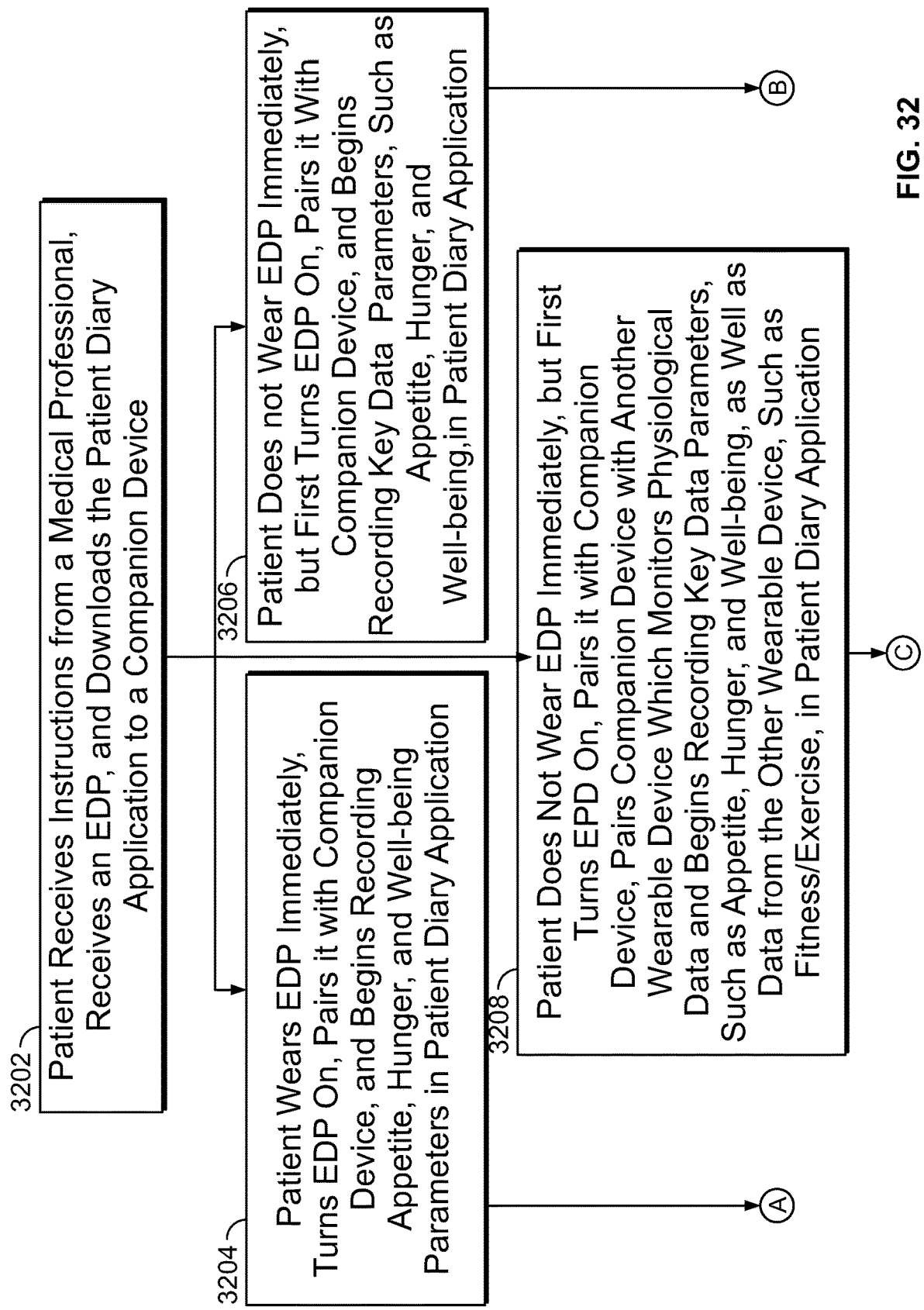
FIG. 32 is a flow chart illustrating the steps involved in methods of using an electro-dermal patch device to suppress appetite in a patient, in various embodiments of the present specification.
Figure 32:
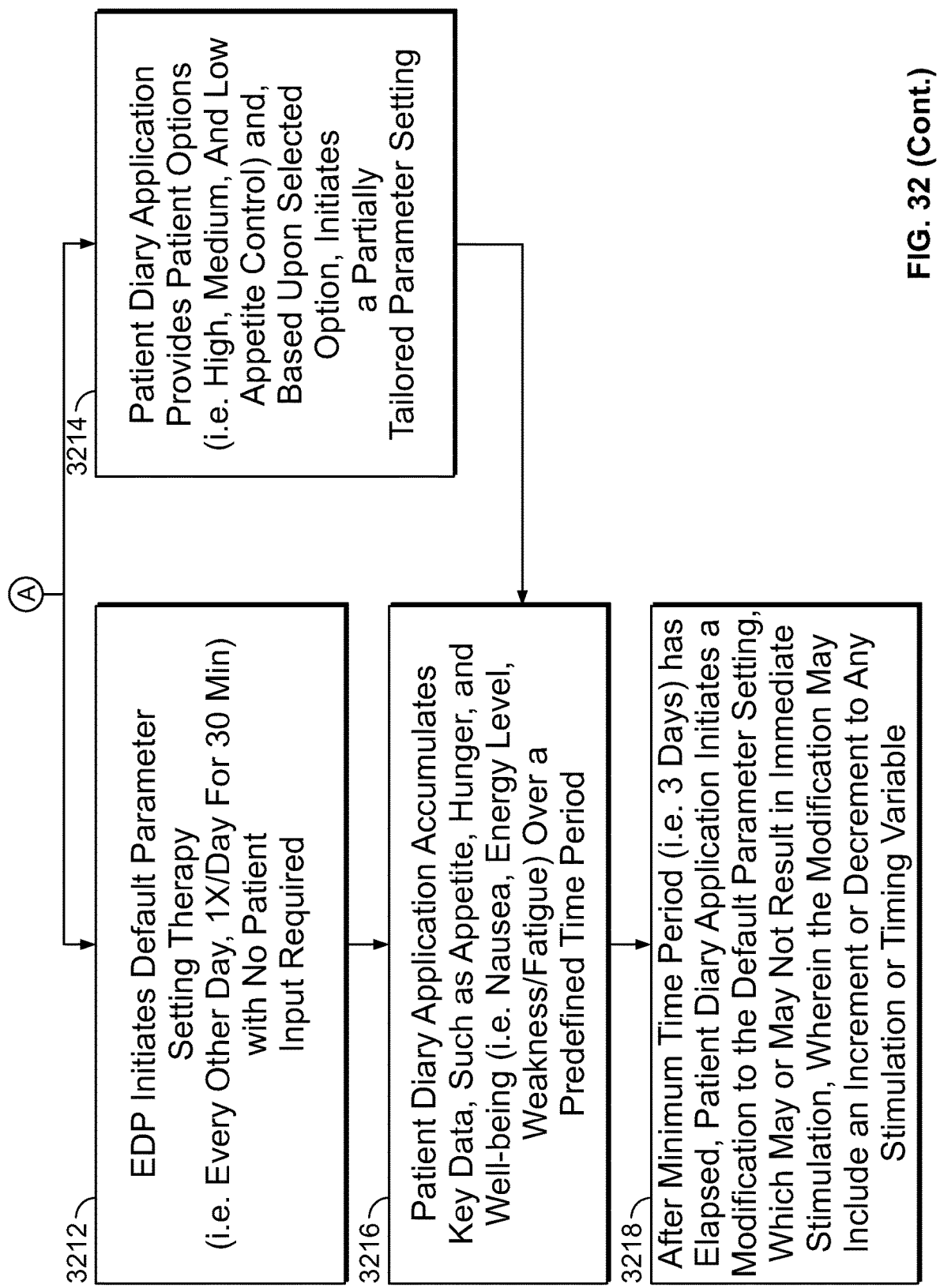
Figure 32:
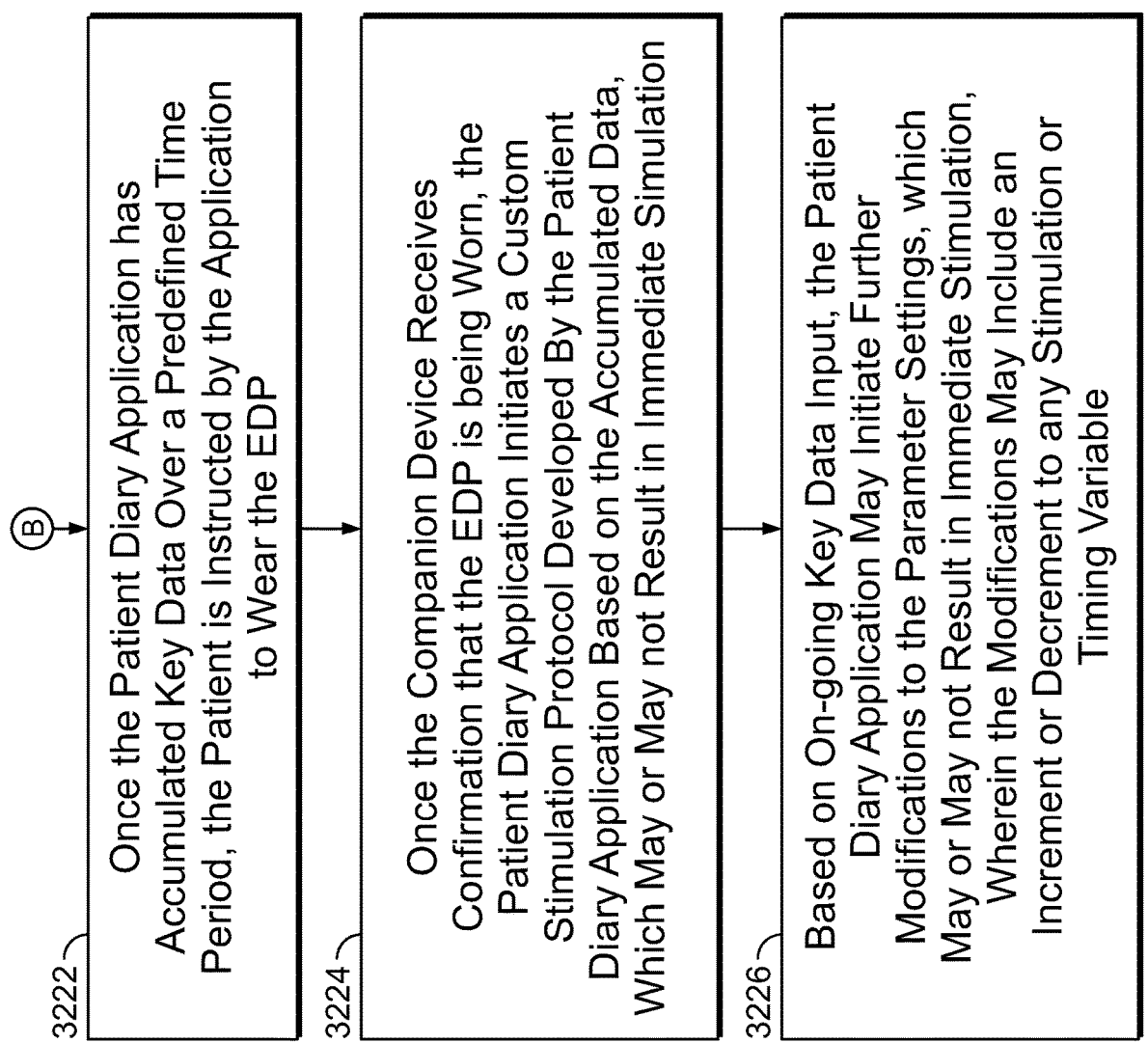

FIG. 32 is a flow chart illustrating the steps involved in yet other embodiments of methods of using an electro-dermal patch device to suppress appetite in a patient. At step 3202, a patient receives instructions from a medical professional, receives an electro-dermal patch (EDP) device, and downloads a patient diary application to a companion device, such as a smartphone. Optionally, at step 3204, the patient wears the EDP immediately, turns it on, and pairs it with the companion device such that the companion device begins recording appetite, hunger, and well-being parameters in the patient diary application. In one embodiment, the EDP then initiates default parameter setting therapy (i.e. every other day, 1×/day for 30 min) with no patient input required at step 3212. The patient diary application then accumulates key data, such as appetite, hunger, and well-being (i.e. nausea, dyspepsia, energy level, weakness/fatigue) over a predefined time period at step 3216. After a minimum time period (i.e. 3 days) has elapsed at step 3218, the patient diary application initiates a modification to the default parameter setting, which may or may not result in immediate stimulation, wherein the modification may include an increment or a decrement to any stimulation or timing variable.

Alternatively, in another embodiment, following step 3204 wherein the patient wears the EDP immediately, the patient diary application provides the patient various options (i.e. high, medium, and low appetite control) at step 3214 and, based upon the selected option, initiates a partially tailored parameter setting. The patient diary application then continues to accumulate key data and initiate parameter setting modifications, as detailed in steps 3216 and 3218 respectively.

Optionally, in another embodiment, following step 3202 wherein the patient receives the EDP and downloads the patient diary application, the patient does not wear the EDP immediately at step 3206, but first turns the EDP on, pairs it with the companion device, and begins recording key data parameters, such as appetite, hunger, and well-being, in the patient diary application. At step 3222, once the patient diary application has accumulated key data over a predefined time period, the patient is instructed by the application to wear the EDP. Then, at step 3224, once the companion device receives confirmation that the EDP is being worn, the patient diary application initiates a custom stimulation protocol developed by the patient diary application based on the accumulated data, which may or may not result in immediate stimulation. Based on on-going key data input, at step 3226, the patient diary application may initiate further modifications to the parameter settings, which may or may not result in immediate stimulation, wherein the modifications may include an increment or a decrement to any stimulation or timing variable.

Still optionally, in another embodiment, following step 3202 wherein the patient receives the EDP and downloads the patient diary application, the patient does not wear the EDP immediately at step 3208, but first turns the EDP on, pairs the EDP with the companion device, pair the companion device with another wearable device, for example, a device, with physiological sensors, configured to be worn on the human body, such as around the wrist, in order to monitor, acquire, record, and/or transmit the physiological data, and begins recording key data parameters, such as appetite, hunger, and well-being, as well as data from the other wearable device, such as fitness/exercise, in the patient diary application. At step 3232, once the patient diary application has accumulated key data and data from the other wearable device over a predefined time period, the patient is instructed by the application to wear the EDP. Then, at step 3234, once the companion device receives confirmation that the EDP is being worn, the patient diary application initiates a custom stimulation protocol developed by the patient diary application based on all accumulated data, which may or may not result in immediate stimulation. Based on on-going key data input and on-going input from the other wearable device, at step 3236, the patient diary application may initiate further modifications to the parameter settings, which may or may not result in immediate stimulation, wherein the modifications may include an increment or a decrement to any stimulation or timing variable.

Figure 33:
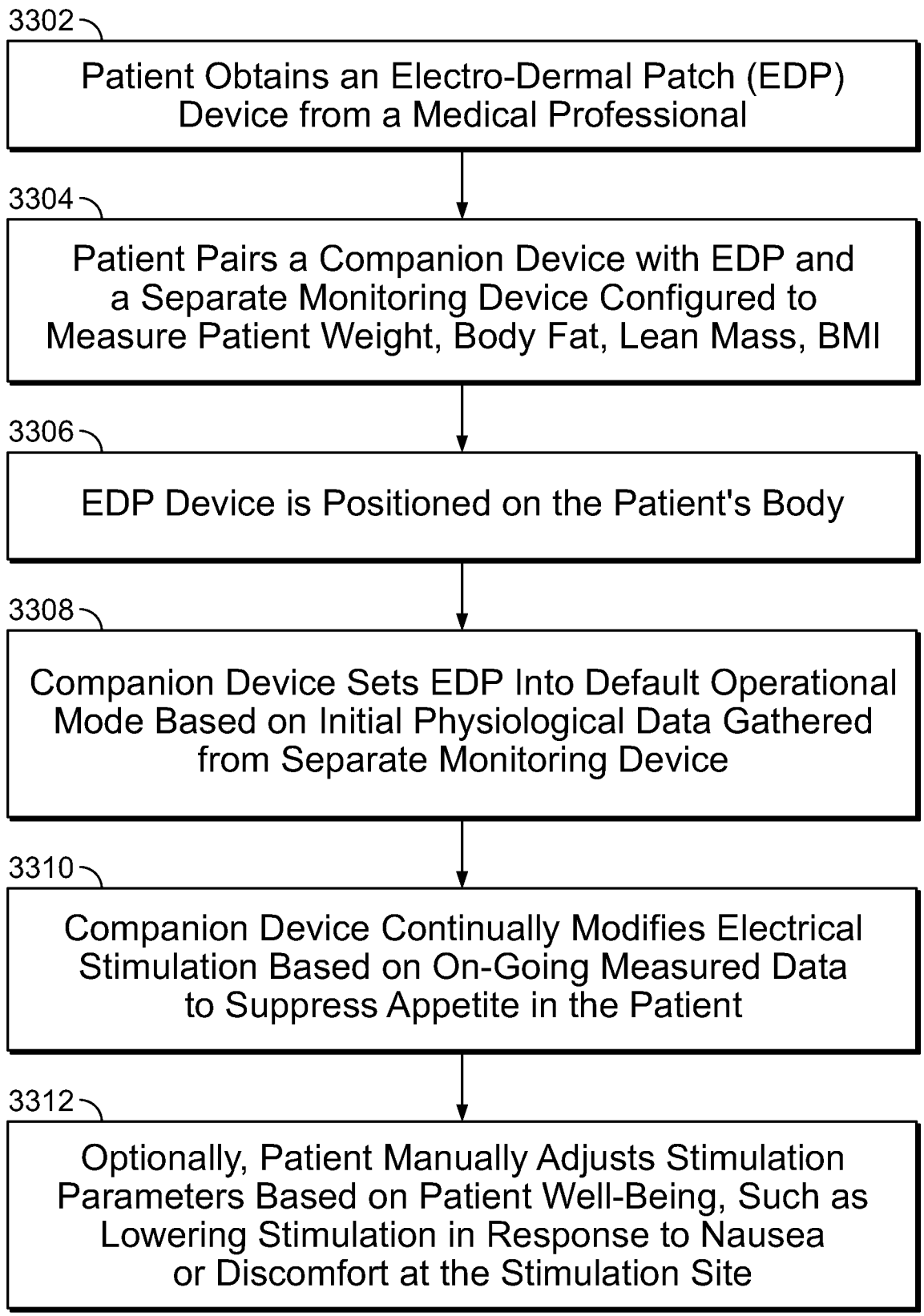
FIG. 33 is a flow chart illustrating the steps involved in a using an electro-dermal patch device and a companion device, paired with a separate monitoring device, to suppress appetite in a patient, in accordance with an embodiment of the present specification.

FIG. 33 is a flow chart illustrating the steps involved in a using an electro-dermal patch device and a companion device, paired with a separate monitoring device, to suppress appetite in a patient, in accordance with one embodiment of the present specification. At step 3302, the patient obtains an EDP from a medical professional. The patient pairs a companion device with the EDP and with a separate monitoring device at step 3304. The separate monitoring device is configured to measure a plurality of physiological parameters, including, but not limited to, patient weight, body fat, lean mass, and BMI, and wirelessly transmit monitored data to the companion device. The patient then positions the EDP on his body at step 3306. At step 3308, the companion device sets the EDP into a default stimulation mode based on initial physiological data gathered from the separate monitoring device. Based on on-going data gathering an input, the companion device continually modifies the electrical stimulation provided by the EDP in an effort to suppress appetite in the patient at step 3310. Optionally, at step 3312, the patient manually adjusts stimulation parameters based on patient well-being, for example, lowering stimulation parameters if the patient is experiencing nausea, dyspepsia or discomfort at the stimulation site.

Figure 34:
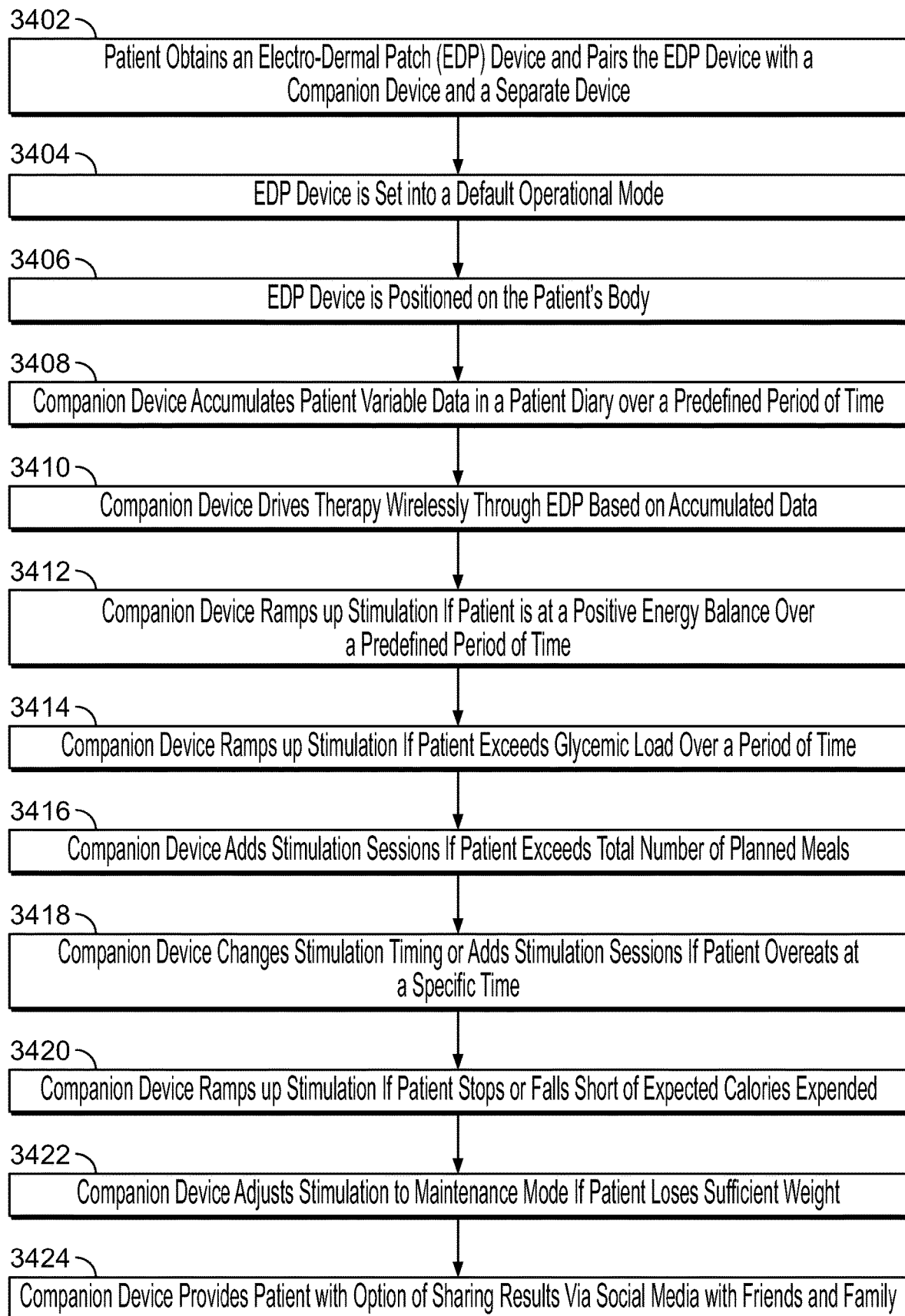
FIG. 34 is a flow chart illustrating steps involved in methods of using an electro-dermal patch device to suppress appetite in a patient, in various embodiments of the present specification.

FIG. 34 is a flow chart illustrating the steps involved in still another embodiment of a method of using an electro-dermal patch device to suppress appetite in a patient. At step 3402, the patient obtains an electro-dermal patch (EDP) device and pairs the EPD device with a companion device, such as a smartphone, and a separate device, for example, a device, with physiological sensors, configured to be worn on the human body, such as around the wrist, in order to monitor, acquire, record, and/or transmit the physiological data. In some embodiments, pairing with the separate device can be done anytime within a treatment cycle. In some embodiments, a treatment cycle lasts 3 months. At step 3404, the device is set into a default operational mode. In some embodiments, the default operational mode includes the stimulation parameters and parameter ranges listed above with respect to FIG. 27C and includes daily stimulation.

The EDP device is positioned on the patient's body at step 3406. At step 3408, the companion device accumulates patient variable data, including, but not limited to, actual eating and meals profile of the user such as the time of consumption of a meal in a day and the type and amount of food eaten at the meal, standard regular eating and meals routine of the user, such as a standard diet plan (such as, but not limited to, Mediterranean, Zone Diet, Atkins Diet, Ketogenic Diet, Intermittent Fasting, Jenny Craig, and Custom Plan), appetite, hunger, well-being, weight, and calories expended/weight loss, in a patient diary over a predefined period of time. In some embodiments, the companion device accumulates data over a range of 1 to 7 days. In one embodiment, the companion device accumulates data for 3 days. Then, at step 3410, the companion device drives stimulation therapy wirelessly through the EDP device based on accumulated patient diary data over the treatment cycle.

During the treatment cycle, if the patient has a positive or surplus energy balance (representative of more actual calories consumed in comparison to the calories expended) over a predefined period of time, for example, 3 days, the companion device ramps up stimulation parameters (such as, by increasing the stimulation duration, intensity and/or number of sessions) at step 3412. During the treatment cycle, if the patient exceeds the glycemic load (calculated based on the patient's actual eating and meals profile input into the patient diary), compared to the allowed glycemic load as estimated based on the patient's standard diet plan, over a predefined period of time, for example, 3 to 5 days, the companion device ramps up stimulation parameters at step 3414. Alternatively or additionally, at steps 3412 and 3414, the companion device ramps up stimulation parameters if the patient records an appetite diary entry with a score of 5, for example, for 3 to 5 days, indicative of poor or no dietary compliance with reference to the patient's standard diet plan. Thus, in some embodiments, the Health Management application uses the appetite parameter, which is indicative of the patient's dietary compliance, to assess if the patient is likely to be at a surplus energy balance and exceed the allowable glycemic load.

During the treatment cycle, if the patient exceeds the total number of meals per day over a predefined period of time, compared to the number of meals allowed according to the patient's standard diet plan, the companion device may include additional stimulation sessions just prior (for example, a half hour or an hour prior) to the extra meal events at step 3416. At step 3418, if the patient overeats at a specific time and continues to depict such overeating behavior over a predefined period of time, for example, 3 to 5 days, the companion device may change the timing of stimulation to just prior (for example, a half hour or an hour prior) to the overeating meal event or time or may include an additional stimulation session just prior to the overeating meal event. In some embodiments, the energy balance and glycemic load are calculated for every meal of the day, which in turn enables calculation of the meal that contributes the highest percentage of calories (or energy surplus) and glycemic load for the day. This meal, which contributes the highest percentage of calories and glycemic load per day over a predefined period of time, is identified as the overeating meal event.

During the treatment cycle, if the patient stops exercising for a predefined period of time, for example 3 to 5 days, or if the patient has an exercise score of 5 (FIG. 12), indicating the least level of expected exercising and therefore calories expended, and is also at a surplus energy balance for a predefined period of time (for example 3 to 5 days), the companion device ramps up stimulation parameters at step 3420. At step 3422, following a treatment course or cycle, once the patient has lost sufficient weight or achieved a target weight, the companion device modifies stimulation parameters to a maintenance mode wherein the stimulation parameters such as stimulation intensity, duration and number of sessions are all lowered.

Optionally, at step 3424, the companion device provides the patient with the option of sharing his results via social media with designated friends and family. In an alternate embodiment, the companion device first accumulates patient diary data before the EDP device is set into the default operation mode. Referring to FIG. 34, in this alternate embodiment, step 3408 is performed prior to step 3404. The remaining steps proceed in the same order.

Figure 49:
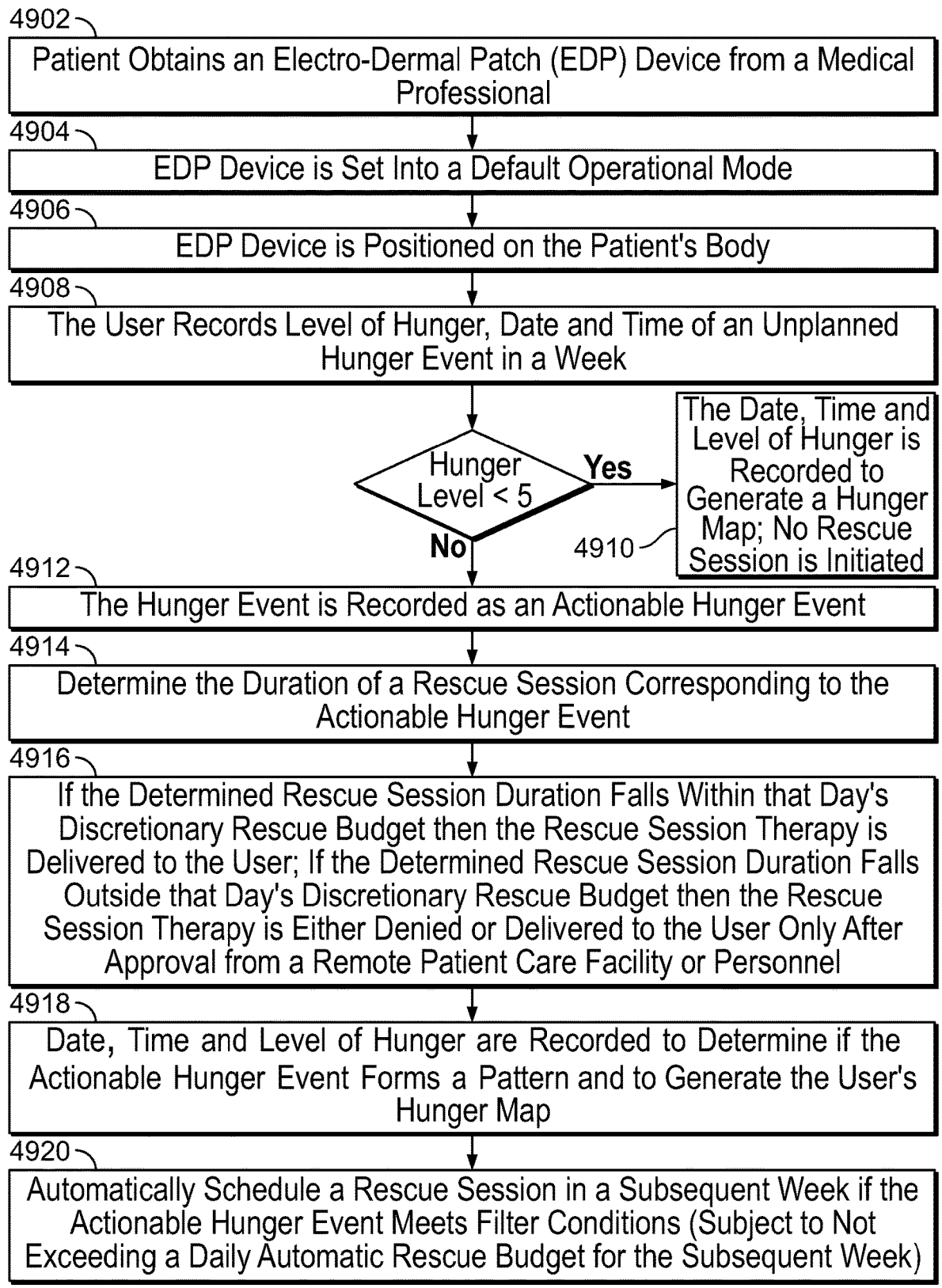

FIG. 49 is a flow chart illustrating the steps involved in one embodiment of a method of using an electro-dermal patch device to automatically drive rescue therapy based on the user's individualized hunger profile or map. At step 4902, a patient obtains an electro-dermal patch (EDP) device, in accordance with the devices disclosed in the present specification, from a medical professional.

The EDP device is set into a default operational mode, either by the patient or by the medical professional, at step 4904. In some embodiments, the default operational mode or the baseline stimulation protocol is set at 3 daily stimulation sessions of 30 minutes each having a pulse amplitude of 20 mA. Each of the three daily stimulation sessions is initiated 30 to 60 minutes and preferably 45 minutes prior to scheduled or planned mealtimes, such as, breakfast, lunch and dinner, for example, or any other scheduled mealtimes in accordance with the user's diet plan. In a preferred embodiment, the baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these post-prandial stimulation sessions are triggered manually by the user. In some alternate embodiments, the pre-prandial and post-prandial stimulation sessions are automatically triggered based on pre-stored meal time schedule. In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B.

At step 4906, the EDP device is positioned on the patient's body, either by the patient or by the medical professional, to begin delivering stimulation treatment in accordance with the baseline stimulation protocol.

At step 4908, in a certain week (for example, the first week of treatment), the user records an intensity or level of hunger as well as the date and time of an unplanned or unscheduled hunger event—that is a hunger event that does not comply with the timings of the user's planned or scheduled mealtimes. In various embodiments, the user uses a light bar Visual Analog Scale (VAS) on his smartphone (that functions as a companion device) to record the level of hunger along with the date and time of the hunger event. In some embodiments, the light bar VAS is configured as a 0 to 10 scale wherein 0 represents no hunger while 10 represents a maximum level of hunger. Thereafter, at step 4910, if the recorded level of hunger intensity is less than 5, on the VAS, the hunger event is recorded as a low intensity hunger event along with the date and time of the hunger event but no corresponding rescue session is triggered. The recorded date, time and level of the hunger event are used to generate and display an individualized hunger profile or map of the user.

However, at step 4912, if the recorded level of hunger intensity is equal to or greater than 5, the hunger event is recorded as an actionable hunger event. Consequently, the following actions are taken: a) at step 4914, a rescue session duration is determined. In various embodiments, the rescue session duration is equal to the level of hunger recorded on the light bar VAS. For example, if the recorded hunger level is 6 then the duration of the corresponding rescue session is determined to be equal to 6 minutes. In some embodiments, the level of hunger recorded on the light bar VAS may alternately or additionally affect the rescue session intensity. For example, if the recorded hunger level is 6 then the duration of corresponding rescue session is 6 minutes and/or the intensity of the rescue session is kept at a first intensity level. Similarly, if the recorded hunger level is 8 then the duration of corresponding rescue session is 8 minutes and/or the intensity of the rescue session is kept at a second intensity level. The first intensity level is different from the second intensity level. In embodiments, the first intensity level is lower than the second intensity level. In embodiments, the first intensity level is greater than the second intensity level. b) At step 4916, the determined rescue session duration is compared with the user's daily discretionary rescue budget. In some embodiments, the user's daily discretionary rescue budget is predefined to be 30 minutes. If the determined rescue session duration falls within that day's discretionary rescue budget then the rescue session therapy is triggered and delivered to the user for the determined rescue duration. On the other hand, if the determined rescue session duration falls outside that day's discretionary rescue budget then the user and a remote patient care facility or personnel are alerted and the rescue session therapy is either denied or delivered to the user only after approval from the remote patient care facility or personnel. c) At step 4918, the date, time and level of hunger are recorded to determine if filter or threshold condition(s) are met to ascertain if the hunger event forms a pattern of recurrent hunger pangs or spikes. As discussed earlier in the specification, the filter or threshold conditions may comprise a predefined period of time (ranging from a few days, say 5 to 7 days, to weeks, say 3 to 6 weeks) and/or a predefined number of rescue sessions (ranging from 1 to 10 sessions). Alternatively or additionally, the filter or threshold condition may comprise a combination of criteria such as, for example, a minimum of, say, 3 hunger events (each triggering a rescue session or bolus—that is, each of the 3 hunger event being of an intensity level greater than or equal to 5 on a 0 to 10 light bar VAS) recorded on 3 separate days in the same week and within, say, 60 minutes of the same time of day. The recorded date, time and level of the hunger event are also used to generate and display an individualized hunger profile or map of the user.

At step 4920, if the actionable hunger event meets or satisfies the filter or threshold condition(s) then a rescue session of, say, 5 or 10 minutes is automatically scheduled, for a subsequent week of therapy (for example, the second week of treatment), at the recorded time of the actionable hunger event. In various embodiments, the automatic scheduling of the rescue session in the subsequent week is subject to a daily automatic rescue budget for the subsequent week. That is, the rescue session is automatically scheduled for the subsequent week only if the duration of the rescue session falls within the automatic rescue budget for the subsequent week. In some embodiments, the user's daily automatic rescue budget is predefined to be 30 minutes.

The steps 4908 to 4920 are repeated for every week, for each occurrence of an unscheduled hunger event, throughout the duration of the stimulation therapy for the user. Thus, by repeating steps 4908 to 4920 for every unscheduled hunger event in a week an automatic rescue delivery plan or schedule is generated that week—for a subsequent week. The automatic rescue delivery plan or schedule progresses along with the baseline stimulation protocol throughout the treatment cycle for the user. It should be appreciated, that since unscheduled hunger events are continued to be recorded throughout the treatment cycle, therefore, if the user records fewer actionable hunger events in a week there will be a reduced number and/or level of automatic rescue deliveries in a subsequent week and vice versa.

As discussed earlier, the user is allowed a predefined amount of daily total rescue budget that, in various embodiments, is a sum of the daily discretionary rescue budget and the daily automatic rescue budget. In some embodiments, the daily total rescue budget is set at, say, 60 minutes while the daily discretionary and automatic rescue budgets are set at, say, 30 minutes each. In alternate embodiments, the daily total rescue budget may be set at lesser or higher values and the daily discretionary and automatic rescue budgets may also comprise different percentages of the total rescue budget.

Figure 50:
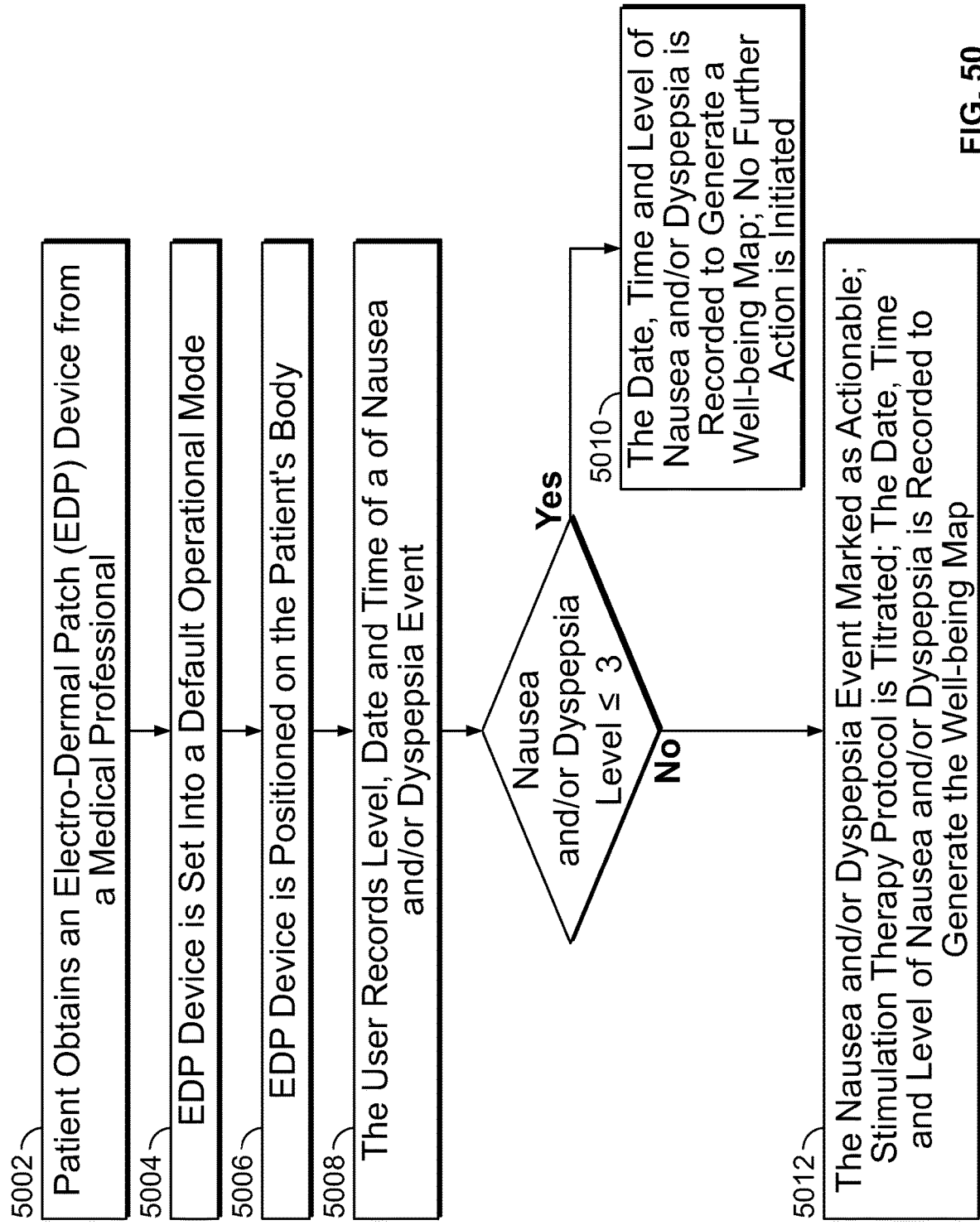

FIG. 50 is a flow chart illustrating the steps involved in one embodiment of a method of using an electro-dermal patch device to automatically titrate or modulate therapy based on the user's dynamic well-being profile representing occurrence of nausea and/or dyspepsia events. At step 5002, a patient obtains an electro-dermal patch (EDP) device, in accordance with the devices disclosed in the present specification, from a medical professional.

The EDP device is set into a default operational mode, either by the patient or by the medical professional, at step 5004. In some embodiments, the default operational mode or the baseline stimulation protocol is set at 3 daily stimulation sessions of 30 minutes each having a pulse amplitude of 20 mA. Each of the three daily stimulation sessions is initiated 30 to 60 minutes and preferably 45 minutes prior to scheduled or planned mealtimes, such as, breakfast, lunch and dinner, for example, or any other scheduled mealtimes in accordance with the user's diet plan. In a preferred embodiment, the baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these post-prandial stimulation sessions are triggered manually by the user. In some alternate embodiments, the pre-prandial and post-prandial stimulation sessions are automatically triggered based on pre-stored meal time schedule. In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B.

At step 5006, the EDP device is positioned on the patient's body, either by the patient or by the medical professional, to begin delivering stimulation treatment in accordance with the baseline stimulation protocol.

At step 5008 the user records an intensity or level of nausea and/or dyspepsia as well as the date and time of occurrence of the nausea and/or dyspepsia event. In various embodiments, the user uses a light bar Visual Analog Scale (VAS) on his smartphone (that functions as a companion device) to record the level of nausea and/or dyspepsia along with the date and time of the event. In some embodiments, the light bar VAS is configured as a 0 to 10 scale wherein 0 represents no nausea and/or dyspepsia (that is, the highest level of well-being) and 10 represents the most intense level of nausea and/or dyspepsia (that is, the worst level of well-being).

Thereafter, at step 5010, if the recorded level of nausea and/or dyspepsia intensity is less than or equal to a threshold level, say 3, on the VAS, the nausea and/or dyspepsia event is recorded as a low intensity event along with the date and time of the event but no action is triggered. The recorded date, time and level of the nausea and/or dyspepsia event are used to generate and display an individualized well-being profile or map of the user. However, at step 5012, if the recorded level of nausea and/or dyspepsia intensity is greater than 3, the nausea and/or dyspepsia event is recorded as a high intensity, and therefore, actionable event resulting in titration or modulation of the ongoing stimulation therapy protocol. The date, time and level of the nausea and/or dyspepsia event are again recorded to feed into generating the user's well-being profile or map.

It should be appreciated that in alternate embodiments, the therapy titration or modulation is based on the user's quality of life VAS level (instead of nausea and/or dyspepsia events) where a low quality of life level may reduce stimulation intensity and/or duration.

FIG. 57 is a flow chart illustrating the steps involved in one embodiment of a method of using an electro-dermal patch device to elicit feedback, coaching or advice related to a medical condition of a patient, from at least one of a social network group (or affinity group) and an online coaching or concierge service, care-provider or physician. In embodiments, the online coaching or concierge service is an algorithm driven automated virtual coach and/or an actual coach person, care-provider, dietician or physician in communication with the affinity group and/or the EDP (or companion device) of the patient. In various embodiments, the patient's medical condition comprises conditions such as, but not limited to, obesity, high levels of hunger, appetite, weight and/or low level of well-being. At step 5702, a patient obtains an electro-dermal patch (EDP) device, in accordance with the devices disclosed in the present specification, from a medical professional.

The EDP device is set into a default operational mode, either by the patient or by the medical professional, at step 5704, and is synced or paired with a corresponding client or companion device implementing a Health Management application (HMA) of the present specification. In some embodiments, the default operational mode or the baseline stimulation protocol is set at 3 daily stimulation sessions of 30 minutes each having a pulse amplitude of 20 mA. Each of the three daily stimulation sessions is initiated 30 to 60 minutes and preferably 45 minutes prior to scheduled or planned mealtimes, such as, breakfast, lunch and dinner, for example, or any other scheduled mealtimes in accordance with the user's diet plan. In a preferred embodiment, the baseline stimulation scheme or protocol is set at 3 daily stimulation sessions of 15 minutes each having a pulse amplitude of 20 mA timed pre-prandial and 60 minutes each having a pulse amplitude of 20 mA timed post-prandial, that is immediately prior to commencement and upon completion of each meal such as breakfast, lunch and dinner. In other words, the baseline stimulation scheme or protocol comprises 3×1.25 hours=3.75 hours total (15 minutes pre-prandial to each meal and 60 minutes post prandial). In some embodiments, the base line pulse amplitude ranges from 5 mA to 10 mA to enable total stimulation durations that are longer than 3.75 hours. In various embodiments, these post-prandial stimulation sessions are triggered manually by the user. In some alternate embodiments, the pre-prandial and post-prandial stimulation sessions are automatically triggered based on pre-stored meal time schedule. In some alternate embodiments, the post-prandial stimulation sessions are automatically triggered with reference to a detection of an eating event by a swallow detection device, such as the device 5605 of FIG. 56, or by the eating moment recognition method (FIG. 58) implemented by the HMA using a plurality of data (representing the user's food intake gestures) captured by an accelerometer, wherein the accelerometer is included in a wrist-band or wristwatch, such as the band 2105 of FIG. 21A or the wristwatch 2106 of FIG. 21B. In some embodiments, the baseline stimulation protocol includes parameters having a pulse width in a range of 10 μsec to 10 msec, a pulse amplitude in a range of 100 μA to 100 mA, and a pulse frequency in a range of 1 Hz and 100 Hz.

At step 5706, the EDP device is positioned on the patient's body, either by the patient or by the medical professional, to begin delivering stimulation treatment in accordance with the baseline stimulation protocol. In various embodiments, the patient, through his EDP, is in communication with one or more remote servers enabling the patient to be in communication with at least one of a social network group (or affinity group) and an online coaching or concierge service, care-provider or physician.

At step 5708 the patient inputs or records (as a result of a prompt by the HMA) an intensity, degree or level of a plurality of health status data or parameters such as a degree or level of appetite, hunger, exercise and well-being. In some embodiments, the HMA prompts the patient to input data indicative of the patient's the degree of appetite, hunger, exercise and well-being via a microphone or display of the client device. In various embodiments, the user uses a light bar Visual Analog Scale (VAS) on his smartphone (that functions as the client or companion device) to record the level of the health status data or parameters. In some embodiments, the light bar VAS is configured as a 0 to 10 or a 0 to 5 scale wherein 0 represents the lowest intensity or degree of the health status parameters and 10 or 5 represent the highest intensity of the health status parameters. In some embodiments, the patient is visually displayed or prompted with a plurality of icons or emoticons wherein each of the plurality of icons is representative of a different degree of health status parameters such as hunger or appetite. In some embodiments, the HMA solicits inputs regarding the health status, such as, degree of appetite or hunger by generating a plurality of auditory inquires played via a speaker of the client device. It should be appreciated that in alternate embodiments, an IPA system (in communication with the HMA) may prompt the patient to receive voice based inputs from the patient regarding his health status, such as, the degree of appetite or hunger.

At step 5710, the patient shares one or more of a plurality of data (shareable date) with at least one of an online social network group or affinity group (to which the patient subscribes to as a member) and an online coaching or concierge service. The plurality of data comprises a level, degree, score or value related to historical and/or current hunger, appetite, exercise, weight, well-being, will-power, urge to eat profile, hunger profile, standard eating and meals profile, actual eating and meals profile, dietary plan, exercise regimen, energy balance, weight changes, glucose data, rescue bolus events, default/baseline or current stimulation parameters, protocols and stimulation induced nausea, dyspepsia, and habituation events. It should be appreciated that in various embodiments, the patient shares any combination, composite function/score (derived from any one or any combination of the shareable data) or sub-set of the aforementioned plurality of data. In some embodiments, the patient shares (manually or automatically as triggered by the HMA) at least one or any combination of: a weight trend of the patient, a plurality of values indicative of the patient's historical degrees of appetite, a plurality of values indicative of the patient's historical amount of exercise and a plurality of values indicative of the patient's historical well-being. Additionally, the HMA determines a composite score of the patient, wherein said composite score is a function of any two or more of the patient's historical degrees of appetite, weight trend, historical well-being, and historical amount of exercise, and causes the composite score to be displayed on the client or companion device. The composite score may additionally or alternatively be shared by the patient manually or automatically, as triggered by the HMA, members of the social network group or affinity group and/or the online coaching service.

In some embodiments, the plurality of data is automatically shared with the online social network group or affinity group if at least a sub-set of the plurality of data is determined to indicate deteriorating or lagging medical condition of the patient. It should be noted that in some embodiments, the online coaching or concierge service is in communication with the social network group and/or the EDP (or companion device) of the patient and is enabled to access or automatically receive the plurality of data related to the patient.

In an embodiment, the plurality of data (shareable data) is automatically shared with the online social network group or affinity group and/or the online coaching service (including an actual coach person, dietician or caregiver) if the patient records an appetite or hunger score/level above a predefined threshold score/level. In some embodiments, the threshold score/level for appetite or hunger is 5.5 (on a scale of 0 to 10). For example, an appetite or hunger score/level in the range of 5.5 to 8.5 would trigger an automatic sharing of the patient's shareable data with the online social network group or affinity group and/or the online coaching service (including an actual coach person, dietician or caregiver). An appetite or hunger score/level above 8.5 would not only trigger automatic sharing of the patient's shareable data but also convey the severity of the condition by, for example, repeatedly flashing the patient's shareable data in bright shades, such as red, to the members of the online social network group or affinity group.

In accordance with an aspect of the present specification, at least one health status data or shareable data, such as for example a hunger event or a rescue therapy event, input or recorded by the patient and/or a composite score or function derived from the patient's health status data or shareable data is automatically shared, in real-time, with the affinity group and/or the online coaching service to trigger real-time coaching, advise or feedback from the online coaching service and/or the affinity group. It should be appreciated that the coaching or advise is with an automated virtual coach or sponsor in some embodiments, while in other embodiments such coaching or advice is provided, additionally or alternatively, by an actual coach person, care-provider, dietician or physician in communication with the affinity group and/or the EDP (or companion device) of the patient.

Members of the social network group or affinity group and/or the online coaching service are enabled to provide a plurality of interventions as advice or response to the shared plurality of data of the patient. In various embodiments, the plurality of interventions or responses comprise elements such as, but not limited to, coaching instructions, encouraging messages (pre-recorded and/or real-time), morale boosting emojis, stimulation parameters and protocols related to members who are determined to have improved their medical condition, modified exercise regimen, and modified dietary plan.

In accordance with aspects of the present specification, the plurality of interventions, advice or responses of the social network group or affinity group and/or the online coaching service varies depending upon the level of deteriorating condition of the patient as indicated by the shared plurality of data. In embodiments, members of the social network group or affinity group and/or the online coaching service are encouraged to input videos, GIFs (Graphics Interchange Format), text messages and/or emojis that may be encouraging or excoriating depending on severity of the patient's condition as indicated through the shared plurality of data. Such videos, GIFs, text messages and/or emojis may be pre-stored for automatic delivery to the patient, when in need and in accordance with the severity of condition of the patient.

At step $5712a$, the HMA determines if the patient's level or degree of appetite or hunger is greater than a first threshold value but less than or equal to a second threshold value. In some embodiments, the first and second threshold values are 0 and 5.5 respectively on a scale of 0 to 10. If the patient's degree of appetite or hunger falls between the first and second threshold values, the members of the social network group or affinity group and/or the online coaching service may respond with a first intervention, at step $5714a$. In some embodiments, the first intervention may comprise encouraging and appreciative pre-recorded messages such as videos, GIFs (Graphics Interchange Format), text based messages and/or emojis from the members of the social network group or affinity group and/or the online coaching service. In some embodiments, the first intervention includes pre-recorded coaching instructions from members of the social network group or affinity group and/or the online coaching service to assist the patient in maintaining dietary compliance. In some embodiments, the first intervention may include displaying the patient's own appetite profile on the patient's client or control device.

At step $5716a$, the HMA determines if the patient's level or degree of appetite or hunger is greater than the second threshold value but less than or equal to a third threshold value. In some embodiments, the second and third threshold values are 5.5 and 8.5 respectively on a scale of 0 to 10. If the patient's degree of appetite or hunger falls between the second and third threshold values, the members of the social network group or affinity group and/or the online coaching service may respond with a second intervention, at step $5718a$. In some embodiments, the second intervention comprises pre-recorded messages such as videos, GIFs, text based messages and/or emojis that are skewed towards being excoriating and perhaps portraying the consequential hazards of not controlling appetite or hunger. The members of the social network group or affinity group and/or the online coaching service may also recommend other measures such as rescue sessions, modified stimulation parameters for the patient and/or coaching instructions to assist the patient in achieving dietary compliance.

At step $5720a$, the HMA determines if the patient's level or degree of hunger or appetite is greater than the third threshold value and less than or equal to a fourth threshold value. In some embodiments, the third and fourth threshold values are 8.5 and 10, respectively, on a scale of 0 to 10. If the patient's degree of appetite or hunger falls between the third and fourth threshold values, the members of the social network group or affinity group and/or the online coaching service may respond with a third intervention, at step $5722a$. The patient's degree of appetite falling between the third and fourth threshold values is construed as a level where the patient needs immediate help and intervention. In some embodiments, in the third intervention a member of the social network group or affinity group and/or a coach person, dietician or caregiver (instead of an automated online coaching service, for example) may call up and/or message the patient in real-time.

Feedback, coaching and advisory responses may additionally or alternatively be elicited, in some embodiments, by enabling the patient to manually share the plurality of data (shareable data) or a sub-set thereof, with one or more users other than the members of social network group or affinity group, via communication channels such as, but not limited to, Facebook Messenger, WhatsApp or any other communication application known to persons of ordinary skill in the art.

It should be appreciated that the first, second, third and fourth threshold values may be different depending at least upon a scale for defining the degree of appetite or hunger. Also, in some embodiments, the interventions may be based on a single threshold value. Thus, in an alternate series of steps, at step $5712b$, the HMA determines if the patient's level or degree of appetite or hunger is above a threshold value. In some embodiments, the threshold value is 5.5 on a scale of 0 to 10. If the degree of appetite or hunger falls below the threshold value, the HMA, at step $5714b$, does not cause any intervention to be delivered to the patient. However, if the degree of appetite or hunger falls above the threshold value, the HMA, at step $5716b$ enables the members of the social network group or affinity group and/or the online coaching service to respond with an intervention. In various embodiments, the intervention comprises coaching instructions to assist the patient in achieving dietary compliance, pre-recorded messages (videos, GIFs, text based messages and/or emojis) from one or more individuals connected with the patient within the social network and/or real-time messages (real-time calling and or real-time videos, GIFs, text based messages and/or emojis) from one or more members of the social network group or affinity group and/or the online coaching service.

In another alternate series of steps and in accordance with aspects of the present specification, the type and nature of feedback, coaching and advice, provided by the online coaching service and/or the coach person, dietician or caregiver, is based on at least one of the level or degree of hunger or appetite, time of day, number of steps taken (that is, exercise score/level), caloric intake taken, and location of patient. For example, at step $5712c$, the patient's reported high level or degree of hunger or appetite (of more than a predefined threshold value—such as 5.5) may be flagged as 'chronic' if the patient frequently reports the high level at a particular time of the day, say, after workouts at a gym. Accordingly, the automated online coaching service detects such 'chronic' correlations and advises the patient, at step $5714c$, to proactively stimulate at or near the particular time of the day. As another example, at step $5712d$, the patient's reported high level of hunger or appetite (of more than the predefined threshold value—such as 5.5) may be flagged as 'acute' if the high level reported by the patient is more random and less frequent. Accordingly, at step 5714*d*, the automated online coaching service response is different such as, but not limited to, distracting the patient (away from the psychological pangs of hunger), reminding the patient of his goals and health hazards of falling prey to the hunger pangs, and/or triggering a media presentation to the patient. The media presentation could be pre-stored GIFs, audio and/or video giving encouragement, for example. The media could be of the patient himself, a friend or a loved one requesting, encouraging and reminding the patient to overcome obesity and/or meet the targeted weight.

In some embodiments, the HMA processes the data indicative of the patient's degree of appetite to determine when, at a future time, the patient will be hungry and transmits a signal to the electrical dermal patch positioned on the patient's skin based upon said future time (as discussed earlier in the specification with reference to Big Data analytics).

At step 5724, the patient is enabled to reply to the interventions or advisory responses or feedback of the members of the social network group and/or the online coaching service to either thank them for the feedback or to update them with the patient's medical condition and, say, improved plurality of data related to the patient's medical condition.

In various embodiments, the titration or modulation of the therapy is directed towards moderating or completely terminating the stimulation therapy in order to reduce and/or prevent further occurrence of nausea and/or dyspepsia events. As discussed earlier in the specification, on occurrence of an actionable nausea and/or dyspepsia event, the Health Management application may modify an existing stimulation protocol, for example may recommend switching a current baseline stimulation protocol to a mild stimulation protocol. Additionally or alternatively, the stimulation continuity profile may be switched to a step-down profile. Still further, the Health Management application may recommend pausing the stimulation sessions for one or more days before restarting with a step-down stimulation protocol. For example, in one embodiment, any single nausea and/or dyspepsia event at an intensity of 10 on the VAS scale will immediately cause all subsequent therapy sessions to be stopped and the user prompted to call their physician. In another embodiment, for example, any cumulative actionable VAS score of 15 in the same week—that is, a score of a 4, and a 5 and a 6 would, in combination, cause the Health Management application to shut down therapy. In yet another embodiment, any actionable cumulative score in the same week greater than 10 would cause the Health Management application to reduce the reducing baseline therapy sessions from 30 to 15 minutes each. In this embodiment, if the frequency of such actionable nausea and/or dyspepsia events continue the therapy is terminated.

While the therapeutic efficacy of the device has been described above in terms of modulating levels of appetite, hunger, satiety, satiation, caloric intake, and/or weight loss, it may also be described in terms of delaying gastric emptying time or increasing gastric retention time. Applying the treatment protocols described above, a patient with a BMI of 25 or greater adheres an electrical dermal patch to his or her epidermal layer such that an electrical field, generated by the electrical dermal patch via a plurality of stimulation sessions, directly contacts at least one of the patient's C5, C6, C7, C8, T1, T2, T3, T4, T5, T6, T7, T8, T9, T10, T11, and T12 frontal and lateral dermatomes and penetrates a range of 0.1 mm to 25 mm through the patient's epidermal layer. The electrical dermal patch has a housing with a base surface, where the base surface is defined by a total base surface area, where at least a portion of the total base surface area is adapted to be adhered to the epidermal layer of the patient, and where the total base surface area is less than 10 in$^2$, has a controller positioned within the housing, has at least one electrode positioned within the housing and adapted to be in electrical contact with said patient's epidermal layer, and has a pulse generator positioned within the housing and in electrical communication with the controller and said at least one electrode.

It should further be appreciated that, preferably, the electro-dermal patch comprises a transceiver in communication with at least one of said controller and pulse generator and a plurality of programmatic instructions, stored in a non-transient computer readable memory of a device physically separate from said electrical dermal patch, wherein, when executed, the programmatic instructions acquire patient status data from an external device (such as a mobile phone running a health management application), generate a modulation signal based upon said patient status data, and wirelessly transmit said modulation signal from the device to the transceiver, wherein said modulation signal comprises data for modulating at least one of said plurality of stimulation parameters. As discussed throughout this specification, the patient status data comprises at least one of the patient's hunger, the patient's hunger appetite, the patient's satiety level, the patient's satiation level, and a degree of well-being being experienced by the patient. The programmatic instructions acquire a first stimulation protocol and use the first stimulation protocol to generate the modulation signal. The programmatic instructions acquire a second stimulation protocol, wherein said second stimulation protocol is different from the first stimulation protocol, and, using said second stimulation protocol, generate a second modulation signal, wherein said second modulation signal comprises data for modulating at least one of the plurality of stimulation parameters. The electrical dermal patch is configured to use the second modulation signal to modify at least one of the first pulse width, the first pulse amplitude, the first pulse frequency, the first pulse shape, the first duty cycle, the first session duration, and the first session frequency to yield a second pulse width, a second pulse amplitude, a second pulse frequency, a second pulse shape, a second duty cycle, a second session duration, or a second session frequency. At least one of the second pulse width is different from the first pulse width, the second pulse amplitude is different from the first pulse amplitude, the second pulse frequency is different from the first pulse frequency, the second pulse shape is different from the first pulse shape, the second duty cycle is different from the first duty cycle, the second session duration is different from the first session duration, and the second session frequency is different from the first session frequency.

Operationally, the pulse generator is configured to generate a plurality of stimulation sessions, wherein each of said plurality of stimulation sessions comprises a plurality of electrical pulses and wherein each of said plurality of electrical pulses is defined by a plurality of stimulation parameters, said plurality of stimulation parameters being defined such that, after applying at least one of said plurality of stimulation sessions to the epidermal layer of the patient within 90 minutes of said patient consuming a meal, a post-prandial time to empty 50% of the patient's stomach contents increases by at least 5% relative to a post-prandial time to empty 50% of the patient's stomach contents without applying at least one of said plurality of stimulation sessions. In other embodiments, it should be appreciated that at least one of said plurality of stimulation sessions may be applied to the epidermal layer of the patient within 3 hours, 2.5 hours, 2 hours, 1.5 hours, 1 hour, 0.5 hours or any increment therein, of consuming a meal. In the examples provided herein, a time period of 90 minutes is used, however, any increment of time as listed above may be used.

It should be appreciated that, in some embodiments, systems of the present specification are used to generate real-time interventions in response to a patient's degree of appetite and include an electrical dermal patch and at least one plurality of programmatic instructions stored in a non-transient memory in a client device separate from the electrical dermal patch. In some embodiments, the electrical dermal patch comprises a housing, a controller positioned within the housing, at least one electrode positioned in physical communication with the housing and adapted to be in electrical contact with the patient's skin, and a pulse generator positioned within the housing and in electrical communication with the controller and the at least one electrode. The pulse generator is configured to generate a plurality of stimulation sessions comprising a plurality of electrical pulses defined by stimulation parameters as discussed in the present specification. In some embodiments, the system includes a first plurality of programmatic instructions, a second plurality of programmatic instructions, and a third plurality of programmatic instructions. The first plurality of programmatic instructions is stored in a non-transient memory in a client device separate from the electrical dermal patch, and, when executed, is adapted to cause the client device to generate a prompt to the patient to input data indicative of the patient's degree of appetite via a microphone or a display of said client device. The second plurality of programmatic instructions is stored in a non-transient memory in the client device or another device separate from the electrical dermal patch, and, when executed, determines an appetite pattern of the patient based upon said inputted data. The third plurality of programmatic instructions is stored in a non-transient memory in the client device or another device separate from the electrical dermal patch, and, when executed, determines an intervention and generates said intervention based on the appetite pattern.

It should further be appreciated that, in some embodiments, systems of the present specification are used to generate real-time interventions in response to a patient's degree of appetite and include an electrical dermal patch and at least one plurality of programmatic instructions stored in a non-transient memory in a client device separate from the electrical dermal patch. In some embodiments, the electrical dermal patch comprises a housing, a controller positioned within the housing, at least one electrode positioned in physical communication with the housing and adapted to be in electrical contact with the patient's skin, and a pulse generator positioned within the housing and in electrical communication with the controller and the at least one electrode. The pulse generator is configured to generate a plurality of stimulation sessions comprising a plurality of electrical pulses defined by stimulation parameters as discussed in the present specification. In some embodiments, the system includes a first plurality of programmatic instructions and a second plurality of programmatic instructions. The first plurality of programmatic instructions is stored in a non-transient memory in a client device separate from the electrical dermal patch, and, when executed, communicates with said electrical dermal patch and prompts the patient to input data indicative of the patient's degree of appetite via a microphone or display of said client device. The second plurality of programmatic instructions is stored in a non-transient memory in the client device or another device separate from the electrical dermal patch, and, when executed, receives the data indicative of the patient's degree of appetite, processes the data indicative of the patient's degree of appetite to develop predictions of whether the patient's degree of appetite will be above or below a threshold value in a future time window, does not generate any intervention in the future time window if the patient's degree of appetite is expected to be below the threshold value, and causes a first intervention to be generated in the future time window if the patient's degree of appetite is expected to be above the threshold value.

The present invention may be defined by a plurality of different therapeutic endpoints related to the delay of gastric emptying time or increase in gastric retention time, including:

Defining the plurality of stimulation parameters such that, after applying at least one of said plurality of stimulation sessions to the epidermal layer of the patient (preferably within 90 minutes of said patient consuming the meal), the post-prandial time to empty 95% of the patient's stomach contents increases by at least 5% minutes relative to the post-prandial time to empty 95% of the patient's stomach contents without applying at least one of said plurality of stimulation sessions.

Defining the plurality of stimulation parameters such that, after applying at least one of said plurality of stimulation sessions to the epidermal layer of the patient (preferably within 90 minutes of said patient consuming the meal), a patient's gastric emptying time is delayed by at least 1%, relative to the patient's gastric emptying time before stimulation.

Defining the plurality of stimulation parameters such that, after applying at least one of said plurality of stimulation sessions for at least 10 minutes of continuous stimulation to the epidermal layer of the patient (preferably within 90 minutes of said patient consuming the meal), a patient's gastric emptying time is delayed by at least 5 minutes, relative to the patient's gastric emptying time before stimulation.

Defining the plurality of stimulation parameters such that, after applying at least one of said plurality of stimulation sessions to the epidermal layer of the patient (preferably within 90 minutes of said patient consuming the meal), a patient's gastric emptying time is delayed by at least 10 minutes, relative to the patient's gastric emptying time before stimulation.

Defining the plurality of stimulation parameters such that, after applying at least one of said plurality of stimulation sessions for at least 40 minutes of continuous stimulation to the epidermal layer of the patient (preferably within 90 minutes of said patient consuming the meal), a patient's gastric emptying time is delayed by at least 20 minutes, relative to the patient's gastric emptying time before stimulation.

Defining the plurality of stimulation parameters such that, after applying at least one of said plurality of stimulation sessions for at least 90 minutes of continuous stimulation to the epidermal layer of the patient (preferably within 60 minutes of said patient consuming the meal), a patient's gastric emptying time is delayed by at least 24 minutes, relative to the patient's gastric emptying time before stimulation.

Defining the plurality of stimulation parameters such that, after applying at least one of said plurality of stimulation sessions to the epidermal layer of the patient (preferably within 90 minutes of said patient consuming the meal), a patient's gastric emptying time (of 50% of stomach solids content) is delayed by at least 15 minutes, relative to the patient's gastric emptying time before stimulation.

Defining the plurality of stimulation parameters such that, after applying at least one of said plurality of stimulation sessions to the epidermal layer of the patient (preferably within 90 minutes of said patient consuming the meal), a patient's gastric emptying time (of 50% of stomach solids content) is delayed by at least 25 minutes, relative to the patient's gastric emptying time before stimulation.

Defining the plurality of stimulation parameters such that, after applying at least one of said plurality of stimulation sessions to the epidermal layer of the patient (preferably within 90 minutes of said patient consuming the meal), a patient's gastric emptying time (of 50% of stomach solids content) is delayed by at least 10%, relative to the patient's gastric emptying time before stimulation.

Defining the plurality of stimulation parameters such that, after applying at least one of said plurality of stimulation sessions for at least 5 minutes of continuous stimulation to the epidermal layer of the patient (preferably within 90 minutes of said patient consuming the meal), a patient's post prandial gastric emptying time (of 50% of stomach solids content) is delayed by at least 5 minutes.

Defining the plurality of stimulation parameters such that, after applying said plurality of stimulation sessions to the epidermal layer of the patient (preferably within 90 minutes of said patient consuming the meal), with a weekly duty cycle of at least 1%, a patient's post prandial gastric emptying time (of 50% of stomach solids content) is delayed by at least 5 minutes.

Defining the plurality of stimulation parameters such that, after applying at least one of said plurality of stimulation sessions to the epidermal layer of the patient (preferably within 90 minutes of said patient consuming the meal), a patient's gastric retention (that is, retention of solid gastric contents) is increased by 50%, 120 minutes after food intake.

Defining the plurality of stimulation parameters such that, after applying at least one of said plurality of stimulation sessions to the epidermal layer of the patient (preferably within 90 minutes of said patient consuming the meal), an amount or rate of a patient's gastric motility is reduced in a range of 5 to 10% relative to the amount or rate of the patient's gastric motility before stimulation.

Defining the plurality of stimulation parameters such that, after applying at least one of said plurality of stimulation sessions to the epidermal layer of the patient (preferably within 90 minutes of said patient consuming the meal), a patient's gastric accommodation or distention is impaired by at least 15%, relative to the patient's gastric accommodation or distention before stimulation.

Defining the plurality of stimulation parameters such that, after applying at least one of said plurality of stimulation sessions to the epidermal layer of the patient (preferably within 90 minutes of said patient consuming the meal), a patient's gastric retention increases by 5% relative to the patient's gastric retention before applying said at least one of said plurality of stimulation sessions.

Defining the plurality of stimulation parameters such that, after applying at least one of said plurality of stimulation sessions to the epidermal layer of the patient (preferably within 90 minutes of said patient consuming the meal), the patient's gastric retention increases relative to the patient's gastric retention before applying said at least one of said plurality of stimulation sessions.

Defining the plurality of stimulation parameters such that, after applying at least one of said plurality of stimulation sessions for at least 5 minutes to the epidermal layer of the patient (preferably within 90 minutes of said patient consuming the meal), a post-prandial time to empty 50% of the patient's stomach contents increases by at least 5 minutes relative to a post-prandial time to empty 50% of the patient's stomach contents without applying at least one of said plurality of stimulation sessions.

Defining the plurality of stimulation parameters such that, after applying at least one of said plurality of stimulation sessions for at least 5 minutes to the epidermal layer of the patient (preferably within 90 minutes of said patient consuming the meal), the post-prandial time to empty 95% of the patient's stomach contents increases by at least 5 minutes relative to the post-prandial time to empty 95% of the patient's stomach contents without applying at least one of said plurality of stimulation sessions.

Defining the plurality of stimulation parameters such that, after applying at least one of said plurality of stimulation sessions to the epidermal layer of the patient, the patient's appetite or hunger decreases relative to the patient's appetite or hunger before applying said at least one of said plurality of stimulation sessions and a nausea level of the patient does not increase relative to the patient's nausea level before applying said at least one of said plurality of stimulation sessions.

Defining the plurality of stimulation parameters such that, after applying at least one of said plurality of stimulation sessions for at least 5 minutes to the epidermal layer of the patient (preferably within 90 minutes of the patient consuming a meal), a post-prandial time to empty 50% of the patient's stomach contents increases by at least 5% relative to a post-prandial time to empty 50% of the patient's stomach contents without applying at least one of said plurality of stimulation sessions.

Defining the plurality of stimulation parameters such that, after applying at least one of said plurality of stimulation sessions to the epidermal layer of the patient (preferably within 90 minutes of the patient consuming a meal), a post-prandial time to empty 25%, 50%, 75%, or 95% of the patient's stomach contents increases by at least 5%, 10%, 15%, 20%, 25% or 50%, or any increment therein, relative to a post-prandial time to empty an equivalent amount of the patient's stomach contents without applying at least one of said plurality of stimulation sessions.

Defining the plurality of stimulation sessions to achieve any of the aforementioned therapeutic objectives such that the total cumulative stimulation in a given day is more than 5 minutes but less than 60 minutes.

Defining the plurality of stimulation sessions to achieve any of the aforementioned therapeutic objectives such that at least a portion of the stimulation in a given day, preferably a majority of the cumulative stimulation in a given day, is applied after 2 pm.

It should be appreciated that, unlike the prior art which attempted to affect gastric emptying time using the direct stimulation of the musculature of the gastrointestinal tract, Applicant's electrical pulses are defined such that 1) the generated electrical field does not directly contact the patient's gastrointestinal tract and does not contact the patient's vagus nerve, 2) each of the electrical pulses are defined by a maximum pulse width of 1 ms, preferably less than 1 ms, preferably less than 0.5 ms, preferably below 0.2 ms, 3) the generated electrical field is configured to activating the patient's somatovisceral reflex and not stimulate parasympathetic nerves, autonomic nerves, the musculature of the gastrointestinal tract, including the stomach, esophagus, duodenum, small intestine, or large intestine, or smooth muscle in general, and 4) the electrical field does not penetrate more than 20 mm through the patient's skin.

Furthermore, the electrical pulses are delivered through a specialized electro-dermal patch device that has a constrained footprint (less than 10 in$^2$), not requiring two disparately positioned electrodes. Preferably, the device has two electrodes with the first electrode and second electrode being separated by a distance of less than 20 mm and has an adhesive layer positioned on the portion of the total base surface area, wherein, when the adhesive layer of the electrical dermal patch is adhered to the patient's epidermal layer, the electrical dermal patch has an average minimum peel strength in a range of 1.0 to 2.1 newtons.

Gastric emptying time may be measured through a plurality of different ways and the therapeutic endpoints described above are equally applicable regardless of what measurement technique is applied. For example, the therapeutic endpoints described above may be evaluated using gastric emptying scintigraphy (GES) that uses radionuclides to measure gastric emptying time. After radiolabeling the solid or liquid component of a meal, the gastric counts measured by scintigraphy correlate directly with the volume of the meal remaining without the need for geometric assumptions about the shape of the stomach. Alternative tests include breath testing and acetaminophen absorption. Breath testing, which assumes normal small bowel absorption and pulmonary function, indirectly measures gastric emptying, as gastric emptying is the rate-limiting step in the processing and excretion of 13C-octanoic acid. Exemplary protocols for measuring gastric emptying rates may be found in "Consensus Recommendations for Gastric Emptying Scintigraphy: A Joint Report of the American Neurogastroenterology and Motility Society and the Society of Nuclear Medicine", Abell et al., American Journal of Gastroenterology, 2007, pages 753-763, which is herein incorporated by reference.

Will Power Conservation

In accordance with an aspect of the present specification, it is recognized that an 'urge to eat' is a function of hunger (a physical need) and appetite (a psychological need). It should therefore be appreciated that the EDP system of the present specification dampens the user's 'urge to eat' so that the user does not has to exert, waste or spend too much 'will power' to comply with diets, exercises or any other therapy related regimen. In other words, the EDP system of the present specification enables users to conserve their will power and improve conservation and therefore reserves of will power as the stimulation therapy progresses.

In accordance with some embodiments, will power is determined or computed as an inverse function of hunger level or score. In other words, as the user's hunger score decreases his will power conserved increases while as the hunger score increases the user's will power is spent or wasted. Accordingly, the HMA presents GUIs showing vertical or horizontal bar graphs, such as in the form of light bar VASs, or any other graphical form evident to persons of ordinary skill in the art, to illustrate the user's hunger score trend over a predefined period of time as well as the user's will power conservation status or trend over the same predefined period of time. In some embodiments, the user's hunger scores over the predefined period of time are together represented as an aggregate hunger score for the period of time. Similarly, the user's will power conservation level or score is determined or computed as an inverse function of the aggregate hunger score for the period of time. FIG. 53A shows a will power VAS 5305 where the colored bar portion 5306 is representative of the amount or level of will power conserved as a result of low or decreased levels of hunger experienced by the user. On the other hand, FIG. 53B shows a will power VAS 5310 where the colored bar portion 5312 represents reduced level or amount of will power conserved as a result of high or increased levels of hunger experienced by the user. In other words, VAS 5310 conveys that the level or amount of will power wasted is high compared to the VAS 5305. Thus, the user's will power conservation status is determined and displayed based upon the user's hunger profile or map over a predefined period of time.

In accordance with some embodiments, will power is determined or computed as a composite function of two sub-parameters such as dietary will power and exercise will power. In accordance with various embodiments, dietary will power is computed as an inverse function of hunger levels or as a directly proportional function of dietary compliance, while exercise will power is computed as a directly proportional function of amount or level of exercise or activity of the user. FIGS. 54A, 54B illustrate dietary will power and exercise will power levels displayed as respective vertical piston bar graphs 5405, 5410 in accordance with an embodiment. The piston 5412 for the exercise will power level 5410 rise the more the user exercises. The piston 5407 for the dietary will power levels 5405 rise the more the user complies with his dietary plan (or the lower the hunger levels are). Thus, depending upon the levels of dietary compliance and exercising, the dietary and exercise will powers are affected and the two piston bars 5405, 5410 accordingly move up or down.

In accordance with some embodiments, dietary will power is determined or computed as a directly proportional composite function of dietary compliance and hunger control or appetite control. The dietary will power status or level is then displayed as a vertical or horizontal bar graph, for example. In various embodiments, the user's score includes at least the amount of calories and the type of calories consumed and is displayed as a vertical bar graph. Similarly, the hunger control or appetite control score is displayed as another vertical bar graph. In accordance with an aspect, if the user's hunger is high and dietary compliance is low, the dietary will power graph is displayed to be in a red zone and/or the EDP flashes red color via LEDs. As hunger moves down and dietary compliance increases, the dietary will power graph is displayed to be in a yellow zone and/or the EDP flashes yellow color. As hunger moves all the way down and dietary compliance is high the dietary will power graph is displayed to be in a green zone and/or the EDP flashes green color.

In accordance with an aspect of the present specification, users are encouraged and rewarded for achieving and maintaining their will power levels, reserves or conservation high, such as by achieving the yellow or green zones, for example. In various embodiments, the rewards are in the form of points, badges, and/or emojis. The users are allowed to share their rewards, such as badges or points, within their social networks. In some embodiments, the users are allowed to redeem their rewards for discounts or, partial or complete waver of their therapy subscription fees and/or earn coupons for other services.

In accordance with some embodiments, will power levels, reserves or conservation is computed or determined as an inverse function of an 'urge to eat' profile or map of the user. In accordance with some embodiments, the 'urge to eat' profile is itself defined as a function of at least one of: total consumption of calories (which is one example of a daily diet plan is less than 1200 calories), type of calories consumed (for example, a diet composition of carbs to proteins in the ratio of 20:80) and the timing of meals (for example, ideally eating at meal times). Thus, the greater the 'urge to eat' the more is the will power wasted or spent and therefore the less is the will power conserved or reserved.

In accordance with still other embodiments, will power levels, reserves or conservation is computed or determined as a composite function of at least two of a plurality of parameters such as, but not limited to, total consumption of calories (which in one example of a daily diet plan is less than 1200 calories), type of calories consumed (for example, a diet composition of carbs to proteins in the ratio of 20:80), the timing of meals (for example, ideally eating at meal times), exercise or activity levels (an ideal goal being 10,000 steps for example) and weight (ideally being, for example, within say 5% of a target weight).

In yet other embodiments, will power levels, reserves or conservation is computed or determined as a composite function of hunger score improvement, dietary compliance and exercise levels. In various embodiments, the composite will power level or score is rated periodically such as, daily or weekly. In accordance with an aspect, to determine the composite will power levels or scores, the user is periodically presented with VAS light bars to enable the user to: rate his success in maintaining a certain diet plan, such as that of a daily consumption of 1200 calories, rate his success in limiting out-of-meal plan snacking, rate his success in eating healthy foods, and rate his success in controlling hunger. Additionally, determination of the composite will power levels or scores involves automatic inputs such as, bonus points earned for each hunger rescue bolus, bonus points earned for exercising or activity, bonus points earned for filling out the daily diary, bonus points earned for favorable daily weight change and/or bonus points earned for positive coaching of other patients within the user's social network group, for example.

It should be appreciated that the user's will power levels, reserves or conservation can be computed or determined as a function of one or more underlying parameters as described above. In alternate embodiments, the user is presented with a light bar VAS to assess the user's dietary will power on a daily, weekly or any other suitable periodic basis. The user's will power levels, scores, reserves or conservation is displayed to the user in a plurality of graphs such as, but not limited to, vertical or horizontal bar graphs, piston bar graphs, VAS light bars, gas tank like graphs, hour glass illustrations or any other suitable display advantageously evident to persons of ordinary skill in the art.

In various embodiments, the user's will power levels, scores, reserves or conservation is archived throughout the stimulation therapy cycle or period to generate the user's will power profile or map. Multiple EDP users' will power profile or map enables determining an average will power level or score of a population or group of EDP users. In accordance with an aspect, the HMA compares a particular user's will power level or score with the average will power level or score of a representative population or group of EDP users, for a predefined period of time, to communicate to the user how his will power levels are faring with reference to the representative population or group of users. In various embodiments, the representative population of group of users may be those of characteristic age, gender, ethnicity, weight, weight loss goal, body mass index, body fat percentage, and/or race.

In accordance with another aspect of the present specification, the user's will power level or score also affects the composite, aggregate or collective will power level or score of the social network group, also referred to as an 'affinity group', that the user may be a member of. Affinity groups that share similar health goals (for example, weight loss) benefit a user member in a plurality of ways such as, but not limited to, enabling sharing of success stories, enabling sharing of non-HIPAA information, enabling sharing progress and compare performance, enabling users to display and share their rewards (points, emojis, badges) earned by achieving high levels of will power, sharing stimulation parameters and/or protocols that lead to better weight loss, improved dietary compliance, higher levels of well-being and increased levels of will power conservation.

In other words, an individual user may not only have a personal will power level or score but may also be associated with a collective will power level or score of the affinity group that he is a member of. The affinity group, in various embodiments, may also strive towards a collective goal associated with will power levels, hunger control, weight loss, and/or dietary compliance. Thus, in some embodiments, if the user's will power level rises it improves the collective will power score of the affinity group and vice versa. In some embodiments, users with at least a predefined minimum score for will power levels are allowed to coach other affinity group members. In some embodiments, a high level or score, above a predefined threshold, for will power of a user can result in one or more rewards such as, but not limited to, reduction of a monthly stimulation therapy fee for the user, free coupons for other services (such as a discounted fee coupon for entry or membership to a gym), free or discounted personalized concierge service, coaching or assistance associated with the EDP device and Health Management application of the present specification. As another example, if the affinity group has a collective goal of, say, achieving 5% total body weight loss, a member user who achieves the goal or is close to achieving the goal may receive encouragement emojis as group support from the group members. To support and encourage the group members, the successful members or high achievers are also enabled to share their therapy credentials such as, but not limited to, diet plans, exercise regimes, stimulation parameters, protocols and will power levels with the group. Again, each time a user triggers a rescue session or bolus and/or fills out his daily diary—he is rewarded bonus will power points, for example, and this event is automatically communicated to other members of the affinity group so that other members can send emojis encouragement to the user.

An online concierge service associated with the EDP device and Health Management application of the present specification may access, process and analyze the user's health related information such as, but not limited to, daily diary entries, a hunger map, a map of daily rescue sessions, dietary compliance, weight trends, exercise data, stimulation protocol, a dietary plan, will power level or score. In accordance with an aspect, the online concierge service functions as an automated online coaching service to educate patients on various functionalities or usage of the EDP device, such as through step-by-step audio-video demos that show the patients how to use the EDP device. In accordance with another aspect, the online concierge service may provide interventions in the form of adjusted or modified stimulation parameters, settings and protocols; modifications to exercising routines, forms, frequency and period; and/or adjustments to the user's dietary plan. In accordance with yet another aspect, the online concierge service would enable automated or personalized encouragement and advice to the patient (for their dietary progress, for example, based on input from their diaries) such as, but not limited to, "you are doing amazingly well compared to your affinity group—your composite score is X versus Y for the group as a whole and by our calculation you will achieve your weight loss goal of Z lbs by D date", "we recommend you add 2000 steps to your daily routine", "you are doing well, your hunger score is down and your weight loss is better than the aggregate weight loss for all users or for your affinity group", "you are showing signs of recurring hunger after dinner around 8:00 pm—we suggest that you eat more protein in your evening meal and apply a rescue stimulation session at 7:30 pm" or any other advice as would be advantageously evident to persons of ordinary skill in the art.

Thus, in various embodiments, the online concierge or dietary coach service algorithmically responds to user input with encouragement and recommendations such as, but not limited to, checking on the user's correct usage of the EDP device and compliance with operating instructions and daily diary completion, suggesting that the user should change timing of stimulation sessions (for example, around mealtimes) or increase usage of rescue sessions, suggesting that the user adopt a calorie counting regimen (from an approved list of Apps), suggesting that the user join an affinity group (from an approved list) for moral support, suggesting that the user go to a prepackaged meal substitution plan (from an approved list, such as, for example Jenny Craig), suggesting that the user exercise more and use a recommended or approved third party device with physiological sensors, and suggesting that the user join an intensive coaching plan from an approved list. In accordance with an aspect, the online coaching and recommendation function via the concierge service enables supporting, providing and therefore selling targeted advertisements as an adjunct to various recommendations such as, but not limited to, the calorie counting App, prepackaged meal plan, and the third party physiological monitoring device.

In various embodiments, status, scores and trends related to collective goals of the affinity group are periodically (such as, daily, weekly, bi-weekly, monthly) aggregated and shared among affinity group members, in the form of graphs for example, and may also be compared with individual member status, scores and trends. The collective goals may include will power levels, hunger scores, weight loss, calorie consumption, exercise score and/or dietary compliance.

In various embodiments, a user is allowed to subscribe to the dietary plans, exercise regimes, or stimulation parameters of affinity group members who have attained certain threshold scores (whether these threshold scores are wellness or will power scores, for example). This encourages affinity group members with high will power scores to get followers by enabling the affinity group members to publish their success credentials such as, but not limited to, diet plans, exercise regimes, stimulation parameters, protocols and will power levels.

In accordance with various aspects, the user's will power score or level can be utilized to participate in games or tournaments such as, for example, among members of the affinity group. In various embodiments, users can earn points and bonuses corresponding to their achieving a plurality of degrees or levels of will power. In various embodiments, as the user accumulates points, to earn progressively higher points the user may be required to not only achieve high levels of will power but also successfully pass a plurality of filters related to various health parameters such as, but not limited to, striking a certain percentage of a weight loss goal, dietary compliance to stay below 1200 Kcal/day, exercise or be active commensurate with 10,000 steps per day. The accumulated points will enable the users to win or be eligible for a plurality of rewards at various levels such as, but not limited to, emojis, electronic badges, reduction of a stimulation therapy fee for the user, free discounted coupons for other services (such as a discounted fee coupon for entry or membership to a gym or entry to a relevant health or fitness camp), free or discounted personalized concierge service, coaching or assistance associated with the EDP device and Health Management application of the present specification.

Composite Dietary Performance, Wellness or Treatment Compliance Score

In accordance with various aspects of the present specification, a combined or composite score is determined that is a function of at least the following categories or groups of metrics: a) adherence to the stimulation treatment regimen, b) actual dietary and well-being performance, and c) effective communication with the TPM and within the affinity or social networking group. In various embodiments the composite score is indicative of how well the patient is complying with the treatment regimen and therefore how well he is faring in terms of his overall health and wellness goal. In various embodiments, the combined, composite or compliance score is a function of a plurality of factors, such as, but not limited to, whether the patient wears the EDP device daily; whether the patient provides or inputs daily diary data, as needed; whether the patient regularly receives the stimulation session therapies as scheduled (that is, does not miss the scheduled sessions); whether the patient reports calories consumed by recording actual calories consumed; how well the patient adheres to a restricted calories diet (that is the planned diet); type or quality of calories consumed (that is, whether the patient is consuming a healthy diet); whether the patient records his actual weight daily; the patient's actual daily weight loss; whether the patient uses wearable devices, for example, a device, with physiological sensors, configured to be worn on the human body, such as around the wrist, in order to monitor, acquire, record, and/or transmit the physiological data; the patient's actual exercise score or metrics, such as steps taken for example, to determine the calories expended; the patient's appetite score; sleep quality of the patient determined at least on the basis of the number of hours the patient slept as detected or recorded by the accelerometer or inclinometer included in the EDP device; whether the patient is proactive enough to request rescue sessions when needed (that is, when feeling hungry at non-scheduled meal times, for example); how participative the patient is within his affinity group and communicative with his TPM—for example, whether the patient is encouraging other affinity group members with emojis and/or whether the patient communicates with his TPM in line with a planned or scheduled feedback call with his TPM.

In embodiments, the patient is incentivized, rewarded and encouraged for achieving high compliance scores not only as an individual but also in comparison to aggregate compliance score of the affinity group to which the patient is associated. In various embodiments, the patient is rewarded through means such as, but not limited to, encouraging or congratulatory text messages (such as from a celebrity or personality), bonus points, emoticons/emojis, gift certificates or coupons, health related accessories, free or discounted enrolment to health management programs (such as Jenny Craig) and gyms. In embodiments, the patient is also incentivized, rewarded and encouraged if the patient enables spreading awareness and adoption of the EDP device to other individuals (currently non-users of the EDP device, for example). For example, the patient is rewarded and encouraged if she invites people on Facebook or WhatsApp, for example, to use the EDP device and/or shares benefits of the EDP device.

In embodiments, the HMA provides a rolling summary of the patient's daily diary input data (such as appetite, hunger, exercise and well-being) or the patient's health status data (comprising a level, score or value related to hunger, appetite, exercise, weight, well-being, will-power, urge to eat profile, hunger profile, standard eating and meals profile, actual eating and meals profile, dietary plan, exercise regimen, energy balance, weight changes, glucose data, rescue bolus events, and stimulation induced nausea, dyspepsia, and habituation events) and uses any one or any combination of these data to create a composite score indicative of an overall health status or performance of the patient.

It should be appreciated that, in various embodiments, the composite score may be a function of a subset of the plurality of factors described above. Also, the composite score is determined not only for individual patients but also aggregated for affinity groups and/or all EDP users to enable a comparison of an individual score against that of an entire affinity group and/or an entire EDP user community. In accordance with an aspect, the composite score of a patient alone or relative to the composite score aggregated for affinity groups and/or all EDP users is used to titrate or adjust stimulation therapy. In accordance with another aspect, the composite score associated with individual patients and/or associated with the affinity group is shared with online automated coaching or concierge service and/or with designated care-providers, physicians, coaches or support groups. Such sharing may automatically trigger online dietary coaching inputs (such as via telephone calls and/or video conferencing, for example) such as, but not limited to, congratulatory and encouraging remarks or emojis in case of improved composite scores, cautionary remarks and/or dietary compliance tips including healthy food options in case of lagging composite scores.

Therapeutic Objectives

In various embodiments, the systems and methods of the present specification employ an electro-dermal patch that provides pre-programmed and/or customized stimulation protocols to induce changes in antral and gastric motility to slow passage of food. In various embodiments, a Health Management application software, as described above, provides and/or enables the programming, either pre-programmed or set 'on demand' by the patient or medical personnel (in real time), of a plurality of therapeutic goals which are also customizable or adjustable in order to modulate gut hormones, modulate gut microbiota, assess antral and gastric motility, suppress appetite, achieve dietary compliance, suppress hunger, or elevate fullness, satiation, or satiety. It should be noted herein that any or a plurality of the methods of use or treatment examples provided above may be employed to achieve the therapeutic objectives.

It should also be noted that the percent changes in value listed below are represented by the following formula: [(New Value)−(Old Value)]/(Old Value)]. Thus, where a certain parameter is measured in percentage, the percentage change is reflected by the above formula and not a delta value.

The following are a plurality of non-limiting, exemplary goals:

In some embodiments, after at least one stimulation session or determinable time period after when stimulation terminates, the rate, level or amount of any patient parameter, as discussed throughout this specification is modified relative to the rate, level or amount of that patient parameter before stimulation. In one instance, after at least one stimulation session or determinable time period after when stimulation terminates, the rate, level or amount of that patient parameter is reduced relative to the rate, level or amount of that patient parameter before stimulation. In another instance, after at least one stimulation session or determinable time period after when stimulation terminates, the rate, level or amount of that patient parameter is increased relative to the rate, level or amount of that patient parameter before stimulation.

In some embodiments, after stimulation terminates, or at least one minute from when stimulation terminates, the patient experiences a decrease in appetite or hunger by at least 5%.

In some embodiments, after at least one minute from when stimulation terminates or after at least one stimulation session, the patient experiences a decrease in appetite or hunger such that it is equal to, or less than, 95% of the pre-stimulation appetite or hunger levels.

In some embodiments, after at least one minute from when stimulation is initiated, the patient experiences a perceptible decrease in appetite or hunger.

In some embodiments, after at least one minute from when stimulation is initiated, the patient experiences an increase in satiety, satiation or fullness levels by at least 5%.

In some embodiments, after at least one minute from when stimulation terminates or after at least one stimulation session, the patient experiences an increase in satiety, satiation or fullness levels such that it is equal to, or greater than, 105% of the pre-stimulation satiety, satiation or fullness levels.

In some embodiments, after at least one stimulation session, a patient's compliance with a target daily caloric intake increases relative to the patient's compliance with the target daily caloric intake before stimulation.

In some embodiments, the systems and methods of the present specification result in a decrease in the post-stimulation daily caloric intake of a patient relative to a pre-stimulation daily caloric intake of the patient, wherein the pre-stimulation daily caloric intake is a function of an amount of calories consumed by the patient over a first predefined period of time prior to stimulation, and wherein the post-stimulation daily caloric intake is a function of an amount of calories consumed by the patient over a second predefined period of time equal in duration to the first predefined period of time, after stimulation is initiated. For example, the decrease may be quantified as equal to or less than 99% of the pre-stimulation caloric intake, where the caloric intake decreases to a range of 600 to 1600 calories, decreases from over 2000 calories per day to less than 2000 calories per day, or decreases from over 1600 calories per day to less than 1600 calories per day.

In some embodiments, after at least one stimulation session, an amount or rate of a patient's antral motility, gastric motility, gastric emptying, hunger or appetite level is modified, relative to the corresponding amount before stimulation.

In some embodiments, after at least one stimulation session, the rate of a patient's antral motility, gastric motility, or gastric emptying is modified relative to the rate of the patient's antral motility, gastric motility, or gastric emptying before stimulation, and preferably the rate of a patient's antral motility, gastric motility, or gastric emptying is reduced relative to the rate of the patient's antral motility, gastric motility, or gastric emptying before stimulation.

In some embodiments, after at least one stimulation session, a patient's gastric emptying time is delayed by at least 1%, relative to the patient's gastric emptying time before stimulation.

In some embodiments, after at least 10 minutes of continuous stimulation, a patient's gastric emptying time is delayed by at least 5 minutes, relative to the patient's gastric emptying time before stimulation.

In some embodiments, after at least 20 minutes of continuous stimulation, a patient's gastric emptying time is delayed by at least 10 minutes, relative to the patient's gastric emptying time before stimulation.

In some embodiments, after at least 40 minutes of continuous stimulation, a patient's gastric emptying time is delayed by at least 20 minutes, relative to the patient's gastric emptying time before stimulation.

In some embodiments, after at least 60 minutes of continuous stimulation, a patient's gastric emptying time is delayed by at least 24 minutes, relative to the patient's gastric emptying time before stimulation.

In some embodiments, after at least one stimulation session, a patient's gastric emptying time is delayed by at least 25 minutes, relative to the patient's gastric emptying time before stimulation.

In some embodiments, after at least one stimulation session, a patient's post prandial gastric emptying time (of 50% of stomach solids content) is delayed by at least 5 minutes, wherein the patient has a BMI of 25 or more.

In some embodiments, after at least one stimulation session, a patient's post prandial gastric emptying time (of 50% of stomach solids content) is delayed by at least 10 minutes, wherein the patient has a BMI of 25 or more.

In some embodiments, after at least 5 minutes of stimulation, a patient's post prandial gastric emptying time (of 50% of stomach solids content) is delayed by at least 5 minutes.

In some embodiments, with a weekly duty cycle of at least 1%, a patient's post prandial gastric emptying time (of 50% of stomach solids content) is delayed by at least 5 minutes.

In some embodiments, with a weekly duty cycle ranging between 1% to 99%, a patient's post prandial gastric emptying time (of 50% of stomach solids content) is delayed by at least 5 minutes.

In some embodiments, after at least one stimulation session, a patient's gastric retention (that is, retention of solid gastric contents) is increased by 50%, 120 minutes after food intake, wherein the patient has a BMI of 25 or more.

In some embodiments, after at least one stimulation session, an amount or rate of a patient's gastric or antral motility is reduced in a range of 8 to 10% on a logarithmic scale, relative to the amount or rate of the patient's gastric or antral motility before stimulation.

In some embodiments, after at least one stimulation session, a patient's gastric accommodation or distention is impaired by at least 15%, relative to the patient's gastric accommodation or distention before stimulation.

In some embodiments, after at least one stimulation session, a patient's glucagon-like peptide 1 (GLP-1) is reduced by at least 20%, relative to the patient's glucagon-like peptide 1 (GLP-1) before stimulation.

In some embodiments, a patient's glucagon-like peptide 1 (GLP-1), in a first state, is greater than the glucagon-like peptide 1 (GLP-1) in a second state, wherein the first state is defined by a first area under the curve (AUC) corresponding to a pre-stimulation glucagon-like peptide 1 (GLP-1) and the second state is defined by a second AUC corresponding to a post-stimulation glucagon-like peptide 1 (GLP-1), and wherein the first AUC differs from the second AUC by at least 10%, thereby representing a decrease in the glucagon-like peptide 1 (GLP-1) of the patient.

In some embodiments, a patient's appetite or hunger level, in a first state, is greater that the appetite or hunger in a second state, wherein the first state is defined by a first area under the curve (AUC) corresponding to a pre-stimulation appetite or hunger level and the second state is defined by a second AUC corresponding to a post-stimulation appetite or hunger level, and wherein the first AUC differs from the second AUC by at least 5%, thereby representing a decrease in the appetite or hunger level of the patient.

In some embodiments, a patient's satiety, satiation or fullness level, in a first state, is less than the satiety, satiation or fullness level in a second state, wherein the first state is defined by a first AUC corresponding to a pre-stimulation satiety, satiation or fullness level and the second state is defined by a second AUC corresponding to a post-stimulation satiety, satiation or fullness level, and wherein the first AUC differs from the second AUC by at least 5%, thereby representing an increase in the satiety, satiation or fullness level of the patient.

In some embodiments, after at least one stimulation session, an amount of a patient's satiety, satiation or fullness levels increases relative to the corresponding amount before stimulation.

In some embodiments, after at least one stimulation session, a patient's appetite or hunger level decreases, over a predefined period of time, relative to the patient's appetite or hunger level before stimulation and the patient's nausea and/or dyspepsia level does not increase, over the predefined period of time, relative to the patient's nausea level before stimulation, wherein the stimulation does not cause the patient to experience a pain sensation.

In some embodiments, after at least one stimulation session, a patient's satiety, satiation or fullness level increases, over a predefined period of time, relative to the patient's satiety, satiation or fullness level before stimulation and the patient's nausea and/or dyspepsia level does not increase, over the predefined period of time, relative to the patient's nausea level before stimulation, wherein the stimulation does not cause the patient to experience a pain sensation.

In some embodiments, after at least one stimulation session, a patient's total body weight reduces by at least 1% relative to the patient's total body weight before stimulation. In some embodiments, after at least one stimulation session, a patient's total body weight reduces by at least 3% relative to the patient's total body weight before stimulation. In some embodiments, after at least one stimulation session, a patient's total body weight reduces by at least 1% relative to the patient's total body weight before stimulation and the patient's well-being level does not reduce more than 5% relative to the patient's well-being level before stimulation. In some embodiments, after at least one stimulation session, a patient's total body weight reduces by at least 3% relative to the patient's total body weight before stimulation and the patient's well-being level does not reduce more than 5% relative to the patient's well-being level before stimulation.

In some embodiments, after at least one stimulation session, a patient's pre-prandial ghrelin level reduces by at least 1%, and preferably at least 3%, relative to the patient's pre-prandial ghrelin level before stimulation. In some embodiments, after at least one stimulation session, a patient's post-prandial ghrelin level reduces by at least 1%, and preferably at least 3%, relative to the patient's post-prandial ghrelin level before stimulation.

In some embodiments, after at least one stimulation session, a post-stimulation ghrelin level of a patient decreases by at least 1%, and preferably at least 3%, relative to a pre-stimulation ghrelin level of the patient, wherein the pre-stimulation ghrelin level is measured prior to stimulation and wherein the post-stimulation ghrelin level is measured more than ten weeks after the at least one stimulation session.

In some embodiments, a patient's Acyl-Ghrelin and Total Ghrelin, in a first state, is greater than the Acyl-Ghrelin and Total Ghrelin in a second state, wherein the first state is defined by a first area under the curve (AUC) corresponding to a pre-stimulation Acyl-Ghrelin and Total Ghrelin and the second state is defined by a second AUC corresponding to a post-stimulation Acyl-Ghrelin and Total Ghrelin, and wherein the first AUC differs from the second AUC by at least 10%, thereby representing a decrease in the Acyl-Ghrelin and Total Ghrelin of the patient.

In some embodiments, after at least one stimulation session, the level of a patient's glucagon-like peptide-1, leptin, serotonin, peptide YY, beta-endorphin levels, resting metabolic rate, and/or cholecystokinin increases relative to the corresponding level of a patient's glucagon-like peptide-1, leptin, serotonin, peptide YY, beta-endorphin levels, resting metabolic rate, and/or cholecystokinin before stimulation.

In some embodiments, after at least one stimulation session, the level of a patient's triglycerides, cholesterol, lipopolysaccharides, and/or motilin-related peptide decreases relative to the corresponding level of a patient's triglycerides, cholesterol, lipopolysaccharides, and/or motilin-related peptide.

In some embodiments, after at least one stimulation session, a patient's plasma motilin level peak value is reduced by at least 20%, relative to the patient's plasma motilin level peak value before stimulation.

In some embodiments, a patient's plasma motilin level peak value, in a first state, is greater than the plasma motilin level peak value in a second state, wherein the first state is defined by a first area under the curve (AUC) corresponding to a pre-stimulation plasma motilin level peak value and the second state is defined by a second AUC corresponding to a post-stimulation plasma motilin level peak value, and wherein the first AUC differs from the second AUC by at least 10%, thereby representing a decrease in the plasma motilin level peak value of the patient.

In some embodiments, after at least one stimulation session, a patient's glucagon-like peptide-1 level increases by at least 1%, and preferably at least 3%, relative to the patient's glucagon-like peptide-1 level before stimulation.

In some embodiments, after at least one stimulation session, a patient's leptin level increases by at least 1%, and preferably at least 3%, relative to the patient's leptin level before stimulation.

In some embodiments, after at least one stimulation session, a patient's serotonin level increases by at least 1%, and preferably at least 3%, relative to the patient's serotonin level before stimulation.

In some embodiments, after at least one stimulation session, a patient's peptide YY level increases by at least 1%, and preferably at least 3%, relative to the patient's peptide YY level before stimulation.

In some embodiments, after at least one stimulation session, a patient's peptide YY level decreases by at least 20%, relative to the patient's peptide YY level before stimulation.

In some embodiments, a patient's peptide YY level, in a first pre-stimulation state, is greater than the peptide YY level in a second post-stimulation state, wherein the first pre-stimulation state is defined by a first area under the curve (AUC) corresponding to a pre-stimulation peptide YY level and the second post-stimulation state is defined by a second AUC corresponding to a post-stimulation peptide YY level, and wherein the first AUC differs from the second AUC by at least 10%, thereby representing a decrease in the peptide YY level of the patient.

In some embodiments, after at least one stimulation session, a patient's beta-endorphin level increases by at least 1%, and preferably at least 3%, relative to the patient's beta-endorphin level before stimulation.

In some embodiments, after at least one stimulation session, a patient's resting metabolic rate increases by at least 1%, and preferably at least 3%, relative to the patient's resting metabolic rate before stimulation.

In some embodiments, after at least one stimulation session, a patient's cholecystokinin (CCK) level increases by at least 1%, and preferably at least 3%, relative to the patient's cholecystokinin level before stimulation.

In some embodiments, after at least one stimulation session, a patient's cholecystokinin level decreases by at least 20%, relative to the patient's cholecystokinin level before stimulation.

In some embodiments, a patient's cholecystokinin level, in a first pre-stimulation state, is greater than the cholecystokinin level in a second post-stimulation state, wherein the first pre-stimulation state is defined by a first area under the curve (AUC) corresponding to a pre-stimulation cholecystokinin level and the second post-stimulation state is defined by a second AUC corresponding to a post-stimulation cholecystokinin level, and wherein the first AUC differs from the second AUC by at least 10%, thereby representing a decrease in the cholecystokinin level of the patient.

In some embodiments, after at least one stimulation session, a patient's lipopolysaccharide level reduces by at least 1%, and preferably at least 3%, relative to the patient's lipopolysaccharide level before stimulation. In some embodiments, a reduction in the lipopolysaccharide level also reduces metabolic inflammation and insulin resistance.

In some embodiments, after at least one stimulation session, a patient's motilin-related peptide level reduces by at least 1%, and preferably at least 3%, relative to the patient's motilin-related peptide level before stimulation.

In some embodiments, after at least one stimulation session, a patient's triglycerides level reduces by at least 1%, and preferably at least 3%, relative to the patient's triglycerides level before stimulation.

In some embodiments, after at least one stimulation session, a patient's degree of glycemia improves by at least 1%, and preferably at least 3% relative to the patient's degree of glycemia before stimulation.

In some embodiments, after at least one stimulation session, a patient's glycemia (GLU) peak lowers by at least 10%, relative to the patient's glycemia (GLU) peak before stimulation.

In some embodiments, after at least one stimulation session, a non-diabetic or a non-pre-diabetic patient's glucose is reduced to a fasting level of less than 100 mg/dl, reducing the overall chances of the patient developing pre-diabetes in the future.

In some embodiments, after at least one stimulation session, a pre-diabetic and diabetic patient's postprandial plasma glucose concentration is lowered by at least 5%, when measured up to 2 hours after a glucose tolerance test.

In some embodiments, after at least one stimulation session, a patient's glycemic control is improved. In some embodiments, after at least one stimulation session, a patient's glycemic control is modified relative to the patient's glycemic control before stimulation, and preferably the patient's glycemic control is increased relative to the patient's glycemic control before stimulation. In some embodiments, after at least one stimulation session, the level of hemoglobin A1C decreases by at least 1%, and preferably at least 3% relative to the patient's level of hemoglobin A1C before stimulation. In some embodiments, after at least one stimulation session, the level of hemoglobin A1C decreases by ≥5% relative to the patient's level of hemoglobin A1C before stimulation. In some embodiments, after at least one stimulation session, the level of hemoglobin A1C decreases by 0.5% relative to the patient's level of hemoglobin A1C before stimulation. Because hemoglobin A1C is measured in terms of percentage, it should be noted that what is described here is the percentage change relative to its level before stimulation. For example, if the baseline hemoglobin A1C level is measured at 7%, a 5% decrease is calculated as a decrement of 0.35% and therefore a decreased hemoglobin A1C level of 6.75%.

In some embodiments, after at least one stimulation session, the level of hemoglobin A1C decreases by at least 1% with a p value of 0.05. In some embodiments, after at least one stimulation session, the level of hemoglobin A1C is completely normalized. In some embodiments, after at least one stimulation session, the level of hemoglobin A1C is ≤7.0% (which equates to 154 mg per dL estimated average glucose in diabetics).

In some embodiments, after at least one stimulation session, a patient's glucose homeostasis improves by at least 1%, and preferably at least 3% relative to the patient's glucose homeostasis before stimulation. Optionally, glucose homeostasis is quantified by decreasing HOMA-IR (Homeostasis Model Assessment—estimated Insulin Resistance) by ≥5% compared to a baseline HOMA-IR and is calculated as described above with respect to hemoglobin A1C. In some embodiments, after at least one stimulation session, a patient's level of HOMA-IR decreases by at least 4% compared to a level of HOMA-IR prior to applying the stimulation session. In some T2DM patients, after at least one stimulation session, fasting blood glucose is decreased by 20 mg/dl.

In some embodiments, after at least one stimulation session, the patient experiences a decrease in a fasting plasma insulin level of ≥5% compared to a baseline fasting plasma insulin level.

In some embodiments, after at least one stimulation session, the patient experiences a decrease in a fasting plasma glucose level of ≥5% compared to a baseline fasting plasma glucose level.

In some embodiments, after at least one stimulation session, a patient's degree of insulin resistance is modified relative to the patient's degree of insulin resistance before stimulation, and preferably the patient's degree of insulin resistance is increased relative to the patient's degree of insulin resistance before stimulation. In some embodiments, after at least one stimulation session, a patient's degree of insulin resistance improves by at least 1%, and preferably at least 3% relative to the patient's degree of insulin resistance before stimulation.

In some embodiments, after at least one stimulation session, a patient's beta cell function of the pancreas is improved relative to the patient's beta cell function before stimulation.

In some embodiments, after at least one stimulation session, a patient's level of total blood cholesterol decreases by at least 1%, and preferably at least 3%, relative to the patient's level of total blood cholesterol before stimulation.

In some embodiments, after at least one stimulation session, a composition of a patient's gut microbiota is modified relative to a composition of a patient's gut microbiota before stimulation. In some embodiments, after at least one stimulation session, a composition of a patient's gut microbiota modulates from a first state to a second state, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 1%, and preferably at least 3%, and wherein the second level of firmicutes is less than the first level of firmicutes by at least 1%, and preferably at least 3%.

In some embodiments, after at least one session of stimulation session, the patient experiences a modification, and preferably, a perceptible decrease in appetite or hunger which lasts for at least one day.

In some embodiments, a patient's appetite is reduced by 5% over at least 1 day of stimulation therapy.

In some embodiments, after at least one session of stimulation, a patient reports "improved" dietary compliance, wherein dietary compliance is achieving a daily caloric consumption target. In some embodiments, "improved" dietary compliance is at least 5% closer to a defined or set daily calorie consumption target using the EDP device of the present specification.

In some embodiments, a patient has reached a therapeutic goal if they achieve greater than at least 1%, and more preferably 2%, 5%, 10%, and any increment therein, TWL (Total Weight Loss) or at least 1%, and more preferably 2%, 5%, 10%, and any increment therein, EWL (Excess Weight Loss) in six months of stimulation therapy.

In some embodiments, a patient has reached a therapeutic goal if they are able to change their metabolism rate (such as RMR or BMR) by 10%. In some embodiments, a stimulation therapy is intended to affect at least 5% improvement in RMR.

In some embodiments, application of electrical stimulation via the EDP embodiments disclosed herein result in a person having an altered perception of gastric fullness or emptiness. Specifically, when the EDP therapy is applied, the stimulation parameters are selected such that, after at least one stimulation session, the perception of gastric fullness or gastric emptiness of the patient increases by at least 1% relative to the perception of gastric fullness or gastric emptiness of the patient before stimulation. This may be measured over a single day, week, month or other time period.

In some embodiments, application of electrical stimulation via the EDP embodiments disclosed herein result in a person having increased exercise output, defined as the amount of calories burned in a given time period or steps taken in a given time period. Specifically, when the EDP therapy is applied, the stimulation parameters are selected such that, after at least one stimulation session, exercise output of the patient increases by at least 1% relative to the exercise output of the patient before stimulation. This exercise output may be measured over a single day, week, month or other time period.

It should be appreciated that the exercise output, in some embodiments, may be measured with a third party device (including a third party application software on an external device), with physiological sensors, configured to be worn on the human body, such as around the wrist or the feet (as smart shoes, for example), in order to monitor, acquire, record, and/or transmit the physiological data, to receive and integrate exercise and weight loss information, along with one or more electro-dermal patch devices of the present specification.

In some embodiments, after at least one stimulation session directed to a patient's T7 dermatome, the patient's hepatic gluconeogenesis (glucose production in liver) is lowered by at least 1% thereby improving glycemia, relative to the patient's hepatic glucogenesis before stimulation. The patient may be pre-diabetic or diabetic.

In some embodiments, after at least one stimulation session, a patient's prolactin level increases by at least 5% within a predetermined time, relative to the patient's prolactin level before stimulation.

In some embodiments, after at least one stimulation session, a patient's dopamine level decreases by at least 5%, relative to the patient's dopamine level before stimulation.

In some embodiments, after at least one stimulation session, a patient's plasma cytokeratin 18 (CK-18) level decreases by at least 5%, relative to the patient's plasma cytokeratin 18 (CK-18) levels before stimulation. It should be appreciated that CK-18 levels correlate with the magnitude of NAFLD (nonalcoholic fatty liver disease), hepatocyte apoptosis and the presence of NASH (nonalcoholic steatohepatitis) in patients.

In some embodiments, at the end of a first therapy phase a patient is at a second metabolic or health state, compared to a first metabolic or health state at the beginning of the first therapy phase, wherein the second metabolic or health state does not deteriorate more than 5% to 50%, and any increment therein, during a vacation period (wherein the patient does not receive any therapy) that extends beyond the end of the first therapy phase, and wherein the vacation period is at least equal to the period associated with the first therapy phase.

Achieving Dietary Compliance

In one embodiment, use of the EDP device, in accordance with the methods described herein, result in patients being able to better comply with a predefined dietary regime, including being better able to restrict daily caloric intake to a predefined amount, being better able to adhere to a diet designed to maximize particular nutritional components, such as vitamins, minerals, and proteins, and decrease undesirable nutritional components, such as carbohydrates, fat, and sugars, and being better able to adhere to a diet designed to have a glycemic index that is equal to or less than a predefined amount. The present specification facilitates adhering to dietary objectives for overweight (body mass index of 25-29.9) or obese (body mass index of 30 or greater) individuals, particularly given that willpower alone or even willpower with exercise is an ineffectual approach to dietary compliance and either weight loss or weight management.

Therapeutically, the EDP device can be used in conjunction with predefined diet plans, comprising a nutritional profile, a set of foods, and/or a maximum number of calories, to ensure that a patient adheres to the predefined plan.

Therefore, in one embodiment, the present specification enables increased dietary compliance. A patient is provided the EDP device, adheres it to his or her epidermal layer, and initiates a stimulation regime. The patient also receives a diet plan, either manually or electronically into an application executing on an external device, that defines a diet plan. The diet plan may establish a maximum daily caloric intake, such as between 600 and 1600 calories, may require a particular nutritional profile, such as a certain number or type of vegetables, proteins, and/or supplements, and/or may require the avoidance of certain types of foods, such as carbohydrates, sugars, and/or foods with high glycemic indexes. The parameters of the diet plan may be based on receiving, electronically into an application executing on an external device or manually, an indication of how active the patient is (sedentary, moderately active, active), the patient's gender, the patient's age, the patient's weight, the patient's height, the patient's percentage of body fat, and/or the patient's body mass index. As the patient uses the device and records his or her food consumption, either into the program in the external device in communication with the EDP device or into a separate third party program which then transmits the information to the program in communication with the EDP device, the program in communication with the EDP device determines if the patient is complying with the diet regimen. If the patient is not avoiding certain types of food, not eating a particular nutritional profile, and/or exceeding the maximum daily caloric intake, the program modulates stimulation parameters in order to decrease appetite and/or hunger levels and transmits those modulated stimulation parameters to the EDP device, which then increases stimulation strength, duration, and/or frequency, thereby causing the decrease appetite and/or hunger levels and enabling the patient to better comply with the diet regimen. Conversely, if the patient is not getting enough calories, the program modulates stimulation parameters in order to increase appetite and/or hunger levels and transmits those modulated stimulation parameters to the EDP device, which then decreases stimulation strength, duration, and/or frequency, thereby causing the increase appetite and/or hunger levels and, again, enabling the patient to better comply with the diet regimen.

In another embodiment, the present specification enables improved dietary management. One substantial problem that physicians and diet programs have is keeping a patient on the prescribed diet. The present specification enables improved dietary management. A third party manager, such as a physician or health care provider, provides a patient with the EDP device and programs the EDP device with an initial stimulation regime based upon a prescribed diet plan. The diet plan may establish a maximum daily caloric intake, such as in the range of 600 to 1600 calories, may require a particular nutritional profile, such as a certain number or type of vegetables, proteins, and/or supplements, and/or may require the avoidance of certain types of foods, such as carbohydrates, sugars, and/or foods with high glycemic indexes. The parameters of the diet plan may be based on receiving, electronically into an application executing on an external device or manually, an indication of how active the patient is (sedentary, moderately active, active), the patient's gender, the patient's age, the patient's weight, the patient's height, the patient's percentage of body fat, and/or the patient's body mass index. As the patient uses the device and records his or her food consumption, either into the program in the external device in communication with the EDP device or into a separate third party program which then transmits the information to the program in communication with the EDP device, the program in communication with the EDP device determines if the patient is complying with the diet regimen. If the patient is not avoiding certain types of food, not eating a particular nutritional profile, and/or exceeding the maximum daily caloric intake, the third party manager may modulate stimulation parameters in order to decrease appetite and/or hunger levels and transmits those modulated stimulation parameters to the EDP device, which then increases stimulation strength, duration, and/or frequency, thereby causing the decrease appetite and/or hunger levels and enabling the patient to better comply with the diet regimen. Conversely, if the patient is not getting enough calories, the third party manager may modulate stimulation parameters in order to increase appetite and/or hunger levels and transmit those modulated stimulation parameters to the EDP device, which then decreases stimulation strength, duration, and/or frequency, thereby causing the increase appetite and/or hunger levels and, again, enabling the patient to better comply with the diet regimen.

In another embodiment, the present specification enables improved dietary maintenance and preventing the regaining of weight. After meeting a weight goal, through any of the aforementioned treatment methods, the patient's diet plan is adjusted to a new diet plan reflecting a weight maintenance, instead of a weight loss, objective. Such a diet plan, which may be received either manually or electronically into an application executing on an external device, may establish a higher maximum daily caloric intake than the previous diet plan, such as between 1600 and 2800 calories, a different nutritional profile, and/or less emphasis on avoiding of certain types of foods, such as carbohydrates, sugars, and/or foods with high glycemic indexes. The parameters of the new diet plan may be based on receiving, electronically into an application executing on an external device or manually, an indication of how active the patient is (sedentary, moderately active, active), the patient's gender, the patient's age, the patient's weight, the patient's height, the patient's percentage of body fat, and/or the patient's body mass index. As the patient uses the device and records his or her food consumption, either into the program in the external device in communication with the EDP device or into a separate third party program which then transmits the information to the program in communication with the EDP device, the program in communication with the EDP device determines if the patient is complying with the new diet regimen. If the patient is not avoiding certain types of food, not eating a particular nutritional profile, and/or exceeding the new maximum daily caloric intake, the program modulates stimulation parameters in order to decrease appetite and/or hunger levels and transmits those modulated stimulation parameters to the EDP device, which then increases stimulation strength, duration, and/or frequency, thereby causing the decrease appetite and/or hunger levels and enabling the patient to better comply with the diet regimen. Conversely, if the patient is not eating enough calories, the program modulates stimulation parameters in order to increase appetite and/or hunger levels and transmits those modulated stimulation parameters to the EDP device, which then decreases stimulation strength, duration, and/or frequency, thereby causing the increase appetite and/or hunger levels and, again, enabling the patient to better comply with the diet regimen.

Alternatively, instead of modulating the stimulation parameters if the patient is not avoiding certain types of food, not eating a particular nutritional profile, and/or exceeding the new maximum daily caloric intake, the program, either in direct communication with the EDP device, a remote server, or a third party application executing on an external device, may change the diet plan itself by increasing or decreasing the maximum daily caloric intake, changing the nutritional profile, and/or changing what types of foods to avoid.

Figure 38A:
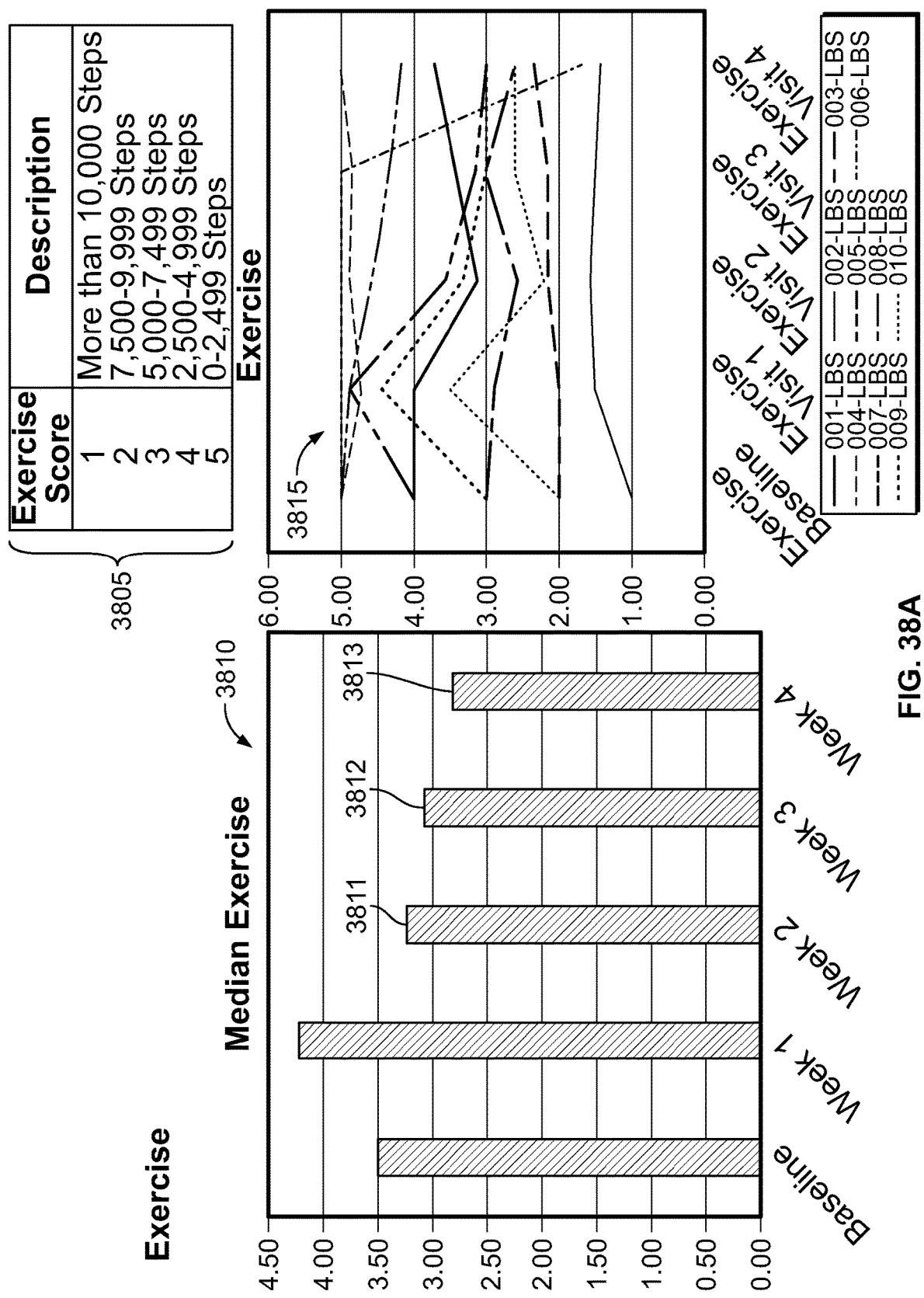
FIG. 38A is a graph illustrating exercise scores of a sample of patients treated with stimulation therapy, in accordance with an embodiment of the present specification.

FIGS. 38A through 38F show charts illustrating how the stimulation therapy of the present specification affects or modulates a plurality of patient variables or parameters such as, weight, BMI (Body Mass Index), appetite, dietary compliance and well-being for a sample of 10 patients. In accordance with an embodiment, the sample of 10 patients, having weight loss as an objective or goal, were treated with the stimulation therapy of the present specification over a duration of 4 weeks and the patients recorded their status on the plurality of variables or parameters throughout the duration of the 4 weeks using their companion devices. As shown in FIG. 38A, the 10 patients also exercised through the duration of 4 weeks and recorded their exercise scores 3805 using their companion devices (as described earlier with reference to FIG. 12). The bar graph 3810 shows median exercise scores per week, calculated from the exercise scores of the sample of 10 patients, while the line graphs 3815 show exercise scores per week of each of the 10 patients. As can be observed from the bar graph 3810, the median exercise scores 3811, 3812, 3813 improved during the second, third and fourth weeks.

Figure 38B:
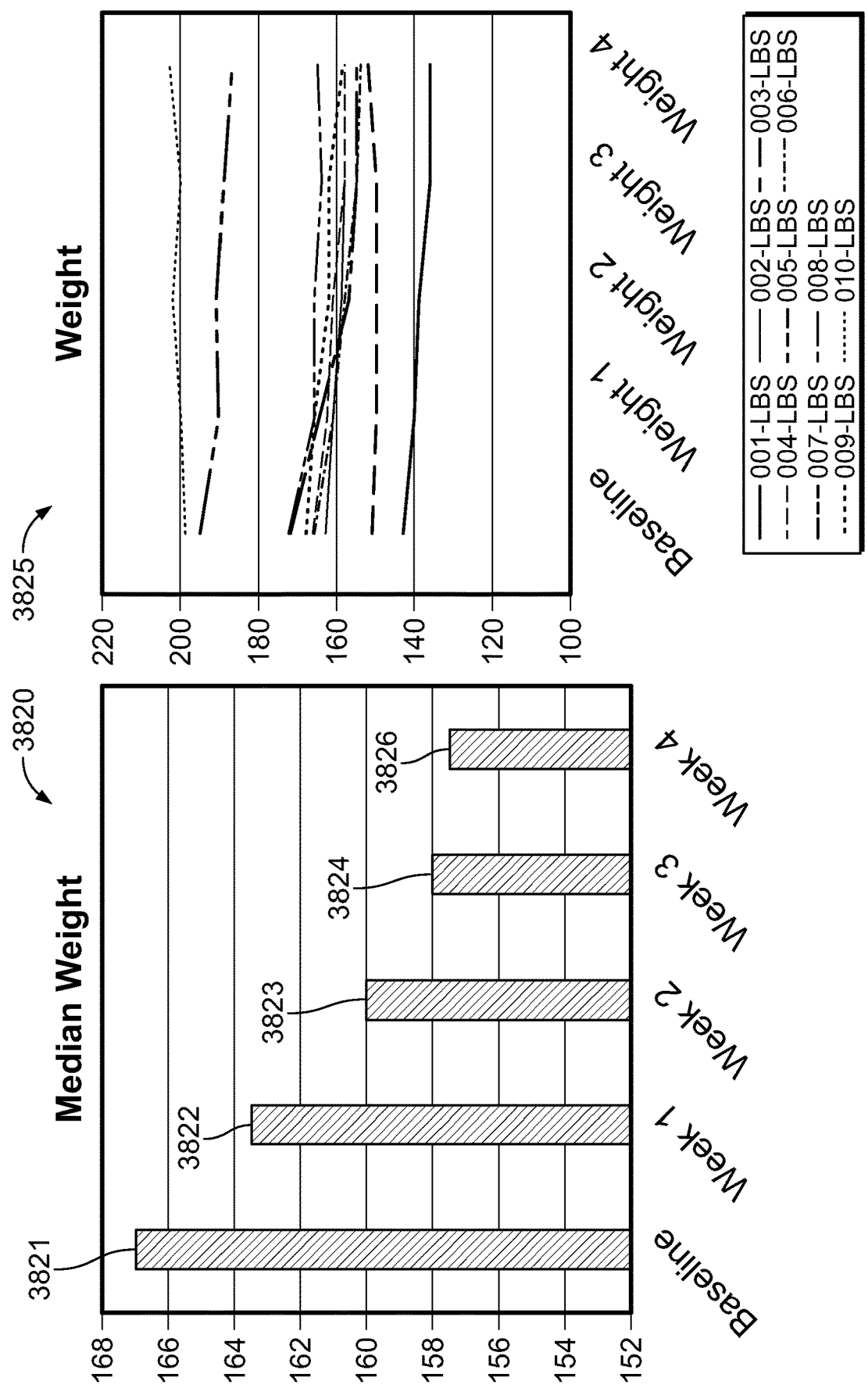
FIG. 38B is a graph illustrating weights of a sample of patients treated with stimulation therapy, in accordance with an embodiment of the present specification.

FIG. 38B shows charts illustrating how the weight parameter, for the sample of 10 patients, varied during the course of the 4 weeks, while the patients exercised, received stimulation therapy and recorded their weight using their companion devices (as described earlier with reference to FIG. 15). The bar graph 3820 shows median weights per week, calculated from the weights of the sample of 10 patients, while the line graphs 3825 show weights per week of each of the 10 patients. As can be observed from the bar graph 3820, the median weights 3822, 3823, 3824, 3826 continued to reduce during the first, second, third and fourth weeks relative to the median weight 3821 at the baseline (that is, prior to receiving stimulation therapy).

Figure 38C:
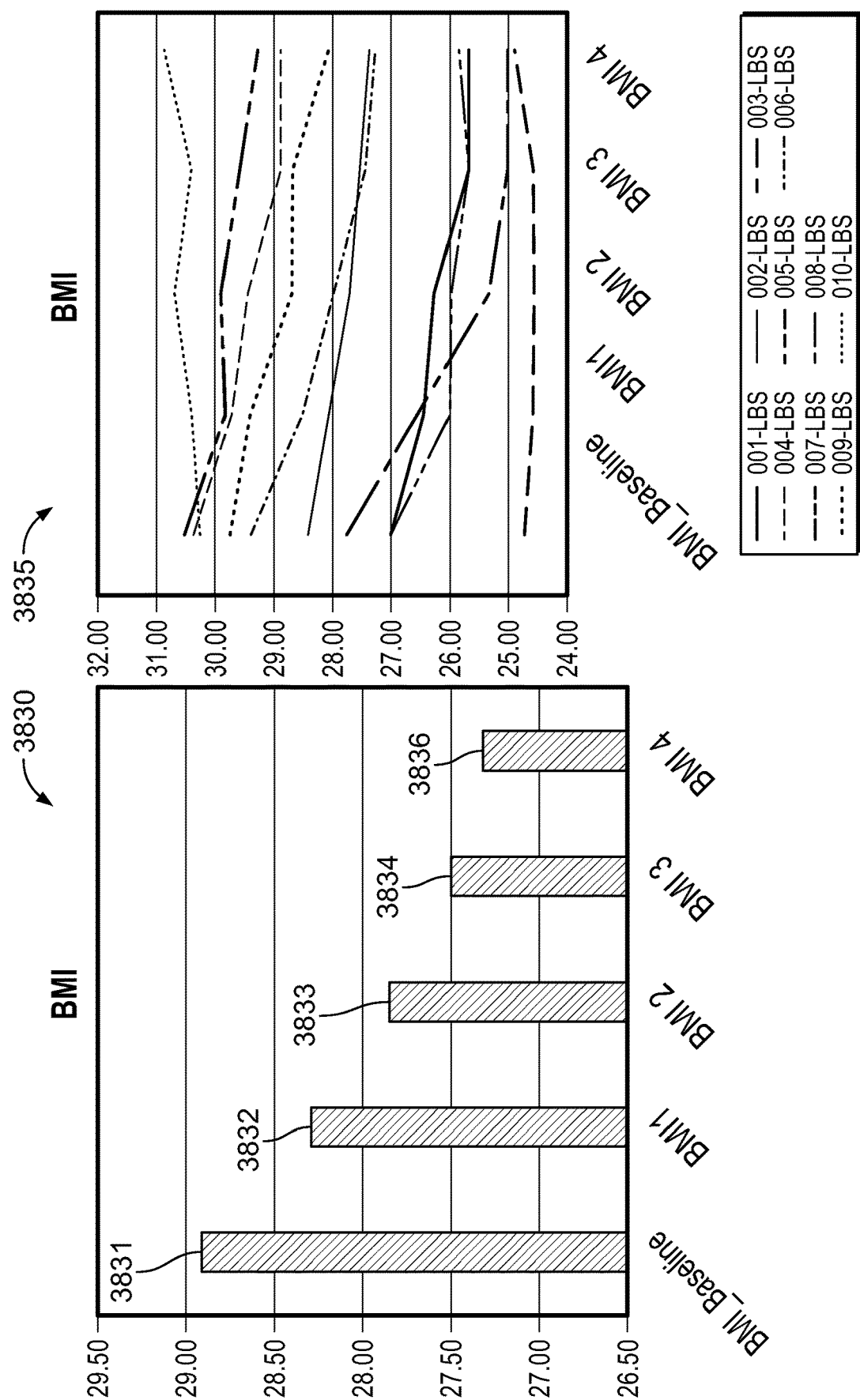
FIG. 38C is a graph illustrating BMIs (Body Mass Index) of a sample of patients treated with stimulation therapy, in accordance with an embodiment of the present specification.

FIG. 38C shows charts illustrating how the BMI parameter, for the sample of 10 patients, varied during the course of the 4 weeks, while the patients exercised and received stimulation therapy. The bar graph 3830 shows median BMI per week, calculated from the BMIs of the sample of 10 patients, while the line graphs 3835 show BMIs per week of each of the 10 patients. As can be observed from the bar graph 3830, the median BMIs 3832, 3833, 3834, 3836 continued to reduce during the first, second, third and fourth weeks relative to the median BMI 3831 at the baseline (that is, prior to receiving stimulation therapy).

Figure 38D:
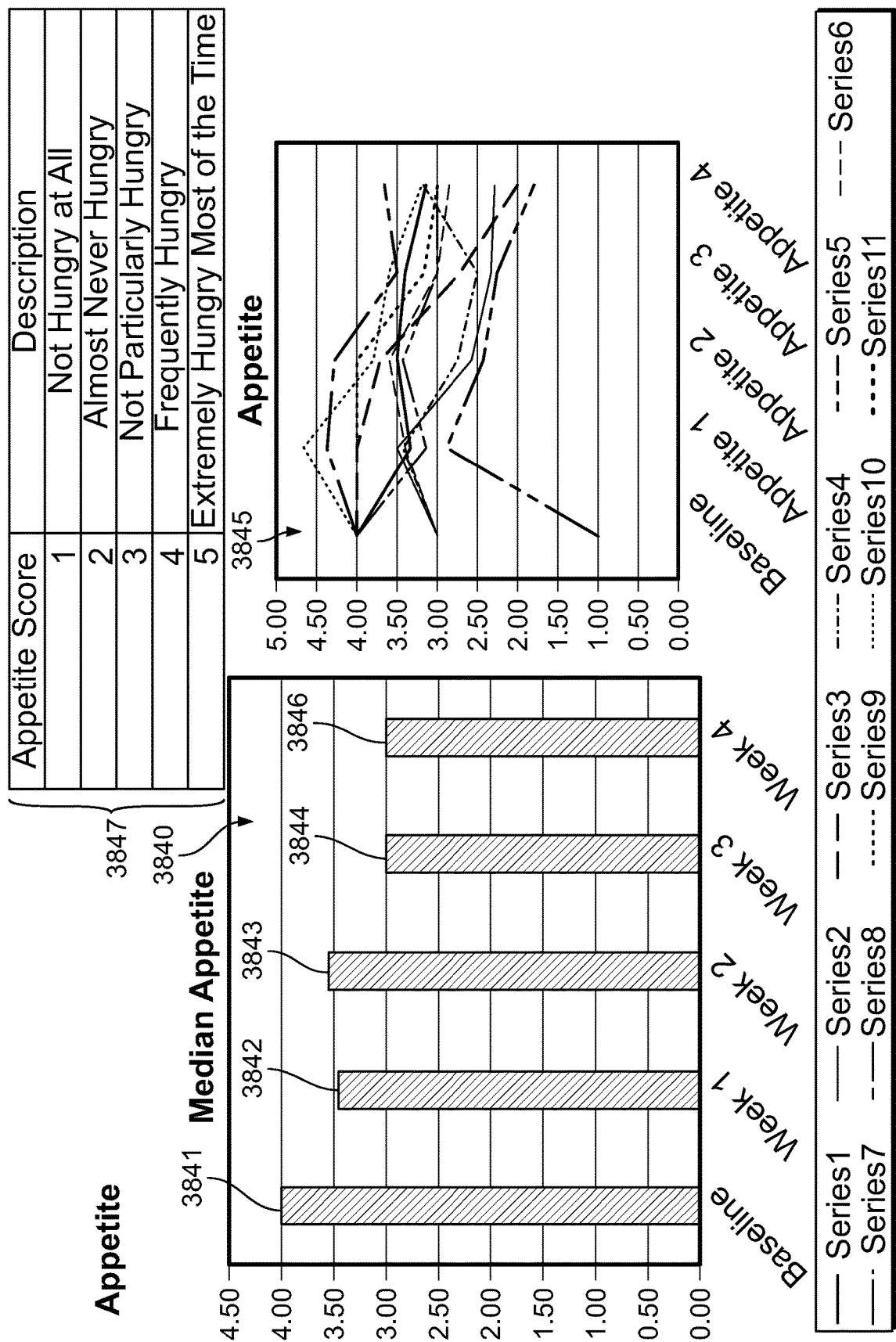
FIG. 38D is a graph illustrating appetite scores of a sample of patients treated with stimulation therapy, in accordance with an embodiment of the present specification.

FIG. 38D shows charts illustrating how the appetite parameter, for the sample of 10 patients, varied during the course of the 4 weeks, while the patients exercised, received stimulation therapy and recorded their appetite scores 3847 using their companion devices (as described earlier with reference to FIG. 11). The bar graph 3840 shows median appetite scores per week, calculated from the appetite scores of the sample of 10 patients, while the line graphs 3845 show appetite scores per week of each of the 10 patients. As can be observed from the bar graph 3840, the median appetite scores 3842, 3843, 3844, 3846 continued to reduce during the first, second, third and fourth weeks relative to the median appetite score 3841 at the baseline (that is, prior to receiving stimulation therapy).

Figure 38E:
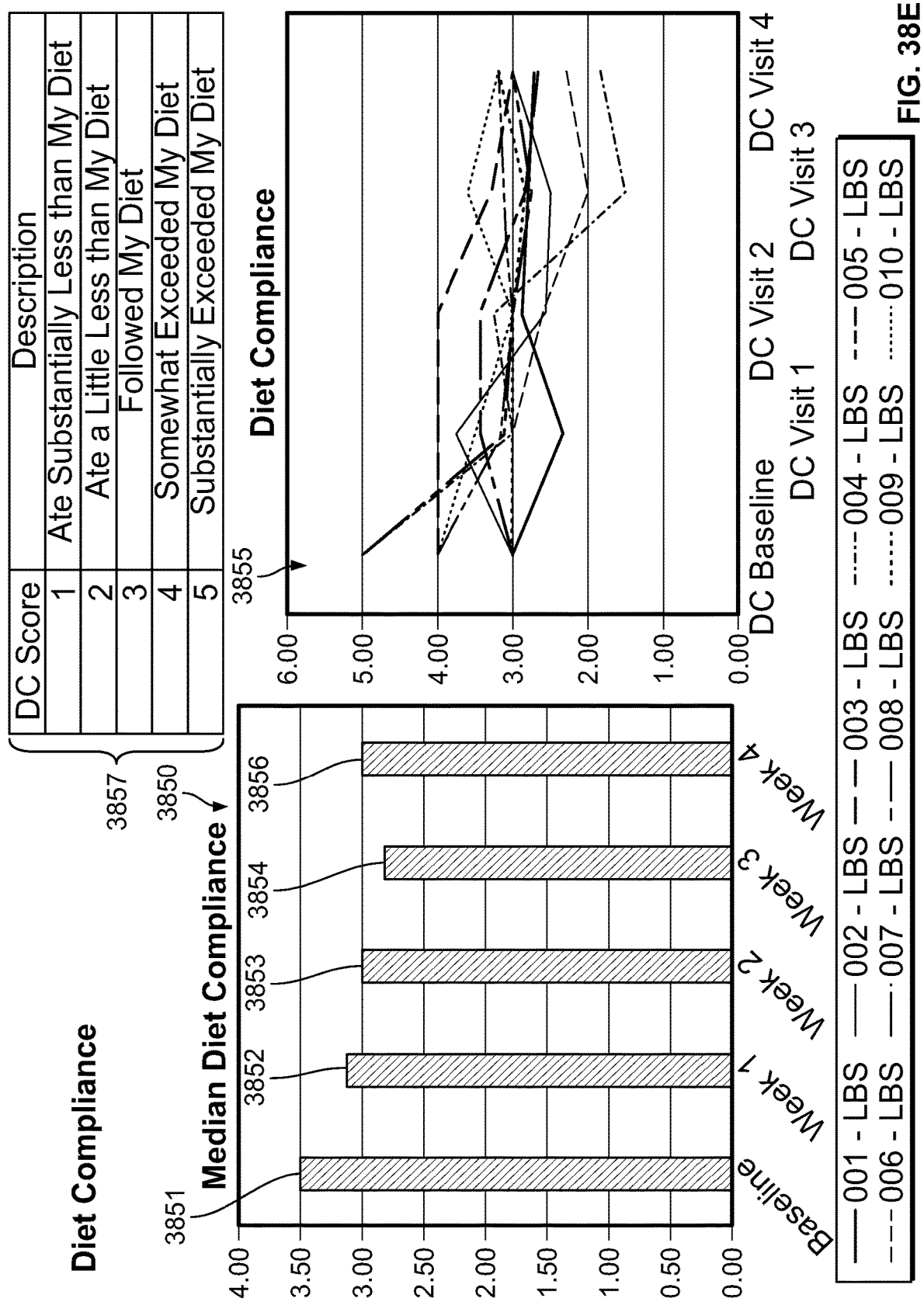
FIG. 38E is a graph illustrating dietary compliance scores of a sample of patients treated with stimulation therapy, in accordance with an embodiment of the present specification.

FIG. 38E shows charts illustrating how the dietary compliance parameter, for the sample of 10 patients, varied during the course of the 4 weeks, while the patients exercised, received stimulation therapy and recorded their dietary compliance scores 3857 using their companion devices. The bar graph 3850 shows median dietary compliance scores per week, calculated from the dietary compliance scores of the sample of 10 patients, while the line graphs 3855 show dietary compliance scores per week of each of the 10 patients. As can be observed from the bar graph 3850, the median dietary compliance scores 3852, 3853, 3854, 3856 improved during the first, second, third and fourth weeks relative to the median dietary compliance score 3851 at the baseline (that is, prior to receiving stimulation therapy). The graph 3850 highlights key advantages of the wearable and self-administered electro-dermal patch device of the present specification, specifically in terms of greater patient independence and improved patient compliance to stimulation protocols, with resultant increased dietary compliance.

Figure 38F:
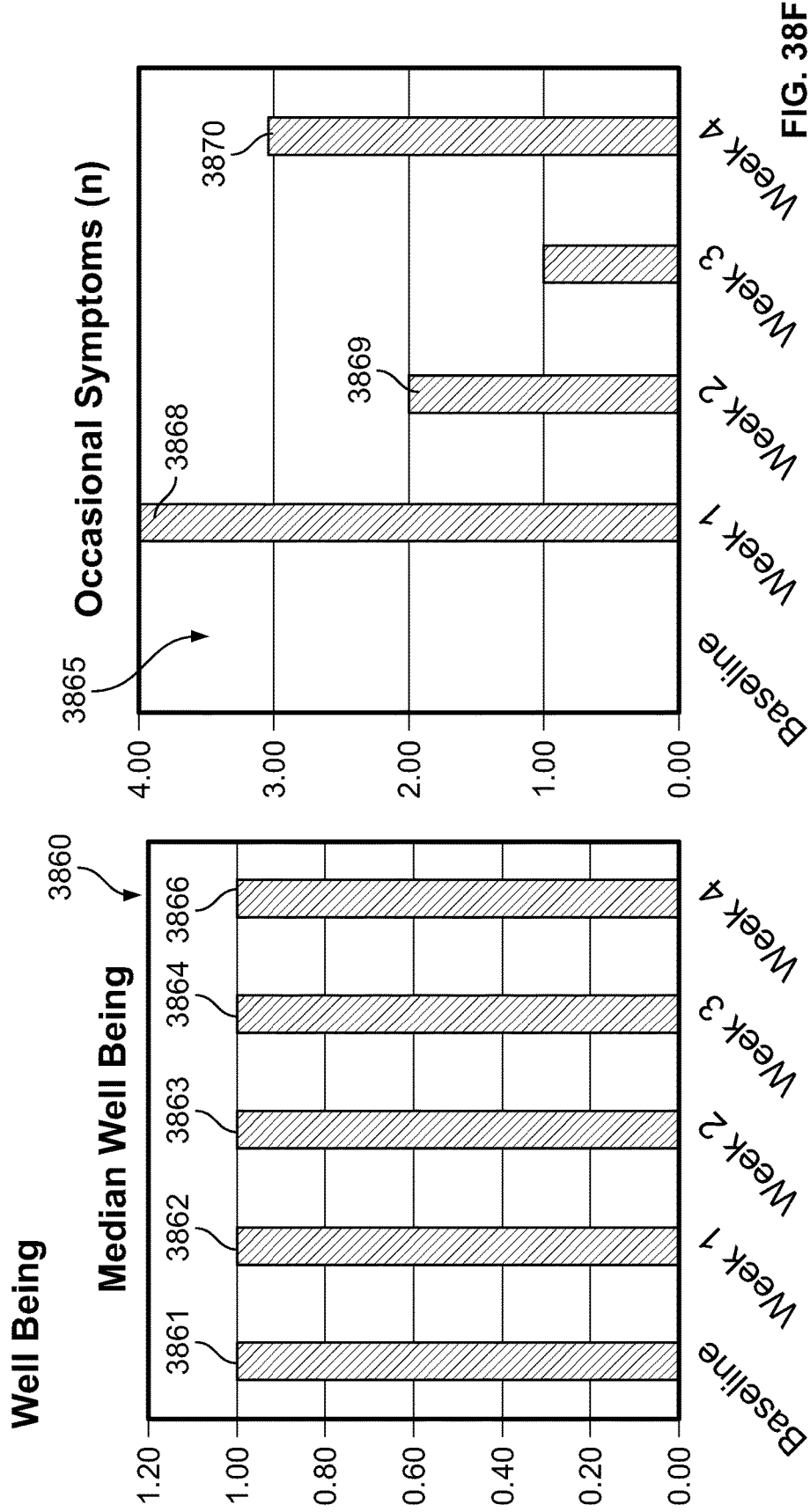
FIG. 38F is a graph illustrating well-being scores of a sample of patients treated with stimulation therapy, in accordance with an embodiment of the present specification.

FIG. 38F shows charts illustrating how the well-being parameter, for the sample of 10 patients, varied during the course of the 4 weeks, while the patients exercised, received stimulation therapy and recorded their well-being scores 3867 using their companion devices (as described earlier with reference to FIG. 16). The bar graph 3860 shows median well-being scores per week, calculated from the well-being scores of the sample of 10 patients, while the bar graphs 3865 show variation in well-being scores for a number of patients (y-axis) reporting symptoms of nausea/abdominal pain at each week. As can be observed from the bar graph 3860, the median well-being scores 3862, 3863, 3864, 3866 remained stable during the first, second, third and fourth weeks relative to the median well-being score 3861 at the baseline (that is, prior to receiving stimulation therapy) although there were occasional deterioration of well-being scores per week (such as the well-being scores 3868, 3869, 3870 for 4, 2 and 3 patients respectively) for some patients, as can be observed from the bar graphs 3865.

It should be appreciated that the pre-stimulation levels of the plurality of patient variables or parameters (such as, but not limited to, weight, BMI (Body Mass Index), appetite, dietary compliance and well-being) are measured using a scale (such as a VAS) at predefined times of the day over a first predefined period of time (such as 4 weeks, for example), and the post-stimulation levels of the patient variables or parameters are measured, after stimulation is initiated, using the scale at the predefined times of the day over a second predefined period of time, equal in duration to the first predefined period of time.

It should be appreciated that each of the pre-stimulation and post-stimulation levels, profiles or measurements may be assessed by comparing data from a single individual or by first aggregating pre-stimulation data from multiple individuals and post-stimulation data from multiple individuals and comparing the two aggregated data sets. Additionally, it should be appreciated that the effects of stimulation may be assessed by comparing measured parameters, as described above, from either an individual or group (in the form of aggregated data) to a control individual or group which has not undergone stimulation. In such cases, one would be comparing post-stimulation effects to no stimulation in a different individual or group of individuals (control) as opposed to comparing post-stimulation effects to pre-stimulation measurements from the same individual or group of individuals.

FIG. 39 is a side view of an EDP device in accordance with a non-preferred embodiment. The EDP device 3900 has all electronics 3902, power 3901, a power transfer mechanism 3903, such as a coil, and electrode 3904 captured within a single unit structure. The EDP device 3900 contains one electrode 3904, in the form of a very fine wire that passes through the cutaneous tissue (skin) to reach the dermatome. The wire is completely coated with an electrical insulator except for the distal end where it is open to create an electrode. This portion is designed to be inserted into or near the dermatome of interest.

The EDP device 3900 is intended to be placed on, and adhered to, the skin over a dermatome of interest. The device 3900 can have different shapes and sizes for different body types. Placement can be accomplished via a biocompatible adhesive on its surface, 3905, a band, a belt, or other such fixturing methods. The proper location of the electrode 3904 may be determined by a sensing mechanism. This sensing mechanism can be feedback from the patient, an electronic sensing mechanism (e.g., biopotential amplifier with analog filtering), or both. Once the proper location is found, the patient can be tattooed to mark the spot for future device placements.

FIG. 40 is another non-preferred embodiment for an EDP device whereby electrodes are fully implanted. The target dermatome(s) are stimulated through a small structure 4005 that has a plurality of anodes and a plurality of cathodes and is placed in the subcutaneous region 4006 of a patient's body 4007 proximate the target dermatome(s). This structure 4005 also has a receiving mechanism to receive power from outside the patient's body 4007. Power is transferred to structure 4005 from the EDP device 4000 which contains a battery 4001, electronics 4002, a power transfer mechanism 4003, such as a coil. The EDP device 4000 is placed with its bottom surface 4004 in close proximity to said subcutaneous region 4006 to enable transfer of power from power transfer mechanism 4003 to structure 4005.

Figure 41:
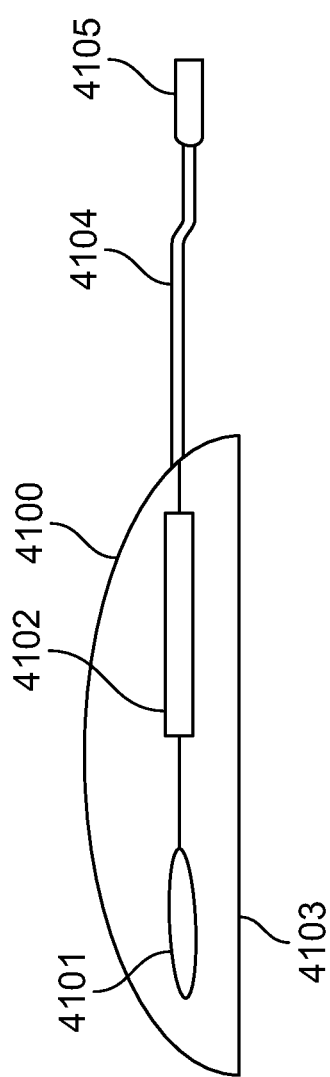
FIG. 41 is a side view illustration of still another EDP device, in accordance with a less preferred embodiment.

FIG. 41 is another non-preferred embodiment for an EDP device whereby the electrodes 4105 are not part of the main device housing. The target dermatome(s) are stimulated through these electrodes 4105, which are operably connected to the EDP device 4100 via a cable 4104. The cable 4104 can either be permanently connected to the device 4100 or detachable. The electrodes can be either cutaneous, percutaneous, or a combination of both. It should be understood that other portions of the device 4100 could be detachable as well. For example, the unit could be constructed such that the power source 4101 and electrodes 4105 are both detachable. This would make the electronics 4102 a reusable element of the device 4100 while the power source 4101 and electrodes 4105 can be disposable. Other such configurations can be envisioned. Optionally, the device 4100 also includes a power transfer mechanism, such as a coil. A bottom surface 4103 of the device includes an adhesive for securing the device 4100 to a skin surface of a patient.

Figure 42:
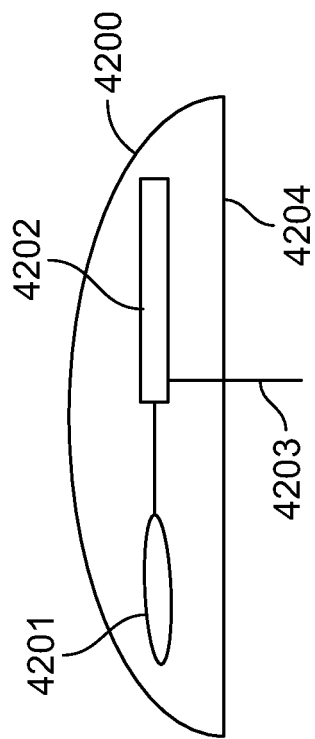

FIG. 42 is another non-preferred embodiment for an EDP device 4200 whereby there are no electrodes disposed on the surface of the device and only one percutaneous element 4203 that extends outward from the surface of the device. The device 4200 contains a battery 4201, electronics 4202 and, optionally, a power transfer mechanism. This embodiment allows for a plurality of electrodes to be on the percutaneous element 4203. A bottom surface 4204 of the device includes an adhesive for securing the device 4200 to a skin surface of a patient.

Figure 43:
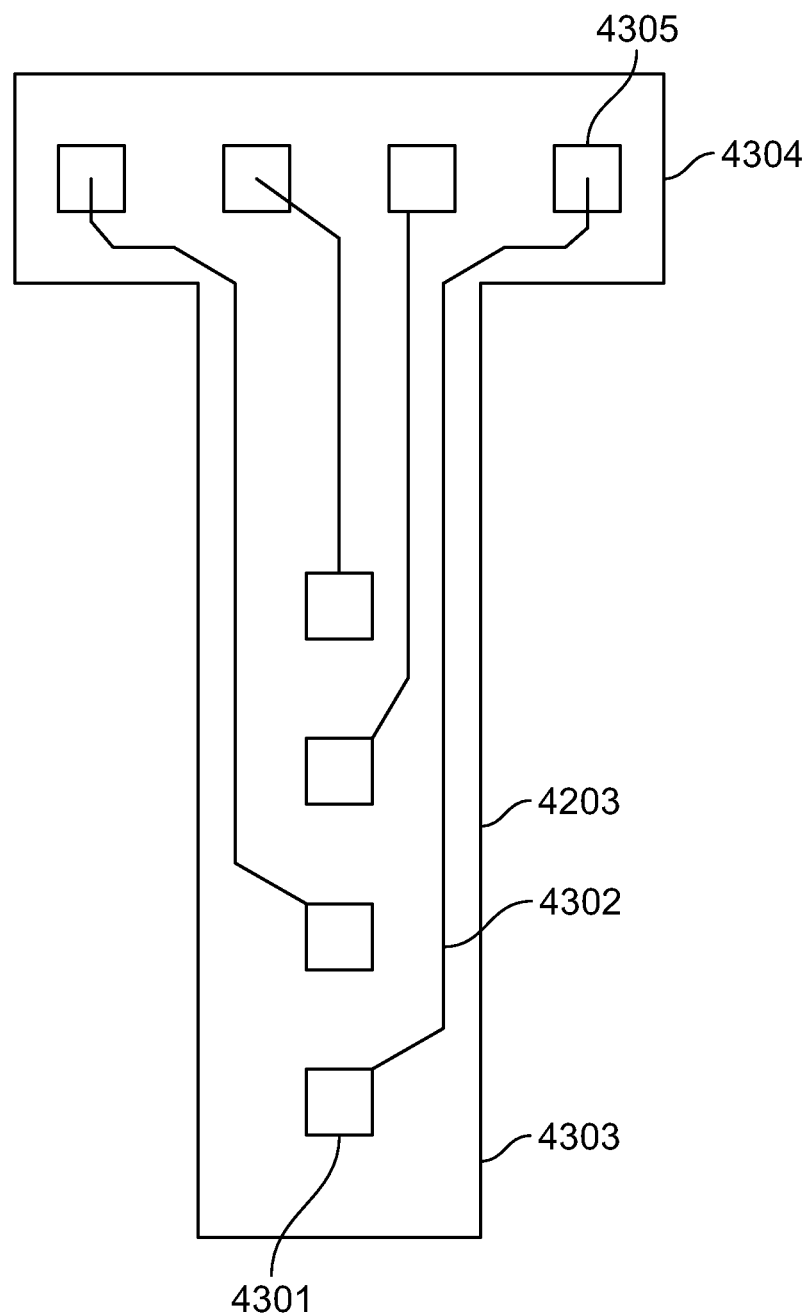

FIG. 43 is an embodiment of the percutaneous element 4203 of FIG. 42. The element 4203 has four electrodes 4301 connected to four pads 4305 via conductors 4302. The element substrate 4303 can be made from a flexible material such as Kapton® (polyimide film) or other such material, and the electrodes 4301 and traces can be made of gold, platinum, etc. An insulate material such as polyimide or parylene can be used to prevent short circuiting of the electrode conductors in tissue.

Figure 44:
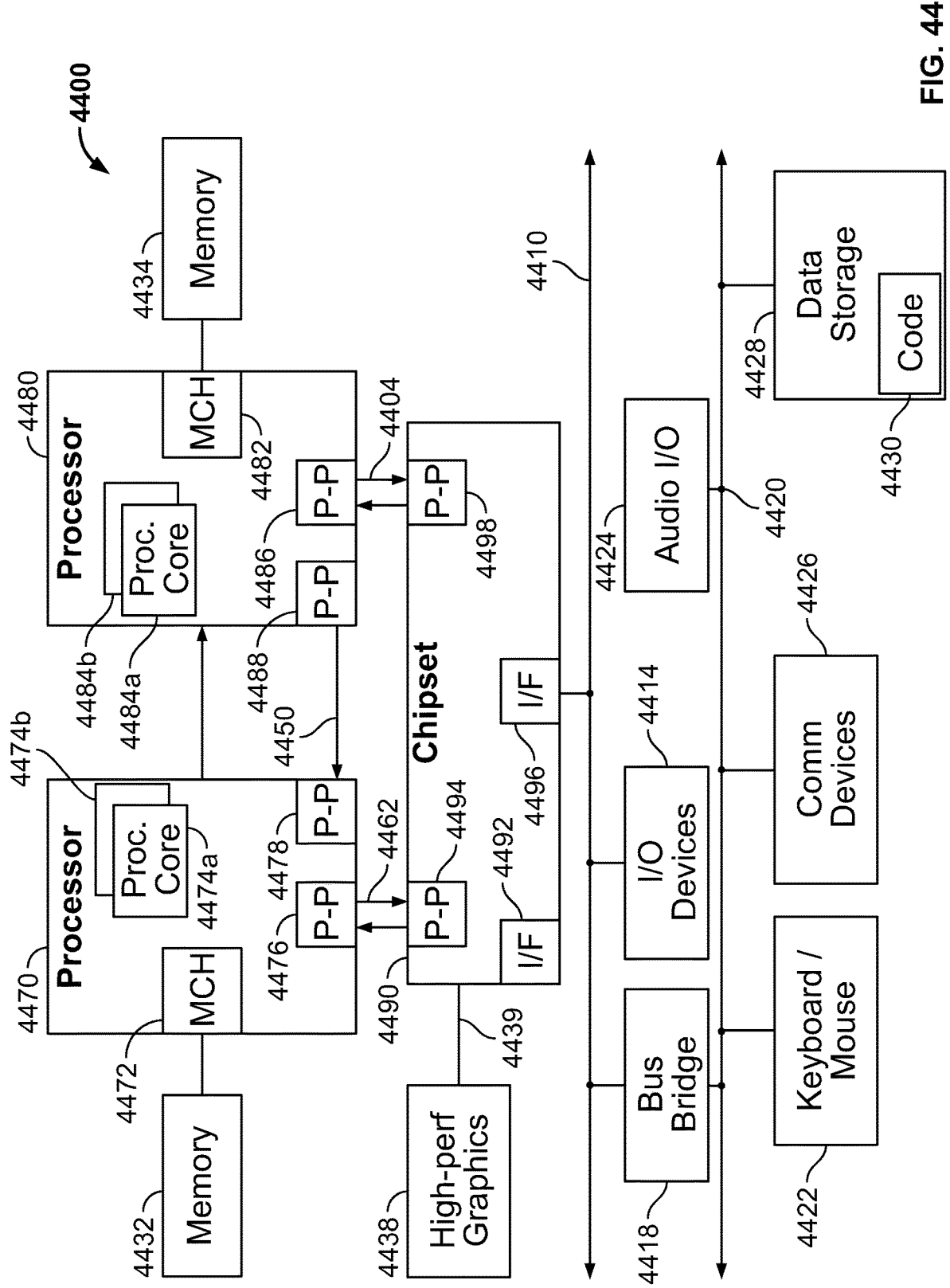

Referring now to FIG. 44, shown is a block diagram of a system 4400 in accordance with a non-preferred embodiment. System 4400 may be included in, for example, a mobile computing node such as a cellular phone, smartphone, tablet, Ultrabook®, notebook, laptop, personal digital assistant, and mobile processor based platform. However, in other embodiments portions thereof may be included in the electronics of the devices of FIGS. 39-42 (e.g., leaving out one of the two cores, the keyboard, and the like).

Shown is a multiprocessor system 4400 that includes a first processing element 4470 and a second processing element 4480. While two processing elements 4470 and 4480 are shown, it is to be understood that an embodiment of system 4400 may also include only one such processing element. System 4400 is illustrated as a point-to-point interconnect system, wherein the first processing element 4470 and second processing element 4480 are coupled via a point-to-point interconnect 4450. It should be understood that any or all of the interconnects illustrated may be implemented as a multi-drop bus rather than point-to-point interconnect. As shown, each of processing elements 4470 and 4480 may be multicore processors, including first and second processor cores (i.e., processor cores 4474a and 4474b and processor cores 4484a and 4484b). Such cores 4474a, 4474b, 4484a, 4484b may be configured to execute instruction code in a manner similar to methods discussed herein.

Each processing element 4470, 4480 may include at least one shared cache. The shared cache may store data (e.g., instructions) that are utilized by one or more components of the processor, such as the cores 4474a, 4474b and 4484a, 4484b, respectively. For example, the shared cache may locally cache data stored in a memory 4432, 4434 for faster access by components of the processor. In one or more embodiments, the shared cache may include one or more mid-level caches, such as level 2 (L2), level 3 (L3), level 4 (L4), or other levels of cache, a last level cache (LLC), and/or combinations thereof.

While shown with only two processing elements 4470, 4480, it is to be understood that the scope of the present specification is not so limited. In other embodiments, one or more additional processing elements may be present in a given processor. Alternatively, one or more of processing elements 4470, 4480 may be an element other than a processor, such as an accelerator or a field programmable gate array. For example, additional processing element(s) may include additional processors(s) that are the same as a first processor 4470, additional processor(s) that are heterogeneous or asymmetric to first processor 4470, accelerators (such as, e.g., graphics accelerators or digital signal processing (DSP) units), field programmable gate arrays, or any other processing element. There can be a variety of differences between the processing elements 4470, 4480 in terms of a spectrum of metrics of merit including architectural, micro-architectural, thermal, power consumption characteristics, and the like. These differences may effectively manifest themselves as asymmetry and heterogeneity amongst the processing elements 4470, 4480. For at least one embodiment, the various processing elements 4470, 4480 may reside in the same die package.

First processing element 4470 may further include memory controller logic (MC) 4472 and point-to-point (P-P) interfaces 4476 and 4478. Similarly, second processing element 4480 may include a MC 4482 and P-P interfaces 4486 and 4488. MC's 4472 and 4482 couple the processors to respective memories, namely a memory 4432 and a memory 4434, which may be portions of main memory locally attached to the respective processors. While MC logic 4472 and 4482 is illustrated as integrated into the processing elements 4470, 4480, for alternative embodiments the MC logic may be discreet logic outside the processing elements 4470, 4480 rather than integrated therein.

First processing element 4470 and second processing element 4480 may be coupled to an I/O subsystem 4490 via P-P interfaces 4476, 4486 via P-P interconnects 4462, 4404, respectively. As shown, I/O subsystem 4490 includes P-P interfaces 4494 and 4498. Furthermore, I/O subsystem 4490 includes an interface 4492 to couple I/O subsystem 4490 with a high performance graphics engine 4438. In one embodiment, a bus may be used to couple graphics engine 4438 to I/O subsystem 4490. Alternately, a point-to-point interconnect 4439 may couple these components.

In turn, I/O subsystem 4490 may be coupled to a first bus 4410 via an interface 4496. In one embodiment, first bus 4410 may be a Peripheral Component Interconnect (PCI) bus, or a bus such as a PCI Express bus or another third generation I/O interconnect bus, although the scope of the present invention is not so limited.

As shown, various I/O devices 4414, 4424 may be coupled to first bus 4410, along with a bus bridge 4418 which may couple first bus 4410 to a second bus 4420. In one embodiment, second bus 4420 may be a low pin count (LPC) bus. Various devices may be coupled to second bus 4420 including, for example, a keyboard/mouse 4422, communication device(s) 4426 (which may in turn be in communication with a computer network), and a data storage unit 4428 such as a disk drive or other mass storage device which may include code 4430, in one embodiment. The code 4430 may include instructions for performing embodiments of one or more of the methods described above. Further, an audio I/O 4424 may be coupled to second bus 4420.

Note that other embodiments are contemplated. For example, instead of the point-to-point architecture shown, a system may implement a multi-drop bus or another such communication topology. Also, the elements of FIG. 44 may alternatively be partitioned using more or fewer integrated chips than shown in the FIG. 44.

Figure 45:
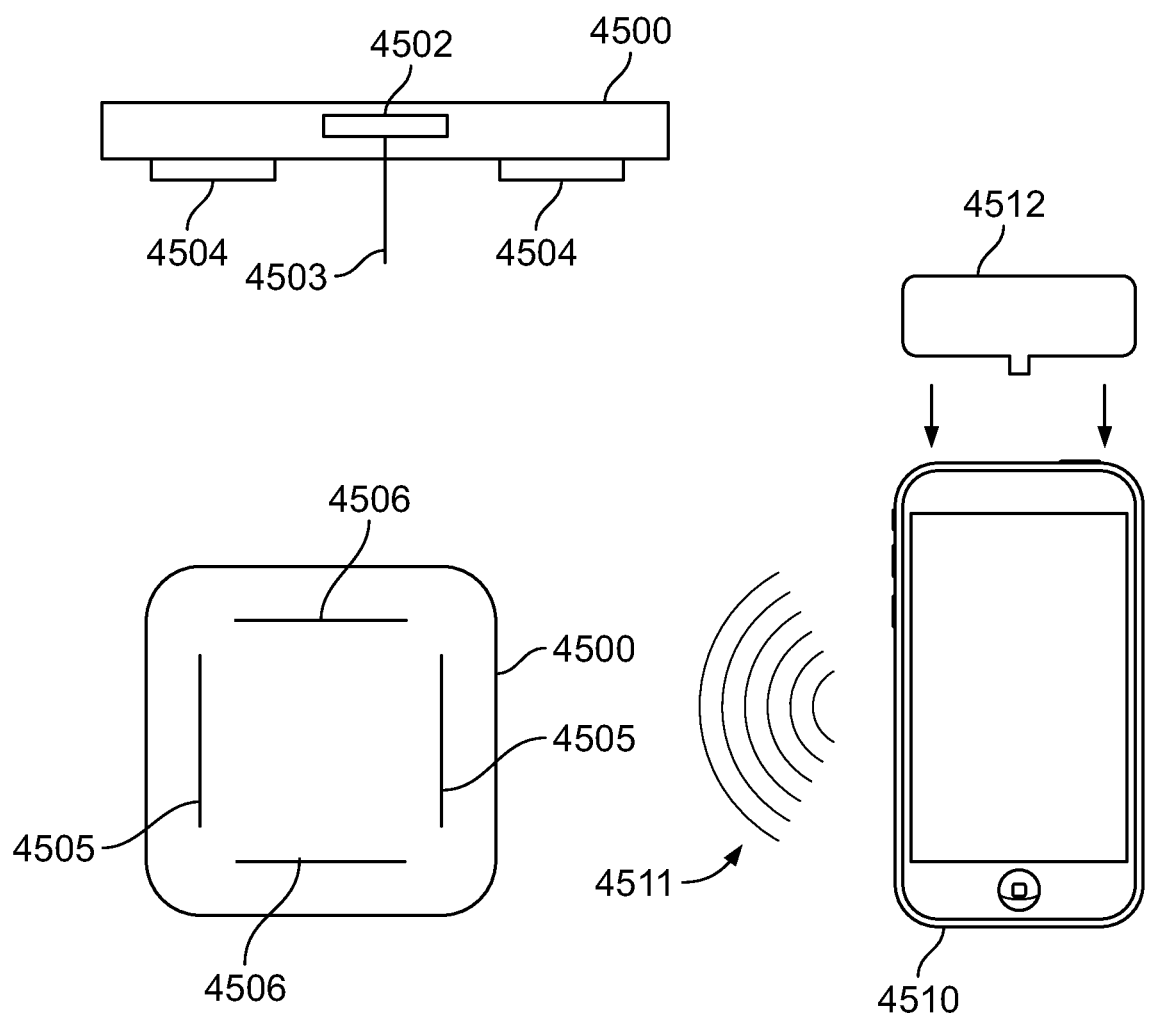

FIG. 45 is another non-preferred embodiment of an EDP device 4500, whereby there are no active electronics incorporated. Instead, an antenna 4505 is connected to a simple passive rectifier circuit 4502 to convert an RF signal 4511 to energy that is delivered to the electrodes 4503 and 4504. The antenna 4505 can be of various designs, such as a dipole antenna, inverted-F antenna, fractal antenna, or other such antenna that can efficiently receive the transmitted RF power. An external wireless device 4510 transmits the RF signal 4511 to the EDP device 4500. It should be appreciated that wireless energy, in the form of electromagnetic energy, RF energy, ultrasound energy, or any combination thereof, is transferred from the external wireless device 4510 (such as a smartphone, for example) to the EDP device 4500. An embodiment can use a half-wave rectifier, a full-wave rectifier, or any other passive rectifier circuits known in the art, for the passive rectifier circuit. An embodiment can have one antenna 4505 or an additional second antenna 4506 to account for RF signal polarization. The electrodes 4503, 4504 can be percutaneous and/or skin surface electrodes. An embodiment would contain sufficient electronic intelligence to avoid unintended stimulation from another external wireless device, whether that be another patient controller or some other wireless device; e.g., airport security scanner, etc. Such intelligence can be in the form of reading a specific data packet encoded in the RF transmission by means of modulation, such as amplitude modulation, frequency shift keying modulation, or other such conventional techniques.

An embodiment for an external wireless device 4510 is a battery powered portable device. An embodiment for the external wireless device can be a smartphone or any other commercially-available mobile electronics platform (such as that shown in FIG. 44). An embodiment can include an attachment 4512 to a smartphone or commercially-available mobile electronics platform which includes one or more of the following: an antenna, an RF signal generator circuit, an RF communication circuit, and an additional portable power source (e.g., battery). An embodiment for the external wireless device can be portable, thereby incorporating a portable power source. An embodiment for the external wireless device can be non-portable, thereby not requiring a portable power source and able to rely on the use of AC mains (connection to electrical wall socket). An embodiment includes the ability to encode data in the RF transmission to enable pairing to a desired EDP device only.

Figure 46:
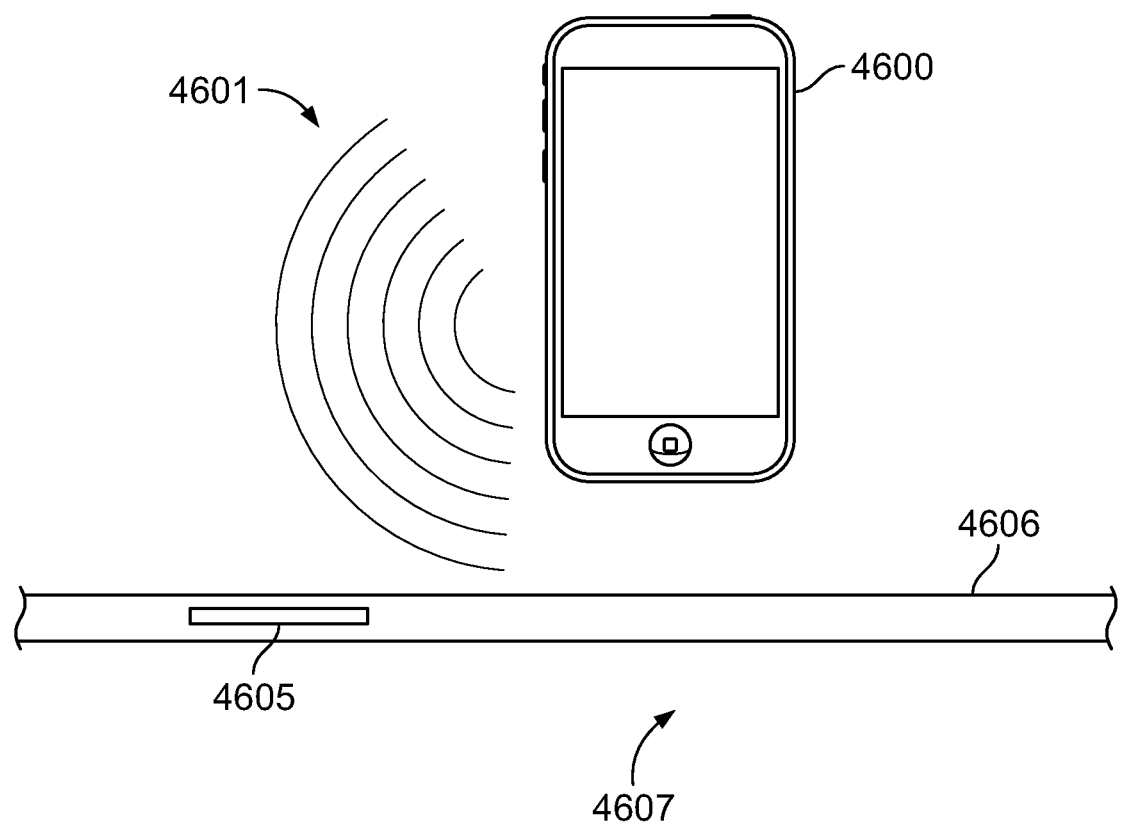

FIG. 46 is another non-preferred embodiment similar to that of FIGS. 40 and 45 combined. More specifically, the EDP device 4605 has the electrodes, antenna, and rectifier circuit fully implanted. The target dermatome(s) are stimulated through this small structure that has a plurality of anodes and a plurality of cathodes and is placed in the subcutaneous region 4606 of patient's body 4607 proximate the target dermatome(s). Wireless energy 4601, in the form of electromagnetic energy, RF energy, ultrasound energy, or any combination thereof, is transferred from an external wireless device 4600 with embodiments as described in FIG. 45.

Telemedicine

As discussed earlier, the electro-dermal patch device is in data communication with and controlled by the companion device. The companion device is further capable of being in data communication with one or more remote patient care facilities and/or patient care personnel enabling telehealth or e-health and therefore allowing health care professionals to evaluate, diagnose and treat patients in remote locations using telecommunications technology.

In accordance with an aspect of the present specification, the user's plurality of health related information, such as the user's hunger profile, standard eating and meals profile, actual eating and meals profile, energy balance, weight trends, glucose data, will power levels, daily or periodic scores related to hunger, appetite, exercise and well-being, daily or periodic composite scores, stimulation induced nausea, dyspepsia and habituation events, including stimulation protocols, setting and parameters are recorded, archived and stored by the Health Management application software on the Cloud (for example). In various embodiments, such recorded and archived health related information as well as stimulation protocols, settings and parameters of the user are communicated to one or more remote care facilities, healthcare industry participants such as insurance companies and/or patient care personnel in real time, on-demand and/or periodically.

This enables the user to communicate his health status, trends, treatment or therapy details as well as therapeutic outcomes to the remote care facility and/or patient care personnel for evaluation, advice, support and further treatment and/or medication options. For example, weight loss programs focused on diets often fail due to weight gain after the termination of the program. However, the Health Management application software, which may be HIPAA compliant, enables continuous weight maintenance by: enabling remote monitoring of the user's weight, blood glucose, blood pressure, and overall activity level, for example; supporting a plurality of modes of communication such as, but not limited to, video-conferencing, tele-conferencing, email, and chat to enable interactive, real-time and/or asynchronous weight maintenance related advice or stimulation regimen for the user. For example, the user's nutrition specialist, fitness trainer and/or a concierge service associated with the EDP device and Health Management application of the present specification may access, process and analyze the user's health related information and provide interventions in the form of adjusted or modified stimulation parameters, settings and protocols; modifications to exercising routines, forms, frequency and period; and/or adjustments to the user's dietary plan.

Hydrolysis of Adipose Tissues

In accordance with an aspect, stimulation of the somato-visceral reflex using the EDP device of the present specification allows for innervation of white adipose tissue to hydrolyze them. Even after losing weight, there are spots or areas that remain with a high amount of adipose tissue (for example hip or upper arm or love handles on the trunk). In some embodiments, these spots or areas are stimulated over long periods of time, for example daily, to hydrolyze the adipose tissue accumulated in these spots or areas.

The above examples are merely illustrative of the many applications of the methods and systems of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for using an electrical dermal patch adapted to be continuously worn by a patient, comprising:
   providing an electrical dermal patch comprising:
      a housing having a controller in electrical communication with a pulse generator; and
      at least two electrodes adapted to be adhered to the patient's skin and in electrical communication with the pulse generator, wherein the controller comprises programmatic instructions that, when executed and transmitted to the pulse generator, cause the pulse generator to generate and transmit to the at least two electrodes a first electrical stimulation pulse and a second electrical stimulation pulse, wherein the first electrical pulse is defined by a first phase having a first polarity and a second phase having a second polarity that is opposite the first polarity, wherein the second electrical pulse follows the first electrical pulse and is defined by a third phase having a third polarity and a fourth phase having a fourth polarity that is opposite the third polarity, and wherein the second polarity is equal to the third polarity, programming the controller such that each of the electrical stimulation pulses comprises a pulse width in a range of 10 μsec to 10 msec, a pulse amplitude in a range of 100 μA to 100 mA, and a pulse frequency in a range of 1 Hz and 10,000 Hz;

determining if the patient experiences a change in appetite as a result of an application of said first set of electrical stimulation pulses or said second set of electrical stimulation pulses to the patient's skin; and determining if the patient experiences erythema, scaling, pruritus, folliculitis, or zintertrigo at a point where the two electrodes adhere to the patient's skin.

2. The method of claim 1, wherein the second electrical pulse follows the first electrical pulse after a predetermined time interval.

3. The method of claim 2 wherein the predefined time interval is in a range of 1 minute to 10 minutes.

4. The method of claim 1, wherein the first polarity is positive, the second polarity is negative, the third polarity is negative, and the fourth polarity is positive.

5. The of claim 1, wherein the first polarity is negative, the second polarity is positive, the third polarity is positive, and the fourth polarity is negative.

6. The method of claim 1, wherein each of the at least two electrodes comprise a hypoallergenic conductive gel with at least one adhesive surface.

7. The method of claim 1, wherein the electrode does not comprise imidazolidinyl urea or diazolidinyl urea.

8. The method of claim 1, wherein the electrode comprises carboxymethylcellulose polymer and propylene glycol.

9. The method of claim 1, wherein the at least one adhesive surface is adapted to adhere to the patient's skin and have a peel strength in a range of 1.0 to 2.1 newtons.

10. The method of claim 1, wherein the at least one adhesive surface is adapted to adhere to the patient's skin and have a total skin contact surface area in a range of 2 $cm^2$ to 4 $cm^2$.

11. The method of claim 1, wherein the at least two electrodes are positioned in a same plane parallel to the patient's skin and separated by an area of 0.05 $cm^2$ to 0.4 $cm^2$.

12. The method of claim 1, wherein an amplitude of the first phase, the second phase, the third phase, and the fourth phase are equal and wherein a pulse width of the first phase, the second phase, the third phase, and the fourth phase are equal.

13. The electrical dermal patch of claim 1, wherein an amplitude of the first phase and the fourth phase are equal, wherein a pulse width of the first phase and the fourth phase are equal, an amplitude of the second phase and the third phase are equal, wherein a pulse width of the second phase and the third phase are equal, and wherein at least one of the amplitude and the pulse width of the first phase is different from the amplitude and pulse width of the second phase.

14. The method of claim 1 wherein the first phase is defined by a waveform characterized by a first period and a second period, wherein the first period comprises a first 10 μs of the waveform and the second period comprises a remainder of the waveform and wherein said waveform is defined by a maximum amplitude during the first period and an amplitude less than said maximum amplitude during the second period.

15. The method of claim 14 wherein the maximum amplitude is in a range of 20 to 40 mA.

16. The method of claim 14 wherein the maximum amplitude is in a range of 20 to 40 mA and an average amplitude across said first period and second period is in a range of 10 mA to 20 mA.

17. The method of claim 1 wherein the pulse generator has a maximum compliance voltage in a range of 40 volts to 60 volts.

18. The method of claim 1 wherein at least one of the first phase, second phase, third phase, and fourth phase is defined by a waveform characterized by a first period, a second period, and a third period, wherein the first period comprises at least a portion of 0 to 10 μs of the waveform, the second period comprises at least a portion of 10 μs to 100 μs of the waveform, and the third period comprises at least a portion of 100 μs to 200 μs of the waveform, wherein the first period is defined by a maximum amplitude and the second and third periods are defined by a remainder amplitude less than said maximum amplitude.

19. The method of claim 18 wherein the maximum amplitude is in a range of 20 mA to 40 mA.

20. The method of claim 18 wherein, in the second period, a decay of the remainder amplitude is defined by a first negative slope having a first magnitude and, in the third period, a decay of said remainder amplitude is defined by a second negative slope having a second magnitude, wherein the first magnitude is less than the second magnitude.

21. The method of claim 18 wherein an average of the maximum amplitude and the remainder amplitude is in a range of 10 mA to 20 mA.

* * * * *